United States Patent
Rush et al.

(10) Patent No.: US 9,885,065 B2
(45) Date of Patent: Feb. 6, 2018

(54) METHODS FOR SUCCINATE PRODUCTION

(71) Applicant: BioAmber International S.à.r.l., Luxembourg (LU)

(72) Inventors: Brian J. Rush, Minneapolis, MN (US); Arlene M. Fosmer, Eden Prairie, MN (US)

(73) Assignee: BIOAMBER INC., St. Paul, MN (US)

( * ) Notice: Subject to any disclaimer, the term of this patent is extended or adjusted under 35 U.S.C. 154(b) by 0 days.

(21) Appl. No.: 14/374,464

(22) PCT Filed: Jan. 25, 2013

(86) PCT No.: PCT/US2013/023300
§ 371 (c)(1),
(2) Date: Jul. 24, 2014

(87) PCT Pub. No.: WO2013/112939
PCT Pub. Date: Aug. 1, 2013

(65) Prior Publication Data
US 2014/0363862 A1    Dec. 11, 2014

Related U.S. Application Data

(60) Provisional application No. 61/590,795, filed on Jan. 25, 2012.

(51) Int. Cl.
*C12P 7/46* (2006.01)
*C12N 1/00* (2006.01)
*C12N 15/52* (2006.01)

(52) U.S. Cl.
CPC ............... *C12P 7/46* (2013.01); *C12N 15/52* (2013.01)

(58) Field of Classification Search
CPC .................................. C12N 15/52; C12P 7/46
USPC ...... 435/145, 254.11, 254.2, 254.21, 254.22, 435/254.23
See application file for complete search history.

(56) References Cited

U.S. PATENT DOCUMENTS

| 2011/0143405 A1 | 6/2011 | Verwaal et al. |
| 2012/0135482 A1* | 5/2012 | Jansen ............... C12N 1/18 435/142 |
| 2012/0165569 A1* | 6/2012 | Verwaal ............. C12N 9/001 562/590 |
| 2013/0302866 A1* | 11/2013 | Finley ............... C12N 9/0006 435/145 |

FOREIGN PATENT DOCUMENTS

| EP | 1751292 B1 | 7/2010 |
| WO | WO 03/102200 A2 * | 12/2003 |
| WO | 2011064151 A1 | 6/2011 |
| WO | WO 2013/004670 A1 * | 1/2013 ............... C12P 7/46 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Zelle et al., Malic acid production by *Saccharomyces cerevisiae*: engineering of pyruvate carboxylation, oxaloacetate reduction and malate export. Appl. Environ. Microbiol., 2008, vol. 74(9): 2766-2777.*
International Application No. PCT/US2013/023300, International Search Report and Written Opinion dated Mar. 22, 2013, 11 pages.
Raab et al., "Oxidative Versus Reductive Succinic Acid Production in the Yeast *Saccharomyces cerevisiae*", Bioengineered Bugs 2:2, Mar.-Apr. 2011, pp. 120-123.
Abbott et al., "Metabolic engineering of *Saccharomyces cerevisiae* for production of carboxylic acids: current status and challenges", FEMS Yeast Res, 2009, 9, 1123-1136.
Nakayama et al., *Candida krusei* produces ethanol without production of succinic acid; a potential advantage for ethanol recovery by pervaporation membrane separation:, FEMS Yeast Res, 2008, 8, 706-714.

* cited by examiner

*Primary Examiner* — Ganapathirama Raghu
(74) *Attorney, Agent, or Firm* — Baker & Hostetler LLP

(57) ABSTRACT

Provided herein are genetically modified yeast cells for the production of succinate, methods of making these yeast cells, and methods of using these cells to produce succinate.

32 Claims, 42 Drawing Sheets

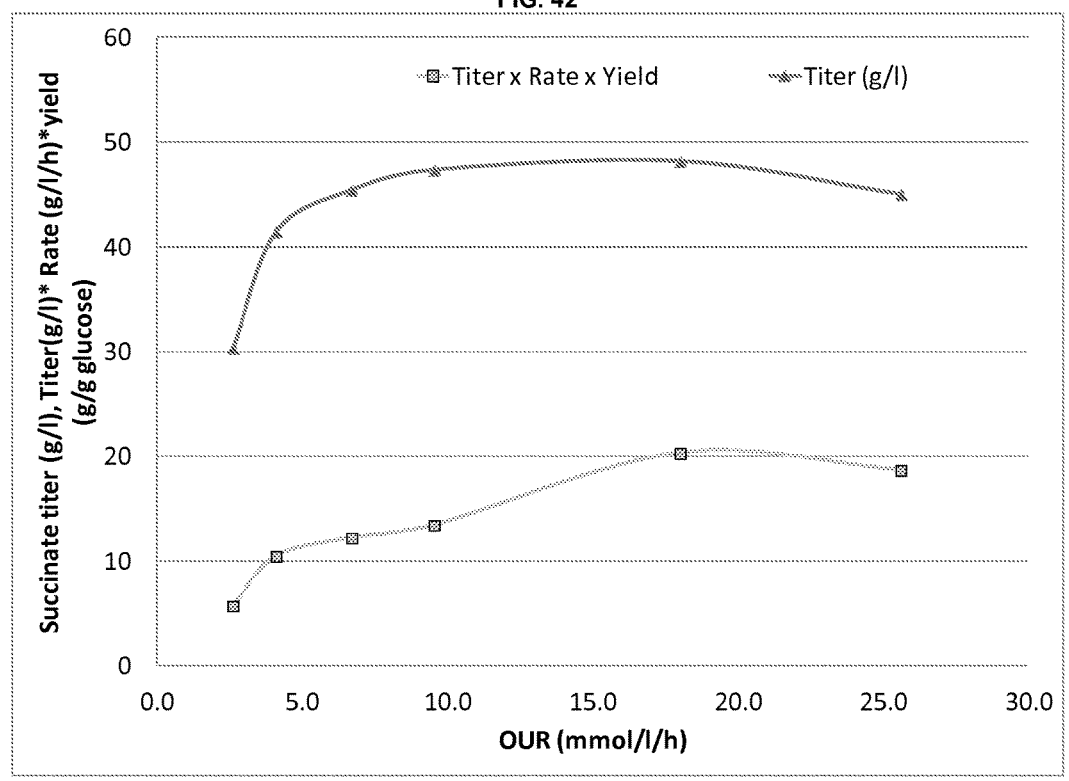

METHODS FOR SUCCINATE PRODUCTION

RELATED APPLICATIONS

The present application claims priority to U.S. Provisional Patent Application No. 61/590,795, filed Jan. 25, 2012, and to PCT/US2013/023300, filed Jan. 25, 2013, the disclosures of which are incorporated by reference herein in their entirety, including drawings.

BACKGROUND

Succinate (butanedioic acid) is a four carbon dicarboxylic acid that plays a key role in the citric acid cycle. Succinate was recently listed by the US Department of Energy at the top of its list of value added chemicals from biomass. Succinate is a precursor for a number of compounds, including tetrahydrofuran, 1,4-butanediol, and γ-butyrolactone. Succinate has a wide variety of potential applications including use in liquid antigels, heat transfer fluids, the solvents gamma butyrolactone (GBL) and dimethyl isosorbide, pigments, the polyesters poly-butylene succinate (PBS) and PEIT, synthesis intermediates and plasticizers.

Succinate has traditionally been derived from maleic anhydride, which is produced by oxidation of butane. In recent years, there have been several attempts to move away from these traditional production methods to biological production methods. Biological production provides several advantages over derivation from petrochemical sources, including increased efficiency and cost effectiveness and decreased environmental impact.

Previously-developed biological succinate production methods have primarily utilized bacterial fermentation hosts. Although several bacterial species have been used successfully to produce succinate, bacteria present certain drawbacks for large-scale organic acid production. As organic acids are produced, the fermentation medium becomes increasingly acidic. These lower pH conditions result in lower costs for organic acid production, because the resultant product is partially or wholly in the acid form. However, most bacteria do not perform well in strongly acidic environments, and therefore either die or begin producing so slowly that they become economically unviable. To prevent this, it becomes necessary to buffer the medium to maintain a higher pH. However, this makes recovery of the organic acid product more difficult and expensive.

SUMMARY

Provided herein in certain embodiments are methods of producing succinate, for example succinic acid, by culturing the genetically modified yeast cells provided herein in the presence of at least one carbon source, then isolating the succinate from the culture. In certain embodiments, the carbon source is one or more of glucose, xylose, arabinose, sucrose, fructose, cellulose, glucose oligomers, and glycerol.

In one aspect, provided is a method of producing a succinate-containing fermentation broth, the method comprising: culturing in a fermenter a genetically modified yeast cell in the presence of at least one carbon source to provide succinate; and introducing into the fermenter sufficient oxygen to provide an oxygen uptake rate of greater than about 5 mmol/L/h (for example, greater than about 6 mmol/L/h, greater than about 8 mmol/L/h, greater than about 10 mmol/L/h, greater than about 12 mmol/L/h, or greater than about 14 mmol/L/h), wherein a final concentration of succinate in the fermentation broth is greater than about 20 g/L (for example, greater than about 40 g/L, greater than about 60 g/L, or greater than about 80 g/L).

In some embodiments, a production rate of succinate is greater than about 0.25 g/L/h (for example, greater than about 1 g/L/h, greater than about 1.5 g/L/h, greater than about 2 g/L/h, or greater than about 3 g/L/h). In some embodiments, a specific production rate of succinate is greater than about 0.1 g/g/h (for example, greater than about 0.15 g/g/h, greater than about 0.5 g/g/h, or greater than about 1.0 g/g/h). In some embodiments, the product yield of succinate is greater than about 25%. In some embodiments, the cell dry weight at end of fermentation is less than about 10 g/L (for example, less than about 7 g/L, less than about 5 g/L, or less than about 3 g/L). In some embodiments, the genetically modified yeast cell dry weight at inoculation is less than about 5 g/L (for example, less than about 3 g/L).

In some embodiments, the genetically modified yeast cell has an active succinate fermentation pathway from phosphoenolpyruvate or pyruvate to succinate. In some embodiments, the active succinate fermentation pathway includes the reactions: (a) pyruvate to oxaloacetate; (b) oxaloacetate to malate; (c) malate to fumarate; and (d) fumarate to succinate. In some embodiments, the succinate fermentation pathway further includes the reaction (e) export of succinate from inside the yeast cell to the extracellular environment. In some embodiments, the genetically modified yeast cell comprises one or more copies of one or more endogenous genes that encode an enzyme that catalyzes any of reactions (a) though (e). In some embodiments, the genetically modified yeast cell comprises one or more copies of one or more endogenous genes selected from the group consisting of pyruvate carboxylase, malate dehydrogenase, fumarase, fumarate reductase, and succinate exporter genes. In some embodiments, one or more of the endogenous genes are operatively linked to an exogenous regulatory element selected from the group consisting of an exogenous promoter and an exogenous terminator. In some embodiments, the genetically modified yeast cell comprises one or more copies of one or more exogenous genes that encode an enzyme that catalyzes any of reactions (a) though (e). In some embodiments, the genetically modified yeast cell comprises one or more copies of one or more exogenous genes selected from the group consisting of pyruvate carboxylase, malate dehydrogenase, fumarase, fumarate reductase, and succinate exporter genes. In some embodiments, the exogenous malate dehydrogenase genes are *Rhizopus delemar* malate dehydrogenase genes encoding the amino acid sequence of SEQ ID NO:167, and in certain of these embodiments the *Rhizopus delemar* malate dehydrogenase genes comprise the nucleotide sequence of SEQ ID NO:166. In some embodiments, the genetically modified yeast cell comprises a genetic modification to enhance succinate export. In some embodiments, the genetically modified yeast cell belongs to a genus selected from the group consisting of *Issatchenkia, Candida, Pichia, Zygosaccharomyces, Kluyveromyces, Saccharomyces, Debaryomyces*, and *Saccharomycopsis*. In some embodiments, the genetically modified yeast cell is a species selected from the group consisting of *Issatchenkia orientalis, Candida lambica, Candida sorboxylosa, Candida zemplinina, Candida geochares, Pichia membranifaciens, Zygosaccharomyces kombuchaensis, Candida sorbosivorans, Kluyveromyces marxianus, Candida vanderwaltii, Candida sorbophila, Zygosaccharomyces bisporus, Zygosaccharomyces lentus, Saccharomyces bayanus, Saccharomyces bulderi, Debaryomyces castellii, Candida boidinii, Candida etchellsii, Kluyveromyces lactis, Pichia jadinii, Pichia anomala, Saccharomycopsis cratae-*

*gensis*, and *Pichia jadinii*. In some embodiments, the genetically modified yeast cell is from the *Pichia fermentans/ Issatchenkia orientalis* clade.

In some embodiments, the carbon source is selected from the group consisting of glucose, xylose, arabinose, sucrose, fructose, cellulose, glucose oligomers, and glycerol. In some embodiments, a final pH of the fermentation broth is less than about 6.0 (for example, less than about 5.5, less than about 5.0, less than about 4.0, or less than about 3.5). In some embodiments, a final concentration of succinate comprises greater than about 20 g/L of succinate (for example, greater than about 40 g/L, greater than about 80 g/L, or greater than about 90 g/L). In some embodiments, the active succinate fermentation pathway further includes step (e) a genetic modification to enhance succinate export. In some embodiments, the genetically modified yeast cell has a deletion or disruption in pyruvate decarboxylase ("PDC") gene. In some embodiments, the genetically modified yeast cell is a succinate resistant yeast cell.

In another aspect, provided is a method of producing succinate, the method comprising: culturing in a fermenter a genetically modified yeast cell in the presence of at least one carbon source to produce succinate; and providing sufficient oxygen to the fermenter to obtain an oxygen uptake rate of from about 8 mmol/L/h to about 25 mmol/L/h, wherein the cell dry weight at end of fermentation is less than about 10 g/L, and wherein the method comprises at least one of the following properties: i) a final concentration of succinate in the fermentation broth is greater than about 20 g/L, ii) a production rate of succinate greater than about 0.25 g/L/h, iii) a product yield of succinate greater than 25%, and iv) a specific succinate production rate greater than about 0.1 g/g/h. In some embodiments, a final pH of the fermentation broth is less than about 6.0, suitably less than about 5.5, desirably less than about 5.0, preferably less than about 4.0, and more preferably less than about 3.5. In some embodiments, the genetically modified yeast cell has an oxygen uptake rate of from about 8 mmol/L/h to about 20 mmol/L/h (for example, from about 8 mmol/L/h to about 15 mmol/L/h). In some embodiments, the production rate of succinate is greater than about 0.25 g/L/h (for example, greater than about 1 g/L/h, greater than about 1.5 g/L/h, greater than about 2 g/L/h, or greater than about 3 g/L/h). In some embodiments, the product yield of succinate is greater than about 50% (for example, greater than about 60%, greater than about 70%, greater than about 80%, or greater than about 90%). In some embodiments, the genetically modified yeast is Crabtree negative. In some embodiments, the dissolved oxygen in the fermentation broth is maintained at less than about 10% of air saturation at one atmosphere for greater than about 10 hours during the batch time.

BRIEF DESCRIPTION OF DRAWINGS

FIG. 42 shows succinate production (g/L) at 90 h: straight batch glucose, pH 3.0, 10% $CO_2$, OUR (mmol/L/h) variable. FIG. 42 also shows the product of: succinate (g/L) multiplied by the succinate production rate (g/L/h) multiplied by the yield (g succinate/g glucose) with OUR as the variable.

DETAILED DESCRIPTION

Figure 1:
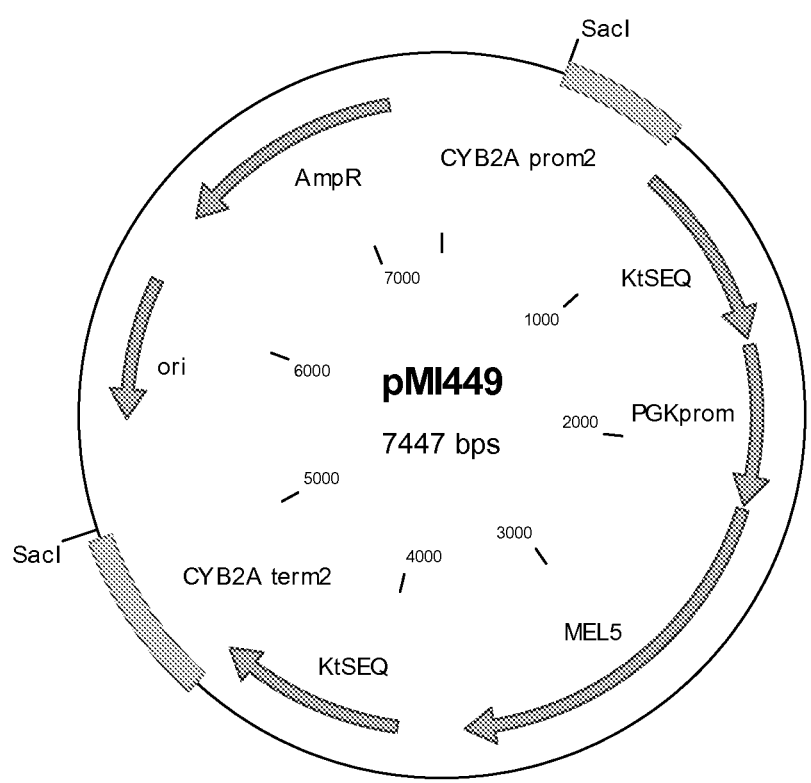
FIG. 1 shows plasmid pMI449, CYB2A deletion construct.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference in their entirety.

ABBREVIATIONS

α-KGDH, α-ketoglutarate dehydrogenase; CYB2, L-(+)-lactate:ferricytochrome c oxidoreductase; CYC, iso-2-cytochrome c; ENO1, enolase; FRD, fumarate reductase; FUM, fumarase; GAPDH, glyceraldehyde-3-phosphate dehydrogenase; GPD, glycerol 3-phosphate dehydrogenase; G6PD, glucose 6-phosphate dehydrogenase; IDH, isocitrate dehydrogenase; MDH, malate dehydrogenase; OAA, oxaloacetate; OUR, oxygen uptake rate; PCK, phosphoenolpyruvate carboxykinase; PDC, pyruvate decarboxylase; PEP, phosphoenolpyruvate; 6PGDH, 6-phosphogluconate dehydrogenase; PGK, phosphoglycerate kinase; PFL, pyruvate formate lyase; PPC, phosphoenolpyruvate carboxylase; PYC, pyruvate carboxylase; RKI, ribose 5-phosphate ketolisomerase; TAL, transaldolase; TCA, tricarboxylic acid; TEF, translation elongate factor; TKL, transketolase; URA3, orotidine 5'-phosphate decarboxylase; XDH, xylitol dehydrogenase; XR, xylose reductase; 6PGDH, 6-phosphogluconate dehydrogenase; SpMAE, succinate exporter.

Definitions

As used herein, "inoculation" is defined as the point in time wherein a microorganism capable of producing succinate is introduced into the fermentation media. This is a term that is well known to those skilled in the art.

As used herein, "end of fermentation" is defined as point in time where the fermentation is stopped to harvest the succinate. This point is triggered by meeting any of the following criteria: exhaustion of the desired fraction of carbon source supplied, cessation of carbon source consumption, or cessation of succinate formation.

As used herein, "cell dry weight at inoculation" refers to the concentration of dry cell mass present in the fermentation medium at inoculation, as measured in a fermentation sample. For fed-batch fermentations, the initial cell dry weight is calculated based on the final volume of fermentation media. Measurement of dry cell weight is a method known to those skilled in the art. Cell dry weight at inoculation is commonly expressed in units of g/L.

As used herein, "cell dry weight at end of fermentation" refers to the concentration of dry cell mass present in the fermentation medium at end of fermentation, as measured in a fermentation sample. Cell dry weight at end of fermentation is commonly expressed in units of g/L.

As used herein, "final titer" shall be defined as the concentration of a substance in the fermentation broth at the end of fermentation. The final titer is commonly expressed in units of grams/liter (g/L).

As used herein, "initial titer" shall be defined as the concentration of a substance present at inoculation. The initial titer is commonly expressed in units of grams/liter (g/L).

As used herein, "batch time" shall be defined as the amount of time that has elapsed between the inoculation and the end of fermentation. The batch time is commonly expressed in units of hours (h).

As used herein, "production rate" shall be defined as the final titer of succinate at end of fermentation divided by the batch time. The production rate is commonly expressed in units of grams per liter per hour (g/L/h).

One skilled in the art will recognize that the unit designation "x/y/z" is equivalent to and represents a shorthand version of the units $xy^{-1}z^{-1}$ or $x/(y*z)$. For example, g/L/h is equivalent to $gL^{-1} h^{-1}$ or $g/(L*h)$.

As used herein, the "specific production rate" refers to the production rate divided by the cell dry weight at the end of fermentation.

As used herein, "product yield" for succinate shall be defined as a ratio of two quantities: a) mass of product (succinate) produced in the course of the batch (numerator) b) the mass of carbon source added to the batch (denominator). The product yield as a percentage is commonly expressed in units of gram per gram (g/g) times 100. Particular note should be taken that product yield is calculated as a ratio of masses (g). The mass of succinate produced should account for the mass of succinate present in the fermentation medium at the end of the batch, as well as the mass of any succinate harvested during the course of the batch, less the mass of succinate present at the start of batch, and further less the mass of any succinate added during the course of the batch. The mass of carbon source added to the batch should include the mass of all carbon source(s) present in the fermenter at the start of the batch in addition to the mass of any carbon source(s) added during the course of the batch less the mass of carbon source(s) present in the fermenter at the end of fermentation.

As used herein, a yeast cell having a Crabtree-negative phenotype is any yeast cell that does not exhibit the Crabtree effect. The term "Crabtree-negative" refers to both naturally-occurring and genetically-modified organisms. Briefly, the Crabtree effect is defined as the inhibition of oxygen consumption by a microorganism when cultured under aerobic conditions due to the presence of glucose (e.g., 50 grams of glucose/L). That is, a yeast cell having a Crabtree-positive phenotype continues to ferment irrespective of oxygen availability due to the presence of glucose, while a yeast cell having a Crabtree-negative phenotype does not exhibit glucose mediated inhibition of oxygen consumption. Examples of yeast cells typically having a Crabtree-negative phenotype include, without limitation, yeast cells from the following genera: *Kluyveromyces, Pichia, Hansenula, Trichosporon,* and *Yamadazyma*.

"Succinate" as used herein includes the anions of a succinate salt and acid forms of succinate such as succinic acid.

"Oxygen uptake rate" ("OUR") as used herein refers to the volumetric rate at which oxygen is consumed during the fermentation. Inlet and outlet oxygen concentrations can be measured with exhaust gas analysis, for instance by mass spectrometers. OUR is calculated by one of ordinary skill in the relevant arts, using the Direct Method described in *Bioreaction Engineering Principles* 2nd Edition, 2003, Kluwer Academic/Plenum Publishers, p. 449, equation 1.

As used herein, "final pH" refers to fermentation medium pH at end of fermentation, as measured in a fermentation sample.

DESCRIPTION

Provided herein are genetically modified yeast cells for the production of succinate, methods of making these yeast cells, and methods of using these cells to produce succinate.

There are three primary fermentation pathways for producing succinate from a microorganism: reductive TCA, oxidative TCA, and glyoxylate shunt.

The reductive TCA pathway begins with carboxylation of the three carbon glycolytic intermediate phosphoenolpyruvate (PEP) or pyruvate to oxaloacetate (OAA) (by PEP carboxylase (PPC) and pyruvate carboxylase (PYC), respectively). OAA is converted to malate by malate dehydrogenase (MDH), malate is converted to fumarate by fumarase (FUM, also known as fumarate hydratase), and fumarate is converted to succinate by fumarate reductase (FRD). When written from the perspective of redox state, the net stoichiometry for this succinate production pathway is: 1 glucose $(C_6H_{12}O_6)+2\ CO_2+2\ (NADH+H^+)\rightarrow 2$ succinic acid $(C_4H_6O_4)+2H_2O+2\ NAD^+$. The reductive TCA pathway provides the highest succinate yield of the three succinate fermentation pathways, but it results in a net deficit in reducing power (NADH). This means that in isolation the pathway results in a redox imbalance. In order to provide redox balance, the reductive TCA pathway can be combined with one or both of the oxidative TCA or glyoxylate shunt pathways, or with one or more unrelated pathways that produce NADH or NADPH.

The oxidative TCA pathway begins with the conversion of OAA and acetyl-CoA to citrate by citrate synthase. OAA can be generated from carboxylation of PEP or pyruvate, while acetyl-CoA is generated from the decarboxylation of pyruvate by PDH or pyruvate formate lyase (PFL). Citrate is converted to isocitrate by aconitase, isocitrate is converted to a-ketoglutarate by isocitrate dehydrogenase (IDH), α-ketoglutarate is converted to succinyl-CoA by α-ketoglutarate dehydrogenase (α-KGDH), and succinyl-CoA is converted to succinate by succinyl coenzyme A synthetase (succinate thiokinase). The net stoichiometry for this succinate production pathway is: 1 glucose $(C_6H_{12}O_6)+2H_2O+5\ NAD^+\rightarrow 1$ succinic acid $(C_4H_6O_4)+2\ CO_2+5\ (NADH+H^+)$. This pathway has a lowest carbon yield of the three succinate fermentation pathways, but the highest yield of reducing power.

Like the oxidative TCA pathway, the glyoxylate shunt pathway begins with the generation of citrate from OAA and acetyl-CoA and the conversion of citrate to isocitrate. Isocitrate is converted to glyoxylate and succinate by isocitrate lyase. Glyoxylate is condensed with acetyl-CoA to form malate by malate synthase, and the resultant malate is converted to succinate via a fumarate intermediate. The net stoichiometry for this succinate production pathway is: 1 glucose $(C_6H_{12}O_6)+\frac{4}{3} H_2O+2\% NAD^+\rightarrow 1\frac{1}{3}$ succinic acid $(C_4H_6O_4)+\frac{2}{3} CO_2+2\frac{2}{3} (NADH+H^+)$.

Previous attempts to produce succinate from microorganisms at commercially viable levels have utilized bacterial fermentation hosts. These bacterial hosts are either native succinate producers or non-native succinate producers that have been genetically engineered to produce succinate. Examples of native succinate producers are *Actinobacillus succinogenes* (see, e.g., U.S. Pat. No. 5,504,004) and *Mannheimia succiniciproducens*, each of which primarily utilizes a reductive TCA pathway. *A. succinogenes* and *M. succiniciproducens* both produce relatively high titers of succinate, but they also produce various organic acid by-products. The presence of these by-products decreases yield and complicates succinate recovery. An example of a non-native succinate producer is *Escherichia coli*. Although *E. coli* is capable of producing trace levels of succinate naturally, genetic modification is required to obtain useful titers. Significant efforts have been made previously to increase succinate yield in genetically modified *E. coli* by decreasing the formation of other organic acids and combining different succinate fermentation pathways. Although *E. coli* strains have been developed that produce fewer organic acid by-products, they still produce lower succinate titers than the native producers. In addition, *E. coli* requires aerobic conditions to grow, but produces succinic acid at high yields only under anaerobic conditions. This means that succinate production in *E. coli* requires a two-phase fermentation.

One drawback common to all of the bacterial hosts developed to date for succinate production is relatively poor performance in strongly acidic environments. However, allowing the low pH conditions to develop as organic acids are produced is preferred for commercial succinate production. The ideal host for commercial succinate production should produce high levels of succinate and relatively low levels of other organic acids, and should possess a high degree of pH resistance and the ability to both grow and ferment under anaerobic or substantially anaerobic conditions.

As disclosed herein, a set of yeast cells from various species were tested for succinate resistance. Cells exhibiting succinate resistance were further evaluated based on their growth rates and glucose consumption rates in media containing varying concentrations of succinate. Based on these experiments, a set of ideal host cells for succinate production were identified. These host cells were then genetically modified to contain an active succinate fermentation pathway, resulting in a set of genetically modified yeast cells that produce succinate under low pH conditions.

Provided herein in certain embodiments are genetically modified succinate-resistant yeast cells having at least one active succinate fermentation pathway from PEP or pyruvate to succinate. A yeast cell having an "active succinate fermentation pathway" as used herein produces active enzymes necessary to catalyze each reaction in a succinate fermentation pathway, and therefore is capable of producing succinate in measurable yields when cultured under fermentation conditions in the presence of at least one fermentable sugar. A yeast cell having an active succinate fermentation pathway comprises one or more succinate fermentation pathway genes. A "succinate fermentation pathway gene" as used herein refers to the coding region of a nucleotide sequence that encodes an enzyme involved in an active succinate fermentation pathway.

In certain embodiments, the yeast cells provided herein have a reductive TCA active succinate fermentation pathway that proceeds through PEP or pyruvate, OAA, malate, and fumarate intermediates. In these embodiments, the yeast cells comprise a set of succinate fermentation pathway genes comprising MDH, FUM, and FRD genes, one or both of PPC and PYC genes, and a succinate exporter.

In those embodiments where the yeast cells provided herein have a reductive TCA active succinate fermentation pathway, the cells may further have an active reduction pathway. An "active reduction pathway" as used herein produces NADH or NADPH from NAD or NADP, respectively, thereby helping to balance out redox imbalances generated by a reductive TCA pathway. A yeast cell having an active reduction pathway comprises one or more reduction pathway genes. A "reduction pathway gene" as used herein refers to the coding region of a nucleotide sequence that encodes an enzyme involved in an active reduction pathway.

In certain embodiments, the yeast cells provided herein have a pentose phosphate active reduction pathway that proceeds through glucose 6-phosphate, 6-phosphogluconaolactone, 6-phosphogluconate, and ribulose 5-phosphate intermediates. In these embodiments, the yeast cells comprise a set of reduction pathway genes comprising glucose 6-phosphate dehydrogenase (G6PD), gluconolactonase, and 6-phosphogluconate dehydrogenase (6PGDH) genes.

In certain embodiments, the yeast cells provided herein may have one or more active succinate fermentation pathways, or portions of such pathways, that are not reductive TCA active succinate fermentation pathways. In these embodiments, the other pathways or portions thereof may be present in addition to or in lieu of the reductive TCA pathway. For example, the cells may comprise a reductive TCA active succinate fermentation pathway and all or a part of an oxidative TCA or glyoxylate shunt active succinate fermentation pathway.

The succinate fermentation pathway and reduction pathway genes in the yeast cells provided herein may be endogenous or exogenous. "Endogenous" as used herein with regard to genetic components such as genes, promoters, and terminator sequences means that the genetic component is present at a particular location in the genome of a native form of a particular yeast cell. "Exogenous" as used herein with regard to genetic components means that the genetic component is not present at a particular location in the genome of a native form of a particular yeast cell. "Native" as used herein with regard to a yeast cell refers to a wild-type yeast cell of a particular yeast species. "Native" as used herein with regard to a metabolic pathway refers to a metabolic pathway that exists and is active in a native yeast cell.

An exogenous genetic component may have either a native or non-native sequence. An exogenous genetic component with a native sequence comprises a sequence identical to (apart from individual-to-individual mutations which do not affect function) a genetic component that is present in the genome of a native cell (i.e., the exogenous genetic component is identical to an endogenous genetic component). However, the exogenous component is present at a different location in the host cell genome than the endogenous component. For example, an exogenous MDH gene that is identical to an endogenous MDH gene may be inserted into a yeast cell, resulting in a modified cell with a non-native (increased) number of MDH gene copies. Similarly, an exogenous PDC promoter that is identical to an endogenous PDC promoter can be inserted into a yeast cell such that it is operatively linked to an endogenous gene such as an MDH gene, resulting in altered expression of the endogenous gene. An exogenous genetic component with a non-native sequence comprises a sequence that is not found in the genome of a native cell. For example, an exogenous MDH gene from a particular species may be inserted into a yeast cell of another species. Similarly, an exogenous PDC promoter from a particular species may be inserted into a yeast cell of another species.

An exogenous gene is preferably integrated into the host cell genome in a functional manner, meaning that it is capable of producing an active protein in the host cell. However, in certain embodiments the exogenous gene may be introduced into the cell as part of a vector that is stably maintained in the host cytoplasm.

In certain embodiments, the genetically modified yeast cells provided herein comprise one or more exogenous succinate fermentation and/or reduction pathway genes.

In certain embodiments, the yeast cells provided herein comprise one or more endogenous succinate fermentation and/or reduction pathway genes.

In certain embodiments, the yeast cells provided herein comprise one or more endogenous succinate fermentation and/or reduction pathway genes and one or more exogenous succinate fermentation and/or reduction pathway genes. In certain embodiments, the yeast cells may comprise both endogenous and exogenous copies of a single succinate fermentation pathway gene. For example, a yeast cell may comprise both endogenous and exogenous copies of an MDH gene.

Succinate fermentation and/or reduction pathway genes in the modified yeast cells provided herein may be operatively linked to one or more regulatory elements such as a promoter or terminator. As used herein, the term "promoter" refers to an untranslated sequence located upstream (i.e., 5') to the translation start codon of a gene (generally within about 1 to 1000 base pairs (bp), preferably within about 1 to 500 bp) which controls the start of transcription of the gene. The term "terminator" as used herein refers to an untranslated sequence located downstream (i.e., 3') to the translation finish codon of a gene (generally within about 1 to 1000 bp, preferably within about 1 to 500 bp, and especially within about 1 to 100 bp) which controls the end of transcription of the gene. A promoter or terminator is "operatively linked" to a gene if its position in the genome relative to that of the gene is such that the promoter or terminator, as the case may be, performs its transcriptional control function. Suitable promoters and terminators are described, for example, in WO99/14335, WO00/71738, WO02/42471, WO03/102201, WO03/102152 and WO03/049525 (all incorporated by reference herein in their entirety).

Regulatory elements linked to succinate fermentation and/or reduction pathway genes in the yeast cells provided herein may be endogenous or exogenous. In certain embodiments, exogenous regulatory elements may comprise a sequence with a relatively high degree of sequence identity to a native regulatory element. For example, an exogenous gene may be linked to an exogenous promoter or terminator having at least 50%, at least 60%, at least 70%, at least 80%, or at least 90% sequence identity to a native promoter or terminator. Sequence identity percentages for nucleotide or amino acid sequences can be calculated by methods known in the art, such as for example using BLAST (National Center for Biological Information (NCBI) Basic Local Alignment Search Tool) version 2.2.1 software with default parameters. For example, a sequence having an identity score of at least 90% using the BLAST version 2.2.1 algorithm with default parameters is considered to have at least 90% sequence identity. The BLAST software is available from the NCBI, Bethesda, Md. In those embodiments wherein multiple exogenous genes are inserted into a host cell, each exogenous gene may be under the control of a different regulatory element, or two or more exogenous genes may be under the control of the same regulatory elements.

Examples of promoters that may be linked to one or more succinate fermentation and/or reduction pathway genes in the yeast cells provided herein include, but are not limited to, promoters for pyruvate decarboxylase (PDC1), phosphoglycerate kinase (PGK), xylose reductase (XR), xylitol dehydrogenase (XDH), L-(+)-lactate-cytochrome c oxidoreductase (CYB2), translation elongation factor-1 or -2 (TEF1, TEF2), enolase (ENO1), glyceraldehyde-3-phosphate dehydrogenase (GAPDH), and orotidine 5'-phosphate decarboxylase (URA3) genes. In these examples, the succinate fermentation and/or reduction pathway genes may be linked to endogenous or exogenous promoters for PDC1, PGK, XR, XDH, CYB2, TEF1, TEF2, ENO1, GAPDH, or URA3 genes. Where the promoters are exogenous, they may be identical to or share a high degree of sequence identity (i.e., at least about 80%, at least about 85%, at least about 90%, at least about 95%, or at least about 99%) with native promoters for PDC1, PGK, XR, XDH, CYB2, TEF1, TEF2, ENO1, GAPDH, or URA3 genes.

Examples of terminators that may be linked to one or more succinate fermentation and/or reduction pathway genes in the yeast cells provided herein include, but are not limited to, terminators for PDC1, XR, XDH, transaldolase (TAL), transketolase (TKL), ribose 5-phosphate ketolisomerase (RKI), CYB2, or iso-2-cytochrome c (CYC) genes or the galactose family of genes (especially the GAL10 terminator). In these examples, the succinate fermentation and/or reduction pathway genes may be linked to endogenous or exogenous terminators for PDC1, XR, XDH, TAL, TKL, RKI, CYB2, or CYC genes or galactose family genes. Where the terminators are exogenous, they may be identical to or share a high degree of sequence identity (i.e., at least about 80%, at least about 85%, at least about 90%, at least about 95%, or at least about 99%) with native terminators for PDC1, XR, XDH, TAL, TKL, RKI, CYB2, or CYC genes or galactose family genes. In certain embodiments, succinate fermentation and/or reduction pathway fermentation pathway genes are linked to a terminator that comprises a functional portion of a native GAL10 gene native to the host cell or a sequence that shares at least 80%, at least 85%, at least 90%, or at least 95% sequence identity with a native GAL10 terminator.

Exogenous genes may be inserted into a yeast host cell via any method known in the art. In preferred embodiments, the genes are integrated into the host cell genome. Exogenous genes may be integrated into the genome in a targeted or a random manner. In those embodiments where the gene is integrated in a targeted manner, it may be integrated into the loci for a particular gene, such that integration of the exogenous gene is coupled to deletion or disruption of a native gene. Alternatively, the exogenous gene may be integrated into a portion of the genome that does not correspond to a gene.

Targeted integration and/or deletion may utilize an integration construct. The term "construct" as used herein refers to a DNA sequence that is used to transform a cell. The construct may be, for example, a circular plasmid or vector, a portion of a circular plasmid or vector (such as a restriction enzyme digestion product), a linearized plasmid or vector, or a PCR product prepared using a plasmid or genomic DNA as a template. Methods for transforming a yeast cell with an exogenous construct are described in, for example, WO99/14335, WO00/71738, WO02/42471, WO03/102201, WO03/102152, and WO03/049525.

An integration or deletion construct may comprise one or more selection marker cassettes cloned into the construct between the two target DNA sequences. The selection marker cassette contains at least one selection marker gene that allows for selection of transformants. A "selection marker gene" is a gene that encodes a protein needed for the survival and/or growth of the transformed cell in a selective culture medium, and therefore can be used to apply selection pressure to the cell. Successful transformants will contain the selection marker gene, which imparts to the successfully transformed cell at least one characteristic that provides a basis for selection. Typical selection marker genes encode proteins that (a) confer resistance to antibiotics or other toxins (e.g., resistance to bleomycin or zeomycin (e.g., *Streptoalloteichus hindustanus* ble gene), aminoglycosides such as G418 or kanamycin (e.g., kanamycin resistance gene from transposon Tn903), or hygromycin (e.g., aminoglycoside antibiotic resistance gene from *E. coli*)), (b) complement auxotrophic deficiencies of the cell (e.g., deficiencies in leucine (e.g., *Kluyveromyces marxianus* LEU2 gene), uracil (e.g., *K. marxianus, Saccharomyces cerevisiae*, or *Issatchenkia orientalis* URA3 gene), or tryptophan (e.g., *K. marxianus, S. cerevisiae*, or *I. orientalis* TRP gene)), (c) enable the cell to synthesize critical nutrients not available from simple media, or (d) confer the ability for the cell to grow on a particular carbon source (e.g., MEL5 gene from *S. cerevisiae*, which encodes the alpha-galactosidase (melibiose) enzyme and confers the ability to grow on melibiose as the sole carbon source). Preferred selection markers include the URA3 gene, zeocin resistance gene, G418 resistance gene, MEL5 gene, and hygromycin resistance gene. Another preferred selection marker is a CYB2 gene cassette, provided that the host cell either natively lacks such a gene or that its native CYB2 gene(s) are first deleted or disrupted. A selection marker gene is operatively linked to one or more promoter and/or terminator sequences that are operable in the host cell. In certain embodiments, these promoter and/or terminator sequences are exogenous promoter and/or terminator sequences that are included in the selection marker cassette. Suitable promoters and terminators are as described above.

An integration or deletion construct is used to transform the host cell. Transformation may be accomplished using, for example, electroporation and/or chemical transformation (e.g., calcium chloride, lithium acetate-based, etc.) methods. Selection or screening based on the presence or absence of the selection marker may be performed to identify successful transformants. In successful transformants, a homologous recombination event at the locus of the target site results in the disruption or the deletion of the target site sequence. Where the construct targets a native gene for deletion or disruption, all or a portion of the native target gene, its promoter, and/or its terminator may be deleted during this recombination event. The expression cassette, selection marker cassette, and any other genetic material between the target sequences in the integration construct is inserted into the host genome at the locus corresponding to the target sequences. Analysis by PCR or Southern analysis can be performed to confirm that the desired insertion/deletion has taken place.

In some embodiments, cell transformation may be performed using DNA from two or more constructs, PCR products, or a combination thereof, rather than a single construct or PCR product. In these embodiments, the 3' end of one integration fragment overlaps with the 5' end of another integration fragment. In one example, one construct will contain the first sequence from the locus of the target sequence and a non-functional part of the marker gene cassette, while the other will contain the second sequence from the locus of the target sequence and a second non-functional part of the marker gene cassette. The parts of the marker gene cassette are selected such that they can be combined to form a complete cassette. The cell is transformed with these pieces simultaneously, resulting in the formation of a complete, functional marker or structural gene cassette. Successful transformants can be selected for on the basis of the characteristic imparted by the selection marker. In another example, the selection marker resides on one fragment but the target sequences are on separate fragments, so that the integration fragments have a high probability of integrating at the site of interest. In other embodiments, transformation from three linear DNAs can be used to integrate exogenous genetic material. In these embodiments, one fragment overlaps on the 5' end with a second fragment and on the 3' end with a third fragment.

An exogenous succinate fermentation or reduction pathway gene in the modified yeast cells provided herein may be derived from a source gene from any suitable source organism. For example, an exogenous gene may be derived from a yeast, fungal, bacterial, plant, insect, or mammalian source. As used herein, an exogenous gene that is "derived from" a source gene encodes a polypeptide that 1) is identical to a polypeptide encoded by the source gene, 2) shares at least 50%, at least 60%, at least 70%, at least 80%, at least 85%, at least 90%, at least 95%, at least 97%, or at least 99% sequence identity with a polypeptide encoded by the source gene, and/or 3) has the same function in a succinate fermentation or reduction pathway as the polypeptide encoded by the source gene. For example, a FUM gene that is derived from an I. orientalis FUM gene may encode a polypeptide comprising the amino acid sequence of SEQ ID NO:2, a polypeptide with at least 50%, at least 60%, at least 70%, at least 80%, at least 85%, at least 90%, at least 95%, at least 97%, or at least 99% sequence identity to the amino acid sequence of SEQ ID NO:2, and/or a polypeptide that has the ability to catalyze the conversion of malate to fumarate. A gene derived from a source gene may comprise a nucleotide sequence with at least 50%, at least 60%, at least 70%, at least 80%, at least 85%, at least 90%, at least 95%, at least 97%, or at least 99% sequence identity to the coding region of the source gene. In certain embodiments, a gene derived from a source gene may comprise a nucleotide sequence that is identical to the coding region of the source gene. For example, a FUM gene that is derived from an I. orientalis FUM gene may comprise the nucleotide sequence of SEQ ID NO:1 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:1.

In certain embodiments of the modified yeast cells provided herein, an exogenous succinate fermentation or reduction pathway gene may be derived from the host yeast species. For example, where the host cell is I. orientalis, an exogenous gene may be derived from a native I. orientalis gene. In these embodiments, the exogenous gene may comprise a nucleotide sequence identical to the coding region of the native gene, such that incorporation of the exogenous gene into the host cell increases the copy number of a native gene sequence and/or changes the regulation or expression level of the gene if under the control of a promoter that is different from the promoter that drives expression of the gene in a wild-type cell. In other embodiments, the exogenous gene may comprise a nucleotide sequence that differs from the coding region of a native gene, but nonetheless encodes a polypeptide that is identical to the polypeptide encoded by the native gene. In still other embodiments, the exogenous gene may comprise a nucleotide sequence that encodes a polypeptide with at least 50%, at least 60%, at least 70%, at least 80%, at least 85%, at least 90%, at least 95%, at least 97%, or at least 99% sequence identity to a polypeptide encoded by one or more native genes. In certain of these embodiments, the exogenous gene comprises a nucleotide sequence with at least 50%, at least 60%, at least 70%, at least 80%, at least 85%, at least 90%, at least 95%, at least 97%, or at least 99% sequence identity to the coding region of one or more native genes. In still other embodiments, the exogenous gene may encode a polypeptide that has less than 50% sequence identity to a polypeptide encoded by a native gene, but which nonetheless has the same function as the native polypeptide in a succinate fermentation or reduction pathway (i.e., the ability to catalyze the same reaction between reaction intermediates).

In other embodiments, an exogenous succinate fermentation or reduction pathway gene may be derived from a species that is different than that of the host yeast cell. In certain of these embodiments, the exogenous gene may be derived from a different yeast species than the host cell. For example, where the host cell is I. orientalis, the exogenous gene may be derived from S. cerevisiae. In other embodiments, the exogenous gene may be derived from a fungal, bacterial, plant, insect, or mammalian source. For example, where the host cell is I. orientalis, the exogenous gene may be derived from a bacterial source such as E. coli. In those embodiments where the exogenous gene is derived from a non-yeast source, the exogenous gene sequence may be codon optimized for expression in a yeast host cell.

In those embodiments where the exogenous succinate fermentation or reduction pathway gene is derived from a species other than the host cell species, the exogenous gene may encode a polypeptide identical to a polypeptide encoded by a native gene from the source organism. In certain of these embodiments, the exogenous gene may be identical to a native gene from the source organism. In other embodiments, the exogenous gene may share at least 50%, at least 60%, at least 70%, at least 80%, at least 85%, at least 90%, at least 95%, at least 97%, or at least 99% sequence identity to the coding region of a native gene from the source organism. In other embodiments, the exogenous gene may encode a polypeptide that shares at least 50%, at least 60%, at least 70%, at least 80%, at least 85%, at least 90%, at least 95%, at least 97%, or at least 99% sequence identity with a polypeptide encoded by a native gene from the source organism. In certain of these embodiments, the exogenous gene may comprise a nucleotide sequence with at least 50%, at least 60%, at least 70%, at least 80%, at least 85%, at least 90%, at least 95%, at least 97%, or at least 99% sequence identity to the coding region of one or more native genes from the source organism. In still other embodiments, the exogenous gene may encode a polypeptide that has less than 50% sequence identity to a polypeptide encoded by a native gene from the source organism, but which nonetheless has the same function as the native polypeptide from the source organism in an active succinate fermentation or active reduction pathway. An exogenous source gene may be subjected to mutagenesis if necessary to provide a coding sequence starting with the usual eukaryotic starting codon (ATG), or for other purposes.

In certain embodiments, the genetically modified yeast cells provided herein have a reductive TCA active succinate fermentation pathway that proceeds via PEP or pyruvate, OAA, malate, and fumarate intermediates. In these embodiments, the cells comprise one or more succinate fermentation pathway genes encoding enzymes selected from the group consisting PPC, PYC, MDH, FUM, FRD, and succinate exporter genes. In certain embodiments, the cells also have one or more active reduction pathways. In these embodiments, the cells comprise one or more reduction pathway genes encoding enzymes selected from the group consisting of G6PD, gluconolactonase, and 6PGDH. In certain embodiments, the cells may comprise all or part of an active oxidative TCA or glyoxylate shunt succinate fermentation pathway. In these embodiments, the cells comprise one or more genes encoding enzymes selected from the group consisting of citrate synthase, PDH, PFL, aconitase, IDH, α-KGDH, succinate thiokinase, isocitrate lyase, and malate synthase. In certain embodiments, the cells have reduced activity for the endogenous succinate dehydrogenase (SDH) gene.

A "PEP carboxylase gene" or "PPC gene" as used herein refers to any gene that encodes a polypeptide with PEP carboxylase activity, meaning the ability to catalyze the conversion of PEP to OAA. In certain embodiments, a PPC gene may be derived from a bacterial source. For example, a PPC gene may be derived from an *E. coli* PPC gene encoding the amino acid sequence set forth in SEQ ID NO:4 or a *Mannheimia succiniciproducens* PPC gene encoding the amino acid sequence set forth in SEQ ID NO:6. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:4 or 6. In certain embodiments, a PPC gene may comprise the nucleotide sequence set forth in SEQ ID NOs:3 or 5, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:3 or 5. In other embodiments, a PPC gene may be derived from a plant source.

A "pyruvate carboxylase gene" or "PYC gene" as used herein refers to any gene that encodes a polypeptide with pyruvate carboxylase activity, meaning the ability to catalyze the conversion of pyruvate to OAA. In certain embodiments, a PYC gene may be derived from a yeast source. For example, the PYC gene may be derived from an *I. orientalis* PYC gene encoding the amino acid sequence set forth in SEQ ID NO:8, an *S. cerevisiae* PYC1 gene encoding the amino acid sequence set forth in SEQ ID NO:10, or a *K. marxianus* PYC1 gene encoding the amino acid sequence set forth in SEQ ID NO:12. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:8, 10, or 12. In certain embodiments, a PYC gene may comprise the nucleotide sequence set forth in SEQ ID NOs:7, 9, or 11, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:7, 9, or 11. In other embodiments, a PYC gene may be derived from a fungal source other than *R. oryzae*.

A "malate dehydrogenase gene" or "MDH gene" as used herein refers to any gene that encodes a polypeptide with malate dehydrogenase activity, meaning the ability to catalyze the conversion of OAA to malate. In certain embodiments, an MDH gene may be derived from a yeast source. For example, the MDH gene may be derived from an *I. orientalis* MDH1, MDH2, or MDH3 gene encoding the amino acid sequence set forth in SEQ ID NOs:14, 16, or 18, respectively, a *K. marxianus* MDH1, MDH2, or MDH3 gene encoding the amino acid sequence set forth in SEQ ID NOs:20, 22, or 24, respectively, a *Zygosaccharomyces rouxii* MDH1 gene encoding the amino acid sequence set forth in SEQ ID NO:26, an *E. coli* MDH gene encoding the amino acid sequence set forth in SEQ ID NO:28, or a *Rhizopus delemar* MDH gene encoding the amino acid sequence set forth in SEQ ID NO:167. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:14, 16, 18, 20, 22, 24, 26, 28, or 167. In certain embodiments, an MDH gene may comprise the nucleotide sequence set forth in SEQ ID NOs:13, 15, 17, 19, 21, 23, 25, 27, or 166 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:13, 15, 17, 19, 21, 23, 25, 27, or 166.

A "fumarase gene" or "FUM gene" as used herein refers to any gene that encodes a polypeptide with fumarase activity, meaning the ability to catalyze the conversion of malate to fumarate. In certain embodiments, a FUM gene may be derived from a yeast source. For example, the FUM gene may be derived from an *I. orientalis* FUM gene encoding the amino acid sequence set forth in SEQ ID NO:2. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO:2. In certain embodiments, a FUM gene may comprise the nucleotide sequence set forth in SEQ ID NO:1 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO:1. In other embodiments, a FUM gene may be derived from a bacterial source outside of the *Mannheimia* genus.

A "fumarate reductase gene" or "FRD gene" as used herein refers to any gene that encodes a polypeptide with fumarate reductase activity, meaning the ability to catalyze the conversion of fumarate to succinate. In certain embodiments, an FRD gene may be derived from a yeast source. For example, the FRD gene may be derived from an *S. cerevisiae* FRD1 gene encoding the amino acid sequence set forth in SEQ ID NO:30, a *Saccharomyces mikatae* FRD1 gene encoding the amino acid sequence set forth in SEQ ID NO:32, a *Kluyveromyces polyspora* FRD1 gene encoding the amino acid sequence set forth in SEQ ID NO:34, or a *K. marxianus* FRD1 gene encoding the amino acid sequence set forth in SEQ ID NO:36. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:30, 32, 34, or 36. In certain embodiments, a yeast-derived FRD gene may comprise the nucleotide sequence set forth in SEQ ID NOs:29, 31, 33, or 35, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs: 29, 31, 33, or 35. In other embodiments, an FRD gene may be derived from a protozoan source. For example, the FRD gene may be derived from a *Trypanosoma brucei* FRD1 gene encoding the amino acid sequence set forth in SEQ ID NO:38, a *Trypanosoma cruzi* FRD1 gene encoding the amino acid sequence set forth in SEQ ID NO:40, a *Leishmania braziliensis* FRD1 gene encoding the amino acid sequence set forth in SEQ ID NO:42, or a *Leishmania mexicana* FRD1 gene encoding the amino acid sequence set forth in SEQ ID NO:44. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:38, 40, 42, or 44. In certain embodiments, a protozoan-derived FRD gene may comprise the nucleotide sequence set forth in SEQ ID NOs:37, 39, 41, or 43, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:37, 39, 41, or 43.

A "succinate exporter gene" as used herein refers to any gene that encodes a polypeptide which gives cells the ability to transport succinate out of the cell into the extracellular environment. In certain embodiments, the succinate exporter gene may be derived from a fungal source. For example, the MAE (malic anion exporter) gene is a characterized succinate transporter and may be derived from an *Schizosaccharomyces pombe* gene encoding the amino acid sequence set forth in SEQ ID NO:46 or an *Aspergillus oryzae* malic anion transporter (MAE) gene encoding the amino acid sequence set forth in SEQ ID NO:48. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:46 or 48. In certain embodiments, a succinate exporter gene may comprise the nucleotide sequence set forth in SEQ ID NOs:45 or 47, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:45 or 47.

In certain embodiments, the genetically modified yeast cells provided herein further comprise a deletion or disruption of one or more native genes. "Deletion or disruption" with regard to a native gene means that either the entire coding region of the gene is eliminated (deletion) or the coding region of the gene, its promoter, and/or its terminator region is modified (such as by deletion, insertion, or mutation) such that the gene no longer produces an active enzyme, produces a severely reduced quantity (at least 75% reduction, preferably at least 90% reduction) of an active enzyme, or produces an enzyme with severely reduced (at least 75% reduced, preferably at least 90% reduced) activity.

In certain embodiments, deletion or disruption of one or more native genes results in a deletion or disruption of one or more native metabolic pathways. "Deletion or disruption" with regard to a metabolic pathway means that the pathway is either inoperative or else exhibits activity that is reduced by at least 75%, at least 85%, or at least 95% relative to the native pathway. In certain embodiments, deletion or disruption of a native metabolic pathway is accomplished by incorporating one or more genetic modifications that result in decreased expression of one or more native genes that reduce succinate production.

In certain embodiments, deletion or disruption of native gene can be accomplished by forced evolution, mutagenesis, or genetic engineering methods, followed by appropriate selection or screening to identify the desired mutants. In certain embodiments, deletion or disruption of a native host cell gene may be coupled to the incorporation of one or more exogenous genes into the host cell, i.e., the exogenous genes may be incorporated using a gene expression integration construct that is also a deletion construct. In other embodiments, deletion or disruption may be accomplished using a deletion construct that does not contain an exogenous gene or by other methods known in the art.

In certain embodiments, the modified yeast cells provided herein comprise a deletion or disruption of one or more native genes encoding an enzyme involved in ethanol fermentation or consumption, including for example pyruvate decarboxylase (PDC, catalyzes the conversion of pyruvate to acetaldehyde) and/or alcohol dehydrogenase 1 (ADH1, catalyzes the conversion of acetaldehyde to ethanol) or 2 (ADH2, catalyzes the conversion of ethanol to acetaldehyde). Such modifications decrease the ability of the yeast cell to produce ethanol, thereby maximizing succinate production. In certain embodiments wherein the modified yeast cell is *I. orientalis*, the cells comprise a deletion of a PDC gene encoding the amino acid sequence of SEQ ID NO:50, an ADHa gene encoding the amino acid sequence of SEQ ID NO:52, and/or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NOs:50 or 52. In certain of these embodiments, the deleted gene may comprise the nucleotide sequence of SEQ ID NOs:49 or 51, or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:49 or 51.

In certain embodiments, the modified yeast cells provided herein comprise a deletion or disruption of one or more native genes encoding an enzyme involved in producing alternate fermentative products such as glycerol or other by-products such as acetate or diols, including for example glycerol 3-phosphate dehydrogenase (GPD, catalyzes the conversion of dihydroxyacetone phosphate to glycerol 3-phosphate). In certain embodiments wherein the modified yeast cell is *I. orientalis*, the cells comprise a deletion of a GPD gene encoding the amino acid sequence of SEQ ID NO:54 or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO:54. In certain of these embodiments, the deleted GPD gene may comprise the nucleotide sequence of SEQ ID NO:53 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:53.

In certain embodiments, the modified yeast cells provided herein comprise a deletion or disruption of one or more native genes encoding an enzyme that catalyzes a reverse reaction in a succinate fermentation pathway. For example, in certain embodiments the modified yeast cells provided herein comprise a deletion or disruption of a native PEP carboxykinase (PCK) gene, which encodes an enzyme that converts OAA to PEP. In certain embodiments wherein the modified yeast cell is *I. orientalis*, the cells comprise a deletion of a PCK gene encoding the amino acid sequence of SEQ ID NO:56 or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO:56. In certain of these embodiments, the deleted PCK gene may comprise the nucleotide sequence of SEQ ID NO:55 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:55. In another example, the modified yeast cells provided herein comprise a deletion or disruption of a native malic enzyme gene, which encodes an enzyme that converts malate to pyruvate. In certain embodiments wherein the modified yeast cell is *I. orientalis*, the cells comprise a deletion of a malic enzyme gene encoding the amino acid sequence of SEQ ID NO:58 or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO:58. In certain of these embodiments, the deleted malic enzyme gene may comprise the nucleotide sequence of SEQ ID NO:57 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:57. In another embodiment, the modified yeast cells provided herein comprise a deletion or disruption of an endogenous succinate importer gene (RIOR43690), which encodes an protein that allows for growth on and consumption of succinate. In certain embodiments, wherein the modified yeast cell is *I. orientalis*, the cells comprise a deletion of a RIOR43690 gene encoding the amino acid sequence of SEQ ID NO:60 or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO:60. In certain of these embodiments, the deleted RIOR43690 gene may comprise the nucleotide sequence of SEQ ID NO:59 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:59.

In certain embodiments, the genetically modified yeast cells provided herein comprise a deletion or disruption of one or more native genes encoding an enzyme involved in an undesirable reaction with a succinate fermentation pathway product or intermediate.

In certain embodiments, the genetically modified yeast cells provided herein comprise a deletion or disruption of one or more native genes encoding an enzyme that has a neutral effect on a succinate fermentation pathway, including for example native genes encoding an enzyme selected from the group consisting of ammonia transport outward (ATO), L-lactate cytochrome-c oxidoreductase (CYB2A or CYB2B, catalyzes the conversion of lactate to pyruvate), and alcohol dehydrogenase (ADHa, ADHb catalyzes conversion between acetaldehyde and ethanol). Deletion or disruption of neutral genes allows for insertion of one or more exogenous genes without affecting succinate fermentation pathways. In certain embodiments wherein the modified yeast cell is *I. orientalis*, the cells comprise a deletion of a CYB2A gene encoding the amino acid sequence of SEQ ID NO:62, a CYB2B gene encoding the amino acid sequence of SEQ ID NO:64, an ATO2 gene encoding the amino acid sequence of SEQ ID NO:66, an ADHb gene encoding the amino acid sequence of SEQ ID NO:68, and/or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NOs:62, 64, 66, or 68. In certain of these embodiments, the deleted gene may comprise the nucleotide sequence of SEQ ID NOs:61, 63, 65, or 67 or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:61, 63, 65, or 67.

In certain embodiments, the genetically modified yeast cells provided herein are succinate resistant yeast cells. A "succinate-resistant yeast cell" (which may also be referred to as "succinate-resistant yeast") as used herein refers to a yeast cell that exhibits a growth rate (as described in Example 1) in media containing 75 g/L or greater succinate at pH 2.8 that is at least 50% as high as its growth rate in the same media containing 0 g/L succinate. In certain of these embodiments, the yeast cells may exhibit succinate resistance in their native form. In other embodiments, the cells may have undergone mutation and/or selection before, during, or after introduction of genetic modifications related to an active succinate fermentation pathway, such that the mutated and/or selected cells possess a higher degree of resistance to succinate than wild-type cells of the same species. In certain embodiments, mutation and/or selection may be carried out on cells that exhibit succinate resistance in their native form. Cells that have undergone mutation and/or selection may be tested for sugar consumption and other characteristics in the presence of varying levels of succinate in order to determine their potential as industrial hosts for succinate production. In addition to succinate resistance, the yeast cells provided herein may have undergone mutation and/or selection for resistance to one or more additional organic acids or to other fermentation products, by-products, or media components.

Selection for resistance to succinate or other compounds may be accomplished using methods well known in the art. For example, selection may be carried out using a chemostat. A chemostat is a device that allows for a continuous culture of microorganisms (e.g., yeast) wherein the specific growth rate and cell number can be controlled independently. A continuous culture is essentially a flow system of constant volume to which medium is added continuously and from which continuous removal of any overflow can occur. Once such a system is in equilibrium, cell number and nutrient status remain constant, and the system is in a steady state. A chemostat allows control of both the population density and the specific growth rate of a culture through dilution rate and alteration of the concentration of a limiting nutrient, such as a carbon or nitrogen source. By altering the conditions as a culture is grown (e.g., decreasing the concentration of a secondary carbon source necessary to the growth of the inoculum strain, among others), microorganisms in the population that are capable of growing faster at the altered conditions will be selected and will outgrow microorganisms that do not function as well under the new conditions. Typically such selection requires the progressive increase or decrease of at least one culture component over the course of growth of the chemostat culture. The operation of chemostats and their use in the directed evolution of microorganisms is well known in the art (see, e.g., Novick Proc Natl Acad Sci USA 36:708-719 (1950), Harder J Appl Bacteriol 43:1-24 (1977).

As disclosed herein, yeast strains exhibiting succinate resistance were identified based on their growth rate and glucose consumption rates in succinate containing media. One such succinate resistant strain was *I. orientalis* strain CD1822. Strain CD1822 was generated by evolving *I. orientalis* ATCC PTA-6658 for 91 days in a glucose limited chemostat. The system was fed with 15 g/L glucose in a DM medium, and operated at a dilution rate of 0.06 $h^{-1}$ at pH=3 with added lactic acid in the feed medium. The conditions were maintained with a low oxygen transfer rate of approximately 2 mmol L$^{-1}$ h$^{-1}$, and dissolved oxygen concentration remained constant at 0% of air saturation. Single colony isolates from the final time point were characterized in two shake flask assays. In the first assay, the strains were characterized for their ability to ferment glucose to ethanol in the presence of 25 g/L total lactic acid with no pH adjustment in the DM defined medium. In the second assay, the growth rate of the isolates were measured in the presence of 25, 32 and 45 g/L of total lactic, with no pH adjustment in DM defined medium. Strain CD1822 was a single isolate selected based on the measured fermentation rates and growth rates.

Yeast strains exhibiting the best combinations of growth and glucose consumption in succinate media as disclosed in the examples below are preferred host cells for various genetic modifications relating to succinate fermentation pathways. Yeast genera that possess the potential for a high degree of succinate resistance, as indicated by growth in the presence of 150 g/L succinate at a pH of 2.8, include for example *Issatchenkia* and *Candida*. Other yeast genera with the potential for a relatively high degree of succinate resistance, as indicated by growth in the presence of 100 g/L succinate, include for example *Pichia*, *Zygosaccharomyces*, *Kluyveromyces*, *Saccharomyces*, *Debaryomyces*, and *Saccharomycopsis*. Species exhibiting a high degree of succinate resistance included *I. orientalis* (also known as *Candida krusei*), *Candida lambica* (also known as *Pichia fermentans*), *Candida sorboxylosa*, *Candida zemplinina*, *Candida geochares*, *Pichia membranifaciens*, *Zygosaccharomyces kombuchaensis*, *Candida sorbosivorans*, *Kluyveromyces marxianus*, *Candida vanderwaltii*, *Candida sorbophila*, *Zygosaccharomyces bisporus*, *Zygosaccharomyces lentus*, *Saccharomyces bayanus*, *Saccharomyces bulderi*, *Debaryomyces castellii*, *Candida boidinii*, *Candida etchellsii*, *Kluyveromyces lactis*, *Pichia jadinii*, *Pichia anomala*, *Saccharomycopsis crataegensis*, and *Pichia jadinii*. *I. orientalis* and *C. lambica* belong to the *I. orientalis/P. fermentans* clade. Specific strains exhibiting succinate resistance included *I. orientalis* strains PTA-6658, 60585, and 24210, *C. lambica* strain 38617, and *C. sorboxylosa* strain 24120.

Other wild-type yeast or fungi may be tested in a similar manner and identified to have acceptable levels of growth and glucose utilization in the presence of high levels of succinate as described herein. For example, Gross and Robbins (Hydrobiologia 433(103):91-109) have compiled a list of 81 fungal species identified in low pH (<4) environments that could be relevant to test as potential production hosts.

In certain embodiments, the modified yeast cells provided herein are generated by incorporating one or more genetic modifications into a Crabtree-negative host yeast cell. In certain of these embodiments the host yeast cell belongs to the genus *Issatchenkia* or *Candida*, and in certain of these embodiments the host cell belongs to the *I. orientalis/P. fermentans* clade. In certain of embodiments, the host cell is *I. orientalis* or *C. lambica*.

The *I. orientalis/P. fermentans* clade is the most terminal clade that contains at least the species *I. orientalis*, *Pichia galeiformis*, *Pichia* sp. YB-4149 (NRRL designation), *Candida ethanolica*, *Pichia deserticola*, *Pichia membranifaciens*, and *P. fermentans*. Members of the *I. orientalis/P. fermentans* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences," *Antonie van Leeuwenhoek* 73:331-371, 1998, incorporated herein by reference (see especially p. 349). Analysis of the variable D1/D2 domain of the 26S ribosomal DNA from hundreds of ascomycetes has revealed that the *I. orientalis/P. fermentans* clade contains very closely related species. Members of the *I. orientalis/P. fermentans* clade exhibit greater similarity in the variable D1/D2 domain of the 26S ribosomal DNA to other members of the clade than to yeast species outside of the clade. Therefore, other members of the *I. orientalis/P. fermentans* clade can be identified by comparison of the D1/D2 domains of their respective ribosomal DNA and comparing to that of other members of the clade and closely related species outside of the clade, using Kurtzman and Robnett's methods.

In certain embodiments, the genetically modified yeast cells provided herein belong to the genus *Issatchenkia*, and in certain of these embodiments the yeast cells are *I. orientalis*. When first characterized, the species *I orientalis* was assigned the name *Pichia kudriavzevii*. The anamorph (asexual form) of *I. orientalis* is known as *C. krusei*. Numerous additional synonyms for the species *I. orientalis* have been listed elsewhere (Kurtzman and Fell, The Yeasts, a Taxonomic Study. Section 35. *Issatchenkia Kudryavtsev*, pp 222-223 (1998)).

The ideal yeast cell for succinate production is ideally capable of conducting fermentation at low pH levels. The ability to conduct fermentation at a low pH decreases downstream recovery costs, resulting in more economical production. Therefore, in certain embodiments the yeast host cell is capable of conducting fermentation at low pH levels.

A suitable host cell may possess one or more favorable characteristics in addition to succinate resistance and/or low pH growth capability. For example, potential host cells exhibiting succinate resistance may be further selected based on glycolytic rates, specific growth rates, thermotolerance, tolerance to biomass hydrolysate inhibitors, overall process robustness, and so on. These criteria may be evaluated prior to any genetic modification relating to a succinate fermentation or reduction pathway, or they may be evaluated after one or more such modifications have taken place.

The level of gene expression and/or the number of exogenous genes to be utilized in a given cell will vary depending upon the identity of the host cell. For fully genome-sequenced yeasts, whole-genome stoichiometric models may be used to determine which enzymes should be expressed to develop a desired pathway succinate fermentation pathway. Whole-genome stoichiometric models are described in, for example, Hjersted Biotechnol Bioeng 97:1190 (2007) and Famili Proc Natl Acad Sci USA 100:13134 (2003).

For yeasts without a known genome sequence, sequences for genes of interest (either as overexpression candidates or as insertion sites) can typically be obtained using techniques known in the art. Routine experimental design can be employed to test expression of various genes and activity of various enzymes, including genes and enzymes that function in a succinate fermentation or reduction pathway. Experiments may be conducted in which each enzyme is expressed in the yeast individually and in blocks of enzymes up to and including preferably all pathway enzymes, to establish which are needed (or desired) for improved succinate production. One illustrative experimental design tests expression of each individual enzyme as well as of each unique pair of enzymes, and further can test expression of all required enzymes, or each unique combination of enzymes. A number of approaches can be taken, as will be appreciated.

In certain embodiments, methods are provided for producing succinate from a genetically modified yeast cell as provided herein. In certain embodiments, these methods comprise providing a modified yeast cell as provided herein with at least one carbon source and culturing the yeast cell such that succinate is produced. The carbon source may be any carbon source that can be fermented by the yeast cell. Examples include, but are not limited to, twelve carbon sugars such as sucrose, hexose sugars such as glucose or fructose, glycan, starch or other polymer of glucose, glucose oligomers such as maltose, maltotriose and isomaltotriose, panose, and fructose oligomers, and pentose sugars such as xylose, xylan, other oligomers of xylose, or arabinose. In certain embodiments, more than one type of genetically modified yeast cell may be present in the culture. Likewise, in certain embodiments one or more native yeast cells of the same or a different species than the genetically modified yeast cell may be present in the culture.

In certain embodiments, culturing of the cells provided herein to produce succinate may be divided up into phases. For example, the cell culture process may be divided into a cultivation phase, a production phase, and a recovery phase. The following represent examples of specific conditions that may be used for each of these phases. One of ordinary skill in the art will recognize that these conditions may be varied based on factors such as the species of yeast being used, the desired yield, or other factors. The medium will typically contain nutrients as required by the particular cell, including a source of nitrogen (such as amino acids, proteins, inorganic nitrogen sources such as ammonia or ammonium salts, and the like), and various vitamins, minerals and the like. In some embodiments, the cells of the invention can be cultured in a chemically defined medium. In one example, the medium is a DM medium containing around 5 g/L ammonium sulfate, around 3 g/L potassium dihydrogen phosphate, around 0.5 g/L magnesium sulfate, trace elements, vitamins and around 150 g/L glucose. The pH is adjusted may be allowed to range freely during cultivation, or may be buffered if necessary to prevent the pH from falling below or rising above predetermined levels. For example, the medium may be buffered to prevent the pH of the solution from falling below around 2.0 or rising above around 8.0 during cultivation. In certain of these embodiments, the medium may be buffered to prevent the pH of the solution from falling below around 3.0 or rising above around 7.0, and in certain of these embodiments the medium may be buffered to prevent the pH of the solution from falling below around 4.0 or rising above around 6.0. In certain embodiments, the fermentation medium is inoculated with sufficient yeast cells that are the subject of the evaluation to produce an $OD_{600}$ of 1.0. In some embodiments, the genetically modified yeast cell dry weight at inoculation is less than about 5 g/L and desirably less than about 3 g/L. Unless explicitly noted otherwise, $OD_{600}$ as used herein refers to an optical density measured at a wavelength of 600 nm with a 1 cm pathlength using a model DU600 spectrophotometer (Beckman Coulter). The cultivation temperature may range from about 25 to about 50° C., and the cultivation time may be up to about 120 hours. During cultivation, aeration, and agitation, conditions are selected to produce a desired OUR such as, for example, from about 2 to about 25 mmol/L/hr, from about 5 to about 20 mmol/L/h, from about 8 mmol/L/h to about 25 mmol/L/h, from about 8 mmol/L/h to about 20 mmol/L/h, or from about 8 to about 15 mmol/L/h. In some embodiments, oxygen uptake rate may be greater than about 2 mmol/L/h, greater than about 5 mmol/L/h, or greater than about 8 mmol/L/h. In some embodiments, the oxygen uptake rate may be less than about 25 mmol/L/h, less than about 20 mmol/L/h, or less than about 15 mmol/L/h.

In one example, the cell dry weight at end of fermentation is typically in the range of about 0.1 to 20 g dry cells/liter, preferably from 0.1 to 10 g dry cells/liter, even more preferably from 2 to 5 g dry cells/liter of fermentation medium during the production phase. In some embodiments, the cell dry weight at end of fermentation is less than about 10 g/L, suitably less than about 7 g/L, desirably less than about 5 g/L, and preferably less than about 3 g/L. The fermentation may be conducted microaerobically, as described herein. If desired, oxygen uptake rate can be varied throughout fermentation as a process control (see, e.g., WO03/102200). In certain embodiments, the modified yeast cells provided herein may perform especially well when cultivated under microaerobic conditions characterized by an OUR of from about 2 to about 25 mmol/L/hr. The medium may be buffered during the production phase such that the pH typically is maintained in a range of about 2.0 to about 7.0, about 2.0 to 6.0, about 3.0 to about 6.0, or about 3.0 to about 5.0. In some embodiments, a final pH of the fermentation broth is less than about 6.0, suitably less than about 5.5, desirably less than about 5.0, preferably less than about 4.0, and more preferably less than about 3.5.

Suitable buffering agents are basic materials that neutralize the acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here.

In those embodiments where a buffered fermentation is utilized, acidic fermentation products may be neutralized to the corresponding salt as they are formed. In these embodiments, recovery of the acid involves regeneration of the free acid. This may be done by removing the cells and acidulating the fermentation broth with a strong acid such as sulfuric acid. This results in the formation of a salt by-product. For example, where a calcium salt is utilized as the neutralizing agent and sulfuric acid is utilized as the acidulating agent, gypsum is produced as a salt by-product. This by-product is separated from the broth, and the acid is recovered using techniques such as liquid-liquid extraction, distillation, absorption, and others (see, e.g., T. B. Vickroy, Vol. 3, Chapter 38 of *Comprehensive Biotechnology*, (ed. M. Moo-Young), Pergamon, Oxford, 1985; R. Datta, et al., FEMS Microbiol Rev, 1995, 16:221-231; U.S. Pat. Nos. 4,275,234, 4,771,001, 5,132,456, 5,420,304, 5,510,526, 5,641,406, and 5,831,122, and WO93/00440.

In other embodiments, the pH of the fermentation medium may be permitted to drop during cultivation from a starting pH that is at or above the lower pKa (4.207) of succinate, typically 4.5 or higher, to at or below the lower pKa of the acid fermentation product, such as in the range of about 2.0 to about 4.2, in the range of from about 3.0 to about 4.2, or in the range from about 3.8 to about 4.2.

In still other embodiments, fermentation may be carried out to produce a product acid by adjusting the pH of the fermentation broth to at or below the lower pKa of the product acid prior to or at the start of the fermentation process. The pH may thereafter be maintained at or below the lower pKa of the product acid throughout the cultivation. In certain embodiments, the pH may be maintained at a range of about 2.0 to about 4.2, in the range of from about 3.0 to about 4.2, or in the range from about 3.8 to about 4.2.

In certain embodiments of the methods provided herein, the genetically modified yeast cells produce relatively low levels of ethanol. In certain embodiments, ethanol may be produced in a yield of 10% or less, preferably in a yield of 2% or less. In certain of these embodiments, ethanol is not detectably produced. In other embodiments, however, succinate and ethanol may be co-produced. In these embodiments, ethanol may be produced at a yield of greater than 10%, greater than 25%, or greater than 50% of the theoretical mass yield.

In some embodiments, a production rate of succinate is greater than about 0.25 g/L/h, greater than about 1 g/L/h, greater than about 1.5 g/L/h, greater than about 2 g/L/h, or greater than about 3 g/L/h. In some embodiments, the production rate may be less than about 4 g/L/h or less than about 3 g/L/h. In some embodiments, the production rate may be about 0.25 g/L/h to about 4 g/L/h or about 1 g/L/h to about 3 g/L/h.

In some embodiments, a specific production rate of succinate is greater than about 0.1 g/g/h, greater than about 0.15 g/g/h, greater than about 0.5 g/g/h, and greater than about 1.0 g/g/h. In some embodiments, the specific production rate of succinate is less than about 2 g/g/h and less than about 1 g/g/h. In some embodiments, the specific production rate of succinate is about 0.1 g/g/h to about 2 g/g/h or about 0.15 g/g/h to about 1.0 g/g/h.

In certain embodiments of the methods provided herein, the product yield of succinate on the carbon source is at least 10%, at least 20%, at least 30%, at least 40%, at least 50%, or greater than 50% of the theoretical yield. In some embodiments, the product yield of succinate is greater than about 50%, suitably greater than about 60%, desirably greater than about 70%, preferably greater than about 80%, and more preferably greater than about 90%. In some embodiments, the product yield of succinate is less than about 100%, less than about 90%, less than about 80%, or less than about 70%. In some embodiments, the product yield of succinate is about 10% to about 100%, about 20% to about 90%, about 30% to about 80%, or about 40% to about 70%.

In certain embodiments, the cells provided herein are capable of converting at least 80% or at least 90% by weight of a carbon source to succinate. The concentration, or titer, of succinate will be a function of the yield as well as the starting concentration of the carbon source. In certain embodiments, the titer may reach at least about 1 to about 3, at least about 5, at least about 10, at least about 20, at least about 30, at least about 40, at least about 50, or greater than 50 g/L at some point during the fermentation, and preferably at the end of the fermentation. In some embodiments, a final concentration of succinate in the fermentation broth is greater than about 20 g/L, greater than about 40 g/L, greater than about 60 g/L, greater than about 70 g/L, greater than about 80 g/L, and greater than about 90 g/L. In some embodiments, the final concentration of succinate in the fermentation broth is less than about 90 g/L, less than about 80 g/L, or less than about 70 g/L. In some embodiments, the final concentration of succinate in the fermentation broth is about 20 g/L to about 90 g/L, about 40 g/L to about 80 g/L, or about 40 g/L to about 70 g/L. In certain embodiments, the final yield of succinate may be increased by decreasing the temperature of the fermentation medium, particularly during the production phase.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1A: Selection of Host Yeast Cells Based on Succinate Tolerance

A set of wild-type yeast strains were tested for their ability to grow in the presence of succinate.

The range of succinate concentrations to utilize in primary screening procedures was determined by evaluating the ability of seven wild-type yeast strains (*Candida sonorensis*, *Candida zemplinina*, *I. orientalis* strain PTA-6658, *Kluyveromyces lactis*, *K. marxianus*, *S. cerevisiae* strain CENPK 113-7D, and *I. orientalis* strain CD1822) to grow on media containing varying levels of succinate. Cells were streaked onto YPD plates and grown overnight. A cell slurry with an $OD_{600}$ of around 4 was made in YPD media, pH 3.0, and this slurry was used to inoculate microtiter wells containing various concentrations of succinate to an $OD_{600}$ of 0.05. Plates were covered with a gas permeable membrane and incubated in a 30° C./300 rpm shaker overnight. The optical densities of each well were measured at a wavelength of 600 nm in a GENios model plate reader (Tecan), and plates were observed visually for growth. The highest succinate concentration that one or more of the strains grew in (150 g/L) was chosen as the upper range for primary screening procedure.

For the primary screening procedure, 91 yeast strains were screened for growth on microtiter plates at 0 g/L, 100 g/L, or 150 g/L succinate and pH 2.8 using the same protocol used for range finding. Solubility issues presented challenges when trying to test succinate concentrations greater than 150 g/L, so low pH rather than higher succinate concentration was used to test more stringent conditions. For these samples, strains were screened for growth at 150 g/L succinate and pH 2.5.

A fresh YPD plate was used for each strain, and a slurry with an $OD_{600}$ of around 4 was made in YPD media, pH 3.0. The slurry was used to inoculate each well to an $OD_{600}$ of 0.05. Plates were covered with a gas permeable membrane, and incubated in a 30° C./300 rpm shaker overnight. Optical densities of each well were measured at 600 nm in a GENios model plate reader, and plates were observed visually for growth.

A similar protocol was run to evaluate growth at lactic acid concentration of 0 g/L, 30 g/L, 45 g/L, and 60 g/L. Table 1 summarizes the highest concentrations of succinate or lactic acid at which growth was observed.

TABLE 1

Primary Screen for Growth on Succinate or Lactic Acid

| ATCC# | Genus/species | Lactic acid (g/L) | Succinate (g/L) |
|---|---|---|---|
| PTA-6658 | *Issatchenkia orientalis* | 60 | 150 (pH 2.5) |
| CD1822 (Cargill collection) | *Issatchenkia orientalis* | 60 | 150 (pH 2.5) |

TABLE 1-continued

Primary Screen for Growth on Succinate or Lactic Acid

| ATCC# | Genus/species | Lactic acid (g/L) | Succinate (g/L) |
|---|---|---|---|
| PYCC 04-501 | Candida zemplinina | 60 | 100 |
| Cargill | Candida geochares | 60 | 100 |
| NCYC 2696 | Pichia membranifaciens | 60 | 100 |
| NCYC 2897 | Zygosaccharomyces kombuchaensis | 60 | 100 |
| mya-402 | Saccharomyces bulderi | 60 | 0 |
| 38619 | Candida sorbosivorans | 60 | 100 |
| NCYC 535 | Schizosaccharomyces pombe | 60 | 0 |
| 52486 | Kluyveromyces marxianus | 45 | 100 |
| 113-7D | Saccharomyces cerevisiae-CENPK | 45 | 0 |
| MUCL 300000 | Candida vanderwaltii | 45 | 100 |
| Cargill | Candida sorbophila | 45 | 100 |
| NCYC 3134 | Zygosaccharomyces bisporus | 45 | 100 |
| NCYC 2928 | Zygosaccharomyces lentus | 45 | 100 |
| NCYC 734 | Saccharomyces ludwigii | 45 | 0 |
| 60585 | Issatchenkia orientalis | 45 | 150 (pH 2.8) |
| 46330 | Yarrowia lipolytica | 45 | 0 |
| 36946 | Zygosaccharomyces bailii | 45 | 0 |
| 60592 | Candida milleri | 45 | 0 |
| 38617 | Candida lambica | 45 | 150 (pH 2.8) |
| 20306 | Candida rugosa | 45 | 0 |
| 28525 | Candida valida | 45 | 0 |
| 20347 | Candida zeylanoides | 45 | 0 |
| 24210 | Issatchenkia orientalis | 45 | 150 (pH 2.5) |
| 20282 | Kodamaea ohmeri | 45 | 0 |
| 90739 | Saccharomyces bayanus | 45 | 100 |
| MYA-404 | Saccharomyces bulderi | 45 | 0/100 |
| MUCL 31237 | Saccharomycopsis javensis | 45 | 0 |
| 32109 | Candida sonorensis | 30 | 0 |
| PYCC 70-1022 | Debaryomyces castellii | 30 | 100 |
| PYCC 70-104 | Candida boidinii | 30 | 100 |
| PYCC 60-8 | Candida etchellsii | 30 | 100 |
| 44691 | Candida kefyr | 30 | 0 |
| 34890 | Zygosaccharomyces rouxii | 30 | 0 |
| 60591 | Candida milleri | 30 | 0 |
| 24120 | Candida sorboxylosa | 30 | 150 (pH 2.5) |
| 28526 | Pichia fermentans | 30 | 0 |
| 96784 | Saccharomyces cerevisiae | 0/30 | 0 |
| 52709 | Kluyveromyces thermotolerans | 0/30 | 0 |
| NCYC 614 | Pachysolen tannophilus | 0/30 | 0 |
| CBS 8452 | Wickerhamiella occidentalis | 0/30 | 0 |
| 18735 | Candida blankii | 0/30 | 0 |
| 8585 | Kluyveromyces lactis | 0 | 100 |
| 9950 | Pichia jadinii | 0 | 100 |
| 38623 | Candida fluviatilis | 0 | 0 |
| 20033 | Saccharomyces capsularis | 0 | NG |
| 20284 | Candida famata | 0 | NG |
| 20118 | Candida guilliermondii | 0 | 0 |
| 20178 | Candida intermedia | 0 | 0 |
| 20179 | Candida parapsilosis | 0 | 0 |
| 96309 | Candida pseudolambica | 0 | 0 |
| 20280 | Debaryomyces polymorphus | 0 | 0 |
| 20277 | Dekkera anomala | 0 | 0 |
| 10563 | Dekkera lambica | 0 | 0 |
| 20030 | Hyphopichia burtonii | 0 | 0 |
| 9889 | Metschnikowia pulcherrima | 0 | 0 |
| 2102 | Pichia anomala | 0 | 0/100 |
| 24116 | Pichia nakasei | 0 | 0 |
| 16768 | Pichia silvicola | 0 | 0 |
| 34024 | Pichia strasburgensis | 0 | 0 |
| 2261 | Pichia tannicola | 0 | 0 |
| 76514 | Saccharomyces uvarum | 0 | 0 |
| 52714 | Torulaspora delbrueckii | 0 | 0 |
| 90197 | Yamadazyma guilliermondii | 0 | 0 |
| 20321 | Yamadazyma halophila | 0 | 0 |
| MUCL 44417 | Saccharomycopsis crataegensis | 0 | 100 |
| NRRL Y-7290 | Saccharomycopsis vini | 0 | 0 |
| 9950 | Pichia jadinii | 0 | 100 |
| CBS 6054 | Pichia stipitis | 0 | 0 |
| NCYC 2389 | Candida shehatae | 0 | 0 |
| 201225 | Yamadazyma stipites | 0 | 0 |
| 10660 | Schizosaccharomyces japonicus | 0 | NG |
| 12659 | Lipomyces starkeyi | 0 | 0 |
| 42479 | Torulaspora pretoriensis | 0 | 0 |
| 90624 | Debaryomyces hansenii | NG | NG |
| 20117 | Candida catenulata | NG | NG |
| 96927 | Candida lactiscondensi | NG | NG |
| 36592 | Candida pignaliae | NG | NG |
| 34087 | Citeromyces matritensis | NG | NG |
| 36591 | Kluyveromyces yarrowii | NG | NG |
| 20292 | Nematospora coryli | NG | NG |
| 28778 | Pichia fluxuum | NG | NG |
| 58362 | Pichia toletana | NG | NG |
| 96272 | Bulleromyces albus | NG | NG |
| MUCL 47216 or MUCL 31253B | Candida tenuis | NG | NG |
| 20361 | Candida methanosorbosa | NG | NG |
| NCYC 813 | Brettanomyces naardenensis | NG | NG/0 |
| 76214 | Myxozyma kluyveri | NG | NG |
| 56306 | Lipomyces tetrasporus | NG | NG |
| 56465 | Candida naeodendra | NG | NG |

All six strains that exhibited growth at 150 g/L succinate were selected for secondary screening. For the first secondary screen, growth rates were measured in YPD media containing 0 g/L succinate at pH 3.0 or 75 g/L succinate at pH 2.85. Shaken flasks were inoculated with biomass harvested from seed flasks grown overnight to an $OD_{600}$ of 6 to 10. 250 mL baffled growth rate flasks (50 mL working volume) were inoculated to an $OD_{600}$ of 0.1 and grown at 250 rpm and 30° C. Samples were taken throughout the time course of the assay and analyzed for biomass growth via $OD_{600}$. The resulting $OD_{600}$ data was plotted and growth rates were established. Results are summarized in Table 2.

TABLE 2

Growth Rate in Succinate

| Strain | 0 g/L succinate (pH 3.0) ($h^{-1}$) | 75 g/L succinate (pH 2.85) ($h^{-1}$) |
|---|---|---|
| Issatchenkia orientalis ATCC PTA-6658 | 0.71 | 0.50 |
| Issatchenkia orientalis CD1822 | 0.69 | 0.47 |
| Issatchenkia orientalis ATCC 60585 | 0.73 | 0.46 |
| Candida lambica ATCC 38617 | 0.81 | 0.48 |
| Candida sorboxylosa ATCC 24120 | 0.66 | 0.36 |
| Issatchenkia orientalis ATCC 24210 | 0.74 | 0.45 |

For the second secondary screen, glucose consumption was measured in YPD media containing 0 g/L succinate at pH 3.0 or 75 g/L succinate at pH 2.85. Shake flasks were inoculated with biomass harvested from seed flasks grown overnight to an $OD_{600}$ of 6 to 10. 250 mL baffled glycolytic assay flasks (50 mL working volume) were inoculated to an $OD_{600}$ of 0.1 and grown at 250 RPM and 30° C. Samples were taken throughout the time course of the assay and analyzed for glucose consumption using a 2700 Biochemistry Analyzer (Yellow Springs Instruments, YSI). The resulting data was plotted and glucose consumption rates were established. Results are summarized in Table 3.

TABLE 3

Glucose Consumption Rate in Succinate

| Strain | 0 g/L succinate (pH 3.0) (g L$^{-1}$ h$^{-1}$) | 75 g/L succinate (pH 2.85) (g L$^{-1}$ h$^{-1}$) |
|---|---|---|
| Issatchenkia orientalis ATCC PTA-6658 | >4.2 g/L/h | >2.3 g/L/h |
| Issatchenkia orientalis CD1822 | >4.2 g/L/h | >2.3 g/L/h |
| Issatchenkia orientalis ATCC 60585 | >4.2 g/L/h | 2.3-2.8 g/L/h |
| Candida lambica ATCC 38617 | >4.2 g/L/h | >2.3 g/L/h |
| Candida sorboxylosa ATCC 24120 | 3.1 g/L/h | 0.7 g/L/h |
| Issatchenkia orientalis ATCC 24210 | >4.2 g/L/h | >2.3 g/L/h |

To identify the most attractive candidates for succinate production, strain performance was graded in three categories. Two of these categories were based on different aspects of growth rate: 1) growth rate at highest acid concentration and 2) slope of the growth rates plotted against acid concentration. The third category was the glycolytic rate at the highest acid concentration. Grading was done on a normalized scale using the highest and lowest value for each rating as the normalized boundaries. Each strain thus received a grade of 0 to 1 for each category, with 1 being the highest possible score. The overall rating of a strain was the sum of the normalized value for the three categories. A weighted score was made in which the growth rate and glycolytic rate were equally weighted. In this case the glycolytic rate at the highest acid concentration was weighted at 50%, while the two growth rate ratings were weighted at 25% each. In accordance with the description above, the final score for each strain was calculated as follows:

Final score for strain $X$ =

(actual growth rate in highest acid concentration − slowest growth rate) ∗ 0.25

(fastest growth rate − slowest growth rate) +

(slope of growth rates of strain $X$ − lowest growth rate slope) ∗

0.25(largest growth rate slope − lowest growth rate slope) +

(actual glycolytic rate in highest acid concentration − slowest glycolytic rate) ∗ 0.50

(fastest glycolytic rate − slowest glycolytic rate)

Normalized values for each category and the final weighted score for each strain are summarized in Table 4.

TABLE 4

Normalized Strain Grades in Succinate

| Strain | Growth rate @ 75 g/L succinate | Growth rate slope | Glycolic rate | Weighted score |
|---|---|---|---|---|
| Issatchenkia orientalis ATCC PTA-6658 | 1.00 | 1.00 | 0.76 | 0.88 |
| Issatchenkia orientalis CD1822 | 0.79 | 0.94 | 0.76 | 0.81 |
| Issatchenkia orientalis ATCC 60585 | 0.71 | 0.50 | 1.00 | 0.80 |
| Candida lambica ATCC 38617 | 0.86 | 0.00 | 0.76 | 0.60 |
| Candida sorboxylosa ATCC 24120 | 0.00 | 0.25 | 0.00 | 0.06 |
| Issatchenkia orientalis ATCC 24210 | 0.64 | 0.31 | 0.79 | 0.63 |

The same procedures were utilized to screen, rate, and score the original 91 yeast strains from the primary screen with media containing 0, 30, 45, and 60 g/L lactic acid at pH 3.0 (about 80% free acid). Due to difficulties in properly scoring some very weak growth that occasionally occurred at 60 g/L, 21 strains were re-tested in the primary screen. Of these 21 strains, eight were eliminated due to very slow growth relative to the rest of the test group. The remaining 13 strains were advanced into secondary screening, and normalized values and weighted and summed scores were derived for each strain. These results are summarized in Table 5.

TABLE 5

Normalized Strain Grades in Lactic acid

| Strain | Growth rate 50 g/L lactic acid | Growth rate slope | Glycolic rate | Weighted score |
|---|---|---|---|---|
| Candida lambica ATCC 38617 | 0.92 | 1 | 1 | 0.98 |
| Issatchenkia orientalis ATCC PTA-6658 | 0.94 | 0.95 | 1 | 0.97 |
| Issatchenkia orientalis CD1822 | 1.00 | 0.86 | 1 | 0.97 |
| Issatchenkia orientalis ATCC 24210 | 0.89 | 0.73 | 1 | 0.91 |
| Candida zemplinina | 0.22 | 0.95 | 1 | 0.79 |
| Saccharomyces bulderi ATCC MYA-404 | 0.47 | 0.45 | 1 | 0.73 |
| Saccharomyces bayanus | 0.08 | 0.91 | 0.96 | 0.73 |
| Saccharomyces bulderi ATCC MYA-402 | 0.5 | 0.23 | 1 | 0.68 |
| Candida milleri ATCC 60592 | 0 | 0.64 | 0.92 | 0.62 |
| Candida sorbosivorans | 0.28 | 0.95 | 0.59 | 0.60 |
| Kodamaea ohmeri | 0.42 | 0 | 0.76 | 0.49 |
| Candida geochares | 0.17 | 0.27 | 0.69 | 0.46 |
| Saccharomyces javensis | 0.11 | 0.68 | 0 | 0.20 |

Of the strains tested in lactic acid, only *S. javensis* did not achieve a 2.5 g/L/hr glucose utilization rate at pH 2.85 in media with 50 g/L lactic acid. While *I. orientalis* and *C. lambica* showed tolerance for both succinic and lactic acids, there were a number of species and strains that were tolerant for only one of the acids. Additionally, the rank order of the strains is different for each acid. This is even more clearly illustrated in the primary screen results (Table 1), where more strains were included. The most succinate tolerant strains are scattered among the top three tiers for lactic acid tolerance. Further, one of the strains that grew at the highest lactic acid concentration in the primary screen and scored highly in the secondary screen (*S. bulderi*) did not grow even at the lowest non-zero concentration of succinic acid tested. Thus, tolerance to lactic acid was shown to be a very poor predictor of tolerance to succinic acid, meaning that ideal strains for succinate production cannot be identified based on tolerance to lactic acid. This is further highlighted by comparing the strains that showed succinate resistance above with the list of eight strains identified as preferred hosts for organic acid production in WO03/049525. While two of those strains (*C. diddensiae* and *C. entomophila*) could not be obtained for testing, the other six (*C. sonorensis, C. methanosorbosa, C. parapsilosis, C. naeodendra, C krusei*, and *C. blankii*) were included in the primary screen described above. Of these six, only *C. krusei* (tested as *I. orientalis*) was able to grow in the presence of 150 g/L succinate at either pH 2.5 or pH 2.8.

Example 1B: Mutagenesis and Selection of Mutant Strains Having Succinate Resistance Yeast cells selected in Example 1A are subjected to mutagenesis and exposed to selection pressure in order to identify mutants with high succinate tolerance.

For example, yeast cells from a fresh YP (yeast extract/peptone)+20 g/L glucose plate or liquid culture ($OD_{600}$ 1-4) are resuspended in sterile water to an $OD_{600}$ of around 10. 200 µL aliquots of this cell suspension are pipetted into individual tubes and exposed to 3 µL ethane methyl sulfonate (EMS) for approximately one hour, which kills around 65% of the cells. Higher EMS concentrations can also be used to increase the kill rate. After exposure, cells are neutralized with 5% sodium thiosulfate, washed in PBS buffer, recovered in rich media for approximately four hours, and cultured on selective media. Mock samples (no EMS) are also run to ensure that the conditions are selective. Alternatively, cell can be mutagenized using UV irradiation.

To select for succinate resistant mutant strains, aliquots of the EMS-treated cell suspension (approximately $2 \times 10^8$ of mutagenized cells) are plated onto a potato glucose agar (PDA) or another media containing succinate at a level at which the parental strain does not grow or grows very slowly. These plates are incubated for several days until colonies appear. Single colonies are purified, streaked on non-selective media to eliminate any adaptive effects of the selection, and re-tested on selective media to confirm increased resistance. Resistant strains are then tested in a shake flask format with periodic sampling for HPLC analysis of products and substrates. Alternatively, selection for succinate tolerance may be done by chemostat or serial shake flask evolution. Additional rounds of mutagenesis and selection can be performed. Mutagenesis can be used to increase the resistance of a host that does not natively meet succinate production requirements so that it has the necessary attributes for commercial succinate production.

Example 2: Deletion of Both Alleles of CYB2A from *I. orientalis* Strain CD1822

Both alleles of CYB2A are deleted from *I. orientalis* strain CD1822. As discussed above, CD1822 is an evolved lactic acid resistant strain isolated from a chemostat that also exhibited a high degree of succinate tolerance.

Figure 2:
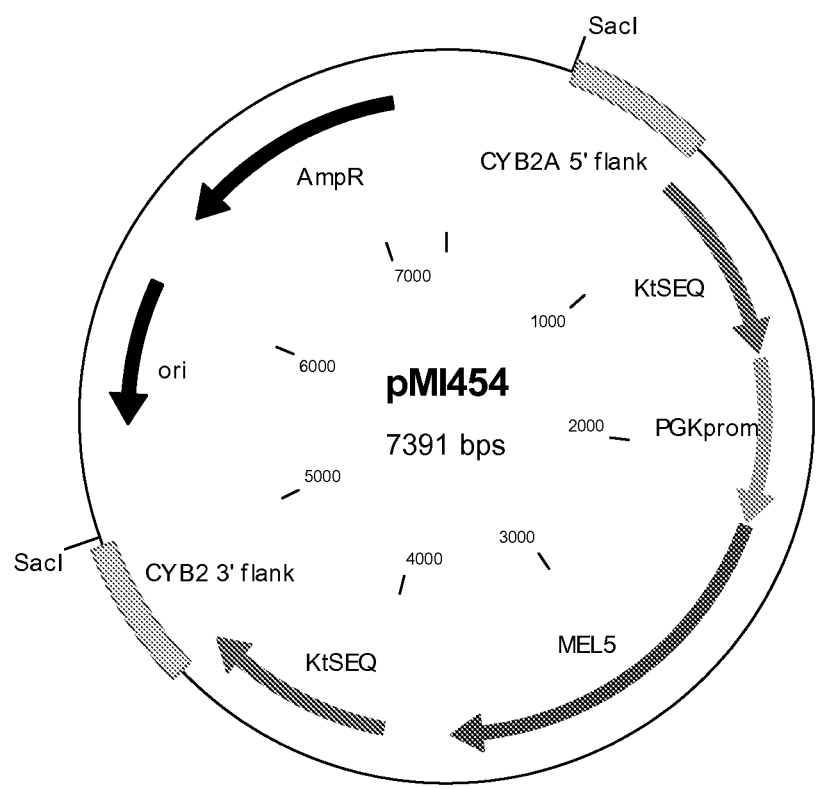
FIG. 2 shows plasmid pMI454, CYB2A deletion construct.

Plasmids pMI449 (FIG. 1) and pMI454 (FIG. 2) are used to delete both copies of the L-lactate:ferricytochrome c oxidoreductase (CYB2A) gene (SEQ ID NO:61) in *I. orientalis* strain CD1822, a lactic acid resistant strain of *I. orientalis* isolated from the environment. pMI449 and pMI454 were both described in WO07/106524. Each plasmid contains 5' and 3' flanking regions from *I. orientalis* CYB2A separated by a selection marker cassette comprising the *S. cerevisiae* MEL5 gene operatively linked to a PGK promoter. This selection marker cassette is flanked on either end by a sequence ("KtSEQ") from *K. thermotolerans*. The 5' and 3' CYB2A flanking regions in pMI449 correspond to nucleotides from 913 to 487 bp upstream of the start of the predicted ORF and nucleotides from 90 to 676 bp downstream of the stop codon of the predicted ORF, respectively. The 5' and 3' CYB2A flanking regions in pMI454 correspond to nucleotides from 466 to 7 bp upstream of the predicted ORF and nucleotides from 402 bp upstream to 77 bp downstream of the predicted stop codon, respectively.

The first CYB2A allele is deleted by transforming strain CD1822 with pMI449 digested with SacI using lithium acetate transformation (Gietz Met Enzymol 350:87 (2002)). Transformants are selected on yeast nitrogen base (YNB) (Becton, Dickinson and Co, Sparks, Md.; REF#239210)+ 2% melibiose plate containing x-α-gal (5-bromo-4-chloro-3-indolyl-α-D-galactoside). Blue-colored transformants are visible after around 4 days of growth at 30° C. Transformants are picked and plated for single colonies on Yeast Extract/Peptone/20 g/L glucose plates (YPD) containing x-α-gal. A single blue colony for each transformant is picked and re-streaked to YPD plates. Genomic DNA is isolated from the purified transformants, and replacement of the CYB2A gene is confirmed by PCR. To obtain strains where the MEL5 marker has undergone spontaneous recombination to excise it from the chromosome, the transformant is grown for several rounds in liquid YPD (100 g/L glucose) at 250 rpm and 30° C. A dilution series is plated onto YPD plates overlaid with x-α-gal, and grown overnight at 30° C. A white colony (indicative of the loop-out of the MEL5 marker cassette) is selected and re-streaked to YPD+x-α-gal plates. A white colony is selected and genomic DNA is prepared. Disruption of one allele of the native CYB2A gene is verified by PCR using primers oMM173 (SEQ ID NO:69) and oTM123 (SEQ ID NO:70).

The second CYB2A allele is deleted from this transformant by transforming with pMI454 digested with SacI. Transformants are obtained and purified as described above and analyzed by PCR for the absence of a 1000 bp CYB2A-specific PCR product using primers oMM175 (SEQ ID NO:71) and oMM176 (SEQ ID NO:72). The MEL5 marker derived from plasmid pMI454 is looped out of a transformant having a deletion of both CYB2A alleles via recombination as before, and confirmed by PCR using primers oMM172 (SEQ ID NO:73) and oMM173 (SEQ ID NO:69). This transformant is designated strain 2610.

The CYB2A deletion strain generated in Example 2 are summarized in Table 6.

TABLE 6

| *I. orientalis* CYB2A Deletion Strain | | |
|---|---|---|
| Strain name | Description | Parent strain |
| CD1822 | Lactic acid-resistant parent strain | — |
| 2610 | CYB2A deletion (2) | 1822 |

Example 3: Construction of Cre Expression Plasmids pVB10 and pVB32

Figure 3:
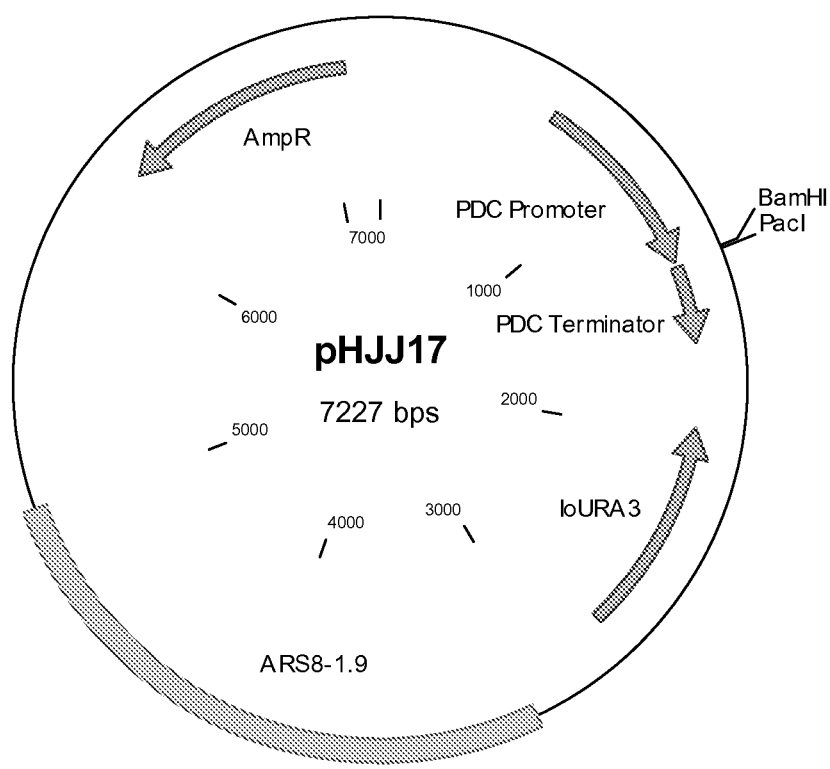
FIG. 3 shows plasmid pHJJ17.
Figure 4:
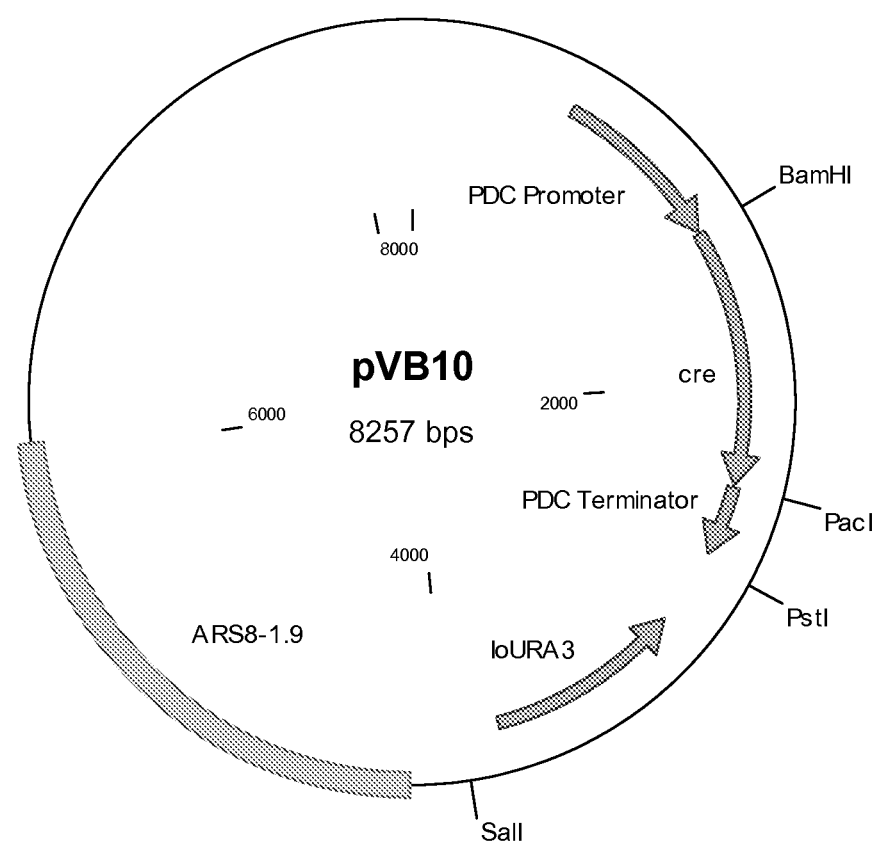
FIG. 4 shows plasmid pVB10, PDC:cre construct.

The cre recombinase gene is synthesized using the native cre protein sequence as a reference. This gene is PCR amplified from template DNA (Blue Heron Biotechnology, Bothell, Wash.) representing a codon-optimized version of the bacteriophage P1 CRE gene (SEQ ID NO:74, encoding polypeptide of SEQ ID NO:75) using PCR primers oVB5 (SEQ ID NO:76) and oVB6 (SEQ ID NO:77) and cloned into pCR2.1-TOPO (Invitrogen) to produce pVB15a. pVB15a is digested with BamHI and PacI to generate a 1 kb cre fragment, and this fragment is ligated into similarly digested pHJJ17 (FIG. 3). The resultant vector, pVB10 (FIG. 4), contains the cre gene operatively linked to a PDC promoter and terminator. The vector also contains a URA3 selection marker gene from I. orientalis.

Figure 5:
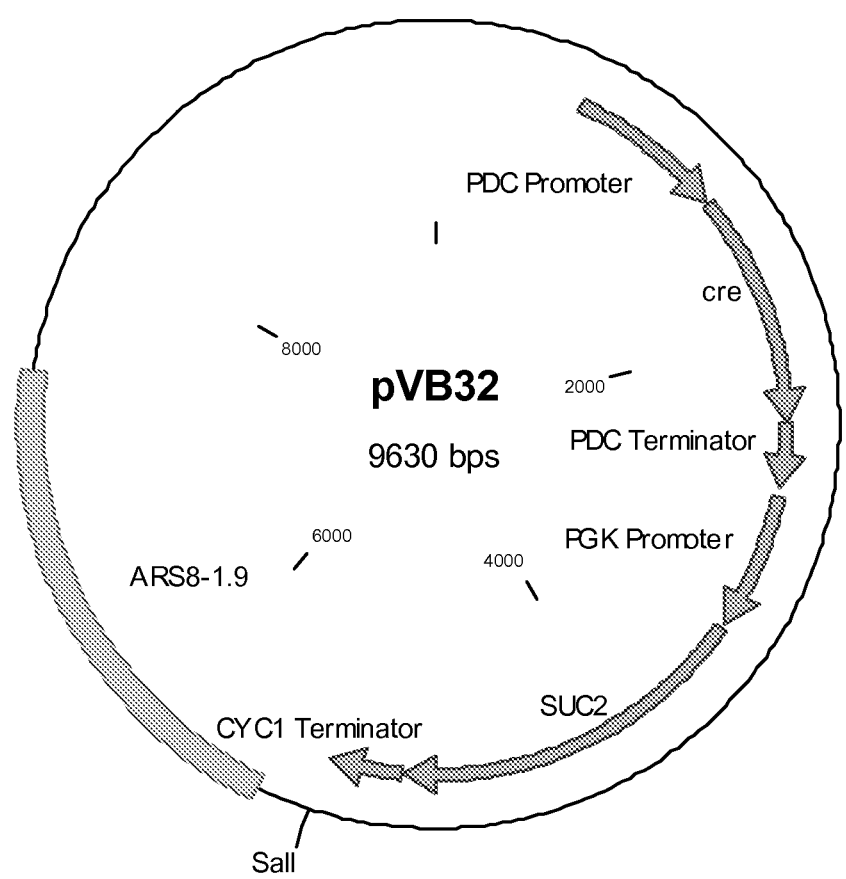
FIG. 5 shows plasmid pVB32.

To replace the URA3 selection marker in pVB10 with the SUC2 selection marker, a SUC2 expression cassette was amplified from pTMC82. This SUC2 expression cassette contains the S. cerevisiae SUC2 gene operatively linked to the I. orientalis PGK1 promoter and the S. cerevisiae CYC1 terminator. Amplification was performed using primers oTM298 (SEQ ID NO:78) and oTM299 (SEQ ID NO:79), which add NsiI and SalI restriction sites to the product. The PCR product was digested with NsiI and SalI and ligated to pVB10 digested with SalI and PstI (NsiI and PstI have compatible cohesive ends) to produce pVB32 (FIG. 5).

Example 4: Insertion of PYC1 at the PDC1 Locus in I. orientalis Strain 2610

A PYC1 expression cassette is inserted at one or both PDC1 alleles in I. orientalis strain 2610 (Example 2).

Example 4A: Construction of I. orientalis PYC1 Expression Constructs pKF043 and pKF045

Figure 6:
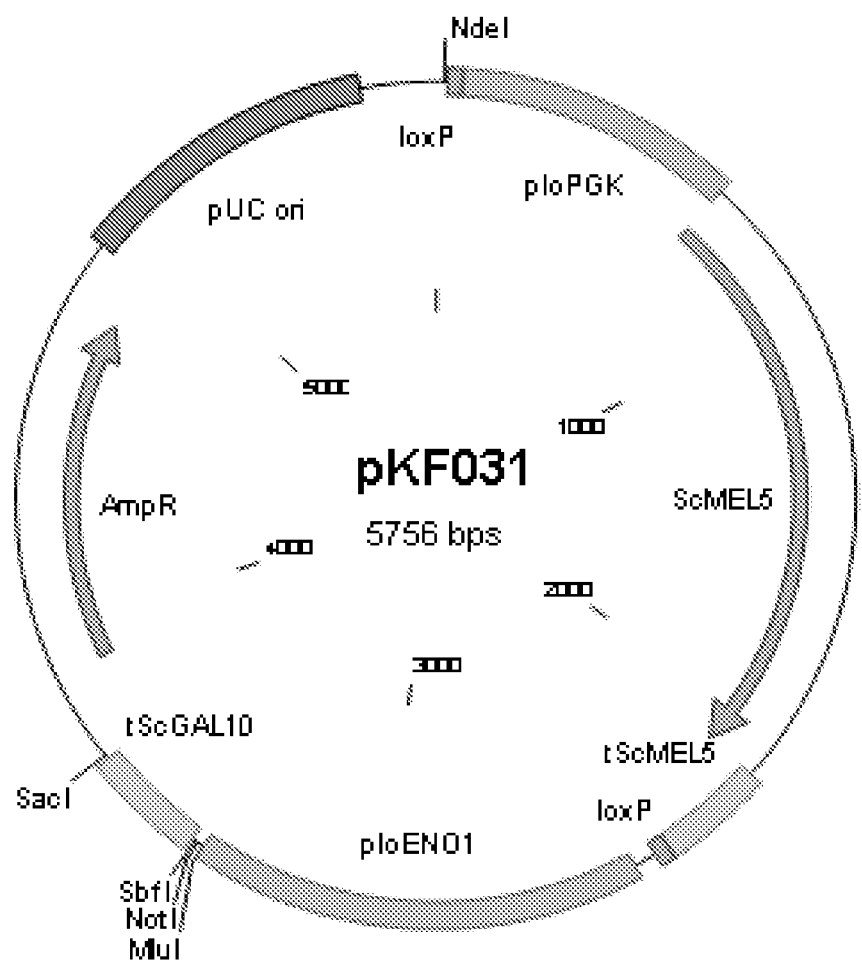
FIG. 6 shows plasmid pKF031, PGK:MEL5 construct.
Figure 7:
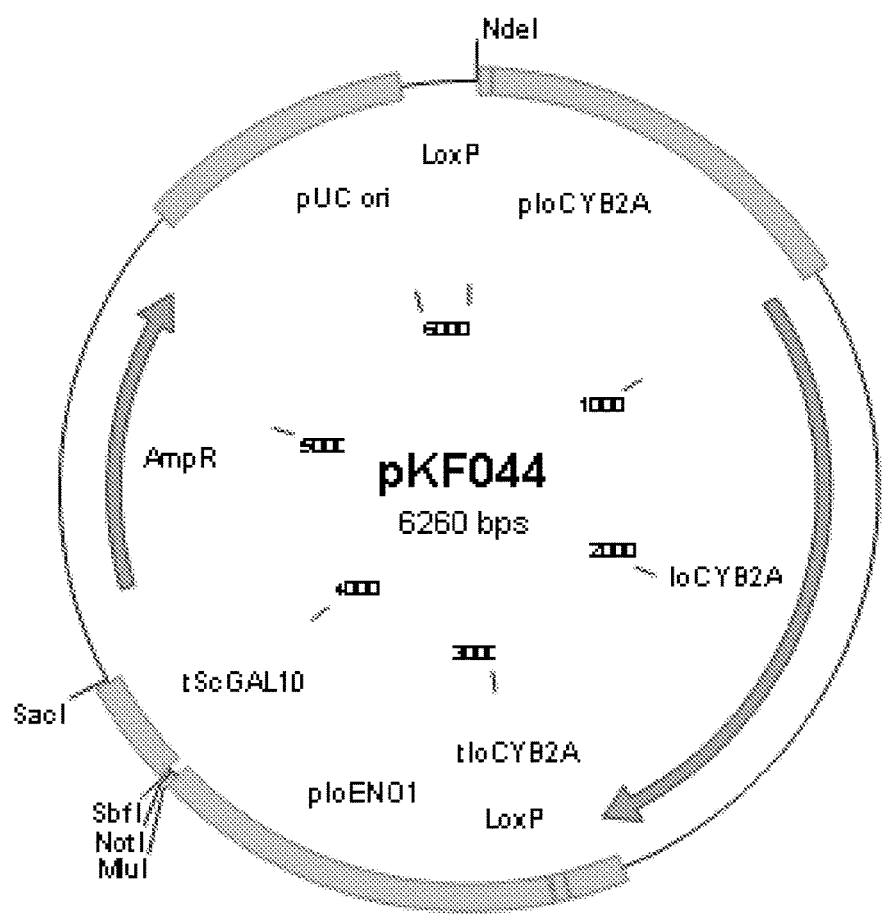
FIG. 7 shows plasmid pKF044, CYB2A construct.

The PYC1 gene from I. orientalis (SEQ ID NO:7) is amplified from genomic DNA using Phusion polymerase and primers oKF245 (SEQ ID NO:80) and oKF246 (SEQ ID NO:81), which contain an MluI site and an SbfI site, respectively. After amplification, the product is gel purified, digested with MluI and SbfI, and ligated to similarly digested pKF031 and pKF044. pKF031 (FIG. 6) and pKF044 (FIG. 7) are constructed from pUC19 backbones, and both contain a multiple cloning site containing MluI, NotI, and SbfI sites operatively linked to the I. orientalis $P_{ENO}$ promoter and the S. cerevisiae GAL10 terminator. pKF031 also contains a selection marker cassette comprising the S. cerevisiae MEL5 gene operatively linked to the I. orientalis $P_{PGK}$ promoter. This selection marker cassette is flanked by loxP sites. pKF044 contains an expression cassette comprising the I. orientalis CYB2A promoter, gene, and terminator. This expression cassette is flanked by loxP sites.

Figure 8:
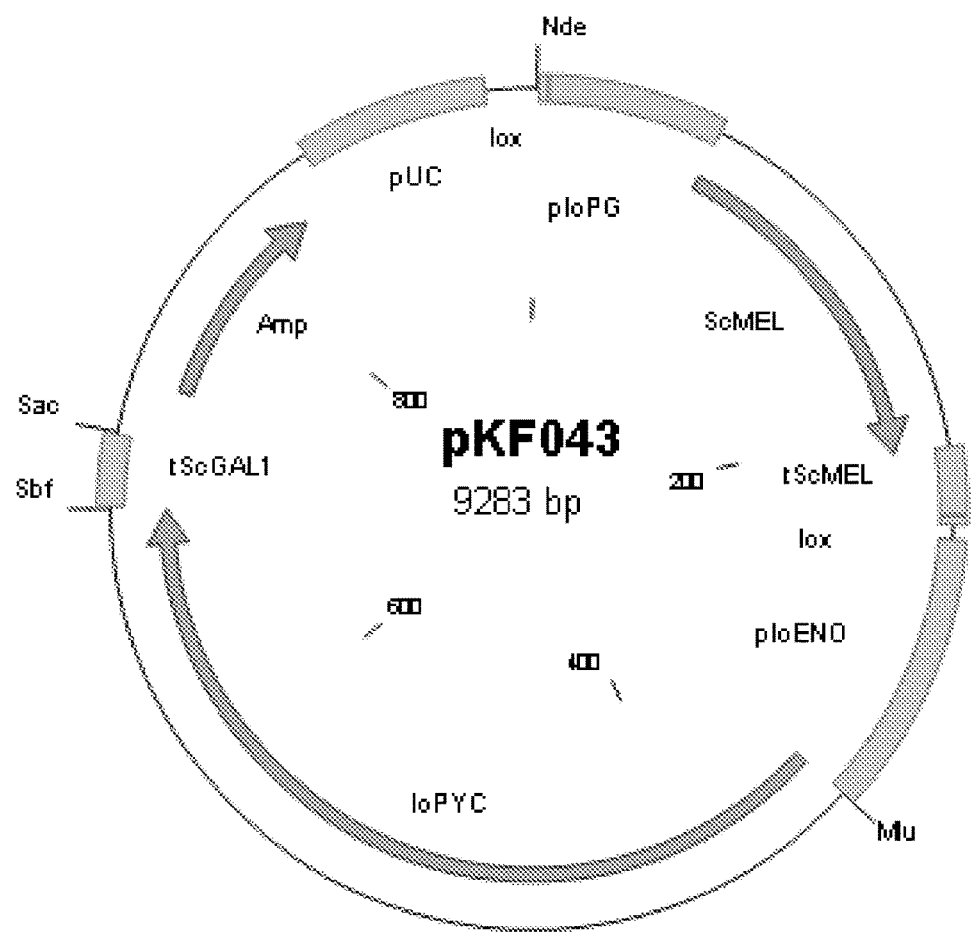
FIG. 8 shows plasmid pKF043, *I. orientalis* PYC1 expression construct.
Figure 9:
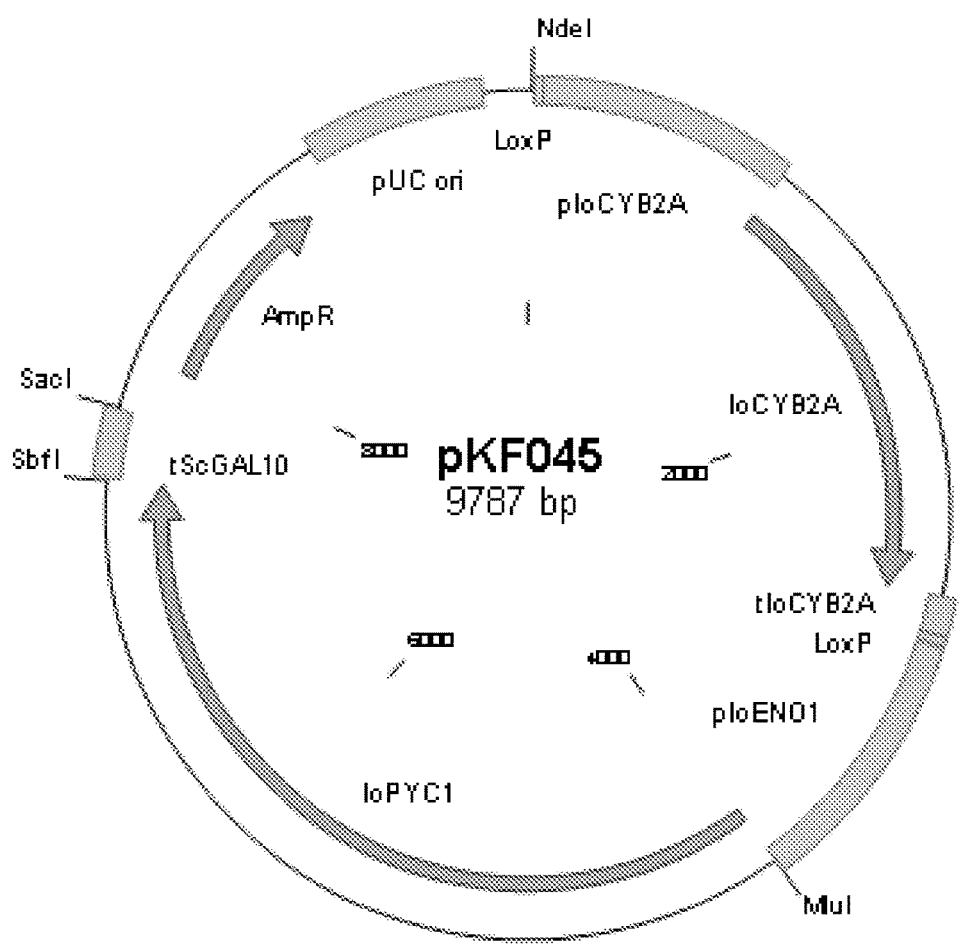
FIG. 9 shows plasmid pKF045, *I. orientalis* PYC1 expression construct.

The plasmids are transformed into E. coli, and transformants are selected on LB plates containing 100 µg/ml carbenicillin and screened using primers flanking the NotI site of pKF031 and pKF044 (oKW93 (SEQ ID NO:82) and oKW95 (SEQ ID NO:83)). Quickchange PCR is performed using primers oKW96 (SEQ ID NO:84) and oKW97 (SEQ ID NO:85) to eliminate an internal NdeI site (T2847C). Correct plasmids are confirmed by sequencing, and the final constructs are designated pKF043 (MEL5 marker) (FIG. 8) and pKF045 (CYB2A marker) (FIG. 9).

Example 4B: Insertion of I. orientalis PYC1 at the First and Second PDC1 Loci in I. orientalis Strain 2610 pKF043 and pKF045 are both amplified from the loxP site on the 5' end to the GAL10 terminator on the 3' end. pKF043 is amplified using primers oKF243 (SEQ ID NO:86) and oKF244 (SEQ ID NO:87), and pKF045 is amplified using primers oKF255 (SEQ ID NO:88) and oKF244 (SEQ ID NO:87). Each of these primers contains on their 5' end 65 bp of sequence specific to the 65 bp immediately upstream and downstream of the PDC1 locus in I. orientalis. This recombination sequence enables double recombination and integration at the PDC1 locus.

The PCR product amplified from pKF043 is used to transform I. orientalis strain 2610. Transformants are selected on YNB+2% melibiose+x-α-gal and, and integration of PYC1 at a first PDC1 allele is confirmed by PCR using primers oCM566 (SEQ ID NO:89), oKF151 (SEQ ID NO:90), oKF252 (SEQ ID NO:91), and oCM587 (SEQ ID NO:92). The correct heterozygous strain is designated ySBCK43.

Strain ySBCK43 is transformed with the PCR product from pKF045 amplification to generate a homozygous strain with PYC1 inserted at both PDC1 alleles. Integration is confirmed by PCR using the primers oCM566 (SEQ ID NO:89), oMM174 (SEQ ID NO:93), oCM587 (SEQ ID NO:92), and oCA397 (SEQ ID NO:94). The correct homozygous strain is designated 12629.

For marker recycling, I. orientalis 12629 was grown to around $OD_{600}$ of 1.0 in YP+100 g/L glucose (50 ml media in a 250 ml flask; 30° C./250 rpm). Cells were transformed with pVB32 using lithium acetate transformation, and transformants were selected on YNB+2% sucrose plates overlaid with x-α-gal. After 4 to 5 days, white colonies were streaked to YP+20 g/L glucose plates overlaid with x-α-gal and grown at 37° C. for 2 days. Genomic DNA from white colonies was screened for retention of the expression cassette at the I. orientalis PDC1 locus and for loss of the selectable markers using PCR primers oGPB9 (SEQ ID NO:95), oGPB10 (SEQ ID NO:96), oGPB11 (SEQ ID NO:97), and oGPB12 (SEQ ID NO:98). Positive transformants were confirmed to have lost the marker by a phenotypic screen showing no growth on YNB+2% lactic (pH 5.5), 2% melabiose, or 2% sucrose. The homozygous strain with both markers removed was designated 12481.

The various PYC1 insertion/PDC1 deletion strains generated in Example 4 are summarized in Table 7.

TABLE 7

PYC1 Insertion Strains

| Strain name | Description | Parent strain |
| --- | --- | --- |
| ySBCK43 | CYB2A deletion (2) | 2610 |
|  | I. orientalis PYC1 insertion at PDC1 (1) |  |
| 12629 | CYB2A deletion (2) | ySBCK43 |
|  | I. orientalis PYC1 insertion at PDC1 (2) |  |
| 12481 | CYB2A deletion (2) | 12629 |
|  | I. orientalis PYC1 insertion at PDC1 (2) |  |

Example 5: Insertion of FRD1 at the ADHa Locus in I. orientalis Strains 12481

An FRD1 expression cassette is inserted at one or both ADHa alleles of I. orientalis strains 12481 (Example 4).

Figure 10:
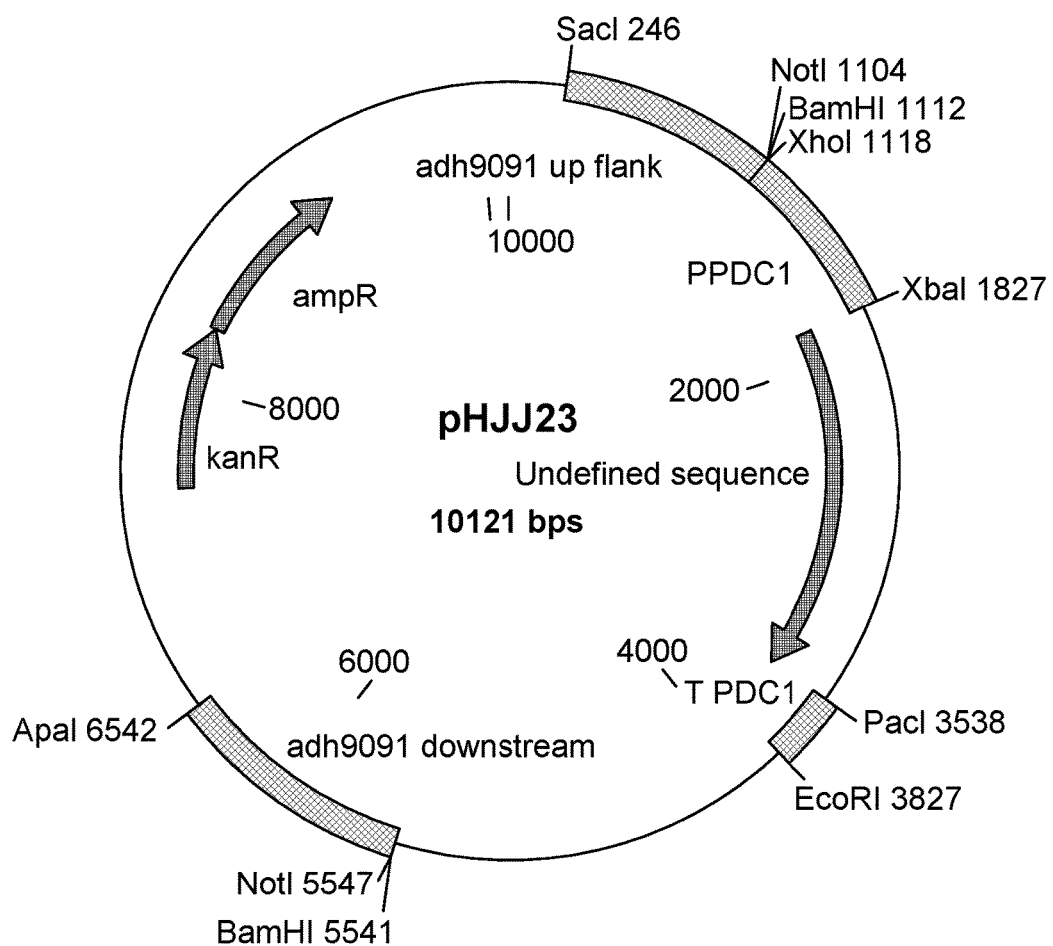
FIG. 10 shows plasmid pHJJ23.
Figure 11:
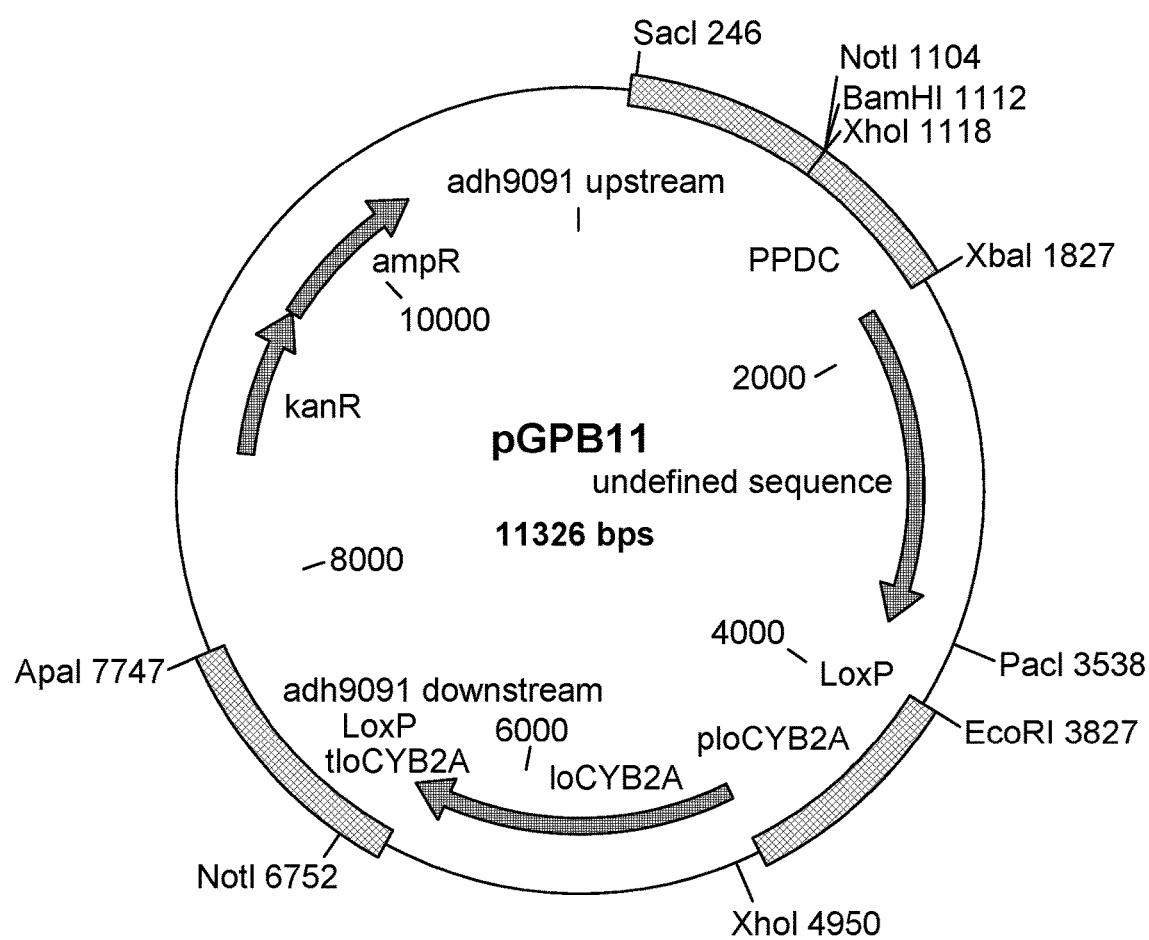
FIG. 11 shows plasmid pGPB11, ADHa deletion construct.
Figure 12:
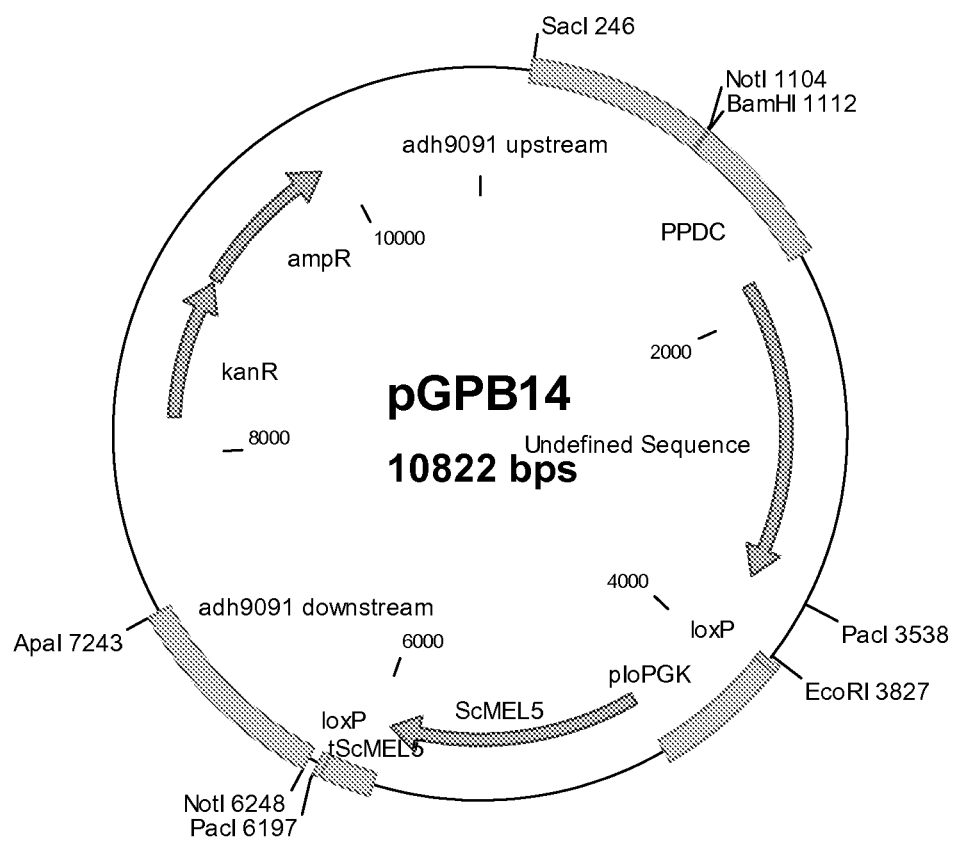
FIG. 12 shows plasmid pGPB14, ADHa deletion construct.
Figure 13:
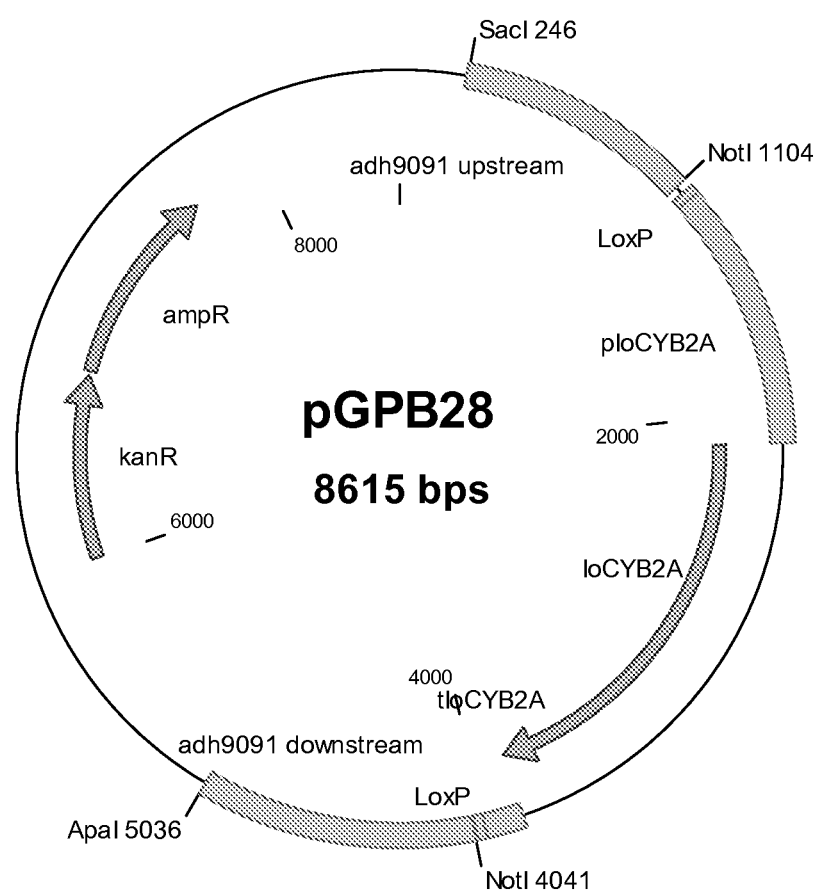
FIG. 13 shows plasmid pGPB28, ADHa deletion construct.
Figure 14:
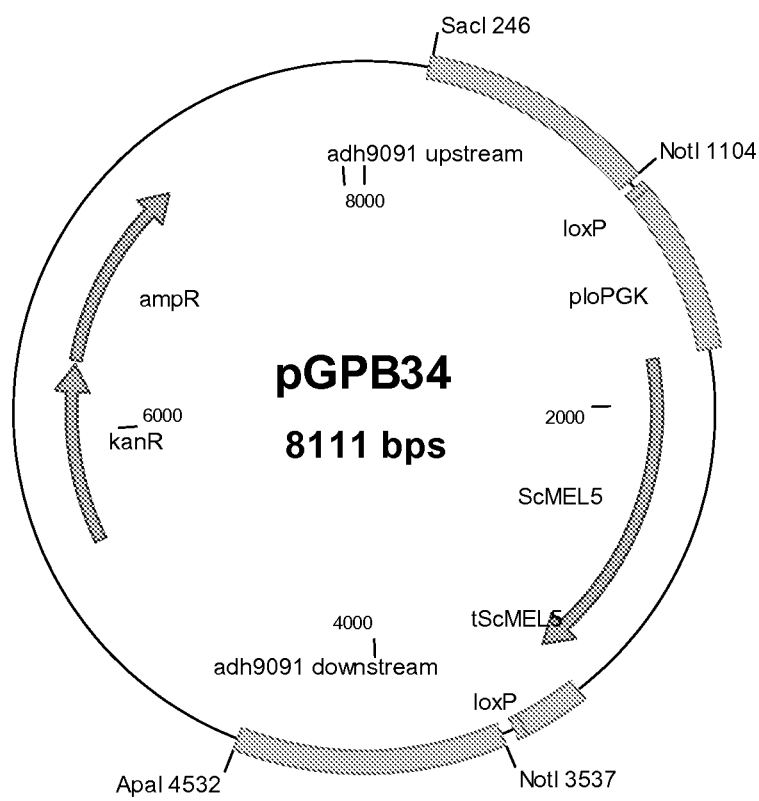
FIG. 14 shows plasmid pGPB34, ADHa deletion construct.

Example 5A: Construction of ADHa Deletion Constructs pGPB11, pGPB14, pGPB28, and pGPB34 pKF044 was used as a template for quickchange mutagenesis using oligonucleotides oKW64 (SEQ ID NO:99) and oKW65 (SEQ ID NO:100) to delete an EcoRI site at nucleotide 932 of the *I. orientalis* CYB2A gene. The resulting plasmid was designated pKW49. pKW49 was digested with EcoRI and BglII and the resultant fragment ligated to EcoRI and BamHI digested pHJJ23 (FIG. 10). The resulting ADHa deletion construct, designated pGPB11 (FIG. 11), contains the *I. orientalis* PDC1 promoter (amplified using primers oJLJ3 (SEQ ID NO:101) and oJLJ19 (SEQ ID NO:102)) and terminator (amplified using primers oJLJ1 (SEQ ID NO:103) and oJLJ2 (SEQ ID NO:104)) and a CYB2A marker element between an 858 bp fragment corresponding to the region immediately 5' of the *I. orientalis* AHD2a open reading frame (amplified using primers oHJJ71 (SEQ ID NO:105) and oHJJ72 (SEQ ID NO:106)) and a 996 bp fragment corresponding to the region immediately 3' of the *I. orientalis* ADHa open reading frame (amplified using primer oHJJ73 (SEQ ID NO:107) and oHJJ74 (SEQ ID NO:108)).

pKF046, which contains an *S. cerevisiae* MEL5 marker gene operatively linked to a *I. orientalis* PGK promoter and an *S. cerevisiae* MEL5 terminator and flanked by LoxP sites, was used as a template for quickchange mutagenesis using oligonucleotides oKW74 (SEQ ID NO:109) and oKW75 (SEQ ID NO:110) to delete an EcoRI site at nucleotide 2392 of the plasmid. The resulting plasmid was designated pKW50. pKW50 was digested with EcoRI and BglII and the resultant fragment ligated to EcoRI and BamHI digested pHJJ23. The resulting plasmid, designated pGPB14 (FIG. 12), contains the same elements as pGPB11, but with the CYB2A selectable marker element replaced by the *S. cerevisiae* MEL5 selectable marker element.

pGPB11 and pGPB14 were each digested with EcoRI and BamHI to remove those portions of the plasmids corresponding to the PDC promoter and terminator, and each plasmid backbone was blunted with Klenow fragment and ligated to recircularize the plasmid. The plasmids were then transformed into *E. coli*. Plasmid isolated from positive colonies was designated pGPB28 (FIG. 13, derived from pGPB11) and pGPB34 (FIG. 14, derived from pGPB14).

Example 5B: Construction of FRD1 Expression Constructs pGPB26, pGPB39

Expression cassettes for the FRD1 gene from *S. cerevisiae* (SEQ ID NO:29) is inserted into the ADHa deletion construct pGPB11.

Figure 15:
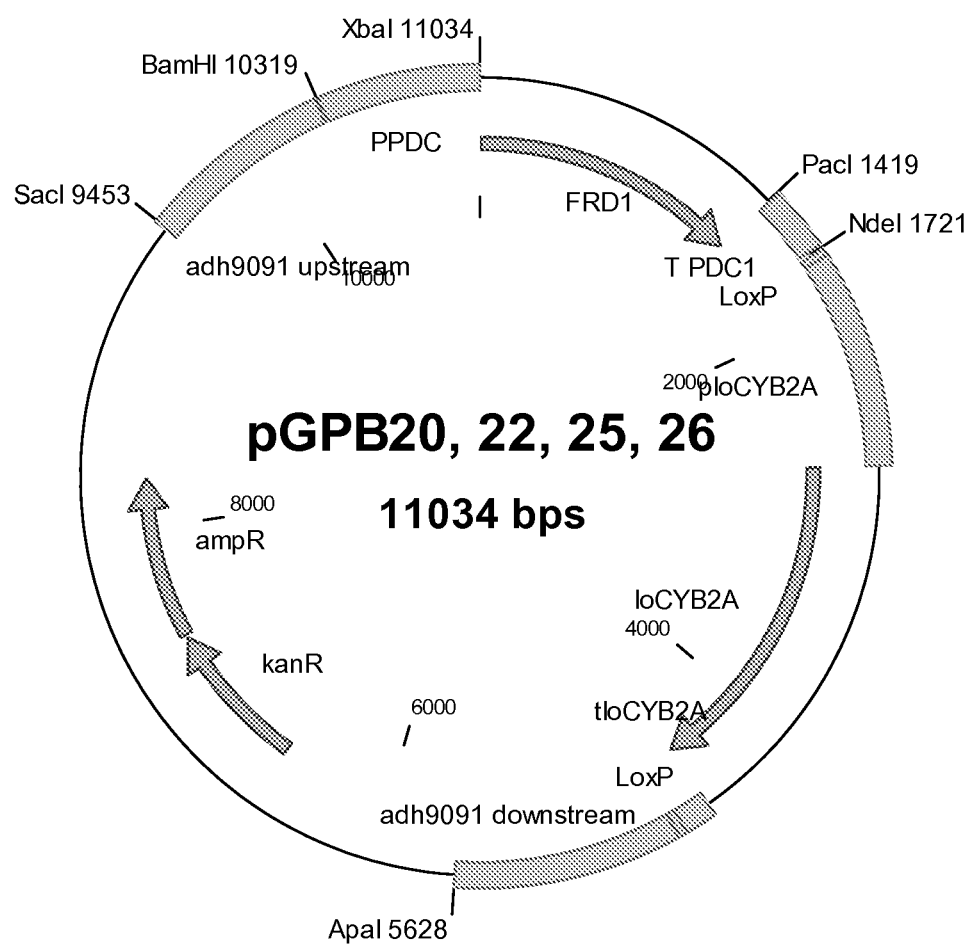
FIG. 15 shows plasmid pGPB20, 22, 25, and 26, FRD1 expression constructs.
Figure 16:
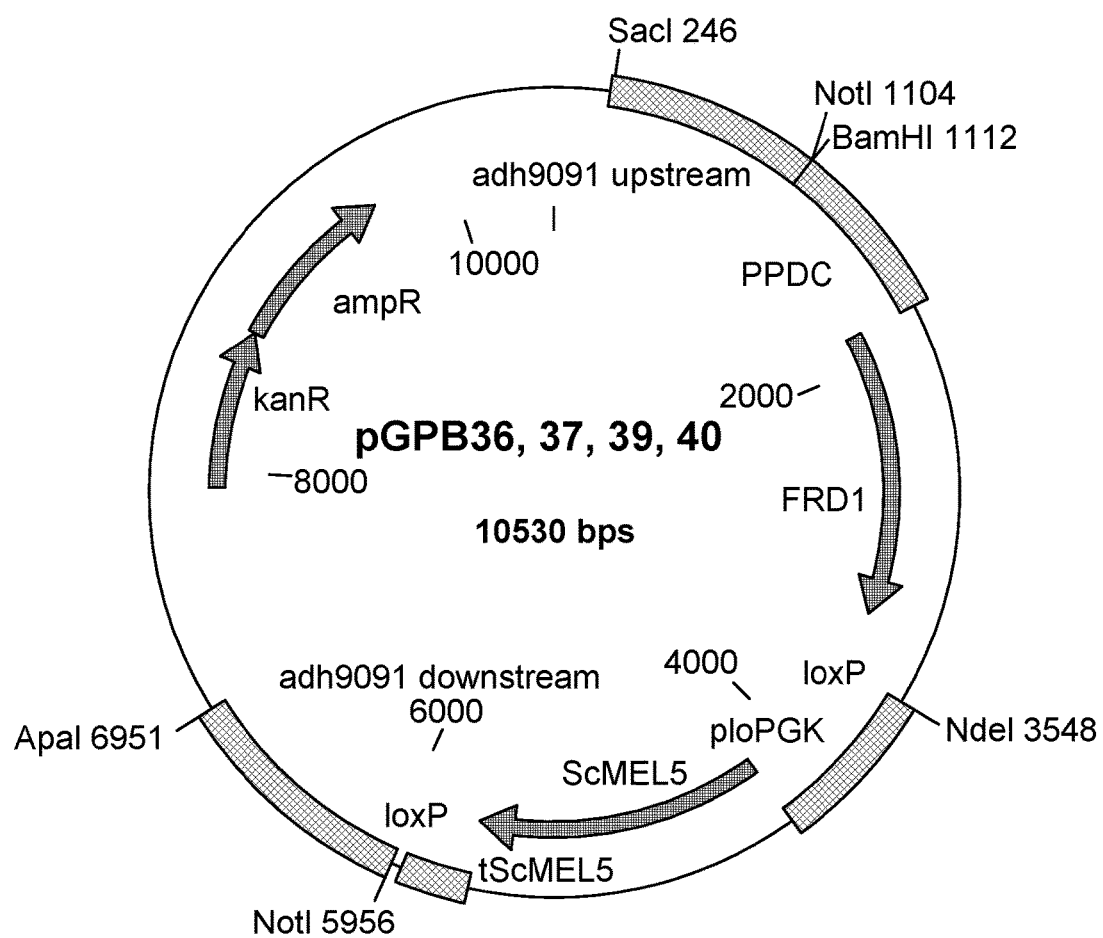
FIG. 16 shows plasmid pGPB36, 37, 39, and 40, FRD1 expression constructs.

Plasmids containing *S. cerevisiae* FRD1 gene was digested with XbaI and PacI, and the FRD1 fragments were ligated to similarly digested pGPB11. The resulting plasmid, which contained the FRD1 coding sequence flanked by the *I. orientalis* PDC1 promoter and terminator and also contained the *I. orientalis* CYB2A selectable marker, was designated pGPB26 (*S. cerevisiae* FRD1) (FIG. 15).

pGPB26 was digested with BamHI and NdeI and ligated to similarly digested pGPB14. The resulting plasmids, which contained the FRD1 coding sequence flanked by the *I. orientalis* PDC1 promoter and terminator and also contained the *S. cerevisiae* MEL5 selectable marker was designated pGPB39 (*S. cerevisiae* FRD1) (FIG. 16).

Example 5C: Insertion of FRD1 at First and Second ADHa Loci of *I. orientalis* Strain 12481 pGPB39, was digested with SacI and ApaI and transformed into *I. orientalis* strain 12481 by lithium acetate transformation. Transformants are selected on YNB+2% melibiose plates overlaid with x-α-gal. After around six days, blue transformants are picked and plated for single colonies on YP+20 g/L glucose plates containing x-α-gal. Blue colonies are picked, and genomic DNA is isolated and screened by PCR to confirm integration of the FRD1 expression cassette at the ADHa locus using primers oGPB47 (SEQ ID NO:111), oGPB56 (SEQ ID NO:112), oGPB54 (SEQ ID NO:113), and oGPB46 (SEQ ID NO:114). Strains with the correct integration of the FRD1 gene are designated ySBCG101.

pGPB26 (*S. cerevisiae* FRD1) are digested with SacI and ApaI and transformed into strain ySBCG101 by lithium acetate transformation. Transformants are screened by PCR to confirm correct integration of the FRD1 expression cassette at a first ADHa locus using primers oGPB47 (SEQ ID NO:111), oGPB53 (SEQ ID NO:115), oGPB52 (SEQ ID NO:116), oGPB54 (SEQ ID NO:113), and oGPB46 (SEQ ID NO:114). The resulting strains are designated ySBCG126.

Marker recycling is carried out with plasmid pVB32. The correct homozygous strain with both markers removed is designated 12752.

The various FRD1 insertion/ADHa deletion strains generated in Example 5 are summarized in Table 8.

TABLE 8

*I. orientalis* FRD1 Insertion Strains

| Strain name | Description | Parent strain |
| --- | --- | --- |
| ySBCG101 | CYB2A deletion (2)<br>*I. orientalis* PYC1 insertion at PDC1 (2)<br>*S. cerevisiae* FRD1 insertion at ADHa (1) | 12481 |
| ySBCG126 | CYB2A deletion (2)<br>*I. orientalis* PYC1 insertion at PDC1 (2)<br>*S. cerevisiae* FRD1 insertion at ADHa (2) | ySBCG101 |
| 12752 | CYB2A deletion (2)<br>*I. orientalis* PYC1 insertion at PDC1 (2)<br>*S. cerevisiae* FRD1 insertion at ADHa (2) | ySBCG126 |

Example 6: Insertion of MDH at the ATO2 Locus in *I. orientalis* Strain 12752

An MDH expression cassette is inserted at one or both ATO2 alleles of *I. orientalis* strain 12752 (Example 5).

Example 6A: Construction of ATO2 Deletion Construct pKWB18, pKWB23, and pKWB28

Figure 17:
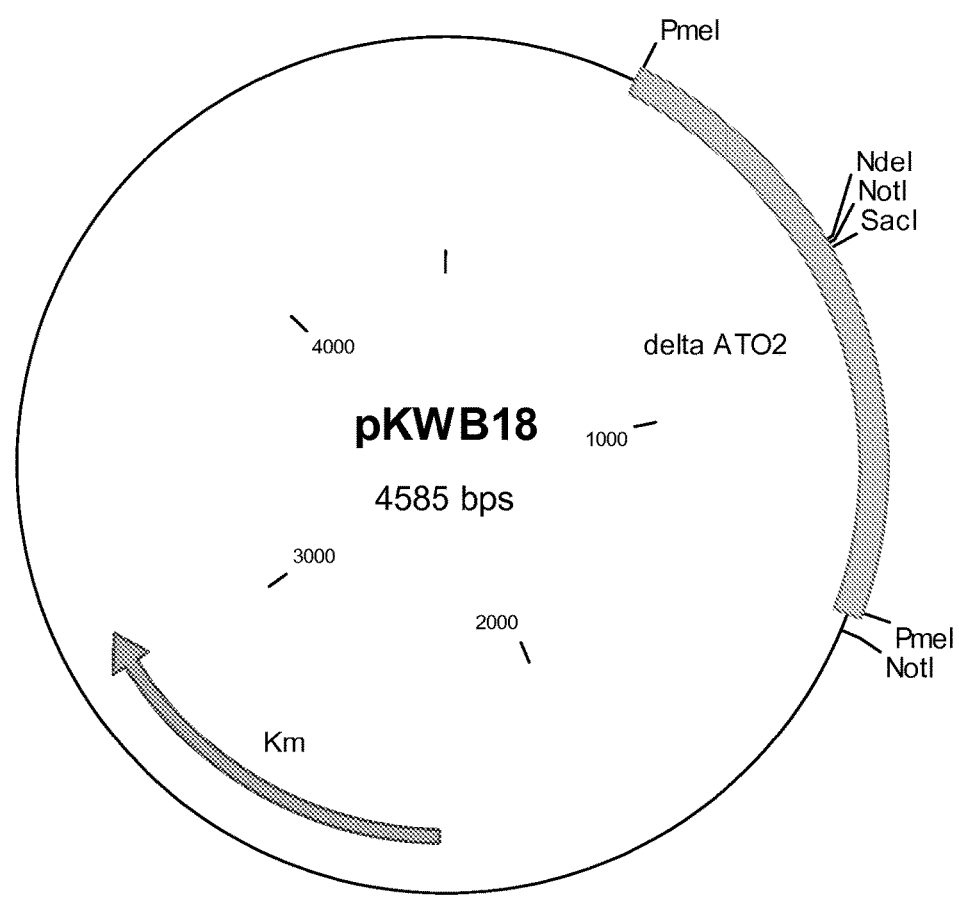
FIG. 17 shows plasmid pKWB18, ATO2 deletion construct.
Figure 18:
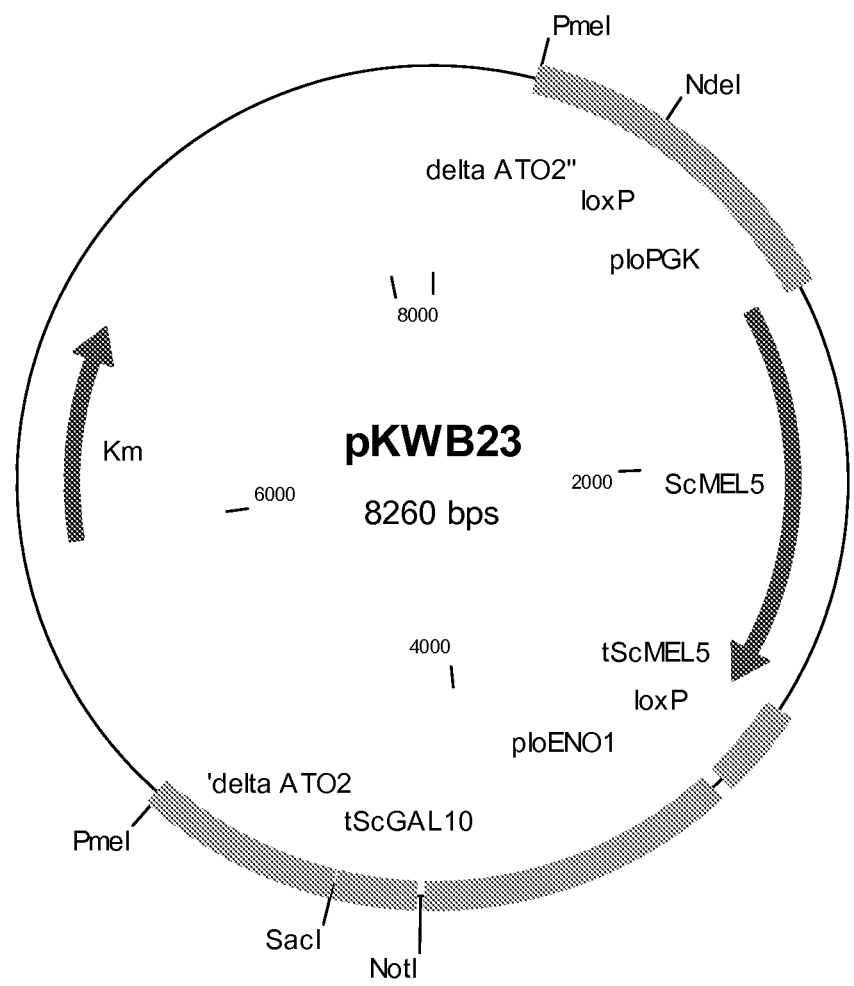
FIG. 18 shows plasmid pKWB23, ATO2 deletion construct.
Figure 19:
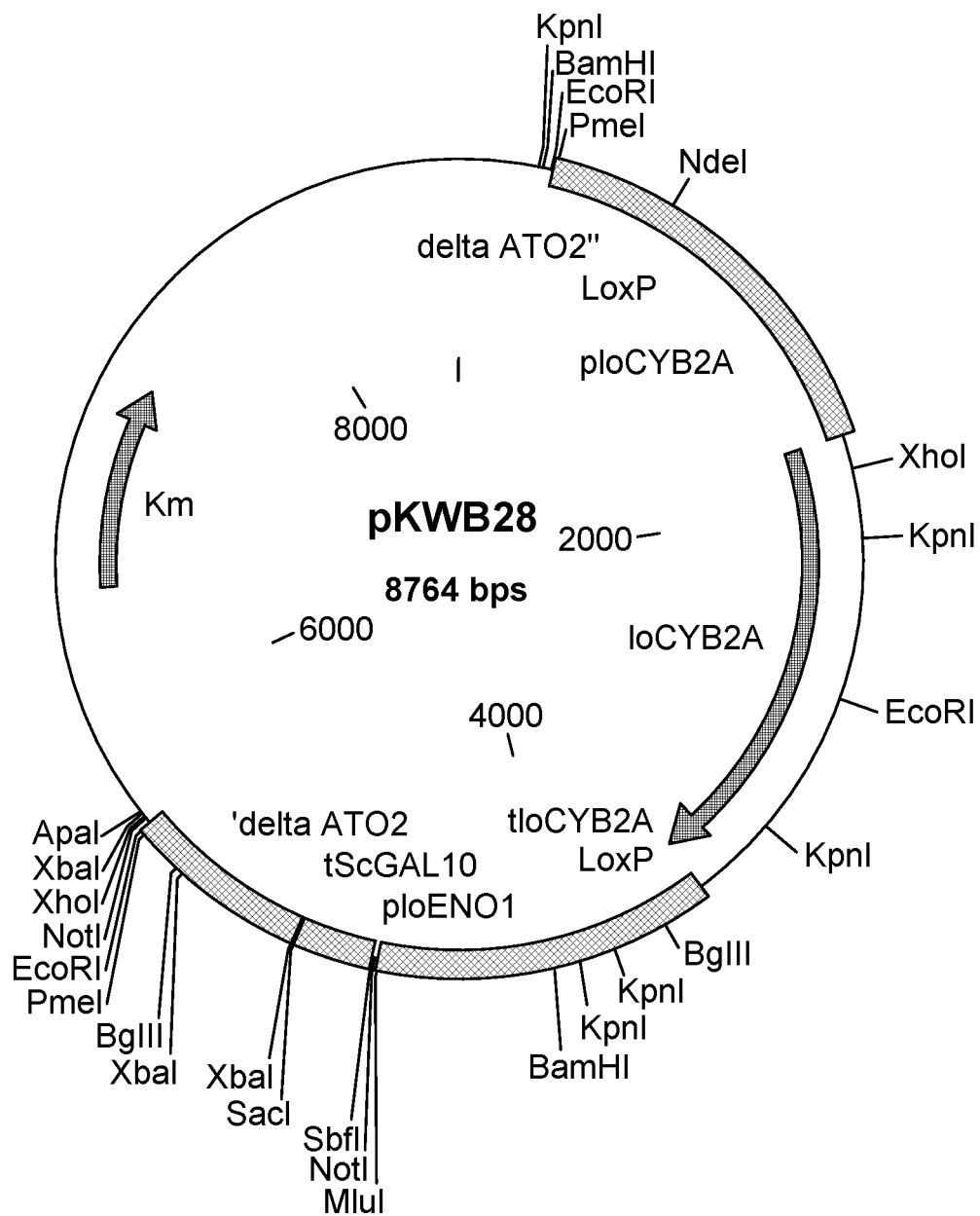
FIG. 19 shows plasmid pKWB28, ATO2 deletion construct.

Upstream and downstream regions of *I. orientalis* ATO2 (SEQ ID NO:65) were amplified in order to generate an ATO2 deletion construct. The upstream and downstream regions correspond to nucleotides from 419 bp upstream to the start codon of ATO2 and from the stop codon to 625 bp downstream, respectively. Amplification of the upstream region is performed using primers oKW66 (forward, SEQ ID NO:117) and oKW67 (reverse, SEQ ID NO:118), which adds a PmeI restriction site and NdeI, NotI, and SacI restriction sites, respectively, to the product. Amplification of the downstream region is performed using primers oKW68 (forward, SEQ ID NO:119) and oKW69 (reverse, SEQ ID NO:120), which adds NdeI, NotI, and SacI restriction sites and a PmeI restriction site, respectively, to the product. The two fragments are amplified independently, then assembled into a full-length product with a two stage PCR protocol. The first stage uses 10 cycles (98° C. 10 s, 55° C. 20 s, 72° C. 60 s) with no primers, and the second stage uses 20 cycles (98° C. 10 s, 55° C. 20 s, 72° C. 60 s) with upstream forward and downstream reverse primers. The full-length product is gel purified, cloned into pCR-BluntII (Invitrogen), and sequenced. The plasmid confirmed to have correct sequence is subjected to quickchange PCR using Phusion polymerase to eliminate the plasmid-borne SacI site. Correct plasmids are confirmed by digestion with SacI and sequencing. The final ATO2 deletion construct is designated pKWB18 (FIG. 17). pKWB18 was digested with NdeI and SacI restriction enzymes and ligated to like cut pKF031 (ScMEL5 selectable marker) and pKF044 (CYB2A selectable marker). The resulting ATO2 deletion constructs with ScMEL5 and CYB2A selectable markers are designated pKWB23 (ScMEL5) and pKWB28 (CYB2A) (FIG. 18 and FIG. 19 respectively).

Example 6B: Construction of MDH Expression Constructs pGPB64 and 66

Figure 20:
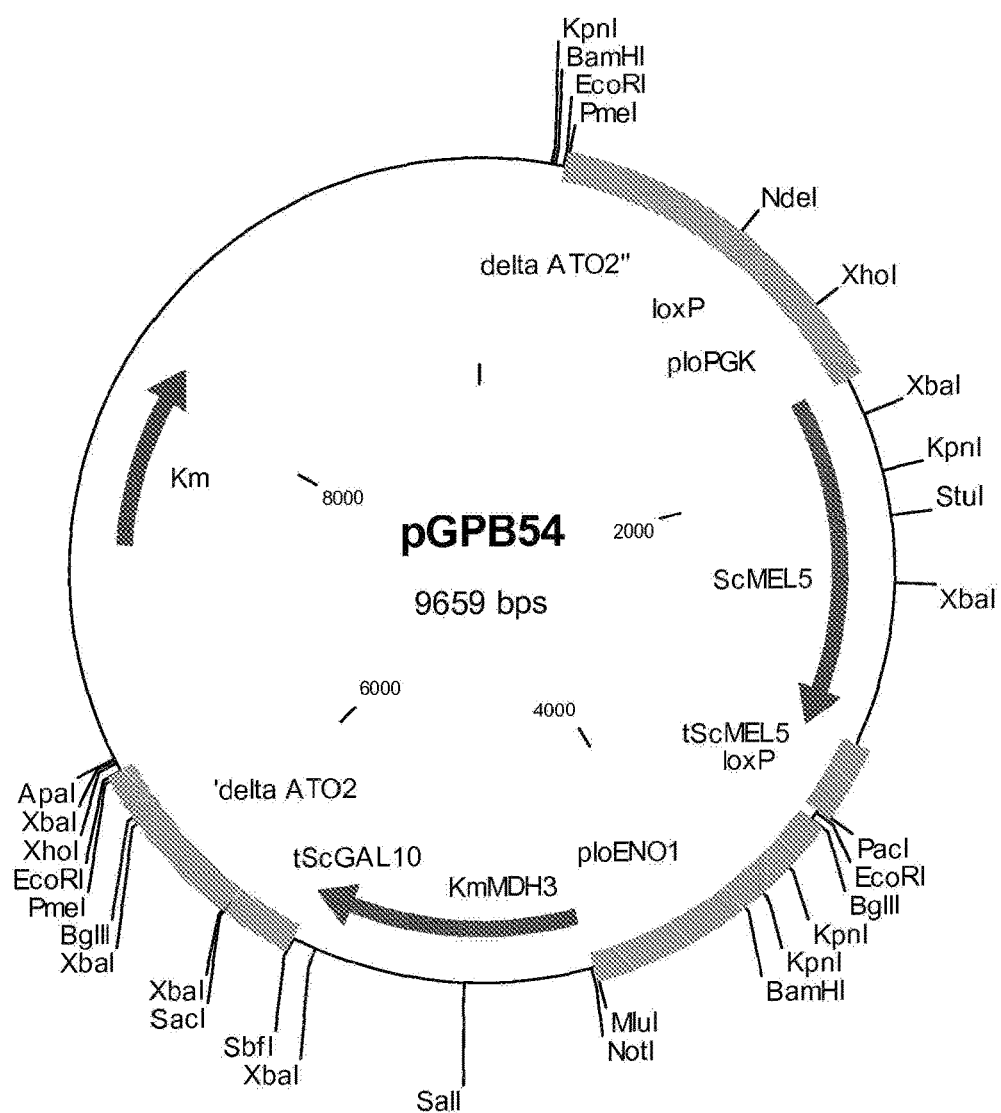
FIG. 20 shows plasmid pGPB54, MDH expression construct.
Figure 21:
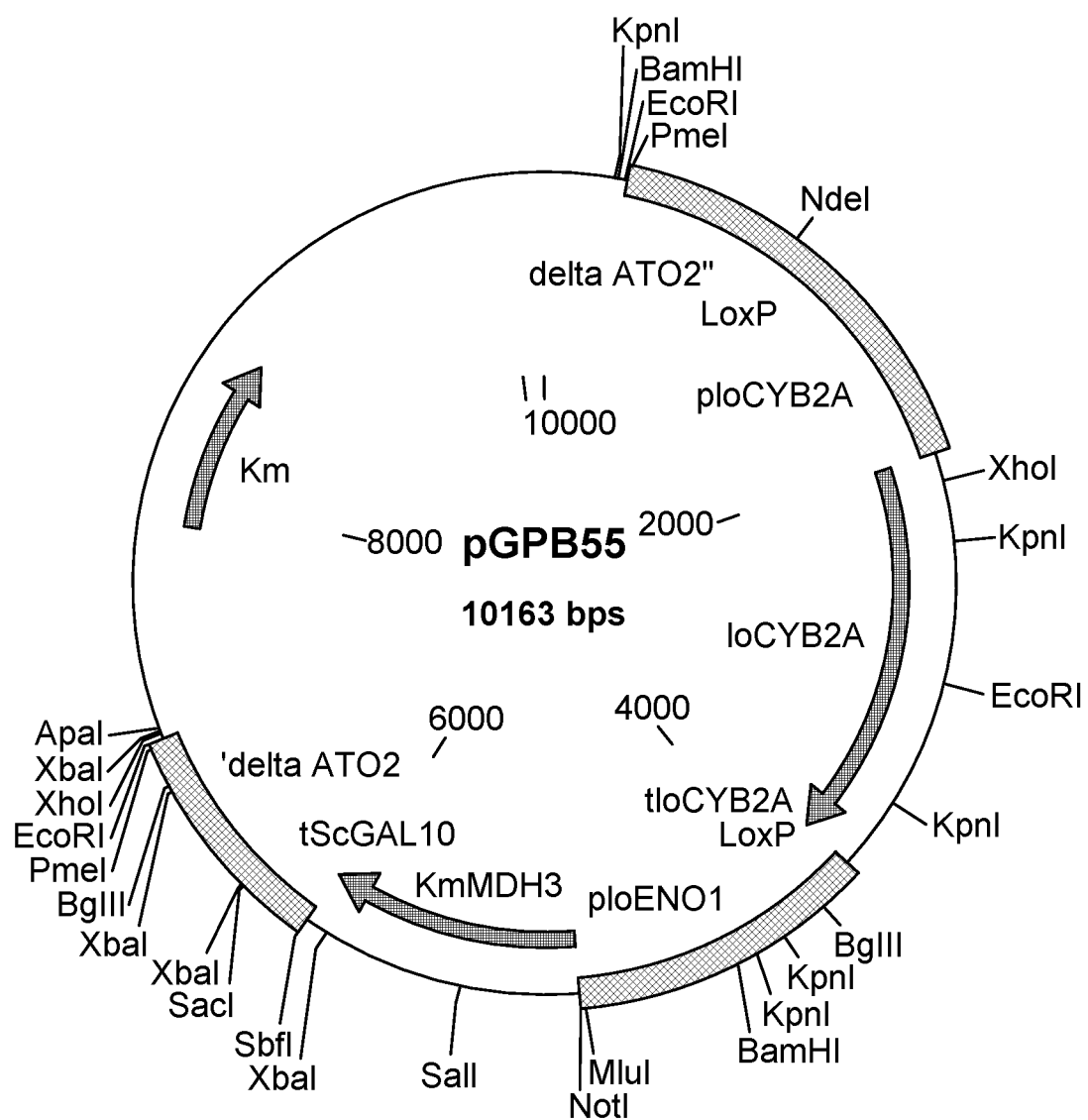
FIG. 21 shows plasmid pGPB55, MDH expression construct.
Figure 22:
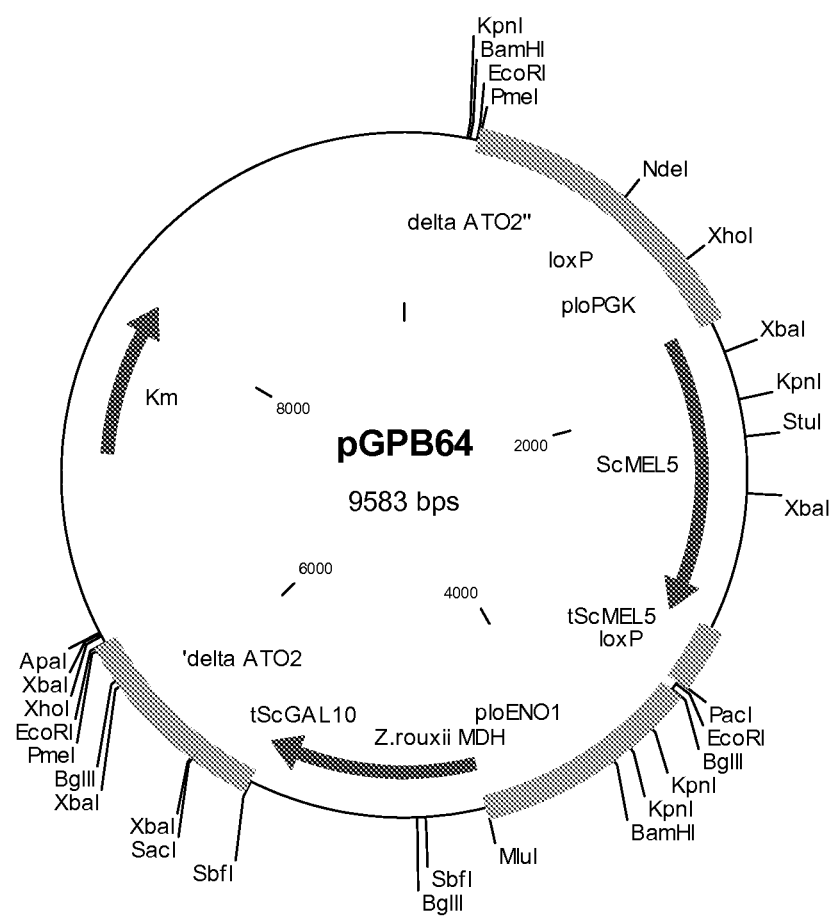
FIG. 22 shows plasmid pGPB64, *Z. rouxii* MDH expression construct.
Figure 23:
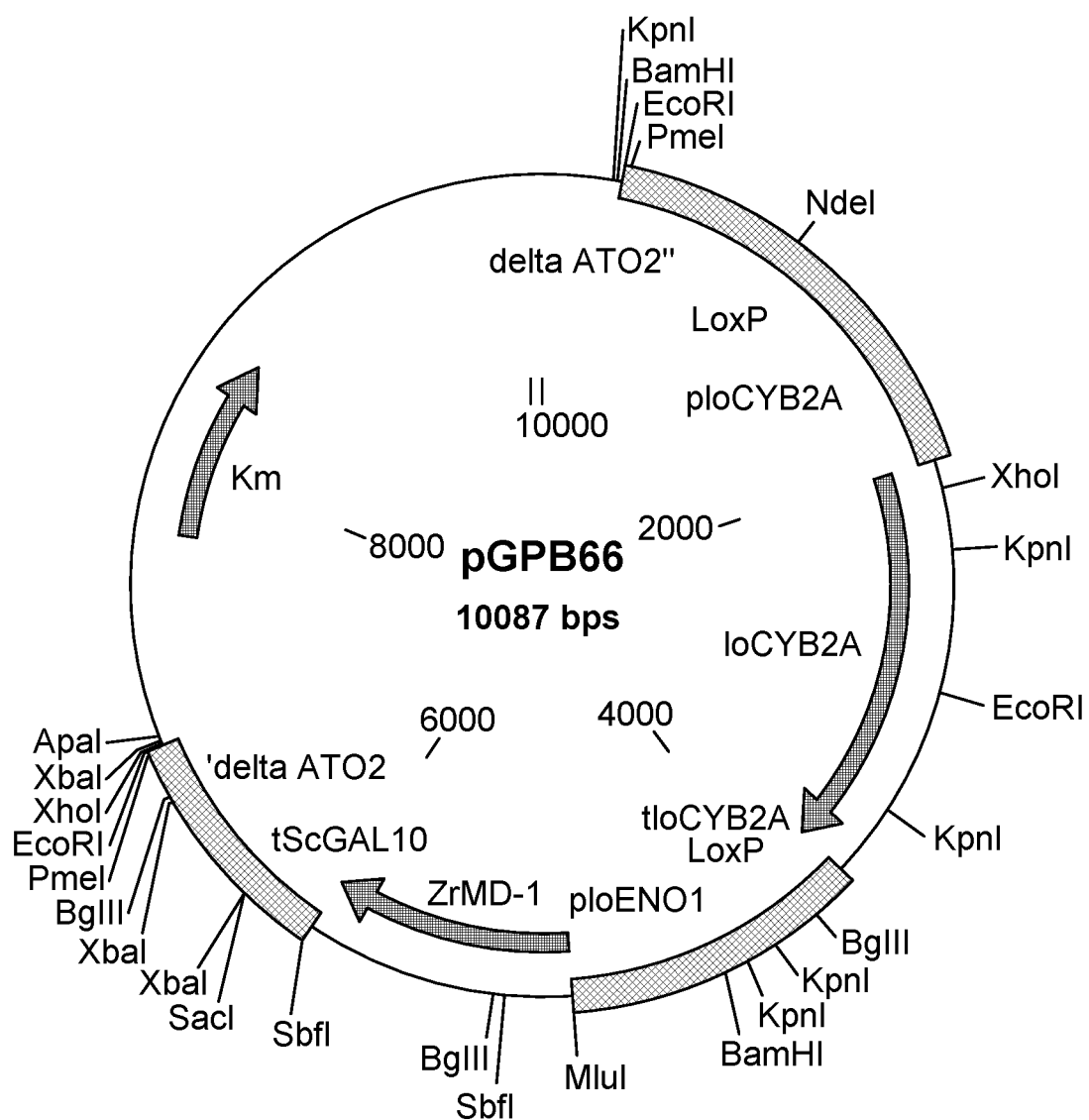
FIG. 23 shows plasmid pGPB66, *Z. rouxii* MDH expression construct.

The MDH gene from *Z. rouxii* (SEQ ID NO:25) is amplified from genomic DNA using primers designed to add a MluI restriction enzyme site 5' end of the start codon, and a SbfI restriction enzyme site to the 3' end of the stop codon. *Z. rouxii* MDH is amplified using primers oGPB67 (SEQ ID NO:121) and oGPB68 (SEQ ID NO:122) After amplification, the product is gel purified and cloned into pZeroBluntII and transformed into *E. coli*. Transformants are selected on LB plates containing 50 μg/ml kanamycin. The correct plasmid is confirmed by sequencing, and the final construct is designated pGPB58 (*Z. rouxii* MDH). pGPB58 is digested with MluI and SbfI to liberate the fragment containing the MDH gene. The fragment is gel purified and cloned into like cut pGPB54 and pGPB55 (FIG. 20 and FIG. 21). The resulting plasmids are designated pGPB64 (*Z. rouxii* MDH, MEL5 marker, FIG. 22) and pGPB66 (*Z. rouxii* MDH, CYB2A selectable marker, FIG. 23).

Example 6C: Insertion of MDH at First and Second ATO2 Loci in *I. orientalis* Strain 12752 pGPB64 is digested with PmeI and the appropriate fragments are used to transform *I. orientalis* strain 12752 (Example 5) by lithium acetate transformation. Transformants are selected by growth on YNB+2% melibiose and screened by PCR with primers flanking the ATO2 locus (oKW214 (SEQ ID NO:123) and oKWB155 (SEQ ID NO:124)) along with nested primers specific to the MEL5 integration cassette (oGPB55 (SEQ ID NO:125), and oGPB11 (SEQ ID NO:97). Colony with the correct insertion of MDH at a first ATO2 locus is designated ySBCG160.

pGPB66 is digested with PmeI and the appropriate fragments are used to transform *I. orientalis* strain ySBCG160. Transformants are selected by growth on YNB+2% lactic+ x-α-gal and screened by PCR with primers flanking the ATO2 locus (oKW214 (SEQ ID NO:123) and oKWB155 (SEQ ID NO:124)) along with nested primers specific to the MEL5 integration cassette (oGPB55 (SEQ ID NO:125), and the CYB2A integration cassette oGPB52 (SEQ ID NO:116), oGPB53 (SEQ ID NO:115). A strain homozygous for MDH at the ATO2 loci is designated 12787.

Marker recycling is carried out using pVB32, and homozygous strain with both markers removed is designated 12792.

The various MDH insertion/ATO2 deletion strains generated in Example 6 are summarized in Table 9.

TABLE 9

*I. orientalis* MDH Insertion Strains

| Strain name | Description | Parent strain |
| --- | --- | --- |
| ySBCG160 | CYB2A deletion (2) *I. orientalis* PYC1 insertion at PDC1 (2) *S. cerevisiae* FRD1 insertion at ADHa (2) *Z. rouxii* MDH insertion at ATO2 (1) | 12752 |
| 12787 | CYB2A deletion (2) *I. orientalis* PYC1 insertion at PDC1 (2) *S. cerevisiae* FRD1 insertion at ADHa (2) *Z. rouxii* MDH insertion at ATO2 (2) | ySBCG160 |
| 12792 | CYB2A deletion (2) *I. orientalis* PYC1 insertion at PDC1 (2) *S. cerevisiae* FRD1 insertion at ADHa (2) *Z. rouxii* MDH insertion at ATO2 (2) | 12787 |

Example 7: Insertion of *I. orientalis* FUM1 Genes at the CYB2B Locus in *I. orientalis* Strains 12790-12792

*I. orientalis* FUM1 expression cassettes are inserted at both alleles of CYB2A of *I. orientalis* strain 12792 (Example 6).

Example 7A: Construction of *I. orientalis* FUM1 Expression Constructs pGPB30, pGPB42, pGPB44, and pGPB47

Figure 24:
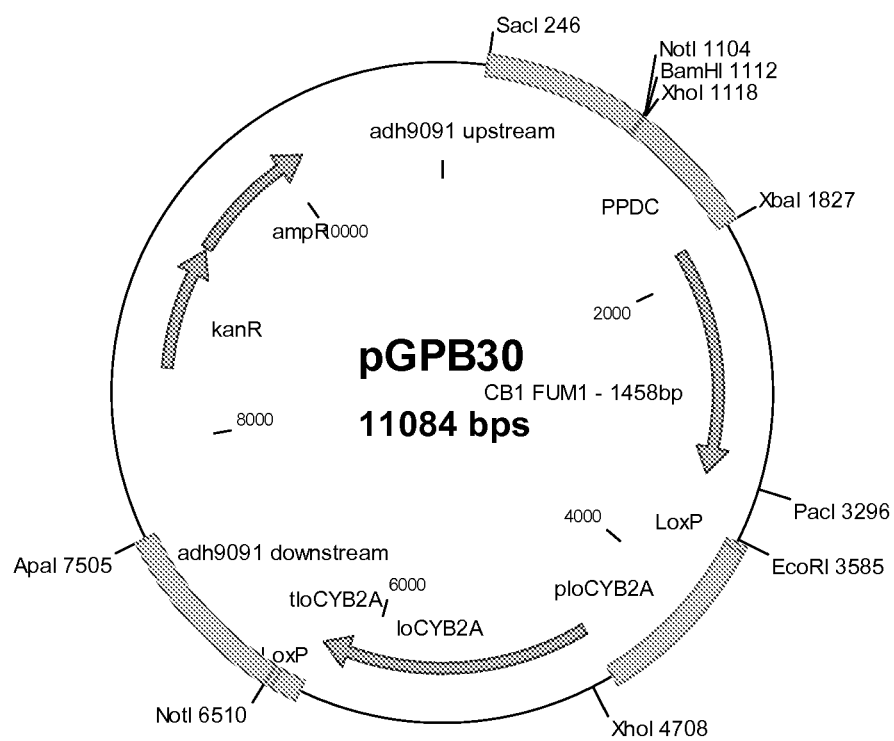
FIG. 24 shows plasmid pGPB30, FUM1 expression constructs.
Figure 25:
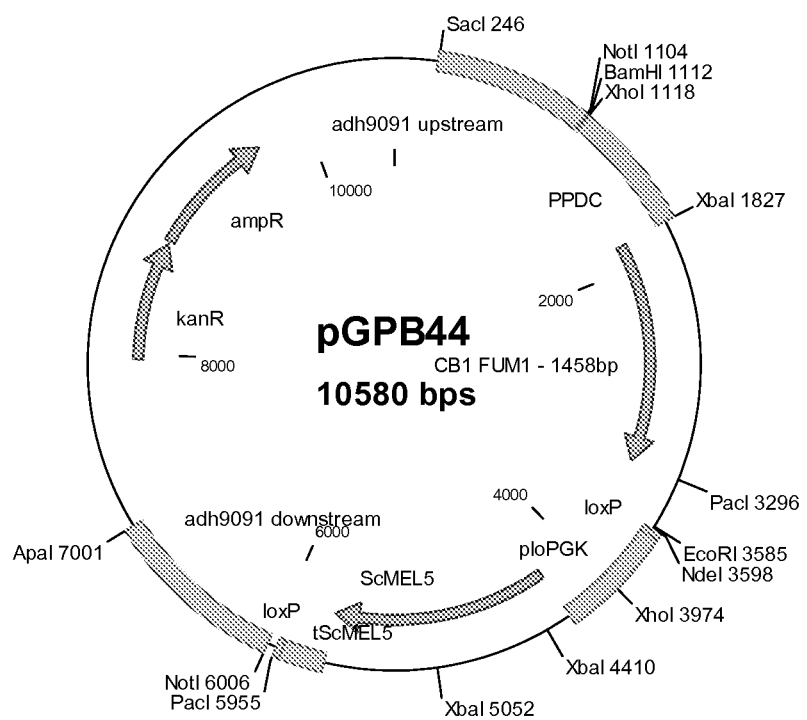
FIG. 25 shows plasmid pGPB44, FUM1 expression constructs.

An expression cassette for the *I. orientalis* FUM1 gene (SEQ ID NO:1) is inserted into the ADHa deletion construct pGPB11. PCR primers oGPB38 (SEQ ID NO:127) and oGPB40 (SEQ ID NO:128) are used to amplify FUM1 using *I. orientalis* genomic DNA as the template. The 5' primer adds an XbaI site at the start site of the coding sequence and the 3' primer adds a PacI site 3' of the stop codon. The resulting PCR product is digested with XbaI and PacI and ligated to similarly digested pGPB11. The resulting plasmid, which contains the FUM1 coding sequence flanked by the *I. orientalis* PDC1 promoter and terminator and the CYB2A selectable marker, is designated pGPB30 (FIG. 24).

pGPB30 is digested with BamHI and NdeI and ligated into similarly digested pGPB14. The resulting plasmid is designated pGPB44 (FIG. 25).

Figure 26:
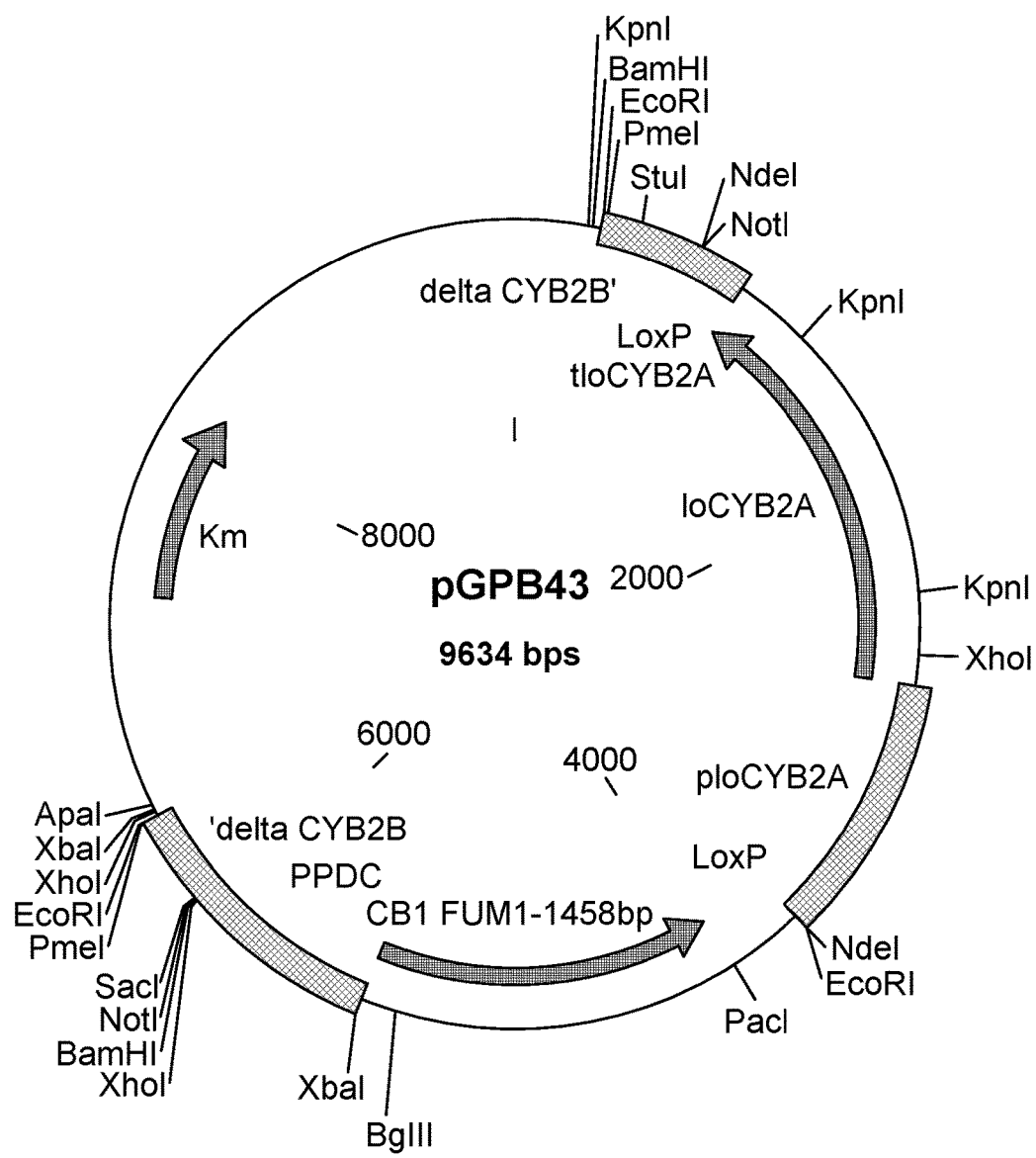
FIG. 26 shows plasmid pGPB43, FUM1 expression constructs.

The expression cassette from pGPB30 is excised using NotI and ligated to the NotI cut pKW22. The resulting plasmid is designated pGPB43 (FIG. 26).

Figure 27:
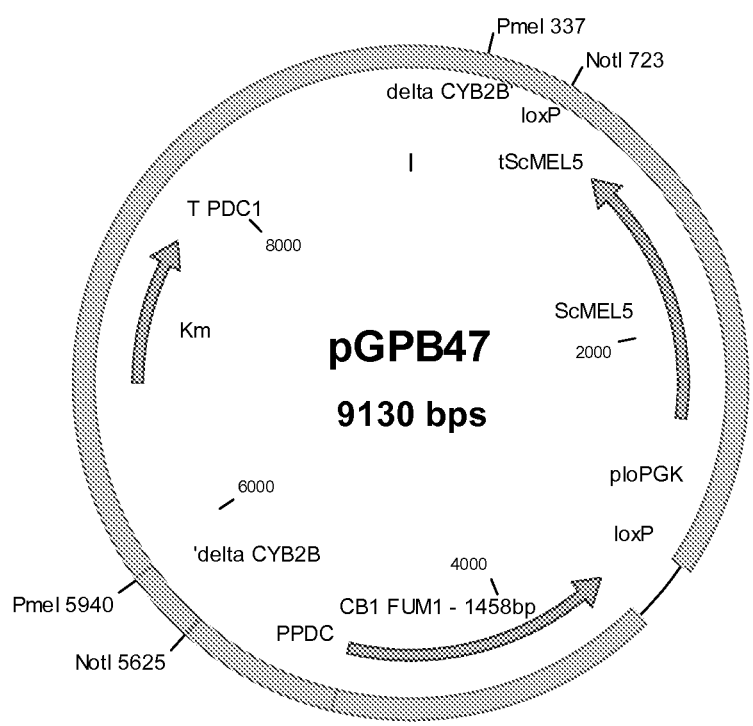
FIG. 27 shows plasmid pGPB47, FUM1 expression constructs.

The expression cassette from pGPB44 is excised using NotI and ligated to the NotI cut pKW22. The resulting plasmid is designated pGPB47 (FIG. 27).

Example 7B: Insertion of *I. orientalis* FUM1 at One or Both *I. orientalis* CYB2B Loci Integration of the first copy of the FUM1 expression cassette at the CYB2B locus is performed using plasmids containing the MEL5 selectable marker. pGPB47 is digested with SacI and ApaI and transformed into 12792 using lithium acetate transformation. Transformants are screened by PCR to confirm correct integration of the FUM1 expression cassette at the second CYB2B locus using primers oKW202 (SEQ ID NO:129), oGPB54 (SEQ ID NO:113), oKW195 (SEQ ID NO:130), and oGPB56 (SEQ ID NO:112). The resulting strains is designated 12826.

Integration of the second copy of the FUM1 expression cassette at the CYB2B locus is performed using plasmids containing the CYB2A selectable marker. pGPB43 is digested with SacI and ApaI and transformed into *I. orientalis* strain 12826 using lithium acetate transformation. Transformants are screened by PCR to confirm correct integration of the FUM1 expression cassette at the first CYB2B locus using primers oKW202 (SEQ ID NO:129), oGPB54 (SEQ ID NO:113), oGPB52 (SEQ ID NO:116), oKW195 (SEQ ID NO:130), and oGPB53 (SEQ ID NO:115). The resulting strain is designated 12833.

Marker recycling is carried out with plasmid pVB32. The correct homozygous strain with both markers removed is designated 12868.

The various FUM1 insertion/CYB2B deletion strains generated in Example 7 are summarized in Table 10.

TABLE 10

*I. orientalis* FUM1 Insertion Strains

| Strain name | Description | Parent strain |
| --- | --- | --- |
| 12826 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (1) | 12792 |
| 12833 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2) | 12826 |
| 12868 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2) | 12833 |

Example 8: Insertion of SpMAE at the Putative RIOR43690 Locus in *I. orientalis* Strain 12868

A SpMAE expression cassette was inserted at one or both RIOR43690 alleles in *I. orientalis* strain 12868 (Example 7).

Example 8A: Synthesis of RIOR43690 Deletion Construct pVMB54

Figure 28:
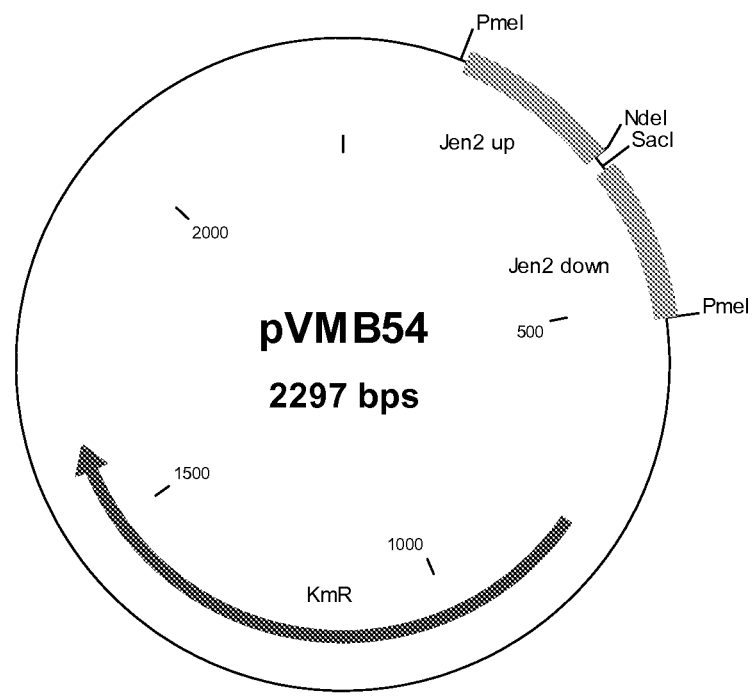
FIG. 28 shows plasmid pVMB54, RIOR43690 deletion construct.

Deletion constructs for RIOR43690 (SEQ ID NO:59) were created. Oligonucleotide sequences identical to the upstream and downstream regions of the RIOR43690 locus (SEQ ID NOs:131 and 132, respectively) was synthesized to create the RIOR43690 deletion construct. The upstream and downstream regions correspond to nucleotides from 180 bp upstream to the start codon of RIOR43690 and from the stop codon to 180 bp downstream, respectively. PmeI restriction sites were added to the 5' end of the upstream identity sequence and to the 3' end of the downstream identity sequence. A multiple cloning site was added between the two sequences which include the following restriction sites, ordered from 5' to 3': NdeI, and SacI. The full length construct oligonucleotide fragment (SEQ ID NO:133) was cloned into the pIDTSMART Kan vector (Integrated DNA Technologies ("IDT"), Coralville, Iowa). The resulting plasmid was confirmed to have the correct sequence via Sanger sequencing. The final RIOR43690 deletion construct was designated pVMB54 (FIG. 28).

Example 8B: Construction of *S. pombe* SpMAE Bipartite Integration Constructs pKWB95, pKWB96 and pKWB97

The SpMAE gene from *S. pombe* (SEQ ID NO:45) was synthesized such that the coding sequence was segmented into five fragments with overlapping regions of homology. Fragments 2-5 (SEQ ID NO:134) were joined into one larger fragment via multi-fragment primerless PCR. The resulting fragment, which encoded the last 1154 bp of the *S. pombe* transporter, was topo cloned and sequenced for verification. Fragment 1 (SEQ ID NO:135) was topo cloned separately and encoded the first 384 bp of the *S. pombe* transporter. Each of the fragments was flanked by mluI and sbfI restriction sites. After restriction digest, the fragments were gel purified, and ligated to similarly digested pKWB86 and pKWB87. pKWB86 and pKWB87 are constructed from pVMB54 backbones, and both contain a multiple cloning site containing MluI, NotI, and SbfI sites operatively linked to the *I. orientalis* ENO promoter and the *S. cerevisiae* GAL10 terminator. pKWB86 also contains a selection marker cassette comprising the *S. cerevisiae* MEL5 gene operatively linked to the *I. orientalis* PGK promoter. This selection marker cassette is flanked by loxP sites. pKWB87 contains an expression cassette comprising the *I. orientalis* CYB2A promoter, gene, and terminator. This expression cassette is flanked by loxP sites.

Figure 29:
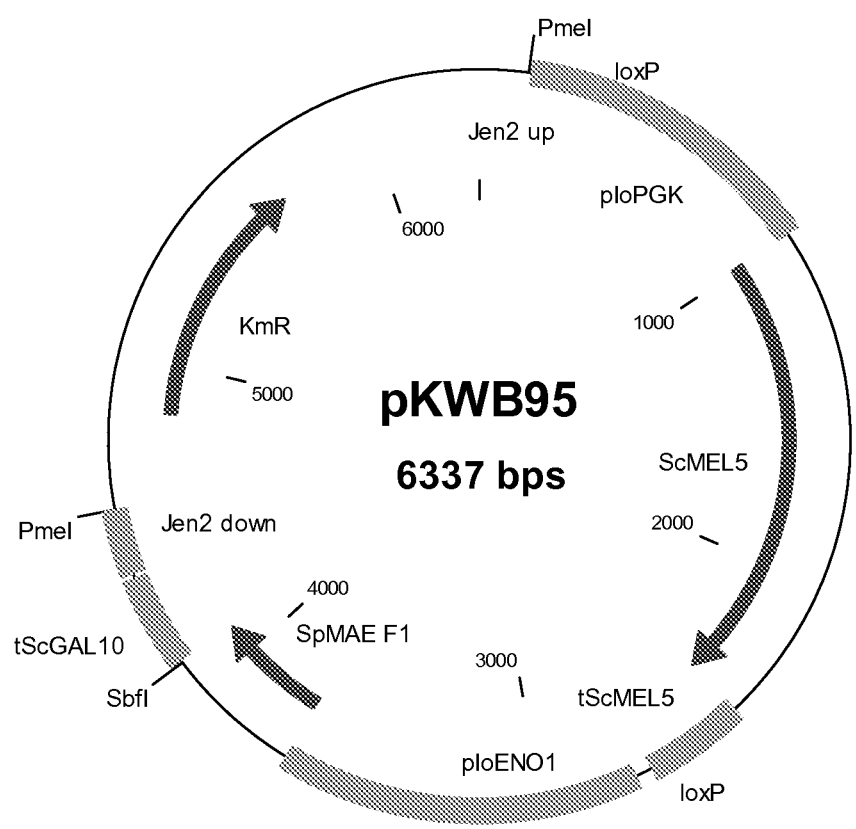
FIG. 29 shows plasmid pKWB95, SpMAE expression construct.
Figure 30:
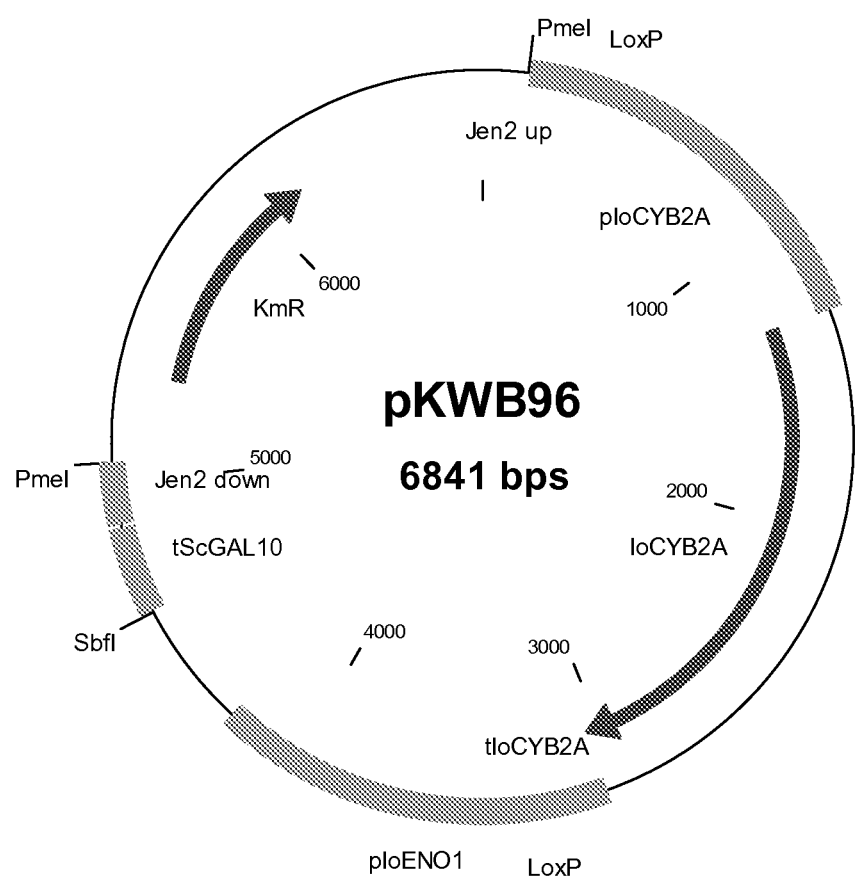
FIG. 30 shows plasmid pKWB96, SpMAE expression construct.
Figure 31:
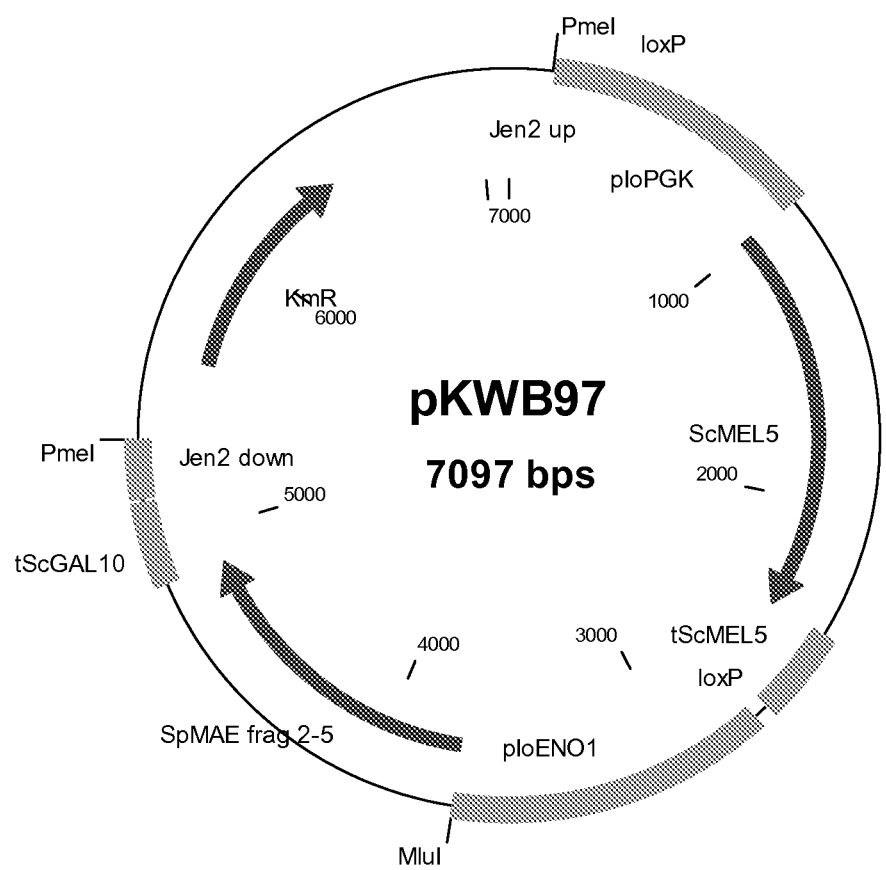
FIG. 31 shows plasmid pKWB97, SpMAE expression construct.

The plasmids were transformed into *E. coli*, and transformants were selected on LB plates containing 50 µg/ml Kanamycin and screened using primers flanking the NotI site of pKWB87 and pKWB86 (oKW93 (SEQ ID NO:82) and oKWB95 (SEQ ID NO:126)). Correct plasmids were designated pKWB95 (fragment 1 with MEL5 marker) (FIG. 29 pKWB95), pKWB96 (fragment 1 with CYB2A marker) (FIG. 30 pKWB96) and pKWB97 (Fragment 2 with MEL5 marker) (FIG. 31 pKWB97).

Example 8C: Integration of SpMAE at CB1 RIOR43690 in 12868

Plasmids pKWB95 and pKWB96 were digested with pmeI and sbfI and gel purified. Each of these digests served to liberate a DNA fragment containing the upstream flanking region, the selective marker and fragment 1 from the vector backbone. pKWB97 was digested with pmeI and mluI. This digest served to liberate fragment 2 through the gal10 terminator and the downstream flanking region from the vector backbone. Strain 12868 (example 8) was transformed with the fragments purified from both pKWB95 and pKWB97 simultaneously. This transformation was designed such that integration of both fragments reconstitutes the intact coding sequence intracellularly to produce a functional transport protein. Crossover events occur between the flanking regions of the fragments and genomic DNA as well as the overlapping regions of the SpMAE gene. Transformants are selected on YNB+2% melibiose+x-α-gal and, and integration of SpMAE at a first RIOR43690 allele is confirmed by PCR. The correct heterozygous strain is designated strain 13050.

A second integration, targeting the second RIOR43690 allele is performed using the fragment purified from pKWB96 and pKWB97. Transformants are selected on YNB+2% lactic+x-α-gal and, and integration of SpMAE at the second RIOR43690 allele is confirmed by PCR. The correct heterozygous strain is designated strain 13051.

Marker recycling is carried out with plasmid pVB32. The correct homozygous strains with both markers removed are designated 13053.

The various SpMAE insertion/RIOR43690 deletion strains generated in Example 8 are summarized in Table 11.

TABLE 11

*I. orientalis* SpMAE Strains

| Strain name | Description | Parent strain |
|---|---|---|
| 13050 | I. CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*S. pombe* MAE insertion at RIOR43690 (1) | 12868 |
| 13051 | I. CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*S. pombe* MAE insertion at RIOR43690 (2) | 13050 |
| 13053 | I. CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*S. pombe* MAE insertion at RIOR43690 (2) | 13051 |

Example 9: Insertion of the FRD1 from *Trypanosoma brucei*, *Trypanosoma cruzi*, *Leishmania braziliensis*, or *Leishmania mexicana* at the ADHb Locus in *I. orientalis* Strain 13053

A FRD1 expression cassette is inserted at one or both ADHb alleles of *I. orientalis* strains 13053 (Example 8).

Figure 32:
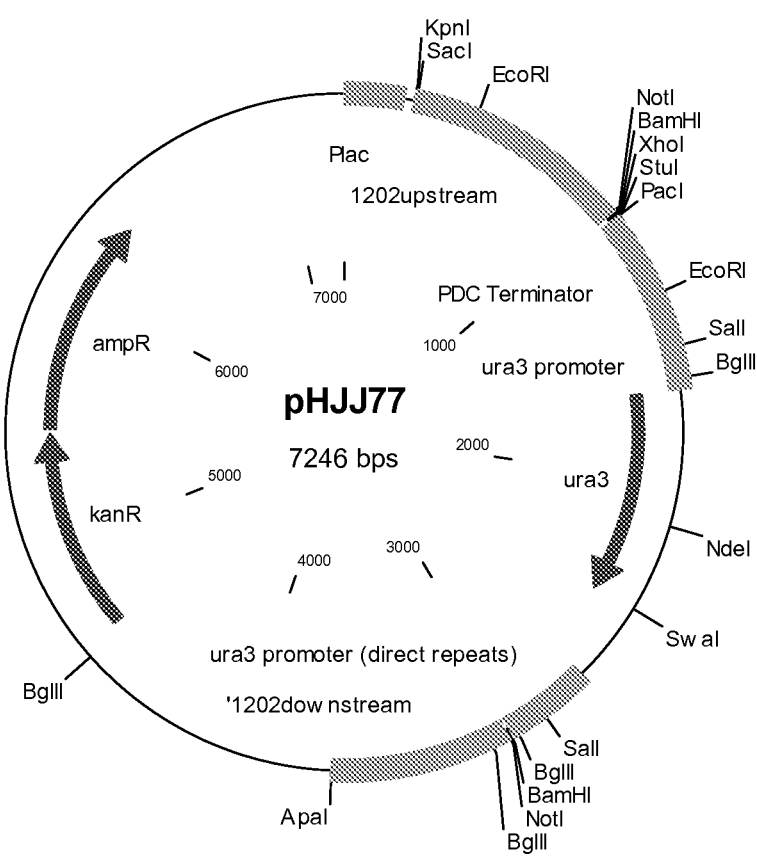
FIG. 32 shows plasmid pHJJ77.
Figure 33:
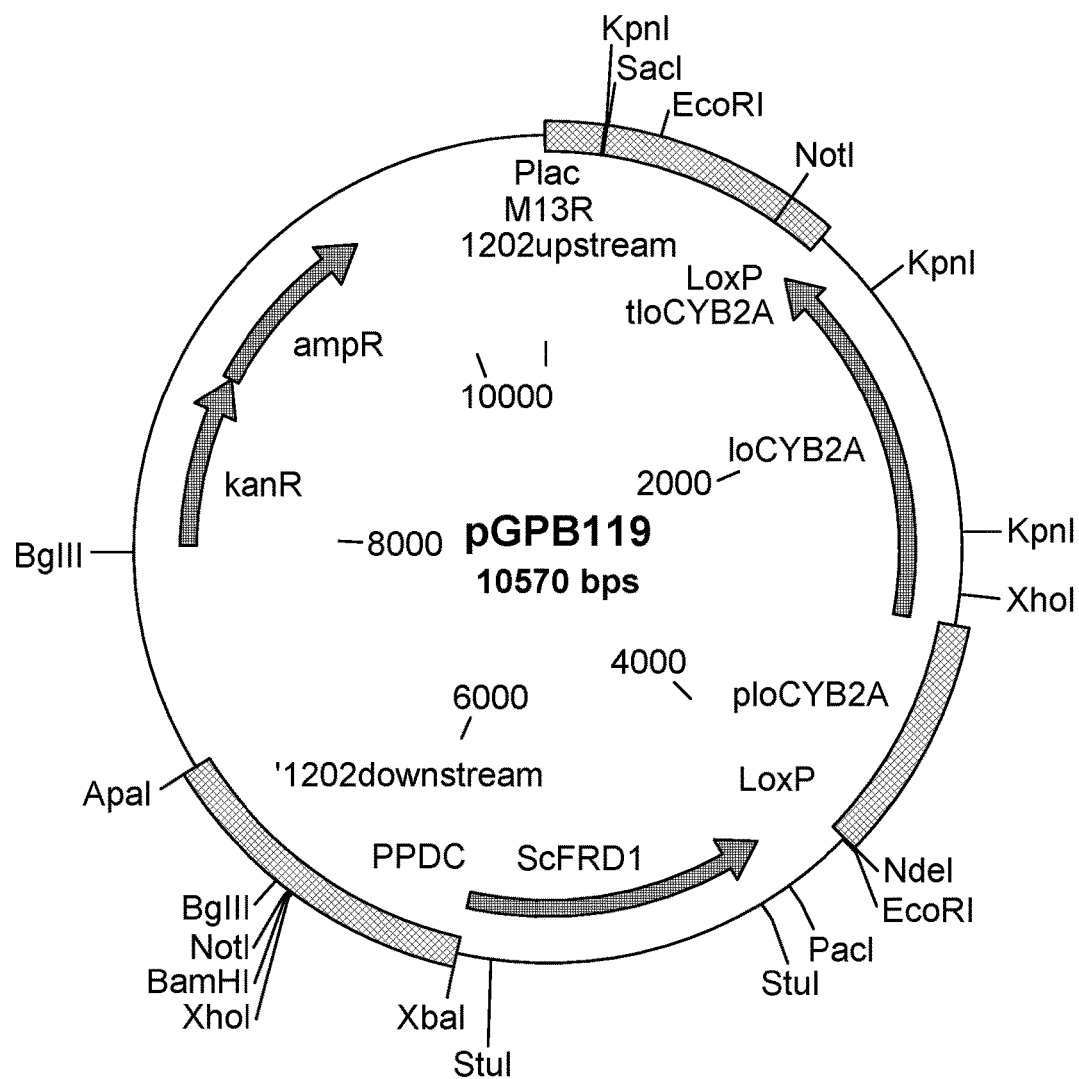
FIG. 33 shows plasmid pGPB119, ADHb deletion construct.

Example 9A: Construction of ADHb Deletion Construct pGPB119 pGPB26 was digested with NotI and the resultant fragment ligated to NotI digested pHJJ77 (FIG. 32). The resulting ADHb deletion construct, designated pGPB119 (FIG. 33), contains the *I. orientalis* PDC1 promoter (amplified using primers oJLJ3 (SEQ ID NO:101) and oJLJ19 (SEQ ID NO:102)) and terminator (amplified using primers oJLJ1 (SEQ ID NO:103) and oJLJ2 (SEQ ID NO:104)) and a CYB2A marker element between a 770 bp fragment corresponding to the region immediately 5' of the *I. orientalis* AHD2b open reading frame (amplified using primers oHJJ124 (SEQ ID NO:137) and oHJJ125 (SEQ ID NO:138)) and a 615 bp fragment corresponding to the region immediately 3' of the *I. orientalis* ADHb open reading frame (amplified using primer oHJJ126 (SEQ ID NO:139) and oHJJ127 (SEQ ID NO:140)).

Example 9B: Construction of FRD Expression Constructs pGPB126, pGPB127, pGPB159, pGPb160, pGPB161, and ADHb Null Constructs pGPB148 and pGPB168

Expression cassettes for the FRD1 genes were inserted into the ADHb deletion construct pGPB119 (Example 9A); the FRD1 genes from *T. brucei* (SEQ ID NO:37), *T. cruzi* (SEQ ID NO:39), *L. braziliensis* (SEQ ID NO:41), and *L. mexicana* (SEQ ID NO:43), were codon optimized to *I. orientalis*, and lacked the C-terminal glyoxysomal targeting sequence from the native gene.

Figure 34:
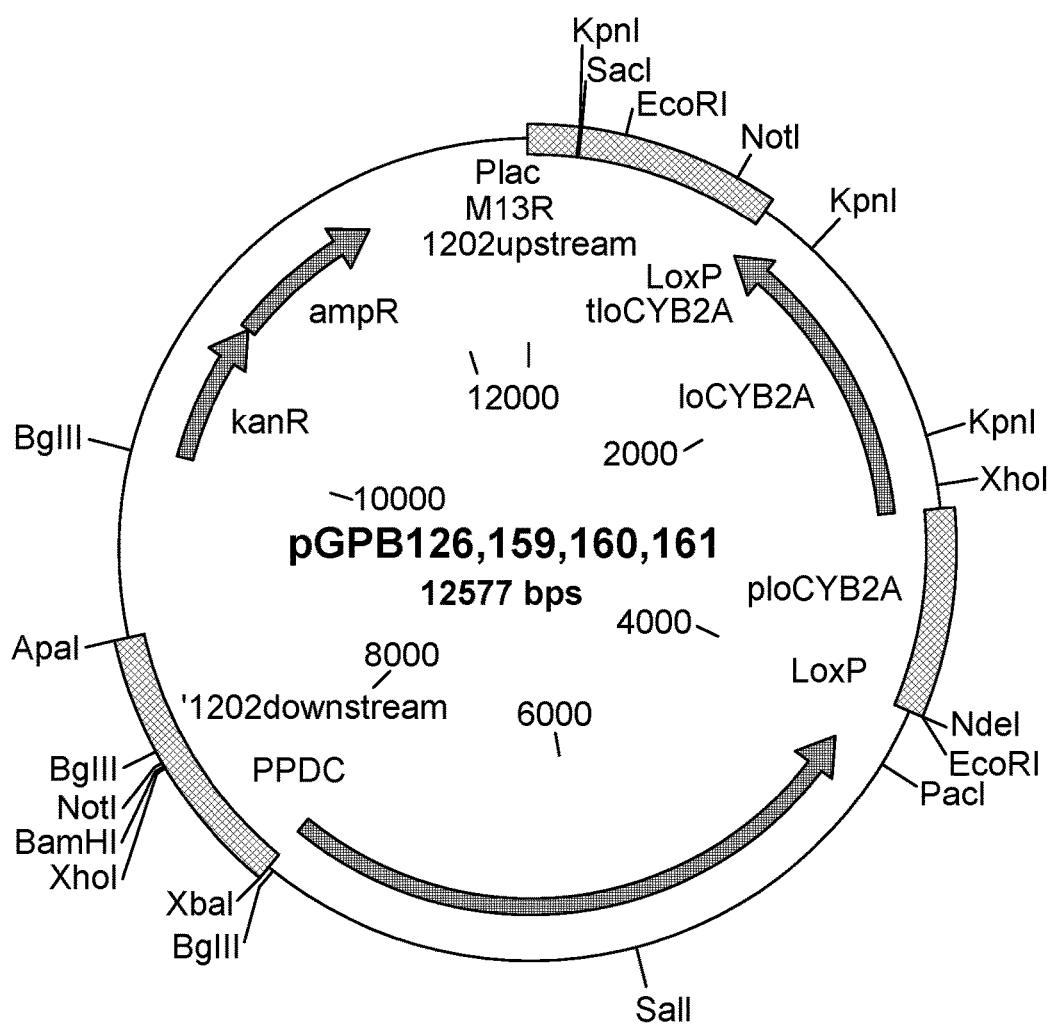
FIG. 34 shows plasmid pGPB126 (*Trypanosoma brucei*), pGPB159 (*Trypanosoma cruzi*), pGPB160 (*Leishmania braziliensis*), and pGPB161 (*Leishmania mexicana*) FRD expression constructs.
Figure 35:
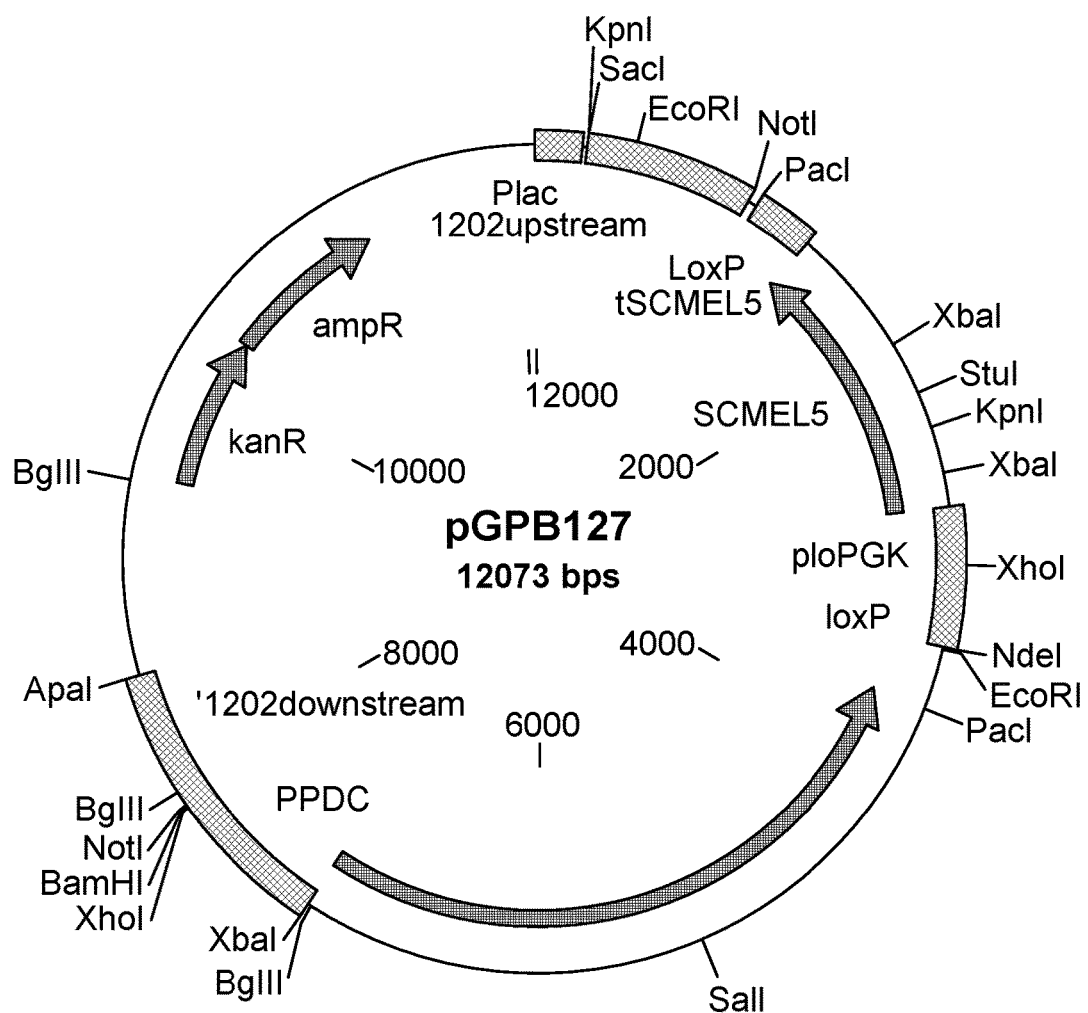
FIG. 35 shows plasmid pGPB127, *Trypanosoma brucei* expression construct.
Figure 36:
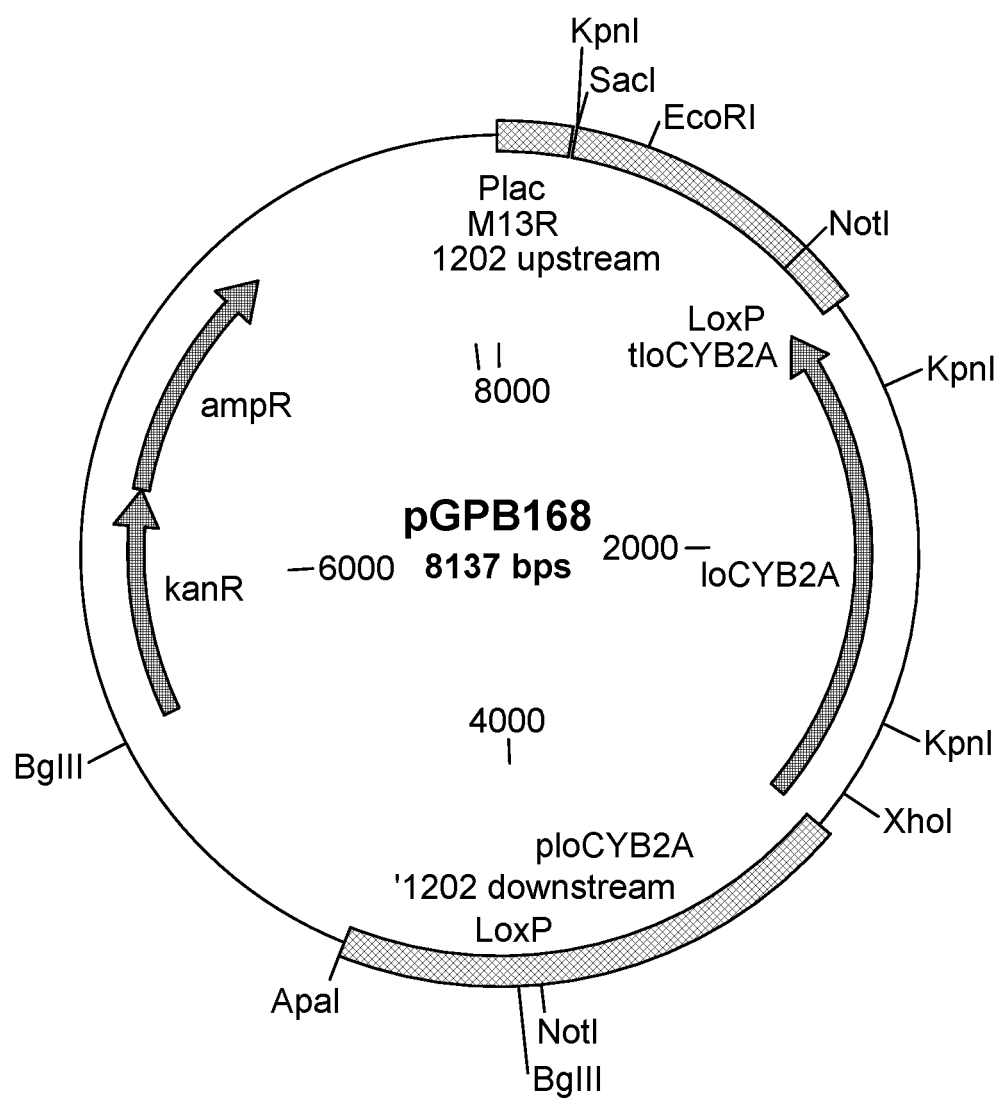
FIG. 36 shows plasmid pGPB168, ADHb deletion construct.
Figure 37:
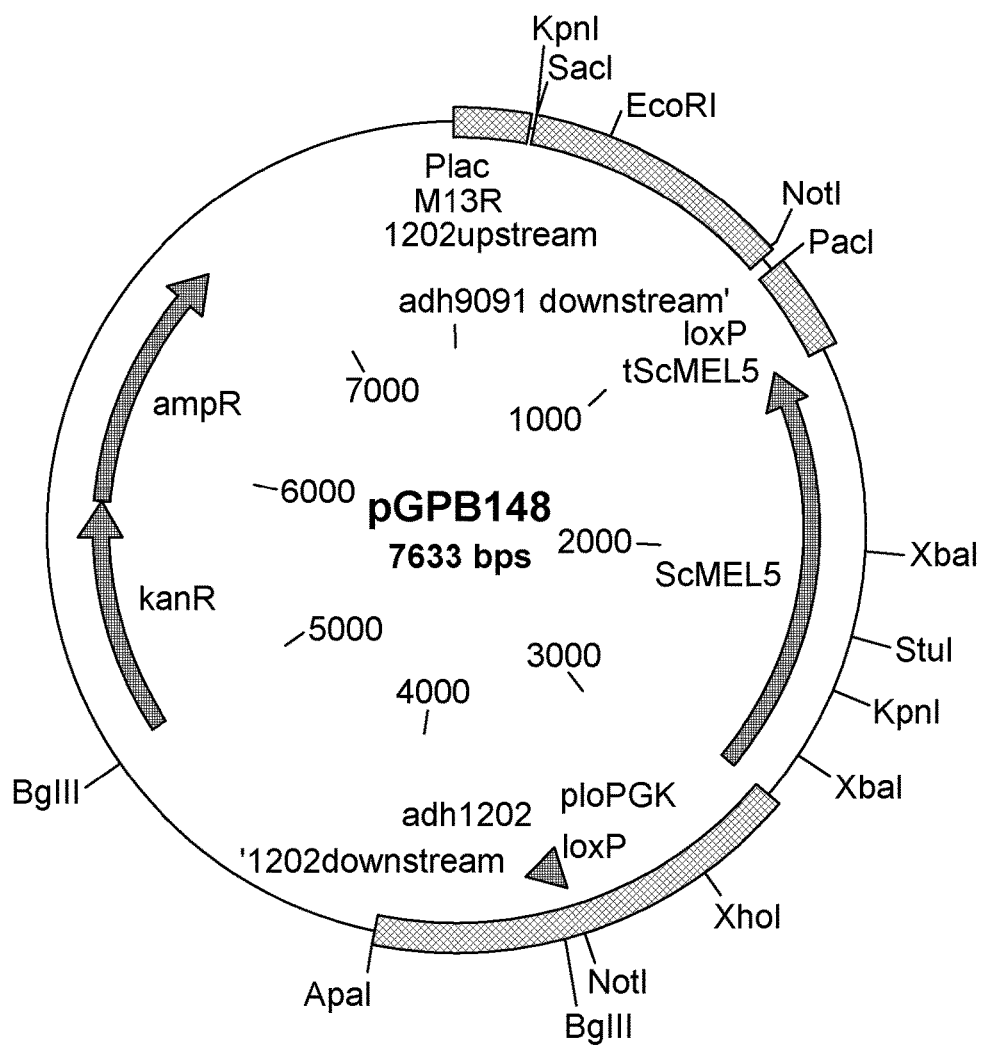
FIG. 37 shows plasmid pGPB148, ADHb deletion construct.

Plasmids containing the codon optimized FRD1 genes were digested with XbaI and PacI, and the FRD1 fragments were ligated to similarly digested pGPB119. The resulting plasmids, containing the FRD1 coding sequence flanked by the *I. orientalis* PDC1 promoter and terminator and the *I. orientalis* CYB2A selectable marker, were designated pGPB126 (*T. brucei*), pGPB159 (*T. cruzi*), pGPB160 (*L. braziliensis*), and pGPB161 (*L. mexicana*) (FIG. 34).

pGPB126 was digested with NdeI and a partial NotI digest to remove the CYB2A selectable marker, and the resulting vector was ligated to the NdeI and NotI fragment from pGPB14 which contained the MEL5 selectable marker. The resulting plasmid, which contained the FRD1 coding sequence flanked by the *I. orientalis* PDC1 promoter and terminator and the *S. cerevisiae* MEL5 selectable marker was designated pGPB127 (FIG. 35).

pGPB126 (CYB2A) and pGPB127 (MEL5) were each digested with NdeI and BamHI to remove those portions of the plasmids corresponding to the PDC promoter, *T. brucei* FRD and PDC terminator, and each plasmid backbone was blunted with Klenow fragment and ligated to recircularize the plasmid. The plasmids were then transformed into *E. coli*. Plasmids isolated from positive colonies are designated pGPB168 (FIG. 36, derived from pGPB126) and pGPB148 (FIG. 37, derived from pGPB127).

Example 9C: Insertion of FRD at First and Second ADHb Loci of *I. orientalis* Strain 13053 pGPB126pGPB159, pGPB160, pGPB161 and pGPB148 were digested with SacI and ApaI and transformed into *I. orientalis* strain 13053 by lithium acetate transformation. Transformants are selected on YNB+2% lactic plates or YNB+2% melibiose plates (pGPB148). After around six days, transformants were picked and plated for single colonies on YP+20 g/L glucose plates. Colonies are picked, and genomic DNA was isolated and screened by PCR to confirm integration of the FRD1 expression cassette at the ADHb locus using primers oGPB106 (SEQ ID NO:141), oGPB56 (SEQ ID NO:112), oGPB52 (SEQ ID NO:116), oGPB54 (SEQ ID NO:113), oGPB55 (SEQ ID NO:125), and oGPB107 (SEQ ID NO:142). Strains with the correct integration of the FRD1 gene are designated 13171 (Tb FRD), 13256 (Tc FRD), 13257 (Lb FRD), and 13258 (Lm FRD).

The various FRD1 insertion/ADHb deletion strains generated in Example 9 are summarized in Table 12.

TABLE 12

*I. orientalis* FRD1 Insertion Strains

| Strain name | Description | Parent strain |
|---|---|---|
| 13171 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*T. brucei* FRD1 insertion at ADHb (1) | 13053 |

TABLE 12-continued

*I. orientalis* FRD1 Insertion Strains

| Strain name | Description | Parent strain |
|---|---|---|
| 13256 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*T. cruzi* FRD1 insertion at ADHb (1) | 13053 |
| 13257 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*L. braziliensis* FRD1 insertion at ADHb (1) | 13053 |
| 13258 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*L. mexicana* FRD1 insertion at ADHb (1) | 13053 |

Example 10: Succinic Acid Production of Strain 13171

The yeast strain 13171 is run in fermenters to test succinic acid production. Fermenters are inoculated with biomass grown in defined medium (adapted from Verduyn, et. al, 1992, Yeast 8, 501-517, see Tables 13, 15, and 16). Seeds are run in 1 L baffled flasks (250 mL working volume) at 250 rpm and 30° C. The contents of the flasks are harvested at approximately 24 hours incubation time with 10% v/v inoculum used to start fermenters. Fermenter initial working volume is 1.2 L for fed-batch glucose and 1.5 L for straight batch glucose. The cell dry weight at inoculation is found in Table 17. Fermenter media is outlined in Table 14, 15, 16. Glucose is either provided by either a) the addition of 115 g/L at the start of the batch (straight batch). or b) providing a glucose feed addition to the fermenter controlled to maintain the glucose concentration at <10 g/L residual glucose (fed-batch). pH is controlled at 3.0 with 5 N KOH. The fermenter systems are sparged at 0.24 slpm with a blend of pure $CO_2$ and air to target 10% $CO_2$ in the inlet gas stream. Different oxygen uptake rates are applied to the vessels by changing vessel agitation rate. These fermentations are operated such that after the cells achieve a sufficient density, oxygen limitation is achieved and subsequently maintained throughout the rest of the fermentation (e.g., dissolved oxygen less than about 10%). A DO curve is demonstrated in FIG. 36. Dissolved oxygen is measured using Mettler Toledo INPRO® 6800 sensor (Mettler-Toledo GmbH, Urdorf, Switzerland), calibrated prior to inoculation. 0% is calibrated by sparging nitrogen at 0.24 slpm, 100% is calibrated using the run conditions in the vessel as detailed above (prior to inoculation).

TABLE 13

Defined Media for Seed Flask Cultures

| Compound | Concentration (g/kg) |
|---|---|
| $C_6H_{12}O_6$ | 20.0 |
| $(NH_2)_2CO$ | 2.3 |
| $KH_2PO_4$ | 3.0 |
| $MgSO_4$—$7H_2O$ | 0.5 |
| 1000x Vitamin Solution | 1 |
| 1000x Trace Solution | 1 |

TABLE 14

Defined Media for 2 L Fermenters

| Compound | Concentration (g/kg) |
|---|---|
| $C_6H_{12}O_6$ | Fed-batch at <10 g/L or straight batch at 115 g/L initial glucose |
| $(NH_4)_2SO_4$ | 2.3 |
| $KH_2PO_4$ | 3.0 |
| $MgSO_4$—$7H_2O$ | 0.5 |
| 1000x Vitamin Solution | 1 |
| 100x Trace Solution | 1 |

TABLE 15

Trace Element 1000x Stock Solution

| Chemical | g/1.0 L |
|---|---|
| $C_{10}H_{14}N_2Na_2O_8 \cdot 2H_2O$ | 15.00 |
| $ZnSO_4 \cdot 7H_2O$ | 4.50 |
| $MnCl_2 \cdot 2H_2O$ | 0.84 |
| $CoCl_2 \cdot 6H_2O$ | 0.30 |
| $CuSO_4 \cdot 5H_2O$ | 0.30 |
| $Na_2MoO_4 \cdot 2H_2O$ | 0.40 |
| $CaCl_2 \cdot 2H_2O$ | 4.50 |
| $FeSO_4 \cdot 7H_2O$ | 3.00 |
| $H_3BO_3$ | 1.00 |
| KI | 0.10 |

TABLE 16

Vitamin 1000x Stock Solution

| Chemical | g/1.0 L |
|---|---|
| Biotin (D-) | 0.05 |
| Ca D(+) panthothenate | 1.00 |
| Nicotinic acid | 1.00 |
| Myo-inositol | 25.00 |
| Thiamine chloride hydrochloride | 1.00 |
| Pyridoxol hydrochloride | 1.00 |
| p-aminobenzoic acid | 0.20 |

Cell concentration is obtained from an optical density measurement using an established conversion factor between dry cell mass and optical density. Optical density is measured at wavelength of 600 nm with a 1 cm pathlength using a model Genesys20 spectrophotometer (Thermo Scientific). Unless explicitly noted otherwise, an experimentally derived conversion factor of 1.68 $OD_{600}$ units per 1 g dry cell mass is used to estimate cell dry weight.

OUR is calculated using methods known to those in the art as described above. For this example, oxygen and $CO_2$ values are measured by an EGAS L instrument (Sartorious). While a mass spectrometer was not used, the results obtained by the EGAS L are believed to be substantially the same. Nitrogen value was calculated as 100% less % measured $CO_2$ minus, less % measured Oxygen.

Samples are taken at 90 h batch time and analyzed for biomass growth via $OD_{600}$, succinate via gas chromatography with flame ionization detector and glucose by high performance liquid chromatography with refractive index detector.

Table 17 illustrates the concentration of cells in straight batch at end of fermentation is variable with oxygen concentration, ranging from 0.4 to 2.3 g/L.

TABLE 17

Final Cell Concentration (g/L) at 90 h Fermentation Time: Straight Batch Glucose at pH 3.0, 10% $CO_2$, OUR (mmol/L/h) Variable

| OUR (mmol/L/h) | Cell Dry Weight at Inoculation (g/L) | Cell Dry Weight at End of Fermentation (g/L) | Mode of Operation |
|---|---|---|---|
| 1.9 | 0.14 | 0.4 | Straight Batch |
| 4.2 | 0.16 | 1.1 | Straight Batch |
| 6.1 | 0.14 | 1.7 | Straight Batch |
| 10.2 | 0.17 | 2.3 | Straight Batch |

Figure 38:
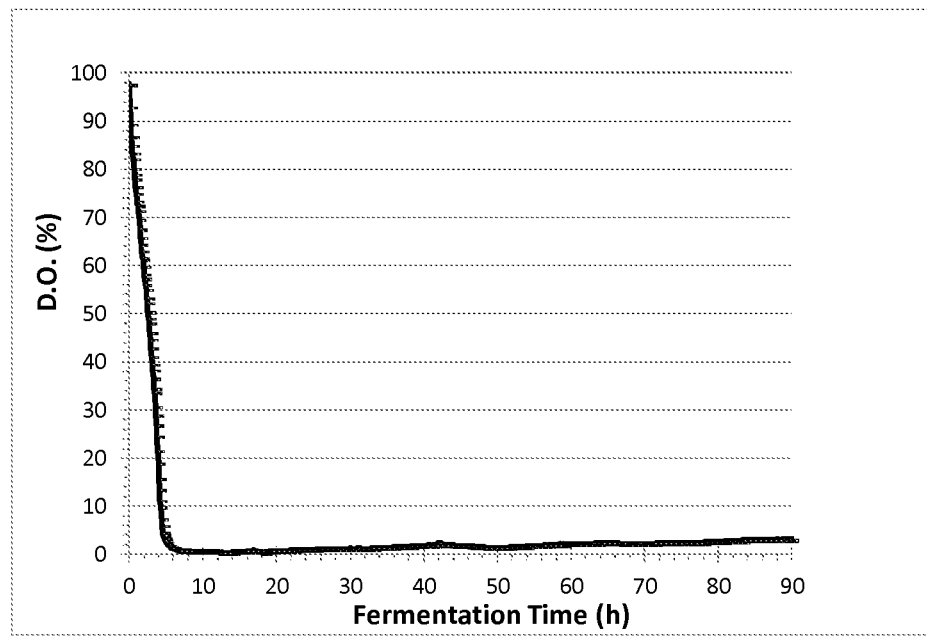
FIG. 38 shows a dissolved oxygen profile of fermentation; straight batch glucose, pH 3.0, 8.6% $CO_2$, OUR 10.2 (mmol/L/h).

FIG. 37 and FIG. 38 illustrate succinate acid production for both straight batch and fed batch fermentations. A previous example (WO2010/003728, pg 9, line 15-18), tells us that "an OUR above 5 mmol/L/h resulted in lower succinic acid production". Surprisingly, in both modes of operation, we find improving production above 5 mmol/L/h, with succinic acid titer increasing with increasing OUR, such that the no decrease in succinic production is observed even at the highest OUR tested, 20 mmol/L/h.

Figure 39:
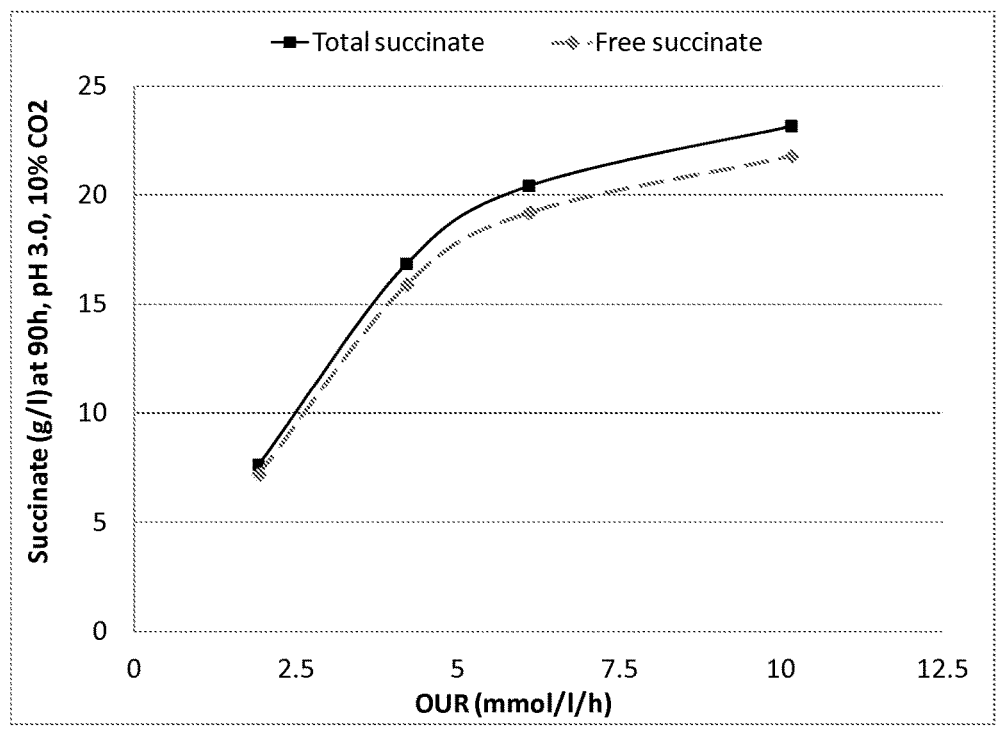
FIG. 39 shows succinate and free sucinate production (g/L) at 90 h: straight batch glucose, pH 3.0, 10% $CO_2$, OUR (mmol/L/h) variable.
Figure 40:
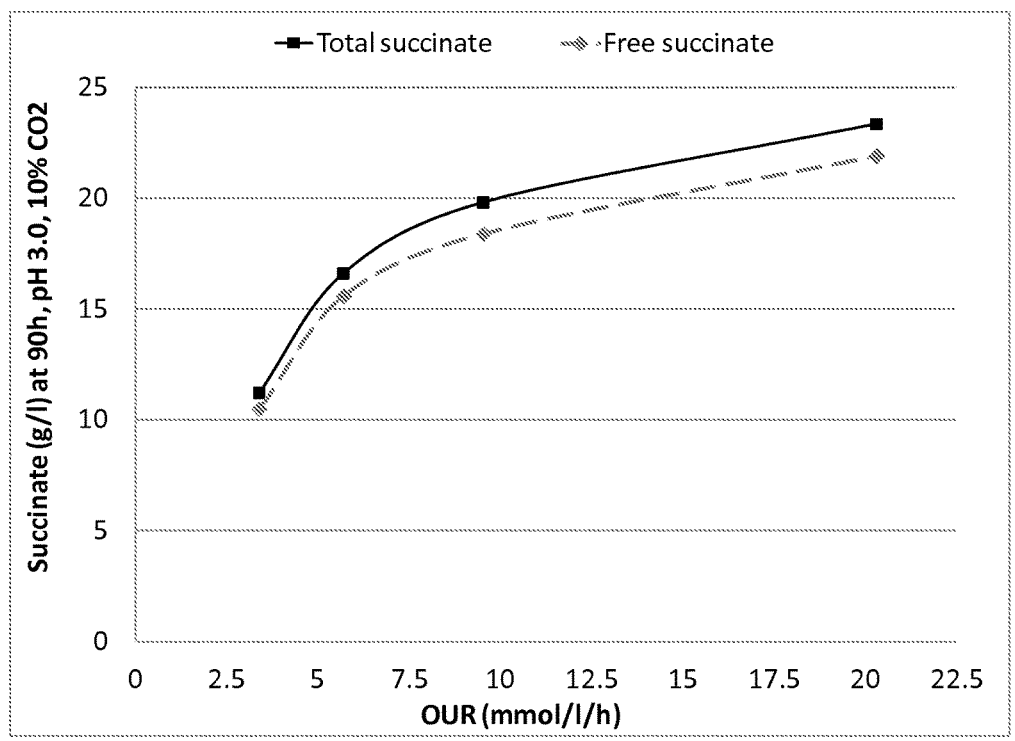
FIG. 40 shows succinate and free sucinate production (g/L) at 90 h: fed-batch glucose, pH 3.0, 10% $CO_2$, OUR (mmol/L/h) variable.
Figure 41:
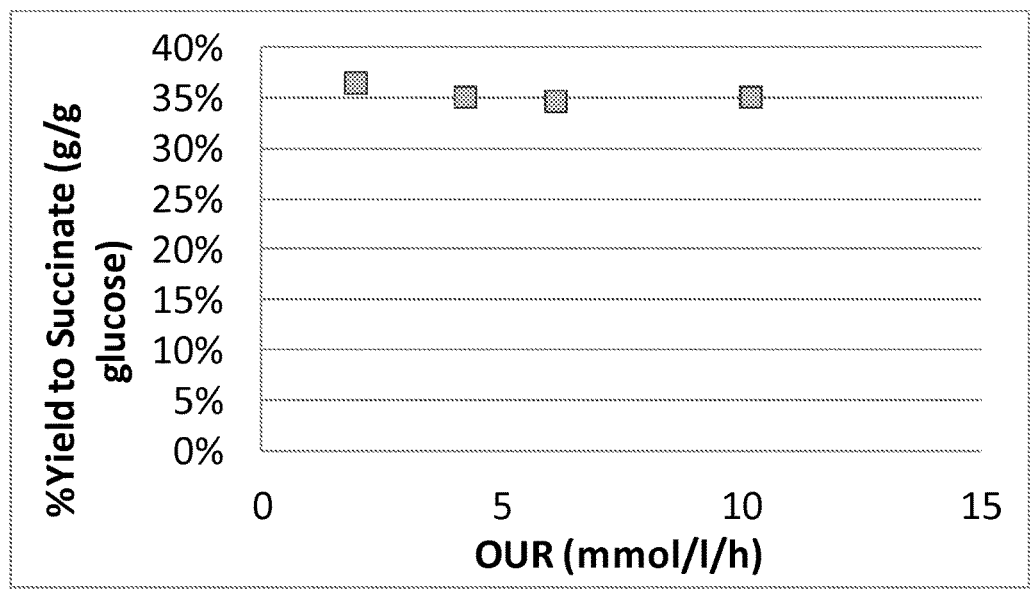
FIG. 41 shows yield to succinate (g/g glucose) at 90 h fermentation time at pH 3.0, 10% $CO_2$, OUR (mmol/L/h) variable, straight batch glucose.

Furthermore, FIG. 39 indicates no significant reduction in succinate yield on carbon source associated with increasing OUR across the range tested. These data indicate OUR greater than about 10 mmol/L/h to be a preferred condition for succinate production.

Example 11: Construction of Preparatory Strains 11-1 to 11-6

An *I. orientalis* host strain is generated by evolving *I. orientalis* strain ATCC PTA-6658 for 91 days in a glucose-limited chemostat. The system is fed 15 g/L glucose in a defined medium and operated at a dilution rate of 0.06 $h^{-1}$ at pH 3 with added lactic acid in the feed medium. The conditions are maintained with an oxygen transfer rate of approximately 2 mmol $L^{-1}$ $h^{-1}$, and dissolved oxygen concentration remains constant at 0% of air saturation. Single colony isolates from the final time point are characterized in two shake flask assays. In the first assay, the isolates are characterized for their ability to ferment glucose to ethanol in the presence of 25 g/L total lactic acid with no pH adjustment in the defined medium. In the second assay, the growth rate of the isolates is measured in the presence of 45 g/L of total lactic acid, with no pH adjustment in the defined medium. Strain 11-1 is a single isolate exhibiting the highest glucose consumption rate in the first assay and the highest growth rate in the second assay.

Strain 11-1 is transformed with linearized integration fragment P2 (having nucleotide sequence SEQ ID NO:143) designed to disrupt the URA3 gene, using the LiOAc transformation method as described by Gietz et al., in Met. Enzymol. 350:87 (2002). Integration fragment P2 includes a MEL5 selection marker gene. Transformants are selected on YNB+2% melibiose plates and screened by PCR to confirm the integration of the integration piece and deletion of a copy of the URA3 gene. A URA3-deletant strain is grown for several rounds until PCR screening identifies an isolate in which the MEL5 selection marker gene has looped out. The PCR screening is performed using the primers of SEQ ID NOs:144 and 145 to confirm the 5'-crossover and the primers of SEQ ID NOs:146 and 147 to confirm the 3' crossover. That isolate is again grown for several rounds until PCR screening using the primers of SEQ ID NOs:144 and 147 identifies an isolate in which both URA3 alleles have been deleted. This isolate is named strain 11-2.

Strain 11-2 is transformed with integration fragment P3 (SEQ ID NO:148), which is designed to disrupt the PDC gene. Integration piece P2 contains the following elements, 5' to 3': a DNA fragment with homology for integration corresponding to the region immediately upstream of the *I. orientalis* PDC open reading frame, a PDC transcriptional terminator, the URA3 promoter, the *I. orientalis* URA3 gene, an additional URA3 promoter direct repeat for marker recycling, and a DNA fragment with homology for integration corresponding to the region directly downstream of the *I. orientalis* PDC open reading frame. A successful integrant (and single-copy PDC deletant) is identified on selection plates lacking uracil and confirmed by PCR using the primers of SEQ ID NOs:149 and 150 to confirm the 5'-crossover and the primers of SEQ ID NOs:151 and 152 to confirm the 3'-crossover. That integrant is grown for several rounds and plated on 5-fluoroorotic acid (FOA) plates to identify a strain in which the URA3 marker has looped out. Loopout of the URA3 marker is confirmed by PCR. The resultant strain is again transformed with integration fragment P3 to delete the second copy of the native PDC gene. A successful transformant is again identified by selection on selection plates lacking uracil, and further confirmed by culturing the strain over two days and measuring ethanol production. Lack of ethanol production further demonstrates a successful deletion of both copies of the PDC gene in a transformant. The resultant transformant is grown for several rounds and plated on FOA plates until PCR identifies a strain in which the URA3 marker has looped out. That strain is plated on selection plates lacking uracil to confirm the loss of the URA3 marker, and is designated strain 11-3.

Integration fragment P4-1 (SEQ ID NO:153) contains the following elements, 5' to 3': a DNA fragment with homology for integration corresponding to the region immediately upstream of the *I. orientalis* ADHa open reading frame, an *I. orientalis* PDC1 promoter, the *I. orientalis* PYC gene (SEQ ID NO:7), the *I. orientalis* TAL terminator, the *I. orientalis* URA3 promoter, and the first 530 bp of the *I. orientalis* URA3 open reading frame.

Integration fragment P4-2 (SEQ ID NO:155) contains the following elements, 5' to 3': a DNA fragment corresponding to the last 568 bp of the *I. orientalis* URA3 open reading frame, the *I. orientalis* URA3 terminator, the *I. orientalis* URA3 promoter, the *I. orientalis* TDH3 promoter, the *S. pombe* MAE gene (SEQ ID NO:45), the *I. orientalis* TKL terminator, and a DNA fragment with homology for integration corresponding to the region immediately downstream of the *I. orientalis* ADHa open reading frame.

Strain 11-3 is transformed simultaneously with integration fragments P4-1 and P4-2 using lithium acetate methods to insert the *I. orientalis* PYC gene and the *S. pombe* MAE gene at the ADHa locus. Integration occurs via three crossover events: in the regions of the ADHa upstream homology, in the regions of the ADHa downstream homology, and in the region of URA3 homology between SEQ ID NO:153 and SEQ ID NO:155. Transformants are streaked to isolates and the correct integration of the cassette at the AHD9091 locus is confirmed in a strain by PCR. PCR screening is performed using the primers of SEQ ID NOs:111 and 112)

to confirm the 5'-crossover and the primers of SEQ ID NOs:159 and 114 to confirm the 3'-crossover. That strain is grown and plated on FOA as before until the loopout of the URA3 marker from an isolate is confirmed by PCR.

The resultant isolate is then transformed simultaneously with integration fragments P4-3 and P4-4 using LiOAc transformation methods to insert a second copy of each of the *I. orientalis* PYC gene and the *S. pombe* MAE gene at the ADHa locus.

Integration fragment P4-3 (SEQ ID NO:161) contains the following elements, 5' to 3': a DNA fragment with homology for integration corresponding to the region immediately downstream of the *I. orientalis* ADHa open reading frame, an *I. orientalis* PDC1 promoter, the *I. orientalis* PYC gene (SEQ ID NO:7), the *I. orientalis* TAL terminator, the *I. orientalis* URA3 promoter, and the first 530 bp of the *I. orientalis* URA3 open reading frame.

Integration fragment P4-4 (SEQ ID NO:163) contains the following elements, 5' to 3': a DNA fragment corresponding to the last 568 bp of the *I. orientalis* URA3 open reading frame, the *I. orientalis* URA3 terminator, the *I. orientalis* URA3 promoter, the *I. orientalis* TDH3 promoter, the *S. pombe* MAE gene (SEQ ID NO:45), the *I. orientalis* TKL terminator, and a DNA fragment with homology for integration corresponding to the region immediately upstream of the *I. orientalis* ADHa open reading frame.

Integration again occurs via three crossover events. Transformants are streaked to isolates and screened by PCR to identify a strain containing both copies of the *I. orientalis* PYC and *S. pombe* MAE genes at the ADHa locus. PCR screening to confirm the first copy is performed using the primers of SEQ ID NOs:111 and 112) to confirm the 5'-crossover and the primers of SEQ ID NOs:159 and 114 to confirm the 3'-crossover. PCR screening to confirm the second copy is performed using the primers of SEQ ID NOs:111 and 159 to confirm the 5'-crossover and the primers of SEQ ID NOs:112 and 114 to confirm the 3'-crossover. The resultant strain is grown and replated on FOA until a strain in which the URA3 marker has looped out is identified. That strain is designated strain 11-4.

Strain 11-4 is transformed with integration fragment P5-1 (SEQ ID NO:165) using LiOAc transformation methods as described in previous examples to integrate the *L. mexicana* FRD gene at the locus of the native CYB2B open reading frame. The integration fragment P5-1 contains the following elements, 5' to 3': a DNA fragment with homology for integration corresponding to the region immediately downstream of the *I. orientalis* CYB2B open reading frame, an *I. orientalis* PDC1 promoter, the *L. mexicana* FRD gene (SEQ ID NO:43), the *I. orientalis* PDC1 terminator, the *I. orientalis* URA3 promoter, gene, and terminator in succession, followed by an additional URA3 promoter which serves as a direct repeat for marker recycling, and a region immediately upstream of the *I. orientalis* CYB2B open reading frame.

Successful integration of a single copy of the *L. mexicana* FRD gene in one isolate is identified by selection on selection plates lacking uracil and confirmed by PCR using the primers of SEQ ID NOs:152 and 129 to confirm the 5'-crossover and the primers of SEQ ID NOs:112 and 130 to confirm the 3'-crossover. That isolate is grown and plated on FOA as before until a strain in which the URA3 marker has looped out is identified by PCR. That isolate is transformed with the integration fragment P5-2 in the same manner as before to integrate a second copy of the *L. mexicana* FRD gene downstream of the CYB2 open reading frame.

Integration fragment P5-2 (SEQ ID NO:169) contains the following elements, 5' to 3': a DNA fragment with homology for integration corresponding to the region immediately upstream of the *I. orientalis* CYB2B open reading frame, an *I. orientalis* PDC1 promoter, the *L. mexicana* FRD gene (SEQ ID NO:43), the *I. orientalis* PDC1 terminator, the *I. orientalis* URA3 promoter, gene, and terminator in succession, followed by an additional URA3 promoter which serves as a direct repeat for marker recycling, and a region immediately downstream of the *I. orientalis* CYB2B open reading frame.

PCR is performed using the primers of SEQ ID NOs:112 and 129 to confirm the 5'-crossover and the primers of SEQ ID NOs:152 and 130 to confirm the 3'-crossover to confirm correct integration of both copies of the *L. mexicana* FRD gene in one isolate. That isolate is grown and plated on FOA as before until the loop out of the URA3 marker is confirmed by PCR in one isolate. That isolate is designated strain 11-5.

TABLE 18

*I. orientalis* URA and PDC Deletion Strains

| Strain name | Description | Parent strain |
|---|---|---|
| 11-1 | Organic acid tolerant isolate | Wild-type |
| 11-2 | URA3 deletion (2) | 11-1 |
| 11-3 | URA3 deletion (2) PDC deletion (2) | 11-2 |
| 11-4 | URA deletion (2) PDC deletion (2) *I. orientalis* PYC1 insertion at ADHa (2) *S. pombe* MAE insertion at ADHa (2) | 11-3 |
| 11-5 | URA deletion (2) PDC deletion (2) *I. orientalis* PYC1 insertion at ADHa (2) *S. pombe* MAE insertion at ADHa (2) *L. mexicana* FRD insertion at CYB2B (2) | 11-4 |

Example 12: Integration of MDH and FUM Genes

Example 12A: First Copy *R. delemar* MDH Integration Fragment

Integration fragment 12A (SEQ ID NO:168) contains the *R. delemar* MDH gene (SEQ ID NO:166), ADHb upstream integration arm, ENO promoter, URA3 promoter, and first 583 base pairs of the URA3 marker.

Example 12B: First Copy *I. orientalis* FUM Integration Fragment

Integration fragment 12B (SEQ ID NO:164) contains the *I. orientalis* FUM gene (SEQ ID NO:1), the last 568 base pairs of the URA3 marker, URA3 promoter, PGK promoter, and ADHb downstream integration arm.

Example 12C: Second Copy *R. delemar* MDH Integration Fragment

Integration fragment 12C (SEQ ID NO:162) contains the *R. delemar* MDH gene (SEQ ID NO:166), ADHb downstream integration arm, ENO promoter, URA3 promoter, and first 583 base pairs of the URA3 marker.

Example 12D: Second Copy *I. orientalis* FUM Integration Fragment

Integration fragment 12D (SEQ ID NO:160) contains the *I. orientalis* FUM gene (SEQ ID NO:1) the last 568 base pairs of the URA3 marker, URA3 promoter, PGK promoter, and ADHb upstream integration arm.

Example 12E: Preparation of Strain 13723

Strain 11-5 is simultaneously transformed with integration fragments 12A and 12B using the standard lithium acetate process described before. Successful transformants are selected on selection plates lacking uracil and confirmed by PCR using the primers of SEQ ID NOs:141 and 158 to confirm the 5'-crossover, the primers of SEQ ID NOs:82 and 157 to confirm the junction of integration fragments 12A and 12B, and the primers of SEQ ID NOs:136 and 142 to confirm the 3'-crossover. These transformants are grown and plated on FOA as before until a strain in which the URA3 marker has looped out is identified. That strain is simultaneously transformed with each of integration fragments 12C and 12D using the standard lithium acetate process described before. Successful transformants are selected on selection plates lacking uracil and confirmed by PCR using the primers of SEQ ID NOs:141 and 154 to confirm the 5'-crossover, the primers of SEQ ID NOs:82 and 157 to confirm the junction of integration fragments 12C and 12D, and the primers of SEQ ID NOs:142 and 156 to confirm the 3'-crossover. The resultant strain, which contains the *L. Mexicana* FRD gene (SEQ. ID. NO:43), is designated strain 13723.

TABLE 19

*I. orientalis* MDH/FUM Insertion Strains

| Strain No | Integration Fragments | Description (in addition to transformations as indicated for Examples 1-4) |
|---|---|---|
| 13723 | 12A/12B | *R. delemar* MDH insertion at ADHb (2) *I. orientalis* FUM insertion at ADHb (2) |

Example 13: Succinate Production of Strain 13723

Strain 13723 was characterized across a range of oxygen transfer rates from 2.6 to 25.6 mmol/L/h using the straight batch fermentation method described in Example 10. Oxygen transfer rate was varied by vessel agitation as described in Example 10. An experimentally derived conversion factor for strain 13723 of 1.51 $OD_{600}$ units per 1 g dry cell mass is used to estimate cell dry weight using methods and instruments as described in Example 10. Samples are taken at 90 hours batch time or when glucose concentration in the batch is >5 g/L and <15 g/L if this occurs prior to 90 hours batch time. Table 20 shows the cell dry weight at inoculation and at the end of fermentation.

TABLE 20

| OUR (mmol/L/h) | Cell dry weight at inoculation (g/L) | Cell dry weight at end of fermentation (g/L) | Strain | Mode of operation |
|---|---|---|---|---|
| 2.6 | 0.14 | 1.19 | 13723 | Straight Batch |
| 4.1 | 0.14 | 1.52 | 13723 | Straight Batch |
| 6.7 | 0.10 | 2.98 | 13723 | Straight Batch |
| 9.5 | 0.15 | 3.91 | 13723 | Straight Batch |
| 18.0 | 0.10 | 8.41 | 13723 | Straight Batch |
| 25.6 | 0.11 | 16.29 | 13723 | Straight Batch |

Succinate production is summarized in Table 21 and FIG. 42. Table 21 shows total succinate production (g/L), rate of succinate production (g/L/h), and total succinate yield per gram of glucose (g/g) for strain 13723. Total succinate yield decreases slowly from an OUR of about 9.5 mmol/L/h to an OUR of about 25.6 mmol/L/h. However, the product of succinate production rate times succinate yield times total succinate titer produced increases as the OUR increases from about 5 mmol/L/h to about 18 mmol/L/h (or about 20 mmol/L/h). This confirms that the strains and fermentation processes disclosed herein can be used to produce succinate with a high production rate, high final titer of succinate in the fermentation broth, and an acceptable yield.

TABLE 21

| OUR (mmol/L/h) | Succinate titer (g/L) | Yield (g succinate/ g glucose) | Rate of succinate production (g/L/h) | Rate × yield × titer | Cells (g/L - 1.5 conversion) |
|---|---|---|---|---|---|
| 2.6 | 30.3 | 0.57 | 0.33 | 5.7 | 1.19 |
| 4.1 | 41.5 | 0.55 | 0.46 | 10.5 | 1.52 |
| 6.7 | 45.4 | 0.54 | 0.5 | 12.3 | 2.98 |
| 9.5 | 47.4 | 0.55 | 0.52 | 13.5 | 3.91 |
| 18.0 | 48.2 | 0.45 | 0.97 | 20.3 | 8.41 |
| 25.6 | 45.0 | 0.4 | 1.03 | 18.6 | 16.29 |

What is claimed is:

1. A method of producing a succinate, succinic acid, or succinate/succinic acid-containing fermentation broth, the method comprising:
   (i) culturing in a fermenter a recombinant yeast in the presence of at least one carbon source to produce succinate, wherein the recombinant yeast is genetically engineered to produce succinate through a reductive tricarboxylic acid (TCA) active succinate fermentation pathway from phosphoenolpyruvate or pyruvate to succinate, wherein the active succinate fermentation pathway comprises the reactions:
   (a) pyruvate to oxaloacetate;
   (b) oxaloacetate to malate;
   (c) malate to fumarate;
   (d) fumarate to succinate; and
   (e) export of succinate from inside the cell to the extracellular environment, and
   (ii) introducing into the fermenter sufficient oxygen to provide an oxygen uptake rate (OUR) of greater than 8 mmol/L/h,
wherein the recombinant yeast produces more succinate when cultured under an OUR of greater than 8 mmol/L/h as compared to when the recombinant yeast is cultured at an OUR of 5 mmol/L/h, and
wherein a final concentration of succinate, succinic acid, or succinate/succinic acid in the fermentation broth is greater than 20 g/L.

2. The method of claim 1, wherein the recombinant yeast is a yeast of the species: *Issatchenkia orientalis* (*Pichia kudriavzevii* or *Candida krusei*), *Candida lambica*, *Candida sorboxylosa*, *Candida zemplinina*, *Candida geochares*, *Pichia membranifaciens*, *Zygosaccharomyces kombuchaensis*, *Candida sorbosivorans*, *Kluyveromyces marxianus*, *Candida vanderwaltii*, *Candida sorbophila*, *Zygosaccharomyces bisporus*, *Zygosaccharomyces lentus*, *Saccharomyces bayanus*, *Saccharomyces bulderi*, *Debaryomyces castellii*, *Candida boidinii*, *Candida etchellsii*, *Kluyveromyces lactis*, *Pichia jadinii*, *Pichia anomala*, *Saccharomycopsis crataegensis*, or *Pichia jadinii*.

3. The method of claim 1, wherein a production rate of succinate, succinic acid, or succinate/succinic acid is greater than 0.25 g/L/h, or a specific production rate of succinate, succinic acid, or succinate/succinic acid is greater than 0.1 g/g/h.

4. The method of claim 1, wherein the product yield of succinate, succinic acid, or succinate/succinic acid is greater than 25%.

5. The method of claim 1, wherein the cell dry weight at the end of fermentation is less than 10 g/L.

6. The method of claim 1, wherein the recombinant yeast dry weight at inoculation is less than 5 g/L.

7. The method of claim 1, wherein the recombinant yeast comprises one or more endogenous genes that encode an enzyme that catalyzes any one of reactions (a) though (e).

8. The method of claim 7, wherein the recombinant yeast comprises one or more copies of one or more endogenous genes encoding pyruvate carboxylase, malate dehydrogenase, fumarase, fumarate reductase, or a succinate exporter.

9. The method of claim 8, wherein the one or more of the endogenous genes are operatively linked to an exogenous regulatory element which is an exogenous promoter or an exogenous terminator.

10. The method of claim 1, wherein the recombinant yeast is genetically engineered to comprise one or more exogenous genes that encode an enzyme that catalyzes any one of reactions (a) through (e).

11. The method of claim 10, wherein the recombinant yeast comprises one or more copies of one or more exogenous genes encoding pyruvate carboxylase, malate dehydrogenase, fumarase, fumarate reductase, or a succinate exporter.

12. The method of claim 1, wherein the recombinant yeast is from a species which is *Issatchenkia orientalis* (*Pichia kudriavzevii* or *Candida krusei*) or *Candida lambica*.

13. The method of claim 1, wherein the recombinant yeast is from the *Pichia fermentans/Issatchenkia orientalis* clade.

14. The method of claim 1, wherein the carbon source is glucose, xylose, arabinose, sucrose, fructose, cellulose, glucose oligomers, or glycerol.

15. The method of claim 1, wherein a final pH of the fermentation broth is less than 6.0.

16. The method of claim 1, wherein a final concentration of succinic acid in the fermentation broth is greater than 20 g/L.

17. The method of claim 1, wherein the recombinant yeast comprises a genetic modification to enhance succinate export.

18. The method of claim 1, wherein the recombinant yeast has a deletion or disruption in a native pyruvate decarboxylase (PDC) gene.

19. The method of claim 1, wherein the OUR is between 8 mmol/L/h and 25 mmol/L/h.

20. The method of claim 1, wherein the OUR is greater than 10 mmol/L/h.

21. The method of claim 20, wherein the OUR is greater than 12 mmol/L/h.

22. A method of producing succinate, succinic acid, or succinate/succinic acid, the method comprising:
   culturing in a fermenter a recombinant yeast in the presence of at least one carbon source to produce succinate, wherein the recombinant yeast is from the species *Issatchenkia orientalis* (*Pichia kudriavzevii* or *Candida krusei*) and is genetically engineered to produce succinate through a reductive tricarboxylic acid (TCA) active succinate fermentation pathway from phosphoenolpyruvate or pyruvate to succinate; and
   providing sufficient oxygen to the fermenter to obtain an oxygen uptake rate (OUR) of 8 mmol/L/h to 25 mmol/L/h,
   wherein the recombinant yeast produces more succinate when cultured under an OUR of between 8 mmol/L/h and 25 mmol/L/h, as compared to when the recombinant yeast is cultured at an OUR of 5 mmol/L/h.

23. The method of claim 22, wherein a final pH of the fermentation broth is less than 6.0.

24. The method of claim 22, wherein the OUR is from 8 mmol/L/h to 20 mmol/L/h.

25. The method of claim 22, wherein the production rate of succinate, succinic acid, or succinate/succinic acid is greater than 1 g/L/h.

26. The method of claim 22, wherein the product yield of succinate, succinic acid, or succinate/succinic acid is greater than 50%.

27. The method of claim 1, wherein the dissolved oxygen in the fermentation broth is maintained at less than 10% of air saturation at one atmosphere for greater than 10 hours during the batch time.

28. The method of claim 22, wherein the dissolved oxygen in the fermentation broth is maintained at less than 10% of air saturation at one atmosphere for greater than 10 hours during the batch time.

29. The method of claim 1, wherein a final pH of the fermentation broth is less than 5.5.

30. The method of claim 1, wherein a final pH of the fermentation broth is less than 5.0.

31. The method of claim 1, wherein a final pH of the fermentation broth is less than 4.0.

32. The method of claim 1, wherein a final pH of the fermentation broth is less than 3.5.

* * * * *

SEQUENCE LISTING

<160> NUMBER OF SEQ ID NOS: 169

<210> SEQ ID NO 1
<211> LENGTH: 1458
<212> TYPE: DNA
<213> ORGANISM: Issatchenkia orientalis
<220> FEATURE:
<221> NAME/KEY: CDS
<222> LOCATION: (1)..(1458)

<400> SEQUENCE: 1

```
atg tta gct gct aga tca tta aag gca aga atg tca aca aga gct ttc        48
Met Leu Ala Ala Arg Ser Leu Lys Ala Arg Met Ser Thr Arg Ala Phe
1               5                  10                  15 tca act acc tca att gca aaa aga atc gaa aaa gat gca ttt ggt gac        96
Ser Thr Thr Ser Ile Ala Lys Arg Ile Glu Lys Asp Ala Phe Gly Asp
            20                  25                  30
```

```
att gaa gtc cca aat gag aaa tat tgg ggt gct caa act caa aga tct      144
Ile Glu Val Pro Asn Glu Lys Tyr Trp Gly Ala Gln Thr Gln Arg Ser
        35                  40                  45 tta caa aat ttc aaa att ggt ggt aag aga gaa gtt atg cca gaa cca      192
Leu Gln Asn Phe Lys Ile Gly Gly Lys Arg Glu Val Met Pro Glu Pro
 50                  55                  60 atc atc aaa tct ttt ggt att tta aag aag gct act gct aag atc aat      240
Ile Ile Lys Ser Phe Gly Ile Leu Lys Lys Ala Thr Ala Lys Ile Asn
65                  70                  75                  80 gct gag tct ggt gct tta gac cca aag tta tct gaa gcc atc caa caa      288
Ala Glu Ser Gly Ala Leu Asp Pro Lys Leu Ser Glu Ala Ile Gln Gln
                85                  90                  95 gct gca acc gaa gtt tat gaa ggt aaa cta atg gac cat ttc cca tta      336
Ala Ala Thr Glu Val Tyr Glu Gly Lys Leu Met Asp His Phe Pro Leu
            100                 105                 110 gtt gtc ttt caa acc ggt tct ggt act caa tct aac atg aat gcc aat      384
Val Val Phe Gln Thr Gly Ser Gly Thr Gln Ser Asn Met Asn Ala Asn
        115                 120                 125 gaa gtc atc tct aat aga gca att gaa atc ttg ggt ggt gaa tta ggc      432
Glu Val Ile Ser Asn Arg Ala Ile Glu Ile Leu Gly Gly Glu Leu Gly
130                 135                 140 tct aaa act cca gtc cat cct aat gat cat gtt aat atg tcc caa tct      480
Ser Lys Thr Pro Val His Pro Asn Asp His Val Asn Met Ser Gln Ser
145                 150                 155                 160 tct aat gat act ttc cct act gtc atg cat att gca gca gtt aca gaa      528
Ser Asn Asp Thr Phe Pro Thr Val Met His Ile Ala Ala Val Thr Glu
                165                 170                 175 gtt tca tcc cat tta tta cca gaa tta act gca cta aga gat gca ttg      576
Val Ser Ser His Leu Leu Pro Glu Leu Thr Ala Leu Arg Asp Ala Leu
            180                 185                 190 caa aag aaa tcc gat gaa ttt aag aat att atc aaa atc ggt aga acc      624
Gln Lys Lys Ser Asp Glu Phe Lys Asn Ile Ile Lys Ile Gly Arg Thr
        195                 200                 205 cat tta caa gat gca act cct tta act tta ggt caa gaa ttt tct ggt      672
His Leu Gln Asp Ala Thr Pro Leu Thr Leu Gly Gln Glu Phe Ser Gly
210                 215                 220 tat gtt caa caa tgt act aat ggt atc aaa aga atc gaa att gct ctt      720
Tyr Val Gln Gln Cys Thr Asn Gly Ile Lys Arg Ile Glu Ile Ala Leu
225                 230                 235                 240 gaa cat ttg aga tac tta gct caa ggt ggt act gcc gtt ggt act ggt      768
Glu His Leu Arg Tyr Leu Ala Gln Gly Gly Thr Ala Val Gly Thr Gly
                245                 250                 255 ctt aac acc aag aaa ggt ttt gct gaa aag gtt gca aat gaa gtc act      816
Leu Asn Thr Lys Lys Gly Phe Ala Glu Lys Val Ala Asn Glu Val Thr
            260                 265                 270 aaa ttg act ggt tta caa ttc tat acc gct cca aat aaa ttc gaa gcc      864
Lys Leu Thr Gly Leu Gln Phe Tyr Thr Ala Pro Asn Lys Phe Glu Ala
        275                 280                 285 ctt gca gct cac gat gct gtt gtt gaa atg tct ggt gct ttg aat acc      912
Leu Ala Ala His Asp Ala Val Val Glu Met Ser Gly Ala Leu Asn Thr
290                 295                 300 gtt gca gtc tca tta ttc aaa atc gct caa gat atc aga tat ttg ggt      960
Val Ala Val Ser Leu Phe Lys Ile Ala Gln Asp Ile Arg Tyr Leu Gly
305                 310                 315                 320 tcc ggc cca aga tgt ggt tat ggt gaa ttg gct tta cca gaa aat gaa     1008
Ser Gly Pro Arg Cys Gly Tyr Gly Glu Leu Ala Leu Pro Glu Asn Glu
                325                 330                 335 cca ggt tct tcc atc atg ccg ggt aaa gtt aac cca act caa aac gaa     1056
Pro Gly Ser Ser Ile Met Pro Gly Lys Val Asn Pro Thr Gln Asn Glu
```

```
                340                 345                 350
gct ttg act atg ctt tgt acc caa gtc ttt ggt aac cac tct tgt att    1104
Ala Leu Thr Met Leu Cys Thr Gln Val Phe Gly Asn His Ser Cys Ile
            355                 360                 365 acc ttt gca ggt gct tca ggt caa ttc gaa ttg aat gtc ttt aag cca    1152
Thr Phe Ala Gly Ala Ser Gly Gln Phe Glu Leu Asn Val Phe Lys Pro
370                 375                 380 gtt atg atc tcc aac ttg tta tct tct att agg tta tta ggt gat ggt    1200
Val Met Ile Ser Asn Leu Leu Ser Ser Ile Arg Leu Leu Gly Asp Gly
385                 390                 395                 400 tgt aat tct ttt aga atc cac tgt gtt gaa ggt atc att gca aat acc    1248
Cys Asn Ser Phe Arg Ile His Cys Val Glu Gly Ile Ile Ala Asn Thr
                405                 410                 415 gac aag att gat aaa tta cta cat gaa tct ctc atg tta gtt act gct    1296
Asp Lys Ile Asp Lys Leu Leu His Glu Ser Leu Met Leu Val Thr Ala
            420                 425                 430 ttg aac cca cac att ggt tac gat aag gct tcc aag att gca aag aat    1344
Leu Asn Pro His Ile Gly Tyr Asp Lys Ala Ser Lys Ile Ala Lys Asn
        435                 440                 445 gca cac aag aag ggc ttg aca ttg aaa caa tct gca ttg gaa tta ggt    1392
Ala His Lys Lys Gly Leu Thr Leu Lys Gln Ser Ala Leu Glu Leu Gly
450                 455                 460 tac ttg acc gaa gaa caa ttc aat gaa tgg gtt aga cca gaa aac atg    1440
Tyr Leu Thr Glu Glu Gln Phe Asn Glu Trp Val Arg Pro Glu Asn Met
465                 470                 475                 480 att ggt cca aag gat taa                                             1458
Ile Gly Pro Lys Asp
            485

<210> SEQ ID NO 2
<211> LENGTH: 485
<212> TYPE: PRT
<213> ORGANISM: Issatchenkia orientalis

<400> SEQUENCE: 2

Met Leu Ala Ala Arg Ser Leu Lys Ala Arg Met Ser Thr Arg Ala Phe
1               5                   10                  15

Ser Thr Thr Ser Ile Ala Lys Arg Ile Glu Lys Asp Ala Phe Gly Asp
            20                  25                  30

Ile Glu Val Pro Asn Glu Lys Tyr Trp Gly Ala Gln Thr Gln Arg Ser
        35                  40                  45

Leu Gln Asn Phe Lys Ile Gly Gly Lys Arg Glu Val Met Pro Glu Pro
    50                  55                  60

Ile Ile Lys Ser Phe Gly Ile Leu Lys Lys Ala Thr Ala Lys Ile Asn
65                  70                  75                  80

Ala Glu Ser Gly Ala Leu Asp Pro Lys Leu Ser Glu Ala Ile Gln Gln
                85                  90                  95

Ala Ala Thr Glu Val Tyr Glu Gly Lys Leu Met Asp His Phe Pro Leu
            100                 105                 110

Val Val Phe Gln Thr Gly Ser Gly Thr Gln Ser Asn Met Asn Ala Asn
        115                 120                 125

Glu Val Ile Ser Asn Arg Ala Ile Glu Ile Leu Gly Gly Glu Leu Gly
    130                 135                 140

Ser Lys Thr Pro Val His Pro Asn Asp His Val Asn Met Ser Gln Ser
145                 150                 155                 160

Ser Asn Asp Thr Phe Pro Thr Val Met His Ile Ala Ala Val Thr Glu
                165                 170                 175
```

```
Val Ser Ser His Leu Leu Pro Glu Leu Thr Ala Leu Arg Asp Ala Leu
            180                 185                 190

Gln Lys Lys Ser Asp Glu Phe Lys Asn Ile Ile Lys Ile Gly Arg Thr
        195                 200                 205

His Leu Gln Asp Ala Thr Pro Leu Thr Leu Gly Gln Glu Phe Ser Gly
    210                 215                 220

Tyr Val Gln Gln Cys Thr Asn Gly Ile Lys Arg Ile Glu Ile Ala Leu
225                 230                 235                 240

Glu His Leu Arg Tyr Leu Ala Gln Gly Gly Thr Ala Val Gly Thr Gly
                245                 250                 255

Leu Asn Thr Lys Lys Gly Phe Ala Glu Lys Val Ala Asn Glu Val Thr
        260                 265                 270

Lys Leu Thr Gly Leu Gln Phe Tyr Thr Ala Pro Asn Lys Phe Glu Ala
    275                 280                 285

Leu Ala Ala His Asp Ala Val Val Glu Met Ser Gly Ala Leu Asn Thr
    290                 295                 300

Val Ala Val Ser Leu Phe Lys Ile Ala Gln Asp Ile Arg Tyr Leu Gly
305                 310                 315                 320

Ser Gly Pro Arg Cys Gly Tyr Gly Glu Leu Ala Leu Pro Glu Asn Glu
                325                 330                 335

Pro Gly Ser Ser Ile Met Pro Gly Lys Val Asn Pro Thr Gln Asn Glu
        340                 345                 350

Ala Leu Thr Met Leu Cys Thr Gln Val Phe Gly Asn His Ser Cys Ile
    355                 360                 365

Thr Phe Ala Gly Ala Ser Gly Gln Phe Glu Leu Asn Val Phe Lys Pro
    370                 375                 380

Val Met Ile Ser Asn Leu Leu Ser Ser Ile Arg Leu Leu Gly Asp Gly
385                 390                 395                 400

Cys Asn Ser Phe Arg Ile His Cys Val Glu Gly Ile Ile Ala Asn Thr
                405                 410                 415

Asp Lys Ile Asp Lys Leu Leu His Glu Ser Leu Met Leu Val Thr Ala
        420                 425                 430

Leu Asn Pro His Ile Gly Tyr Asp Lys Ala Ser Lys Ile Ala Lys Asn
    435                 440                 445

Ala His Lys Lys Gly Leu Thr Leu Lys Gln Ser Ala Leu Glu Leu Gly
    450                 455                 460

Tyr Leu Thr Glu Glu Gln Phe Asn Glu Trp Val Arg Pro Glu Asn Met
465                 470                 475                 480

Ile Gly Pro Lys Asp
                485

<210> SEQ ID NO 3
<211> LENGTH: 2652
<212> TYPE: DNA
<213> ORGANISM: Escherichia coli
<220> FEATURE:
<221> NAME/KEY: CDS
<222> LOCATION: (1)..(2652)

<400> SEQUENCE: 3 atg aac gaa caa tat tcc gca ttg cgt agt aat gtc agt atg ctc ggc      48
Met Asn Glu Gln Tyr Ser Ala Leu Arg Ser Asn Val Ser Met Leu Gly
1               5                   10                  15 aaa gtg ctg gga gaa acc atc aag gat gcg ttg gga gaa cac att ctt      96
Lys Val Leu Gly Glu Thr Ile Lys Asp Ala Leu Gly Glu His Ile Leu
            20                  25                  30
```

```
gaa cgc gta gaa act atc cgt aag ttg tcg aaa tct tca cgc gct ggc       144
Glu Arg Val Glu Thr Ile Arg Lys Leu Ser Lys Ser Ser Arg Ala Gly
         35                  40                  45 aat gat gct aac cgc cag gag ttg ctc acc acc tta caa aat ttg tcg       192
Asn Asp Ala Asn Arg Gln Glu Leu Leu Thr Thr Leu Gln Asn Leu Ser
 50                  55                  60 aac gac gag ctg ctg ccc gtt gcg cgt gcg ttt agt cag ttc ctg aac       240
Asn Asp Glu Leu Leu Pro Val Ala Arg Ala Phe Ser Gln Phe Leu Asn
 65                  70                  75                  80 ctg gcc aac acc gcc gag caa tac cac agc att tcg ccg aaa ggc gaa       288
Leu Ala Asn Thr Ala Glu Gln Tyr His Ser Ile Ser Pro Lys Gly Glu
                 85                  90                  95 gct gcc agc aac ccg gaa gtg atc gcc cgc acc ctg cgt aaa ctg aaa       336
Ala Ala Ser Asn Pro Glu Val Ile Ala Arg Thr Leu Arg Lys Leu Lys
            100                 105                 110 aac cag ccg gaa ctg agc gaa gac acc atc aaa aaa gca gtg gaa tcg       384
Asn Gln Pro Glu Leu Ser Glu Asp Thr Ile Lys Lys Ala Val Glu Ser
        115                 120                 125 ctg tcg ctg gaa ctg gtc ctc acg gct cac cca acc gaa att acc cgt       432
Leu Ser Leu Glu Leu Val Leu Thr Ala His Pro Thr Glu Ile Thr Arg
    130                 135                 140 cgt aca ctg atc cac aaa atg gtg gaa gtg aac gcc tgt tta aaa cag       480
Arg Thr Leu Ile His Lys Met Val Glu Val Asn Ala Cys Leu Lys Gln
145                 150                 155                 160 ctc gat aac aaa gat atc gct gac tac gaa cac aac cag ctg atg cgt       528
Leu Asp Asn Lys Asp Ile Ala Asp Tyr Glu His Asn Gln Leu Met Arg
                165                 170                 175 cgc ctg cgc cag ttg atc gcc cag tca tgg cat acc gat gaa atc cgt       576
Arg Leu Arg Gln Leu Ile Ala Gln Ser Trp His Thr Asp Glu Ile Arg
            180                 185                 190 aag ctg cgt cca agc ccg gta gat gaa gcc aaa tgg ggc ttt gcc gta       624
Lys Leu Arg Pro Ser Pro Val Asp Glu Ala Lys Trp Gly Phe Ala Val
        195                 200                 205 gtg gaa aac agc ctg tgg caa ggc gta cca aat tac ctg cgc gaa ctg       672
Val Glu Asn Ser Leu Trp Gln Gly Val Pro Asn Tyr Leu Arg Glu Leu
    210                 215                 220 aac gaa caa ctg gaa gag aac ctc ggc tac aaa ctg ccc gtc gaa ttt       720
Asn Glu Gln Leu Glu Glu Asn Leu Gly Tyr Lys Leu Pro Val Glu Phe
225                 230                 235                 240 gtt ccg gtc cgt ttt act tcg tgg atg ggc ggc gac cgc gac ggc aac       768
Val Pro Val Arg Phe Thr Ser Trp Met Gly Gly Asp Arg Asp Gly Asn
                245                 250                 255 ccg aac gtc act gcc gat atc acc cgc cac gtc ctg cta ctc agc cgc       816
Pro Asn Val Thr Ala Asp Ile Thr Arg His Val Leu Leu Leu Ser Arg
            260                 265                 270 tgg aaa gcc acc gat ttg ttc ctg aaa gat att cag gtg ctg gtt tct       864
Trp Lys Ala Thr Asp Leu Phe Leu Lys Asp Ile Gln Val Leu Val Ser
        275                 280                 285 gaa ctg tcg atg gtt gaa gcg acc cct gaa ctg ctg gcg ctg gtt ggc       912
Glu Leu Ser Met Val Glu Ala Thr Pro Glu Leu Leu Ala Leu Val Gly
    290                 295                 300 gaa gaa ggt gcc gca gaa ccg tat cgc tat ctg atg aaa aac ctg cgt       960
Glu Glu Gly Ala Ala Glu Pro Tyr Arg Tyr Leu Met Lys Asn Leu Arg
305                 310                 315                 320 tct cgc ctg atg gcg aca cag gca tgg ctg gaa gcg cgc ctg aaa ggc      1008
Ser Arg Leu Met Ala Thr Gln Ala Trp Leu Glu Ala Arg Leu Lys Gly
                325                 330                 335 gaa gaa ctg cca aaa cca gaa ggc ctg ctg aca caa aac gaa gaa ctg      1056
Glu Glu Leu Pro Lys Pro Glu Gly Leu Leu Thr Gln Asn Glu Glu Leu
            340                 345                 350
```

```
tgg gaa ccg ctc tac gct tgc tac cag tca ctt cag gcg tgt ggc atg       1104
Trp Glu Pro Leu Tyr Ala Cys Tyr Gln Ser Leu Gln Ala Cys Gly Met
            355                 360                 365 ggt att atc gcc aac ggc gat ctg ctc gac acc ctg cgc cgc gtg aaa       1152
Gly Ile Ile Ala Asn Gly Asp Leu Leu Asp Thr Leu Arg Arg Val Lys
    370                 375                 380 tgt ttc ggc gta ccg ctg gtc cgt att gat atc cgt cag gag agc acg       1200
Cys Phe Gly Val Pro Leu Val Arg Ile Asp Ile Arg Gln Glu Ser Thr
385                 390                 395                 400 cgt cat acc gaa gcg ctg ggc gag ctg acc cgc tac ctc ggt atc ggc       1248
Arg His Thr Glu Ala Leu Gly Glu Leu Thr Arg Tyr Leu Gly Ile Gly
                405                 410                 415 gac tac gaa agc tgg tca gag gcc gac aaa cag gcg ttc ctg atc cgc       1296
Asp Tyr Glu Ser Trp Ser Glu Ala Asp Lys Gln Ala Phe Leu Ile Arg
            420                 425                 430 gaa ctg aac tcc aaa cgt ccg ctt ctg ccg cgc aac tgg caa cca agc       1344
Glu Leu Asn Ser Lys Arg Pro Leu Leu Pro Arg Asn Trp Gln Pro Ser
        435                 440                 445 gcc gaa acg cgc gaa gtg ctc gat acc tgc cag gtg att gcc gaa gca       1392
Ala Glu Thr Arg Glu Val Leu Asp Thr Cys Gln Val Ile Ala Glu Ala
450                 455                 460 ccg caa ggc tcc att gcc gcc tac gtg atc tcg atg gcg aaa acg ccg       1440
Pro Gln Gly Ser Ile Ala Ala Tyr Val Ile Ser Met Ala Lys Thr Pro
465                 470                 475                 480 tcc gac gta ctg gct gtc cac ctg ctg ctg aaa gaa gcg ggt atc ggg       1488
Ser Asp Val Leu Ala Val His Leu Leu Leu Lys Glu Ala Gly Ile Gly
                485                 490                 495 ttt gcg atg ccg gtt gct ccg ctg ttt gaa acc ctc gat gat ctg aac       1536
Phe Ala Met Pro Val Ala Pro Leu Phe Glu Thr Leu Asp Asp Leu Asn
            500                 505                 510 aac gcc aac gat gtc atg acc cag ctg ctc aat att gac tgg tat cgt       1584
Asn Ala Asn Asp Val Met Thr Gln Leu Leu Asn Ile Asp Trp Tyr Arg
        515                 520                 525 ggc ctg att cag ggc aaa cag atg gtg atg att ggc tat tcc gac tca       1632
Gly Leu Ile Gln Gly Lys Gln Met Val Met Ile Gly Tyr Ser Asp Ser
530                 535                 540 gca aaa gat gcg gga gtg atg gca gct tcc tgg gcg caa tat cag gca       1680
Ala Lys Asp Ala Gly Val Met Ala Ala Ser Trp Ala Gln Tyr Gln Ala
545                 550                 555                 560 cag gat gca tta atc aaa acc tgc gaa aaa gcg ggt att gag ctg acg       1728
Gln Asp Ala Leu Ile Lys Thr Cys Glu Lys Ala Gly Ile Glu Leu Thr
                565                 570                 575 ttg ttc cac ggt cgc ggc ggt tcc att ggt cgc ggc ggc gca cct gct       1776
Leu Phe His Gly Arg Gly Gly Ser Ile Gly Arg Gly Gly Ala Pro Ala
            580                 585                 590 cat gcg gcg ctg ctg tca caa ccg cca gga agc ctg aaa ggc ggc ctg       1824
His Ala Ala Leu Leu Ser Gln Pro Pro Gly Ser Leu Lys Gly Gly Leu
        595                 600                 605 cgc gta acc gaa cag ggc gag atg atc cgc ttt aaa tat ggt ctg cca       1872
Arg Val Thr Glu Gln Gly Glu Met Ile Arg Phe Lys Tyr Gly Leu Pro
610                 615                 620 gaa atc acc gtc agc agc ctg tcg ctt tat acc ggg gcg att ctg gaa       1920
Glu Ile Thr Val Ser Ser Leu Ser Leu Tyr Thr Gly Ala Ile Leu Glu
625                 630                 635                 640 gcc aac ctg ctg cca ccg ccg gag ccg aaa gag agc tgg cgt cgc att       1968
Ala Asn Leu Leu Pro Pro Pro Glu Pro Lys Glu Ser Trp Arg Arg Ile
                645                 650                 655 atg gat gaa ctg tca gtc atc tcc tgc gat gtc tac cgc ggc tac gta       2016
Met Asp Glu Leu Ser Val Ile Ser Cys Asp Val Tyr Arg Gly Tyr Val
```

```
                    660                 665                 670
cgt gaa aac aaa gat ttt gtg cct tac ttc cgc tcc gct acg ccg gaa    2064
Arg Glu Asn Lys Asp Phe Val Pro Tyr Phe Arg Ser Ala Thr Pro Glu
        675                 680                 685 caa gaa ctg ggc aaa ctg ccg ttg ggt tca cgt ccg gcg aaa cgt cgc    2112
Gln Glu Leu Gly Lys Leu Pro Leu Gly Ser Arg Pro Ala Lys Arg Arg
        690                 695                 700 cca acc ggc ggc gtc gag tca cta cgc gcc att ccg tgg atc ttc gcc    2160
Pro Thr Gly Gly Val Glu Ser Leu Arg Ala Ile Pro Trp Ile Phe Ala
705                 710                 715                 720 tgg acg caa aac cgt ctg atg ctc ccc gcc tgg ctg ggt gca ggt acg    2208
Trp Thr Gln Asn Arg Leu Met Leu Pro Ala Trp Leu Gly Ala Gly Thr
                725                 730                 735 gcg ctg caa aaa gtg gtc gaa gac ggc aaa cag agc gag ctg gag gct    2256
Ala Leu Gln Lys Val Val Glu Asp Gly Lys Gln Ser Glu Leu Glu Ala
            740                 745                 750 atg tgc cgc gat tgg cca ttc ttc tcg acg cgt ctc ggc atg ctg gag    2304
Met Cys Arg Asp Trp Pro Phe Phe Ser Thr Arg Leu Gly Met Leu Glu
        755                 760                 765 atg gtc ttc gcc aaa gca gac ctg tgg ctg gcg gaa tac tat gac caa    2352
Met Val Phe Ala Lys Ala Asp Leu Trp Leu Ala Glu Tyr Tyr Asp Gln
770                 775                 780 cgc ctg gta gac aaa gca ctg tgg ccg tta ggt aaa gag tta cgc aac    2400
Arg Leu Val Asp Lys Ala Leu Trp Pro Leu Gly Lys Glu Leu Arg Asn
785                 790                 795                 800 ctg caa gaa gaa gac atc aaa gtg gtg ctg gcg att gcc aac gat tcc    2448
Leu Gln Glu Glu Asp Ile Lys Val Val Leu Ala Ile Ala Asn Asp Ser
                805                 810                 815 cat ctg atg gcc gat ctg ccg tgg att gca gag tct att cag cta cgg    2496
His Leu Met Ala Asp Leu Pro Trp Ile Ala Glu Ser Ile Gln Leu Arg
            820                 825                 830 aat att tac acc gac ccg ctg aac gta ttg cag gcc gag ttg ctg cac    2544
Asn Ile Tyr Thr Asp Pro Leu Asn Val Leu Gln Ala Glu Leu Leu His
        835                 840                 845 cgc tcc cgc cag gca gaa aaa gaa ggc cag gaa ccg gat cct cgc gtc    2592
Arg Ser Arg Gln Ala Glu Lys Glu Gly Gln Glu Pro Asp Pro Arg Val
850                 855                 860 gaa caa gcg tta atg gtc act att gcc ggg att gcg gca ggt atg cgt    2640
Glu Gln Ala Leu Met Val Thr Ile Ala Gly Ile Ala Ala Gly Met Arg
865                 870                 875                 880 aat acc ggc taa                                                    2652
Asn Thr Gly <210> SEQ ID NO 4
<211> LENGTH: 883
<212> TYPE: PRT
<213> ORGANISM: Escherichia coli

<400> SEQUENCE: 4

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80
```

```
Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495
```

```
Phe Ala Met Pro Val Ala Pro Leu Phe Glu Thr Leu Asp Asp Leu Asn
            500                 505                 510
Asn Ala Asn Asp Val Met Thr Gln Leu Leu Asn Ile Asp Trp Tyr Arg
        515                 520                 525
Gly Leu Ile Gln Gly Lys Gln Met Val Met Ile Gly Tyr Ser Asp Ser
    530                 535                 540
Ala Lys Asp Ala Gly Val Met Ala Ala Ser Trp Ala Gln Tyr Gln Ala
545                 550                 555                 560
Gln Asp Ala Leu Ile Lys Thr Cys Glu Lys Ala Gly Ile Glu Leu Thr
                565                 570                 575
Leu Phe His Gly Arg Gly Gly Ser Ile Gly Arg Gly Gly Ala Pro Ala
            580                 585                 590
His Ala Ala Leu Leu Ser Gln Pro Pro Gly Ser Leu Lys Gly Gly Leu
        595                 600                 605
Arg Val Thr Glu Gln Gly Glu Met Ile Arg Phe Lys Tyr Gly Leu Pro
    610                 615                 620
Glu Ile Thr Val Ser Ser Leu Ser Leu Tyr Thr Gly Ala Ile Leu Glu
625                 630                 635                 640
Ala Asn Leu Leu Pro Pro Pro Glu Pro Lys Glu Ser Trp Arg Arg Ile
                645                 650                 655
Met Asp Glu Leu Ser Val Ile Ser Cys Asp Val Tyr Arg Gly Tyr Val
            660                 665                 670
Arg Glu Asn Lys Asp Phe Val Pro Tyr Phe Arg Ser Ala Thr Pro Glu
        675                 680                 685
Gln Glu Leu Gly Lys Leu Pro Leu Gly Ser Arg Pro Ala Lys Arg Arg
    690                 695                 700
Pro Thr Gly Gly Val Glu Ser Leu Arg Ala Ile Pro Trp Ile Phe Ala
705                 710                 715                 720
Trp Thr Gln Asn Arg Leu Met Leu Pro Ala Trp Leu Gly Ala Gly Thr
                725                 730                 735
Ala Leu Gln Lys Val Val Glu Asp Gly Lys Gln Ser Glu Leu Glu Ala
            740                 745                 750
Met Cys Arg Asp Trp Pro Phe Phe Ser Thr Arg Leu Gly Met Leu Glu
        755                 760                 765
Met Val Phe Ala Lys Ala Asp Leu Trp Leu Ala Glu Tyr Tyr Asp Gln
    770                 775                 780
Arg Leu Val Asp Lys Ala Leu Trp Pro Leu Gly Lys Glu Leu Arg Asn
785                 790                 795                 800
Leu Gln Glu Glu Asp Ile Lys Val Val Leu Ala Ile Ala Asn Asp Ser
                805                 810                 815
His Leu Met Ala Asp Leu Pro Trp Ile Ala Glu Ser Ile Gln Leu Arg
            820                 825                 830
Asn Ile Tyr Thr Asp Pro Leu Asn Val Leu Gln Ala Glu Leu Leu His
        835                 840                 845
Arg Ser Arg Gln Ala Glu Lys Glu Gly Gln Glu Pro Asp Pro Arg Val
    850                 855                 860
Glu Gln Ala Leu Met Val Thr Ile Ala Gly Ile Ala Ala Gly Met Arg
865                 870                 875                 880
Asn Thr Gly

<210> SEQ ID NO 5
<211> LENGTH: 2643
<212> TYPE: DNA
<213> ORGANISM: Mannheimia succiniciproducens
```

```
<220> FEATURE:
<221> NAME/KEY: CDS
<222> LOCATION: (1)..(2643)

<400> SEQUENCE: 5 atg aca gaa gaa tat tta atg atg cgt aat aac atc aat atg ctg ggg       48
Met Thr Glu Glu Tyr Leu Met Met Arg Asn Asn Ile Asn Met Leu Gly
1               5                   10                  15 cgc ttt ttg ggc gaa act att cag gag gcg caa ggt gac gat att ctc       96
Arg Phe Leu Gly Glu Thr Ile Gln Glu Ala Gln Gly Asp Asp Ile Leu
            20                  25                  30 gaa ctg att gaa aat atc cgc gta ctg tcc cgc aat tcc cgt agc ggc      144
Glu Leu Ile Glu Asn Ile Arg Val Leu Ser Arg Asn Ser Arg Ser Gly
        35                  40                  45 gat gac aaa gcc cgg gcg gca tta tta gac acc ctt tcc act att tcg      192
Asp Asp Lys Ala Arg Ala Ala Leu Leu Asp Thr Leu Ser Thr Ile Ser
50                  55                  60 gcg gat aat att att ccg gtt gcc cgc gct ttc agc cag ttt ctg aac      240
Ala Asp Asn Ile Ile Pro Val Ala Arg Ala Phe Ser Gln Phe Leu Asn
65                  70                  75                  80 ctg aca aat gtg gcg gaa caa tat caa acc atg tct cgc tcc cat gaa      288
Leu Thr Asn Val Ala Glu Gln Tyr Gln Thr Met Ser Arg Ser His Glu
                85                  90                  95 gat aag gtt tct gcg gaa cgt tcc act gct gcg ctg ttc gcc cgc ctg      336
Asp Lys Val Ser Ala Glu Arg Ser Thr Ala Ala Leu Phe Ala Arg Leu
            100                 105                 110 aaa gaa caa cat gtt tct cag gaa gaa atc att aaa acc gta cag aaa      384
Lys Glu Gln His Val Ser Gln Glu Glu Ile Ile Lys Thr Val Gln Lys
        115                 120                 125 ctg ttg att gaa atc gtc ctt acc gct cac ccg acg gaa gtt acc cgc      432
Leu Leu Ile Glu Ile Val Leu Thr Ala His Pro Thr Glu Val Thr Arg
130                 135                 140 cgt tca tta atg cac aaa cag gtt gaa atc aac aaa tgt ctg gct cag      480
Arg Ser Leu Met His Lys Gln Val Glu Ile Asn Lys Cys Leu Ala Gln
145                 150                 155                 160 ctg gat cat acg gat tta acc gcc gaa gaa caa aaa aat att gag tat      528
Leu Asp His Thr Asp Leu Thr Ala Glu Glu Gln Lys Asn Ile Glu Tyr
                165                 170                 175 aaa tta ctt cgt ctt atc gcc gaa gcc tgg cat acc aat gaa atc cgt      576
Lys Leu Leu Arg Leu Ile Ala Glu Ala Trp His Thr Asn Glu Ile Arg
            180                 185                 190 acc aat cgg ccg aca cct ctg gaa gaa gcc aaa tgg ggt ttt gcc gtt      624
Thr Asn Arg Pro Thr Pro Leu Glu Glu Ala Lys Trp Gly Phe Ala Val
        195                 200                 205 atc gaa aac agt tta tgg gaa ggt ttg ccc gcc ttt atc cgc aaa ctt      672
Ile Glu Asn Ser Leu Trp Glu Gly Leu Pro Ala Phe Ile Arg Lys Leu
210                 215                 220 aac gat gcc gcc gtc gaa cat tta aat tat gct ttg ccg gta gac ctc      720
Asn Asp Ala Ala Val Glu His Leu Asn Tyr Ala Leu Pro Val Asp Leu
225                 230                 235                 240 aca ccg gta cgc ttc tct tcc tgg atg ggc ggt gac cgt gac ggc aac      768
Thr Pro Val Arg Phe Ser Ser Trp Met Gly Gly Asp Arg Asp Gly Asn
                245                 250                 255 ccc ttc gtt acc gca aaa att acc cgg gaa gcg ctg caa ctt gcg cgc      816
Pro Phe Val Thr Ala Lys Ile Thr Arg Glu Ala Leu Gln Leu Ala Arg
            260                 265                 270 tgg aaa gcg gcg gat tta ttt tta acc gat att cag gaa ctc tgc gac      864
Trp Lys Ala Ala Asp Leu Phe Leu Thr Asp Ile Gln Glu Leu Cys Asp
        275                 280                 285 gag ttg tca atg aca caa tgc act gcg gaa ttc cga gaa aaa tac ggt      912
```

```
                Glu Leu Ser Met Thr Gln Cys Thr Ala Glu Phe Arg Glu Lys Tyr Gly
                    290                 295                 300 gat cat tta gaa ccc tat cgt gta gtt gtg aag gat tta cgc agc aaa        960
Asp His Leu Glu Pro Tyr Arg Val Val Val Lys Asp Leu Arg Ser Lys
305                 310                 315                 320 tta aaa aat acg ctg gat tat tac aac gat ata ctt gcg ggt cgc att       1008
Leu Lys Asn Thr Leu Asp Tyr Tyr Asn Asp Ile Leu Ala Gly Arg Ile
                325                 330                 335 ccg ccg ttt aaa caa gat gaa atc atc agt gaa gac caa caa ctc tgg       1056
Pro Pro Phe Lys Gln Asp Glu Ile Ile Ser Glu Asp Gln Gln Leu Trp
            340                 345                 350 caa ccg ctt tat gac tgt tat caa tcc cta acc gcc tgc ggt atg cgt       1104
Gln Pro Leu Tyr Asp Cys Tyr Gln Ser Leu Thr Ala Cys Gly Met Arg
        355                 360                 365 att att gcc aat gga tta ttg ctg gat acc tta cgc cgc gtt cgt tgt       1152
Ile Ile Ala Asn Gly Leu Leu Leu Asp Thr Leu Arg Arg Val Arg Cys
    370                 375                 380 ttc ggc gtc aca tta ctg cgt tta gat atc cgt cag gaa agc acc cgc       1200
Phe Gly Val Thr Leu Leu Arg Leu Asp Ile Arg Gln Glu Ser Thr Arg
385                 390                 395                 400 cat agc gac gcc atc ggc gaa att acc cgc tac atc ggt tta ggc gat       1248
His Ser Asp Ala Ile Gly Glu Ile Thr Arg Tyr Ile Gly Leu Gly Asp
                405                 410                 415 tac agc caa tgg aca gaa gat gac aaa caa gcc ttc ctg atc cgg gaa       1296
Tyr Ser Gln Trp Thr Glu Asp Asp Lys Gln Ala Phe Leu Ile Arg Glu
            420                 425                 430 tta agt tcc cgt cgt ccg cta att ccc cat aac tgg acg cct tcg gaa       1344
Leu Ser Ser Arg Arg Pro Leu Ile Pro His Asn Trp Thr Pro Ser Glu
        435                 440                 445 cac act cgg gaa att tta gac acc tgt aaa gtc att gca aaa cag ccg       1392
His Thr Arg Glu Ile Leu Asp Thr Cys Lys Val Ile Ala Lys Gln Pro
    450                 455                 460 gaa ggc gtt att tcc tgc tat atc att tcc atg gcg cgc acc gct tcc       1440
Glu Gly Val Ile Ser Cys Tyr Ile Ile Ser Met Ala Arg Thr Ala Ser
465                 470                 475                 480 gat gtt ttg gcg gtg cat tta tta ttg aaa gaa gcg ggc att tca tac       1488
Asp Val Leu Ala Val His Leu Leu Leu Lys Glu Ala Gly Ile Ser Tyr
                485                 490                 495 cat ctg ccg gta gtt cct cta ttt gaa aca ttg gac gac ctg gac gct       1536
His Leu Pro Val Val Pro Leu Phe Glu Thr Leu Asp Asp Leu Asp Ala
            500                 505                 510 tct aaa gaa gtg atg acg caa ctg ttt aac gta ggc tgg tat cgc ggc       1584
Ser Lys Glu Val Met Thr Gln Leu Phe Asn Val Gly Trp Tyr Arg Gly
        515                 520                 525 gta atc aaa aac cgc caa atg atc atg atc ggc tat tcc gat agc gcc       1632
Val Ile Lys Asn Arg Gln Met Ile Met Ile Gly Tyr Ser Asp Ser Ala
    530                 535                 540 aaa gat gcg ggc atg atg gcg gcc tca tgg gcg caa tac cgg gcg cag       1680
Lys Asp Ala Gly Met Met Ala Ala Ser Trp Ala Gln Tyr Arg Ala Gln
545                 550                 555                 560 gac gct tta gtc aaa ctt tgc gaa caa acc ggc atc gaa ctt acc ctc       1728
Asp Ala Leu Val Lys Leu Cys Glu Gln Thr Gly Ile Glu Leu Thr Leu
                565                 570                 575 ttc cac ggc cgc ggc ggc acc gta gga cgt ggc ggt gca ccg gct cac       1776
Phe His Gly Arg Gly Gly Thr Val Gly Arg Gly Gly Ala Pro Ala His
            580                 585                 590 gcc gca tta tta tcc caa ccg cca cgt tct ctg aaa aac ggc tta cgg       1824
Ala Ala Leu Leu Ser Gln Pro Pro Arg Ser Leu Lys Asn Gly Leu Arg
        595                 600                 605
```

```
gta acc gaa caa ggg gaa atg atc cgc ttc aaa ctg gga tta ccg gct    1872
Val Thr Glu Gln Gly Glu Met Ile Arg Phe Lys Leu Gly Leu Pro Ala
610             615                 620 atc gcc gca gaa agt ctg gat ctc tac gcc agc gcc att ctt gag gcc    1920
Ile Ala Ala Glu Ser Leu Asp Leu Tyr Ala Ser Ala Ile Leu Glu Ala
625             630                 635                 640 aac ctc ctg ccg ccg ccg gaa ccg aaa gcc agc tgg tgc cgg gta atg    1968
Asn Leu Leu Pro Pro Pro Glu Pro Lys Ala Ser Trp Cys Arg Val Met
            645                 650                 655 gac gaa ctt gcc gtc gct tct tgc gaa atc tat cgc aat gtg gtg cgc    2016
Asp Glu Leu Ala Val Ala Ser Cys Glu Ile Tyr Arg Asn Val Val Arg
660             665                 670 ggc gat aaa gat ttt gtg cct tac ttc cgc agc gcc aca ccg gaa cag    2064
Gly Asp Lys Asp Phe Val Pro Tyr Phe Arg Ser Ala Thr Pro Glu Gln
    675                 680                 685 gaa ctg gca aaa ctg cct tta ggt tcc cga ccg gca aaa cgc aat ccg    2112
Glu Leu Ala Lys Leu Pro Leu Gly Ser Arg Pro Ala Lys Arg Asn Pro
690             695                 700 aac ggc ggc gtt gaa agc ctg cgt gcc att ccc tgg atc ttc gcc tgg    2160
Asn Gly Gly Val Glu Ser Leu Arg Ala Ile Pro Trp Ile Phe Ala Trp
705                 710                 715                 720 atg caa aac cgc ctg atg ctg ccc gcc tgg ctc ggt gcc ggc gcc tca    2208
Met Gln Asn Arg Leu Met Leu Pro Ala Trp Leu Gly Ala Gly Ala Ser
            725                 730                 735 atc cgt cag gcg atg gaa agc ggc aaa gcg gcg gtg att gaa gaa atg    2256
Ile Arg Gln Ala Met Glu Ser Gly Lys Ala Ala Val Ile Glu Glu Met
                740                 745                 750 tgc aac cat tgg ccg ttt ttc aat acc cga atc ggc atg ctt gaa atg    2304
Cys Asn His Trp Pro Phe Phe Asn Thr Arg Ile Gly Met Leu Glu Met
        755                 760                 765 gta ttc agt aaa acc gat agc tgg ctg tcc gaa tat tac gac cag cgt    2352
Val Phe Ser Lys Thr Asp Ser Trp Leu Ser Glu Tyr Tyr Asp Gln Arg
770                 775                 780 tta gtg aaa aaa gag ctt tgg tat tta ggc gaa tcg ctg cgc aaa cag    2400
Leu Val Lys Lys Glu Leu Trp Tyr Leu Gly Glu Ser Leu Arg Lys Gln
785                 790                 795                 800 tta agc gaa gat atc gct acc gtg tta cgg ctt tcc ggc aaa ggc gat    2448
Leu Ser Glu Asp Ile Ala Thr Val Leu Arg Leu Ser Gly Lys Gly Asp
            805                 810                 815 caa tta atg tcg gat ttg cct tgg gtg gcg gaa tct att gca ctg cgt    2496
Gln Leu Met Ser Asp Leu Pro Trp Val Ala Glu Ser Ile Ala Leu Arg
        820                 825                 830 aac gtt tac acc gac ccg tta aac tta ttg caa gtg gaa tta ttg cgt    2544
Asn Val Tyr Thr Asp Pro Leu Asn Leu Leu Gln Val Glu Leu Leu Arg
    835                 840                 845 cgt ttg cga gcg gat ccc gaa cat ccg aat ccg gat atc gag caa gcg    2592
Arg Leu Arg Ala Asp Pro Glu His Pro Asn Pro Asp Ile Glu Gln Ala
850                 855                 860 ctg atg atc acc att acc ggt atc gcc gcg ggt atg cgt aat acg ggt    2640
Leu Met Ile Thr Ile Thr Gly Ile Ala Ala Gly Met Arg Asn Thr Gly
865                 870                 875                 880 tag                                                                2643

<210> SEQ ID NO 6
<211> LENGTH: 880
<212> TYPE: PRT
<213> ORGANISM: Mannheimia succiniciproducens

<400> SEQUENCE: 6

Met Thr Glu Glu Tyr Leu Met Met Arg Asn Asn Ile Asn Met Leu Gly
```

```
  1               5                   10                  15
Arg Phe Leu Gly Glu Thr Ile Gln Glu Ala Gln Gly Asp Asp Ile Leu
                20                  25                  30
Glu Leu Ile Glu Asn Ile Arg Val Leu Ser Arg Asn Ser Arg Ser Gly
                35                  40                  45
Asp Asp Lys Ala Arg Ala Ala Leu Leu Asp Thr Leu Ser Thr Ile Ser
 50                  55                  60
Ala Asp Asn Ile Ile Pro Val Ala Arg Ala Phe Ser Gln Phe Leu Asn
 65                  70                  75                  80
Leu Thr Asn Val Ala Glu Gln Tyr Gln Thr Met Ser Arg Ser His Glu
                85                  90                  95
Asp Lys Val Ser Ala Glu Arg Ser Thr Ala Ala Leu Phe Ala Arg Leu
                100                 105                 110
Lys Glu Gln His Val Ser Gln Glu Ile Ile Lys Thr Val Gln Lys
                115                 120                 125
Leu Leu Ile Glu Ile Val Leu Thr Ala His Pro Thr Glu Val Thr Arg
                130                 135                 140
Arg Ser Leu Met His Lys Gln Val Glu Ile Asn Lys Cys Leu Ala Gln
145                 150                 155                 160
Leu Asp His Thr Asp Leu Thr Ala Glu Glu Gln Lys Asn Ile Glu Tyr
                165                 170                 175
Lys Leu Leu Arg Leu Ile Ala Glu Ala Trp His Thr Asn Glu Ile Arg
                180                 185                 190
Thr Asn Arg Pro Thr Pro Leu Glu Glu Ala Lys Trp Gly Phe Ala Val
                195                 200                 205
Ile Glu Asn Ser Leu Trp Glu Gly Leu Pro Ala Phe Ile Arg Lys Leu
210                 215                 220
Asn Asp Ala Ala Val Glu His Leu Asn Tyr Ala Leu Pro Val Asp Leu
225                 230                 235                 240
Thr Pro Val Arg Phe Ser Ser Trp Met Gly Gly Asp Arg Asp Gly Asn
                245                 250                 255
Pro Phe Val Thr Ala Lys Ile Thr Arg Glu Ala Leu Gln Leu Ala Arg
                260                 265                 270
Trp Lys Ala Ala Asp Leu Phe Leu Thr Asp Ile Gln Glu Leu Cys Asp
                275                 280                 285
Glu Leu Ser Met Thr Gln Cys Thr Ala Glu Phe Arg Glu Lys Tyr Gly
                290                 295                 300
Asp His Leu Glu Pro Tyr Arg Val Val Lys Asp Leu Arg Ser Lys
305                 310                 315                 320
Leu Lys Asn Thr Leu Asp Tyr Tyr Asn Asp Ile Leu Ala Gly Arg Ile
                325                 330                 335
Pro Pro Phe Lys Gln Asp Glu Ile Ile Ser Glu Asp Gln Leu Trp
                340                 345                 350
Gln Pro Leu Tyr Asp Cys Tyr Gln Ser Leu Thr Ala Cys Gly Met Arg
                355                 360                 365
Ile Ile Ala Asn Gly Leu Leu Leu Asp Thr Leu Arg Arg Val Arg Cys
                370                 375                 380
Phe Gly Val Thr Leu Leu Arg Leu Asp Ile Arg Gln Glu Ser Thr Arg
385                 390                 395                 400
His Ser Asp Ala Ile Gly Glu Ile Thr Arg Tyr Ile Gly Leu Gly Asp
                405                 410                 415
Tyr Ser Gln Trp Thr Glu Asp Asp Lys Gln Ala Phe Leu Ile Arg Glu
                420                 425                 430
```

```
Leu Ser Ser Arg Arg Pro Leu Ile Pro His Asn Trp Thr Pro Ser Glu
        435                 440                 445

His Thr Arg Glu Ile Leu Asp Thr Cys Lys Val Ile Ala Lys Gln Pro
    450                 455                 460

Glu Gly Val Ile Ser Cys Tyr Ile Ile Ser Met Ala Arg Thr Ala Ser
465                 470                 475                 480

Asp Val Leu Ala Val His Leu Leu Lys Glu Ala Gly Ile Ser Tyr
                485                 490                 495

His Leu Pro Val Val Pro Leu Phe Glu Thr Leu Asp Asp Leu Asp Ala
            500                 505                 510

Ser Lys Glu Val Met Thr Gln Leu Phe Asn Val Gly Trp Tyr Arg Gly
        515                 520                 525

Val Ile Lys Asn Arg Gln Met Ile Met Ile Gly Tyr Ser Asp Ser Ala
        530                 535                 540

Lys Asp Ala Gly Met Met Ala Ala Ser Trp Ala Gln Tyr Arg Ala Gln
545                 550                 555                 560

Asp Ala Leu Val Lys Leu Cys Glu Gln Thr Gly Ile Glu Leu Thr Leu
                565                 570                 575

Phe His Gly Arg Gly Gly Thr Val Gly Arg Gly Gly Ala Pro Ala His
            580                 585                 590

Ala Ala Leu Leu Ser Gln Pro Pro Arg Ser Leu Lys Asn Gly Leu Arg
            595                 600                 605

Val Thr Glu Gln Gly Glu Met Ile Arg Phe Lys Leu Gly Leu Pro Ala
        610                 615                 620

Ile Ala Ala Glu Ser Leu Asp Leu Tyr Ala Ser Ala Ile Leu Glu Ala
625                 630                 635                 640

Asn Leu Leu Pro Pro Pro Glu Pro Lys Ala Ser Trp Cys Arg Val Met
                645                 650                 655

Asp Glu Leu Ala Val Ala Ser Cys Glu Ile Tyr Arg Asn Val Val Arg
            660                 665                 670

Gly Asp Lys Asp Phe Val Pro Tyr Phe Arg Ser Ala Thr Pro Glu Gln
        675                 680                 685

Glu Leu Ala Lys Leu Pro Leu Gly Ser Arg Pro Ala Lys Arg Asn Pro
        690                 695                 700

Asn Gly Gly Val Glu Ser Leu Arg Ala Ile Pro Trp Ile Phe Ala Trp
705                 710                 715                 720

Met Gln Asn Arg Leu Met Leu Pro Ala Trp Leu Gly Ala Gly Ala Ser
                725                 730                 735

Ile Arg Gln Ala Met Glu Ser Gly Lys Ala Ala Val Ile Glu Glu Met
            740                 745                 750

Cys Asn His Trp Pro Phe Phe Asn Thr Arg Ile Gly Met Leu Glu Met
        755                 760                 765

Val Phe Ser Lys Thr Asp Ser Trp Leu Ser Glu Tyr Tyr Asp Gln Arg
        770                 775                 780

Leu Val Lys Lys Glu Leu Trp Tyr Leu Gly Glu Ser Leu Arg Lys Gln
785                 790                 795                 800

Leu Ser Glu Asp Ile Ala Thr Val Leu Arg Leu Ser Gly Lys Gly Asp
                805                 810                 815

Gln Leu Met Ser Asp Leu Pro Trp Val Ala Glu Ser Ile Ala Leu Arg
            820                 825                 830

Asn Val Tyr Thr Asp Pro Leu Asn Leu Gln Val Glu Leu Leu Arg
            835                 840                 845
```

-continued

```
Arg Leu Arg Ala Asp Pro Glu His Pro Asn Pro Asp Ile Glu Gln Ala
850                 855                 860

Leu Met Ile Thr Ile Thr Gly Ile Ala Ala Gly Met Arg Asn Thr Gly
865                 870                 875                 880

<210> SEQ ID NO 7
<211> LENGTH: 3543
<212> TYPE: DNA
<213> ORGANISM: Issatchenkia orientalis
<220> FEATURE:
<221> NAME/KEY: CDS
<222> LOCATION: (1)..(3543)

<400> SEQUENCE: 7 atg tca act gtg gaa gat cac tcc tcc cta cat aaa ttg aga aag gaa      48
Met Ser Thr Val Glu Asp His Ser Ser Leu His Lys Leu Arg Lys Glu
1               5                   10                  15 tct gag att ctt tcc aat gca aac aaa atc tta gtg gct aat aga ggt      96
Ser Glu Ile Leu Ser Asn Ala Asn Lys Ile Leu Val Ala Asn Arg Gly
            20                  25                  30 gaa att cca att aga att ttc agg tca gcc cat gaa ttg tca atg cat     144
Glu Ile Pro Ile Arg Ile Phe Arg Ser Ala His Glu Leu Ser Met His
        35                  40                  45 act gtg gcg atc tat tcc cat gaa gat cgg ttg tcc atg cat agg ttg     192
Thr Val Ala Ile Tyr Ser His Glu Asp Arg Leu Ser Met His Arg Leu
    50                  55                  60 aag gcc gac gag gct tat gca atc ggt aag act ggt caa tat tcg cca     240
Lys Ala Asp Glu Ala Tyr Ala Ile Gly Lys Thr Gly Gln Tyr Ser Pro
65                  70                  75                  80 gtt caa gct tat cta caa att gac gaa att atc aaa ata gca aag gaa     288
Val Gln Ala Tyr Leu Gln Ile Asp Glu Ile Ile Lys Ile Ala Lys Glu
                85                  90                  95 cat gat gtt tcc atg atc cat cca ggt tat ggt ttc tta tct gaa aac     336
His Asp Val Ser Met Ile His Pro Gly Tyr Gly Phe Leu Ser Glu Asn
            100                 105                 110 tcc gaa ttc gca aag aag gtt gaa gaa tcc ggt atg att tgg gtt ggg     384
Ser Glu Phe Ala Lys Lys Val Glu Glu Ser Gly Met Ile Trp Val Gly
        115                 120                 125 cct cct gct gaa gtt att gat tct gtt ggt gac aag gtt tct gca aga     432
Pro Pro Ala Glu Val Ile Asp Ser Val Gly Asp Lys Val Ser Ala Arg
    130                 135                 140 aat ttg gca att aaa tgt gac gtt cct gtt gtt cct ggt acc gat ggt     480
Asn Leu Ala Ile Lys Cys Asp Val Pro Val Val Pro Gly Thr Asp Gly
145                 150                 155                 160 cca att gaa gac att gaa cag gct aaa cag ttt gtg gaa caa tat ggt     528
Pro Ile Glu Asp Ile Glu Gln Ala Lys Gln Phe Val Glu Gln Tyr Gly
                165                 170                 175 tat cct gtc att ata aag gct gca ttt ggt ggt ggt gga aga ggt atg     576
Tyr Pro Val Ile Ile Lys Ala Ala Phe Gly Gly Gly Gly Arg Gly Met
            180                 185                 190 aga gtt gtt aga gaa ggt gat gat ata gtt gat gct ttc caa aga gcg     624
Arg Val Val Arg Glu Gly Asp Asp Ile Val Asp Ala Phe Gln Arg Ala
        195                 200                 205 tca tct gaa gca aag tct gcc ttt ggt aat ggt act tgt ttt att gaa     672
Ser Ser Glu Ala Lys Ser Ala Phe Gly Asn Gly Thr Cys Phe Ile Glu
    210                 215                 220 aga ttt ttg gat aag cca aaa cat att gag gtt caa tta ttg gct gat     720
Arg Phe Leu Asp Lys Pro Lys His Ile Glu Val Gln Leu Leu Ala Asp
225                 230                 235                 240 aat tat ggt aac aca atc cat ctc ttt gaa aga gat tgt tct gtt caa     768
Asn Tyr Gly Asn Thr Ile His Leu Phe Glu Arg Asp Cys Ser Val Gln
```

```
                    245                 250                 255
aga aga cat caa aag gtt gtt gaa att gca cct gcc aaa act tta cct       816
Arg Arg His Gln Lys Val Val Glu Ile Ala Pro Ala Lys Thr Leu Pro
            260                 265                 270 gtt gaa gtt aga aat gct ata tta aag gat gct gta acg tta gct aaa       864
Val Glu Val Arg Asn Ala Ile Leu Lys Asp Ala Val Thr Leu Ala Lys
                275                 280                 285 acc gct aac tat aga aat gct ggt act gca gaa ttt tta gtt gat tcc       912
Thr Ala Asn Tyr Arg Asn Ala Gly Thr Ala Glu Phe Leu Val Asp Ser
        290                 295                 300 caa aac aga cat tat ttt att gaa att aat cca aga att caa gtt gaa       960
Gln Asn Arg His Tyr Phe Ile Glu Ile Asn Pro Arg Ile Gln Val Glu
305                 310                 315                 320 cat aca att act gaa gaa atc acg ggt gtt gat att gtt gcc gct caa      1008
His Thr Ile Thr Glu Glu Ile Thr Gly Val Asp Ile Val Ala Ala Gln
                325                 330                 335 att caa att gct gca ggt gca tca ttg gaa caa ttg ggt cta tta caa      1056
Ile Gln Ile Ala Ala Gly Ala Ser Leu Glu Gln Leu Gly Leu Leu Gln
            340                 345                 350 aac aaa att aca act aga ggt ttt gca att caa tgt aga att aca acc      1104
Asn Lys Ile Thr Thr Arg Gly Phe Ala Ile Gln Cys Arg Ile Thr Thr
        355                 360                 365 gag gat cct gct aag aat ttt gcc cca gat aca ggt aaa att gag gtt      1152
Glu Asp Pro Ala Lys Asn Phe Ala Pro Asp Thr Gly Lys Ile Glu Val
370                 375                 380 tat aga tct gca ggt ggt aac ggt gtc aga tta gat ggt ggt aat ggg      1200
Tyr Arg Ser Ala Gly Gly Asn Gly Val Arg Leu Asp Gly Gly Asn Gly
385                 390                 395                 400 ttt gcc ggt gct gtt ata tct cct cat tat gac tcg atg ttg gtt aaa      1248
Phe Ala Gly Ala Val Ile Ser Pro His Tyr Asp Ser Met Leu Val Lys
                405                 410                 415 tgt tca aca tct ggt tct aac tat gaa att gcc aga aga aag atg att      1296
Cys Ser Thr Ser Gly Ser Asn Tyr Glu Ile Ala Arg Arg Lys Met Ile
            420                 425                 430 aga gct tta gtt gaa ttt aga atc aga ggt gtc aag acc aat att cct      1344
Arg Ala Leu Val Glu Phe Arg Ile Arg Gly Val Lys Thr Asn Ile Pro
        435                 440                 445 ttc tta ttg gca ttg cta act cat cca gtt ttc att tcg ggt gat tgt      1392
Phe Leu Leu Ala Leu Leu Thr His Pro Val Phe Ile Ser Gly Asp Cys
    450                 455                 460 tgg aca act ttt att gat gat acc cct tcg tta ttc gaa atg gtt tct      1440
Trp Thr Thr Phe Ile Asp Asp Thr Pro Ser Leu Phe Glu Met Val Ser
465                 470                 475                 480 tca aag aat aga gcc caa aaa tta ttg gca tat att ggt gac ttg tgt      1488
Ser Lys Asn Arg Ala Gln Lys Leu Leu Ala Tyr Ile Gly Asp Leu Cys
                485                 490                 495 gtc aat ggt tct tca att aaa ggt caa att ggt ttc cct aaa ttg aac      1536
Val Asn Gly Ser Ser Ile Lys Gly Gln Ile Gly Phe Pro Lys Leu Asn
            500                 505                 510 aag gaa gca gaa atc cca gat ttg ttg gat cca aat gat gag gtt att      1584
Lys Glu Ala Glu Ile Pro Asp Leu Leu Asp Pro Asn Asp Glu Val Ile
        515                 520                 525 gat gtt tct aaa cct tct acc aat ggt cta aga ccg tat cta tta aag      1632
Asp Val Ser Lys Pro Ser Thr Asn Gly Leu Arg Pro Tyr Leu Leu Lys
    530                 535                 540 tat gga cca gat gcg ttt tcc aaa aaa gtt cgt gaa ttc gat ggt tgt      1680
Tyr Gly Pro Asp Ala Phe Ser Lys Lys Val Arg Glu Phe Asp Gly Cys
545                 550                 555                 560 atg att atg gat acc acc tgg aga gat gca cat caa tca tta ttg gct      1728
```

```
                Met Ile Met Asp Thr Thr Trp Arg Asp Ala His Gln Ser Leu Leu Ala
                                    565                 570                 575 aca aga gtt aga act att gat tta ctg aga att gct cca acg act agt         1776
Thr Arg Val Arg Thr Ile Asp Leu Leu Arg Ile Ala Pro Thr Thr Ser
            580                 585                 590 cat gcc tta caa aat gca ttt gca tta gaa tgt tgg ggt ggc gca aca         1824
His Ala Leu Gln Asn Ala Phe Ala Leu Glu Cys Trp Gly Gly Ala Thr
                595                 600                 605 ttt gat gtt gcg atg agg ttc ctc tat gaa gat cct tgg gag aga tta         1872
Phe Asp Val Ala Met Arg Phe Leu Tyr Glu Asp Pro Trp Glu Arg Leu
            610                 615                 620 aga caa ctt aga aag gca gtt cca aat att cct ttc caa atg tta ttg         1920
Arg Gln Leu Arg Lys Ala Val Pro Asn Ile Pro Phe Gln Met Leu Leu
625                 630                 635                 640 aga ggt gct aat ggt gtt gct tat tcg tca tta cct gat aat gca att         1968
Arg Gly Ala Asn Gly Val Ala Tyr Ser Ser Leu Pro Asp Asn Ala Ile
            645                 650                 655 gat cat ttt gtt aag caa gca aag gat aat ggt gtt gat att ttc aga         2016
Asp His Phe Val Lys Gln Ala Lys Asp Asn Gly Val Asp Ile Phe Arg
                660                 665                 670 gtc ttt gat gct ttg aac gat ttg gaa caa ttg aag gtt ggt gtt gat         2064
Val Phe Asp Ala Leu Asn Asp Leu Glu Gln Leu Lys Val Gly Val Asp
            675                 680                 685 gct gtc aag aaa gcc gga ggt gtt gtt gaa gct aca gtt tgt tac tca         2112
Ala Val Lys Lys Ala Gly Gly Val Val Glu Ala Thr Val Cys Tyr Ser
        690                 695                 700 ggt gat atg tta att cca ggt aaa aag tat aac ttg gat tat tat tta         2160
Gly Asp Met Leu Ile Pro Gly Lys Lys Tyr Asn Leu Asp Tyr Tyr Leu
705                 710                 715                 720 gag act gtt gga aag att gtg gaa atg ggt acc cat att tta ggt att         2208
Glu Thr Val Gly Lys Ile Val Glu Met Gly Thr His Ile Leu Gly Ile
            725                 730                 735 aag gat atg gct ggc acg tta aag cca aag gct gct aag ttg ttg att         2256
Lys Asp Met Ala Gly Thr Leu Lys Pro Lys Ala Ala Lys Leu Leu Ile
                740                 745                 750 ggc tcg atc aga tca aaa tac cct gac ttg gtt atc cat gtc cat acc         2304
Gly Ser Ile Arg Ser Lys Tyr Pro Asp Leu Val Ile His Val His Thr
            755                 760                 765 cat gac tct gct ggt acc ggt att tca act tat gtt gca tgc gca ttg         2352
His Asp Ser Ala Gly Thr Gly Ile Ser Thr Tyr Val Ala Cys Ala Leu
        770                 775                 780 gca ggt gcc gac att gtc gat tgt gca atc aat tcg atg tct ggt tta         2400
Ala Gly Ala Asp Ile Val Asp Cys Ala Ile Asn Ser Met Ser Gly Leu
785                 790                 795                 800 acc tct caa cct tca atg agt gct ttt att gct gct tta gat ggt gat         2448
Thr Ser Gln Pro Ser Met Ser Ala Phe Ile Ala Ala Leu Asp Gly Asp
            805                 810                 815 atc gaa act ggt gtt cca gaa cat ttt gca aga caa tta gat gca tac         2496
Ile Glu Thr Gly Val Pro Glu His Phe Ala Arg Gln Leu Asp Ala Tyr
                820                 825                 830 tgg gca gaa atg aga ttg tta tac tca tgt ttc gaa gcc gac ttg aag         2544
Trp Ala Glu Met Arg Leu Leu Tyr Ser Cys Phe Glu Ala Asp Leu Lys
            835                 840                 845 gga cca gac cca gaa gtt tat aaa cat gaa att cca ggt gga cag ttg         2592
Gly Pro Asp Pro Glu Val Tyr Lys His Glu Ile Pro Gly Gly Gln Leu
        850                 855                 860 act aac cta atc ttc caa gcc caa caa gtt ggt ttg ggt gaa caa tgg         2640
Thr Asn Leu Ile Phe Gln Ala Gln Gln Val Gly Leu Gly Glu Gln Trp
865                 870                 875                 880
```

| | | |
|---|---|---|
| gaa gaa act aag aag aag tat gaa gat gct aac atg ttg ttg ggt gat<br>Glu Glu Thr Lys Lys Lys Tyr Glu Asp Ala Asn Met Leu Leu Gly Asp<br>885 890 895 | | 2688 |
| att gtc aag gtt acc cca acc tcc aag gtt gtt ggt gat tta gcc caa<br>Ile Val Lys Val Thr Pro Thr Ser Lys Val Val Gly Asp Leu Ala Gln<br>900 905 910 | | 2736 |
| ttt atg gtt tct aat aaa tta gaa aaa gaa gat gtt gaa aaa ctt gct<br>Phe Met Val Ser Asn Lys Leu Glu Lys Glu Asp Val Glu Lys Leu Ala<br>915 920 925 | | 2784 |
| aat gaa tta gat ttc cca gat tca gtt ctt gat ttc ttt gaa gga tta<br>Asn Glu Leu Asp Phe Pro Asp Ser Val Leu Asp Phe Phe Glu Gly Leu<br>930 935 940 | | 2832 |
| atg ggt aca cca tat ggt gga ttc cca gag cct ttg aga aca aat gtc<br>Met Gly Thr Pro Tyr Gly Gly Phe Pro Glu Pro Leu Arg Thr Asn Val<br>945 950 955 960 | | 2880 |
| att tcc ggc aag aga aga aaa tta aag ggt aga cca ggt tta gaa tta<br>Ile Ser Gly Lys Arg Arg Lys Leu Lys Gly Arg Pro Gly Leu Glu Leu<br>965 970 975 | | 2928 |
| gaa cct ttc aac ctc gag gaa atc aga gaa aat ttg gtt tcc aga ttt<br>Glu Pro Phe Asn Leu Glu Glu Ile Arg Glu Asn Leu Val Ser Arg Phe<br>980 985 990 | | 2976 |
| ggt cca ggt att act gaa tgt gat gtt gca tct tat aac atg tat cca<br>Gly Pro Gly Ile Thr Glu Cys Asp Val Ala Ser Tyr Asn Met Tyr Pro<br>995 1000 1005 | | 3024 |
| aag gtt tac gag caa tat cgt aag gtg gtt gaa aaa tat ggt gat<br>Lys Val Tyr Glu Gln Tyr Arg Lys Val Val Glu Lys Tyr Gly Asp<br>1010 1015 1020 | | 3069 |
| tta tct gtt tta cca aca aaa gca ttt ttg gct cct cca act att<br>Leu Ser Val Leu Pro Thr Lys Ala Phe Leu Ala Pro Pro Thr Ile<br>1025 1030 1035 | | 3114 |
| ggt gaa gaa gtt cat gtg gaa att gag caa ggt aag act ttg att<br>Gly Glu Glu Val His Val Glu Ile Glu Gln Gly Lys Thr Leu Ile<br>1040 1045 1050 | | 3159 |
| att aag tta tta gcc att tct gac ttg tct aaa tct cat ggt aca<br>Ile Lys Leu Leu Ala Ile Ser Asp Leu Ser Lys Ser His Gly Thr<br>1055 1060 1065 | | 3204 |
| aga gaa gta tac ttt gaa ttg aat ggt gaa atg aga aag gtt aca<br>Arg Glu Val Tyr Phe Glu Leu Asn Gly Glu Met Arg Lys Val Thr<br>1070 1075 1080 | | 3249 |
| att gaa gat aaa aca gct gca att gag act gtt aca aga gca aag<br>Ile Glu Asp Lys Thr Ala Ala Ile Glu Thr Val Thr Arg Ala Lys<br>1085 1090 1095 | | 3294 |
| gct gac gga cac aat cca aat gaa gtt ggt gcg cca atg gct ggt<br>Ala Asp Gly His Asn Pro Asn Glu Val Gly Ala Pro Met Ala Gly<br>1100 1105 1110 | | 3339 |
| gtc gtt gtt gaa gtt aga gtg aag cat gga aca gaa gtt aag aag<br>Val Val Val Glu Val Arg Val Lys His Gly Thr Glu Val Lys Lys<br>1115 1120 1125 | | 3384 |
| ggt gat cca tta gcc gtt ttg agt gca atg aaa atg gaa atg gtt<br>Gly Asp Pro Leu Ala Val Leu Ser Ala Met Lys Met Glu Met Val<br>1130 1135 1140 | | 3429 |
| att tct gct cct gtt agt ggt agg gtc ggt gaa gtt ttt gtc aac<br>Ile Ser Ala Pro Val Ser Gly Arg Val Gly Glu Val Phe Val Asn<br>1145 1150 1155 | | 3474 |
| gaa ggc gat tcc gtt gat atg ggt gat ttg ctt gtg aaa att gcc<br>Glu Gly Asp Ser Val Asp Met Gly Asp Leu Leu Val Lys Ile Ala<br>1160 1165 1170 | | 3519 |
| aaa gat gaa gcg cca gca gct taa<br>Lys Asp Glu Ala Pro Ala Ala<br>1175 1180 | | 3543 |

<210> SEQ ID NO 8
<211> LENGTH: 1180
<212> TYPE: PRT
<213> ORGANISM: Issatchenkia orientalis

<400> SEQUENCE: 8

```
Met Ser Thr Val Glu Asp His Ser Ser Leu His Lys Leu Arg Lys Glu
1               5                   10                  15

Ser Glu Ile Leu Ser Asn Ala Asn Lys Ile Leu Val Ala Asn Arg Gly
            20                  25                  30

Glu Ile Pro Ile Arg Ile Phe Arg Ser Ala His Glu Leu Ser Met His
        35                  40                  45

Thr Val Ala Ile Tyr Ser His Glu Asp Arg Leu Ser Met His Arg Leu
    50                  55                  60

Lys Ala Asp Glu Ala Tyr Ala Ile Gly Lys Thr Gly Gln Tyr Ser Pro
65                  70                  75                  80

Val Gln Ala Tyr Leu Gln Ile Asp Glu Ile Ile Lys Ile Ala Lys Glu
                85                  90                  95

His Asp Val Ser Met Ile His Pro Gly Tyr Gly Phe Leu Ser Glu Asn
            100                 105                 110

Ser Glu Phe Ala Lys Lys Val Glu Glu Ser Gly Met Ile Trp Val Gly
        115                 120                 125

Pro Pro Ala Glu Val Ile Asp Ser Val Gly Asp Lys Val Ser Ala Arg
    130                 135                 140

Asn Leu Ala Ile Lys Cys Asp Val Pro Val Pro Gly Thr Asp Gly
145                 150                 155                 160

Pro Ile Glu Asp Ile Glu Gln Ala Lys Gln Phe Val Glu Gln Tyr Gly
                165                 170                 175

Tyr Pro Val Ile Ile Lys Ala Ala Phe Gly Gly Gly Arg Gly Met
            180                 185                 190

Arg Val Val Arg Glu Gly Asp Asp Ile Val Asp Ala Phe Gln Arg Ala
        195                 200                 205

Ser Ser Glu Ala Lys Ser Ala Phe Gly Asn Gly Thr Cys Phe Ile Glu
    210                 215                 220

Arg Phe Leu Asp Lys Pro Lys His Ile Glu Val Gln Leu Leu Ala Asp
225                 230                 235                 240

Asn Tyr Gly Asn Thr Ile His Leu Phe Glu Arg Asp Cys Ser Val Gln
                245                 250                 255

Arg Arg His Gln Lys Val Val Ile Ala Pro Ala Lys Thr Leu Pro
            260                 265                 270

Val Glu Val Arg Asn Ala Ile Leu Lys Asp Ala Val Thr Leu Ala Lys
        275                 280                 285

Thr Ala Asn Tyr Arg Asn Ala Gly Thr Ala Glu Phe Leu Val Asp Ser
    290                 295                 300

Gln Asn Arg His Tyr Phe Ile Glu Ile Asn Pro Arg Ile Gln Val Glu
305                 310                 315                 320

His Thr Ile Thr Glu Glu Ile Thr Gly Val Asp Ile Val Ala Ala Gln
                325                 330                 335

Ile Gln Ile Ala Ala Gly Ala Ser Leu Glu Gln Leu Gly Leu Leu Gln
            340                 345                 350

Asn Lys Ile Thr Thr Arg Gly Phe Ala Ile Gln Cys Arg Ile Thr Thr
        355                 360                 365

Glu Asp Pro Ala Lys Asn Phe Ala Pro Asp Thr Gly Lys Ile Glu Val
```

```
              370                 375                 380
Tyr Arg Ser Ala Gly Gly Asn Gly Val Arg Leu Asp Gly Gly Asn Gly
385                 390                 395                 400

Phe Ala Gly Ala Val Ile Ser Pro His Tyr Asp Ser Met Leu Val Lys
                405                 410                 415

Cys Ser Thr Ser Gly Ser Asn Tyr Glu Ile Ala Arg Arg Lys Met Ile
                420                 425                 430

Arg Ala Leu Val Glu Phe Arg Ile Arg Gly Val Lys Thr Asn Ile Pro
            435                 440                 445

Phe Leu Leu Ala Leu Leu Thr His Pro Val Phe Ile Ser Gly Asp Cys
450                 455                 460

Trp Thr Thr Phe Ile Asp Asp Thr Pro Ser Leu Phe Glu Met Val Ser
465                 470                 475                 480

Ser Lys Asn Arg Ala Gln Lys Leu Leu Ala Tyr Ile Gly Asp Leu Cys
                485                 490                 495

Val Asn Gly Ser Ser Ile Lys Gly Gln Ile Gly Phe Pro Lys Leu Asn
                500                 505                 510

Lys Glu Ala Glu Ile Pro Asp Leu Leu Asp Pro Asn Asp Glu Val Ile
            515                 520                 525

Asp Val Ser Lys Pro Ser Thr Asn Gly Leu Arg Pro Tyr Leu Leu Lys
530                 535                 540

Tyr Gly Pro Asp Ala Phe Ser Lys Lys Val Arg Glu Phe Asp Gly Cys
545                 550                 555                 560

Met Ile Met Asp Thr Thr Trp Arg Asp Ala His Gln Ser Leu Leu Ala
                565                 570                 575

Thr Arg Val Arg Thr Ile Asp Leu Leu Arg Ile Ala Pro Thr Thr Ser
            580                 585                 590

His Ala Leu Gln Asn Ala Phe Ala Leu Glu Cys Trp Gly Gly Ala Thr
            595                 600                 605

Phe Asp Val Ala Met Arg Phe Leu Tyr Glu Asp Pro Trp Glu Arg Leu
            610                 615                 620

Arg Gln Leu Arg Lys Ala Val Pro Asn Ile Pro Phe Gln Met Leu Leu
625                 630                 635                 640

Arg Gly Ala Asn Gly Val Ala Tyr Ser Ser Leu Pro Asp Asn Ala Ile
                645                 650                 655

Asp His Phe Val Lys Gln Ala Lys Asp Asn Gly Val Asp Ile Phe Arg
                660                 665                 670

Val Phe Asp Ala Leu Asn Asp Leu Glu Gln Leu Lys Val Gly Val Asp
            675                 680                 685

Ala Val Lys Lys Ala Gly Gly Val Val Glu Ala Thr Val Cys Tyr Ser
            690                 695                 700

Gly Asp Met Leu Ile Pro Gly Lys Lys Tyr Asn Leu Asp Tyr Tyr Leu
705                 710                 715                 720

Glu Thr Val Gly Lys Ile Val Glu Met Gly Thr His Ile Leu Gly Ile
                725                 730                 735

Lys Asp Met Ala Gly Thr Leu Lys Pro Lys Ala Ala Lys Leu Leu Ile
                740                 745                 750

Gly Ser Ile Arg Ser Lys Tyr Pro Asp Leu Val Ile His Val His Thr
            755                 760                 765

His Asp Ser Ala Gly Thr Gly Ile Ser Thr Tyr Val Ala Cys Ala Leu
            770                 775                 780

Ala Gly Ala Asp Ile Val Asp Cys Ala Ile Asn Ser Met Ser Gly Leu
785                 790                 795                 800
```

Thr Ser Gln Pro Ser Met Ser Ala Phe Ile Ala Ala Leu Asp Gly Asp
            805                 810                 815

Ile Glu Thr Gly Val Pro Glu His Phe Ala Arg Gln Leu Asp Ala Tyr
        820                 825                 830

Trp Ala Glu Met Arg Leu Leu Tyr Ser Cys Phe Glu Ala Asp Leu Lys
            835                 840                 845

Gly Pro Asp Pro Glu Val Tyr Lys His Glu Ile Pro Gly Gly Gln Leu
        850                 855                 860

Thr Asn Leu Ile Phe Gln Ala Gln Gln Val Gly Leu Gly Glu Gln Trp
865                 870                 875                 880

Glu Glu Thr Lys Lys Tyr Glu Asp Ala Asn Met Leu Leu Gly Asp
                885                 890                 895

Ile Val Lys Val Thr Pro Thr Ser Lys Val Val Gly Asp Leu Ala Gln
            900                 905                 910

Phe Met Val Ser Asn Lys Leu Glu Lys Glu Asp Val Glu Lys Leu Ala
        915                 920                 925

Asn Glu Leu Asp Phe Pro Asp Ser Val Leu Asp Phe Phe Glu Gly Leu
    930                 935                 940

Met Gly Thr Pro Tyr Gly Gly Phe Pro Glu Pro Leu Arg Thr Asn Val
945                 950                 955                 960

Ile Ser Gly Lys Arg Arg Lys Leu Lys Gly Arg Pro Gly Leu Glu Leu
                965                 970                 975

Glu Pro Phe Asn Leu Glu Glu Ile Arg Glu Asn Leu Val Ser Arg Phe
            980                 985                 990

Gly Pro Gly Ile Thr Glu Cys Asp Val Ala Ser Tyr Asn Met Tyr Pro
        995                 1000                1005

Lys Val Tyr Glu Gln Tyr Arg Lys Val Val Glu Lys Tyr Gly Asp
    1010                1015                1020

Leu Ser Val Leu Pro Thr Lys Ala Phe Leu Ala Pro Pro Thr Ile
    1025                1030                1035

Gly Glu Glu Val His Val Glu Ile Glu Gln Gly Lys Thr Leu Ile
    1040                1045                1050

Ile Lys Leu Leu Ala Ile Ser Asp Leu Ser Lys Ser His Gly Thr
    1055                1060                1065

Arg Glu Val Tyr Phe Glu Leu Asn Gly Glu Met Arg Lys Val Thr
    1070                1075                1080

Ile Glu Asp Lys Thr Ala Ala Ile Glu Thr Val Thr Arg Ala Lys
    1085                1090                1095

Ala Asp Gly His Asn Pro Asn Glu Val Gly Ala Pro Met Ala Gly
    1100                1105                1110

Val Val Val Glu Val Arg Val Lys His Gly Thr Glu Val Lys Lys
    1115                1120                1125

Gly Asp Pro Leu Ala Val Leu Ser Ala Met Lys Met Glu Met Val
    1130                1135                1140

Ile Ser Ala Pro Val Ser Gly Arg Val Gly Glu Val Phe Val Asn
    1145                1150                1155

Glu Gly Asp Ser Val Asp Met Gly Asp Leu Leu Val Lys Ile Ala
    1160                1165                1170

Lys Asp Glu Ala Pro Ala Ala
    1175                1180

<210> SEQ ID NO 9
<211> LENGTH: 3537

```
<212> TYPE: DNA
<213> ORGANISM: Saccharomyces cerevisiae
<220> FEATURE:
<221> NAME/KEY: CDS
<222> LOCATION: (1)..(3537)

<400> SEQUENCE: 9 atg tcg caa aga aaa ttc gcc ggc ttg aga gat aac ttc aat ctc ttg      48
Met Ser Gln Arg Lys Phe Ala Gly Leu Arg Asp Asn Phe Asn Leu Leu
1               5                   10                  15 ggt gaa aag aac aaa ata ttg gtg gct aat aga gga gaa att cca atc      96
Gly Glu Lys Asn Lys Ile Leu Val Ala Asn Arg Gly Glu Ile Pro Ile
            20                  25                  30 aga att ttt cgt acc gct cat gaa ctg tct atg cag acg gta gct ata     144
Arg Ile Phe Arg Thr Ala His Glu Leu Ser Met Gln Thr Val Ala Ile
        35                  40                  45 tat tct cat gaa gat cgt ctt tca acg cac aaa caa aag gct gac gaa     192
Tyr Ser His Glu Asp Arg Leu Ser Thr His Lys Gln Lys Ala Asp Glu
    50                  55                  60 gca tac gtc ata ggt gaa gta ggc caa tat acc ccc gtc ggc gct tat     240
Ala Tyr Val Ile Gly Glu Val Gly Gln Tyr Thr Pro Val Gly Ala Tyr
65                  70                  75                  80 ttg gcc att gac gaa atc att tcc att gcc caa aaa cac cag gta gat     288
Leu Ala Ile Asp Glu Ile Ile Ser Ile Ala Gln Lys His Gln Val Asp
                85                  90                  95 ttc atc cat cca ggt tat ggg ttc ttg tct gaa aat tcg gaa ttt gcc     336
Phe Ile His Pro Gly Tyr Gly Phe Leu Ser Glu Asn Ser Glu Phe Ala
            100                 105                 110 gac aaa gta gtg aag gcc ggt atc act tgg att ggc cct cca gct gaa     384
Asp Lys Val Val Lys Ala Gly Ile Thr Trp Ile Gly Pro Pro Ala Glu
        115                 120                 125 gtt att gac tcc gtg ggt gat aag gtc tca gct aga aac ctg gca gca     432
Val Ile Asp Ser Val Gly Asp Lys Val Ser Ala Arg Asn Leu Ala Ala
    130                 135                 140 aaa gct aat gtg ccc acc gtt cct ggt aca cca ggt cct ata gaa act     480
Lys Ala Asn Val Pro Thr Val Pro Gly Thr Pro Gly Pro Ile Glu Thr
145                 150                 155                 160 gta gag gaa gca ctt gac ttc gtc aat gaa tac ggc tac ccg gtg atc     528
Val Glu Glu Ala Leu Asp Phe Val Asn Glu Tyr Gly Tyr Pro Val Ile
                165                 170                 175 att aag gcc gcc ttt ggt ggt ggt gga aga ggt atg aga gtc gtt aga     576
Ile Lys Ala Ala Phe Gly Gly Gly Gly Arg Gly Met Arg Val Val Arg
            180                 185                 190 gaa ggt gac gac gtg gca gat gcc ttt caa cgt gct acc tcc gaa gcc     624
Glu Gly Asp Asp Val Ala Asp Ala Phe Gln Arg Ala Thr Ser Glu Ala
        195                 200                 205 cgt act gcc ttc ggt aat ggt acc tgc ttt gtg gaa aga ttc ttg gac     672
Arg Thr Ala Phe Gly Asn Gly Thr Cys Phe Val Glu Arg Phe Leu Asp
    210                 215                 220 aag cca aag cat att gaa gtt caa ttg ttg gcc gat aac cac gga aac     720
Lys Pro Lys His Ile Glu Val Gln Leu Leu Ala Asp Asn His Gly Asn
225                 230                 235                 240 gtg gtt cat ctt ttc gaa aga gac tgt tcc gtg cag aga aga cac caa     768
Val Val His Leu Phe Glu Arg Asp Cys Ser Val Gln Arg Arg His Gln
                245                 250                 255 aag gtt gtc gaa gtg gcc cca gca aag act tta ccc cgt gaa gtc cgt     816
Lys Val Val Glu Val Ala Pro Ala Lys Thr Leu Pro Arg Glu Val Arg
            260                 265                 270 gac gcc att ttg aca gat gca gtt aaa ttg gcc aaa gag tgt ggc tac     864
Asp Ala Ile Leu Thr Asp Ala Val Lys Leu Ala Lys Glu Cys Gly Tyr
        275                 280                 285
```

```
aga aat gcg ggt act gct gaa ttc ttg gtt gat aac caa aat aga cac      912
Arg Asn Ala Gly Thr Ala Glu Phe Leu Val Asp Asn Gln Asn Arg His
    290             295                 300 tat ttc att gaa att aat cca aga atc caa gtg gaa cat acc atc aca      960
Tyr Phe Ile Glu Ile Asn Pro Arg Ile Gln Val Glu His Thr Ile Thr
305             310                 315                 320 gaa gaa att acc ggt ata gat att gtg gcg gct cag atc caa att gcg     1008
Glu Glu Ile Thr Gly Ile Asp Ile Val Ala Ala Gln Ile Gln Ile Ala
            325                 330                 335 gca ggt gcc tct cta ccc cag ctg ggc cta ttc cag gac aaa att acg     1056
Ala Gly Ala Ser Leu Pro Gln Leu Gly Leu Phe Gln Asp Lys Ile Thr
        340                 345                 350 act cgt ggc ttt gcc att cag tgc cgt att acc acg gaa gac cct gct     1104
Thr Arg Gly Phe Ala Ile Gln Cys Arg Ile Thr Thr Glu Asp Pro Ala
    355                 360                 365 aag aac ttc caa cca gat acc ggt aga ata gaa gtg tac cgt tct gca     1152
Lys Asn Phe Gln Pro Asp Thr Gly Arg Ile Glu Val Tyr Arg Ser Ala
370             375                 380 ggt ggt aat ggt gtt aga ctg gat ggt ggt aac gcc tat gca gga aca     1200
Gly Gly Asn Gly Val Arg Leu Asp Gly Gly Asn Ala Tyr Ala Gly Thr
385             390                 395                 400 ata atc tca cct cat tac gac tca atg ctg gtc aaa tgc tca tgc tcc     1248
Ile Ile Ser Pro His Tyr Asp Ser Met Leu Val Lys Cys Ser Cys Ser
            405                 410                 415 ggt tcc acc tac gaa atc gtt cgt aga aaa atg att cgt gca tta atc     1296
Gly Ser Thr Tyr Glu Ile Val Arg Arg Lys Met Ile Arg Ala Leu Ile
        420                 425                 430 gag ttc aga att aga ggt gtc aag acc aac att ccc ttc cta ttg act     1344
Glu Phe Arg Ile Arg Gly Val Lys Thr Asn Ile Pro Phe Leu Leu Thr
    435                 440                 445 ctt ttg acc aat cca gta ttt att gag ggt aca tac tgg acg act ttt     1392
Leu Leu Thr Asn Pro Val Phe Ile Glu Gly Thr Tyr Trp Thr Thr Phe
450             455                 460 att gac gac acc cca caa ctg ttc caa atg gtt tca tca caa aac aga     1440
Ile Asp Asp Thr Pro Gln Leu Phe Gln Met Val Ser Ser Gln Asn Arg
465             470                 475                 480 gcc caa aaa ctt tta cat tac ctc gcc gac gtg gca gtc aat ggt tca     1488
Ala Gln Lys Leu Leu His Tyr Leu Ala Asp Val Ala Val Asn Gly Ser
            485                 490                 495 tct atc aag ggt caa att ggc ttg cca aaa tta aaa tca aat cca agt     1536
Ser Ile Lys Gly Gln Ile Gly Leu Pro Lys Leu Lys Ser Asn Pro Ser
        500                 505                 510 gtc ccc cat ttg cac gat gct cag ggc aat gtc atc aac gtt aca aag     1584
Val Pro His Leu His Asp Ala Gln Gly Asn Val Ile Asn Val Thr Lys
    515                 520                 525 tct gca cca cca tcc gga tgg agg caa gtg cta cta gaa aag ggg cca     1632
Ser Ala Pro Pro Ser Gly Trp Arg Gln Val Leu Leu Glu Lys Gly Pro
530             535                 540 gct gaa ttt gcc aga caa gtt aga cag ttc aat ggt act tta ttg atg     1680
Ala Glu Phe Ala Arg Gln Val Arg Gln Phe Asn Gly Thr Leu Leu Met
545             550                 555                 560 gac acc acc tgg aga gac gct cat caa tct cta ctt gca aca aga gtc     1728
Asp Thr Thr Trp Arg Asp Ala His Gln Ser Leu Leu Ala Thr Arg Val
            565                 570                 575 aga acc cac gat ttg gct aca atc gct cca aca acc gca cat gcc ctt     1776
Arg Thr His Asp Leu Ala Thr Ile Ala Pro Thr Thr Ala His Ala Leu
        580                 585                 590 gca ggt cgt ttc gcc tta gaa tgt tgg ggt ggt gcc aca ttc gat gtt     1824
Ala Gly Arg Phe Ala Leu Glu Cys Trp Gly Gly Ala Thr Phe Asp Val
```

-continued

```
                  595                 600                 605
gca atg aga ttt ttg cat gag gat cca tgg gaa cgt ttg aga aaa tta      1872
Ala Met Arg Phe Leu His Glu Asp Pro Trp Glu Arg Leu Arg Lys Leu
    610                 615                 620 aga tct ctg gtg cct aat att cca ttc caa atg tta ttg cgt ggt gcc      1920
Arg Ser Leu Val Pro Asn Ile Pro Phe Gln Met Leu Leu Arg Gly Ala
625                 630                 635                 640 aat ggt gtg gct tat tct tca ttg cct gac aat gct att gac cat ttc      1968
Asn Gly Val Ala Tyr Ser Ser Leu Pro Asp Asn Ala Ile Asp His Phe
                645                 650                 655 gtc aag caa gcc aag gat aat ggt gtt gat ata ttt aga gtc ttt gat      2016
Val Lys Gln Ala Lys Asp Asn Gly Val Asp Ile Phe Arg Val Phe Asp
        660                 665                 670 gcc tta aat gac ttg gaa caa ttg aag gtc ggt gta gat gct gtg aag      2064
Ala Leu Asn Asp Leu Glu Gln Leu Lys Val Gly Val Asp Ala Val Lys
    675                 680                 685 aag gca ggt ggt gtt gta gaa gcc act gtt tgt ttc tct ggg gat atg      2112
Lys Ala Gly Gly Val Val Glu Ala Thr Val Cys Phe Ser Gly Asp Met
690                 695                 700 ctt cag cca ggc aag aaa tac aat ttg gat tac tac ttg gaa att gct      2160
Leu Gln Pro Gly Lys Lys Tyr Asn Leu Asp Tyr Tyr Leu Glu Ile Ala
705                 710                 715                 720 gaa aaa att gtc caa atg ggc act cat atc ctg ggt atc aaa gat atg      2208
Glu Lys Ile Val Gln Met Gly Thr His Ile Leu Gly Ile Lys Asp Met
                725                 730                 735 gca ggt acc atg aag cca gca gct gcc aaa cta ctg att gga tct ttg      2256
Ala Gly Thr Met Lys Pro Ala Ala Ala Lys Leu Leu Ile Gly Ser Leu
        740                 745                 750 agg gct aag tac cct gat ctc cca ata cat gtt cac act cac gat tct      2304
Arg Ala Lys Tyr Pro Asp Leu Pro Ile His Val His Thr His Asp Ser
    755                 760                 765 gca ggt act gct gtt gca tca atg act gcg tgt gct ctg gcg ggc gcc      2352
Ala Gly Thr Ala Val Ala Ser Met Thr Ala Cys Ala Leu Ala Gly Ala
770                 775                 780 gat gtc gtt gat gtt gcc atc aac tca atg tct ggt tta act tca caa      2400
Asp Val Val Asp Val Ala Ile Asn Ser Met Ser Gly Leu Thr Ser Gln
785                 790                 795                 800 cca tca atc aat gct ctg ttg gct tca tta gaa ggt aat att gac act      2448
Pro Ser Ile Asn Ala Leu Leu Ala Ser Leu Glu Gly Asn Ile Asp Thr
                805                 810                 815 ggt att aac gtt gag cat gtc cgt gaa cta gat gca tat tgg gca gag      2496
Gly Ile Asn Val Glu His Val Arg Glu Leu Asp Ala Tyr Trp Ala Glu
        820                 825                 830 atg aga ttg tta tac tct tgt ttc gag gct gac ttg aag ggc cca gat      2544
Met Arg Leu Leu Tyr Ser Cys Phe Glu Ala Asp Leu Lys Gly Pro Asp
    835                 840                 845 cca gaa gtt tat caa cat gaa atc cca ggt ggt caa ttg aca aac ttg      2592
Pro Glu Val Tyr Gln His Glu Ile Pro Gly Gly Gln Leu Thr Asn Leu
850                 855                 860 ttg ttt caa gcc caa caa ttg ggt ctt gga gaa caa tgg gcc gaa aca      2640
Leu Phe Gln Ala Gln Gln Leu Gly Leu Gly Glu Gln Trp Ala Glu Thr
865                 870                 875                 880 aaa aga gct tac aga gaa gcc aat tat tta ttg ggt gat att gtc aaa      2688
Lys Arg Ala Tyr Arg Glu Ala Asn Tyr Leu Leu Gly Asp Ile Val Lys
                885                 890                 895 gtt acc cca act tcg aag gtc gtt ggt gat ctg gca caa ttt atg gtc      2736
Val Thr Pro Thr Ser Lys Val Val Gly Asp Leu Ala Gln Phe Met Val
        900                 905                 910 tcc aat aaa tta act tcc gat gat gtg aga cgc ctg gct aat tct ttg      2784
Ser Asn Lys Leu Thr Ser Asp Asp Val Arg Arg Leu Ala Asn Ser Leu
```

```
Ser Asn Lys Leu Thr Ser Asp Asp Val Arg Arg Leu Ala Asn Ser Leu
        915                 920                 925 gat ttc cct gac tct gtt atg gat ttc ttc gaa ggc tta atc ggc caa       2832
Asp Phe Pro Asp Ser Val Met Asp Phe Phe Glu Gly Leu Ile Gly Gln
930                 935                 940 cca tac ggt ggg ttc cca gaa cca ttt aga tca gac gtt tta agg aac       2880
Pro Tyr Gly Gly Phe Pro Glu Pro Phe Arg Ser Asp Val Leu Arg Asn
945                 950                 955                 960 aag aga aga aag ttg act tgt cgt cca ggc ctg gaa cta gag cca ttt       2928
Lys Arg Arg Lys Leu Thr Cys Arg Pro Gly Leu Glu Leu Glu Pro Phe
                965                 970                 975 gat ctc gaa aaa att aga gaa gac ttg cag aat aga ttt ggt gat gtt       2976
Asp Leu Glu Lys Ile Arg Glu Asp Leu Gln Asn Arg Phe Gly Asp Val
            980                 985                 990 gat gag tgc gac gtt gct tct tat aac atg tac cca aga gtt tat gaa       3024
Asp Glu Cys Asp Val Ala Ser Tyr Asn Met Tyr Pro Arg Val Tyr Glu
        995                 1000                1005 gac ttc caa aag atg aga gaa acg tat ggt gat tta tct gta ttg            3069
Asp Phe Gln Lys Met Arg Glu Thr Tyr Gly Asp Leu Ser Val Leu
    1010                1015                1020 cca aca aga agc ttt ttg tct cca cta gag act gac gaa gaa att            3114
Pro Thr Arg Ser Phe Leu Ser Pro Leu Glu Thr Asp Glu Glu Ile
    1025                1030                1035 gaa gtt gta atc gaa caa ggt aaa acg cta att atc aag cta cag            3159
Glu Val Val Ile Glu Gln Gly Lys Thr Leu Ile Ile Lys Leu Gln
    1040                1045                1050 gct gtg ggt gat ttg aac aaa aag acc ggt gaa aga gaa gtt tac            3204
Ala Val Gly Asp Leu Asn Lys Lys Thr Gly Glu Arg Glu Val Tyr
    1055                1060                1065 ttt gat ttg aat ggt gaa atg aga aaa att cgt gtt gct gac aga            3249
Phe Asp Leu Asn Gly Glu Met Arg Lys Ile Arg Val Ala Asp Arg
    1070                1075                1080 tca caa aaa gtg gaa act gtt act aaa tcc aaa gca gac atg cat            3294
Ser Gln Lys Val Glu Thr Val Thr Lys Ser Lys Ala Asp Met His
    1085                1090                1095 gat cca tta cac att ggt gca cca atg gca ggt gtc att gtt gaa            3339
Asp Pro Leu His Ile Gly Ala Pro Met Ala Gly Val Ile Val Glu
    1100                1105                1110 gtt aaa gtt cat aaa gga tca cta ata aag aag ggc caa cct gta            3384
Val Lys Val His Lys Gly Ser Leu Ile Lys Lys Gly Gln Pro Val
    1115                1120                1125 gcc gta tta agc gcc atg aaa atg gaa atg att ata tct tct cca            3429
Ala Val Leu Ser Ala Met Lys Met Glu Met Ile Ile Ser Ser Pro
    1130                1135                1140 tcc gat gga caa gtt aaa gaa gtg ttt gtc tct gat ggt gaa aat            3474
Ser Asp Gly Gln Val Lys Glu Val Phe Val Ser Asp Gly Glu Asn
    1145                1150                1155 gtg gac tct tct gat tta tta gtt cta tta gaa gac caa gtt cct            3519
Val Asp Ser Ser Asp Leu Leu Val Leu Leu Glu Asp Gln Val Pro
    1160                1165                1170 gtt gaa act aag gca taa                                                3537
Val Glu Thr Lys Ala
    1175

<210> SEQ ID NO 10
<211> LENGTH: 1178
<212> TYPE: PRT
<213> ORGANISM: Saccharomyces cerevisiae

<400> SEQUENCE: 10
```

```
Met Ser Gln Arg Lys Phe Ala Gly Leu Arg Asp Asn Phe Asn Leu Leu
1               5                   10                  15

Gly Glu Lys Asn Lys Ile Leu Val Ala Asn Arg Gly Glu Ile Pro Ile
                20                  25                  30

Arg Ile Phe Arg Thr Ala His Glu Leu Ser Met Gln Thr Val Ala Ile
            35                  40                  45

Tyr Ser His Glu Asp Arg Leu Ser Thr His Lys Gln Lys Ala Asp Glu
50                  55                  60

Ala Tyr Val Ile Gly Glu Val Gly Gln Tyr Thr Pro Val Gly Ala Tyr
65                  70                  75                  80

Leu Ala Ile Asp Glu Ile Ile Ser Ile Ala Gln Lys His Gln Val Asp
                85                  90                  95

Phe Ile His Pro Gly Tyr Gly Phe Leu Ser Glu Asn Ser Glu Phe Ala
                100                 105                 110

Asp Lys Val Val Lys Ala Gly Ile Thr Trp Ile Gly Pro Pro Ala Glu
            115                 120                 125

Val Ile Asp Ser Val Gly Asp Lys Val Ser Ala Arg Asn Leu Ala Ala
            130                 135                 140

Lys Ala Asn Val Pro Thr Val Pro Gly Thr Pro Gly Pro Ile Glu Thr
145                 150                 155                 160

Val Glu Glu Ala Leu Asp Phe Val Asn Glu Tyr Gly Tyr Pro Val Ile
                165                 170                 175

Ile Lys Ala Ala Phe Gly Gly Gly Gly Arg Gly Met Arg Val Val Arg
                180                 185                 190

Glu Gly Asp Asp Val Ala Asp Ala Phe Gln Arg Ala Thr Ser Glu Ala
            195                 200                 205

Arg Thr Ala Phe Gly Asn Gly Thr Cys Phe Val Glu Arg Phe Leu Asp
210                 215                 220

Lys Pro Lys His Ile Glu Val Gln Leu Leu Ala Asp Asn His Gly Asn
225                 230                 235                 240

Val Val His Leu Phe Glu Arg Asp Cys Ser Val Gln Arg Arg His Gln
                245                 250                 255

Lys Val Val Glu Val Ala Pro Ala Lys Thr Leu Pro Arg Glu Val Arg
            260                 265                 270

Asp Ala Ile Leu Thr Asp Ala Val Lys Leu Ala Lys Glu Cys Gly Tyr
            275                 280                 285

Arg Asn Ala Gly Thr Ala Glu Phe Leu Val Asp Asn Gln Asn Arg His
290                 295                 300

Tyr Phe Ile Glu Ile Asn Pro Arg Ile Gln Val Glu His Thr Ile Thr
305                 310                 315                 320

Glu Glu Ile Thr Gly Ile Asp Ile Val Ala Ala Gln Ile Gln Ile Ala
                325                 330                 335

Ala Gly Ala Ser Leu Pro Gln Leu Gly Leu Phe Gln Asp Lys Ile Thr
                340                 345                 350

Thr Arg Gly Phe Ala Ile Gln Cys Arg Ile Thr Thr Glu Asp Pro Ala
            355                 360                 365

Lys Asn Phe Gln Pro Asp Thr Gly Arg Ile Glu Val Tyr Arg Ser Ala
            370                 375                 380

Gly Gly Asn Gly Val Arg Leu Asp Gly Gly Asn Ala Tyr Ala Gly Thr
385                 390                 395                 400

Ile Ile Ser Pro His Tyr Asp Ser Met Leu Val Lys Cys Ser Cys Ser
                405                 410                 415

Gly Ser Thr Tyr Glu Ile Val Arg Arg Lys Met Ile Arg Ala Leu Ile
```

```
                420             425             430
Glu Phe Arg Ile Arg Gly Val Lys Thr Asn Ile Pro Phe Leu Leu Thr
            435             440             445
Leu Leu Thr Asn Pro Val Phe Ile Glu Gly Thr Tyr Trp Thr Thr Phe
        450             455             460
Ile Asp Asp Thr Pro Gln Leu Phe Gln Met Val Ser Ser Gln Asn Arg
465             470             475             480
Ala Gln Lys Leu Leu His Tyr Leu Ala Asp Val Ala Val Asn Gly Ser
            485             490             495
Ser Ile Lys Gly Gln Ile Gly Leu Pro Lys Leu Lys Ser Asn Pro Ser
        500             505             510
Val Pro His Leu His Asp Ala Gln Gly Asn Val Ile Asn Val Thr Lys
    515             520             525
Ser Ala Pro Pro Ser Gly Trp Arg Gln Val Leu Glu Lys Gly Pro
    530             535             540
Ala Glu Phe Ala Arg Gln Val Arg Gln Phe Asn Gly Thr Leu Leu Met
545             550             555             560
Asp Thr Thr Trp Arg Asp Ala His Gln Ser Leu Leu Ala Thr Arg Val
            565             570             575
Arg Thr His Asp Leu Ala Thr Ile Ala Pro Thr Thr Ala His Ala Leu
        580             585             590
Ala Gly Arg Phe Ala Leu Glu Cys Trp Gly Gly Ala Thr Phe Asp Val
        595             600             605
Ala Met Arg Phe Leu His Glu Asp Pro Trp Glu Arg Leu Arg Lys Leu
    610             615             620
Arg Ser Leu Val Pro Asn Ile Pro Phe Gln Met Leu Leu Arg Gly Ala
625             630             635             640
Asn Gly Val Ala Tyr Ser Ser Leu Pro Asp Asn Ala Ile Asp His Phe
            645             650             655
Val Lys Gln Ala Lys Asp Asn Gly Val Asp Ile Phe Arg Val Phe Asp
            660             665             670
Ala Leu Asn Asp Leu Glu Gln Leu Lys Val Gly Val Asp Ala Val Lys
        675             680             685
Lys Ala Gly Gly Val Val Glu Ala Thr Val Cys Phe Ser Gly Asp Met
    690             695             700
Leu Gln Pro Gly Lys Lys Tyr Asn Leu Asp Tyr Tyr Leu Glu Ile Ala
705             710             715             720
Glu Lys Ile Val Gln Met Gly Thr His Ile Leu Gly Ile Lys Asp Met
            725             730             735
Ala Gly Thr Met Lys Pro Ala Ala Lys Leu Leu Ile Gly Ser Leu
        740             745             750
Arg Ala Lys Tyr Pro Asp Leu Pro Ile His Val His Thr His Asp Ser
        755             760             765
Ala Gly Thr Ala Val Ala Ser Met Thr Ala Cys Ala Leu Ala Gly Ala
    770             775             780
Asp Val Val Asp Val Ala Ile Asn Ser Met Ser Gly Leu Thr Ser Gln
785             790             795             800
Pro Ser Ile Asn Ala Leu Leu Ala Ser Leu Glu Gly Asn Ile Asp Thr
            805             810             815
Gly Ile Asn Val Glu His Val Arg Glu Leu Asp Ala Tyr Trp Ala Glu
            820             825             830
Met Arg Leu Leu Tyr Ser Cys Phe Glu Ala Asp Leu Lys Gly Pro Asp
        835             840             845
```

```
Pro Glu Val Tyr Gln His Glu Ile Pro Gly Gly Gln Leu Thr Asn Leu
    850                 855                 860

Leu Phe Gln Ala Gln Gln Leu Gly Leu Gly Glu Gln Trp Ala Glu Thr
865                 870                 875                 880

Lys Arg Ala Tyr Arg Glu Ala Asn Tyr Leu Leu Gly Asp Ile Val Lys
                885                 890                 895

Val Thr Pro Thr Ser Lys Val Val Gly Asp Leu Ala Gln Phe Met Val
            900                 905                 910

Ser Asn Lys Leu Thr Ser Asp Asp Val Arg Arg Leu Ala Asn Ser Leu
        915                 920                 925

Asp Phe Pro Asp Ser Val Met Asp Phe Glu Gly Leu Ile Gly Gln
    930                 935                 940

Pro Tyr Gly Gly Phe Pro Glu Pro Phe Arg Ser Asp Val Leu Arg Asn
945                 950                 955                 960

Lys Arg Arg Lys Leu Thr Cys Arg Pro Gly Leu Glu Leu Glu Pro Phe
                965                 970                 975

Asp Leu Glu Lys Ile Arg Glu Asp Leu Gln Asn Arg Phe Gly Asp Val
            980                 985                 990

Asp Glu Cys Asp Val Ala Ser Tyr Asn Met Tyr Pro Arg Val Tyr Glu
        995                 1000                1005

Asp Phe Gln Lys Met Arg Glu Thr Tyr Gly Asp Leu Ser Val Leu
    1010                1015                1020

Pro Thr Arg Ser Phe Leu Ser Pro Leu Glu Thr Asp Glu Glu Ile
    1025                1030                1035

Glu Val Val Ile Glu Gln Gly Lys Thr Leu Ile Ile Lys Leu Gln
    1040                1045                1050

Ala Val Gly Asp Leu Asn Lys Lys Thr Gly Glu Arg Glu Val Tyr
    1055                1060                1065

Phe Asp Leu Asn Gly Glu Met Arg Lys Ile Arg Val Ala Asp Arg
    1070                1075                1080

Ser Gln Lys Val Glu Thr Val Thr Lys Ser Lys Ala Asp Met His
    1085                1090                1095

Asp Pro Leu His Ile Gly Ala Pro Met Ala Gly Val Ile Val Glu
    1100                1105                1110

Val Lys Val His Lys Gly Ser Leu Ile Lys Lys Gly Gln Pro Val
    1115                1120                1125

Ala Val Leu Ser Ala Met Lys Met Glu Met Ile Ile Ser Ser Pro
    1130                1135                1140

Ser Asp Gly Gln Val Lys Glu Val Phe Val Ser Asp Gly Glu Asn
    1145                1150                1155

Val Asp Ser Ser Asp Leu Leu Val Leu Leu Glu Asp Gln Val Pro
    1160                1165                1170

Val Glu Thr Lys Ala
    1175

<210> SEQ ID NO 11
<211> LENGTH: 3528
<212> TYPE: DNA
<213> ORGANISM: Kluyveromyces marxianus
<220> FEATURE:
<221> NAME/KEY: CDS
<222> LOCATION: (1)..(3528)

<400> SEQUENCE: 11 atg tct acc caa aac gat ctg gcc ggg ttg cgt gat aac tcg aac cta        48
```

```
Met Ser Thr Gln Asn Asp Leu Ala Gly Leu Arg Asp Asn Ser Asn Leu
1               5                   10                  15 tta ggt gaa aag aac aag att ctt gtt gcc aac cgt ggt gaa att cca        96
Leu Gly Glu Lys Asn Lys Ile Leu Val Ala Asn Arg Gly Glu Ile Pro
            20                  25                  30 att aga atc ttt aga acg gct cat gaa ctt tcg atg aag act gtt gcg       144
Ile Arg Ile Phe Arg Thr Ala His Glu Leu Ser Met Lys Thr Val Ala
            35                  40                  45 atc tat tcg cac gag gat aga cta tct atg cac aga ttg aag gca gac       192
Ile Tyr Ser His Glu Asp Arg Leu Ser Met His Arg Leu Lys Ala Asp
50                  55                  60 gaa gct tac gtt att ggt gag cca gga aaa tac act cca gtt ggt gcg       240
Glu Ala Tyr Val Ile Gly Glu Pro Gly Lys Tyr Thr Pro Val Gly Ala
65                  70                  75                  80 tat ttg gcg atc gat gag att atc aag att gct caa ttg cac gga gtg       288
Tyr Leu Ala Ile Asp Glu Ile Ile Lys Ile Ala Gln Leu His Gly Val
                85                  90                  95 agc ttc atc cac cct ggt tat ggg ttc tta tcg gaa aac tct gag ttt       336
Ser Phe Ile His Pro Gly Tyr Gly Phe Leu Ser Glu Asn Ser Glu Phe
            100                 105                 110 gcc aag aag gtg gcc gac tct ggt atc acg tgg gtt ggt cct cca gcc       384
Ala Lys Lys Val Ala Asp Ser Gly Ile Thr Trp Val Gly Pro Pro Ala
            115                 120                 125 gat gtg atc gat gct gtt ggt gac aag gtt tct gcc aga aac ttg gcc       432
Asp Val Ile Asp Ala Val Gly Asp Lys Val Ser Ala Arg Asn Leu Ala
130                 135                 140 gag aga gcg gat gtt cca gtg gtt cca ggt acg cct ggt cca ata gag       480
Glu Arg Ala Asp Val Pro Val Val Pro Gly Thr Pro Gly Pro Ile Glu
145                 150                 155                 160 aca gtt gaa gaa gca gtt gaa ttt gtg gag aag tac gga tac cca gtc       528
Thr Val Glu Glu Ala Val Glu Phe Val Glu Lys Tyr Gly Tyr Pro Val
                165                 170                 175 atc atc aag gct gcc ttc ggt ggt ggt ggt cgt ggt atg aga gtt gtt       576
Ile Ile Lys Ala Ala Phe Gly Gly Gly Gly Arg Gly Met Arg Val Val
            180                 185                 190 cgt gaa ggt gat gat atc gcc gat gct ttc caa aga gcc aag tcc gaa       624
Arg Glu Gly Asp Asp Ile Ala Asp Ala Phe Gln Arg Ala Lys Ser Glu
            195                 200                 205 gct gtt act gct ttc ggt aac ggt act tgt ttc gtt gaa aga ttc ttg       672
Ala Val Thr Ala Phe Gly Asn Gly Thr Cys Phe Val Glu Arg Phe Leu
210                 215                 220 gac aag cca aag cac atc gaa gtt cag ttg ttg gct gat cac tac ggt       720
Asp Lys Pro Lys His Ile Glu Val Gln Leu Leu Ala Asp His Tyr Gly
225                 230                 235                 240 aat gtc atc cat cta ttc gaa aga gac tgt tct gtg caa aga aga cat       768
Asn Val Ile His Leu Phe Glu Arg Asp Cys Ser Val Gln Arg Arg His
                245                 250                 255 caa aag gtc gtt gaa gta gcg cca gcc aag act ttg cca gag agc gtg       816
Gln Lys Val Val Glu Val Ala Pro Ala Lys Thr Leu Pro Glu Ser Val
            260                 265                 270 cgt aat gca atc ttg act gac gct gtc aag ttg gct aag gag gca gga       864
Arg Asn Ala Ile Leu Thr Asp Ala Val Lys Leu Ala Lys Glu Ala Gly
            275                 280                 285 tac aga aat gct ggt acc gct gaa ttt ttg gtc gac aac caa aac aga       912
Tyr Arg Asn Ala Gly Thr Ala Glu Phe Leu Val Asp Asn Gln Asn Arg
            290                 295                 300 cac tac ttt att gaa atc aac cca aga att caa gtc gaa cat acc atc       960
His Tyr Phe Ile Glu Ile Asn Pro Arg Ile Gln Val Glu His Thr Ile
305                 310                 315                 320
```

| | | |
|---|---|---|
| acc gaa gaa att acc ggt atc gac att gtc gcc gca caa att caa atc<br>Thr Glu Glu Ile Thr Gly Ile Asp Ile Val Ala Ala Gln Ile Gln Ile<br>325 330 335 | | 1008 |
| gca gca ggt gct tcc ttg gaa caa ttg gga cta ttg caa gat aga atc<br>Ala Ala Gly Ala Ser Leu Glu Gln Leu Gly Leu Leu Gln Asp Arg Ile<br>340 345 350 | | 1056 |
| acc acc cgt ggt ttc gct att caa tgt cgt atc act act gaa gat cct<br>Thr Thr Arg Gly Phe Ala Ile Gln Cys Arg Ile Thr Thr Glu Asp Pro<br>355 360 365 | | 1104 |
| tcc aag aac ttc cag cca gat act ggt cgt atc gat gtt tac cgt tcc<br>Ser Lys Asn Phe Gln Pro Asp Thr Gly Arg Ile Asp Val Tyr Arg Ser<br>370 375 380 | | 1152 |
| gct ggt ggt aac ggt gtc aga ttg gat ggt ggt aac gca ttc gct ggt<br>Ala Gly Gly Asn Gly Val Arg Leu Asp Gly Gly Asn Ala Phe Ala Gly<br>385 390 395 400 | | 1200 |
| tcg gtc att tca cct cat tat gat tcc atg ttg gtc aaa tgt tct tgt<br>Ser Val Ile Ser Pro His Tyr Asp Ser Met Leu Val Lys Cys Ser Cys<br>405 410 415 | | 1248 |
| tcc ggt tcc act tac gaa atc gtt cgt cgt aag atg ttg cgt gcc ttg<br>Ser Gly Ser Thr Tyr Glu Ile Val Arg Arg Lys Met Leu Arg Ala Leu<br>420 425 430 | | 1296 |
| atc gaa ttc aga atc aga ggt gtg aag aca aac att cca ttc ttg cta<br>Ile Glu Phe Arg Ile Arg Gly Val Lys Thr Asn Ile Pro Phe Leu Leu<br>435 440 445 | | 1344 |
| acg ttg ttg act cat cct gtg ttc aag tcc ggt gac tac tgg act acc<br>Thr Leu Leu Thr His Pro Val Phe Lys Ser Gly Asp Tyr Trp Thr Thr<br>450 455 460 | | 1392 |
| ttc atc gat gac act cca caa ttg ttc gaa atg gtt tct tct caa aac<br>Phe Ile Asp Asp Thr Pro Gln Leu Phe Glu Met Val Ser Ser Gln Asn<br>465 470 475 480 | | 1440 |
| aga gca caa aaa cta ttg cac tac ttg gcc gat ctt gcc gtt aac ggt<br>Arg Ala Gln Lys Leu Leu His Tyr Leu Ala Asp Leu Ala Val Asn Gly<br>485 490 495 | | 1488 |
| tca tcg atc aag ggt caa att ggt cta cca aag tta aag act cat cct<br>Ser Ser Ile Lys Gly Gln Ile Gly Leu Pro Lys Leu Lys Thr His Pro<br>500 505 510 | | 1536 |
| act atc cca cat ttg cat aag gcc gat ggc tcc att cta gat gtg tct<br>Thr Ile Pro His Leu His Lys Ala Asp Gly Ser Ile Leu Asp Val Ser<br>515 520 525 | | 1584 |
| gcc aag cct cct gcc ggg tgg aga gat gtt cta ttg caa cac ggc cca<br>Ala Lys Pro Pro Ala Gly Trp Arg Asp Val Leu Leu Gln His Gly Pro<br>530 535 540 | | 1632 |
| gaa gaa ttt gca aag caa gtt aga aag ttc aag ggt act ttg cta atg<br>Glu Glu Phe Ala Lys Gln Val Arg Lys Phe Lys Gly Thr Leu Leu Met<br>545 550 555 560 | | 1680 |
| gac acc acc tgg aga gat gct cat caa tct cta ttg gcc act aga gtc<br>Asp Thr Thr Trp Arg Asp Ala His Gln Ser Leu Leu Ala Thr Arg Val<br>565 570 575 | | 1728 |
| aga act tac gat ttg gct gcc atc gct cca act act gct cat gct ttg<br>Arg Thr Tyr Asp Leu Ala Ala Ile Ala Pro Thr Thr Ala His Ala Leu<br>580 585 590 | | 1776 |
| agc ggt gct ttc gct ttg gaa tgt tgg ggt ggt gcc act ttc gat gtc<br>Ser Gly Ala Phe Ala Leu Glu Cys Trp Gly Gly Ala Thr Phe Asp Val<br>595 600 605 | | 1824 |
| tcc atg aga ttc ttg cac gaa gat cca tgg gaa cgt ttg aga act ttg<br>Ser Met Arg Phe Leu His Glu Asp Pro Trp Glu Arg Leu Arg Thr Leu<br>610 615 620 | | 1872 |
| aga aag ttg gtt cct aac att cca ttc caa atg ttg cta cgt ggt gcc<br>Arg Lys Leu Val Pro Asn Ile Pro Phe Gln Met Leu Leu Arg Gly Ala<br>625 630 635 640 | | 1920 |

-continued

| | | |
|---|---|---|
| aac ggt gtt gca tac tct tct cta cca gat aac gct atc gac cac ttt<br>Asn Gly Val Ala Tyr Ser Ser Leu Pro Asp Asn Ala Ile Asp His Phe<br>645 650 655 | | 1968 |
| gtc aag caa gca aag gat aac ggt gtt gac att ttc aga gtc ttc gat<br>Val Lys Gln Ala Lys Asp Asn Gly Val Asp Ile Phe Arg Val Phe Asp<br>660 665 670 | | 2016 |
| gct cta aac gat ttg gag caa ttg act gtc ggt gtt gac gct gtc aag<br>Ala Leu Asn Asp Leu Glu Gln Leu Thr Val Gly Val Asp Ala Val Lys<br>675 680 685 | | 2064 |
| aag gct ggt ggt gtt gtc gaa gct acc att tgt tac tcc ggt gac atg<br>Lys Ala Gly Gly Val Val Glu Ala Thr Ile Cys Tyr Ser Gly Asp Met<br>690 695 700 | | 2112 |
| cta gca cca ggt aag aag tac aac ctt gac tac tac ttg gac att gtt<br>Leu Ala Pro Gly Lys Lys Tyr Asn Leu Asp Tyr Tyr Leu Asp Ile Val<br>705 710 715 720 | | 2160 |
| gaa caa gtg gtt aag aga ggt acc cat att ctt ggt atc aag gat atg<br>Glu Gln Val Val Lys Arg Gly Thr His Ile Leu Gly Ile Lys Asp Met<br>725 730 735 | | 2208 |
| gca ggt act ttg aag cca tct gct gct aag ctc ttg atc ggt tct atc<br>Ala Gly Thr Leu Lys Pro Ser Ala Ala Lys Leu Leu Ile Gly Ser Ile<br>740 745 750 | | 2256 |
| aga aca aag tac cct gac ttg cca att cac gtc cat acc cat gac tcc<br>Arg Thr Lys Tyr Pro Asp Leu Pro Ile His Val His Thr His Asp Ser<br>755 760 765 | | 2304 |
| gcc ggt acc ggt gtt gct tcc atg gct gca tgt gct ttc gct ggt gct<br>Ala Gly Thr Gly Val Ala Ser Met Ala Ala Cys Ala Phe Ala Gly Ala<br>770 775 780 | | 2352 |
| gat gtt gtt gat gtt gca acc aac tct atg tct ggt atg act tct caa<br>Asp Val Val Asp Val Ala Thr Asn Ser Met Ser Gly Met Thr Ser Gln<br>785 790 795 800 | | 2400 |
| cca tct gtc aat gca cta ttg gct gct ctt gat ggt gaa atc gac tgt<br>Pro Ser Val Asn Ala Leu Leu Ala Ala Leu Asp Gly Glu Ile Asp Cys<br>805 810 815 | | 2448 |
| aat gtc aac gtc agc tac atc agt cag cta gat gct tac tgg gct gaa<br>Asn Val Asn Val Ser Tyr Ile Ser Gln Leu Asp Ala Tyr Trp Ala Glu<br>820 825 830 | | 2496 |
| atg aga cta ttg tac tca tgt ttc gaa gcc gac ttg aag ggt cct gat<br>Met Arg Leu Leu Tyr Ser Cys Phe Glu Ala Asp Leu Lys Gly Pro Asp<br>835 840 845 | | 2544 |
| cca gaa gtt tac gtc cat gaa att cca ggt ggt caa ttg acc aac ttg<br>Pro Glu Val Tyr Val His Glu Ile Pro Gly Gly Gln Leu Thr Asn Leu<br>850 855 860 | | 2592 |
| ctc ttc caa gcc caa caa ttg ggt ctt ggt gag caa tgg gct gaa acc<br>Leu Phe Gln Ala Gln Gln Leu Gly Leu Gly Glu Gln Trp Ala Glu Thr<br>865 870 875 880 | | 2640 |
| aag aga gct tac cgt gaa gca aac ctg ttg ttg ggt gat gtt gtt aag<br>Lys Arg Ala Tyr Arg Glu Ala Asn Leu Leu Leu Gly Asp Val Val Lys<br>885 890 895 | | 2688 |
| gtc act cca aca tcc aag gtt gtc ggt gat ttg gct caa ttc atg gtc<br>Val Thr Pro Thr Ser Lys Val Val Gly Asp Leu Ala Gln Phe Met Val<br>900 905 910 | | 2736 |
| act aac aag ttg acc tcg gat gat gtt aag aga tta gct tca tct ttg<br>Thr Asn Lys Leu Thr Ser Asp Asp Val Lys Arg Leu Ala Ser Ser Leu<br>915 920 925 | | 2784 |
| gat ttc cca gac tcc gtc atg gac ttc ttt gaa ggt tta atc ggt caa<br>Asp Phe Pro Asp Ser Val Met Asp Phe Phe Glu Gly Leu Ile Gly Gln<br>930 935 940 | | 2832 |
| cca tac ggt ggt ttc cca gaa cct cta aga tct gat gtt ttg aag aac<br>Pro Tyr Gly Gly Phe Pro Glu Pro Leu Arg Ser Asp Val Leu Lys Asn | | 2880 |

```
                 945                 950                 955                 960
aag aga aga aag ttg acc aag aga cca ggt ttg gaa ttg gct cca ttc      2928
Lys Arg Arg Lys Leu Thr Lys Arg Pro Gly Leu Glu Leu Ala Pro Phe
                965                 970                 975 gat ttg gaa ggc att aag gaa gat ttg act aac aga ttt ggt gac att      2976
Asp Leu Glu Gly Ile Lys Glu Asp Leu Thr Asn Arg Phe Gly Asp Ile
            980                 985                 990 gac gac tgt gat gtt gct tct tac aac atg tat cca aag gtc tac gaa     3024
Asp Asp Cys Asp Val Ala Ser Tyr Asn Met Tyr Pro Lys Val Tyr Glu
        995                 1000                1005 gat ttc cgt aag atc aga gaa aag tac ggt gat cta tct gtt ttg         3069
Asp Phe Arg Lys Ile Arg Glu Lys Tyr Gly Asp Leu Ser Val Leu
    1010                1015                1020 cca acc aag aac ttc ttg tct cca cct tca atc ggt gaa gaa atc         3114
Pro Thr Lys Asn Phe Leu Ser Pro Pro Ser Ile Gly Glu Glu Ile
    1025                1030                1035 gtc gtt aca att gaa caa ggt aag act ttg atc att aag cca caa         3159
Val Val Thr Ile Glu Gln Gly Lys Thr Leu Ile Ile Lys Pro Gln
    1040                1045                1050 gct att ggt gat ttg aac aag gag act ggt atc aga gaa gtt tac         3204
Ala Ile Gly Asp Leu Asn Lys Glu Thr Gly Ile Arg Glu Val Tyr
    1055                1060                1065 ttc gaa ttg aac ggt gaa ttg aga aag gtc tct gtt gct gac aga         3249
Phe Glu Leu Asn Gly Glu Leu Arg Lys Val Ser Val Ala Asp Arg
    1070                1075                1080 tct caa aag gtt gaa acg atc tcc aag cca aag gct gac gcc cac         3294
Ser Gln Lys Val Glu Thr Ile Ser Lys Pro Lys Ala Asp Ala His
    1085                1090                1095 gat cca ttc caa gtt ggt tct cca atg gca ggt gtt gtc gtc gaa         3339
Asp Pro Phe Gln Val Gly Ser Pro Met Ala Gly Val Val Val Glu
    1100                1105                1110 gtc aag gta cac aag ggt tct ttg atc tcc aag ggc caa cca gtc         3384
Val Lys Val His Lys Gly Ser Leu Ile Ser Lys Gly Gln Pro Val
    1115                1120                1125 gct gtc cta agt gcc atg aag atg gaa atg gtt atc tcc tcc cca         3429
Ala Val Leu Ser Ala Met Lys Met Glu Met Val Ile Ser Ser Pro
    1130                1135                1140 tct gat ggt caa gtc aag gaa gtg ctt gtc aag gat ggt gaa aac         3474
Ser Asp Gly Gln Val Lys Glu Val Leu Val Lys Asp Gly Glu Asn
    1145                1150                1155 gtt gac gct tct gac ttg ctc gtt gtt ttg gaa gaa gct cca gct         3519
Val Asp Ala Ser Asp Leu Leu Val Val Leu Glu Glu Ala Pro Ala
    1160                1165                1170 aaa gaa taa                                                          3528
Lys Glu
    1175

<210> SEQ ID NO 12
<211> LENGTH: 1175
<212> TYPE: PRT
<213> ORGANISM: Kluyveromyces marxianus

<400> SEQUENCE: 12

Met Ser Thr Gln Asn Asp Leu Ala Gly Leu Arg Asp Asn Ser Asn Leu
1               5                   10                  15

Leu Gly Glu Lys Asn Lys Ile Leu Val Ala Asn Arg Gly Glu Ile Pro
            20                  25                  30

Ile Arg Ile Phe Arg Thr Ala His Glu Leu Ser Met Lys Thr Val Ala
        35                  40                  45
```

-continued

```
Ile Tyr Ser His Glu Asp Arg Leu Ser Met His Arg Leu Lys Ala Asp
 50                  55                  60

Glu Ala Tyr Val Ile Gly Glu Pro Gly Lys Tyr Thr Pro Val Gly Ala
 65                  70                  75                  80

Tyr Leu Ala Ile Asp Glu Ile Ile Lys Ile Ala Gln Leu His Gly Val
                 85                  90                  95

Ser Phe Ile His Pro Gly Tyr Gly Phe Leu Ser Glu Asn Ser Glu Phe
            100                 105                 110

Ala Lys Lys Val Ala Asp Ser Gly Ile Thr Trp Val Gly Pro Pro Ala
        115                 120                 125

Asp Val Ile Asp Ala Val Gly Asp Lys Val Ser Ala Arg Asn Leu Ala
130                 135                 140

Glu Arg Ala Asp Val Pro Val Pro Gly Thr Pro Gly Pro Ile Glu
145                 150                 155                 160

Thr Val Glu Glu Ala Val Glu Phe Val Glu Lys Tyr Gly Tyr Pro Val
                165                 170                 175

Ile Ile Lys Ala Ala Phe Gly Gly Gly Arg Gly Met Arg Val Val
            180                 185                 190

Arg Glu Gly Asp Asp Ile Ala Asp Ala Phe Gln Arg Ala Lys Ser Glu
        195                 200                 205

Ala Val Thr Ala Phe Gly Asn Gly Thr Cys Phe Val Glu Arg Phe Leu
210                 215                 220

Asp Lys Pro Lys His Ile Glu Val Gln Leu Leu Ala Asp His Tyr Gly
225                 230                 235                 240

Asn Val Ile His Leu Phe Glu Arg Asp Cys Ser Val Gln Arg Arg His
                245                 250                 255

Gln Lys Val Val Glu Val Ala Pro Ala Lys Thr Leu Pro Glu Ser Val
            260                 265                 270

Arg Asn Ala Ile Leu Thr Asp Ala Val Lys Leu Ala Lys Glu Ala Gly
        275                 280                 285

Tyr Arg Asn Ala Gly Thr Ala Glu Phe Leu Val Asp Asn Gln Asn Arg
290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ala Ala Gln Ile Gln Ile
                325                 330                 335

Ala Ala Gly Ala Ser Leu Glu Gln Leu Gly Leu Leu Gln Asp Arg Ile
            340                 345                 350

Thr Thr Arg Gly Phe Ala Ile Gln Cys Arg Ile Thr Thr Glu Asp Pro
        355                 360                 365

Ser Lys Asn Phe Gln Pro Asp Thr Gly Arg Ile Asp Val Tyr Arg Ser
370                 375                 380

Ala Gly Gly Asn Gly Val Arg Leu Asp Gly Gly Asn Ala Phe Ala Gly
385                 390                 395                 400

Ser Val Ile Ser Pro His Tyr Asp Ser Met Leu Val Lys Cys Ser Cys
                405                 410                 415

Ser Gly Ser Thr Tyr Glu Ile Val Arg Arg Lys Met Leu Arg Ala Leu
            420                 425                 430

Ile Glu Phe Arg Ile Arg Gly Val Lys Thr Asn Ile Pro Phe Leu Leu
        435                 440                 445

Thr Leu Leu Thr His Pro Val Phe Lys Ser Gly Asp Tyr Trp Thr Thr
450                 455                 460

Phe Ile Asp Asp Thr Pro Gln Leu Phe Glu Met Val Ser Ser Gln Asn
```

```
                465                 470                 475                 480
        Arg Ala Gln Lys Leu Leu His Tyr Leu Ala Asp Leu Ala Val Asn Gly
                        485                 490                 495

Ser Ser Ile Lys Gly Gln Ile Gly Leu Pro Lys Leu Lys Thr His Pro
                        500                 505                 510

Thr Ile Pro His Leu His Lys Ala Asp Gly Ser Ile Leu Asp Val Ser
                        515                 520                 525

Ala Lys Pro Pro Ala Gly Trp Arg Asp Val Leu Leu Gln His Gly Pro
                530                 535                 540

Glu Glu Phe Ala Lys Gln Val Arg Lys Phe Lys Gly Thr Leu Leu Met
        545                 550                 555                 560

Asp Thr Thr Trp Arg Asp Ala His Gln Ser Leu Leu Ala Thr Arg Val
                                565                 570                 575

Arg Thr Tyr Asp Leu Ala Ala Ile Ala Pro Thr Thr Ala His Ala Leu
                        580                 585                 590

Ser Gly Ala Phe Ala Leu Glu Cys Trp Gly Gly Ala Thr Phe Asp Val
                        595                 600                 605

Ser Met Arg Phe Leu His Glu Asp Pro Trp Glu Arg Leu Arg Thr Leu
                610                 615                 620

Arg Lys Leu Val Pro Asn Ile Pro Phe Gln Met Leu Leu Arg Gly Ala
        625                 630                 635                 640

Asn Gly Val Ala Tyr Ser Ser Leu Pro Asp Asn Ala Ile Asp His Phe
                        645                 650                 655

Val Lys Gln Ala Lys Asp Asn Gly Val Asp Ile Phe Arg Val Phe Asp
                        660                 665                 670

Ala Leu Asn Asp Leu Glu Gln Leu Thr Val Gly Val Asp Ala Val Lys
                        675                 680                 685

Lys Ala Gly Gly Val Val Glu Ala Thr Ile Cys Tyr Ser Gly Asp Met
                690                 695                 700

Leu Ala Pro Gly Lys Lys Tyr Asn Leu Asp Tyr Tyr Leu Asp Ile Val
        705                 710                 715                 720

Glu Gln Val Val Lys Arg Gly Thr His Ile Leu Gly Ile Lys Asp Met
                        725                 730                 735

Ala Gly Thr Leu Lys Pro Ser Ala Ala Lys Leu Leu Ile Gly Ser Ile
                        740                 745                 750

Arg Thr Lys Tyr Pro Asp Leu Pro Ile His Val His Thr His Asp Ser
                        755                 760                 765

Ala Gly Thr Gly Val Ala Ser Met Ala Ala Cys Ala Phe Ala Gly Ala
                        770                 775                 780

Asp Val Val Asp Val Ala Thr Asn Ser Met Ser Gly Met Thr Ser Gln
        785                 790                 795                 800

Pro Ser Val Asn Ala Leu Leu Ala Ala Leu Asp Gly Glu Ile Asp Cys
                        805                 810                 815

Asn Val Asn Val Ser Tyr Ile Ser Gln Leu Asp Ala Tyr Trp Ala Glu
                        820                 825                 830

Met Arg Leu Leu Tyr Ser Cys Phe Glu Ala Asp Leu Lys Gly Pro Asp
                835                 840                 845

Pro Glu Val Tyr Val His Glu Ile Pro Gly Gly Gln Leu Thr Asn Leu
                        850                 855                 860

Leu Phe Gln Ala Gln Gln Leu Gly Leu Gly Glu Gln Trp Ala Glu Thr
        865                 870                 875                 880

Lys Arg Ala Tyr Arg Glu Ala Asn Leu Leu Leu Gly Asp Val Val Lys
                        885                 890                 895
```

```
Val Thr Pro Thr Ser Lys Val Val Gly Asp Leu Ala Gln Phe Met Val
            900                 905                 910

Thr Asn Lys Leu Thr Ser Asp Asp Val Lys Arg Leu Ala Ser Ser Leu
            915                 920                 925

Asp Phe Pro Asp Ser Val Met Asp Phe Glu Gly Leu Ile Gly Gln
            930                 935                 940

Pro Tyr Gly Gly Phe Pro Glu Pro Leu Arg Ser Asp Val Leu Lys Asn
945                 950                 955                 960

Lys Arg Arg Lys Leu Thr Lys Arg Pro Gly Leu Glu Leu Ala Pro Phe
            965                 970                 975

Asp Leu Glu Gly Ile Lys Glu Asp Leu Thr Asn Arg Phe Gly Asp Ile
            980                 985                 990

Asp Asp Cys Asp Val Ala Ser Tyr Asn Met Tyr Pro Lys Val Tyr Glu
            995                 1000                1005

Asp Phe Arg Lys Ile Arg Glu Lys Tyr Gly Asp Leu Ser Val Leu
    1010                1015                1020

Pro Thr Lys Asn Phe Leu Ser Pro Pro Ser Ile Gly Glu Glu Ile
    1025                1030                1035

Val Val Thr Ile Glu Gln Gly Lys Thr Leu Ile Ile Lys Pro Gln
    1040                1045                1050

Ala Ile Gly Asp Leu Asn Lys Glu Thr Gly Ile Arg Glu Val Tyr
    1055                1060                1065

Phe Glu Leu Asn Gly Glu Leu Arg Lys Val Ser Val Ala Asp Arg
    1070                1075                1080

Ser Gln Lys Val Glu Thr Ile Ser Lys Pro Lys Ala Asp Ala His
    1085                1090                1095

Asp Pro Phe Gln Val Gly Ser Pro Met Ala Gly Val Val Val Glu
    1100                1105                1110

Val Lys Val His Lys Gly Ser Leu Ile Ser Lys Gly Gln Pro Val
    1115                1120                1125

Ala Val Leu Ser Ala Met Lys Met Glu Met Val Ile Ser Ser Pro
    1130                1135                1140

Ser Asp Gly Gln Val Lys Glu Val Leu Val Lys Asp Gly Glu Asn
    1145                1150                1155

Val Asp Ala Ser Asp Leu Leu Val Val Leu Glu Glu Ala Pro Ala
    1160                1165                1170

Lys Glu
    1175

<210> SEQ ID NO 13
<211> LENGTH: 1029
<212> TYPE: DNA
<213> ORGANISM: Issatchenkia orientalis
<220> FEATURE:
<221> NAME/KEY: CDS
<222> LOCATION: (1)..(1029)

<400> SEQUENCE: 13 atg tcc aat gtt aaa gta gct cta cta ggt gcc gct ggt ggt atc ggc      48
Met Ser Asn Val Lys Val Ala Leu Leu Gly Ala Ala Gly Gly Ile Gly
1               5                   10                  15 caa cca ctt gct cta tta ctt aag ctt aat cca aac ata acc cat ttg      96
Gln Pro Leu Ala Leu Leu Leu Lys Leu Asn Pro Asn Ile Thr His Leu
            20                  25                  30 gca ctc tat gac gtt gtg cat gtt cct gga gtg gct gcc gac cta cac     144
Ala Leu Tyr Asp Val Val His Val Pro Gly Val Ala Ala Asp Leu His
```

```
                35                  40                  45
cat ata gac aca gat gta gtg att acc cac cat ttg aaa gat gaa gac    192
His Ile Asp Thr Asp Val Val Ile Thr His His Leu Lys Asp Glu Asp
     50                  55                  60 ggt acg gcc ttg gca aac gcc ctc aag gac gct acg ttt gtt att gtc    240
Gly Thr Ala Leu Ala Asn Ala Leu Lys Asp Ala Thr Phe Val Ile Val
 65                  70                  75                  80 ccc gcc ggt gtt ccg aga aag ccc ggc atg act aga ggt gat ttg ttc    288
Pro Ala Gly Val Pro Arg Lys Pro Gly Met Thr Arg Gly Asp Leu Phe
                 85                  90                  95 aca att aat gcc ggt ata tgt gcc gaa ttg gct aat gct att agt ttg    336
Thr Ile Asn Ala Gly Ile Cys Ala Glu Leu Ala Asn Ala Ile Ser Leu
            100                 105                 110 aac gct cct aat gca ttc acc ctt gtc att acc aat ccg gtc aac tcg    384
Asn Ala Pro Asn Ala Phe Thr Leu Val Ile Thr Asn Pro Val Asn Ser
        115                 120                 125 acc gtt cct ata ttt aag gaa ata ttt gct aaa aat gaa gcc ttc aat    432
Thr Val Pro Ile Phe Lys Glu Ile Phe Ala Lys Asn Glu Ala Phe Asn
    130                 135                 140 cca agg aga ctg ttt ggt gta act gct cta gat cat gtt aga tca aat    480
Pro Arg Arg Leu Phe Gly Val Thr Ala Leu Asp His Val Arg Ser Asn
145                 150                 155                 160 act ttt ctc tcg gaa tta att gac ggt aaa aat ccc caa cat ttt gat    528
Thr Phe Leu Ser Glu Leu Ile Asp Gly Lys Asn Pro Gln His Phe Asp
                165                 170                 175 gtc act gtt gtt ggc gga cac tct ggt aac tca att gtc ccc cta ttc    576
Val Thr Val Val Gly Gly His Ser Gly Asn Ser Ile Val Pro Leu Phe
            180                 185                 190 tcc ctt gtt aag gct gcc gaa aat tta gac gat gaa att ata gat gcc    624
Ser Leu Val Lys Ala Ala Glu Asn Leu Asp Asp Glu Ile Ile Asp Ala
        195                 200                 205 ttg att cat aga gtt caa tac ggt gga gat gaa gtt gtg gaa gca aag    672
Leu Ile His Arg Val Gln Tyr Gly Gly Asp Glu Val Val Glu Ala Lys
    210                 215                 220 agc ggt gcg ggc tcg gca act ctt tca atg gct tat gcc gct aac aag    720
Ser Gly Ala Gly Ser Ala Thr Leu Ser Met Ala Tyr Ala Ala Asn Lys
225                 230                 235                 240 ttc ttc aat ata ttg ctt aat gga tac ttg ggt ttg aag aag aca atg    768
Phe Phe Asn Ile Leu Leu Asn Gly Tyr Leu Gly Leu Lys Lys Thr Met
                245                 250                 255 att tca agt tat gtc ttt tta gac gat tca atc aac ggc gtc cct caa    816
Ile Ser Ser Tyr Val Phe Leu Asp Asp Ser Ile Asn Gly Val Pro Gln
            260                 265                 270 tta aag gaa aat ttg tct aaa ctt ttg aaa ggt tcc gag gtt gag tta    864
Leu Lys Glu Asn Leu Ser Lys Leu Leu Lys Gly Ser Glu Val Glu Leu
        275                 280                 285 cca agt tat ttg gct gtt cca atg acc tat ggt aaa gaa ggt att gaa    912
Pro Ser Tyr Leu Ala Val Pro Met Thr Tyr Gly Lys Glu Gly Ile Glu
    290                 295                 300 caa gtc ttt tac gat tgg gtg ttt gaa atg tca cca aag gaa aag gaa    960
Gln Val Phe Tyr Asp Trp Val Phe Glu Met Ser Pro Lys Glu Lys Glu
305                 310                 315                 320 aac ttc att aca gcg att gaa tac att gat caa aat att gaa aaa ggt    1008
Asn Phe Ile Thr Ala Ile Glu Tyr Ile Asp Gln Asn Ile Glu Lys Gly
                325                 330                 335 ctg aat ttt atg gta cgt taa                                        1029
Leu Asn Phe Met Val Arg
            340
```

<210> SEQ ID NO 14
<211> LENGTH: 342
<212> TYPE: PRT
<213> ORGANISM: Issatchenkia orientalis

<400> SEQUENCE: 14

Met Ser Asn Val Lys Val Ala Leu Leu Gly Ala Ala Gly Gly Ile Gly
1               5                   10                  15

Gln Pro Leu Ala Leu Leu Leu Lys Leu Asn Pro Asn Ile Thr His Leu
            20                  25                  30

Ala Leu Tyr Asp Val Val His Val Pro Gly Val Ala Ala Asp Leu His
        35                  40                  45

His Ile Asp Thr Asp Val Val Ile Thr His His Leu Lys Asp Glu Asp
    50                  55                  60

Gly Thr Ala Leu Ala Asn Ala Leu Lys Asp Ala Thr Phe Val Ile Val
65                  70                  75                  80

Pro Ala Gly Val Pro Arg Lys Pro Gly Met Thr Arg Gly Asp Leu Phe
                85                  90                  95

Thr Ile Asn Ala Gly Ile Cys Ala Glu Leu Ala Asn Ala Ile Ser Leu
            100                 105                 110

Asn Ala Pro Asn Ala Phe Thr Leu Val Ile Thr Asn Pro Val Asn Ser
        115                 120                 125

Thr Val Pro Ile Phe Lys Glu Ile Phe Ala Lys Asn Glu Ala Phe Asn
    130                 135                 140

Pro Arg Arg Leu Phe Gly Val Thr Ala Leu Asp His Val Arg Ser Asn
145                 150                 155                 160

Thr Phe Leu Ser Glu Leu Ile Asp Gly Lys Asn Pro Gln His Phe Asp
                165                 170                 175

Val Thr Val Val Gly Gly His Ser Gly Asn Ser Ile Val Pro Leu Phe
            180                 185                 190

Ser Leu Val Lys Ala Ala Glu Asn Leu Asp Asp Glu Ile Ile Asp Ala
        195                 200                 205

Leu Ile His Arg Val Gln Tyr Gly Gly Asp Glu Val Val Glu Ala Lys
    210                 215                 220

Ser Gly Ala Gly Ser Ala Thr Leu Ser Met Ala Tyr Ala Ala Asn Lys
225                 230                 235                 240

Phe Phe Asn Ile Leu Leu Asn Gly Tyr Leu Gly Leu Lys Lys Thr Met
                245                 250                 255

Ile Ser Ser Tyr Val Phe Leu Asp Asp Ser Ile Asn Gly Val Pro Gln
            260                 265                 270

Leu Lys Glu Asn Leu Ser Lys Leu Lys Gly Ser Glu Val Glu Leu
        275                 280                 285

Pro Ser Tyr Leu Ala Val Pro Met Thr Tyr Gly Lys Glu Gly Ile Glu
    290                 295                 300

Gln Val Phe Tyr Asp Trp Val Phe Glu Met Ser Pro Lys Glu Lys Glu
305                 310                 315                 320

Asn Phe Ile Thr Ala Ile Glu Tyr Ile Asp Gln Asn Ile Glu Lys Gly
                325                 330                 335

Leu Asn Phe Met Val Arg
            340

<210> SEQ ID NO 15
<211> LENGTH: 1011
<212> TYPE: DNA
<213> ORGANISM: Issatchenkia orientalis
<220> FEATURE:

<221> NAME/KEY: CDS
<222> LOCATION: (1)..(1011)

<400> SEQUENCE: 15

| | | | | | | | | | | | | | | | | |
|---|---|---|---|---|---|---|---|---|---|---|---|---|---|---|---|---|
| atg | gtc | aag | gtg | act | att | tta | ggc | gct | gcc | ggt | gga | att | gga | caa | cca | 48 |
| Met | Val | Lys | Val | Thr | Ile | Leu | Gly | Ala | Ala | Gly | Gly | Ile | Gly | Gln | Pro | |
| 1 | | | | 5 | | | | | 10 | | | | | 15 | | |
| ctc | tca | ttg | tta | ttg | aga | ctt | aat | cca | tgg | att | gac | gaa | ttg | gcc | ttg | 96 |
| Leu | Ser | Leu | Leu | Leu | Arg | Leu | Asn | Pro | Trp | Ile | Asp | Glu | Leu | Ala | Leu | |
| | | | 20 | | | | | 25 | | | | | 30 | | | |
| ttt | gat | att | gtc | aat | acc | ccc | ggc | gtg | agt | tgt | gat | ttg | tcg | cat | att | 144 |
| Phe | Asp | Ile | Val | Asn | Thr | Pro | Gly | Val | Ser | Cys | Asp | Leu | Ser | His | Ile | |
| | | 35 | | | | | 40 | | | | | 45 | | | | |
| cct | gca | tca | cag | gtt | gtt | aat | ggc | tat | gct | ccg | aaa | tcg | aaa | tca | gat | 192 |
| Pro | Ala | Ser | Gln | Val | Val | Asn | Gly | Tyr | Ala | Pro | Lys | Ser | Lys | Ser | Asp | |
| | 50 | | | | | 55 | | | | | 60 | | | | | |
| aca | gag | aca | atc | aag | act | gcc | ttg | aaa | ggt | gct | gat | att | gtt | gtt | att | 240 |
| Thr | Glu | Thr | Ile | Lys | Thr | Ala | Leu | Lys | Gly | Ala | Asp | Ile | Val | Val | Ile | |
| 65 | | | | | 70 | | | | | 75 | | | | | 80 | |
| cct | gca | gga | att | cca | cgt | aaa | cct | ggt | atg | aca | aga | aac | gat | ctc | ttt | 288 |
| Pro | Ala | Gly | Ile | Pro | Arg | Lys | Pro | Gly | Met | Thr | Arg | Asn | Asp | Leu | Phe | |
| | | | | 85 | | | | | 90 | | | | | 95 | | |
| aaa | atc | aat | gcc | gga | atc | gtt | aag | agt | ttg | att | cat | agt | gca | gga | acc | 336 |
| Lys | Ile | Asn | Ala | Gly | Ile | Val | Lys | Ser | Leu | Ile | His | Ser | Ala | Gly | Thr | |
| | | | 100 | | | | | 105 | | | | | 110 | | | |
| act | tgc | cct | gat | gca | ttt | att | tgt | gtc | att | tcg | aac | cct | gtc | aac | tcg | 384 |
| Thr | Cys | Pro | Asp | Ala | Phe | Ile | Cys | Val | Ile | Ser | Asn | Pro | Val | Asn | Ser | |
| | | 115 | | | | | 120 | | | | | 125 | | | | |
| aca | gtt | cca | att | gcc | gtt | gaa | gaa | cta | aag | cgt | ttg | aat | gtt | ttt | aat | 432 |
| Thr | Val | Pro | Ile | Ala | Val | Glu | Glu | Leu | Lys | Arg | Leu | Asn | Val | Phe | Asn | |
| | 130 | | | | | 135 | | | | | 140 | | | | | |
| cca | cat | aaa | gtt | ttc | ggt | att | acc | aca | ttg | gac | aat | ttc | aga | tta | gaa | 480 |
| Pro | His | Lys | Val | Phe | Gly | Ile | Thr | Thr | Leu | Asp | Asn | Phe | Arg | Leu | Glu | |
| 145 | | | | | 150 | | | | | 155 | | | | | 160 | |
| gaa | ttt | ctg | agt | gga | gaa | ctt | ggt | gga | att | gtc | aaa | cca | aat | gat | tta | 528 |
| Glu | Phe | Leu | Ser | Gly | Glu | Leu | Gly | Gly | Ile | Val | Lys | Pro | Asn | Asp | Leu | |
| | | | | 165 | | | | | 170 | | | | | 175 | | |
| tat | ggt | gat | gta | gtt | gct | ata | ggt | ggc | cat | tcg | ggc | gac | tct | ata | gta | 576 |
| Tyr | Gly | Asp | Val | Val | Ala | Ile | Gly | Gly | His | Ser | Gly | Asp | Ser | Ile | Val | |
| | | | 180 | | | | | 185 | | | | | 190 | | | |
| ccg | atc | ttg | aat | tcg | tgg | aat | ttg | aat | ttc | atc | aat | gat | gga | gat | tct | 624 |
| Pro | Ile | Leu | Asn | Ser | Trp | Asn | Leu | Asn | Phe | Ile | Asn | Asp | Gly | Asp | Ser | |
| | | 195 | | | | | 200 | | | | | 205 | | | | |
| tat | aac | aat | ttg | gtc | aag | agg | gtc | cag | ttt | gga | ggc | gat | gag | gtt | gtc | 672 |
| Tyr | Asn | Asn | Leu | Val | Lys | Arg | Val | Gln | Phe | Gly | Gly | Asp | Glu | Val | Val | |
| | 210 | | | | | 215 | | | | | 220 | | | | | |
| aag | gca | aag | gac | ggg | aaa | ggt | tcg | gct | aca | ttg | tca | atg | gct | aca | gct | 720 |
| Lys | Ala | Lys | Asp | Gly | Lys | Gly | Ser | Ala | Thr | Leu | Ser | Met | Ala | Thr | Ala | |
| 225 | | | | | 230 | | | | | 235 | | | | | 240 | |
| gca | tac | agg | ttt | gtc | aac | aac | ctc | ttg | gac | gcc | att | gtc | aat | aac | aag | 768 |
| Ala | Tyr | Arg | Phe | Val | Asn | Asn | Leu | Leu | Asp | Ala | Ile | Val | Asn | Asn | Lys | |
| | | | | 245 | | | | | 250 | | | | | 255 | | |
| aaa | gtc | aag | gaa | gtg | gcc | ttt | gtg | aaa | atc | gac | caa | ttg | cca | act | aca | 816 |
| Lys | Val | Lys | Glu | Val | Ala | Phe | Val | Lys | Ile | Asp | Gln | Leu | Pro | Thr | Thr | |
| | | | 260 | | | | | 265 | | | | | 270 | | | |
| agg | gtt | cct | tat | ttt | gtt | gtt | gat | gaa | act | cag | tat | ttt | agt | cta | ccc | 864 |
| Arg | Val | Pro | Tyr | Phe | Val | Val | Asp | Glu | Thr | Gln | Tyr | Phe | Ser | Leu | Pro | |
| | | 275 | | | | | 280 | | | | | 285 | | | | |
| att | att | ctc | ggt | aga | cag | ggg | att | gag | agg | gtc | acg | ttc | cca | gaa | tct | 912 |
| Ile | Ile | Leu | Gly | Arg | Gln | Gly | Ile | Glu | Arg | Val | Thr | Phe | Pro | Glu | Ser | |

```
                290                 295                 300
ctg aca gag caa gag gtg aga atg aca aag cac gct gtt gct aaa gtt        960
Leu Thr Glu Gln Glu Val Arg Met Thr Lys His Ala Val Ala Lys Val
305                 310                 315                 320 aaa gtt gac gtt aat aaa ggc ttc aat ttt gtc cat ggc cca aaa ctg       1008
Lys Val Asp Val Asn Lys Gly Phe Asn Phe Val His Gly Pro Lys Leu
                325                 330                 335 taa                                                                    1011

<210> SEQ ID NO 16
<211> LENGTH: 336
<212> TYPE: PRT
<213> ORGANISM: Issatchenkia orientalis

<400> SEQUENCE: 16

Met Val Lys Val Thr Ile Leu Gly Ala Ala Gly Gly Ile Gly Gln Pro
1               5                   10                  15

Leu Ser Leu Leu Leu Arg Leu Asn Pro Trp Ile Asp Glu Leu Ala Leu
            20                  25                  30

Phe Asp Ile Val Asn Thr Pro Gly Val Ser Cys Asp Leu Ser His Ile
        35                  40                  45

Pro Ala Ser Gln Val Val Asn Gly Tyr Ala Pro Lys Ser Lys Ser Asp
    50                  55                  60

Thr Glu Thr Ile Lys Thr Ala Leu Lys Gly Ala Asp Ile Val Val Ile
65                  70                  75                  80

Pro Ala Gly Ile Pro Arg Lys Pro Gly Met Thr Arg Asn Asp Leu Phe
                85                  90                  95

Lys Ile Asn Ala Gly Ile Val Lys Ser Leu Ile His Ser Ala Gly Thr
            100                 105                 110

Thr Cys Pro Asp Ala Phe Ile Cys Val Ile Ser Asn Pro Val Asn Ser
        115                 120                 125

Thr Val Pro Ile Ala Val Glu Glu Leu Lys Arg Leu Asn Val Phe Asn
    130                 135                 140

Pro His Lys Val Phe Gly Ile Thr Thr Leu Asp Asn Phe Arg Leu Glu
145                 150                 155                 160

Glu Phe Leu Ser Gly Glu Leu Gly Gly Ile Val Lys Pro Asn Asp Leu
                165                 170                 175

Tyr Gly Asp Val Val Ala Ile Gly Gly His Ser Gly Asp Ser Ile Val
            180                 185                 190

Pro Ile Leu Asn Ser Trp Asn Leu Asn Phe Ile Asn Asp Gly Asp Ser
        195                 200                 205

Tyr Asn Asn Leu Val Lys Arg Val Gln Phe Gly Gly Asp Glu Val Val
    210                 215                 220

Lys Ala Lys Asp Gly Lys Gly Ser Ala Thr Leu Ser Met Ala Thr Ala
225                 230                 235                 240

Ala Tyr Arg Phe Val Asn Asn Leu Leu Asp Ala Ile Val Asn Asn Lys
                245                 250                 255

Lys Val Lys Glu Val Ala Phe Val Lys Ile Asp Gln Leu Pro Thr Thr
            260                 265                 270

Arg Val Pro Tyr Phe Val Asp Glu Thr Gln Tyr Phe Ser Leu Pro
        275                 280                 285

Ile Ile Leu Gly Arg Gln Gly Ile Glu Arg Val Thr Phe Pro Glu Ser
    290                 295                 300

Leu Thr Glu Gln Glu Val Arg Met Thr Lys His Ala Val Ala Lys Val
305                 310                 315                 320
```

```
                    Lys Val Asp Val Asn Lys Gly Phe Asn Phe Val His Gly Pro Lys Leu
                                    325                 330                 335

<210> SEQ ID NO 17
<211> LENGTH: 1005
<212> TYPE: DNA
<213> ORGANISM: Issatchenkia orientalis
<220> FEATURE:
<221> NAME/KEY: CDS
<222> LOCATION: (1)..(1005)

<400> SEQUENCE: 17 atg ttc tcc aga atc tct gct aga caa ttc tcc tcc tct gct gct tcc         48
Met Phe Ser Arg Ile Ser Ala Arg Gln Phe Ser Ser Ser Ala Ala Ser
1               5                  10                  15 gct tac aag gtc acc gtt tta ggt gct gca ggt ggt att ggc caa cca         96
Ala Tyr Lys Val Thr Val Leu Gly Ala Ala Gly Gly Ile Gly Gln Pro
                20                  25                  30 cta tct ctt ttg atg aag ttg aac cac aag gtc acc aac tta tcc ttg        144
Leu Ser Leu Leu Met Lys Leu Asn His Lys Val Thr Asn Leu Ser Leu
        35                  40                  45 tac gac ttg aga ttg ggt gct ggt gtt gcc act gac ttg tcc cac att        192
Tyr Asp Leu Arg Leu Gly Ala Gly Val Ala Thr Asp Leu Ser His Ile
50                  55                  60 cca acc aac tcc gtt gtc aag ggc tat ggt cca gaa aac aat ggt ttg        240
Pro Thr Asn Ser Val Val Lys Gly Tyr Gly Pro Glu Asn Asn Gly Leu
65                  70                  75                  80 aag gac gcc ttg acc ggc tcc gat gtt gtt ctt att cca gct ggt gtt        288
Lys Asp Ala Leu Thr Gly Ser Asp Val Val Leu Ile Pro Ala Gly Val
                85                  90                  95 cca aga aaa cca ggt atg act aga gac gat ctc ttc aac acc aat gca        336
Pro Arg Lys Pro Gly Met Thr Arg Asp Asp Leu Phe Asn Thr Asn Ala
            100                 105                 110 tcg att gtc aga gac ttg gca aag gct gct gca gac cac tgt cca aac        384
Ser Ile Val Arg Asp Leu Ala Lys Ala Ala Ala Asp His Cys Pro Asn
        115                 120                 125 gcc gtc ttg ttg atc att tca aac cct gtc aac tca act gtc cca att        432
Ala Val Leu Leu Ile Ile Ser Asn Pro Val Asn Ser Thr Val Pro Ile
    130                 135                 140 gtt gct gag gtt ttg aaa tca aag ggc gtc tac aac cca aag aag ttg        480
Val Ala Glu Val Leu Lys Ser Lys Gly Val Tyr Asn Pro Lys Lys Leu
145                 150                 155                 160 ttt ggt gtc acc act ttg gac gtt ttg aga tcc tcg aga ttc ttg agt        528
Phe Gly Val Thr Thr Leu Asp Val Leu Arg Ser Ser Arg Phe Leu Ser
                165                 170                 175 gaa gtc gtc aac acc gac cca acc acc gaa acc gtc act gtt gtt ggt        576
Glu Val Val Asn Thr Asp Pro Thr Thr Glu Thr Val Thr Val Val Gly
            180                 185                 190 ggc cac tct ggt gtc acc att gtt cct tta atc tcc caa acc aaa cac        624
Gly His Ser Gly Val Thr Ile Val Pro Leu Ile Ser Gln Thr Lys His
        195                 200                 205 aag gac ttg cca aag gaa acc tac gaa gca ttg gtc cac aga atc caa        672
Lys Asp Leu Pro Lys Glu Thr Tyr Glu Ala Leu Val His Arg Ile Gln
    210                 215                 220 ttc ggt ggt gat gag gtt gtc aag gcc aag gac ggt gca ggt tcc gct        720
Phe Gly Gly Asp Glu Val Val Lys Ala Lys Asp Gly Ala Gly Ser Ala
225                 230                 235                 240 acc ttg tcc atg gcc caa gcc ggt gca aga atg gcc tcc tcc gtc ttg        768
Thr Leu Ser Met Ala Gln Ala Gly Ala Arg Met Ala Ser Ser Val Leu
                245                 250                 255
```

```
aag ggt ttg gct ggt gaa gtt gac att gtc gaa cca acc ttt att gac    816
Lys Gly Leu Ala Gly Glu Val Asp Ile Val Glu Pro Thr Phe Ile Asp
    260                 265                 270 tct cca ttg ttc aag tcc gaa ggt gtc gaa ttc ttc tcc tcc aga gtc    864
Ser Pro Leu Phe Lys Ser Glu Gly Val Glu Phe Phe Ser Ser Arg Val
275                 280                 285 acc ctt ggt cca gaa ggt gtc caa gaa gtc cac cca ttg ggc gtc tta    912
Thr Leu Gly Pro Glu Gly Val Gln Glu Val His Pro Leu Gly Val Leu
        290                 295                 300 tct act gct gaa gaa gaa atg gtt gct act gct aag gaa acc ttg aag    960
Ser Thr Ala Glu Glu Glu Met Val Ala Thr Ala Lys Glu Thr Leu Lys
305                 310                 315                 320 aag aac atc caa aag ggt gtc gac ttt gtc aag gct aac cca taa       1005
Lys Asn Ile Gln Lys Gly Val Asp Phe Val Lys Ala Asn Pro
                325                 330

<210> SEQ ID NO 18
<211> LENGTH: 334
<212> TYPE: PRT
<213> ORGANISM: Issatchenkia orientalis

<400> SEQUENCE: 18

Met Phe Ser Arg Ile Ser Ala Arg Gln Phe Ser Ser Ala Ala Ser
1               5                   10                  15

Ala Tyr Lys Val Thr Val Leu Gly Ala Ala Gly Gly Ile Gly Gln Pro
            20                  25                  30

Leu Ser Leu Leu Met Lys Leu Asn His Lys Val Thr Asn Leu Ser Leu
        35                  40                  45

Tyr Asp Leu Arg Leu Gly Ala Gly Val Ala Thr Asp Leu Ser His Ile
    50                  55                  60

Pro Thr Asn Ser Val Val Lys Gly Tyr Gly Pro Glu Asn Asn Gly Leu
65                  70                  75                  80

Lys Asp Ala Leu Thr Gly Ser Asp Val Val Leu Ile Pro Ala Gly Val
                85                  90                  95

Pro Arg Lys Pro Gly Met Thr Arg Asp Asp Leu Phe Asn Thr Asn Ala
            100                 105                 110

Ser Ile Val Arg Asp Leu Ala Lys Ala Ala Ala Asp His Cys Pro Asn
        115                 120                 125

Ala Val Leu Leu Ile Ile Ser Asn Pro Val Asn Ser Thr Val Pro Ile
    130                 135                 140

Val Ala Glu Val Leu Lys Ser Lys Gly Val Tyr Asn Pro Lys Lys Leu
145                 150                 155                 160

Phe Gly Val Thr Thr Leu Asp Val Leu Arg Ser Ser Arg Phe Leu Ser
                165                 170                 175

Glu Val Val Asn Thr Asp Pro Thr Thr Glu Thr Val Thr Val Val Gly
            180                 185                 190

Gly His Ser Gly Val Thr Ile Val Pro Leu Ile Ser Gln Thr Lys His
        195                 200                 205

Lys Asp Leu Pro Lys Glu Thr Tyr Glu Ala Leu Val His Arg Ile Gln
    210                 215                 220

Phe Gly Gly Asp Glu Val Val Lys Ala Lys Asp Gly Ala Gly Ser Ala
225                 230                 235                 240

Thr Leu Ser Met Ala Gln Ala Gly Ala Arg Met Ala Ser Ser Val Leu
                245                 250                 255

Lys Gly Leu Ala Gly Glu Val Asp Ile Val Glu Pro Thr Phe Ile Asp
            260                 265                 270
```

```
Ser Pro Leu Phe Lys Ser Glu Gly Val Glu Phe Phe Ser Arg Val
            275                 280                 285

Thr Leu Gly Pro Glu Gly Val Gln Glu Val His Pro Leu Gly Val Leu
        290                 295                 300

Ser Thr Ala Glu Glu Met Val Ala Thr Ala Lys Glu Thr Leu Lys
305                 310                 315                 320

Lys Asn Ile Gln Lys Gly Val Asp Phe Val Lys Ala Asn Pro
                325                 330

<210> SEQ ID NO 19
<211> LENGTH: 1017
<212> TYPE: DNA
<213> ORGANISM: Kluyveromyces marxianus
<220> FEATURE:
<221> NAME/KEY: CDS
<222> LOCATION: (1)..(1017)

<400> SEQUENCE: 19
```

| | | | | | | | | | | | | | | | | |
|---|---|---|---|---|---|---|---|---|---|---|---|---|---|---|---|---|
| atg | ctt | aga | gcc | cta | act | cgc | cgt | caa | ttt | tcc | tcc | act | gcc | ttc | aac | 48 |
| Met | Leu | Arg | Ala | Leu | Thr | Arg | Arg | Gln | Phe | Ser | Ser | Thr | Ala | Phe | Asn | |
| 1 | | | | 5 | | | | | 10 | | | | | 15 | | |
| cca | tac | aag | gtc | acc | gtt | cta | ggt | gct | ggt | ggt | ggt | att | ggt | caa | cca | 96 |
| Pro | Tyr | Lys | Val | Thr | Val | Leu | Gly | Ala | Gly | Gly | Gly | Ile | Gly | Gln | Pro |  |
| | | | 20 | | | | | 25 | | | | | 30 | | | |
| ttg | tcc | ttg | ttg | ttg | aag | cta | aac | cac | aag | gtc | act | gac | ttg | aga | cta | 144 |
| Leu | Ser | Leu | Leu | Leu | Lys | Leu | Asn | His | Lys | Val | Thr | Asp | Leu | Arg | Leu | |
| | | 35 | | | | | 40 | | | | | 45 | | | | |
| tac | gac | ttg | aag | ggt | gcc | aag | ggt | gtc | gct | gct | gac | ttg | tct | cac | atc | 192 |
| Tyr | Asp | Leu | Lys | Gly | Ala | Lys | Gly | Val | Ala | Ala | Asp | Leu | Ser | His | Ile | |
| | 50 | | | | | 55 | | | | | 60 | | | | | |
| cca | acc | aac | tct | acc | gtt | act | ggt | tac | act | cca | gaa | tcc | aag | gac | tct | 240 |
| Pro | Thr | Asn | Ser | Thr | Val | Thr | Gly | Tyr | Thr | Pro | Glu | Ser | Lys | Asp | Ser | |
| 65 | | | | | 70 | | | | | 75 | | | | | 80 | |
| caa | gaa | gaa | ttg | gct | gct | gct | ttg | aag | gac | act | gag | gtt | gtt | ttg | atc | 288 |
| Gln | Glu | Glu | Leu | Ala | Ala | Ala | Leu | Lys | Asp | Thr | Glu | Val | Val | Leu | Ile | |
| | | | | 85 | | | | | 90 | | | | | 95 | | |
| cca | gct | ggt | gtg | cca | aga | aag | cca | ggt | atg | acc | cgt | gac | gat | ttg | ttc | 336 |
| Pro | Ala | Gly | Val | Pro | Arg | Lys | Pro | Gly | Met | Thr | Arg | Asp | Asp | Leu | Phe | |
| | | | | 100 | | | | | 105 | | | | | 110 | | |
| gcc | atc | aat | gcc | ggt | att | gtc | aga | gat | ttg | gcc | act | tcc | atc | gcc | aag | 384 |
| Ala | Ile | Asn | Ala | Gly | Ile | Val | Arg | Asp | Leu | Ala | Thr | Ser | Ile | Ala | Lys | |
| | | 115 | | | | | 120 | | | | | 125 | | | | |
| aac | gct | cca | aac | gcc | gcc | atc | ttg | gtc | atc | tcc | aac | cca | gtc | aac | tct | 432 |
| Asn | Ala | Pro | Asn | Ala | Ala | Ile | Leu | Val | Ile | Ser | Asn | Pro | Val | Asn | Ser | |
| | 130 | | | | | 135 | | | | | 140 | | | | | |
| act | gtc | cca | atc | gtc | gcc | gag | gtc | ttg | aag | caa | aac | ggc | gtc | tac | aac | 480 |
| Thr | Val | Pro | Ile | Val | Ala | Glu | Val | Leu | Lys | Gln | Asn | Gly | Val | Tyr | Asn | |
| 145 | | | | | 150 | | | | | 155 | | | | | 160 | |
| cca | aag | aag | ttg | ttc | ggt | gtc | acc | act | ttg | gac | gtt | atc | cgt | gcc | tcc | 528 |
| Pro | Lys | Lys | Leu | Phe | Gly | Val | Thr | Thr | Leu | Asp | Val | Ile | Arg | Ala | Ser | |
| | | | | 165 | | | | | 170 | | | | | 175 | | |
| aga | ttc | atc | tcc | gag | gtt | aga | ggt | acc | gac | cca | acc | act | gag | cac | gtg | 576 |
| Arg | Phe | Ile | Ser | Glu | Val | Arg | Gly | Thr | Asp | Pro | Thr | Thr | Glu | His | Val | |
| | | | | | 180 | | | | | 185 | | | | | 190 | |
| acc | gtc | gtc | ggt | ggt | cac | tcc | ggt | atc | acc | atc | ttg | ccg | cta | gtg | tcc | 624 |
| Thr | Val | Val | Gly | Gly | His | Ser | Gly | Ile | Thr | Ile | Leu | Pro | Leu | Val | Ser | |
| | | | 195 | | | | | 200 | | | | | 205 | | | |
| cag | acc | aag | cac | aag | tcc | gtc | atc | aag | ggc | gag | gaa | ttg | gac | aac | ttg | 672 |
| Gln | Thr | Lys | His | Lys | Ser | Val | Ile | Lys | Gly | Glu | Glu | Leu | Asp | Asn | Leu | |
| | 210 | | | | | 215 | | | | | 220 | | | | | |

```
atc cac aga atc caa ttc ggt ggt gac gaa gtc gtc cag gca aag aac    720
Ile His Arg Ile Gln Phe Gly Gly Asp Glu Val Val Gln Ala Lys Asn
225                 230                 235                 240 ggt gct ggt tct gcc act ttg tcc atg gcc caa gcc ggt gcc cgt ttc    768
Gly Ala Gly Ser Ala Thr Leu Ser Met Ala Gln Ala Gly Ala Arg Phe
        245                 250                 255 gct aac agc gtt cta agc ggt ttc gaa ggt gaa aga gac gtc att gag    816
Ala Asn Ser Val Leu Ser Gly Phe Glu Gly Glu Arg Asp Val Ile Glu
    260                 265                 270 cca act ttc gtc gac tcc cca ttg ttc aag gac gaa ggt atc gaa ttc    864
Pro Thr Phe Val Asp Ser Pro Leu Phe Lys Asp Glu Gly Ile Glu Phe
275                 280                 285 ttc gct tcc cca gtc act ttg ggc cca gaa ggt gtc gaa aag atc cac    912
Phe Ala Ser Pro Val Thr Leu Gly Pro Glu Gly Val Glu Lys Ile His
        290                 295                 300 ggt ttg ggt gtc ttg tcc gac aag gaa gaa caa atg ttg gcc act tgt    960
Gly Leu Gly Val Leu Ser Asp Lys Glu Glu Gln Met Leu Ala Thr Cys
305                 310                 315                 320 aag gaa acc ttg aag aag aac atc gaa aag ggt caa aac ttt gtc aag   1008
Lys Glu Thr Leu Lys Lys Asn Ile Glu Lys Gly Gln Asn Phe Val Lys
        325                 330                 335 caa aac taa                                                        1017
Gln Asn

<210> SEQ ID NO 20
<211> LENGTH: 338
<212> TYPE: PRT
<213> ORGANISM: Kluyveromyces marxianus

<400> SEQUENCE: 20

Met Leu Arg Ala Leu Thr Arg Arg Gln Phe Ser Ser Thr Ala Phe Asn
1               5                   10                  15

Pro Tyr Lys Val Thr Val Leu Gly Ala Gly Gly Ile Gly Gln Pro
            20                  25                  30

Leu Ser Leu Leu Leu Lys Leu Asn His Lys Val Thr Asp Leu Arg Leu
        35                  40                  45

Tyr Asp Leu Lys Gly Ala Lys Gly Val Ala Ala Asp Leu Ser His Ile
50                  55                  60

Pro Thr Asn Ser Thr Val Thr Gly Tyr Thr Pro Glu Ser Lys Asp Ser
65                  70                  75                  80

Gln Glu Glu Leu Ala Ala Ala Leu Lys Asp Thr Glu Val Val Leu Ile
            85                  90                  95

Pro Ala Gly Val Pro Arg Lys Pro Gly Met Thr Arg Asp Asp Leu Phe
            100                 105                 110

Ala Ile Asn Ala Gly Ile Val Arg Asp Leu Ala Thr Ser Ile Ala Lys
        115                 120                 125

Asn Ala Pro Asn Ala Ala Ile Leu Val Ile Ser Asn Pro Val Asn Ser
130                 135                 140

Thr Val Pro Ile Val Ala Glu Val Leu Lys Gln Asn Gly Val Tyr Asn
145                 150                 155                 160

Pro Lys Lys Leu Phe Gly Val Thr Thr Leu Asp Val Ile Arg Ala Ser
                165                 170                 175

Arg Phe Ile Ser Glu Val Arg Gly Thr Asp Pro Thr Thr Glu His Val
            180                 185                 190

Thr Val Val Gly Gly His Ser Gly Ile Thr Ile Leu Pro Leu Val Ser
        195                 200                 205

Gln Thr Lys His Lys Ser Val Ile Lys Gly Glu Glu Leu Asp Asn Leu
```

```
                    210                 215                 220
Ile His Arg Ile Gln Phe Gly Gly Asp Glu Val Val Gln Ala Lys Asn
225                 230                 235                 240

Gly Ala Gly Ser Ala Thr Leu Ser Met Ala Gln Ala Gly Ala Arg Phe
                245                 250                 255

Ala Asn Ser Val Leu Ser Gly Phe Glu Gly Arg Asp Val Ile Glu
                260                 265                 270

Pro Thr Phe Val Asp Ser Pro Leu Phe Lys Asp Glu Gly Ile Glu Phe
                275                 280                 285

Phe Ala Ser Pro Val Thr Leu Gly Pro Glu Gly Val Glu Lys Ile His
                290                 295                 300

Gly Leu Gly Val Leu Ser Asp Lys Glu Glu Gln Met Leu Ala Thr Cys
305                 310                 315                 320

Lys Glu Thr Leu Lys Lys Asn Ile Glu Lys Gly Gln Asn Phe Val Lys
                325                 330                 335

Gln Asn

<210> SEQ ID NO 21
<211> LENGTH: 1017
<212> TYPE: DNA
<213> ORGANISM: Kluyveromyces marxianus
<220> FEATURE:
<221> NAME/KEY: CDS
<222> LOCATION: (1)..(1017)

<400> SEQUENCE: 21 atg gtt agc gtt gca gta tta gga tca tcc gga ggc att ggc caa cca       48
Met Val Ser Val Ala Val Leu Gly Ser Ser Gly Gly Ile Gly Gln Pro
1               5                   10                  15 ctc tca ctc ttg ttg aag ctg gac cct cgc gtg tcc agc ttg aga ttg       96
Leu Ser Leu Leu Leu Lys Leu Asp Pro Arg Val Ser Ser Leu Arg Leu
                20                  25                  30 tac gat ttg aag atg tcc cac ggg atc gcc acc gat ttg tcg cac atg      144
Tyr Asp Leu Lys Met Ser His Gly Ile Ala Thr Asp Leu Ser His Met
            35                  40                  45 gac tcc aac tcc atc tgc gag ggc ttc aac acc gac gag atc gcg ctc      192
Asp Ser Asn Ser Ile Cys Glu Gly Phe Asn Thr Asp Glu Ile Ala Leu
        50                  55                  60 gcg ctc aag ggc gcc cag atc gtc gtc atc ccc gcg ggt gtc cca aga      240
Ala Leu Lys Gly Ala Gln Ile Val Val Ile Pro Ala Gly Val Pro Arg
65                  70                  75                  80 aag ccc ggg atg tca cgt gac gac ctt ttc aag atc aac gcc aag atc      288
Lys Pro Gly Met Ser Arg Asp Asp Leu Phe Lys Ile Asn Ala Lys Ile
                85                  90                  95 atc aag tcg ttg gcg ttg caa ata gcc gag cac gcg ccc gag gcg cgc      336
Ile Lys Ser Leu Ala Leu Gln Ile Ala Glu His Ala Pro Glu Ala Arg
            100                 105                 110 gtc ctc gtg atc tcg aac ccg gtc aac tcc ttg gtg ccc att gtg tac      384
Val Leu Val Ile Ser Asn Pro Val Asn Ser Leu Val Pro Ile Val Tyr
        115                 120                 125 gag act ttg aag agc gtc ggc aag ttc gag ccg ggt aaa gtg atg gga      432
Glu Thr Leu Lys Ser Val Gly Lys Phe Glu Pro Gly Lys Val Met Gly
    130                 135                 140 att acc aca ttg gac att atc cgc tca cac acg ttc ctg gtg gac gtc      480
Ile Thr Thr Leu Asp Ile Ile Arg Ser His Thr Phe Leu Val Asp Val
145                 150                 155                 160 ttg ggc cgc aag gcg tac agc gtc gag aag ttg cgc agc gcg gtt act      528
Leu Gly Arg Lys Ala Tyr Ser Val Glu Lys Leu Arg Ser Ala Val Thr
                165                 170                 175
```

```
gtg gtg ggc ggc cac tcg ggc gag acc att gtt ccg att ttc acc gac      576
Val Val Gly Gly His Ser Gly Glu Thr Ile Val Pro Ile Phe Thr Asp
        180                 185                 190 cag aag ttc tac agg cgt ctc aga gac aga gag ctc tat gac gcg tac      624
Gln Lys Phe Tyr Arg Arg Leu Arg Asp Arg Glu Leu Tyr Asp Ala Tyr
            195                 200                 205 gtg cat agg gtc caa ttc ggc gga gac gag gtc gtg aag gcc aag gac      672
Val His Arg Val Gln Phe Gly Gly Asp Glu Val Val Lys Ala Lys Asp
    210                 215                 220 ggc agc ggt agt gct act ttg tct atg gcc tgg gcg ggt tac agt ttt      720
Gly Ser Gly Ser Ala Thr Leu Ser Met Ala Trp Ala Gly Tyr Ser Phe
225                 230                 235                 240 gtg aag cag ttg ctc aac agc ttg cac cta gaa aca ggc gaa gac gtg      768
Val Lys Gln Leu Leu Asn Ser Leu His Leu Glu Thr Gly Glu Asp Val
                245                 250                 255 cat ccg atc cca acg ttt gtg tac ttg ccg ggt tta ccg ggc ggg aag      816
His Pro Ile Pro Thr Phe Val Tyr Leu Pro Gly Leu Pro Gly Gly Lys
            260                 265                 270 gag ctc cag cag aag ttg ggc acc tct gtt gag ttt ttt gcc gcg ccc      864
Glu Leu Gln Gln Lys Leu Gly Thr Ser Val Glu Phe Phe Ala Ala Pro
        275                 280                 285 gtg aag ctt tcc aag ggt att gtg gtt gaa gtt gag cac gac tgg gtc      912
Val Lys Leu Ser Lys Gly Ile Val Val Glu Val Glu His Asp Trp Val
    290                 295                 300 gac aag ttg aac gat gcc gag aag aag ttg att gca aag tgt ctt cca      960
Asp Lys Leu Asn Asp Ala Glu Lys Lys Leu Ile Ala Lys Cys Leu Pro
305                 310                 315                 320 atc ctt gac aag aac atc aag aag ggt ctc gcc ttt tcg cag cag aca     1008
Ile Leu Asp Lys Asn Ile Lys Lys Gly Leu Ala Phe Ser Gln Gln Thr
                325                 330                 335 aag ttg tga                                                         1017
Lys Leu <210> SEQ ID NO 22
<211> LENGTH: 338
<212> TYPE: PRT
<213> ORGANISM: Kluyveromyces marxianus

<400> SEQUENCE: 22

Met Val Ser Val Ala Val Leu Gly Ser Ser Gly Gly Ile Gly Gln Pro
1               5                   10                  15

Leu Ser Leu Leu Leu Lys Leu Asp Pro Arg Val Ser Ser Leu Arg Leu
            20                  25                  30

Tyr Asp Leu Lys Met Ser His Gly Ile Ala Thr Asp Leu Ser His Met
        35                  40                  45

Asp Ser Asn Ser Ile Cys Glu Gly Phe Asn Thr Asp Glu Ile Ala Leu
    50                  55                  60

Ala Leu Lys Gly Ala Gln Ile Val Val Pro Ala Gly Val Pro Arg
65                  70                  75                  80

Lys Pro Gly Met Ser Arg Asp Asp Leu Phe Lys Ile Asn Ala Lys Ile
                85                  90                  95

Ile Lys Ser Leu Ala Leu Gln Ile Ala Glu His Ala Pro Glu Ala Arg
            100                 105                 110

Val Leu Val Ile Ser Asn Pro Val Asn Ser Leu Val Pro Ile Val Tyr
        115                 120                 125

Glu Thr Leu Lys Ser Val Gly Lys Phe Glu Pro Gly Lys Val Met Gly
    130                 135                 140
```

```
Ile Thr Thr Leu Asp Ile Ile Arg Ser His Thr Phe Leu Val Asp Val
145                 150                 155                 160

Leu Gly Arg Lys Ala Tyr Ser Val Glu Lys Leu Arg Ser Ala Val Thr
            165                 170                 175

Val Val Gly Gly His Ser Gly Glu Thr Ile Val Pro Ile Phe Thr Asp
            180                 185                 190

Gln Lys Phe Tyr Arg Arg Leu Arg Asp Arg Glu Leu Tyr Asp Ala Tyr
            195                 200                 205

Val His Arg Val Gln Phe Gly Gly Asp Glu Val Val Lys Ala Lys Asp
            210                 215                 220

Gly Ser Gly Ser Ala Thr Leu Ser Met Ala Trp Ala Gly Tyr Ser Phe
225                 230                 235                 240

Val Lys Gln Leu Leu Asn Ser Leu His Leu Glu Thr Gly Glu Asp Val
            245                 250                 255

His Pro Ile Pro Thr Phe Val Tyr Leu Pro Gly Leu Pro Gly Gly Lys
            260                 265                 270

Glu Leu Gln Gln Lys Leu Gly Thr Ser Val Glu Phe Phe Ala Ala Pro
            275                 280                 285

Val Lys Leu Ser Lys Gly Ile Val Val Glu Val Glu His Asp Trp Val
            290                 295                 300

Asp Lys Leu Asn Asp Ala Glu Lys Lys Leu Ile Ala Lys Cys Leu Pro
305                 310                 315                 320

Ile Leu Asp Lys Asn Ile Lys Lys Gly Leu Ala Phe Ser Gln Gln Thr
            325                 330                 335

Lys Leu

<210> SEQ ID NO 23
<211> LENGTH: 1125
<212> TYPE: DNA
<213> ORGANISM: Kluyveromyces marxianus
<220> FEATURE:
<221> NAME/KEY: CDS
<222> LOCATION: (1)..(1125)

<400> SEQUENCE: 23 atg cca gca gta tca tat gat gtc cag caa cgg gat atc ctc aag atc      48
Met Pro Ala Val Ser Tyr Asp Val Gln Gln Arg Asp Ile Leu Lys Ile
1               5                   10                  15 gca gtt cta ggg gcg gca ggc ggt att ggc caa tcc ttg tcg ctc ttg      96
Ala Val Leu Gly Ala Ala Gly Gly Ile Gly Gln Ser Leu Ser Leu Leu
            20                  25                  30 ttg aag tcg aac gct tct ttt ttg tta cca cgt gac tcg tca aga cac     144
Leu Lys Ser Asn Ala Ser Phe Leu Leu Pro Arg Asp Ser Ser Arg His
        35                  40                  45 ata agc cta gcg cta tac gac gtg aac aaa gat gcc atc gtg ggc aca     192
Ile Ser Leu Ala Leu Tyr Asp Val Asn Lys Asp Ala Ile Val Gly Thr
    50                  55                  60 gca gca gac ttg tca cac ata gac acc cct atc acc acc act cca cac     240
Ala Ala Asp Leu Ser His Ile Asp Thr Pro Ile Thr Thr Thr Pro His
65                  70                  75                  80 tac cca aat gat ggg aat ggc ggt atc gca cgg tgc ttg caa gat gca     288
Tyr Pro Asn Asp Gly Asn Gly Gly Ile Ala Arg Cys Leu Gln Asp Ala
                85                  90                  95 gac atg gtc atc atc cca gca ggt gtg ccc aga aaa ccc ggt atg tca     336
Asp Met Val Ile Ile Pro Ala Gly Val Pro Arg Lys Pro Gly Met Ser
            100                 105                 110 cgt gat gac cta atc ggt gtc aac gcc aag atc atc aag tcg cta gga     384
Arg Asp Asp Leu Ile Gly Val Asn Ala Lys Ile Ile Lys Ser Leu Gly
        115                 120                 125
```

```
aac gac atc gca gag tac tgt gac ttg tct aaa gtg cat gta ttg gtt      432
Asn Asp Ile Ala Glu Tyr Cys Asp Leu Ser Lys Val His Val Leu Val
            130                 135                 140 att tcg aac cca gtg aac tcg ttg gtc cca ctg atg gtg tcg act ttg      480
Ile Ser Asn Pro Val Asn Ser Leu Val Pro Leu Met Val Ser Thr Leu
145                 150                 155                 160 gca aac agc cca cac agt gcg aac aca aac atc gag gct aga gtg tac      528
Ala Asn Ser Pro His Ser Ala Asn Thr Asn Ile Glu Ala Arg Val Tyr
                165                 170                 175 ggg atc acc cat ttg gac cta gtg aga gct tcc acc ttt gtg caa cag      576
Gly Ile Thr His Leu Asp Leu Val Arg Ala Ser Thr Phe Val Gln Gln
            180                 185                 190 cta aac tct ttc aaa tca aat aac gca cct gac att ccg gtc att ggt      624
Leu Asn Ser Phe Lys Ser Asn Asn Ala Pro Asp Ile Pro Val Ile Gly
            195                 200                 205 ggt cat tcc gga gat acc atc atc ccc gtt ttt tcc gtc ttg aat cac      672
Gly His Ser Gly Asp Thr Ile Ile Pro Val Phe Ser Val Leu Asn His
210                 215                 220 cgc gct tct aac tcc gga tac gct aat ttg cta gat aat ggc gtt agg      720
Arg Ala Ser Asn Ser Gly Tyr Ala Asn Leu Leu Asp Asn Gly Val Arg
225                 230                 235                 240 caa aag ttg gtc cac aga gtt caa tat ggt ggg gac gaa atc gtc caa      768
Gln Lys Leu Val His Arg Val Gln Tyr Gly Gly Asp Glu Ile Val Gln
                245                 250                 255 gca aag aac ggt aac ggg agc gcg aca tta tcc atg gca tac gcg ggc      816
Ala Lys Asn Gly Asn Gly Ser Ala Thr Leu Ser Met Ala Tyr Ala Gly
            260                 265                 270 ttc aaa atc gca gca caa ttc atc gac ctt ttg gtc gga aat atc cgc      864
Phe Lys Ile Ala Ala Gln Phe Ile Asp Leu Leu Val Gly Asn Ile Arg
            275                 280                 285 act atc gaa aat att tgc atg tat gtt ccg ctc act aac agg tat aat      912
Thr Ile Glu Asn Ile Cys Met Tyr Val Pro Leu Thr Asn Arg Tyr Asn
290                 295                 300 acc gag atc gcc cca ggc tct gac gaa tta aga tca aag tac atc aac      960
Thr Glu Ile Ala Pro Gly Ser Asp Glu Leu Arg Ser Lys Tyr Ile Asn
305                 310                 315                 320 gga acc ctt tat ttc tcg att cca ctt tcc atc gga ata aac ggt atc     1008
Gly Thr Leu Tyr Phe Ser Ile Pro Leu Ser Ile Gly Ile Asn Gly Ile
                325                 330                 335 gaa aga gtc cac tac gag atc atg gaa cat cta gac agc tac gag cgt     1056
Glu Arg Val His Tyr Glu Ile Met Glu His Leu Asp Ser Tyr Glu Arg
            340                 345                 350 gag acg cta cta ccg atc tgc ttg gaa act cta aag ggt aat att gac     1104
Glu Thr Leu Leu Pro Ile Cys Leu Glu Thr Leu Lys Gly Asn Ile Asp
            355                 360                 365 aag ggt cta agc ttg gta taa                                         1125
Lys Gly Leu Ser Leu Val
        370

<210> SEQ ID NO 24
<211> LENGTH: 374
<212> TYPE: PRT
<213> ORGANISM: Kluyveromyces marxianus

<400> SEQUENCE: 24

Met Pro Ala Val Ser Tyr Asp Val Gln Gln Arg Asp Ile Leu Lys Ile
1               5                   10                  15

Ala Val Leu Gly Ala Ala Gly Gly Ile Gly Gln Ser Leu Ser Leu Leu
            20                  25                  30
```

```
Leu Lys Ser Asn Ala Ser Phe Leu Leu Pro Arg Asp Ser Arg His
         35                  40                  45

Ile Ser Leu Ala Leu Tyr Asp Val Asn Lys Asp Ala Ile Val Gly Thr
 50                  55                  60

Ala Ala Asp Leu Ser His Ile Asp Thr Pro Ile Thr Thr Thr Pro His
 65                  70                  75                  80

Tyr Pro Asn Asp Gly Asn Gly Gly Ile Ala Arg Cys Leu Gln Asp Ala
                 85                  90                  95

Asp Met Val Ile Ile Pro Ala Gly Val Pro Arg Lys Pro Gly Met Ser
            100                 105                 110

Arg Asp Asp Leu Ile Gly Val Asn Ala Lys Ile Ile Lys Ser Leu Gly
            115                 120                 125

Asn Asp Ile Ala Glu Tyr Cys Asp Leu Ser Lys Val His Val Leu Val
        130                 135                 140

Ile Ser Asn Pro Val Asn Ser Leu Val Pro Leu Met Val Ser Thr Leu
145                 150                 155                 160

Ala Asn Ser Pro His Ser Ala Asn Thr Asn Ile Glu Ala Arg Val Tyr
                165                 170                 175

Gly Ile Thr His Leu Asp Leu Val Arg Ala Ser Thr Phe Val Gln Gln
            180                 185                 190

Leu Asn Ser Phe Lys Ser Asn Asn Ala Pro Asp Ile Pro Val Ile Gly
        195                 200                 205

Gly His Ser Gly Asp Thr Ile Ile Pro Val Phe Ser Val Leu Asn His
210                 215                 220

Arg Ala Ser Asn Ser Gly Tyr Ala Asn Leu Leu Asp Asn Gly Val Arg
225                 230                 235                 240

Gln Lys Leu Val His Arg Val Gln Tyr Gly Gly Asp Glu Ile Val Gln
                245                 250                 255

Ala Lys Asn Gly Asn Gly Ser Ala Thr Leu Ser Met Ala Tyr Ala Gly
            260                 265                 270

Phe Lys Ile Ala Ala Gln Phe Ile Asp Leu Leu Val Gly Asn Ile Arg
        275                 280                 285

Thr Ile Glu Asn Ile Cys Met Tyr Val Pro Leu Thr Asn Arg Tyr Asn
290                 295                 300

Thr Glu Ile Ala Pro Gly Ser Asp Glu Leu Arg Ser Lys Tyr Ile Asn
305                 310                 315                 320

Gly Thr Leu Tyr Phe Ser Ile Pro Leu Ser Ile Gly Ile Asn Gly Ile
                325                 330                 335

Glu Arg Val His Tyr Glu Ile Met Glu His Leu Asp Ser Tyr Glu Arg
            340                 345                 350

Glu Thr Leu Leu Pro Ile Cys Leu Glu Thr Leu Lys Gly Asn Ile Asp
        355                 360                 365

Lys Gly Leu Ser Leu Val
    370

<210> SEQ ID NO 25
<211> LENGTH: 1071
<212> TYPE: DNA
<213> ORGANISM: Zygosaccharomyces rouxii
<220> FEATURE:
<221> NAME/KEY: CDS
<222> LOCATION: (1)..(1071)

<400> SEQUENCE: 25 atg cct cat tct atc aac ggt gat gtt aaa atc gca gta ttg gga gct      48
```

```
                Met Pro His Ser Ile Asn Gly Asp Val Lys Ile Ala Val Leu Gly Ala
                1               5                   10                  15 gca ggt ggt att gga caa tca ctt tcg cta ctt ttg aag acc cag tta          96
Ala Gly Gly Ile Gly Gln Ser Leu Ser Leu Leu Leu Lys Thr Gln Leu
                20                  25                  30 act aga gaa ttg cca aat cat cgt cat gct cag tta gcc cta tac gac         144
Thr Arg Glu Leu Pro Asn His Arg His Ala Gln Leu Ala Leu Tyr Asp
                35                  40                  45 gtc aat gct gac gca gtt cgg ggt gtc gca gcc gac tta tct cat att         192
Val Asn Ala Asp Ala Val Arg Gly Val Ala Ala Asp Leu Ser His Ile
        50                  55                  60 gat aca ggt gtt act gta aca gga tat gaa ggt gat agg atc ggc gaa         240
Asp Thr Gly Val Thr Val Thr Gly Tyr Glu Gly Asp Arg Ile Gly Glu
65                  70                  75                  80 gcg tta gaa ggt acg gat atc gtc ctg atc cct gca ggt gtt cct aga         288
Ala Leu Glu Gly Thr Asp Ile Val Leu Ile Pro Ala Gly Val Pro Arg
                85                  90                  95 aaa cct ggt atg aca aga gaa gat cta ttg gtt gtt aat gca aag att         336
Lys Pro Gly Met Thr Arg Glu Asp Leu Leu Val Val Asn Ala Lys Ile
                100                 105                 110 gtc aag agt ata ggg tca tcg att gcg cag cat tgc gat tta aac aaa         384
Val Lys Ser Ile Gly Ser Ser Ile Ala Gln His Cys Asp Leu Asn Lys
                115                 120                 125 gtg ttc att cta cta atc tca aac cca ata aat tcc ctt gtt cca gta         432
Val Phe Ile Leu Leu Ile Ser Asn Pro Ile Asn Ser Leu Val Pro Val
        130                 135                 140 ctc gtt aag gaa ctg gaa tct aaa tct caa ggc act caa gtt gag aga         480
Leu Val Lys Glu Leu Glu Ser Lys Ser Gln Gly Thr Gln Val Glu Arg
145                 150                 155                 160 cgt gtg ctt ggt ctc act aag ttg gat tcc gtt aga gca agt gca ttt         528
Arg Val Leu Gly Leu Thr Lys Leu Asp Ser Val Arg Ala Ser Ala Phe
                165                 170                 175 ttg cac gag gtt acg att aaa cat ggt cta aaa cct aaa tct aat act         576
Leu His Glu Val Thr Ile Lys His Gly Leu Lys Pro Lys Ser Asn Thr
                180                 185                 190 ctt gat gat gtt cca gta gtt ggt ggt cat tct ggt gaa act att gta         624
Leu Asp Asp Val Pro Val Val Gly Gly His Ser Gly Glu Thr Ile Val
        195                 200                 205 cct tta ttc tcc caa gcc cct aat ggt aac cgt tta tca cag gac gcc         672
Pro Leu Phe Ser Gln Ala Pro Asn Gly Asn Arg Leu Ser Gln Asp Ala
210                 215                 220 ttg gaa gct ctt gtt cag cgt gta caa ttc gga ggc gat gaa gtc gtt         720
Leu Glu Ala Leu Val Gln Arg Val Gln Phe Gly Gly Asp Glu Val Val
225                 230                 235                 240 aga gct aaa aat ggt gct ggt agt gcc act ctg tgt atg gcc cat gcc         768
Arg Ala Lys Asn Gly Ala Gly Ser Ala Thr Leu Cys Met Ala His Ala
                245                 250                 255 gct tat act gtt gct gca tct ttt att cca ctt atc act ggt caa aag         816
Ala Tyr Thr Val Ala Ala Ser Phe Ile Pro Leu Ile Thr Gly Gln Lys
                260                 265                 270 cgt tcc atc tct ggt aca ttc tat gtt gcc tta aag gat gct caa ggt         864
Arg Ser Ile Ser Gly Thr Phe Tyr Val Ala Leu Lys Asp Ala Gln Gly
        275                 280                 285 cag cct atc aac agt agc gct aag cgt ctt ttg ggc tca atc aac gat         912
Gln Pro Ile Asn Ser Ser Ala Lys Arg Leu Leu Gly Ser Ile Asn Asp
        290                 295                 300 tta cca tat ttt gca gtg cca ttg gag att act tct cag ggt gtg gat         960
Leu Pro Tyr Phe Ala Val Pro Leu Glu Ile Thr Ser Gln Gly Val Asp
305                 310                 315                 320
```

```
gaa tta gat acc agc gtt ttg gaa aga atg acc aag tat gag aga gaa    1008
Glu Leu Asp Thr Ser Val Leu Glu Arg Met Thr Lys Tyr Glu Arg Glu
            325                 330                 335 aga ctc tta gct cct tgt ctg ggt aaa ttg gaa ggt ggt atc aga aac    1056
Arg Leu Leu Ala Pro Cys Leu Gly Lys Leu Glu Gly Gly Ile Arg Asn
            340                 345                 350 ggt ttg agt ttg tga                                                1071
Gly Leu Ser Leu
            355

<210> SEQ ID NO 26
<211> LENGTH: 356
<212> TYPE: PRT
<213> ORGANISM: Zygosaccharomyces rouxii

<400> SEQUENCE: 26

Met Pro His Ser Ile Asn Gly Asp Val Lys Ile Ala Val Leu Gly Ala
1               5                   10                  15

Ala Gly Gly Ile Gly Gln Ser Leu Ser Leu Leu Leu Lys Thr Gln Leu
            20                  25                  30

Thr Arg Glu Leu Pro Asn His Arg His Ala Gln Leu Ala Leu Tyr Asp
        35                  40                  45

Val Asn Ala Asp Ala Val Arg Gly Val Ala Ala Asp Leu Ser His Ile
    50                  55                  60

Asp Thr Gly Val Thr Val Thr Gly Tyr Glu Gly Asp Arg Ile Gly Glu
65                  70                  75                  80

Ala Leu Glu Gly Thr Asp Ile Val Leu Ile Pro Ala Gly Val Pro Arg
                85                  90                  95

Lys Pro Gly Met Thr Arg Glu Asp Leu Leu Val Val Asn Ala Lys Ile
            100                 105                 110

Val Lys Ser Ile Gly Ser Ser Ile Ala Gln His Cys Asp Leu Asn Lys
        115                 120                 125

Val Phe Ile Leu Leu Ile Ser Asn Pro Ile Asn Ser Leu Val Pro Val
    130                 135                 140

Leu Val Lys Glu Leu Glu Ser Lys Ser Gln Gly Thr Gln Val Glu Arg
145                 150                 155                 160

Arg Val Leu Gly Leu Thr Lys Leu Asp Ser Val Arg Ala Ser Ala Phe
                165                 170                 175

Leu His Glu Val Thr Ile Lys His Gly Leu Lys Pro Lys Ser Asn Thr
            180                 185                 190

Leu Asp Asp Val Pro Val Val Gly Gly His Ser Gly Glu Thr Ile Val
        195                 200                 205

Pro Leu Phe Ser Gln Ala Pro Asn Gly Asn Arg Leu Ser Gln Asp Ala
    210                 215                 220

Leu Glu Ala Leu Val Gln Arg Val Gln Phe Gly Gly Asp Glu Val Val
225                 230                 235                 240

Arg Ala Lys Asn Gly Ala Gly Ser Ala Thr Leu Cys Met Ala His Ala
                245                 250                 255

Ala Tyr Thr Val Ala Ala Ser Phe Ile Pro Leu Ile Thr Gly Gln Lys
            260                 265                 270

Arg Ser Ile Ser Gly Thr Phe Tyr Val Ala Leu Lys Asp Ala Gln Gly
        275                 280                 285

Gln Pro Ile Asn Ser Ser Ala Lys Arg Leu Leu Gly Ser Ile Asn Asp
    290                 295                 300

Leu Pro Tyr Phe Ala Val Pro Leu Glu Ile Thr Ser Gln Gly Val Asp
305                 310                 315                 320
```

```
Glu Leu Asp Thr Ser Val Leu Glu Arg Met Thr Lys Tyr Glu Arg Glu
            325                 330                 335

Arg Leu Leu Ala Pro Cys Leu Gly Lys Leu Glu Gly Gly Ile Arg Asn
            340                 345                 350

Gly Leu Ser Leu
        355

<210> SEQ ID NO 27
<211> LENGTH: 939
<212> TYPE: DNA
<213> ORGANISM: Escherichia coli
<220> FEATURE:
<221> NAME/KEY: CDS
<222> LOCATION: (1)..(939)

<400> SEQUENCE: 27 atg aaa gtc gca gtc ctc ggc gct gct ggc ggt att ggc cag gcg ctt    48
Met Lys Val Ala Val Leu Gly Ala Ala Gly Gly Ile Gly Gln Ala Leu
1               5                   10                  15 gca cta ctg tta aaa acc caa ctg cct tca ggt tca gaa ctc tct ctg    96
Ala Leu Leu Leu Lys Thr Gln Leu Pro Ser Gly Ser Glu Leu Ser Leu
            20                  25                  30 tat gat atc gct cca gtg act ccc ggt gtg gct gtc gat ctg agc cat   144
Tyr Asp Ile Ala Pro Val Thr Pro Gly Val Ala Val Asp Leu Ser His
        35                  40                  45 atc cct act gct gtg aaa atc aaa ggt ttt tct ggt gaa gat gcg act   192
Ile Pro Thr Ala Val Lys Ile Lys Gly Phe Ser Gly Glu Asp Ala Thr
    50                  55                  60 ccg gcg ctg gaa ggc gca gat gtc gtt ctt atc tct gca ggc gta gcg   240
Pro Ala Leu Glu Gly Ala Asp Val Val Leu Ile Ser Ala Gly Val Ala
65                  70                  75                  80 cgt aaa ccg ggt atg gat cgt tcc gac ctg ttt aac gtt aac gcc ggc   288
Arg Lys Pro Gly Met Asp Arg Ser Asp Leu Phe Asn Val Asn Ala Gly
                85                  90                  95 atc gtg aaa aac ctg gta cag caa gtt gcg aaa acc tgc ccg aaa gcg   336
Ile Val Lys Asn Leu Val Gln Gln Val Ala Lys Thr Cys Pro Lys Ala
            100                 105                 110 tgc att ggt att atc act aac ccg gtt aac acc aca gtt gca att gct   384
Cys Ile Gly Ile Ile Thr Asn Pro Val Asn Thr Thr Val Ala Ile Ala
        115                 120                 125 gct gaa gtg ctg aaa aaa gcc ggt gtt tat gac aaa aac aaa ctg ttc   432
Ala Glu Val Leu Lys Lys Ala Gly Val Tyr Asp Lys Asn Lys Leu Phe
    130                 135                 140 ggc gtt acc acg ctg gat atc att cgt tcc aac acc ttt gtt gcg gaa   480
Gly Val Thr Thr Leu Asp Ile Ile Arg Ser Asn Thr Phe Val Ala Glu
145                 150                 155                 160 ctg aaa ggc aaa cag cca ggc gaa gtt gaa gtg ccg gtt att ggc ggt   528
Leu Lys Gly Lys Gln Pro Gly Glu Val Glu Val Pro Val Ile Gly Gly
                165                 170                 175 cac tct ggt gtt acc att ctg ccg ctg ctg tca cag gtt cct ggc gtt   576
His Ser Gly Val Thr Ile Leu Pro Leu Leu Ser Gln Val Pro Gly Val
            180                 185                 190 agt ttt acc gag cag gaa gtg gct gat ctg acc aaa cgc atc cag aac   624
Ser Phe Thr Glu Gln Glu Val Ala Asp Leu Thr Lys Arg Ile Gln Asn
        195                 200                 205 gcg ggt act gaa gtg gtt gaa gcg aag gcc ggt ggc ggg tct gca acc   672
Ala Gly Thr Glu Val Val Glu Ala Lys Ala Gly Gly Gly Ser Ala Thr
    210                 215                 220 ctg tct atg ggc cag gca gct gca cgt ttt ggt ctg tct ctg gtt cgt   720
Leu Ser Met Gly Gln Ala Ala Ala Arg Phe Gly Leu Ser Leu Val Arg
```

```
gca ctg cag ggc gaa caa ggc gtt gtc gaa tgt gcc tac gtt gaa ggc      768
Ala Leu Gln Gly Glu Gln Gly Val Val Glu Cys Ala Tyr Val Glu Gly
            245                 250                 255 gac ggt cag tac gcc cgt ttc ttc tct caa ccg ctg ctg ggt aaa          816
Asp Gly Gln Tyr Ala Arg Phe Phe Ser Gln Pro Leu Leu Leu Gly Lys
        260                 265                 270 aac ggc gtg gaa gag cgt aaa tct atc ggt acc ctg agc gca ttt gaa      864
Asn Gly Val Glu Glu Arg Lys Ser Ile Gly Thr Leu Ser Ala Phe Glu
    275                 280                 285 cag aac gcg ctg gaa ggt atg ctg gat acg ctg aag aaa gat atc gcc      912
Gln Asn Ala Leu Glu Gly Met Leu Asp Thr Leu Lys Lys Asp Ile Ala
290                 295                 300 ctg ggc gaa gag ttc gtt aat aag taa                                  939
Leu Gly Glu Glu Phe Val Asn Lys
305                 310

<210> SEQ ID NO 28
<211> LENGTH: 312
<212> TYPE: PRT
<213> ORGANISM: Escherichia coli

<400> SEQUENCE: 28

Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Arg Lys Pro Gly Met Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140

Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
                165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Gly Ser Ala Thr
    210                 215                 220

Leu Ser Met Gly Gln Ala Ala Ala Arg Phe Gly Leu Ser Leu Val Arg
225                 230                 235                 240

Ala Leu Gln Gly Glu Gln Gly Val Val Glu Cys Ala Tyr Val Glu Gly
                245                 250                 255

Asp Gly Gln Tyr Ala Arg Phe Phe Ser Gln Pro Leu Leu Leu Gly Lys
```

```
                260                 265                 270
Asn Gly Val Glu Glu Arg Lys Ser Ile Gly Thr Leu Ser Ala Phe Glu
            275                 280                 285

Gln Asn Ala Leu Glu Gly Met Leu Asp Thr Leu Lys Lys Asp Ile Ala
        290                 295                 300

Leu Gly Glu Glu Phe Val Asn Lys
305                 310

<210> SEQ ID NO 29
<211> LENGTH: 1413
<212> TYPE: DNA
<213> ORGANISM: Saccharomyces cerevisiae
<220> FEATURE:
<221> NAME/KEY: CDS
<222> LOCATION: (1)..(1413)

<400> SEQUENCE: 29 atg tct ctc tct ccc gtt gtt gtt att gga acc ggt ttg gcc ggg ctg     48
Met Ser Leu Ser Pro Val Val Val Ile Gly Thr Gly Leu Ala Gly Leu
1               5                   10                  15 gct gct gcc aac gaa ttg gtt aac aag tat aac atc cct gta acc atc     96
Ala Ala Ala Asn Glu Leu Val Asn Lys Tyr Asn Ile Pro Val Thr Ile
                20                  25                  30 ctc gaa aag gct tcc tcg atc ggt ggg aac tct atc aag gcc tcc agt    144
Leu Glu Lys Ala Ser Ser Ile Gly Gly Asn Ser Ile Lys Ala Ser Ser
            35                  40                  45 ggt att aac ggt gct tgc acc gag act caa cgt cac ttc cac atc gag    192
Gly Ile Asn Gly Ala Cys Thr Glu Thr Gln Arg His Phe His Ile Glu
        50                  55                  60 gac tcc cca cgc tta ttt gaa gat gac acc atc aag tct gct aaa ggt    240
Asp Ser Pro Arg Leu Phe Glu Asp Asp Thr Ile Lys Ser Ala Lys Gly
65                  70                  75                  80 aaa ggt gtc caa gag tta atg gct aag ttg gcc aat gat tct ccc ctg    288
Lys Gly Val Gln Glu Leu Met Ala Lys Leu Ala Asn Asp Ser Pro Leu
                85                  90                  95 gct att gaa tgg ttg aaa aac gaa ttt gat ttg aaa ttg gac cta ttg    336
Ala Ile Glu Trp Leu Lys Asn Glu Phe Asp Leu Lys Leu Asp Leu Leu
                100                 105                 110 gct caa ttg ggt ggc cac tct gtg gca aga act cac aga tcg tct ggg    384
Ala Gln Leu Gly Gly His Ser Val Ala Arg Thr His Arg Ser Ser Gly
            115                 120                 125 aag ttg cct cca ggt ttc gaa att gtt tct gcc tta tct aac aat ttg    432
Lys Leu Pro Pro Gly Phe Glu Ile Val Ser Ala Leu Ser Asn Asn Leu
        130                 135                 140 aag aaa tta gct gag act aaa cca gag tta gtt aag att aac tta gac    480
Lys Lys Leu Ala Glu Thr Lys Pro Glu Leu Val Lys Ile Asn Leu Asp
145                 150                 155                 160 agt aaa gtc gta gac atc cat gaa aag gat ggc tcc att tct gct gta    528
Ser Lys Val Val Asp Ile His Glu Lys Asp Gly Ser Ile Ser Ala Val
                165                 170                 175 gtg tac gag gat aag aat ggc gaa aag cac atg gtg agt gct aac gat    576
Val Tyr Glu Asp Lys Asn Gly Glu Lys His Met Val Ser Ala Asn Asp
                180                 185                 190 gtc gtt ttt tgt tct gga ggg ttt ggc ttt tct aag gaa atg ctt aaa    624
Val Val Phe Cys Ser Gly Gly Phe Gly Phe Ser Lys Glu Met Leu Lys
            195                 200                 205 gaa tat gca ccc gaa ctg gtg aac ttg cca acg aca aac ggg caa caa    672
Glu Tyr Ala Pro Glu Leu Val Asn Leu Pro Thr Thr Asn Gly Gln Gln
        210                 215                 220 aca act ggt gat ggt caa agg ctt ctg cag aag tta ggc gct gat ctg    720
Thr Thr Gly Asp Gly Gln Arg Leu Leu Gln Lys Leu Gly Ala Asp Leu
```

```
                        Thr Thr Gly Asp Gly Gln Arg Leu Leu Gln Lys Leu Gly Ala Asp Leu
                        225                 230                 235                 240 att gac atg gac caa att caa gtt cat cca act ggg ttc att gat cca           768
Ile Asp Met Asp Gln Ile Gln Val His Pro Thr Gly Phe Ile Asp Pro
                245                 250                 255 aat gac cgt agc tca agc tgg aaa ttc ttg gct gcc gaa tcc tta aga           816
Asn Asp Arg Ser Ser Ser Trp Lys Phe Leu Ala Ala Glu Ser Leu Arg
            260                 265                 270 ggt ctt ggt ggt atc cta tta aac cct att acc ggt aga aga ttt gtc           864
Gly Leu Gly Gly Ile Leu Leu Asn Pro Ile Thr Gly Arg Arg Phe Val
        275                 280                 285 aac gaa ttg acc aca aga gat gta gtc act gca gct att caa aag gtt           912
Asn Glu Leu Thr Thr Arg Asp Val Val Thr Ala Ala Ile Gln Lys Val
    290                 295                 300 tgt cct caa gag gat aac aga gca cta ttg gtt atg ggc gaa aaa atg           960
Cys Pro Gln Glu Asp Asn Arg Ala Leu Leu Val Met Gly Glu Lys Met
305                 310                 315                 320 tac aca gat ttg aag aat aat tta gat ttt tac atg ttc aag aaa ctt          1008
Tyr Thr Asp Leu Lys Asn Asn Leu Asp Phe Tyr Met Phe Lys Lys Leu
                325                 330                 335 gta cag aaa ttg aca tta tct caa gtt gtg tct gaa tat aat tta cca          1056
Val Gln Lys Leu Thr Leu Ser Gln Val Val Ser Glu Tyr Asn Leu Pro
            340                 345                 350 atc act gtc acc caa tta tgc gag gaa ttg caa aca tac tct tcg ttc          1104
Ile Thr Val Thr Gln Leu Cys Glu Glu Leu Gln Thr Tyr Ser Ser Phe
        355                 360                 365 act acc aag gct gat ccg ttg gga cgt acc gtt att ctc aac gaa ttt          1152
Thr Thr Lys Ala Asp Pro Leu Gly Arg Thr Val Ile Leu Asn Glu Phe
    370                 375                 380 ggc tct gac gtt act cca gaa acc gtg gtt ttt att ggt gaa gta aca          1200
Gly Ser Asp Val Thr Pro Glu Thr Val Val Phe Ile Gly Glu Val Thr
385                 390                 395                 400 ccg gtt gtc cat ttc acc atg ggt ggt gct aga atc aat gtc aag gct          1248
Pro Val Val His Phe Thr Met Gly Gly Ala Arg Ile Asn Val Lys Ala
                405                 410                 415 caa gtc att ggc aag aac gac gaa agg cta cta aaa ggc ctg tac gcg          1296
Gln Val Ile Gly Lys Asn Asp Glu Arg Leu Leu Lys Gly Leu Tyr Ala
            420                 425                 430 gcc ggt gaa gtt tct ggc ggt gtt cat ggc gcc aat agg ttg ggt ggt          1344
Ala Gly Glu Val Ser Gly Gly Val His Gly Ala Asn Arg Leu Gly Gly
        435                 440                 445 tca agt ttg tta gaa tgc gtt gtc ttt ggg aga act gca gct gaa tct          1392
Ser Ser Leu Leu Glu Cys Val Val Phe Gly Arg Thr Ala Ala Glu Ser
    450                 455                 460 att gcc aat gac cgc aag taa                                              1413
Ile Ala Asn Asp Arg Lys
465                 470

<210> SEQ ID NO 30
<211> LENGTH: 470
<212> TYPE: PRT
<213> ORGANISM: Saccharomyces cerevisiae

<400> SEQUENCE: 30

Met Ser Leu Ser Pro Val Val Ile Gly Thr Gly Leu Ala Gly Leu
1               5                   10                  15

Ala Ala Ala Asn Glu Leu Val Asn Lys Tyr Asn Ile Pro Val Thr Ile
                20                  25                  30

Leu Glu Lys Ala Ser Ser Ile Gly Gly Asn Ser Ile Lys Ala Ser Ser
            35                  40                  45
```

```
Gly Ile Asn Gly Ala Cys Thr Glu Thr Gln Arg His Phe His Ile Glu
         50                  55                  60

Asp Ser Pro Arg Leu Phe Glu Asp Asp Thr Ile Lys Ser Ala Lys Gly
 65                  70                  75                  80

Lys Gly Val Gln Glu Leu Met Ala Lys Leu Ala Asn Asp Ser Pro Leu
                     85                  90                  95

Ala Ile Glu Trp Leu Lys Asn Glu Phe Asp Leu Lys Leu Asp Leu Leu
                100                 105                 110

Ala Gln Leu Gly Gly His Ser Val Ala Arg Thr His Arg Ser Ser Gly
            115                 120                 125

Lys Leu Pro Pro Gly Phe Glu Ile Val Ser Ala Leu Ser Asn Asn Leu
        130                 135                 140

Lys Lys Leu Ala Glu Thr Lys Pro Glu Leu Val Lys Ile Asn Leu Asp
145                 150                 155                 160

Ser Lys Val Val Asp Ile His Glu Lys Asp Gly Ser Ile Ser Ala Val
                165                 170                 175

Val Tyr Glu Asp Lys Asn Gly Glu Lys His Met Val Ser Ala Asn Asp
                180                 185                 190

Val Val Phe Cys Ser Gly Gly Phe Gly Phe Ser Lys Glu Met Leu Lys
            195                 200                 205

Glu Tyr Ala Pro Glu Leu Val Asn Leu Pro Thr Thr Asn Gly Gln Gln
        210                 215                 220

Thr Thr Gly Asp Gly Gln Arg Leu Leu Gln Lys Leu Gly Ala Asp Leu
225                 230                 235                 240

Ile Asp Met Asp Gln Ile Gln Val His Pro Thr Gly Phe Ile Asp Pro
                245                 250                 255

Asn Asp Arg Ser Ser Ser Trp Lys Phe Leu Ala Ala Glu Ser Leu Arg
                260                 265                 270

Gly Leu Gly Gly Ile Leu Leu Asn Pro Ile Thr Gly Arg Arg Phe Val
            275                 280                 285

Asn Glu Leu Thr Thr Arg Asp Val Val Thr Ala Ala Ile Gln Lys Val
        290                 295                 300

Cys Pro Gln Glu Asp Asn Arg Ala Leu Leu Val Met Gly Glu Lys Met
305                 310                 315                 320

Tyr Thr Asp Leu Lys Asn Asn Leu Asp Phe Tyr Met Phe Lys Lys Leu
                325                 330                 335

Val Gln Lys Leu Thr Leu Ser Gln Val Val Ser Glu Tyr Asn Leu Pro
            340                 345                 350

Ile Thr Val Thr Gln Leu Cys Glu Glu Leu Gln Thr Tyr Ser Ser Phe
        355                 360                 365

Thr Thr Lys Ala Asp Pro Leu Gly Arg Thr Val Ile Leu Asn Glu Phe
370                 375                 380

Gly Ser Asp Val Thr Pro Glu Thr Val Val Phe Ile Gly Glu Val Thr
385                 390                 395                 400

Pro Val Val His Phe Thr Met Gly Gly Ala Arg Ile Asn Val Lys Ala
                405                 410                 415

Gln Val Ile Gly Lys Asn Asp Glu Arg Leu Leu Lys Gly Leu Tyr Ala
            420                 425                 430

Ala Gly Glu Val Ser Gly Gly Val His Gly Ala Asn Arg Leu Gly Gly
        435                 440                 445

Ser Ser Leu Leu Glu Cys Val Val Phe Gly Arg Thr Ala Ala Glu Ser
450                 455                 460
```

```
Ile Ala Asn Asp Arg Lys
465                 470

<210> SEQ ID NO 31
<211> LENGTH: 1413
<212> TYPE: DNA
<213> ORGANISM: Saccharomyces mikatae
<220> FEATURE:
<221> NAME/KEY: CDS
<222> LOCATION: (1)..(1413)

<400> SEQUENCE: 31 atg tca tct tct cca gtt gtc gtt att ggt aca ggc ttg gca ggt ttg      48
Met Ser Ser Ser Pro Val Val Val Ile Gly Thr Gly Leu Ala Gly Leu
1               5                   10                  15 gca act gct aat gag tta gtc aat aag tac aac att cct gtt acc att      96
Ala Thr Ala Asn Glu Leu Val Asn Lys Tyr Asn Ile Pro Val Thr Ile
            20                  25                  30 ttg gaa aag gca tcc tct atc ggt ggc aat tcc att aag gca tct tct     144
Leu Glu Lys Ala Ser Ser Ile Gly Gly Asn Ser Ile Lys Ala Ser Ser
        35                  40                  45 ggt atc aat ggt gca tgt aca gaa acc caa cgt cat ttt cac att gaa     192
Gly Ile Asn Gly Ala Cys Thr Glu Thr Gln Arg His Phe His Ile Glu
    50                  55                  60 gat act cct aga ctt ttt gaa gat gat act gtt caa tcc gcc aag ggc     240
Asp Thr Pro Arg Leu Phe Glu Asp Asp Thr Val Gln Ser Ala Lys Gly
65                  70                  75                  80 aaa ggt gtt caa gag tta atg ggt aaa ctt gct aat gat tct cca ctt     288
Lys Gly Val Gln Glu Leu Met Gly Lys Leu Ala Asn Asp Ser Pro Leu
                85                  90                  95 gct att gaa tgg tta aag act gaa ttc gac tta aag tta gac ctt ttg     336
Ala Ile Glu Trp Leu Lys Thr Glu Phe Asp Leu Lys Leu Asp Leu Leu
            100                 105                 110 gct cag tta ggt ggt cac tct gtt gct aga act cat aga tct tcc ggt     384
Ala Gln Leu Gly Gly His Ser Val Ala Arg Thr His Arg Ser Ser Gly
        115                 120                 125 aaa ctt cca cca ggt ttc gaa atc gtt tcc gcc tta tcc aat aac ttg     432
Lys Leu Pro Pro Gly Phe Glu Ile Val Ser Ala Leu Ser Asn Asn Leu
    130                 135                 140 aaa aag ttg gca gaa acc aag cca gag tta gtt aag att aac tta gac     480
Lys Lys Leu Ala Glu Thr Lys Pro Glu Leu Val Lys Ile Asn Leu Asp
145                 150                 155                 160 tca aag gtc gtt gac atc cac aaa aag gac ggc tct att tcc gca att     528
Ser Lys Val Val Asp Ile His Lys Lys Asp Gly Ser Ile Ser Ala Ile
                165                 170                 175 gtc tat gat gac aaa aac ggt gaa aga cat acc tta tcc act tca aat     576
Val Tyr Asp Asp Lys Asn Gly Glu Arg His Thr Leu Ser Thr Ser Asn
            180                 185                 190 gtt gtt ttc tgc tct ggt ggt ttc ggt ttt tct aag gaa atg tta aac     624
Val Val Phe Cys Ser Gly Gly Phe Gly Phe Ser Lys Glu Met Leu Asn
        195                 200                 205 gag tat gct cca caa ttg gtc aac ttg cca acc act aac ggt cag caa     672
Glu Tyr Ala Pro Gln Leu Val Asn Leu Pro Thr Thr Asn Gly Gln Gln
    210                 215                 220 aca aca ggt gac ggc caa aga ttg tta caa aag ctt ggt gca gat ttg     720
Thr Thr Gly Asp Gly Gln Arg Leu Leu Gln Lys Leu Gly Ala Asp Leu
225                 230                 235                 240 att gat atg gat caa att caa gtc cat cct act ggt ttc atc gac cca     768
Ile Asp Met Asp Gln Ile Gln Val His Pro Thr Gly Phe Ile Asp Pro
                245                 250                 255 aac gat aga aac tcc tct tgg aag ttt ttg gct gct gaa tct tta aga     816
Asn Asp Arg Asn Ser Ser Trp Lys Phe Leu Ala Ala Glu Ser Leu Arg
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | Asn | Asp | Arg | Asn | Ser | Ser | Trp | Lys | Phe | Leu | Ala | Ala | Glu | Ser | Leu Arg |
|     |     |     |     | 260 |     |     |     | 265 |     |     |     |     | 270 |     |     |      |

```
ggt ttg ggt ggt atc tta ttg aat cca att act ggt cgt aga ttt gtc      864
Gly Leu Gly Gly Ile Leu Leu Asn Pro Ile Thr Gly Arg Arg Phe Val
        275                 280                 285 aac gaa ttg acc act aga gat gtc gtt act gaa gca atc cag aag cac      912
Asn Glu Leu Thr Thr Arg Asp Val Val Thr Glu Ala Ile Gln Lys His
290                 295                 300 tgt cca caa gat gat aac aga gct ttg tta gtt atg tcc gaa aag atg      960
Cys Pro Gln Asp Asp Asn Arg Ala Leu Leu Val Met Ser Glu Lys Met
305                 310                 315                 320 tat aca gat ttg aaa aac aat ttg gac ttc tac atg ttc aaa aag tta     1008
Tyr Thr Asp Leu Lys Asn Asn Leu Asp Phe Tyr Met Phe Lys Lys Leu
            325                 330                 335 gtt caa aag tta tct ttg tcc caa gtt gtt tcc gag tat aag tta cca     1056
Val Gln Lys Leu Ser Leu Ser Gln Val Val Ser Glu Tyr Lys Leu Pro
        340                 345                 350 att act gtt tcc caa ttg tgt cag gaa tta caa acc tac tca tct ttt     1104
Ile Thr Val Ser Gln Leu Cys Gln Glu Leu Gln Thr Tyr Ser Ser Phe
    355                 360                 365 act tca aaa gcc gat cct ctt ggt aga acc gtt gtc tta aac gaa ttc     1152
Thr Ser Lys Ala Asp Pro Leu Gly Arg Thr Val Val Leu Asn Glu Phe
370                 375                 380 ggt gct gac atc acc cca gaa aca atg gtt ttc atc ggc gaa gtt acc     1200
Gly Ala Asp Ile Thr Pro Glu Thr Met Val Phe Ile Gly Glu Val Thr
385                 390                 395                 400 cca gtc gtt cac ttt acc atg ggt ggt gct aga atc aat gtt aag gct     1248
Pro Val Val His Phe Thr Met Gly Gly Ala Arg Ile Asn Val Lys Ala
            405                 410                 415 caa gtt atc ggc aaa aac gat gag cct ttg tta aac ggt ttg tac gca     1296
Gln Val Ile Gly Lys Asn Asp Glu Pro Leu Leu Asn Gly Leu Tyr Ala
        420                 425                 430 gca ggt gaa gtt tct ggt ggt gtc cat ggt gcc aat aga tta ggt ggt     1344
Ala Gly Glu Val Ser Gly Gly Val His Gly Ala Asn Arg Leu Gly Gly
    435                 440                 445 tca tct ttg ctt gaa tgt gtc gtt ttt ggt aga act gca gca gaa tca     1392
Ser Ser Leu Leu Glu Cys Val Val Phe Gly Arg Thr Ala Ala Glu Ser
450                 455                 460 att gcc aat aac cac aag taa                                         1413
Ile Ala Asn Asn His Lys
465                 470

<210> SEQ ID NO 32
<211> LENGTH: 470
<212> TYPE: PRT
<213> ORGANISM: Saccharomyces mikatae

<400> SEQUENCE: 32

Met Ser Ser Ser Pro Val Val Ile Gly Thr Gly Leu Ala Gly Leu
1               5                   10                  15

Ala Thr Ala Asn Glu Leu Val Asn Lys Tyr Asn Ile Pro Val Thr Ile
                20                  25                  30

Leu Glu Lys Ala Ser Ser Ile Gly Gly Asn Ser Ile Lys Ala Ser Ser
            35                  40                  45

Gly Ile Asn Gly Ala Cys Thr Glu Thr Gln Arg His Phe His Ile Glu
        50                  55                  60

Asp Thr Pro Arg Leu Phe Glu Asp Asp Thr Val Gln Ser Ala Lys Gly
65                  70                  75                  80

Lys Gly Val Gln Glu Leu Met Gly Lys Leu Ala Asn Asp Ser Pro Leu
```

```
                85                  90                  95
Ala Ile Glu Trp Leu Lys Thr Glu Phe Asp Leu Lys Leu Asp Leu Leu
            100                 105                 110

Ala Gln Leu Gly Gly His Ser Val Ala Arg Thr His Arg Ser Ser Gly
        115                 120                 125

Lys Leu Pro Pro Gly Phe Glu Ile Val Ser Ala Leu Ser Asn Asn Leu
    130                 135                 140

Lys Lys Leu Ala Glu Thr Lys Pro Glu Leu Val Lys Ile Asn Leu Asp
145                 150                 155                 160

Ser Lys Val Val Asp Ile His Lys Lys Asp Gly Ser Ile Ser Ala Ile
                165                 170                 175

Val Tyr Asp Asp Lys Asn Gly Glu Arg His Thr Leu Ser Thr Ser Asn
            180                 185                 190

Val Val Phe Cys Ser Gly Gly Phe Gly Phe Ser Lys Glu Met Leu Asn
        195                 200                 205

Glu Tyr Ala Pro Gln Leu Val Asn Leu Pro Thr Thr Asn Gly Gln Gln
    210                 215                 220

Thr Thr Gly Asp Gly Gln Arg Leu Leu Gln Lys Leu Gly Ala Asp Leu
225                 230                 235                 240

Ile Asp Met Asp Gln Ile Gln Val His Pro Thr Gly Phe Ile Asp Pro
                245                 250                 255

Asn Asp Arg Asn Ser Ser Trp Lys Phe Leu Ala Ala Glu Ser Leu Arg
            260                 265                 270

Gly Leu Gly Gly Ile Leu Leu Asn Pro Ile Thr Gly Arg Arg Phe Val
        275                 280                 285

Asn Glu Leu Thr Thr Arg Asp Val Val Thr Glu Ala Ile Gln Lys His
    290                 295                 300

Cys Pro Gln Asp Asp Asn Arg Ala Leu Leu Val Met Ser Glu Lys Met
305                 310                 315                 320

Tyr Thr Asp Leu Lys Asn Asn Leu Asp Phe Tyr Met Phe Lys Lys Leu
                325                 330                 335

Val Gln Lys Leu Ser Leu Ser Gln Val Val Ser Glu Tyr Lys Leu Pro
            340                 345                 350

Ile Thr Val Ser Gln Leu Cys Gln Glu Leu Gln Thr Tyr Ser Ser Phe
        355                 360                 365

Thr Ser Lys Ala Asp Pro Leu Gly Arg Thr Val Leu Asn Glu Phe
    370                 375                 380

Gly Ala Asp Ile Thr Pro Glu Thr Met Val Phe Ile Gly Glu Val Thr
385                 390                 395                 400

Pro Val Val His Phe Thr Met Gly Gly Ala Arg Ile Asn Val Lys Ala
                405                 410                 415

Gln Val Ile Gly Lys Asn Asp Glu Pro Leu Leu Asn Gly Leu Tyr Ala
            420                 425                 430

Ala Gly Glu Val Ser Gly Val His Gly Ala Asn Arg Leu Gly Gly
        435                 440                 445

Ser Ser Leu Leu Glu Cys Val Val Phe Gly Arg Thr Ala Ala Glu Ser
    450                 455                 460

Ile Ala Asn Asn His Lys
465                 470

<210> SEQ ID NO 33
<211> LENGTH: 1413
<212> TYPE: DNA
<213> ORGANISM: Kluyveromyces polyspora
```

<220> FEATURE:
<221> NAME/KEY: CDS
<222> LOCATION: (1)..(1413)

<400> SEQUENCE: 33

```
atg tca acc aaa aag cca gtc gtc atc att ggt act ggt tta gcc ggt      48
Met Ser Thr Lys Lys Pro Val Val Ile Ile Gly Thr Gly Leu Ala Gly
1               5                   10                  15 ttg tct gct ggt aat caa ttg gtc aat atg cat aaa gtt cct atc att      96
Leu Ser Ala Gly Asn Gln Leu Val Asn Met His Lys Val Pro Ile Ile
            20                  25                  30 atg ttg gac aag gca tcc tcc att ggt ggt aat tct aca aag gct tcc     144
Met Leu Asp Lys Ala Ser Ser Ile Gly Gly Asn Ser Thr Lys Ala Ser
        35                  40                  45 tct ggt atc aac ggt gct tct act att act caa cag caa ctt aat gtt     192
Ser Gly Ile Asn Gly Ala Ser Thr Ile Thr Gln Gln Gln Leu Asn Val
    50                  55                  60 aaa gac tct cct gac tta ttc ctt caa gat act gtt aag tct gct aag     240
Lys Asp Ser Pro Asp Leu Phe Leu Gln Asp Thr Val Lys Ser Ala Lys
65                  70                  75                  80 ggt aga ggt att gag tcc ctt atg aaa aag tta tca caa gac tcc aac     288
Gly Arg Gly Ile Glu Ser Leu Met Lys Lys Leu Ser Gln Asp Ser Asn
                85                  90                  95 tct gct atc cat tgg ttg caa cag gat ttt gat ttg aag ttg gat ttg     336
Ser Ala Ile His Trp Leu Gln Gln Asp Phe Asp Leu Lys Leu Asp Leu
            100                 105                 110 tta gct caa ttg ggt ggt cat tcc gtt cct aga aca cac cgt tcc tca     384
Leu Ala Gln Leu Gly Gly His Ser Val Pro Arg Thr His Arg Ser Ser
        115                 120                 125 ggc aag tta cct cca ggc ttc gaa att gtc caa gct tta tct aac aag     432
Gly Lys Leu Pro Pro Gly Phe Glu Ile Val Gln Ala Leu Ser Asn Lys
    130                 135                 140 tta aag gct att tct gag tcc gat cca gaa ttc gtt aga atc tta ctt     480
Leu Lys Ala Ile Ser Glu Ser Asp Pro Glu Phe Val Arg Ile Leu Leu
145                 150                 155                 160 aac tcc aag gtt gtt gat gtt tcc gtt aac aat gag ggc aag gtc gaa     528
Asn Ser Lys Val Val Asp Val Ser Val Asn Asn Glu Gly Lys Val Glu
                165                 170                 175 tct att gac tat gtt gat gca gaa ggt aaa cat cac aaa atc gct act     576
Ser Ile Asp Tyr Val Asp Ala Glu Gly Lys His His Lys Ile Ala Thr
            180                 185                 190 gat aac gtt gtc ttt tgt tcc ggt ggt ttc ggt cac tca gca gaa atg     624
Asp Asn Val Val Phe Cys Ser Gly Gly Phe Gly His Ser Ala Glu Met
        195                 200                 205 ttg aac aag tat gca cca gaa tta gct aac ttg cca act act aac ggt     672
Leu Asn Lys Tyr Ala Pro Glu Leu Ala Asn Leu Pro Thr Thr Asn Gly
    210                 215                 220 caa caa acc act ggc gat ggt cag aga atc ttg gag aaa ttg ggt gca     720
Gln Gln Thr Thr Gly Asp Gly Gln Arg Ile Leu Glu Lys Leu Gly Ala
225                 230                 235                 240 gac ttg att gat atg tcc caa att caa gtt cac cca aca ggt ttc atc     768
Asp Leu Ile Asp Met Ser Gln Ile Gln Val His Pro Thr Gly Phe Ile
                245                 250                 255 gat cca gca aac aga gat tct aag tgg aag ttt ttg gct gcc gaa gca     816
Asp Pro Ala Asn Arg Asp Ser Lys Trp Lys Phe Leu Ala Ala Glu Ala
            260                 265                 270 tta aga ggt tta ggt ggt atc tta ctt aat cca tct acc ggc aag aga     864
Leu Arg Gly Leu Gly Gly Ile Leu Leu Asn Pro Ser Thr Gly Lys Arg
        275                 280                 285 ttc gtt aat gag tta acc acc aga gat ttg gtc aca gaa gct atc caa     912
Phe Val Asn Glu Leu Thr Thr Arg Asp Leu Val Thr Glu Ala Ile Gln
```

```
Phe Val Asn Glu Leu Thr Thr Arg Asp Leu Val Thr Glu Ala Ile Gln
    290                 295                 300 tca caa tgt cca aga gat gac aat aag gca ttc ctt gtt atg tct gaa      960
Ser Gln Cys Pro Arg Asp Asp Asn Lys Ala Phe Leu Val Met Ser Glu
305                 310                 315                 320 aag gtc tat gag aat tac aaa aac aac atg gac ttt tac tta ttc aaa     1008
Lys Val Tyr Glu Asn Tyr Lys Asn Asn Met Asp Phe Tyr Leu Phe Lys
                325                 330                 335 aag tta gtt tcc aag atg acc att aag gaa ttt gtc gaa act tac aag     1056
Lys Leu Val Ser Lys Met Thr Ile Lys Glu Phe Val Glu Thr Tyr Lys
            340                 345                 350 ttg cca att tct gcc gac gcc gtt acc caa gac tta atc gac tat tca     1104
Leu Pro Ile Ser Ala Asp Ala Val Thr Gln Asp Leu Ile Asp Tyr Ser
        355                 360                 365 gtt gat aag acc gat aag ttt ggt aga cca ttg gtt atc aac gtt ttt     1152
Val Asp Lys Thr Asp Lys Phe Gly Arg Pro Leu Val Ile Asn Val Phe
    370                 375                 380 gat gaa aag ttg acc gaa gat tcc gaa atc tat gtt ggt gaa gtt aca     1200
Asp Glu Lys Leu Thr Glu Asp Ser Glu Ile Tyr Val Gly Glu Val Thr
385                 390                 395                 400 cca gtt gtc cat ttc act atg ggt ggt gca aag atc aat act gaa tct     1248
Pro Val Val His Phe Thr Met Gly Gly Ala Lys Ile Asn Thr Glu Ser
                405                 410                 415 caa gtt atc aac aaa aac ggt caa gtt ttg gca aag ggt atc tac gca     1296
Gln Val Ile Asn Lys Asn Gly Gln Val Leu Ala Lys Gly Ile Tyr Ala
            420                 425                 430 gca ggt gaa gtc tcc ggt ggt gtt cac ggt tct aat aga tta ggt ggt     1344
Ala Gly Glu Val Ser Gly Gly Val His Gly Ser Asn Arg Leu Gly Gly
        435                 440                 445 tca tct ttg tta gaa tgc gtc gtt tac ggt aga tct gct gca gat aac     1392
Ser Ser Leu Leu Glu Cys Val Val Tyr Gly Arg Ser Ala Ala Asp Asn
450                 455                 460 att gcc aaa aac att gaa taa                                         1413
Ile Ala Lys Asn Ile Glu
465                 470

<210> SEQ ID NO 34
<211> LENGTH: 470
<212> TYPE: PRT
<213> ORGANISM: Kluyveromyces polyspora

<400> SEQUENCE: 34

Met Ser Thr Lys Lys Pro Val Val Ile Ile Gly Thr Gly Leu Ala Gly
1               5                   10                  15

Leu Ser Ala Gly Asn Gln Leu Val Asn Met His Lys Val Pro Ile Ile
                20                  25                  30

Met Leu Asp Lys Ala Ser Ser Ile Gly Gly Asn Ser Thr Lys Ala Ser
            35                  40                  45

Ser Gly Ile Asn Gly Ala Ser Thr Ile Thr Gln Gln Gln Leu Asn Val
        50                  55                  60

Lys Asp Ser Pro Asp Leu Phe Leu Gln Asp Thr Val Lys Ser Ala Lys
65                  70                  75                  80

Gly Arg Gly Ile Glu Ser Leu Met Lys Lys Leu Ser Gln Asp Ser Asn
                85                  90                  95

Ser Ala Ile His Trp Leu Gln Gln Asp Phe Asp Leu Lys Leu Asp Leu
            100                 105                 110

Leu Ala Gln Leu Gly Gly His Ser Val Pro Arg Thr His Arg Ser Ser
        115                 120                 125
```

Gly Lys Leu Pro Pro Gly Phe Glu Ile Val Gln Ala Leu Ser Asn Lys
    130                 135                 140

Leu Lys Ala Ile Ser Glu Ser Asp Pro Glu Phe Val Arg Ile Leu Leu
145                 150                 155                 160

Asn Ser Lys Val Val Asp Val Ser Val Asn Asn Glu Gly Lys Val Glu
                165                 170                 175

Ser Ile Asp Tyr Val Asp Ala Glu Gly Lys His His Lys Ile Ala Thr
            180                 185                 190

Asp Asn Val Val Phe Cys Ser Gly Gly Phe Gly His Ser Ala Glu Met
        195                 200                 205

Leu Asn Lys Tyr Ala Pro Glu Leu Ala Asn Leu Pro Thr Thr Asn Gly
    210                 215                 220

Gln Gln Thr Thr Gly Asp Gly Gln Arg Ile Leu Glu Lys Leu Gly Ala
225                 230                 235                 240

Asp Leu Ile Asp Met Ser Gln Ile Gln Val His Pro Thr Gly Phe Ile
                245                 250                 255

Asp Pro Ala Asn Arg Asp Ser Lys Trp Lys Phe Leu Ala Ala Glu Ala
            260                 265                 270

Leu Arg Gly Leu Gly Gly Ile Leu Leu Asn Pro Ser Thr Gly Lys Arg
        275                 280                 285

Phe Val Asn Glu Leu Thr Thr Arg Asp Leu Val Thr Glu Ala Ile Gln
    290                 295                 300

Ser Gln Cys Pro Arg Asp Asp Asn Lys Ala Phe Leu Val Met Ser Glu
305                 310                 315                 320

Lys Val Tyr Glu Asn Tyr Lys Asn Asn Met Asp Phe Tyr Leu Phe Lys
                325                 330                 335

Lys Leu Val Ser Lys Met Thr Ile Lys Glu Phe Val Glu Thr Tyr Lys
            340                 345                 350

Leu Pro Ile Ser Ala Asp Ala Val Thr Gln Asp Leu Ile Asp Tyr Ser
        355                 360                 365

Val Asp Lys Thr Asp Lys Phe Gly Arg Pro Leu Val Ile Asn Val Phe
    370                 375                 380

Asp Glu Lys Leu Thr Glu Asp Ser Glu Ile Tyr Val Gly Glu Val Thr
385                 390                 395                 400

Pro Val Val His Phe Thr Met Gly Gly Ala Lys Ile Asn Thr Glu Ser
                405                 410                 415

Gln Val Ile Asn Lys Asn Gly Gln Val Leu Ala Lys Gly Ile Tyr Ala
            420                 425                 430

Ala Gly Glu Val Ser Gly Val His Gly Ser Asn Arg Leu Gly Gly
        435                 440                 445

Ser Ser Leu Leu Glu Cys Val Val Tyr Gly Arg Ser Ala Ala Asp Asn
450                 455                 460

Ile Ala Lys Asn Ile Glu
465             470

<210> SEQ ID NO 35
<211> LENGTH: 1464
<212> TYPE: DNA
<213> ORGANISM: Kluyveromyces marxianus
<220> FEATURE:
<221> NAME/KEY: CDS
<222> LOCATION: (1)..(1464)

<400> SEQUENCE: 35 atg ttg cac aga tac atc cgt ttg ttc tcc ttc tgc gtc atc ttg tac    48
Met Leu His Arg Tyr Ile Arg Leu Phe Ser Phe Cys Val Ile Leu Tyr -continued

```
1               5                   10                  15 tta gtc tat ttg tta ctt act aag gag tca aac gtc atg tct aag cct        96
Leu Val Tyr Leu Leu Leu Thr Lys Glu Ser Asn Val Met Ser Lys Pro
            20                  25                  30 gtt gtt gtt att ggt tct ggt tta gca ggc tta aca aca tct tca caa       144
Val Val Val Ile Gly Ser Gly Leu Ala Gly Leu Thr Thr Ser Ser Gln
                35                  40                  45 tta gca aag ttt aac att cca atc gtc ctt tta gaa aag aca tct tcc       192
Leu Ala Lys Phe Asn Ile Pro Ile Val Leu Leu Glu Lys Thr Ser Ser
    50                  55                  60 att ggt ggt aat tcc att aag gca tct tct ggt atc aat ggc gca ggc       240
Ile Gly Gly Asn Ser Ile Lys Ala Ser Ser Gly Ile Asn Gly Ala Gly
65                  70                  75                  80 acc gaa act caa tct cgt tta cac gtt gaa gat cac cca gaa ttg ttt       288
Thr Glu Thr Gln Ser Arg Leu His Val Glu Asp His Pro Glu Leu Phe
                85                  90                  95 gct gat gat acc att aag tct gca aaa ggt aaa ggt gtt gtc gct ttg       336
Ala Asp Asp Thr Ile Lys Ser Ala Lys Gly Lys Gly Val Val Ala Leu
                100                 105                 110 atg gaa aag tta tct aaa gac tcc tct gat gct att tcc tgg tta caa       384
Met Glu Lys Leu Ser Lys Asp Ser Ser Asp Ala Ile Ser Trp Leu Gln
            115                 120                 125 aac gac ttc aag att cct ttg gat aag tta gct caa tta ggc ggt cat       432
Asn Asp Phe Lys Ile Pro Leu Asp Lys Leu Ala Gln Leu Gly Gly His
130                 135                 140 tcc gtt cct aga acc cat aga tca tcc ggc aag ctt cca cca ggt ttc       480
Ser Val Pro Arg Thr His Arg Ser Ser Gly Lys Leu Pro Pro Gly Phe
145                 150                 155                 160 caa att gtc gat acc ttg aaa aag gcc ttg gag tct tat gac tct aaa       528
Gln Ile Val Asp Thr Leu Lys Lys Ala Leu Glu Ser Tyr Asp Ser Lys
                165                 170                 175 gca gtt aag atc caa ttg aat tct aag gtc gtt gat gtt aag ctt gat       576
Ala Val Lys Ile Gln Leu Asn Ser Lys Val Val Asp Val Lys Leu Asp
                180                 185                 190 tcc aat aac aga gtt tca tct gtt gtt ttc gaa gat caa gat ggt act       624
Ser Asn Asn Arg Val Ser Ser Val Val Phe Glu Asp Gln Asp Gly Thr
            195                 200                 205 cac acc att gaa acc aac aac gtc gtt ttc tgt act ggt ggt ttc ggt       672
His Thr Ile Glu Thr Asn Asn Val Val Phe Cys Thr Gly Gly Phe Gly
    210                 215                 220 ttc aac aaa aag tta ttg gag aag tat gca cca cac ttg gtc gac ttg       720
Phe Asn Lys Lys Leu Leu Glu Lys Tyr Ala Pro His Leu Val Asp Leu
225                 230                 235                 240 cca act acc aac ggt gag caa acc tta ggt gaa ggt cag gtc tta ttg       768
Pro Thr Thr Asn Gly Glu Gln Thr Leu Gly Glu Gly Gln Val Leu Leu
                245                 250                 255 gaa aaa ctt ggt gct aag ttg att gat atg gac caa att caa gtt cat       816
Glu Lys Leu Gly Ala Lys Leu Ile Asp Met Asp Gln Ile Gln Val His
            260                 265                 270 cca act ggc ttt atc gat cca gcc aat cca gat tct aat tgg aag ttt       864
Pro Thr Gly Phe Ile Asp Pro Ala Asn Pro Asp Ser Asn Trp Lys Phe
        275                 280                 285 ttg gct gcc gag gcc tta aga ggt tta ggt ggt gtc ttg atc aat cca       912
Leu Ala Ala Glu Ala Leu Arg Gly Leu Gly Gly Val Leu Ile Asn Pro
290                 295                 300 cac act ggt cag aga ttt gtt aac gaa ttg aca act aga gac atg gtc       960
His Thr Gly Gln Arg Phe Val Asn Glu Leu Thr Thr Arg Asp Met Val
305                 310                 315                 320 acc gaa gct atc cag tct aag tcc gaa tcc aag act gct tac ttg gtt      1008
```

-continued

```
              Thr Glu Ala Ile Gln Ser Lys Ser Glu Ser Lys Thr Ala Tyr Leu Val
                              325                 330                 335 atg tcc gag tcc tta tac gag aac tac aag cca aac atg gac ttc tat       1056
Met Ser Glu Ser Leu Tyr Glu Asn Tyr Lys Pro Asn Met Asp Phe Tyr
                340                 345                 350 atg ttc aaa aag ctt gtt tcc aaa aag acc gtt gct gaa ttt gct gaa       1104
Met Phe Lys Lys Leu Val Ser Lys Lys Thr Val Ala Glu Phe Ala Glu
            355                 360                 365 gat ttg cca gtt tct gtt gac caa ctt att gca gaa ctt tca act tat       1152
Asp Leu Pro Val Ser Val Asp Gln Leu Ile Ala Glu Leu Ser Thr Tyr
        370                 375                 380 tcc gac ttg tct aag gat gat cat ttg ggt aga aag ttt aga gaa aac       1200
Ser Asp Leu Ser Lys Asp Asp His Leu Gly Arg Lys Phe Arg Glu Asn
385                 390                 395                 400 act ttt ggt tcc tca tta tca tca gac tca acc att ttc gtt ggc aag       1248
Thr Phe Gly Ser Ser Leu Ser Ser Asp Ser Thr Ile Phe Val Gly Lys
                405                 410                 415 att act cct gtt gtt cac ttc aca atg ggt ggt gca aag att gat gaa       1296
Ile Thr Pro Val Val His Phe Thr Met Gly Gly Ala Lys Ile Asp Glu
                420                 425                 430 caa gct aga gtc ttg aat gca gaa ggt aaa cca tta gct act ggt atc       1344
Gln Ala Arg Val Leu Asn Ala Glu Gly Lys Pro Leu Ala Thr Gly Ile
            435                 440                 445 tac gcc gct ggt gaa gtt tct ggt ggt gtc cat ggt gct aat aga tta       1392
Tyr Ala Ala Gly Glu Val Ser Gly Gly Val His Gly Ala Asn Arg Leu
        450                 455                 460 ggt ggt tcc tct ttg tta gaa tgt gtt gtc ttt ggt aga caa gca gca       1440
Gly Gly Ser Ser Leu Leu Glu Cys Val Val Phe Gly Arg Gln Ala Ala
465                 470                 475                 480 aaa tcc att aga gca aac ttg taa                                       1464
Lys Ser Ile Arg Ala Asn Leu
                485
```

<210> SEQ ID NO 36
<211> LENGTH: 487
<212> TYPE: PRT
<213> ORGANISM: Kluyveromyces marxianus

<400> SEQUENCE: 36

```
Met Leu His Arg Tyr Ile Arg Leu Phe Ser Phe Cys Val Ile Leu Tyr
1               5                   10                  15

Leu Val Tyr Leu Leu Thr Lys Glu Ser Asn Val Met Ser Lys Pro
            20                  25                  30

Val Val Val Ile Gly Ser Gly Leu Ala Gly Leu Thr Thr Ser Ser Gln
        35                  40                  45

Leu Ala Lys Phe Asn Ile Pro Ile Val Leu Glu Lys Thr Ser Ser
    50                  55                  60

Ile Gly Gly Asn Ser Ile Lys Ala Ser Ser Gly Ile Asn Gly Ala Gly
65                  70                  75                  80

Thr Glu Thr Gln Ser Arg Leu His Val Glu Asp His Pro Glu Leu Phe
                85                  90                  95

Ala Asp Asp Thr Ile Lys Ser Ala Lys Gly Lys Gly Val Val Ala Leu
            100                 105                 110

Met Glu Lys Leu Ser Lys Asp Ser Ser Asp Ala Ile Ser Trp Leu Gln
        115                 120                 125

Asn Asp Phe Lys Ile Pro Leu Asp Lys Leu Ala Gln Leu Gly Gly His
    130                 135                 140

Ser Val Pro Arg Thr His Arg Ser Ser Gly Lys Leu Pro Pro Gly Phe
```

```
                    145                 150                 155                 160
         Gln Ile Val Asp Thr Leu Lys Lys Ala Leu Glu Ser Tyr Asp Ser Lys
                        165                 170                 175

Ala Val Lys Ile Gln Leu Asn Ser Lys Val Asp Val Lys Leu Asp
                     180                 185                 190

Ser Asn Asn Arg Val Ser Ser Val Phe Glu Asp Gln Asp Gly Thr
                     195                 200                 205

His Thr Ile Glu Thr Asn Asn Val Val Phe Cys Thr Gly Phe Gly
             210                 215                 220

Phe Asn Lys Lys Leu Leu Glu Lys Tyr Ala Pro His Leu Val Asp Leu
         225                 230                 235                 240

Pro Thr Thr Asn Gly Glu Gln Thr Leu Gly Glu Gly Gln Val Leu Leu
                         245                 250                 255

Glu Lys Leu Gly Ala Lys Leu Ile Asp Met Asp Gln Ile Gln Val His
                         260                 265                 270

Pro Thr Gly Phe Ile Asp Pro Ala Asn Pro Asp Ser Asn Trp Lys Phe
                         275                 280                 285

Leu Ala Ala Glu Ala Leu Arg Gly Leu Gly Gly Val Leu Ile Asn Pro
                         290                 295                 300

His Thr Gly Gln Arg Phe Val Asn Glu Leu Thr Thr Arg Asp Met Val
         305                 310                 315                 320

Thr Glu Ala Ile Gln Ser Lys Ser Glu Ser Lys Thr Ala Tyr Leu Val
                         325                 330                 335

Met Ser Glu Ser Leu Tyr Glu Asn Tyr Lys Pro Asn Met Asp Phe Tyr
                         340                 345                 350

Met Phe Lys Lys Leu Val Ser Lys Lys Thr Val Ala Glu Phe Ala Glu
                         355                 360                 365

Asp Leu Pro Val Ser Val Asp Gln Leu Ile Ala Glu Leu Ser Thr Tyr
                         370                 375                 380

Ser Asp Leu Ser Lys Asp Asp His Leu Gly Arg Lys Phe Arg Glu Asn
         385                 390                 395                 400

Thr Phe Gly Ser Ser Leu Ser Ser Asp Ser Thr Ile Phe Val Gly Lys
                         405                 410                 415

Ile Thr Pro Val Val His Phe Thr Met Gly Gly Ala Lys Ile Asp Glu
                         420                 425                 430

Gln Ala Arg Val Leu Asn Ala Glu Gly Lys Pro Leu Ala Thr Gly Ile
                         435                 440                 445

Tyr Ala Ala Gly Glu Val Ser Gly Gly Val His Gly Ala Asn Arg Leu
                         450                 455                 460

Gly Gly Ser Ser Leu Leu Glu Cys Val Val Phe Gly Arg Gln Ala Ala
         465                 470                 475                 480

Lys Ser Ile Arg Ala Asn Leu
                         485

<210> SEQ ID NO 37
<211> LENGTH: 3429
<212> TYPE: DNA
<213> ORGANISM: Trypanosoma brucei
<220> FEATURE:
<221> NAME/KEY: CDS
<222> LOCATION: (1)..(3429)

<400> SEQUENCE: 37 atg gtt gat ggt aga tct tca gct tct att gtt gca gtt gat cca gaa     48
Met Val Asp Gly Arg Ser Ser Ala Ser Ile Val Ala Val Asp Pro Glu
1               5                  10                  15
```

| | | |
|---|---|---|
| aga gca gca aga gaa aga gat gct gca gct aga gct ttg tta caa gat<br>Arg Ala Ala Arg Glu Arg Asp Ala Ala Ala Arg Ala Leu Leu Gln Asp<br>20 25 30 | | 96 |
| tct cca ttg cac act acc atg caa tat gct acc tcc ggt tta gaa ttg<br>Ser Pro Leu His Thr Thr Met Gln Tyr Ala Thr Ser Gly Leu Glu Leu<br>35 40 45 | | 144 |
| acc gtc cct tat gca ttg aaa gtt gtt gca tct gcc gac acc ttc gat<br>Thr Val Pro Tyr Ala Leu Lys Val Val Ala Ser Ala Asp Thr Phe Asp<br>50 55 60 | | 192 |
| aga gct aag gaa gtt gca gat gaa gtc ctt aga tgt gcc tgg caa ttg<br>Arg Ala Lys Glu Val Ala Asp Glu Val Leu Arg Cys Ala Trp Gln Leu<br>65 70 75 80 | | 240 |
| gct gat aca gtc ctt aac tcc ttt aac cca aac tct gaa gtc tct ctt<br>Ala Asp Thr Val Leu Asn Ser Phe Asn Pro Asn Ser Glu Val Ser Leu<br>85 90 95 | | 288 |
| gtt ggt aga ctt cca gtc ggt cag aag cat caa atg tcc gcc cca ctt<br>Val Gly Arg Leu Pro Val Gly Gln Lys His Gln Met Ser Ala Pro Leu<br>100 105 110 | | 336 |
| aag aga gtt atg gct tgt tgt caa aga gtt tac aat tcc tct gct ggt<br>Lys Arg Val Met Ala Cys Cys Gln Arg Val Tyr Asn Ser Ser Ala Gly<br>115 120 125 | | 384 |
| tgt ttc gac cca tcc acc gcc cca gtt gca aag gct ttg cgt gaa atc<br>Cys Phe Asp Pro Ser Thr Ala Pro Val Ala Lys Ala Leu Arg Glu Ile<br>130 135 140 | | 432 |
| gct tta ggc aag gag aga aac aat gcc tgt ttg gag gct tta aca caa<br>Ala Leu Gly Lys Glu Arg Asn Asn Ala Cys Leu Glu Ala Leu Thr Gln<br>145 150 155 160 | | 480 |
| gca tgc act ttg cca aac tct ttc gtc att gac ttt gaa gca ggt act<br>Ala Cys Thr Leu Pro Asn Ser Phe Val Ile Asp Phe Glu Ala Gly Thr<br>165 170 175 | | 528 |
| atc tca cgt aaa cat gaa cat gct tca ctt gac tta ggt ggt gtt tca<br>Ile Ser Arg Lys His Glu His Ala Ser Leu Asp Leu Gly Gly Val Ser<br>180 185 190 | | 576 |
| aag ggt tac atc gtt gac tat gtt att gat aac att aac gca gct ggt<br>Lys Gly Tyr Ile Val Asp Tyr Val Ile Asp Asn Ile Asn Ala Ala Gly<br>195 200 205 | | 624 |
| ttc caa aat gtc ttt ttc gat tgg ggt ggt gat tgt aga gcc tcc ggt<br>Phe Gln Asn Val Phe Phe Asp Trp Gly Gly Asp Cys Arg Ala Ser Gly<br>210 215 220 | | 672 |
| atg aat gct aga aat acc cct tgg gtt gtt ggt att act aga cca cca<br>Met Asn Ala Arg Asn Thr Pro Trp Val Val Gly Ile Thr Arg Pro Pro<br>225 230 235 240 | | 720 |
| tca tta gat atg tta cca aac cca cca aag gaa gca tcc tat atc tct<br>Ser Leu Asp Met Leu Pro Asn Pro Pro Lys Glu Ala Ser Tyr Ile Ser<br>245 250 255 | | 768 |
| gtt atc tca ttg gac aac gaa gct ttg gca acc tcc ggt gat tac gag<br>Val Ile Ser Leu Asp Asn Glu Ala Leu Ala Thr Ser Gly Asp Tyr Glu<br>260 265 270 | | 816 |
| aat ttg atc tac aca gct gat gac aag cct tta act tgt act tac gat<br>Asn Leu Ile Tyr Thr Ala Asp Asp Lys Pro Leu Thr Cys Thr Tyr Asp<br>275 280 285 | | 864 |
| tgg aag ggc aag gaa ctt atg aag cca tct caa tca aac att gcc caa<br>Trp Lys Gly Lys Glu Leu Met Lys Pro Ser Gln Ser Asn Ile Ala Gln<br>290 295 300 | | 912 |
| gtt tca gtt aag tgc tat tca gca atg tac gct gac gct tta gcc acc<br>Val Ser Val Lys Cys Tyr Ser Ala Met Tyr Ala Asp Ala Leu Ala Thr<br>305 310 315 320 | | 960 |
| gct tgt ttc atc aaa aga gat cca gcc aag gtt aga caa ttg tta gat<br>Ala Cys Phe Ile Lys Arg Asp Pro Ala Lys Val Arg Gln Leu Leu Asp | | 1008 |

-continued

```
                    325                 330                 335
ggt tgg aga tac gtt aga gat act gtc aga gat tac aga gtt tat gtt    1056
Gly Trp Arg Tyr Val Arg Asp Thr Val Arg Asp Tyr Arg Val Tyr Val
        340                 345                 350 aga gaa aat gag aga gtc gct aag atg ttt gaa att gca acc gaa gat    1104
Arg Glu Asn Glu Arg Val Ala Lys Met Phe Glu Ile Ala Thr Glu Asp
    355                 360                 365 gct gaa atg aga aaa aga cgt atc tct aat act ttg cct gca aga gtc    1152
Ala Glu Met Arg Lys Arg Arg Ile Ser Asn Thr Leu Pro Ala Arg Val
370                 375                 380 atc gtt gtc ggt ggc ggt tta gca ggt tta tct gca gca att gaa gct    1200
Ile Val Val Gly Gly Gly Leu Ala Gly Leu Ser Ala Ala Ile Glu Ala
385                 390                 395                 400 gca ggc tgc ggt gca caa gtc gtt ttg atg gaa aag gaa gct aag tta    1248
Ala Gly Cys Gly Ala Gln Val Val Leu Met Glu Lys Glu Ala Lys Leu
            405                 410                 415 ggt ggt aac tct gca aag gca acc tct ggt atc aat ggt tgg ggt act    1296
Gly Gly Asn Ser Ala Lys Ala Thr Ser Gly Ile Asn Gly Trp Gly Thr
            420                 425                 430 aga gcc caa gca aag gct tcc att gtt gac ggt ggc aag tat ttc gaa    1344
Arg Ala Gln Ala Lys Ala Ser Ile Val Asp Gly Gly Lys Tyr Phe Glu
        435                 440                 445 aga gat act tac aaa tct ggt att ggt ggt aat acc gac cca gct tta    1392
Arg Asp Thr Tyr Lys Ser Gly Ile Gly Gly Asn Thr Asp Pro Ala Leu
    450                 455                 460 gtt aag act ctt tcc atg aag tct gct gac gct att ggt tgg tta aca    1440
Val Lys Thr Leu Ser Met Lys Ser Ala Asp Ala Ile Gly Trp Leu Thr
465                 470                 475                 480 tca tta ggt gtt cct tta aca gtc tta tca caa ttg ggt ggt cat tcc    1488
Ser Leu Gly Val Pro Leu Thr Val Leu Ser Gln Leu Gly Gly His Ser
                485                 490                 495 aga aag aga act cac aga gca cca gac aaa aag gat ggc acc cca tta    1536
Arg Lys Arg Thr His Arg Ala Pro Asp Lys Lys Asp Gly Thr Pro Leu
            500                 505                 510 cct att ggt ttt acc att atg aaa acc tta gaa gat cac gtc aga ggt    1584
Pro Ile Gly Phe Thr Ile Met Lys Thr Leu Glu Asp His Val Arg Gly
        515                 520                 525 aat ctt tct ggt aga att act atc atg gaa aac tgt tcc gtt acc tct    1632
Asn Leu Ser Gly Arg Ile Thr Ile Met Glu Asn Cys Ser Val Thr Ser
    530                 535                 540 tta ctt tct gaa act aag gaa aga cca gat ggt act aaa caa atc aga    1680
Leu Leu Ser Glu Thr Lys Glu Arg Pro Asp Gly Thr Lys Gln Ile Arg
545                 550                 555                 560 gtt acc ggt gtt gag ttc act caa gca ggc tct ggc aaa act acc att    1728
Val Thr Gly Val Glu Phe Thr Gln Ala Gly Ser Gly Lys Thr Thr Ile
                565                 570                 575 ttg gcc gac gca gtc atc ttg gcc act ggt ggt ttc tct aac gac aag    1776
Leu Ala Asp Ala Val Ile Leu Ala Thr Gly Gly Phe Ser Asn Asp Lys
            580                 585                 590 acc gca gac tct ttg ttg aga gaa cat gcc cct cac tta gtt aac ttt    1824
Thr Ala Asp Ser Leu Leu Arg Glu His Ala Pro His Leu Val Asn Phe
        595                 600                 605 cct aca act aac ggt cct tgg gca act ggt gac ggt gtt aag ctt gct    1872
Pro Thr Thr Asn Gly Pro Trp Ala Thr Gly Asp Gly Val Lys Leu Ala
    610                 615                 620 caa aga tta ggt gca caa ttg gtc gac atg gat aag gtt caa ttg cat    1920
Gln Arg Leu Gly Ala Gln Leu Val Asp Met Asp Lys Val Gln Leu His
625                 630                 635                 640 cca act ggt ttg att aac cca aaa gat cca gct aat cca aca aag ttt    1968
Pro Thr Gly Leu Ile Asn Pro Lys Asp Pro Ala Asn Pro Thr Lys Phe
```

-continued

```
Pro Thr Gly Leu Ile Asn Pro Lys Asp Pro Ala Asn Pro Thr Lys Phe
            645             650             655 ttg ggt cca gaa gct tta aga ggt tcc ggt ggt gtc ttg tta aac aaa      2016
Leu Gly Pro Glu Ala Leu Arg Gly Ser Gly Gly Val Leu Leu Asn Lys
        660             665             670 cag ggt aaa aga ttt gtt aac gaa tta gat ttg cgt tct gtt gtt tcc      2064
Gln Gly Lys Arg Phe Val Asn Glu Leu Asp Leu Arg Ser Val Val Ser
    675             680             685 aag gcc att atg gaa caa ggt gct gaa tac cca ggc tct ggt ggt tct      2112
Lys Ala Ile Met Glu Gln Gly Ala Glu Tyr Pro Gly Ser Gly Gly Ser
690             695             700 atg ttc gca tat tgt gtc ctt aat gca gct gca caa aag ttg ttt ggt      2160
Met Phe Ala Tyr Cys Val Leu Asn Ala Ala Ala Gln Lys Leu Phe Gly
705             710             715             720 gtc tct tcc cac gag ttc tac tgg aaa aag atg ggt ttg ttc gtt aag      2208
Val Ser Ser His Glu Phe Tyr Trp Lys Lys Met Gly Leu Phe Val Lys
            725             730             735 gct gat act atg aga gat ttg gca gca ttg att ggt tgt cca gtc gag      2256
Ala Asp Thr Met Arg Asp Leu Ala Ala Leu Ile Gly Cys Pro Val Glu
        740             745             750 tct gtt caa caa act tta gag gaa tat gaa aga tta tct att tct cag      2304
Ser Val Gln Gln Thr Leu Glu Glu Tyr Glu Arg Leu Ser Ile Ser Gln
    755             760             765 aga tcc tgt cca atc act aga aaa tct gtt tac cca tgt gtt ttg ggc      2352
Arg Ser Cys Pro Ile Thr Arg Lys Ser Val Tyr Pro Cys Val Leu Gly
770             775             780 act aag ggt cca tac tac gtt gct ttc gtc acc cca tct att cac tat      2400
Thr Lys Gly Pro Tyr Tyr Val Ala Phe Val Thr Pro Ser Ile His Tyr
785             790             795             800 aca atg ggt ggt tgt ttg att tcc cca tca gca gaa att cag atg aaa      2448
Thr Met Gly Gly Cys Leu Ile Ser Pro Ser Ala Glu Ile Gln Met Lys
            805             810             815 aac acc tcc tcc cgt gct cca ttg tcc cat tcc aac cct atc ttg ggt      2496
Asn Thr Ser Ser Arg Ala Pro Leu Ser His Ser Asn Pro Ile Leu Gly
        820             825             830 ttg ttc ggt gct ggt gaa gtt act ggt ggt gtc cac ggt ggc aat aga      2544
Leu Phe Gly Ala Gly Glu Val Thr Gly Gly Val His Gly Gly Asn Arg
    835             840             845 tta ggt ggt aac tca ttg tta gaa tgt gtt gtc ttt ggt aga att gct      2592
Leu Gly Gly Asn Ser Leu Leu Glu Cys Val Val Phe Gly Arg Ile Ala
850             855             860 ggt gat aga gct tct acc att ttg cag aga aag tcc tcc gca tta tct      2640
Gly Asp Arg Ala Ser Thr Ile Leu Gln Arg Lys Ser Ser Ala Leu Ser
865             870             875             880 ttc aag gtc tgg act acc gtt gtt ttg aga gaa gtt aga gaa ggt ggc      2688
Phe Lys Val Trp Thr Thr Val Val Leu Arg Glu Val Arg Glu Gly Gly
            885             890             895 gtc tat ggt gcc ggt tca aga gtt ttg aga ttc aac ttg cct ggt gct      2736
Val Tyr Gly Ala Gly Ser Arg Val Leu Arg Phe Asn Leu Pro Gly Ala
        900             905             910 tta caa aga tcc ggt ttg tcc ttg ggt caa ttc atc gca atc aga ggt      2784
Leu Gln Arg Ser Gly Leu Ser Leu Gly Gln Phe Ile Ala Ile Arg Gly
    915             920             925 gac tgg gat ggt caa caa ttg att ggt tac tat tcc cca att aca ttg      2832
Asp Trp Asp Gly Gln Gln Leu Ile Gly Tyr Tyr Ser Pro Ile Thr Leu
930             935             940 cca gat gac ttg ggt atg att gac att ttg gct aga tcc gat aaa ggt      2880
Pro Asp Asp Leu Gly Met Ile Asp Ile Leu Ala Arg Ser Asp Lys Gly
945             950             955             960
```

| | | |
|---|---|---|
| act tta aga gaa tgg att tct gct tta gaa cca ggc gac gct gtt gag<br>Thr Leu Arg Glu Trp Ile Ser Ala Leu Glu Pro Gly Asp Ala Val Glu<br>965 970 975 | 2928 | |
| atg aaa gca tgc ggt ggt tta gtc atc gag aga aga ttg tca gat aag<br>Met Lys Ala Cys Gly Gly Leu Val Ile Glu Arg Arg Leu Ser Asp Lys<br>980 985 990 | 2976 | |
| cac ttt gtc ttt atg ggt cac atc att aac aag tta tgt ttg atc gct<br>His Phe Val Phe Met Gly His Ile Ile Asn Lys Leu Cys Leu Ile Ala<br>995 1000 1005 | 3024 | |
| ggt ggt aca ggc gtt gca cct atg tta caa atc att aag gca gca<br>Gly Gly Thr Gly Val Ala Pro Met Leu Gln Ile Ile Lys Ala Ala<br>1010 1015 1020 | 3069 | |
| ttc atg aaa cct ttt atc gat acc tta gaa tct gtc cat ctt atc<br>Phe Met Lys Pro Phe Ile Asp Thr Leu Glu Ser Val His Leu Ile<br>1025 1030 1035 | 3114 | |
| tat gct gca gaa gat gtt acc gag tta act tat aga gaa gtt tta<br>Tyr Ala Ala Glu Asp Val Thr Glu Leu Thr Tyr Arg Glu Val Leu<br>1040 1045 1050 | 3159 | |
| gag gag cgt aga aga gag tct cgt ggc aag ttc aaa aag acc ttt<br>Glu Glu Arg Arg Arg Glu Ser Arg Gly Lys Phe Lys Lys Thr Phe<br>1055 1060 1065 | 3204 | |
| gtt ttg aac aga cct cca cca ctt tgg act gat ggt gtt ggt ttc<br>Val Leu Asn Arg Pro Pro Pro Leu Trp Thr Asp Gly Val Gly Phe<br>1070 1075 1080 | 3249 | |
| atc gat aga ggt atc tta act aat cat gtc caa cca cca tcc gat<br>Ile Asp Arg Gly Ile Leu Thr Asn His Val Gln Pro Pro Ser Asp<br>1085 1090 1095 | 3294 | |
| aac ctt ttg gtt gca atc tgt ggt cca cct gtc atg cag cgt att<br>Asn Leu Leu Val Ala Ile Cys Gly Pro Pro Val Met Gln Arg Ile<br>1100 1105 1110 | 3339 | |
| gtt aag gcc acc tta aag act ttg ggt tac aat atg aat ctt gtt<br>Val Lys Ala Thr Leu Lys Thr Leu Gly Tyr Asn Met Asn Leu Val<br>1115 1120 1125 | 3384 | |
| aga aca gtt gac gaa aca gaa cca tcc ggt tcc taa tta att aac<br>Arg Thr Val Asp Glu Thr Glu Pro Ser Gly Ser Leu Ile Asn<br>1130 1135 1140 | 3429 | |

<210> SEQ ID NO 38
<211> LENGTH: 1139
<212> TYPE: PRT
<213> ORGANISM: Trypanosoma brucei

<400> SEQUENCE: 38

Met Val Asp Gly Arg Ser Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30

Ser Pro Leu His Thr Thr Met Gln Tyr Ala Thr Ser Gly Leu Glu Leu
        35                  40                  45

Thr Val Pro Tyr Ala Leu Lys Val Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
        115                 120                 125

```
Cys Phe Asp Pro Ser Thr Ala Pro Val Ala Lys Ala Leu Arg Glu Ile
        130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                    165                 170                 175

Ile Ser Arg Lys His Glu His Ala Ser Leu Asp Leu Gly Gly Val Ser
                180                 185                 190

Lys Gly Tyr Ile Val Asp Tyr Val Ile Asp Asn Ile Asn Ala Ala Gly
            195                 200                 205

Phe Gln Asn Val Phe Phe Asp Trp Gly Asp Cys Arg Ala Ser Gly
    210                 215                 220

Met Asn Ala Arg Asn Thr Pro Trp Val Gly Ile Thr Arg Pro Pro
225                 230                 235                 240

Ser Leu Asp Met Leu Pro Asn Pro Pro Lys Glu Ala Ser Tyr Ile Ser
                    245                 250                 255

Val Ile Ser Leu Asp Asn Glu Ala Leu Ala Thr Ser Gly Asp Tyr Glu
                260                 265                 270

Asn Leu Ile Tyr Thr Ala Asp Asp Lys Pro Leu Thr Cys Thr Tyr Asp
            275                 280                 285

Trp Lys Gly Lys Glu Leu Met Lys Pro Ser Gln Ser Asn Ile Ala Gln
        290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                    325                 330                 335

Gly Trp Arg Tyr Val Arg Asp Thr Val Arg Asp Tyr Arg Val Tyr Val
                340                 345                 350

Arg Glu Asn Glu Arg Val Ala Lys Met Phe Glu Ile Ala Thr Glu Asp
            355                 360                 365

Ala Glu Met Arg Lys Arg Arg Ile Ser Asn Thr Leu Pro Ala Arg Val
        370                 375                 380

Ile Val Val Gly Gly Gly Leu Ala Gly Leu Ser Ala Ala Ile Glu Ala
385                 390                 395                 400

Ala Gly Cys Gly Ala Gln Val Val Leu Met Glu Lys Glu Ala Lys Leu
                    405                 410                 415

Gly Gly Asn Ser Ala Lys Ala Thr Ser Gly Ile Asn Gly Trp Gly Thr
                420                 425                 430

Arg Ala Gln Ala Lys Ala Ser Ile Val Asp Gly Gly Lys Tyr Phe Glu
            435                 440                 445

Arg Asp Thr Tyr Lys Ser Gly Ile Gly Gly Asn Thr Asp Pro Ala Leu
        450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
                    485                 490                 495

Arg Lys Arg Thr His Arg Ala Pro Asp Lys Lys Asp Gly Thr Pro Leu
                500                 505                 510

Pro Ile Gly Phe Thr Ile Met Lys Thr Leu Glu Asp His Val Arg Gly
            515                 520                 525

Asn Leu Ser Gly Arg Ile Thr Ile Met Glu Asn Cys Ser Val Thr Ser
        530                 535                 540
```

-continued

```
Leu Leu Ser Glu Thr Lys Glu Arg Pro Asp Gly Thr Lys Gln Ile Arg
545                 550                 555                 560

Val Thr Gly Val Glu Phe Thr Gln Ala Gly Ser Gly Lys Thr Thr Ile
                565                 570                 575

Leu Ala Asp Ala Val Ile Leu Ala Thr Gly Gly Phe Ser Asn Asp Lys
            580                 585                 590

Thr Ala Asp Ser Leu Leu Arg Glu His Ala Pro His Leu Val Asn Phe
        595                 600                 605

Pro Thr Thr Asn Gly Pro Trp Ala Thr Gly Asp Gly Val Lys Leu Ala
    610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
                645                 650                 655

Leu Gly Pro Glu Ala Leu Arg Gly Ser Gly Val Leu Leu Asn Lys
            660                 665                 670

Gln Gly Lys Arg Phe Val Asn Glu Leu Asp Leu Arg Ser Val Val Ser
        675                 680                 685

Lys Ala Ile Met Glu Gln Gly Ala Glu Tyr Pro Gly Ser Gly Gly Ser
    690                 695                 700

Met Phe Ala Tyr Cys Val Leu Asn Ala Ala Gln Lys Leu Phe Gly
705                 710                 715                 720

Val Ser Ser His Glu Phe Tyr Trp Lys Lys Met Gly Leu Phe Val Lys
                725                 730                 735

Ala Asp Thr Met Arg Asp Leu Ala Ala Leu Ile Gly Cys Pro Val Glu
            740                 745                 750

Ser Val Gln Gln Thr Leu Glu Glu Tyr Glu Arg Leu Ser Ile Ser Gln
        755                 760                 765

Arg Ser Cys Pro Ile Thr Arg Lys Ser Val Tyr Pro Cys Val Leu Gly
    770                 775                 780

Thr Lys Gly Pro Tyr Tyr Val Ala Phe Val Thr Pro Ser Ile His Tyr
785                 790                 795                 800

Thr Met Gly Gly Cys Leu Ile Ser Pro Ser Ala Glu Ile Gln Met Lys
                805                 810                 815

Asn Thr Ser Ser Arg Ala Pro Leu Ser His Ser Asn Pro Ile Leu Gly
            820                 825                 830

Leu Phe Gly Ala Gly Glu Val Thr Gly Gly Val His Gly Gly Asn Arg
        835                 840                 845

Leu Gly Gly Asn Ser Leu Leu Glu Cys Val Val Phe Gly Arg Ile Ala
    850                 855                 860

Gly Asp Arg Ala Ser Thr Ile Leu Gln Arg Lys Ser Ser Ala Leu Ser
865                 870                 875                 880

Phe Lys Val Trp Thr Thr Val Leu Arg Glu Val Arg Glu Gly Gly
                885                 890                 895

Val Tyr Gly Ala Gly Ser Arg Val Leu Arg Phe Asn Leu Pro Gly Ala
            900                 905                 910

Leu Gln Arg Ser Gly Leu Ser Leu Gly Gln Phe Ile Ala Ile Arg Gly
        915                 920                 925

Asp Trp Asp Gly Gln Gln Leu Ile Gly Tyr Tyr Ser Pro Ile Thr Leu
    930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
```

-continued

```
            965              970              975
Met Lys Ala Cys Gly Gly Leu Val Ile Glu Arg Arg Leu Ser Asp Lys
              980              985              990

His Phe Val Phe Met Gly His Ile Ile Asn Lys Leu Cys Leu Ile Ala
              995             1000             1005

Gly Gly Thr Gly Val Ala Pro Met Leu Gln Ile Ile Lys Ala Ala
         1010             1015             1020

Phe Met Lys Pro Phe Ile Asp Thr Leu Glu Ser Val His Leu Ile
         1025             1030             1035

Tyr Ala Ala Glu Asp Val Thr Glu Leu Thr Tyr Arg Glu Val Leu
         1040             1045             1050

Glu Glu Arg Arg Arg Glu Ser Arg Gly Lys Phe Lys Lys Thr Phe
         1055             1060             1065

Val Leu Asn Arg Pro Pro Leu Trp Thr Asp Gly Val Gly Phe
         1070             1075             1080

Ile Asp Arg Gly Ile Leu Thr Asn His Val Gln Pro Pro Ser Asp
         1085             1090             1095

Asn Leu Leu Val Ala Ile Cys Gly Pro Pro Val Met Gln Arg Ile
         1100             1105             1110

Val Lys Ala Thr Leu Lys Thr Leu Gly Tyr Asn Met Asn Leu Val
         1115             1120             1125

Arg Thr Val Asp Glu Thr Glu Pro Ser Gly Ser
         1130             1135
```

<210> SEQ ID NO 39
<211> LENGTH: 3420
<212> TYPE: DNA
<213> ORGANISM: Trypanosoma cruzi
<220> FEATURE:
<221> NAME/KEY: CDS
<222> LOCATION: (1)..(3420)

<400> SEQUENCE: 39

```
atg gct gac ggt aga tcc tct gca tct gtt gtt gca gtt gat cca gaa      48
Met Ala Asp Gly Arg Ser Ser Ala Ser Val Val Ala Val Asp Pro Glu
1               5                  10                  15 aag gct gca aga gaa aga gat gaa gca gct cgt gct ttg tta aga gac      96
Lys Ala Ala Arg Glu Arg Asp Glu Ala Ala Arg Ala Leu Leu Arg Asp
                20                  25                  30 tct cca tta caa act cat ctt cag tac atg act aat ggt tta gag ttg     144
Ser Pro Leu Gln Thr His Leu Gln Tyr Met Thr Asn Gly Leu Glu Leu
            35                  40                  45 act gtc cca ttc acc tta aag gtt gtc gct gaa gca gtt gca ttt tcc     192
Thr Val Pro Phe Thr Leu Lys Val Val Ala Glu Ala Val Ala Phe Ser
        50                  55                  60 aga gca aag gaa gtt gct gac gaa gtt ttg agg tca gcc tgg cat ctt     240
Arg Ala Lys Glu Val Ala Asp Glu Val Leu Arg Ser Ala Trp His Leu
65                  70                  75                  80 gca gac acc gtc ttg aac aac ttt aac cct aac tcc gag att tct atg     288
Ala Asp Thr Val Leu Asn Asn Phe Asn Pro Asn Ser Glu Ile Ser Met
                85                  90                  95 att ggt aga tta cca gtt ggt caa aaa cat aca atg tcc gct aca ttg     336
Ile Gly Arg Leu Pro Val Gly Gln Lys His Thr Met Ser Ala Thr Leu
                100                 105                 110 aag tct gtt atc aca tgc tgt cag cat gtt ttc aat tca tcc aga ggt     384
Lys Ser Val Ile Thr Cys Cys Gln His Val Phe Asn Ser Ser Arg Gly
            115                 120                 125 gtt ttt gat cca gct act ggt cct atc att gaa gct tta aga gct aag     432
Val Phe Asp Pro Ala Thr Gly Pro Ile Ile Glu Ala Leu Arg Ala Lys
```

-continued

```
              Val Phe Asp Pro Ala Thr Gly Pro Ile Ile Glu Ala Leu Arg Ala Lys
                  130                 135                 140 gtt gct gag aaa gcc tct gtt tct gat gaa cag atg gag aag ttg ttt         480
Val Ala Glu Lys Ala Ser Val Ser Asp Glu Gln Met Glu Lys Leu Phe
145                 150                 155                 160 cgt gtt tgt aac ttc tct tcc tca ttc atc gtt gat ttg gaa atg ggt         528
Arg Val Cys Asn Phe Ser Ser Ser Phe Ile Val Asp Leu Glu Met Gly
                165                 170                 175 act att gcc aga aaa cac gaa gat gca aga ttt gac tta ggt ggt gtt         576
Thr Ile Ala Arg Lys His Glu Asp Ala Arg Phe Asp Leu Gly Gly Val
            180                 185                 190 tcc aag ggt tac atc gtt gac tac gtt gtt gaa aga ttg aac gct gct         624
Ser Lys Gly Tyr Ile Val Asp Tyr Val Val Glu Arg Leu Asn Ala Ala
        195                 200                 205 ggt att gtc gat gtc tac ttc gaa tgg ggt ggt gac tgt aga gct tcc         672
Gly Ile Val Asp Val Tyr Phe Glu Trp Gly Gly Asp Cys Arg Ala Ser
    210                 215                 220 ggt act aac gca aga cgt acc cca tgg atg gtt ggt atc att aga cct         720
Gly Thr Asn Ala Arg Arg Thr Pro Trp Met Val Gly Ile Ile Arg Pro
225                 230                 235                 240 cca tct tta gaa caa ttg aga aac cca cca aaa gat cca tcc tac att         768
Pro Ser Leu Glu Gln Leu Arg Asn Pro Pro Lys Asp Pro Ser Tyr Ile
                245                 250                 255 agg gtt tta cca ctt aac gat gaa gca ctt tgt acc tct ggt gac tat         816
Arg Val Leu Pro Leu Asn Asp Glu Ala Leu Cys Thr Ser Gly Asp Tyr
                260                 265                 270 gag aat ttg acc gaa ggc tct aac aaa aag ttg tat aca tcc att ttc         864
Glu Asn Leu Thr Glu Gly Ser Asn Lys Lys Leu Tyr Thr Ser Ile Phe
            275                 280                 285 gat tgg aaa aag aga tcc ttg ttg gaa cca gtt gaa tca gaa ttg gcc         912
Asp Trp Lys Lys Arg Ser Leu Leu Glu Pro Val Glu Ser Glu Leu Ala
        290                 295                 300 caa gtt tcc att aga tgt tat tct gcc atg tat gca gac gca tta gca         960
Gln Val Ser Ile Arg Cys Tyr Ser Ala Met Tyr Ala Asp Ala Leu Ala
305                 310                 315                 320 aca gct tct ctt atc aag aga gat atc aaa aag gtt aga caa atg ttg        1008
Thr Ala Ser Leu Ile Lys Arg Asp Ile Lys Lys Val Arg Gln Met Leu
                325                 330                 335 gaa gat tgg aga cac gtc cgt aat agg gtt act aac tat gtt acc tat        1056
Glu Asp Trp Arg His Val Arg Asn Arg Val Thr Asn Tyr Val Thr Tyr
                340                 345                 350 acc aga caa ggt gaa aga gtc gca cgt atg ttt gaa att gct act gat        1104
Thr Arg Gln Gly Glu Arg Val Ala Arg Met Phe Glu Ile Ala Thr Asp
            355                 360                 365 aac gct gag att agg aaa aag aga att gca ggc tct tta cct gct agg        1152
Asn Ala Glu Ile Arg Lys Lys Arg Ile Ala Gly Ser Leu Pro Ala Arg
        370                 375                 380 gtt att gtt gtc ggt ggt ggt tta gct ggt ttg tct gca gca att gaa        1200
Val Ile Val Val Gly Gly Gly Leu Ala Gly Leu Ser Ala Ala Ile Glu
385                 390                 395                 400 gca act gca tgt ggt gcc caa gtt atc ctt tta gaa aag gaa cct aaa        1248
Ala Thr Ala Cys Gly Ala Gln Val Ile Leu Leu Glu Lys Glu Pro Lys
                405                 410                 415 gtt ggt ggt aat tcc gca aag gct aca tct ggt atc aac ggt tgg ggt        1296
Val Gly Gly Asn Ser Ala Lys Ala Thr Ser Gly Ile Asn Gly Trp Gly
                420                 425                 430 act aga gca caa gct gaa caa gat gtc tac gac tct ggc aag tac ttc        1344
Thr Arg Ala Gln Ala Glu Gln Asp Val Tyr Asp Ser Gly Lys Tyr Phe
            435                 440                 445
```

```
gaa aga gat aca cac aaa tct ggt tta ggt ggt tct acc gat cca ggc    1392
Glu Arg Asp Thr His Lys Ser Gly Leu Gly Gly Ser Thr Asp Pro Gly
    450                 455                 460 tta gtt cgt act tta tca gtc aag tct ggt gac gct att tca tgg tta    1440
Leu Val Arg Thr Leu Ser Val Lys Ser Gly Asp Ala Ile Ser Trp Leu
465                 470                 475                 480 tct tct ctt ggt gtt cca tta act gtc ttg tca caa tta ggc ggt cat    1488
Ser Ser Leu Gly Val Pro Leu Thr Val Leu Ser Gln Leu Gly Gly His
                485                 490                 495 tcc aga aaa agg act cac aga gcc cct gat aag gca gat ggt act cca    1536
Ser Arg Lys Arg Thr His Arg Ala Pro Asp Lys Ala Asp Gly Thr Pro
            500                 505                 510 gtt cca att ggt ttc acc att atg caa acc tta gaa cag cat gtt aga    1584
Val Pro Ile Gly Phe Thr Ile Met Gln Thr Leu Glu Gln His Val Arg
        515                 520                 525 acc aag tta gca gac aga gtt act atc atg gag aat acc acc gtt acc    1632
Thr Lys Leu Ala Asp Arg Val Thr Ile Met Glu Asn Thr Thr Val Thr
    530                 535                 540 tcc ttg ctt tct aag tcc aga gtt aga cat gat ggt gca aag caa gtt    1680
Ser Leu Leu Ser Lys Ser Arg Val Arg His Asp Gly Ala Lys Gln Val
545                 550                 555                 560 aga gtc tac ggt gtt gaa gtc tta caa gac gaa ggt gtc gtt tct cgt    1728
Arg Val Tyr Gly Val Glu Val Leu Gln Asp Glu Gly Val Val Ser Arg
                565                 570                 575 atc ttg gcc gat gct gtc att ttg gca aca ggt ggt ttc tcc aat gac    1776
Ile Leu Ala Asp Ala Val Ile Leu Ala Thr Gly Gly Phe Ser Asn Asp
            580                 585                 590 aaa acc cca aac tcc tta ttg caa gag ttc gct cca caa ttg tca ggt    1824
Lys Thr Pro Asn Ser Leu Leu Gln Glu Phe Ala Pro Gln Leu Ser Gly
        595                 600                 605 ttt cca aca acc aac ggt cca tgg gct act ggc gat ggt gtt aag tta    1872
Phe Pro Thr Thr Asn Gly Pro Trp Ala Thr Gly Asp Gly Val Lys Leu
    610                 615                 620 gca aga gaa ctt ggt gtc aag ttg gtt gat atg gat aag gtc caa ctt    1920
Ala Arg Glu Leu Gly Val Lys Leu Val Asp Met Asp Lys Val Gln Leu
625                 630                 635                 640 cat cca act ggt ttg att gac cct aag gac cca gca aat cca acc aaa    1968
His Pro Thr Gly Leu Ile Asp Pro Lys Asp Pro Ala Asn Pro Thr Lys
                645                 650                 655 tac tta ggt cca gaa gca ttg aga ggt tct ggt ggt gtc ttg tta aac    2016
Tyr Leu Gly Pro Glu Ala Leu Arg Gly Ser Gly Gly Val Leu Leu Asn
            660                 665                 670 aaa aag ggt gaa aga ttt gtc aat gag ttg gac ttg cgt tcc gtc gtt    2064
Lys Lys Gly Glu Arg Phe Val Asn Glu Leu Asp Leu Arg Ser Val Val
        675                 680                 685 tca aat gct atc att gaa caa ggt gat gaa tat cca gat gcc ggt ggt    2112
Ser Asn Ala Ile Ile Glu Gln Gly Asp Glu Tyr Pro Asp Ala Gly Gly
    690                 695                 700 tcc aag ttc gcc ttc tgt gtt ttg aat gat gca gca gtt aag tta ttc    2160
Ser Lys Phe Ala Phe Cys Val Leu Asn Asp Ala Ala Val Lys Leu Phe
705                 710                 715                 720 ggt gtc aac tcc cac ggt ttc tac tgg aag aga ctt ggt ttg ttt gtt    2208
Gly Val Asn Ser His Gly Phe Tyr Trp Lys Arg Leu Gly Leu Phe Val
                725                 730                 735 aag gct gat acc gtt gaa aag tta gcc gca ttg atc ggt tgc cca gtc    2256
Lys Ala Asp Thr Val Glu Lys Leu Ala Ala Leu Ile Gly Cys Pro Val
            740                 745                 750 gaa aat gtt aga aac aca tta ggt gat tat gag caa ttg tcc aag gaa    2304
Glu Asn Val Arg Asn Thr Leu Gly Asp Tyr Glu Gln Leu Ser Lys Glu
        755                 760                 765
```

-continued

```
aac aga caa tgt cca aag act aga aaa gtt gtc tat cca tgt gtt gtt      2352
Asn Arg Gln Cys Pro Lys Thr Arg Lys Val Val Tyr Pro Cys Val Val
770                 775                 780 ggt cca caa ggt cca ttc tat gtt gct ttt gtt acc cca tct att cac      2400
Gly Pro Gln Gly Pro Phe Tyr Val Ala Phe Val Thr Pro Ser Ile His
785                 790                 795                 800 tat acc atg ggt ggt tgt ttg atc tca cca tct gct gag atg caa ttg      2448
Tyr Thr Met Gly Gly Cys Leu Ile Ser Pro Ser Ala Glu Met Gln Leu
            805                 810                 815 gaa gag aac act acc tcc cca ttt ggt cac aga agg cct atc ttc ggt      2496
Glu Glu Asn Thr Thr Ser Pro Phe Gly His Arg Arg Pro Ile Phe Gly
        820                 825                 830 ctt ttc ggt gcc ggt gaa gtt act ggt ggt gtc cat ggt ggt aac aga      2544
Leu Phe Gly Ala Gly Glu Val Thr Gly Gly Val His Gly Gly Asn Arg
    835                 840                 845 tta ggt ggc aac tct ttg ttg gag tgt gtt gtt ttt ggt aga atc gct      2592
Leu Gly Gly Asn Ser Leu Leu Glu Cys Val Val Phe Gly Arg Ile Ala
850                 855                 860 ggt gat aga gct gca acc att ttg caa aag aaa cca gtt cca ctt tcc      2640
Gly Asp Arg Ala Ala Thr Ile Leu Gln Lys Lys Pro Val Pro Leu Ser
865                 870                 875                 880 ttt aag act tgg acc acc gtc att ttg aga gag gtc cgt gaa ggt ggc      2688
Phe Lys Thr Trp Thr Thr Val Ile Leu Arg Glu Val Arg Glu Gly Gly
            885                 890                 895 atg tac ggt act ggt tca aga gtc tta aga ttc aat ttg cca ggt gct      2736
Met Tyr Gly Thr Gly Ser Arg Val Leu Arg Phe Asn Leu Pro Gly Ala
        900                 905                 910 tta caa aga tct ggt ttg caa ttg ggt caa ttc atc gct att aga ggc      2784
Leu Gln Arg Ser Gly Leu Gln Leu Gly Gln Phe Ile Ala Ile Arg Gly
    915                 920                 925 gaa tgg gat ggt caa caa ttg att ggc tac tat tcc cca atc act ttg      2832
Glu Trp Asp Gly Gln Gln Leu Ile Gly Tyr Tyr Ser Pro Ile Thr Leu
930                 935                 940 cca gac gat ttg ggt gtc atc ggc att ttg gct aga tcc gat aag ggt      2880
Pro Asp Asp Leu Gly Val Ile Gly Ile Leu Ala Arg Ser Asp Lys Gly
945                 950                 955                 960 act ttg aag gaa tgg att tct gct ttg gaa cct ggt gat gca gtt gag      2928
Thr Leu Lys Glu Trp Ile Ser Ala Leu Glu Pro Gly Asp Ala Val Glu
            965                 970                 975 atg aag ggt tgt ggc ggt tta gtt att gaa agg aga ttc tct gaa aga      2976
Met Lys Gly Cys Gly Gly Leu Val Ile Glu Arg Arg Phe Ser Glu Arg
        980                 985                 990 tac ttg tac ttt tct ggt cac gct ttg aaa aag tta tgc ctt att gct      3024
Tyr Leu Tyr Phe Ser Gly His Ala Leu Lys Lys Leu Cys Leu Ile Ala
    995                 1000                1005 ggt ggt act ggt gtc gca cca atg tta caa atc att aga gca gca        3069
Gly Gly Thr Gly Val Ala Pro Met Leu Gln Ile Ile Arg Ala Ala
    1010                1015                1020 ttg aaa aag cca ttc ctt gag aat atc gaa tca att aga ctt atc        3114
Leu Lys Lys Pro Phe Leu Glu Asn Ile Glu Ser Ile Arg Leu Ile
    1025                1030                1035 tat gct gct gag gac gtt tct gag ttg aca tac agg gaa ttg tta        3159
Tyr Ala Ala Glu Asp Val Ser Glu Leu Thr Tyr Arg Glu Leu Leu
    1040                1045                1050 gaa cat cac caa aga gat tct aag ggc aag ttt aga tcc atc ttc        3204
Glu His His Gln Arg Asp Ser Lys Gly Lys Phe Arg Ser Ile Phe
    1055                1060                1065 gtt ttg aat aga cca cct cca att tgg act gat ggt gtt ggc ttt        3249
Val Leu Asn Arg Pro Pro Pro Ile Trp Thr Asp Gly Val Gly Phe
```

```
                     1070                1075                1080
atc  gac  aaa  aag  ttg  tta  tct  tca  tcc  gtt  cag  cca  cct  gct  aag     3294
Ile  Asp  Lys  Lys  Leu  Leu  Ser  Ser  Ser  Val  Gln  Pro  Pro  Ala  Lys
     1085                1090                1095 gat  ttg  tta  gtc  gcc  att  tgt  ggt  cct  cct  atc  atg  caa  cgt  gtt     3339
Asp  Leu  Leu  Val  Ala  Ile  Cys  Gly  Pro  Pro  Ile  Met  Gln  Arg  Val
     1100                1105                1110 gtc  aag  act  tgt  ctt  aag  tca  tta  ggt  tat  gat  atg  cag  tta  gtc     3384
Val  Lys  Thr  Cys  Leu  Lys  Ser  Leu  Gly  Tyr  Asp  Met  Gln  Leu  Val
     1115                1120                1125 aga  aca  gtt  gat  gaa  gtc  gaa  act  caa  aac  tcc  taa                    3420
Arg  Thr  Val  Asp  Glu  Val  Glu  Thr  Gln  Asn  Ser
     1130                1135
```

<210> SEQ ID NO 40
<211> LENGTH: 1139
<212> TYPE: PRT
<213> ORGANISM: Trypanosoma cruzi

<400> SEQUENCE: 40

```
Met Ala Asp Gly Arg Ser Ser Ala Ser Val Val Ala Val Asp Pro Glu
1               5                   10                  15

Lys Ala Ala Arg Glu Arg Asp Glu Ala Ala Arg Ala Leu Leu Arg Asp
                20                  25                  30

Ser Pro Leu Gln Thr His Leu Gln Tyr Met Thr Asn Gly Leu Glu Leu
            35                  40                  45

Thr Val Pro Phe Thr Leu Lys Val Val Ala Glu Ala Val Ala Phe Ser
        50                  55                  60

Arg Ala Lys Glu Val Ala Asp Glu Val Leu Arg Ser Ala Trp His Leu
65                  70                  75                  80

Ala Asp Thr Val Leu Asn Asn Phe Asn Pro Asn Ser Glu Ile Ser Met
                85                  90                  95

Ile Gly Arg Leu Pro Val Gly Gln Lys His Thr Met Ser Ala Thr Leu
            100                 105                 110

Lys Ser Val Ile Thr Cys Cys Gln His Val Phe Asn Ser Ser Arg Gly
        115                 120                 125

Val Phe Asp Pro Ala Thr Gly Pro Ile Ile Glu Ala Leu Arg Ala Lys
    130                 135                 140

Val Ala Glu Lys Ala Ser Val Ser Asp Glu Gln Met Glu Lys Leu Phe
145                 150                 155                 160

Arg Val Cys Asn Phe Ser Ser Ser Phe Ile Val Asp Leu Glu Met Gly
                165                 170                 175

Thr Ile Ala Arg Lys His Glu Asp Ala Arg Phe Asp Leu Gly Gly Val
            180                 185                 190

Ser Lys Gly Tyr Ile Val Asp Tyr Val Val Glu Arg Leu Asn Ala Ala
        195                 200                 205

Gly Ile Val Asp Val Tyr Phe Glu Trp Gly Gly Asp Cys Arg Ala Ser
    210                 215                 220

Gly Thr Asn Ala Arg Arg Thr Pro Trp Met Val Gly Ile Ile Arg Pro
225                 230                 235                 240

Pro Ser Leu Glu Gln Leu Arg Asn Pro Lys Asp Pro Ser Tyr Ile
                245                 250                 255

Arg Val Leu Pro Leu Asn Asp Glu Ala Leu Cys Thr Ser Gly Asp Tyr
            260                 265                 270

Glu Asn Leu Thr Glu Gly Ser Asn Lys Lys Leu Tyr Thr Ser Ile Phe
        275                 280                 285
```

```
Asp Trp Lys Lys Arg Ser Leu Leu Glu Pro Val Glu Ser Glu Leu Ala
    290                 295                 300
Gln Val Ser Ile Arg Cys Tyr Ser Ala Met Tyr Ala Asp Ala Leu Ala
305                 310                 315                 320
Thr Ala Ser Leu Ile Lys Arg Asp Ile Lys Lys Val Arg Gln Met Leu
                325                 330                 335
Glu Asp Trp Arg His Val Arg Asn Arg Val Thr Asn Tyr Val Thr Tyr
            340                 345                 350
Thr Arg Gln Gly Glu Arg Val Ala Arg Met Phe Glu Ile Ala Thr Asp
        355                 360                 365
Asn Ala Glu Ile Arg Lys Lys Arg Ile Ala Gly Ser Leu Pro Ala Arg
    370                 375                 380
Val Ile Val Val Gly Gly Gly Leu Ala Gly Leu Ser Ala Ala Ile Glu
385                 390                 395                 400
Ala Thr Ala Cys Gly Ala Gln Val Ile Leu Leu Glu Lys Glu Pro Lys
                405                 410                 415
Val Gly Gly Asn Ser Ala Lys Ala Thr Ser Gly Ile Asn Gly Trp Gly
            420                 425                 430
Thr Arg Ala Gln Ala Glu Gln Asp Val Tyr Asp Ser Gly Lys Tyr Phe
        435                 440                 445
Glu Arg Asp Thr His Lys Ser Gly Leu Gly Gly Ser Thr Asp Pro Gly
    450                 455                 460
Leu Val Arg Thr Leu Ser Val Lys Ser Gly Asp Ala Ile Ser Trp Leu
465                 470                 475                 480
Ser Ser Leu Gly Val Pro Leu Thr Val Leu Ser Gln Leu Gly Gly His
                485                 490                 495
Ser Arg Lys Arg Thr His Arg Ala Pro Asp Lys Ala Asp Gly Thr Pro
            500                 505                 510
Val Pro Ile Gly Phe Thr Ile Met Gln Thr Leu Glu Gln His Val Arg
        515                 520                 525
Thr Lys Leu Ala Asp Arg Val Thr Ile Met Glu Asn Thr Thr Val Thr
    530                 535                 540
Ser Leu Leu Ser Lys Ser Arg Val Arg His Asp Gly Ala Lys Gln Val
545                 550                 555                 560
Arg Val Tyr Gly Val Glu Val Leu Gln Asp Glu Gly Val Val Ser Arg
                565                 570                 575
Ile Leu Ala Asp Ala Val Ile Leu Ala Thr Gly Gly Phe Ser Asn Asp
            580                 585                 590
Lys Thr Pro Asn Ser Leu Leu Gln Glu Phe Ala Pro Gln Leu Ser Gly
        595                 600                 605
Phe Pro Thr Thr Asn Gly Pro Trp Ala Thr Gly Asp Gly Val Lys Leu
    610                 615                 620
Ala Arg Glu Leu Gly Val Lys Leu Val Asp Met Asp Lys Val Gln Leu
625                 630                 635                 640
His Pro Thr Gly Leu Ile Asp Pro Lys Asp Pro Ala Asn Pro Thr Lys
                645                 650                 655
Tyr Leu Gly Pro Glu Ala Leu Arg Gly Ser Gly Gly Val Leu Leu Asn
            660                 665                 670
Lys Lys Gly Glu Arg Phe Val Asn Glu Leu Asp Leu Arg Ser Val Val
        675                 680                 685
Ser Asn Ala Ile Ile Glu Gln Gly Asp Glu Tyr Pro Asp Ala Gly Gly
    690                 695                 700
```

```
Ser Lys Phe Ala Phe Cys Val Leu Asn Asp Ala Ala Val Lys Leu Phe
705                 710                 715                 720

Gly Val Asn Ser His Gly Phe Tyr Trp Lys Arg Leu Gly Leu Phe Val
            725                 730                 735

Lys Ala Asp Thr Val Glu Lys Leu Ala Ala Leu Ile Gly Cys Pro Val
                740                 745                 750

Glu Asn Val Arg Asn Thr Leu Gly Asp Tyr Glu Gln Leu Ser Lys Glu
            755                 760                 765

Asn Arg Gln Cys Pro Lys Thr Arg Lys Val Val Tyr Pro Cys Val Val
770                 775                 780

Gly Pro Gln Gly Pro Phe Tyr Val Ala Phe Val Thr Pro Ser Ile His
785                 790                 795                 800

Tyr Thr Met Gly Gly Cys Leu Ile Ser Pro Ser Ala Glu Met Gln Leu
                805                 810                 815

Glu Glu Asn Thr Thr Ser Pro Phe Gly His Arg Arg Pro Ile Phe Gly
            820                 825                 830

Leu Phe Gly Ala Gly Glu Val Thr Gly Gly Val His Gly Gly Asn Arg
                835                 840                 845

Leu Gly Gly Asn Ser Leu Leu Glu Cys Val Val Phe Gly Arg Ile Ala
850                 855                 860

Gly Asp Arg Ala Ala Thr Ile Leu Gln Lys Lys Pro Val Pro Leu Ser
865                 870                 875                 880

Phe Lys Thr Trp Thr Thr Val Ile Leu Arg Glu Val Arg Glu Gly Gly
                885                 890                 895

Met Tyr Gly Thr Gly Ser Arg Val Leu Arg Phe Asn Leu Pro Gly Ala
            900                 905                 910

Leu Gln Arg Ser Gly Leu Gln Leu Gly Gln Phe Ile Ala Ile Arg Gly
            915                 920                 925

Glu Trp Asp Gly Gln Gln Leu Ile Gly Tyr Tyr Ser Pro Ile Thr Leu
930                 935                 940

Pro Asp Asp Leu Gly Val Ile Gly Ile Leu Ala Arg Ser Asp Lys Gly
945                 950                 955                 960

Thr Leu Lys Glu Trp Ile Ser Ala Leu Glu Pro Gly Asp Ala Val Glu
                965                 970                 975

Met Lys Gly Cys Gly Gly Leu Val Ile Glu Arg Arg Phe Ser Glu Arg
            980                 985                 990

Tyr Leu Tyr Phe Ser Gly His Ala Leu Lys Lys Leu Cys Leu Ile Ala
            995                 1000                1005

Gly Gly Thr Gly Val Ala Pro Met Leu Gln Ile Ile Arg Ala Ala
    1010                1015                1020

Leu Lys Lys Pro Phe Leu Glu Asn Ile Glu Ser Ile Arg Leu Ile
    1025                1030                1035

Tyr Ala Ala Glu Asp Val Ser Glu Leu Thr Tyr Arg Glu Leu Leu
    1040                1045                1050

Glu His His Gln Arg Asp Ser Lys Gly Lys Phe Arg Ser Ile Phe
    1055                1060                1065

Val Leu Asn Arg Pro Pro Ile Trp Thr Asp Gly Val Gly Phe
    1070                1075                1080

Ile Asp Lys Lys Leu Leu Ser Ser Ser Val Gln Pro Pro Ala Lys
    1085                1090                1095

Asp Leu Leu Val Ala Ile Cys Gly Pro Pro Ile Met Gln Arg Val
    1100                1105                1110

Val Lys Thr Cys Leu Lys Ser Leu Gly Tyr Asp Met Gln Leu Val
```

```
            1115                1120               1125
Arg Thr  Val Asp Glu Val Glu  Thr Gln Asn Ser
         1130              1135

<210> SEQ ID NO 41
<211> LENGTH: 3435
<212> TYPE: DNA
<213> ORGANISM: Leishmania braziliensis
<220> FEATURE:
<221> NAME/KEY: CDS
<222> LOCATION: (1)..(3435)

<400> SEQUENCE: 41 atg gct gat ggt aaa acc tct gct tcc gtt gtt gct gtc gac cca gag      48
Met Ala Asp Gly Lys Thr Ser Ala Ser Val Val Ala Val Asp Pro Glu
1               5                   10                  15 cgt gca gca aag gag aga gat gca gca aga gca atg tta caa gac          96
Arg Ala Ala Lys Glu Arg Asp Ala Ala Arg Ala Met Leu Gln Asp
            20                  25                  30 ggt ggt gtt tct cca gtt ggt aaa gct cag ttg ttg aaa aag ggt ttg     144
Gly Gly Val Ser Pro Val Gly Lys Ala Gln Leu Leu Lys Lys Gly Leu
        35                  40                  45 gca tat gct gtc cct tac acc ctt aag att gtt gtt gca gat cct aaa     192
Ala Tyr Ala Val Pro Tyr Thr Leu Lys Ile Val Val Ala Asp Pro Lys
50                  55                  60 gct atg gaa aag acc acc gca gac gtt gag aag gtc ctt caa acc gca     240
Ala Met Glu Lys Thr Thr Ala Asp Val Glu Lys Val Leu Gln Thr Ala
65                  70                  75                  80 ttc caa gtc gtt gac act ttg tta aac aat ttc aac gaa aac tcc gag     288
Phe Gln Val Val Asp Thr Leu Leu Asn Asn Phe Asn Glu Asn Ser Glu
                85                  90                  95 gtt tct cgt atc aac aga atg cca gtc ggt gag gaa cac caa atg tct     336
Val Ser Arg Ile Asn Arg Met Pro Val Gly Glu Glu His Gln Met Ser
            100                 105                 110 gct gca ttg aag aga gtt atg ggt tgc tgt cag cgt gtt tac aat tca     384
Ala Ala Leu Lys Arg Val Met Gly Cys Cys Gln Arg Val Tyr Asn Ser
        115                 120                 125 tct cgt ggt gct ttt gac cca gct gtt ggt cca ttg gtc aga gaa ttg     432
Ser Arg Gly Ala Phe Asp Pro Ala Val Gly Pro Leu Val Arg Glu Leu
130                 135                 140 agg gaa gct gca aga gaa ggc aga act tta cca gca gaa agg att aac     480
Arg Glu Ala Ala Arg Glu Gly Arg Thr Leu Pro Ala Glu Arg Ile Asn
145                 150                 155                 160 gct ttg tta tcc aag tgt acc ttg aat atc tcc ttt tcc att gat ttg     528
Ala Leu Leu Ser Lys Cys Thr Leu Asn Ile Ser Phe Ser Ile Asp Leu
                165                 170                 175 aac aga ggt act att gcc aga aaa cac gca gat gca atg ttg gat ttg     576
Asn Arg Gly Thr Ile Ala Arg Lys His Ala Asp Ala Met Leu Asp Leu
            180                 185                 190 ggt ggt gtc aat aag ggt tat ggt gtt gat tat gtt gtc gaa cat ttg     624
Gly Gly Val Asn Lys Gly Tyr Gly Val Asp Tyr Val Val Glu His Leu
        195                 200                 205 aac aat ttg ggt tat gat gat gtc ttt ttc gaa tgg ggt ggt gat gtt     672
Asn Asn Leu Gly Tyr Asp Asp Val Phe Phe Glu Trp Gly Gly Asp Val
210                 215                 220 aga gca tct ggc aaa aac cca tca aac caa cat tgg gtt gtt ggt att     720
Arg Ala Ser Gly Lys Asn Pro Ser Asn Gln His Trp Val Val Gly Ile
225                 230                 235                 240 gct aga cca cca gca ctt gct gat atc aga acc gtt gtt cca caa gac     768
Ala Arg Pro Pro Ala Leu Ala Asp Ile Arg Thr Val Val Pro Gln Asp
                245                 250                 255
```

```
aag caa tcc ttc atc aga gtt gtt tgt ctt aat gat gaa gca att gcc    816
Lys Gln Ser Phe Ile Arg Val Val Cys Leu Asn Asp Glu Ala Ile Ala
        260                 265                 270 acc tct ggt gat tac gaa aat ctt gtc gaa ggt cct ggt tct aag gtt    864
Thr Ser Gly Asp Tyr Glu Asn Leu Val Glu Gly Pro Gly Ser Lys Val
    275                 280                 285 tac tcc tct acc ttc aac gca acc tct aag tcc tta ttg gaa cca acc    912
Tyr Ser Ser Thr Phe Asn Ala Thr Ser Lys Ser Leu Leu Glu Pro Thr
290                 295                 300 gaa acc aat atc gca caa gtc tct gtt aag tgt tac tca tgc atg tat    960
Glu Thr Asn Ile Ala Gln Val Ser Val Lys Cys Tyr Ser Cys Met Tyr
305                 310                 315                 320 gca gac gca ttg gct acc gct gcc tta ttg aaa aac aat cca act gct   1008
Ala Asp Ala Leu Ala Thr Ala Ala Leu Leu Lys Asn Asn Pro Thr Ala
                325                 330                 335 gtt cgt aga atg tta gat aac tgg aga tat gtt cgt gat act gtt acc   1056
Val Arg Arg Met Leu Asp Asn Trp Arg Tyr Val Arg Asp Thr Val Thr
            340                 345                 350 gac tat aca acc tat tcc aga gaa ggt gaa aga gtt gca aag atg ttt   1104
Asp Tyr Thr Thr Tyr Ser Arg Glu Gly Glu Arg Val Ala Lys Met Phe
        355                 360                 365 gag att gca acc gaa gat aag gaa atg aga gct aag aga att tcc ggt   1152
Glu Ile Ala Thr Glu Asp Lys Glu Met Arg Ala Lys Arg Ile Ser Gly
    370                 375                 380 tcc ttg cca gca aga gtc att atc gtc ggt ggt ggt tta gct ggt tgt   1200
Ser Leu Pro Ala Arg Val Ile Ile Val Gly Gly Gly Leu Ala Gly Cys
385                 390                 395                 400 tct gca gct att gaa gca gtc aac tgt ggt gct caa gtc att ttg tta   1248
Ser Ala Ala Ile Glu Ala Val Asn Cys Gly Ala Gln Val Ile Leu Leu
                405                 410                 415 gaa aag gaa gcc aag att ggt ggc aac tcc gca aag gct acc tct ggt   1296
Glu Lys Glu Ala Lys Ile Gly Gly Asn Ser Ala Lys Ala Thr Ser Gly
            420                 425                 430 atc aac gcc tgg ggt act aga gcc cag gct aaa caa ggt gtt atg gat   1344
Ile Asn Ala Trp Gly Thr Arg Ala Gln Ala Lys Gln Gly Val Met Asp
        435                 440                 445 ggt ggc aag ttt ttc gag aga gac acc cat aga tcc ggt aaa ggt ggt   1392
Gly Gly Lys Phe Phe Glu Arg Asp Thr His Arg Ser Gly Lys Gly Gly
    450                 455                 460 cac tgt gat cct tgt ttg gtt aag aca ctt tcc gtt aag tca tca gac   1440
His Cys Asp Pro Cys Leu Val Lys Thr Leu Ser Val Lys Ser Ser Asp
465                 470                 475                 480 gca gtt aag tgg ttg tct gaa ttg ggt gtt cca tta acc gtc tta tcc   1488
Ala Val Lys Trp Leu Ser Glu Leu Gly Val Pro Leu Thr Val Leu Ser
                485                 490                 495 caa tta ggt ggt gca tcc aga aag agg tgt cat aga gcc cca gat aag   1536
Gln Leu Gly Gly Ala Ser Arg Lys Arg Cys His Arg Ala Pro Asp Lys
            500                 505                 510 tct gat ggt act cct gtt cca att ggt ttt aca atc atg aaa aca tta   1584
Ser Asp Gly Thr Pro Val Pro Ile Gly Phe Thr Ile Met Lys Thr Leu
        515                 520                 525 gaa aat cac atc att aac gat ctt tct cac caa gtt act gtt atg act   1632
Glu Asn His Ile Ile Asn Asp Leu Ser His Gln Val Thr Val Met Thr
    530                 535                 540 ggt atc aag gtt act ggt ttg gag tcc act tct cac gct cgt cca gat   1680
Gly Ile Lys Val Thr Gly Leu Glu Ser Thr Ser His Ala Arg Pro Asp
545                 550                 555                 560 ggt gtt tta gtt aag cac gtt act ggt gtt aga ttg att caa ggt gat   1728
Gly Val Leu Val Lys His Val Thr Gly Val Arg Leu Ile Gln Gly Asp
```

```
                565                 570                 575
ggc caa tcc aga gtt ttg aat gct gat gcc gtt atc tta gca act ggt    1776
Gly Gln Ser Arg Val Leu Asn Ala Asp Ala Val Ile Leu Ala Thr Gly
        580                 585                 590 ggt ttc tcc aat gac cat act gct aac tct tta ctt caa caa tac gct    1824
Gly Phe Ser Asn Asp His Thr Ala Asn Ser Leu Leu Gln Gln Tyr Ala
    595                 600                 605 cca caa ctt tca tcc ttt cca acc act aat ggt gtt tgg gcc act ggt    1872
Pro Gln Leu Ser Ser Phe Pro Thr Thr Asn Gly Val Trp Ala Thr Gly
610                 615                 620 gac ggt gtc aag gca gct aga gaa tta ggt gtt gag ttg gtt gac atg    1920
Asp Gly Val Lys Ala Ala Arg Glu Leu Gly Val Glu Leu Val Asp Met
625                 630                 635                 640 gat aag gtc caa ttg cat cca aca ggt ttg tta gat cca aag gac cca    1968
Asp Lys Val Gln Leu His Pro Thr Gly Leu Leu Asp Pro Lys Asp Pro
            645                 650                 655 tcc aac agg act aag tac ttg ggt cca gaa gct tta agg ggt tca ggc    2016
Ser Asn Arg Thr Lys Tyr Leu Gly Pro Glu Ala Leu Arg Gly Ser Gly
        660                 665                 670 ggt gtc ttg tta aac aaa aac ggt gaa cgt ttc gtc aac gaa ctt gat    2064
Gly Val Leu Leu Asn Lys Asn Gly Glu Arg Phe Val Asn Glu Leu Asp
    675                 680                 685 ttg aga tct gtc gtt tct caa gcc att atc gaa caa aac aac gtt tac    2112
Leu Arg Ser Val Val Ser Gln Ala Ile Ile Glu Gln Asn Asn Val Tyr
690                 695                 700 cct ggt tct ggt ggt tcc aag ttt gct tac tgc gtt ttg aac gaa gca    2160
Pro Gly Ser Gly Gly Ser Lys Phe Ala Tyr Cys Val Leu Asn Glu Ala
705                 710                 715                 720 gca gct aag ttg ttc ggc aaa aac ttt ttg ggt ttc tat tgg cat aga    2208
Ala Ala Lys Leu Phe Gly Lys Asn Phe Leu Gly Phe Tyr Trp His Arg
            725                 730                 735 tta ggt ctt ttt gaa aag gtt gaa gat gtt gct ggt tta gcc aaa ttg    2256
Leu Gly Leu Phe Glu Lys Val Glu Asp Val Ala Gly Leu Ala Lys Leu
        740                 745                 750 atc ggt tgt cca gag gaa aat gtt acc gct aca ttg aag gaa tac aag    2304
Ile Gly Cys Pro Glu Glu Asn Val Thr Ala Thr Leu Lys Glu Tyr Lys
    755                 760                 765 gaa ttg tcc tcc aaa aag ctt cat gcc tgt cct tta acc aac aaa aac    2352
Glu Leu Ser Ser Lys Lys Leu His Ala Cys Pro Leu Thr Asn Lys Asn
770                 775                 780 gtc ttt cct tgc act tta ggt act gaa ggc cct tac tat gtt gct ttc    2400
Val Phe Pro Cys Thr Leu Gly Thr Glu Gly Pro Tyr Tyr Val Ala Phe
785                 790                 795                 800 gtc aca cct tca att cac tac aca atg ggt ggt tgt ttg atc tcc cct    2448
Val Thr Pro Ser Ile His Tyr Thr Met Gly Gly Cys Leu Ile Ser Pro
            805                 810                 815 tca gca gaa atg cag acc att gat aac act ggt gtc aca cca gtt cgt    2496
Ser Ala Glu Met Gln Thr Ile Asp Asn Thr Gly Val Thr Pro Val Arg
        820                 825                 830 aga cca atc ttg ggc tta ttc ggt gct ggt gaa gtt act ggt ggt gtc    2544
Arg Pro Ile Leu Gly Leu Phe Gly Ala Gly Glu Val Thr Gly Gly Val
    835                 840                 845 cat ggt ggt aac aga ttg ggt ggt aat tcc tta ttg gaa tgt gtt gtc    2592
His Gly Gly Asn Arg Leu Gly Gly Asn Ser Leu Leu Glu Cys Val Val
850                 855                 860 ttt ggt aga att gct ggt gat aga gcc gct acc att ttg caa aag aag    2640
Phe Gly Arg Ile Ala Gly Asp Arg Ala Ala Thr Ile Leu Gln Lys Lys
865                 870                 875                 880 aat gct ggt tta tca atg act gag tgg tct aca gtt gtc tta aga gaa    2688
```

```
Asn Ala Gly Leu Ser Met Thr Glu Trp Ser Thr Val Val Leu Arg Glu
                885                 890                 895 gtc aga gaa ggc ggt gtt tac ggt act ggt tct cgt gtc ctt aga ttc      2736
Val Arg Glu Gly Gly Val Tyr Gly Thr Gly Ser Arg Val Leu Arg Phe
        900                 905                 910 aat atg cca ggt gcc tta caa aag act ggc tta gca ttg ggt caa ttc      2784
Asn Met Pro Gly Ala Leu Gln Lys Thr Gly Leu Ala Leu Gly Gln Phe
                915                 920                 925 atc gca atg aga ggt gat tgg gat ggt caa cag tta ttg ggt tac tat      2832
Ile Ala Met Arg Gly Asp Trp Asp Gly Gln Gln Leu Leu Gly Tyr Tyr
            930                 935                 940 tct cca att aca tta cca gac gac att ggt gtt att ggt atc tta gct      2880
Ser Pro Ile Thr Leu Pro Asp Asp Ile Gly Val Ile Gly Ile Leu Ala
945                 950                 955                 960 aga gct gac aaa ggt aga tta gct gaa tgg att tct gca tta caa cca      2928
Arg Ala Asp Lys Gly Arg Leu Ala Glu Trp Ile Ser Ala Leu Gln Pro
                965                 970                 975 ggt gat gct gtt gag atg aag gca tgt ggc ggt ttg att atc cat aga      2976
Gly Asp Ala Val Glu Met Lys Ala Cys Gly Gly Leu Ile Ile His Arg
            980                 985                 990 aga ttc gct gct aga cac ttg ttt ttc cgt tct cac aag att aga aag      3024
Arg Phe Ala Ala Arg His Leu Phe Phe Arg Ser His Lys Ile Arg Lys
        995                 1000                1005 ctt gct ctt att ggt ggt ggt act ggt gtt gca cca atg ttg caa          3069
Leu Ala Leu Ile Gly Gly Gly Thr Gly Val Ala Pro Met Leu Gln
    1010                1015                1020 att gtc agg gct gca gtc aaa aag cca ttt gtt gac tct att gag          3114
Ile Val Arg Ala Ala Val Lys Lys Pro Phe Val Asp Ser Ile Glu
    1025                1030                1035 tct att cag ttc atc tat gca gct gaa gat gtc tcc gaa ctt act          3159
Ser Ile Gln Phe Ile Tyr Ala Ala Glu Asp Val Ser Glu Leu Thr
    1040                1045                1050 tat aga act ttg ttg gaa tca tat gaa aag gaa tac ggt tct ggc          3204
Tyr Arg Thr Leu Leu Glu Ser Tyr Glu Lys Glu Tyr Gly Ser Gly
    1055                1060                1065 aaa ttc aag tgt cat ttc gtc ttg aat aac cca cca tca caa tgg          3249
Lys Phe Lys Cys His Phe Val Leu Asn Asn Pro Pro Ser Gln Trp
    1070                1075                1080 acc gag ggc gtt ggt ttc gtt gat act gct ttg ttg cgt tct gcc          3294
Thr Glu Gly Val Gly Phe Val Asp Thr Ala Leu Leu Arg Ser Ala
    1085                1090                1095 gtt caa gca cct tct aac gac ttg tta gtc gct att tgt ggc cca          3339
Val Gln Ala Pro Ser Asn Asp Leu Leu Val Ala Ile Cys Gly Pro
    1100                1105                1110 cca atc atg caa aga gca gtc aaa tca gcc tta aag ggt tta ggt          3384
Pro Ile Met Gln Arg Ala Val Lys Ser Ala Leu Lys Gly Leu Gly
    1115                1120                1125 tac aat atg aat ttg gtt aga aca gtt gat gaa cca gaa cca ttg          3429
Tyr Asn Met Asn Leu Val Arg Thr Val Asp Glu Pro Glu Pro Leu
    1130                1135                1140 tct taa                                                              3435
Ser

<210> SEQ ID NO 42
<211> LENGTH: 1144
<212> TYPE: PRT
<213> ORGANISM: Leishmania braziliensis

<400> SEQUENCE: 42

Met Ala Asp Gly Lys Thr Ser Ala Ser Val Val Ala Val Asp Pro Glu
```

-continued

```
1               5                   10                  15
Arg Ala Ala Lys Glu Arg Asp Ala Ala Ala Arg Ala Met Leu Gln Asp
                20                  25                  30
Gly Gly Val Ser Pro Val Gly Lys Ala Gln Leu Leu Lys Lys Gly Leu
                35                  40                  45
Ala Tyr Ala Val Pro Tyr Thr Leu Lys Ile Val Val Ala Asp Pro Lys
                50                  55                  60
Ala Met Glu Lys Thr Thr Ala Asp Val Glu Lys Val Leu Gln Thr Ala
 65                 70                  75                  80
Phe Gln Val Val Asp Thr Leu Leu Asn Asn Phe Asn Glu Asn Ser Glu
                    85                  90                  95
Val Ser Arg Ile Asn Arg Met Pro Val Gly Glu His Gln Met Ser
                100                 105                 110
Ala Ala Leu Lys Arg Val Met Gly Cys Cys Gln Arg Val Tyr Asn Ser
                115                 120                 125
Ser Arg Gly Ala Phe Asp Pro Ala Val Gly Pro Leu Val Arg Glu Leu
                130                 135                 140
Arg Glu Ala Ala Arg Glu Gly Arg Thr Leu Pro Ala Glu Arg Ile Asn
145                 150                 155                 160
Ala Leu Leu Ser Lys Cys Thr Leu Asn Ile Ser Phe Ser Ile Asp Leu
                165                 170                 175
Asn Arg Gly Thr Ile Ala Arg Lys His Ala Asp Ala Met Leu Asp Leu
                180                 185                 190
Gly Gly Val Asn Lys Gly Tyr Gly Val Asp Tyr Val Val Glu His Leu
                195                 200                 205
Asn Asn Leu Gly Tyr Asp Asp Val Phe Phe Glu Trp Gly Gly Asp Val
                210                 215                 220
Arg Ala Ser Gly Lys Asn Pro Ser Asn Gln His Trp Val Val Gly Ile
225                 230                 235                 240
Ala Arg Pro Pro Ala Leu Ala Asp Ile Arg Thr Val Val Pro Gln Asp
                245                 250                 255
Lys Gln Ser Phe Ile Arg Val Val Cys Leu Asn Asp Glu Ala Ile Ala
                260                 265                 270
Thr Ser Gly Asp Tyr Glu Asn Leu Val Glu Gly Pro Gly Ser Lys Val
                275                 280                 285
Tyr Ser Ser Thr Phe Asn Ala Thr Ser Lys Ser Leu Leu Glu Pro Thr
                290                 295                 300
Glu Thr Asn Ile Ala Gln Val Ser Val Lys Cys Tyr Ser Cys Met Tyr
305                 310                 315                 320
Ala Asp Ala Leu Ala Thr Ala Ala Leu Leu Lys Asn Asn Pro Thr Ala
                325                 330                 335
Val Arg Arg Met Leu Asp Asn Trp Arg Tyr Val Arg Asp Thr Val Thr
                340                 345                 350
Asp Tyr Thr Thr Tyr Ser Arg Glu Gly Glu Arg Val Ala Lys Met Phe
                355                 360                 365
Glu Ile Ala Thr Glu Asp Lys Glu Met Arg Ala Lys Arg Ile Ser Gly
                370                 375                 380
Ser Leu Pro Ala Arg Val Ile Ile Val Gly Gly Leu Ala Gly Cys
385                 390                 395                 400
Ser Ala Ala Ile Glu Ala Val Asn Cys Gly Ala Gln Val Ile Leu Leu
                405                 410                 415
Glu Lys Glu Ala Lys Ile Gly Gly Asn Ser Ala Lys Ala Thr Ser Gly
                420                 425                 430
```

```
Ile Asn Ala Trp Gly Thr Arg Ala Gln Ala Lys Gln Gly Val Met Asp
        435                 440                 445

Gly Gly Lys Phe Phe Glu Arg Asp Thr His Arg Ser Gly Lys Gly Gly
450                 455                 460

His Cys Asp Pro Cys Leu Val Lys Thr Leu Ser Val Lys Ser Ser Asp
465                 470                 475                 480

Ala Val Lys Trp Leu Ser Glu Leu Gly Val Pro Leu Thr Val Leu Ser
                485                 490                 495

Gln Leu Gly Gly Ala Ser Arg Lys Arg Cys His Arg Ala Pro Asp Lys
            500                 505                 510

Ser Asp Gly Thr Pro Val Pro Ile Gly Phe Thr Ile Met Lys Thr Leu
        515                 520                 525

Glu Asn His Ile Ile Asn Asp Leu Ser His Gln Val Thr Val Met Thr
        530                 535                 540

Gly Ile Lys Val Thr Gly Leu Glu Ser Thr Ser His Ala Arg Pro Asp
545                 550                 555                 560

Gly Val Leu Val Lys His Val Thr Gly Val Arg Leu Ile Gln Gly Asp
                565                 570                 575

Gly Gln Ser Arg Val Leu Asn Ala Asp Ala Val Ile Leu Ala Thr Gly
            580                 585                 590

Gly Phe Ser Asn Asp His Thr Ala Asn Ser Leu Leu Gln Gln Tyr Ala
        595                 600                 605

Pro Gln Leu Ser Ser Phe Pro Thr Thr Asn Gly Val Trp Ala Thr Gly
        610                 615                 620

Asp Gly Val Lys Ala Ala Arg Glu Leu Gly Val Glu Leu Val Asp Met
625                 630                 635                 640

Asp Lys Val Gln Leu His Pro Thr Gly Leu Leu Asp Pro Lys Asp Pro
                645                 650                 655

Ser Asn Arg Thr Lys Tyr Leu Gly Pro Glu Ala Leu Arg Gly Ser Gly
            660                 665                 670

Gly Val Leu Leu Asn Lys Asn Gly Glu Arg Phe Val Asn Glu Leu Asp
        675                 680                 685

Leu Arg Ser Val Val Ser Gln Ala Ile Ile Glu Gln Asn Asn Val Tyr
        690                 695                 700

Pro Gly Ser Gly Gly Ser Lys Phe Ala Tyr Cys Val Leu Asn Glu Ala
705                 710                 715                 720

Ala Ala Lys Leu Phe Gly Lys Asn Phe Leu Gly Phe Tyr Trp His Arg
                725                 730                 735

Leu Gly Leu Phe Glu Lys Val Glu Asp Val Ala Gly Leu Ala Lys Leu
            740                 745                 750

Ile Gly Cys Pro Glu Glu Asn Val Thr Ala Thr Leu Lys Glu Tyr Lys
        755                 760                 765

Glu Leu Ser Ser Lys Lys Leu His Ala Cys Pro Leu Thr Asn Lys Asn
        770                 775                 780

Val Phe Pro Cys Thr Leu Gly Thr Glu Gly Pro Tyr Tyr Val Ala Phe
785                 790                 795                 800

Val Thr Pro Ser Ile His Tyr Thr Met Gly Gly Cys Leu Ile Ser Pro
                805                 810                 815

Ser Ala Glu Met Gln Thr Ile Asp Asn Thr Gly Val Thr Pro Val Arg
            820                 825                 830

Arg Pro Ile Leu Gly Leu Phe Gly Ala Gly Glu Val Thr Gly Gly Val
        835                 840                 845
```

```
His Gly Gly Asn Arg Leu Gly Gly Asn Ser Leu Leu Glu Cys Val Val
    850                 855                 860

Phe Gly Arg Ile Ala Gly Asp Arg Ala Ala Thr Ile Leu Gln Lys Lys
865                 870                 875                 880

Asn Ala Gly Leu Ser Met Thr Glu Trp Ser Thr Val Val Leu Arg Glu
                885                 890                 895

Val Arg Glu Gly Gly Val Tyr Gly Thr Gly Ser Arg Val Leu Arg Phe
            900                 905                 910

Asn Met Pro Gly Ala Leu Gln Lys Thr Gly Leu Ala Leu Gly Gln Phe
        915                 920                 925

Ile Ala Met Arg Gly Asp Trp Asp Gly Gln Gln Leu Leu Gly Tyr Tyr
    930                 935                 940

Ser Pro Ile Thr Leu Pro Asp Asp Ile Gly Val Ile Gly Ile Leu Ala
945                 950                 955                 960

Arg Ala Asp Lys Gly Arg Leu Ala Glu Trp Ile Ser Ala Leu Gln Pro
                965                 970                 975

Gly Asp Ala Val Glu Met Lys Ala Cys Gly Gly Leu Ile Ile His Arg
            980                 985                 990

Arg Phe Ala Ala Arg His Leu Phe  Phe Arg Ser His Lys  Ile Arg Lys
        995                 1000                1005

Leu Ala  Leu Ile Gly Gly Gly  Thr Gly Val Ala Pro  Met Leu Gln
    1010                1015                1020

Ile Val  Arg Ala Ala Val Lys  Lys Pro Phe Val Asp  Ser Ile Glu
    1025                1030                1035

Ser Ile  Gln Phe Ile Tyr Ala  Ala Glu Asp Val Ser  Glu Leu Thr
    1040                1045                1050

Tyr Arg  Thr Leu Leu Glu Ser  Tyr Glu Lys Glu Tyr  Gly Ser Gly
    1055                1060                1065

Lys Phe  Lys Cys His Phe Val  Leu Asn Asn Pro Pro  Ser Gln Trp
    1070                1075                1080

Thr Glu  Gly Val Gly Phe Val  Asp Thr Ala Leu Leu  Arg Ser Ala
    1085                1090                1095

Val Gln  Ala Pro Ser Asn Asp  Leu Leu Val Ala Ile  Cys Gly Pro
    1100                1105                1110

Pro Ile  Met Gln Arg Ala Val  Lys Ser Ala Leu Lys  Gly Leu Gly
    1115                1120                1125

Tyr Asn  Met Asn Leu Val Arg  Thr Val Asp Glu Pro  Glu Pro Leu
    1130                1135                1140

Ser

<210> SEQ ID NO 43
<211> LENGTH: 3435
<212> TYPE: DNA
<213> ORGANISM: Leishmania mexicana
<220> FEATURE:
<221> NAME/KEY: CDS
<222> LOCATION: (1)..(3435)

<400> SEQUENCE: 43 atg gct gat ggc aaa acc tct gca tca gtt gtt gct gtt gat gct gaa    48
Met Ala Asp Gly Lys Thr Ser Ala Ser Val Val Ala Val Asp Ala Glu
1               5                   10                  15 cgt gcc gct aag gaa aga gat gca gca gct aga gct atg ttg caa ggt    96
Arg Ala Ala Lys Glu Arg Asp Ala Ala Ala Arg Ala Met Leu Gln Gly
            20                  25                  30 ggt ggt gtc tct cct gct ggc aag gca caa ttg ttg aaa aag ggt ttg   144
```

|   |   |   |   |   |   |   |   |   |   |   |   |   |   |   |   |
|---|---|---|---|---|---|---|---|---|---|---|---|---|---|---|---|
| Gly | Gly | Val | Ser | Pro | Ala | Gly | Lys | Ala | Gln | Leu | Leu | Lys | Gly | Leu |   |
|   |   | 35 |   |   |   | 40 |   |   |   | 45 |   |   |   |   |   |

```
gtt cac act gtt cca tat acc tta aag gtt gtc gtc gca gat cca aag      192
Val His Thr Val Pro Tyr Thr Leu Lys Val Val Val Ala Asp Pro Lys
     50                  55                  60 gaa atg gag aag gca act gct gac gca gaa gag gtt tta caa gct gca      240
Glu Met Glu Lys Ala Thr Ala Asp Ala Glu Glu Val Leu Gln Ala Ala
 65                  70                  75                  80 ttt caa gtc gtc gac acc ctt ttg aac aac ttt aac gaa aac tca gaa      288
Phe Gln Val Val Asp Thr Leu Leu Asn Asn Phe Asn Glu Asn Ser Glu
                 85                  90                  95 gtt tca aga gtc aat agg ttg gca gtt ggt gag gaa cat caa atg tct      336
Val Ser Arg Val Asn Arg Leu Ala Val Gly Glu Glu His Gln Met Ser
            100                 105                 110 gaa aca ttg aaa cac gtc atg gcc tgt tgt caa aag gtt tat cat tcc      384
Glu Thr Leu Lys His Val Met Ala Cys Cys Gln Lys Val Tyr His Ser
        115                 120                 125 tcc aga ggt gtt ttt gac cca gca gtt ggt cca tta gtc cgt gaa ctt      432
Ser Arg Gly Val Phe Asp Pro Ala Val Gly Pro Leu Val Arg Glu Leu
    130                 135                 140 aga gaa gct gct cac aag ggt aaa act gtt cca gcc gaa aga gtt aat      480
Arg Glu Ala Ala His Lys Gly Lys Thr Val Pro Ala Glu Arg Val Asn
145                 150                 155                 160 gat ttg tta tcc aaa tgt acc ctt aat gca tct ttt tca att gat atg      528
Asp Leu Leu Ser Lys Cys Thr Leu Asn Ala Ser Phe Ser Ile Asp Met
                165                 170                 175 tcc aga ggt atg att gca agg aag cat cca gac gcc atg ttg gat ttg      576
Ser Arg Gly Met Ile Ala Arg Lys His Pro Asp Ala Met Leu Asp Leu
            180                 185                 190 ggt ggt gtc aac aag ggt tat ggt atc gac tac att gtt gaa cac tta      624
Gly Gly Val Asn Lys Gly Tyr Gly Ile Asp Tyr Ile Val Glu His Leu
        195                 200                 205 aac tct ttg ggt tat gat gat gtc ttt ttc gaa tgg ggt ggt gat gtt      672
Asn Ser Leu Gly Tyr Asp Asp Val Phe Phe Glu Trp Gly Gly Asp Val
    210                 215                 220 aga gca tcc ggc aaa aac cag tta tct caa cct tgg gct gtt ggt att      720
Arg Ala Ser Gly Lys Asn Gln Leu Ser Gln Pro Trp Ala Val Gly Ile
225                 230                 235                 240 gtt aga cca cct gcc ttg gcc gac att aga act gtt gtc cca gag gac      768
Val Arg Pro Pro Ala Leu Ala Asp Ile Arg Thr Val Val Pro Glu Asp
                245                 250                 255 aaa aga tcc ttt atc cgt gtc gtc aga ttg aac aac gaa gct att gct      816
Lys Arg Ser Phe Ile Arg Val Val Arg Leu Asn Asn Glu Ala Ile Ala
            260                 265                 270 acc tct ggt gat tat gag aat ttg gtt gaa ggt cct ggt tct aag gtt      864
Thr Ser Gly Asp Tyr Glu Asn Leu Val Glu Gly Pro Gly Ser Lys Val
        275                 280                 285 tac tct tcc acc ttc aat cca act tcc aaa aac ttg ttg gaa cct acc      912
Tyr Ser Ser Thr Phe Asn Pro Thr Ser Lys Asn Leu Leu Glu Pro Thr
    290                 295                 300 gaa gca ggt atg gct caa gtt tct gtc aag tgt tgc tca tgt atc tac      960
Glu Ala Gly Met Ala Gln Val Ser Val Lys Cys Cys Ser Cys Ile Tyr
305                 310                 315                 320 gct gat gct tta gca aca gca gct ttg ttg aaa aac gat cct gct gcc     1008
Ala Asp Ala Leu Ala Thr Ala Ala Leu Leu Lys Asn Asp Pro Ala Ala
                325                 330                 335 gtt aga agg atc tta gat aac tgg aga tat gtc aga gat act gtt act     1056
Val Arg Arg Ile Leu Asp Asn Trp Arg Tyr Val Arg Asp Thr Val Thr
            340                 345                 350
```

```
gac tac acc act tac aca agg gaa ggt gaa aga gtt gct aag atg ttg    1104
Asp Tyr Thr Thr Tyr Thr Arg Glu Gly Glu Arg Val Ala Lys Met Leu
        355                 360                 365 gaa att gct acc gaa gat gct gaa atg aga gca aag aga atc aag ggc    1152
Glu Ile Ala Thr Glu Asp Ala Glu Met Arg Ala Lys Arg Ile Lys Gly
370                 375                 380 tct tta cca gca aga gtt atc att gtt ggt ggt ggt ttg gcc ggt tgt    1200
Ser Leu Pro Ala Arg Val Ile Ile Val Gly Gly Gly Leu Ala Gly Cys
385                 390                 395                 400 tcc gca gct atc gaa gca gct aac tgt ggc gcc cac gtc atc ttg tta    1248
Ser Ala Ala Ile Glu Ala Ala Asn Cys Gly Ala His Val Ile Leu Leu
                405                 410                 415 gaa aag gaa cca aag tta ggt ggt aac tct gca aag gct acc tcc ggt    1296
Glu Lys Glu Pro Lys Leu Gly Gly Asn Ser Ala Lys Ala Thr Ser Gly
            420                 425                 430 atc aac gcc tgg ggt act aga gca caa gca aaa caa ggt gtc atg gac    1344
Ile Asn Ala Trp Gly Thr Arg Ala Gln Ala Lys Gln Gly Val Met Asp
        435                 440                 445 ggc ggc aag ttt ttc gaa aga gat acc cat aga tcc ggc aag ggt ggt    1392
Gly Gly Lys Phe Phe Glu Arg Asp Thr His Arg Ser Gly Lys Gly Gly
    450                 455                 460 aat tgc gat cca tgc ctt gtt aag act ttg tcc gtt aag tcc tct gat    1440
Asn Cys Asp Pro Cys Leu Val Lys Thr Leu Ser Val Lys Ser Ser Asp
465                 470                 475                 480 gca gtt aag tgg tta tct gaa tta ggt gtt cca ttg act gtt ttg tct    1488
Ala Val Lys Trp Leu Ser Glu Leu Gly Val Pro Leu Thr Val Leu Ser
                485                 490                 495 caa tta ggt ggt gct tca agg aaa cgt tgt cac cgt gca cca gat aag    1536
Gln Leu Gly Gly Ala Ser Arg Lys Arg Cys His Arg Ala Pro Asp Lys
            500                 505                 510 tct gat ggt aca cca gtc cca gtt ggt ttc acc att atg aaa acc ctt    1584
Ser Asp Gly Thr Pro Val Pro Val Gly Phe Thr Ile Met Lys Thr Leu
        515                 520                 525 gaa aac cac att gtc aac gat ttg tcc aga cat gtt aca gtt atg aca    1632
Glu Asn His Ile Val Asn Asp Leu Ser Arg His Val Thr Val Met Thr
    530                 535                 540 ggt att acc gtc aca gct tta gaa tct aca tca aga gtc aga cct gat    1680
Gly Ile Thr Val Thr Ala Leu Glu Ser Thr Ser Arg Val Arg Pro Asp
545                 550                 555                 560 ggt gtt tta gtc aag cat gtt act ggt gtt cac ttg att cag gca tct    1728
Gly Val Leu Val Lys His Val Thr Gly Val His Leu Ile Gln Ala Ser
                565                 570                 575 ggt caa tct atg gtt ttg aat gca gac gct gtt atc tta gct act ggt    1776
Gly Gln Ser Met Val Leu Asn Ala Asp Ala Val Ile Leu Ala Thr Gly
            580                 585                 590 ggt ttc tcc aat gat cat acc cca aac tcc ctt tta caa caa tac gcc    1824
Gly Phe Ser Asn Asp His Thr Pro Asn Ser Leu Leu Gln Gln Tyr Ala
        595                 600                 605 cca cag ttg tca tct ttt cca aca acc aat ggt gtc tgg gca act ggc    1872
Pro Gln Leu Ser Ser Phe Pro Thr Thr Asn Gly Val Trp Ala Thr Gly
    610                 615                 620 gat ggt gtt aag atg gct tcc aag ttg ggt gtc gcc tta gtt gat atg    1920
Asp Gly Val Lys Met Ala Ser Lys Leu Gly Val Ala Leu Val Asp Met
625                 630                 635                 640 gat aag gtc caa tta cat cct acc ggc ttg tta gac cca aaa gat cca    1968
Asp Lys Val Gln Leu His Pro Thr Gly Leu Leu Asp Pro Lys Asp Pro
                645                 650                 655 tct aat aga acc aag tat ctt ggt cca gag gcc tta aga ggt tcc ggc    2016
Ser Asn Arg Thr Lys Tyr Leu Gly Pro Glu Ala Leu Arg Gly Ser Gly
            660                 665                 670
```

| | | | | | | | | | | | | | | | |
|---|---|---|---|---|---|---|---|---|---|---|---|---|---|---|---|
| ggt | gtc | ttg | tta | aac | aaa | aac | ggt | gaa | aga | ttt | gtt | aat | gaa | tta | gac | 2064 |
| Gly | Val | Leu | Leu | Asn | Lys | Asn | Gly | Glu | Arg | Phe | Val | Asn | Glu | Leu | Asp | |
| | | | 675 | | | | 680 | | | | 685 | | | | | | tta aga tct gtt gtc tct caa gct atc atc gca caa gat aat gag tac 2112
Leu Arg Ser Val Val Ser Gln Ala Ile Ile Ala Gln Asp Asn Glu Tyr
690         695             700 cca ggc tct ggt ggt tcc aag ttc gca tac tgt gtt ttg aac gaa act 2160
Pro Gly Ser Gly Gly Ser Lys Phe Ala Tyr Cys Val Leu Asn Glu Thr
705         710             715             720 gca gca aag tta ttc ggc aaa aac ttc ctt ggt ttc tac tgg aat aga 2208
Ala Ala Lys Leu Phe Gly Lys Asn Phe Leu Gly Phe Tyr Trp Asn Arg
        725             730             735 tta ggt ctt ttc caa aag gtt gat tcc gtt gct ggt tta gct aag ttg 2256
Leu Gly Leu Phe Gln Lys Val Asp Ser Val Ala Gly Leu Ala Lys Leu
        740             745             750 att ggt tgt cca gaa gct aat gtt gtt gct aca ttg aag caa tat gag 2304
Ile Gly Cys Pro Glu Ala Asn Val Val Ala Thr Leu Lys Gln Tyr Glu
        755             760             765 gag tta tct tcc aaa aag ctt aat cct tgt cca ttg act ggc aag tct 2352
Glu Leu Ser Ser Lys Lys Leu Asn Pro Cys Pro Leu Thr Gly Lys Ser
770         775             780 gtc ttt cct tgt gtt tta ggc act caa ggt cca tac tat gtt gcc ttg 2400
Val Phe Pro Cys Val Leu Gly Thr Gln Gly Pro Tyr Tyr Val Ala Leu
785         790             795             800 gtt acc cca tcc att cac tac act atg ggt ggt tgt ttg att tcc cca 2448
Val Thr Pro Ser Ile His Tyr Thr Met Gly Gly Cys Leu Ile Ser Pro
            805             810             815 tct gct gag atg caa acc att gac aac tct ggt gtt act cct gtc aga 2496
Ser Ala Glu Met Gln Thr Ile Asp Asn Ser Gly Val Thr Pro Val Arg
        820             825             830 cgt cca atc tta ggc tta ttc ggt gct ggt gaa gtt act ggc ggt gtc 2544
Arg Pro Ile Leu Gly Leu Phe Gly Ala Gly Glu Val Thr Gly Gly Val
        835             840             845 cat ggt ggt aac aga tta ggc ggt aac tct ttg tta gaa tgt gtt gtt 2592
His Gly Gly Asn Arg Leu Gly Gly Asn Ser Leu Leu Glu Cys Val Val
850         855             860 ttc ggc aag atc gct ggt gac aga gct gca acc atc ttg caa aag aaa 2640
Phe Gly Lys Ile Ala Gly Asp Arg Ala Ala Thr Ile Leu Gln Lys Lys
865         870             875             880 aac acc ggc tta tca atg aca gaa tgg tct act gtc gtc tta aga gaa 2688
Asn Thr Gly Leu Ser Met Thr Glu Trp Ser Thr Val Val Leu Arg Glu
            885             890             895 gtt aga gaa ggt ggt gtc tat ggt gct ggt tcc aga gtt ttg agg ttt 2736
Val Arg Glu Gly Gly Val Tyr Gly Ala Gly Ser Arg Val Leu Arg Phe
        900             905             910 aac atg cct ggt gca tta cag aga act ggt tta gct tta ggt caa ttc 2784
Asn Met Pro Gly Ala Leu Gln Arg Thr Gly Leu Ala Leu Gly Gln Phe
        915             920             925 atc ggt atc aga ggt gat tgg gac ggt cac aga ttg atc ggt tac tat 2832
Ile Gly Ile Arg Gly Asp Trp Asp Gly His Arg Leu Ile Gly Tyr Tyr
930         935             940 tct cca atc act tta cct gat gat gtt ggt gtt att ggt atc tta gct 2880
Ser Pro Ile Thr Leu Pro Asp Asp Val Gly Val Ile Gly Ile Leu Ala
945         950             955             960 aga gca gac aag ggt aga ttg gca gaa tgg att tct gca ttg cag cca 2928
Arg Ala Asp Lys Gly Arg Leu Ala Glu Trp Ile Ser Ala Leu Gln Pro
        965             970             975 ggt gac gct gtt gag atg aag gcc tgc ggt ggt ctt atc att gac aga 2976
Gly Asp Ala Val Glu Met Lys Ala Cys Gly Gly Leu Ile Ile Asp Arg

```
aga ttc gct gaa aga cat ttc ttt ttc cgt ggt cat aag atc aga aag    3024
Arg Phe Ala Glu Arg His Phe Phe Phe Arg Gly His Lys Ile Arg Lys
            995                 1000                1005 ttg gcc ctt atc ggt ggt ggt act ggt gtt gca cca atg tta caa        3069
Leu Ala Leu Ile Gly Gly Gly Thr Gly Val Ala Pro Met Leu Gln
    1010                1015                1020 atc gtc aga gct gct gtc aaa aag cca ttt gtc gat tca att gag        3114
Ile Val Arg Ala Ala Val Lys Lys Pro Phe Val Asp Ser Ile Glu
    1025                1030                1035 tcc att cag ttc atc tat gct gca gag gat gtt tcc gag ctt aca        3159
Ser Ile Gln Phe Ile Tyr Ala Ala Glu Asp Val Ser Glu Leu Thr
    1040                1045                1050 tac aga acc tta ctt gaa tct tac gaa gag gaa tat ggt tca gaa        3204
Tyr Arg Thr Leu Leu Glu Ser Tyr Glu Glu Glu Tyr Gly Ser Glu
    1055                1060                1065 aag ttt aag tgt cac ttc gtt ttg aat aac cca cca gct caa tgg        3249
Lys Phe Lys Cys His Phe Val Leu Asn Asn Pro Pro Ala Gln Trp
    1070                1075                1080 act gac ggt gtt ggt ttc gtt gat act gca ttg ttg aga tcc gca        3294
Thr Asp Gly Val Gly Phe Val Asp Thr Ala Leu Leu Arg Ser Ala
    1085                1090                1095 gtt caa gca cca tca aat gat ttg ctt gtt gca att tgt ggt cca        3339
Val Gln Ala Pro Ser Asn Asp Leu Leu Val Ala Ile Cys Gly Pro
    1100                1105                1110 cca atc atg caa aga gca gtt aag ggt gca ttg aaa ggt tta ggt        3384
Pro Ile Met Gln Arg Ala Val Lys Gly Ala Leu Lys Gly Leu Gly
    1115                1120                1125 tac aat atg aat ctt gtt aga acc gtt gac gaa act gaa cca cca        3429
Tyr Asn Met Asn Leu Val Arg Thr Val Asp Glu Thr Glu Pro Pro
    1130                1135                1140 tca taa                                                            3435
Ser

<210> SEQ ID NO 44
<211> LENGTH: 1144
<212> TYPE: PRT
<213> ORGANISM: Leishmania mexicana

<400> SEQUENCE: 44

Met Ala Asp Gly Lys Thr Ser Ala Ser Val Val Ala Val Asp Ala Glu
1               5                   10                  15

Arg Ala Ala Lys Glu Arg Asp Ala Ala Ala Arg Ala Met Leu Gln Gly
            20                  25                  30

Gly Gly Val Ser Pro Ala Gly Lys Ala Gln Leu Leu Lys Lys Gly Leu
        35                  40                  45

Val His Thr Val Pro Tyr Thr Leu Lys Val Val Val Ala Asp Pro Lys
    50                  55                  60

Glu Met Glu Lys Ala Thr Ala Asp Ala Glu Glu Val Leu Gln Ala Ala
65                  70                  75                  80

Phe Gln Val Val Asp Thr Leu Leu Asn Asn Phe Asn Glu Asn Ser Glu
                85                  90                  95

Val Ser Arg Val Asn Arg Leu Ala Val Gly Glu Glu His Gln Met Ser
            100                 105                 110

Glu Thr Leu Lys His Val Met Ala Cys Cys Gln Lys Val Tyr His Ser
        115                 120                 125

Ser Arg Gly Val Phe Asp Pro Ala Val Gly Pro Leu Val Arg Glu Leu
    130                 135                 140
```

-continued

```
Arg Glu Ala Ala His Lys Gly Lys Thr Val Pro Ala Glu Arg Val Asn
145                 150                 155                 160

Asp Leu Leu Ser Lys Cys Thr Leu Asn Ala Ser Phe Ser Ile Asp Met
            165                 170                 175

Ser Arg Gly Met Ile Ala Arg Lys His Pro Asp Ala Met Leu Asp Leu
        180                 185                 190

Gly Gly Val Asn Lys Gly Tyr Gly Ile Asp Tyr Ile Val Glu His Leu
    195                 200                 205

Asn Ser Leu Gly Tyr Asp Asp Val Phe Phe Glu Trp Gly Gly Asp Val
210                 215                 220

Arg Ala Ser Gly Lys Asn Gln Leu Ser Gln Pro Trp Ala Val Gly Ile
225                 230                 235                 240

Val Arg Pro Pro Ala Leu Ala Asp Ile Arg Thr Val Val Pro Glu Asp
            245                 250                 255

Lys Arg Ser Phe Ile Arg Val Val Arg Leu Asn Asn Glu Ala Ile Ala
        260                 265                 270

Thr Ser Gly Asp Tyr Glu Asn Leu Val Glu Gly Pro Gly Ser Lys Val
    275                 280                 285

Tyr Ser Ser Thr Phe Asn Pro Thr Ser Lys Asn Leu Leu Glu Pro Thr
290                 295                 300

Glu Ala Gly Met Ala Gln Val Ser Val Lys Cys Cys Ser Cys Ile Tyr
305                 310                 315                 320

Ala Asp Ala Leu Ala Thr Ala Ala Leu Leu Lys Asn Asp Pro Ala Ala
            325                 330                 335

Val Arg Arg Ile Leu Asp Asn Trp Arg Tyr Val Arg Asp Thr Val Thr
        340                 345                 350

Asp Tyr Thr Thr Tyr Thr Arg Glu Gly Glu Arg Val Ala Lys Met Leu
    355                 360                 365

Glu Ile Ala Thr Glu Asp Ala Glu Met Arg Ala Lys Arg Ile Lys Gly
370                 375                 380

Ser Leu Pro Ala Arg Val Ile Val Gly Gly Gly Leu Ala Gly Cys
385                 390                 395                 400

Ser Ala Ala Ile Glu Ala Ala Asn Cys Gly Ala His Val Ile Leu Leu
            405                 410                 415

Glu Lys Glu Pro Lys Leu Gly Gly Asn Ser Ala Lys Ala Thr Ser Gly
        420                 425                 430

Ile Asn Ala Trp Gly Thr Arg Ala Gln Ala Lys Gln Gly Val Met Asp
    435                 440                 445

Gly Gly Lys Phe Phe Glu Arg Asp Thr His Arg Ser Gly Lys Gly Gly
450                 455                 460

Asn Cys Asp Pro Cys Leu Val Lys Thr Leu Ser Val Lys Ser Ser Asp
465                 470                 475                 480

Ala Val Lys Trp Leu Ser Glu Leu Gly Val Pro Leu Thr Val Leu Ser
            485                 490                 495

Gln Leu Gly Gly Ala Ser Arg Lys Arg Cys His Arg Ala Pro Asp Lys
        500                 505                 510

Ser Asp Gly Thr Pro Val Pro Val Gly Phe Thr Ile Met Lys Thr Leu
    515                 520                 525

Glu Asn His Ile Val Asn Asp Leu Ser Arg His Val Thr Val Met Thr
530                 535                 540

Gly Ile Thr Val Thr Ala Leu Glu Ser Thr Ser Arg Val Arg Pro Asp
545                 550                 555                 560
```

-continued

```
Gly Val Leu Val Lys His Val Thr Gly Val His Leu Ile Gln Ala Ser
            565                 570                 575
Gly Gln Ser Met Val Leu Asn Ala Asp Ala Val Ile Leu Ala Thr Gly
        580                 585                 590
Gly Phe Ser Asn Asp His Thr Pro Asn Ser Leu Leu Gln Gln Tyr Ala
    595                 600                 605
Pro Gln Leu Ser Ser Phe Pro Thr Thr Asn Gly Val Trp Ala Thr Gly
610                 615                 620
Asp Gly Val Lys Met Ala Ser Lys Leu Gly Val Ala Leu Val Asp Met
625                 630                 635                 640
Asp Lys Val Gln Leu His Pro Thr Gly Leu Leu Asp Pro Lys Asp Pro
                645                 650                 655
Ser Asn Arg Thr Lys Tyr Leu Gly Pro Glu Ala Leu Arg Gly Ser Gly
            660                 665                 670
Gly Val Leu Leu Asn Lys Asn Gly Glu Arg Phe Val Asn Glu Leu Asp
        675                 680                 685
Leu Arg Ser Val Val Ser Gln Ala Ile Ile Ala Gln Asp Asn Glu Tyr
    690                 695                 700
Pro Gly Ser Gly Gly Ser Lys Phe Ala Tyr Cys Val Leu Asn Glu Thr
705                 710                 715                 720
Ala Ala Lys Leu Phe Gly Lys Asn Phe Leu Gly Phe Tyr Trp Asn Arg
                725                 730                 735
Leu Gly Leu Phe Gln Lys Val Asp Ser Val Ala Gly Leu Ala Lys Leu
            740                 745                 750
Ile Gly Cys Pro Glu Ala Asn Val Val Ala Thr Leu Lys Gln Tyr Glu
        755                 760                 765
Glu Leu Ser Ser Lys Lys Leu Asn Pro Cys Pro Leu Thr Gly Lys Ser
    770                 775                 780
Val Phe Pro Cys Val Leu Gly Thr Gln Gly Pro Tyr Tyr Val Ala Leu
785                 790                 795                 800
Val Thr Pro Ser Ile His Tyr Thr Met Gly Gly Cys Leu Ile Ser Pro
                805                 810                 815
Ser Ala Glu Met Gln Thr Ile Asp Asn Ser Gly Val Thr Pro Val Arg
            820                 825                 830
Arg Pro Ile Leu Gly Leu Phe Gly Ala Gly Glu Val Thr Gly Gly Val
        835                 840                 845
His Gly Gly Asn Arg Leu Gly Gly Asn Ser Leu Leu Glu Cys Val Val
    850                 855                 860
Phe Gly Lys Ile Ala Gly Asp Arg Ala Ala Thr Ile Leu Gln Lys Lys
865                 870                 875                 880
Asn Thr Gly Leu Ser Met Thr Glu Trp Ser Thr Val Val Leu Arg Glu
                885                 890                 895
Val Arg Glu Gly Gly Val Tyr Gly Ala Gly Ser Arg Val Leu Arg Phe
            900                 905                 910
Asn Met Pro Gly Ala Leu Gln Arg Thr Gly Leu Ala Leu Gly Gln Phe
        915                 920                 925
Ile Gly Ile Arg Gly Asp Trp Asp Gly His Arg Leu Ile Gly Tyr Tyr
    930                 935                 940
Ser Pro Ile Thr Leu Pro Asp Asp Val Gly Val Gly Ile Leu Ala
945                 950                 955                 960
Arg Ala Asp Lys Gly Arg Leu Ala Glu Trp Ile Ser Ala Leu Gln Pro
                965                 970                 975
Gly Asp Ala Val Glu Met Lys Ala Cys Gly Gly Leu Ile Ile Asp Arg
```

```
                    980             985                 990
Arg Phe Ala Glu Arg His Phe Phe  Phe Arg Gly His Lys  Ile Arg Lys
            995                 1000                1005

Leu Ala  Leu Ile Gly Gly  Gly  Thr Gly Val Ala  Pro  Met Leu Gln
    1010                 1015                1020

Ile Val  Arg Ala Ala Val  Lys  Lys Pro Phe Val  Asp  Ser Ile Glu
    1025                 1030                1035

Ser Ile  Gln Phe Ile Tyr  Ala  Ala Glu Asp Val  Ser  Glu Leu Thr
    1040                 1045                1050

Tyr Arg  Thr Leu Leu Glu  Ser  Tyr Glu Glu Tyr  Gly  Ser Glu
    1055                 1060                1065

Lys Phe  Lys Cys His Phe  Val  Leu Asn Asn Pro  Pro  Ala Gln Trp
    1070                 1075                1080

Thr Asp  Gly Val Gly Phe  Val  Asp Thr Ala Leu  Leu  Arg Ser Ala
    1085                 1090                1095

Val Gln  Ala Pro Ser Asn  Asp  Leu Leu Val Ala  Ile  Cys Gly Pro
    1100                 1105                1110

Pro Ile  Met Gln Arg Ala  Val  Lys Gly Ala Leu  Lys  Gly Leu Gly
    1115                 1120                1125

Tyr Asn  Met Asn Leu Val  Arg  Thr Val Asp Glu  Thr  Glu Pro Pro
    1130                 1135                1140

Ser

<210> SEQ ID NO 45
<211> LENGTH: 1317
<212> TYPE: DNA
<213> ORGANISM: Schizosaccharomyces pombe
<220> FEATURE:
<221> NAME/KEY: CDS
<222> LOCATION: (1)..(1317)

<400> SEQUENCE: 45 atg ggt gaa ttg aaa gag att ttg aaa caa aga tat cat gaa tta ctt      48
Met Gly Glu Leu Lys Glu Ile Leu Lys Gln Arg Tyr His Glu Leu Leu
1               5                   10                  15 gat tgg aat gtt aag gca cca cat gtc cct tta tcc cag aga ttg aag      96
Asp Trp Asn Val Lys Ala Pro His Val Pro Leu Ser Gln Arg Leu Lys
            20                  25                  30 cac ttt act tgg tca tgg ttt gct tgt act atg gca acc ggt ggt gtt     144
His Phe Thr Trp Ser Trp Phe Ala Cys Thr Met Ala Thr Gly Gly Val
        35                  40                  45 ggt ttg atc att ggt tcc ttc cca ttc aga ttc tac ggt ttg aac acc     192
Gly Leu Ile Ile Gly Ser Phe Pro Phe Arg Phe Tyr Gly Leu Asn Thr
    50                  55                  60 att ggc aag att gtt tac atc tta caa atc ttt ttg ttt tct ctt ttt     240
Ile Gly Lys Ile Val Tyr Ile Leu Gln Ile Phe Leu Phe Ser Leu Phe
65                  70                  75                  80 ggc tct tgt atg ttg ttt cgt ttc atc aag tat cca tct acc att aag     288
Gly Ser Cys Met Leu Phe Arg Phe Ile Lys Tyr Pro Ser Thr Ile Lys
                85                  90                  95 gac tct tgg aat cat cac ttg gaa aag ttg ttt atc gca act tgt ttg     336
Asp Ser Trp Asn His His Leu Glu Lys Leu Phe Ile Ala Thr Cys Leu
            100                 105                 110 tta tct att tcc aca ttc atc gac atg tta gct atc tat gct tat cca     384
Leu Ser Ile Ser Thr Phe Ile Asp Met Leu Ala Ile Tyr Ala Tyr Pro
        115                 120                 125 gat acc ggt gaa tgg atg gtc tgg gtc att aga atc tta tac tac atc     432
Asp Thr Gly Glu Trp Met Val Trp Val Ile Arg Ile Leu Tyr Tyr Ile
```

```
                130                 135                 140
tat gtc gct gtc tct ttc atc tac tgt gtt atg gcc ttt ttc acc att         480
Tyr Val Ala Val Ser Phe Ile Tyr Cys Val Met Ala Phe Phe Thr Ile
145                 150                 155                 160 ttc aac aat cat gtt tac act att gaa act gct tct cca gct tgg att         528
Phe Asn Asn His Val Tyr Thr Ile Glu Thr Ala Ser Pro Ala Trp Ile
                165                 170                 175 ttg cca atc ttc cct cca atg atc tgt ggt gtc att gct ggt gct gtt         576
Leu Pro Ile Phe Pro Pro Met Ile Cys Gly Val Ile Ala Gly Ala Val
            180                 185                 190 aac tcc acc caa cct gct cac caa ttg aaa aac atg gtc att ttc ggt         624
Asn Ser Thr Gln Pro Ala His Gln Leu Lys Asn Met Val Ile Phe Gly
        195                 200                 205 atc ttg ttt caa ggt tta ggt ttt tgg gtt tac ctt tta ctt ttc gcc         672
Ile Leu Phe Gln Gly Leu Gly Phe Trp Val Tyr Leu Leu Leu Phe Ala
    210                 215                 220 gtt aat gtt ttg aga ttc ttc aca gtc ggt tta gca aag cca caa gat         720
Val Asn Val Leu Arg Phe Phe Thr Val Gly Leu Ala Lys Pro Gln Asp
225                 230                 235                 240 aga cca ggt atg ttt atg ttc gtt ggt cca cca gct ttc tct ggt tta         768
Arg Pro Gly Met Phe Met Phe Val Gly Pro Pro Ala Phe Ser Gly Leu
                245                 250                 255 gca ttg att aac att gca aga ggt gca atg ggc tca aga cct tac att         816
Ala Leu Ile Asn Ile Ala Arg Gly Ala Met Gly Ser Arg Pro Tyr Ile
            260                 265                 270 ttc gtt ggt gca aac tct tcc gaa tac tta ggt ttt gtc tca acc ttc         864
Phe Val Gly Ala Asn Ser Ser Glu Tyr Leu Gly Phe Val Ser Thr Phe
        275                 280                 285 atg gcc att ttc atc tgg ggt tta gcc gca tgg tgt tat tgc tta gct         912
Met Ala Ile Phe Ile Trp Gly Leu Ala Ala Trp Cys Tyr Cys Leu Ala
    290                 295                 300 atg gtt tcc ttc ctt gcc ggc ttt ttc act aga gca cca ttg aaa ttc         960
Met Val Ser Phe Leu Ala Gly Phe Phe Thr Arg Ala Pro Leu Lys Phe
305                 310                 315                 320 gct tgt ggt tgg ttc gct ttc atc ttt cca aat gtt ggt ttt gtt aac        1008
Ala Cys Gly Trp Phe Ala Phe Ile Phe Pro Asn Val Gly Phe Val Asn
                325                 330                 335 tgt act atc gaa atc ggc aag atg att gat tct aag gct ttt caa atg        1056
Cys Thr Ile Glu Ile Gly Lys Met Ile Asp Ser Lys Ala Phe Gln Met
            340                 345                 350 ttt ggt cac atc att ggt gtt atc ttg tgt att caa tgg att ttg tta        1104
Phe Gly His Ile Ile Gly Val Ile Leu Cys Ile Gln Trp Ile Leu Leu
        355                 360                 365 atg tac tta atg gtt aga gca ttc ctt gtt aat gac ttg tgc tat cct        1152
Met Tyr Leu Met Val Arg Ala Phe Leu Val Asn Asp Leu Cys Tyr Pro
    370                 375                 380 ggt aaa gac gaa gat gca cac cca cca cca aag cca aac act ggt gtc        1200
Gly Lys Asp Glu Asp Ala His Pro Pro Pro Lys Pro Asn Thr Gly Val
385                 390                 395                 400 tta aac cca act ttc cca cca gag aag gct cca gca tca tta gag aag        1248
Leu Asn Pro Thr Phe Pro Pro Glu Lys Ala Pro Ala Ser Leu Glu Lys
                405                 410                 415 gtt gat act cat gtt aca tca aca ggt ggt gaa tcc gat cct cca tct        1296
Val Asp Thr His Val Thr Ser Thr Gly Gly Glu Ser Asp Pro Pro Ser
            420                 425                 430 tcc gaa cat gaa tcc gtt taa                                            1317
Ser Glu His Glu Ser Val
        435
```

```
<210> SEQ ID NO 46
<211> LENGTH: 438
<212> TYPE: PRT
<213> ORGANISM: Schizosaccharomyces pombe

<400> SEQUENCE: 46
```

| | | | | | | | | | | | | | | | |
|---|---|---|---|---|---|---|---|---|---|---|---|---|---|---|---|
| Met | Gly | Glu | Leu | Lys | Glu | Ile | Leu | Lys | Gln | Arg | Tyr | His | Glu | Leu | Leu |
| 1 | | | | 5 | | | | | 10 | | | | | 15 | |
| Asp | Trp | Asn | Val | Lys | Ala | Pro | His | Val | Pro | Leu | Ser | Gln | Arg | Leu | Lys |
| | | | 20 | | | | | 25 | | | | | 30 | | |
| His | Phe | Thr | Trp | Ser | Trp | Phe | Ala | Cys | Thr | Met | Ala | Thr | Gly | Gly | Val |
| | | 35 | | | | | 40 | | | | | 45 | | | |
| Gly | Leu | Ile | Ile | Gly | Ser | Phe | Pro | Phe | Arg | Phe | Tyr | Gly | Leu | Asn | Thr |
| | 50 | | | | | 55 | | | | | 60 | | | | |
| Ile | Gly | Lys | Ile | Val | Tyr | Ile | Leu | Gln | Ile | Phe | Leu | Phe | Ser | Leu | Phe |
| 65 | | | | | 70 | | | | | 75 | | | | | 80 |
| Gly | Ser | Cys | Met | Leu | Phe | Arg | Phe | Ile | Lys | Tyr | Pro | Ser | Thr | Ile | Lys |
| | | | | 85 | | | | | 90 | | | | | 95 | |
| Asp | Ser | Trp | Asn | His | His | Leu | Glu | Lys | Leu | Phe | Ile | Ala | Thr | Cys | Leu |
| | | | 100 | | | | | 105 | | | | | 110 | | |
| Leu | Ser | Ile | Ser | Thr | Phe | Ile | Asp | Met | Leu | Ala | Ile | Tyr | Ala | Tyr | Pro |
| | | | 115 | | | | | 120 | | | | | 125 | | |
| Asp | Thr | Gly | Glu | Trp | Met | Val | Trp | Val | Ile | Arg | Ile | Leu | Tyr | Tyr | Ile |
| | 130 | | | | | 135 | | | | | 140 | | | | |
| Tyr | Val | Ala | Val | Ser | Phe | Ile | Tyr | Cys | Val | Met | Ala | Phe | Phe | Thr | Ile |
| 145 | | | | | 150 | | | | | 155 | | | | | 160 |
| Phe | Asn | Asn | His | Val | Tyr | Thr | Ile | Glu | Thr | Ala | Ser | Pro | Ala | Trp | Ile |
| | | | | 165 | | | | | 170 | | | | | 175 | |
| Leu | Pro | Ile | Phe | Pro | Pro | Met | Ile | Cys | Gly | Val | Ile | Ala | Gly | Ala | Val |
| | | | 180 | | | | | 185 | | | | | 190 | | |
| Asn | Ser | Thr | Gln | Pro | Ala | His | Gln | Leu | Lys | Asn | Met | Val | Ile | Phe | Gly |
| | | | 195 | | | | | 200 | | | | | 205 | | |
| Ile | Leu | Phe | Gln | Gly | Leu | Gly | Phe | Trp | Val | Tyr | Leu | Leu | Leu | Phe | Ala |
| | 210 | | | | | 215 | | | | | 220 | | | | |
| Val | Asn | Val | Leu | Arg | Phe | Phe | Thr | Val | Gly | Leu | Ala | Lys | Pro | Gln | Asp |
| 225 | | | | | 230 | | | | | 235 | | | | | 240 |
| Arg | Pro | Gly | Met | Phe | Met | Phe | Val | Gly | Pro | Pro | Ala | Phe | Ser | Gly | Leu |
| | | | | 245 | | | | | 250 | | | | | 255 | |
| Ala | Leu | Ile | Asn | Ile | Ala | Arg | Gly | Ala | Met | Gly | Ser | Arg | Pro | Tyr | Ile |
| | | | 260 | | | | | 265 | | | | | 270 | | |
| Phe | Val | Gly | Ala | Asn | Ser | Ser | Glu | Tyr | Leu | Gly | Phe | Val | Ser | Thr | Phe |
| | | | 275 | | | | | 280 | | | | | 285 | | |
| Met | Ala | Ile | Phe | Ile | Trp | Gly | Leu | Ala | Ala | Trp | Cys | Tyr | Cys | Leu | Ala |
| | 290 | | | | | 295 | | | | | 300 | | | | |
| Met | Val | Ser | Phe | Leu | Ala | Gly | Phe | Phe | Thr | Arg | Ala | Pro | Leu | Lys | Phe |
| 305 | | | | | 310 | | | | | 315 | | | | | 320 |
| Ala | Cys | Gly | Trp | Phe | Ala | Phe | Ile | Phe | Pro | Asn | Val | Gly | Phe | Val | Asn |
| | | | | 325 | | | | | 330 | | | | | 335 | |
| Cys | Thr | Ile | Glu | Ile | Gly | Lys | Met | Ile | Asp | Ser | Lys | Ala | Phe | Gln | Met |
| | | | 340 | | | | | 345 | | | | | 350 | | |
| Phe | Gly | His | Ile | Ile | Gly | Val | Ile | Leu | Cys | Ile | Gln | Trp | Ile | Leu | Leu |
| | | | 355 | | | | | 360 | | | | | 365 | | |
| Met | Tyr | Leu | Met | Val | Arg | Ala | Phe | Leu | Val | Asn | Asp | Leu | Cys | Tyr | Pro |
| | 370 | | | | | 375 | | | | | 380 | | | | |

```
Gly Lys Asp Glu Asp Ala His Pro Pro Lys Pro Asn Thr Gly Val
385                 390                 395                 400

Leu Asn Pro Thr Phe Pro Pro Glu Lys Ala Pro Ala Ser Leu Glu Lys
                405                 410                 415

Val Asp Thr His Val Thr Ser Thr Gly Gly Glu Ser Asp Pro Pro Ser
                420                 425                 430

Ser Glu His Glu Ser Val
        435

<210> SEQ ID NO 47
<211> LENGTH: 1205
<212> TYPE: DNA
<213> ORGANISM: Aspergillus oryzae
<220> FEATURE:
<221> NAME/KEY: CDS
<222> LOCATION: (1)..(1197)

<400> SEQUENCE: 47
```

| | | | | | | | | | | | | | | | | |
|---|---|---|---|---|---|---|---|---|---|---|---|---|---|---|---|---|
| atg ttt aac aat gag cac cat att cct cct ggt tcc tct cac tct gat | | | | | | | | | | | | | | | | 48 |
| Met Phe Asn Asn Glu His His Ile Pro Pro Gly Ser Ser His Ser Asp | | | | | | | | | | | | | | | | |
| 1 | | | 5 | | | | | 10 | | | | | 15 | | | |
| atc gaa atg tta aca cca cca aag ttt gag gat gaa aaa cag tta ggt | | | | | | | | | | | | | | | | 96 |
| Ile Glu Met Leu Thr Pro Pro Lys Phe Glu Asp Glu Lys Gln Leu Gly | | | | | | | | | | | | | | | | |
| | | 20 | | | | | 25 | | | | | 30 | | | | |
| cca gtc ggt att aga gaa aga ttg aga cat ttc act tgg gct tgg tat | | | | | | | | | | | | | | | | 144 |
| Pro Val Gly Ile Arg Glu Arg Leu Arg His Phe Thr Trp Ala Trp Tyr | | | | | | | | | | | | | | | | |
| | 35 | | | | | 40 | | | | | 45 | | | | | |
| acc tta acc atg tcc ggt ggt ggt ttg gca gtt ttg att atc tct cag | | | | | | | | | | | | | | | | 192 |
| Thr Leu Thr Met Ser Gly Gly Gly Leu Ala Val Leu Ile Ile Ser Gln | | | | | | | | | | | | | | | | |
| 50 | | | | | 55 | | | | | 60 | | | | | | |
| cca ttc ggt ttt aga ggt tta aga gaa att ggt att gca gtt tac att | | | | | | | | | | | | | | | | 240 |
| Pro Phe Gly Phe Arg Gly Leu Arg Glu Ile Gly Ile Ala Val Tyr Ile | | | | | | | | | | | | | | | | |
| 65 | | | | 70 | | | | | 75 | | | | | 80 | | |
| ttg aac tta atc tta ttc gct ttg gtt tgt tct acc atg gct att cgt | | | | | | | | | | | | | | | | 288 |
| Leu Asn Leu Ile Leu Phe Ala Leu Val Cys Ser Thr Met Ala Ile Arg | | | | | | | | | | | | | | | | |
| | | | | 85 | | | | | 90 | | | | | 95 | | |
| ttc atc ttg cac ggt aac ctt ttg gaa tcc ctt aga cat gac aga gaa | | | | | | | | | | | | | | | | 336 |
| Phe Ile Leu His Gly Asn Leu Leu Glu Ser Leu Arg His Asp Arg Glu | | | | | | | | | | | | | | | | |
| | | | 100 | | | | | 105 | | | | | 110 | | | |
| ggt ttg ttt ttc cct act ttc tgg ttg tct gtt gct acc atc att tgt | | | | | | | | | | | | | | | | 384 |
| Gly Leu Phe Phe Pro Thr Phe Trp Leu Ser Val Ala Thr Ile Ile Cys | | | | | | | | | | | | | | | | |
| | | 115 | | | | | 120 | | | | | 125 | | | | |
| ggt ttg tca aga tac ttt ggt gag gaa tcc aac gaa tcc ttc caa ttg | | | | | | | | | | | | | | | | 432 |
| Gly Leu Ser Arg Tyr Phe Gly Glu Glu Ser Asn Glu Ser Phe Gln Leu | | | | | | | | | | | | | | | | |
| | 130 | | | | | 135 | | | | | 140 | | | | | |
| gca tta gaa gcc ttg ttc tgg atc tat tgc gtt tgt acc ttg ttg gtt | | | | | | | | | | | | | | | | 480 |
| Ala Leu Glu Ala Leu Phe Trp Ile Tyr Cys Val Cys Thr Leu Leu Val | | | | | | | | | | | | | | | | |
| 145 | | | | | 150 | | | | | 155 | | | | | 160 | |
| gca atc att caa tac tct ttt gtt ttc tca tcc cac aag tac ggt tta | | | | | | | | | | | | | | | | 528 |
| Ala Ile Ile Gln Tyr Ser Phe Val Phe Ser Ser His Lys Tyr Gly Leu | | | | | | | | | | | | | | | | |
| | | | | 165 | | | | | 170 | | | | | 175 | | |
| caa aca atg atg cca tct tgg att ttg cca gcc ttt cct atc atg ttg | | | | | | | | | | | | | | | | 576 |
| Gln Thr Met Met Pro Ser Trp Ile Leu Pro Ala Phe Pro Ile Met Leu | | | | | | | | | | | | | | | | |
| | | | 180 | | | | | 185 | | | | | 190 | | | |
| tca ggc aca att gca tct gtt atc ggt gaa caa caa cca gcc aga gct | | | | | | | | | | | | | | | | 624 |
| Ser Gly Thr Ile Ala Ser Val Ile Gly Glu Gln Gln Pro Ala Arg Ala | | | | | | | | | | | | | | | | |
| | | 195 | | | | | 200 | | | | | 205 | | | | |
| gca tta cca atc att ggt gcc ggt gtc acc ttc caa ggt tta ggt ttt | | | | | | | | | | | | | | | | 672 |
| Ala Leu Pro Ile Ile Gly Ala Gly Val Thr Phe Gln Gly Leu Gly Phe | | | | | | | | | | | | | | | | |
| | 210 | | | | | 215 | | | | | 220 | | | | | |

```
tct att tcc ttc atg atg tat gct cat tac att ggc aga ctt atg gaa    720
Ser Ile Ser Phe Met Met Tyr Ala His Tyr Ile Gly Arg Leu Met Glu
225                 230                 235                 240 tcc ggt tta cct cac tcc gac cat aga cca ggc atg ttc atc tgt gtt    768
Ser Gly Leu Pro His Ser Asp His Arg Pro Gly Met Phe Ile Cys Val
            245                 250                 255 ggc cca cca gcc ttt act gct ttg gct tta gtc ggt atg tcc aag ggt    816
Gly Pro Pro Ala Phe Thr Ala Leu Ala Leu Val Gly Met Ser Lys Gly
        260                 265                 270 tta cca gaa gat ttc aag ctt tta cat gac gct cat gca tta gag gat    864
Leu Pro Glu Asp Phe Lys Leu Leu His Asp Ala His Ala Leu Glu Asp
    275                 280                 285 ggt aga atc att gaa ttg tta gca att tca gca ggt gtt ttc ctt tgg    912
Gly Arg Ile Ile Glu Leu Leu Ala Ile Ser Ala Gly Val Phe Leu Trp
290                 295                 300 gca tta tcc ctt tgg ttt ttc tgt att gct att gtc gct gtc att aga    960
Ala Leu Ser Leu Trp Phe Phe Cys Ile Ala Ile Val Ala Val Ile Arg
305                 310                 315                 320 tct cca cca gaa gct ttc cac ttg aac tgg tgg gct atg gtt ttc cca    1008
Ser Pro Pro Glu Ala Phe His Leu Asn Trp Trp Ala Met Val Phe Pro
            325                 330                 335 aat act ggt ttc acc tta gct act atc act ttg ggt aaa gct ttg aac    1056
Asn Thr Gly Phe Thr Leu Ala Thr Ile Thr Leu Gly Lys Ala Leu Asn
        340                 345                 350 tca aat ggt gtc aag ggt gtc ggt tct gca atg tcc att tgt att gtc    1104
Ser Asn Gly Val Lys Gly Val Gly Ser Ala Met Ser Ile Cys Ile Val
    355                 360                 365 tgc atg tac atc ttt gtt ttc gtt aac aat gtt aga gct gtt att cgt    1152
Cys Met Tyr Ile Phe Val Phe Val Asn Asn Val Arg Ala Val Ile Arg
370                 375                 380 aag gat atc atg tat cca ggc aaa gat gag gat gtt tct gat taa        1197
Lys Asp Ile Met Tyr Pro Gly Lys Asp Glu Asp Val Ser Asp
385                 390                 395 cctgcagg                                                           1205
```

<210> SEQ ID NO 48
<211> LENGTH: 398
<212> TYPE: PRT
<213> ORGANISM: Aspergillus oryzae

<400> SEQUENCE: 48

```
Met Phe Asn Asn Glu His His Ile Pro Pro Gly Ser Ser His Ser Asp
1               5                   10                  15

Ile Glu Met Leu Thr Pro Pro Lys Phe Glu Asp Glu Lys Gln Leu Gly
            20                  25                  30

Pro Val Gly Ile Arg Glu Arg Leu Arg His Phe Thr Trp Ala Trp Tyr
        35                  40                  45

Thr Leu Thr Met Ser Gly Gly Leu Ala Val Leu Ile Ile Ser Gln
50                  55                  60

Pro Phe Gly Phe Arg Gly Leu Arg Glu Ile Gly Ile Ala Val Tyr Ile
65                  70                  75                  80

Leu Asn Leu Ile Leu Phe Ala Leu Val Cys Ser Thr Met Ala Ile Arg
                85                  90                  95

Phe Ile Leu His Gly Asn Leu Leu Glu Ser Leu Arg His Asp Arg Glu
            100                 105                 110

Gly Leu Phe Phe Pro Thr Phe Trp Leu Ser Val Ala Thr Ile Ile Cys
        115                 120                 125

Gly Leu Ser Arg Tyr Phe Gly Glu Glu Ser Asn Glu Ser Phe Gln Leu
```

```
              130                 135                 140
Ala Leu Glu Ala Leu Phe Trp Ile Tyr Cys Val Cys Thr Leu Leu Val
145                 150                 155                 160

Ala Ile Ile Gln Tyr Ser Phe Val Phe Ser Ser His Lys Tyr Gly Leu
                165                 170                 175

Gln Thr Met Met Pro Ser Trp Ile Leu Pro Ala Phe Pro Ile Met Leu
            180                 185                 190

Ser Gly Thr Ile Ala Ser Val Ile Gly Glu Gln Gln Pro Ala Arg Ala
        195                 200                 205

Ala Leu Pro Ile Ile Gly Ala Gly Val Thr Phe Gln Gly Leu Gly Phe
    210                 215                 220

Ser Ile Ser Phe Met Met Tyr Ala His Tyr Ile Gly Arg Leu Met Glu
225                 230                 235                 240

Ser Gly Leu Pro His Ser Asp His Arg Pro Gly Met Phe Ile Cys Val
                245                 250                 255

Gly Pro Pro Ala Phe Thr Ala Leu Ala Leu Val Gly Met Ser Lys Gly
            260                 265                 270

Leu Pro Glu Asp Phe Lys Leu Leu His Asp Ala His Ala Leu Glu Asp
        275                 280                 285

Gly Arg Ile Ile Glu Leu Leu Ala Ile Ser Ala Gly Val Phe Leu Trp
    290                 295                 300

Ala Leu Ser Leu Trp Phe Phe Cys Ile Ala Ile Val Ala Val Ile Arg
305                 310                 315                 320

Ser Pro Pro Glu Ala Phe His Leu Asn Trp Trp Ala Met Val Phe Pro
                325                 330                 335

Asn Thr Gly Phe Thr Leu Ala Thr Ile Thr Leu Gly Lys Ala Leu Asn
            340                 345                 350

Ser Asn Gly Val Lys Gly Val Gly Ser Ala Met Ser Ile Cys Ile Val
        355                 360                 365

Cys Met Tyr Ile Phe Val Phe Val Asn Asn Val Arg Ala Val Ile Arg
    370                 375                 380

Lys Asp Ile Met Tyr Pro Gly Lys Asp Glu Asp Val Ser Asp
385                 390                 395

<210> SEQ ID NO 49
<211> LENGTH: 1728
<212> TYPE: DNA
<213> ORGANISM: Issatchenkia orientalis
<220> FEATURE:
<221> NAME/KEY: CDS
<222> LOCATION: (1)..(1728)

<400> SEQUENCE: 49 atg act gac aaa atc tcc cta ggt act tat ctg ttt gaa aag tta aag        48
Met Thr Asp Lys Ile Ser Leu Gly Thr Tyr Leu Phe Glu Lys Leu Lys
1               5                   10                  15 gaa gca ggc tct tat tcc atc ttt ggt gtt cct ggt gat ttc aat ttg        96
Glu Ala Gly Ser Tyr Ser Ile Phe Gly Val Pro Gly Asp Phe Asn Leu
                20                  25                  30 gca ttg ttg gac cac gtc aag gaa gtt gaa ggc att aga tgg gtc ggt       144
Ala Leu Leu Asp His Val Lys Glu Val Glu Gly Ile Arg Trp Val Gly
            35                  40                  45 aac gct aac gag ttg aat gcc ggc tac gaa gct gat ggt tat gca aga       192
Asn Ala Asn Glu Leu Asn Ala Gly Tyr Glu Ala Asp Gly Tyr Ala Arg
        50                  55                  60 atc aat gga ttt gca tcc cta atc acc acc ttt ggt gtc ggt gaa ttg       240
Ile Asn Gly Phe Ala Ser Leu Ile Thr Thr Phe Gly Val Gly Glu Leu
```

```
                65                  70                  75                  80
tct gcc gtc aat gcc att gca ggt tct tat gct gaa cac gtc cca ttg        288
Ser Ala Val Asn Ala Ile Ala Gly Ser Tyr Ala Glu His Val Pro Leu
                    85                  90                  95 atc cat att gtt ggt atg cct tcc ttg tct gct atg aag aac aac ttg        336
Ile His Ile Val Gly Met Pro Ser Leu Ser Ala Met Lys Asn Asn Leu
                    100                 105                 110 ttg tta cac cat acc ttg ggt gac aca aga ttc gac aac ttc acc gaa        384
Leu Leu His His Thr Leu Gly Asp Thr Arg Phe Asp Asn Phe Thr Glu
                    115                 120                 125 atg tca aag aaa atc agt gca aag gtt gaa att gtt tac gat ttg gaa        432
Met Ser Lys Lys Ile Ser Ala Lys Val Glu Ile Val Tyr Asp Leu Glu
        130                 135                 140 tca gct cca aaa tta att aat aac ttg att gaa acc gct tat cac aca        480
Ser Ala Pro Lys Leu Ile Asn Asn Leu Ile Glu Thr Ala Tyr His Thr
145                 150                 155                 160 aag aga cca gtc tac ttg gga ctt cct tcc aac ttt gct gat gaa ttg        528
Lys Arg Pro Val Tyr Leu Gly Leu Pro Ser Asn Phe Ala Asp Glu Leu
                    165                 170                 175 gtt cca gcg gca tta gtt aag gaa aac aag tta cat tta gaa gaa cct        576
Val Pro Ala Ala Leu Val Lys Glu Asn Lys Leu His Leu Glu Glu Pro
                180                 185                 190 cta aac aac ccc gtt gct gaa gaa gaa ttc att cat aac gtt gtt gaa        624
Leu Asn Asn Pro Val Ala Glu Glu Glu Phe Ile His Asn Val Val Glu
            195                 200                 205 atg gtc aag aag gca gaa aaa cca atc att ctc gtt gac gct tgt gct        672
Met Val Lys Lys Ala Glu Lys Pro Ile Ile Leu Val Asp Ala Cys Ala
        210                 215                 220 gca aga cat aac att tct aag gaa gtg aga gag ttg gct aaa ttg act        720
Ala Arg His Asn Ile Ser Lys Glu Val Arg Glu Leu Ala Lys Leu Thr
225                 230                 235                 240 aaa ttc cct gtc ttc acc acc cca atg ggt aaa tct act gtt gat gaa        768
Lys Phe Pro Val Phe Thr Thr Pro Met Gly Lys Ser Thr Val Asp Glu
                    245                 250                 255 gat gat gaa gaa ttc ttt ggc tta tac ttg ggt tct cta tct gct cca        816
Asp Asp Glu Glu Phe Phe Gly Leu Tyr Leu Gly Ser Leu Ser Ala Pro
                260                 265                 270 gat gtt aag gac att gtt ggc cca acc gat tgt atc tta tcc tta ggt        864
Asp Val Lys Asp Ile Val Gly Pro Thr Asp Cys Ile Leu Ser Leu Gly
            275                 280                 285 ggt tta cct tct gat ttc aac acc ggt tcc ttc tca tat ggt tac acc        912
Gly Leu Pro Ser Asp Phe Asn Thr Gly Ser Phe Ser Tyr Gly Tyr Thr
        290                 295                 300 act aag aat gtc gtt gaa ttc cat tcc aac tac tgt aaa ttc aaa tct        960
Thr Lys Asn Val Val Glu Phe His Ser Asn Tyr Cys Lys Phe Lys Ser
305                 310                 315                 320 gca act tat gaa aac ttg atg atg aag ggc gca gtc caa aga ttg atc       1008
Ala Thr Tyr Glu Asn Leu Met Met Lys Gly Ala Val Gln Arg Leu Ile
                    325                 330                 335 agc gaa ttg aag aat att aag tat tcc aat gtc tca act tta tct cca       1056
Ser Glu Leu Lys Asn Ile Lys Tyr Ser Asn Val Ser Thr Leu Ser Pro
                340                 345                 350 cca aaa tct aaa ttt gct tac gaa tct gca aag gtt gct cca gaa ggt       1104
Pro Lys Ser Lys Phe Ala Tyr Glu Ser Ala Lys Val Ala Pro Glu Gly
            355                 360                 365 atc atc act caa gat tac ctg tgg aag aga tta tct tac ttc tta aag       1152
Ile Ile Thr Gln Asp Tyr Leu Trp Lys Arg Leu Ser Tyr Phe Leu Lys
        370                 375                 380 cca aga gat atc att gtc act gaa act ggt act tcc tcc ttt ggt gtc       1200
```

```
Pro Arg Asp Ile Ile Val Thr Glu Thr Gly Thr Ser Ser Phe Gly Val
385                 390                 395                 400 ttg gct acc cac tta cca aga gat tca aag tct atc tcc caa gtc tta      1248
Leu Ala Thr His Leu Pro Arg Asp Ser Lys Ser Ile Ser Gln Val Leu
                405                 410                 415 tgg ggt tcc att ggt ttc tcc tta cca gct gca gtt ggt gct gca ttt      1296
Trp Gly Ser Ile Gly Phe Ser Leu Pro Ala Ala Val Gly Ala Ala Phe
                420                 425                 430 gct gct gaa gat gca cac aaa caa act ggc gaa caa gaa aga aga act      1344
Ala Ala Glu Asp Ala His Lys Gln Thr Gly Glu Gln Glu Arg Arg Thr
                435                 440                 445 gtt ttg ttt att ggt gat ggt tct tta caa ttg act gtc caa tca atc      1392
Val Leu Phe Ile Gly Asp Gly Ser Leu Gln Leu Thr Val Gln Ser Ile
        450                 455                 460 tca gat gct gca aga tgg aac atc aag cca tac atc ttc atc tta aac      1440
Ser Asp Ala Ala Arg Trp Asn Ile Lys Pro Tyr Ile Phe Ile Leu Asn
465                 470                 475                 480 aac aga ggt tac act atc gaa aag ttg atc cac ggt cgt cat gag gac      1488
Asn Arg Gly Tyr Thr Ile Glu Lys Leu Ile His Gly Arg His Glu Asp
                485                 490                 495 tac aac caa att caa cca tgg gat cac caa ttg tta ttg aag ctc ttt      1536
Tyr Asn Gln Ile Gln Pro Trp Asp His Gln Leu Leu Leu Lys Leu Phe
                500                 505                 510 gct gac aag acc caa tat gaa aac cat gtt gtt aaa tcc gct aag gac      1584
Ala Asp Lys Thr Gln Tyr Glu Asn His Val Val Lys Ser Ala Lys Asp
                515                 520                 525 ttg gac gct ttg atg aag gat gaa gca ttc aac aag gaa gat aag att      1632
Leu Asp Ala Leu Met Lys Asp Glu Ala Phe Asn Lys Glu Asp Lys Ile
        530                 535                 540 aga gtc att gaa tta ttc ttg gat gaa ttc gat gct cca gaa atc ttg      1680
Arg Val Ile Glu Leu Phe Leu Asp Glu Phe Asp Ala Pro Glu Ile Leu
545                 550                 555                 560 gtt gct caa gct aaa tta tct gat gaa atc aac tct aaa gcc gct taa      1728
Val Ala Gln Ala Lys Leu Ser Asp Glu Ile Asn Ser Lys Ala Ala
                565                 570                 575

<210> SEQ ID NO 50
<211> LENGTH: 575
<212> TYPE: PRT
<213> ORGANISM: Issatchenkia orientalis

<400> SEQUENCE: 50

Met Thr Asp Lys Ile Ser Leu Gly Thr Tyr Leu Phe Glu Lys Leu Lys
1               5                   10                  15

Glu Ala Gly Ser Tyr Ser Ile Phe Gly Val Pro Gly Asp Phe Asn Leu
            20                  25                  30

Ala Leu Leu Asp His Val Lys Glu Val Glu Gly Ile Arg Trp Val Gly
        35                  40                  45

Asn Ala Asn Glu Leu Asn Ala Gly Tyr Glu Ala Asp Gly Tyr Ala Arg
    50                  55                  60

Ile Asn Gly Phe Ala Ser Leu Ile Thr Thr Phe Gly Val Gly Glu Leu
65                  70                  75                  80

Ser Ala Val Asn Ala Ile Ala Gly Ser Tyr Ala Glu His Val Pro Leu
                85                  90                  95

Ile His Ile Val Gly Met Pro Ser Leu Ser Ala Met Lys Asn Asn Leu
            100                 105                 110

Leu Leu His His Thr Leu Gly Asp Thr Arg Phe Asp Asn Phe Thr Glu
        115                 120                 125
```

-continued

```
Met Ser Lys Lys Ile Ser Ala Lys Val Glu Ile Val Tyr Asp Leu Glu
    130                 135                 140

Ser Ala Pro Lys Leu Ile Asn Asn Leu Ile Glu Thr Ala Tyr His Thr
145                 150                 155                 160

Lys Arg Pro Val Tyr Leu Gly Leu Pro Ser Asn Phe Ala Asp Glu Leu
                165                 170                 175

Val Pro Ala Ala Leu Val Lys Glu Asn Lys Leu His Leu Glu Glu Pro
            180                 185                 190

Leu Asn Asn Pro Val Ala Glu Glu Phe Ile His Asn Val Val Glu
                195                 200                 205

Met Val Lys Lys Ala Glu Lys Pro Ile Ile Leu Val Asp Ala Cys Ala
    210                 215                 220

Ala Arg His Asn Ile Ser Lys Glu Val Arg Glu Leu Ala Lys Leu Thr
225                 230                 235                 240

Lys Phe Pro Val Phe Thr Thr Pro Met Gly Lys Ser Thr Val Asp Glu
                245                 250                 255

Asp Asp Glu Glu Phe Phe Gly Leu Tyr Leu Gly Ser Leu Ser Ala Pro
            260                 265                 270

Asp Val Lys Asp Ile Val Gly Pro Thr Asp Cys Ile Leu Ser Leu Gly
        275                 280                 285

Gly Leu Pro Ser Asp Phe Asn Thr Gly Ser Phe Ser Tyr Gly Tyr Thr
    290                 295                 300

Thr Lys Asn Val Val Glu Phe His Ser Asn Tyr Cys Lys Phe Lys Ser
305                 310                 315                 320

Ala Thr Tyr Glu Asn Leu Met Met Lys Gly Ala Val Gln Arg Leu Ile
                325                 330                 335

Ser Glu Leu Lys Asn Ile Lys Tyr Ser Asn Val Ser Thr Leu Ser Pro
            340                 345                 350

Pro Lys Ser Lys Phe Ala Tyr Glu Ser Ala Lys Val Ala Pro Glu Gly
        355                 360                 365

Ile Ile Thr Gln Asp Tyr Leu Trp Lys Arg Leu Ser Tyr Phe Leu Lys
    370                 375                 380

Pro Arg Asp Ile Ile Val Thr Glu Thr Gly Thr Ser Ser Phe Gly Val
385                 390                 395                 400

Leu Ala Thr His Leu Pro Arg Asp Ser Lys Ser Ile Ser Gln Val Leu
                405                 410                 415

Trp Gly Ser Ile Gly Phe Ser Leu Pro Ala Ala Val Gly Ala Ala Phe
            420                 425                 430

Ala Ala Glu Asp Ala His Lys Gln Thr Gly Glu Gln Glu Arg Arg Thr
        435                 440                 445

Val Leu Phe Ile Gly Asp Gly Ser Leu Gln Leu Thr Val Gln Ser Ile
    450                 455                 460

Ser Asp Ala Ala Arg Trp Asn Ile Lys Pro Tyr Ile Phe Ile Leu Asn
465                 470                 475                 480

Asn Arg Gly Tyr Thr Ile Glu Lys Leu Ile His Gly Arg His Glu Asp
                485                 490                 495

Tyr Asn Gln Ile Gln Pro Trp Asp His Gln Leu Leu Leu Lys Leu Phe
            500                 505                 510

Ala Asp Lys Thr Gln Tyr Glu Asn His Val Val Lys Ser Ala Lys Asp
        515                 520                 525

Leu Asp Ala Leu Met Lys Asp Glu Ala Phe Asn Lys Glu Asp Lys Ile
    530                 535                 540

Arg Val Ile Glu Leu Phe Leu Asp Glu Phe Asp Ala Pro Glu Ile Leu
```

Val Ala Gln Ala Lys Leu Ser Asp Glu Ile Asn Ser Lys Ala Ala
               565                 570                 575

<210> SEQ ID NO 51
<211> LENGTH: 1131
<212> TYPE: DNA
<213> ORGANISM: Issatchenkia orientalis
<220> FEATURE:
<221> NAME/KEY: CDS
<222> LOCATION: (1)..(1131)

<400> SEQUENCE: 51

```
atg ttt gca tca acc ttc aga agt caa gct gta aga gct gca aga ttt      48
Met Phe Ala Ser Thr Phe Arg Ser Gln Ala Val Arg Ala Ala Arg Phe
1               5                   10                  15 act aga ttc caa tcc act ttt gcc att cct gag aag caa atg ggt gtt      96
Thr Arg Phe Gln Ser Thr Phe Ala Ile Pro Glu Lys Gln Met Gly Val
            20                  25                  30 atc ttt gaa act cat ggt ggt cct tta caa tac aag gaa att cca gtt     144
Ile Phe Glu Thr His Gly Gly Pro Leu Gln Tyr Lys Glu Ile Pro Val
        35                  40                  45 cca aaa cca aaa cca act gaa att tta atc aat gtt aaa tac tct ggt     192
Pro Lys Pro Lys Pro Thr Glu Ile Leu Ile Asn Val Lys Tyr Ser Gly
    50                  55                  60 gtc tgc cat acc gat tta cac gca tgg aaa ggt gac tgg cca tta cca     240
Val Cys His Thr Asp Leu His Ala Trp Lys Gly Asp Trp Pro Leu Pro
65                  70                  75                  80 gca aag tta ccc cta gtt ggt ggt cac gaa ggt gcg ggc att gtt gtt     288
Ala Lys Leu Pro Leu Val Gly Gly His Glu Gly Ala Gly Ile Val Val
                85                  90                  95 gcg aaa ggt tct gca gtt acc aac ttt gag att ggc gat tat gct ggt     336
Ala Lys Gly Ser Ala Val Thr Asn Phe Glu Ile Gly Asp Tyr Ala Gly
            100                 105                 110 att aag tgg tta aac ggt tca tgt atg tca tgt gaa ttc tgt gaa caa     384
Ile Lys Trp Leu Asn Gly Ser Cys Met Ser Cys Glu Phe Cys Glu Gln
        115                 120                 125 ggt gat gaa tct aac tgt gaa cat gcc gat ttg agt ggt tat act cat     432
Gly Asp Glu Ser Asn Cys Glu His Ala Asp Leu Ser Gly Tyr Thr His
    130                 135                 140 gat ggt tct ttc caa caa tat gcc act gct gac gct att caa gct gca     480
Asp Gly Ser Phe Gln Gln Tyr Ala Thr Ala Asp Ala Ile Gln Ala Ala
145                 150                 155                 160 aag atc cca aag ggt acc gac tta tct gaa gtt gcg cca att tta tgt     528
Lys Ile Pro Lys Gly Thr Asp Leu Ser Glu Val Ala Pro Ile Leu Cys
                165                 170                 175 gct ggt gtt act gtc tat aaa gct ttg aaa act gct gat tta aga gca     576
Ala Gly Val Thr Val Tyr Lys Ala Leu Lys Thr Ala Asp Leu Arg Ala
            180                 185                 190 ggt caa tgg gtt gcg att tct ggt gcc gct ggt ggt cta ggt tct ctt     624
Gly Gln Trp Val Ala Ile Ser Gly Ala Ala Gly Gly Leu Gly Ser Leu
        195                 200                 205 gct gtc caa tat gca aag gca atg ggt cta aga gtt tta ggt atc gat     672
Ala Val Gln Tyr Ala Lys Ala Met Gly Leu Arg Val Leu Gly Ile Asp
    210                 215                 220 ggt ggt gaa ggt aaa aag gaa ctt ttt gaa caa tgt ggt ggt gat gtg     720
Gly Gly Glu Gly Lys Lys Glu Leu Phe Glu Gln Cys Gly Gly Asp Val
225                 230                 235                 240 ttt atc gat ttc acc aga tac cca aga gat gca cct gaa aag atg gtt     768
Phe Ile Asp Phe Thr Arg Tyr Pro Arg Asp Ala Pro Glu Lys Met Val
                245                 250                 255
```

```
gct gat att aag gct gca act aac ggt ttg ggt cca cac ggt gtt atc      816
Ala Asp Ile Lys Ala Ala Thr Asn Gly Leu Gly Pro His Gly Val Ile
            260                 265                 270 aat gtc tct gtc tcc cca gct gct atc tct caa tca tgt gac tat gtt      864
Asn Val Ser Val Ser Pro Ala Ala Ile Ser Gln Ser Cys Asp Tyr Val
        275                 280                 285 aga gca act ggt aag gtt gtc ctt gtc ggt atg cca tct ggt gct gtc      912
Arg Ala Thr Gly Lys Val Val Leu Val Gly Met Pro Ser Gly Ala Val
    290                 295                 300 tgt aag tct gat gtc ttc act cat gtt gtt aaa tcc tta caa att aaa      960
Cys Lys Ser Asp Val Phe Thr His Val Val Lys Ser Leu Gln Ile Lys
305                 310                 315                 320 ggt tct tat gtt ggt aac aga gca gat acc aga gaa gct ttg gaa ttc     1008
Gly Ser Tyr Val Gly Asn Arg Ala Asp Thr Arg Glu Ala Leu Glu Phe
                325                 330                 335 ttt aat gaa ggt aag gtc aga tct cca atc aag gtt gtc cca tta tct     1056
Phe Asn Glu Gly Lys Val Arg Ser Pro Ile Lys Val Val Pro Leu Ser
            340                 345                 350 act tta cct gaa att tac gaa ttg atg gag caa ggt aag att tta ggt     1104
Thr Leu Pro Glu Ile Tyr Glu Leu Met Glu Gln Gly Lys Ile Leu Gly
        355                 360                 365 aga tac gtt gtt gat act tct aaa taa                                  1131
Arg Tyr Val Val Asp Thr Ser Lys
    370                 375

<210> SEQ ID NO 52
<211> LENGTH: 376
<212> TYPE: PRT
<213> ORGANISM: Issatchenkia orientalis

<400> SEQUENCE: 52

Met Phe Ala Ser Thr Phe Arg Ser Gln Ala Val Arg Ala Ala Arg Phe
1               5                   10                  15

Thr Arg Phe Gln Ser Thr Phe Ala Ile Pro Glu Lys Gln Met Gly Val
            20                  25                  30

Ile Phe Glu Thr His Gly Gly Pro Leu Gln Tyr Lys Glu Ile Pro Val
        35                  40                  45

Pro Lys Pro Lys Pro Thr Glu Ile Leu Ile Asn Val Lys Tyr Ser Gly
    50                  55                  60

Val Cys His Thr Asp Leu His Ala Trp Lys Gly Asp Trp Pro Leu Pro
65                  70                  75                  80

Ala Lys Leu Pro Leu Val Gly Gly His Glu Gly Ala Gly Ile Val Val
                85                  90                  95

Ala Lys Gly Ser Ala Val Thr Asn Phe Glu Ile Gly Asp Tyr Ala Gly
            100                 105                 110

Ile Lys Trp Leu Asn Gly Ser Cys Met Ser Cys Glu Phe Cys Glu Gln
        115                 120                 125

Gly Asp Glu Ser Asn Cys Glu His Ala Asp Leu Ser Gly Tyr Thr His
    130                 135                 140

Asp Gly Ser Phe Gln Gln Tyr Ala Thr Ala Asp Ala Ile Gln Ala Ala
145                 150                 155                 160

Lys Ile Pro Lys Gly Thr Asp Leu Ser Glu Val Ala Pro Ile Leu Cys
                165                 170                 175

Ala Gly Val Thr Val Tyr Lys Ala Leu Lys Thr Ala Asp Leu Arg Ala
            180                 185                 190

Gly Gln Trp Val Ala Ile Ser Gly Ala Ala Gly Gly Leu Gly Ser Leu
        195                 200                 205
```

```
Ala Val Gln Tyr Ala Lys Ala Met Gly Leu Arg Val Leu Gly Ile Asp
    210                 215                 220

Gly Gly Glu Gly Lys Lys Glu Leu Phe Glu Gln Cys Gly Gly Asp Val
225                 230                 235                 240

Phe Ile Asp Phe Thr Arg Tyr Pro Arg Asp Ala Pro Glu Lys Met Val
                245                 250                 255

Ala Asp Ile Lys Ala Ala Thr Asn Gly Leu Gly Pro His Gly Val Ile
            260                 265                 270

Asn Val Ser Val Ser Pro Ala Ala Ile Ser Gln Ser Cys Asp Tyr Val
        275                 280                 285

Arg Ala Thr Gly Lys Val Val Leu Val Gly Met Pro Ser Gly Ala Val
    290                 295                 300

Cys Lys Ser Asp Val Phe Thr His Val Val Lys Ser Leu Gln Ile Lys
305                 310                 315                 320

Gly Ser Tyr Val Gly Asn Arg Ala Asp Thr Arg Glu Ala Leu Glu Phe
                325                 330                 335

Phe Asn Glu Gly Lys Val Arg Ser Pro Ile Lys Val Val Pro Leu Ser
            340                 345                 350

Thr Leu Pro Glu Ile Tyr Glu Leu Met Glu Gln Gly Lys Ile Leu Gly
        355                 360                 365

Arg Tyr Val Val Asp Thr Ser Lys
    370                 375

<210> SEQ ID NO 53
<211> LENGTH: 1167
<212> TYPE: DNA
<213> ORGANISM: Issatchenkia orientalis
<220> FEATURE:
<221> NAME/KEY: CDS
<222> LOCATION: (1)..(1167)

<400> SEQUENCE: 53 atg gtg tcc cct gct gaa aga tta tct act att gcg tcc aca atc aag      48
Met Val Ser Pro Ala Glu Arg Leu Ser Thr Ile Ala Ser Thr Ile Lys
1               5                   10                  15 cca aac aga aaa gat tct aca tca tta caa cca gaa gac tat ccg gaa      96
Pro Asn Arg Lys Asp Ser Thr Ser Leu Gln Pro Glu Asp Tyr Pro Glu
            20                  25                  30 cat ccg ttc aag gtg acg gtt gtt ggt tcc ggt aac tgg ggg tgt aca     144
His Pro Phe Lys Val Thr Val Val Gly Ser Gly Asn Trp Gly Cys Thr
        35                  40                  45 att gcc aag gtt ata gcg gaa aac acc gtt gag aga cct cgt caa ttt     192
Ile Ala Lys Val Ile Ala Glu Asn Thr Val Glu Arg Pro Arg Gln Phe
    50                  55                  60 caa aga gat gtt aat atg tgg gtc tat gaa gaa ttg att gaa ggc gaa     240
Gln Arg Asp Val Asn Met Trp Val Tyr Glu Glu Leu Ile Glu Gly Glu
65                  70                  75                  80 aag ttg act gaa atc ata aat acc aaa cac gaa aac gtc aag tac ttg     288
Lys Leu Thr Glu Ile Ile Asn Thr Lys His Glu Asn Val Lys Tyr Leu
                85                  90                  95 cca ggt atc aag ttg cca gtt aac gtt gtt gca gtt cca gac att gtt     336
Pro Gly Ile Lys Leu Pro Val Asn Val Val Ala Val Pro Asp Ile Val
            100                 105                 110 gag gct tgt gca ggc tca gac ttg att gtc ttt aat att cct cac caa     384
Glu Ala Cys Ala Gly Ser Asp Leu Ile Val Phe Asn Ile Pro His Gln
        115                 120                 125 ttt tta cca aga att tta tcc caa tta aag ggt aag gtg aat cca aag     432
Phe Leu Pro Arg Ile Leu Ser Gln Leu Lys Gly Lys Val Asn Pro Lys
```

```
                  130                 135                 140
gct aga gca att tct tgt ttg aaa ggt ttg gat gtc aat cct aat gga        480
Ala Arg Ala Ile Ser Cys Leu Lys Gly Leu Asp Val Asn Pro Asn Gly
145                 150                 155                 160 tgt aag ttg ctc tcc act gtt att act gaa gag ttg ggt att tat tgt        528
Cys Lys Leu Leu Ser Thr Val Ile Thr Glu Glu Leu Gly Ile Tyr Cys
                165                 170                 175 ggt gcc tta tca ggt gct aat tta gct cct gaa gtt gca caa tgt aaa        576
Gly Ala Leu Ser Gly Ala Asn Leu Ala Pro Glu Val Ala Gln Cys Lys
            180                 185                 190 tgg tcg gaa aca act gtt gca tat aca att ccg gac gat ttc aga ggt        624
Trp Ser Glu Thr Thr Val Ala Tyr Thr Ile Pro Asp Asp Phe Arg Gly
        195                 200                 205 aaa ggc aag gat att gac cat caa att cta aag agt ttg ttc cat aga        672
Lys Gly Lys Asp Ile Asp His Gln Ile Leu Lys Ser Leu Phe His Arg
    210                 215                 220 cct tat ttc cat gtt cgt gtt att agt gat gtt gca ggt att tcc att        720
Pro Tyr Phe His Val Arg Val Ile Ser Asp Val Ala Gly Ile Ser Ile
225                 230                 235                 240 gcc ggt gca ctc aag aat gtc gtt gct atg gct gct gga ttt gtc gaa        768
Ala Gly Ala Leu Lys Asn Val Val Ala Met Ala Ala Gly Phe Val Glu
                245                 250                 255 ggt tta ggt tgg ggt gat aat gca aag gct gca gtc atg aga ata ggt        816
Gly Leu Gly Trp Gly Asp Asn Ala Lys Ala Ala Val Met Arg Ile Gly
            260                 265                 270 ttg gtg gaa acc att caa ttt gcc aag act ttt ttc gat ggc tgt cat        864
Leu Val Glu Thr Ile Gln Phe Ala Lys Thr Phe Phe Asp Gly Cys His
        275                 280                 285 gct gca acc ttt act cat gaa tct gca ggt gtt gcc gac cta atc act        912
Ala Ala Thr Phe Thr His Glu Ser Ala Gly Val Ala Asp Leu Ile Thr
    290                 295                 300 acc tgt gcc ggc ggc cgt aac gtt aga gtt ggt aga tat atg gca caa        960
Thr Cys Ala Gly Gly Arg Asn Val Arg Val Gly Arg Tyr Met Ala Gln
305                 310                 315                 320 cat tct gtc tct gca acg gag gct gaa gaa aag ttg ttg aat ggc caa       1008
His Ser Val Ser Ala Thr Glu Ala Glu Glu Lys Leu Leu Asn Gly Gln
                325                 330                 335 tcc tgt caa ggt atc cac aca act agg gaa gtt tac gag ttc ctc tcc       1056
Ser Cys Gln Gly Ile His Thr Thr Arg Glu Val Tyr Glu Phe Leu Ser
            340                 345                 350 aac atg ggc agg aca gat gag ttc cca cta ttt acc acc acc tac cgt       1104
Asn Met Gly Arg Thr Asp Glu Phe Pro Leu Phe Thr Thr Thr Tyr Arg
        355                 360                 365 atc atc tac gaa aac ttc cca att gag aag ctg cca gaa tgc ctt gaa       1152
Ile Ile Tyr Glu Asn Phe Pro Ile Glu Lys Leu Pro Glu Cys Leu Glu
    370                 375                 380 cct gtg gaa gat taa                                                    1167
Pro Val Glu Asp
385

<210> SEQ ID NO 54
<211> LENGTH: 388
<212> TYPE: PRT
<213> ORGANISM: Issatchenkia orientalis

<400> SEQUENCE: 54

Met Val Ser Pro Ala Glu Arg Leu Ser Thr Ile Ala Ser Thr Ile Lys
1               5                   10                  15

Pro Asn Arg Lys Asp Ser Thr Ser Leu Gln Pro Glu Asp Tyr Pro Glu
            20                  25                  30
```

His Pro Phe Lys Val Thr Val Gly Ser Gly Asn Trp Gly Cys Thr
        35                  40                  45

Ile Ala Lys Val Ile Ala Glu Asn Thr Val Glu Arg Pro Arg Gln Phe
 50                  55                  60

Gln Arg Asp Val Asn Met Trp Val Tyr Glu Leu Ile Glu Gly Glu
 65                  70                  75                  80

Lys Leu Thr Glu Ile Ile Asn Thr Lys His Glu Asn Val Lys Tyr Leu
                 85                  90                  95

Pro Gly Ile Lys Leu Pro Val Asn Val Ala Val Pro Asp Ile Val
                100                 105                 110

Glu Ala Cys Ala Gly Ser Asp Leu Ile Val Phe Asn Ile Pro His Gln
            115                 120                 125

Phe Leu Pro Arg Ile Leu Ser Gln Leu Lys Gly Lys Val Asn Pro Lys
130                 135                 140

Ala Arg Ala Ile Ser Cys Leu Lys Gly Leu Asp Val Asn Pro Asn Gly
145                 150                 155                 160

Cys Lys Leu Leu Ser Thr Val Ile Thr Glu Glu Leu Gly Ile Tyr Cys
                165                 170                 175

Gly Ala Leu Ser Gly Ala Asn Leu Ala Pro Glu Val Ala Gln Cys Lys
            180                 185                 190

Trp Ser Glu Thr Thr Val Ala Tyr Thr Ile Pro Asp Asp Phe Arg Gly
        195                 200                 205

Lys Gly Lys Asp Ile Asp His Gln Ile Leu Lys Ser Leu Phe His Arg
210                 215                 220

Pro Tyr Phe His Val Arg Val Ile Ser Asp Val Ala Gly Ile Ser Ile
225                 230                 235                 240

Ala Gly Ala Leu Lys Asn Val Val Ala Met Ala Ala Gly Phe Val Glu
                245                 250                 255

Gly Leu Gly Trp Gly Asp Asn Ala Lys Ala Ala Val Met Arg Ile Gly
            260                 265                 270

Leu Val Glu Thr Ile Gln Phe Ala Lys Thr Phe Phe Asp Gly Cys His
        275                 280                 285

Ala Ala Thr Phe Thr His Glu Ser Ala Gly Val Ala Asp Leu Ile Thr
290                 295                 300

Thr Cys Ala Gly Gly Arg Asn Val Arg Val Gly Arg Tyr Met Ala Gln
305                 310                 315                 320

His Ser Val Ser Ala Thr Glu Ala Glu Lys Leu Leu Asn Gly Gln
                325                 330                 335

Ser Cys Gln Gly Ile His Thr Thr Arg Glu Val Tyr Glu Phe Leu Ser
            340                 345                 350

Asn Met Gly Arg Thr Asp Glu Phe Pro Leu Phe Thr Thr Thr Tyr Arg
        355                 360                 365

Ile Ile Tyr Glu Asn Phe Pro Ile Glu Lys Leu Pro Glu Cys Leu Glu
370                 375                 380

Pro Val Glu Asp
385

<210> SEQ ID NO 55
<211> LENGTH: 1683
<212> TYPE: DNA
<213> ORGANISM: Issatchenkia orientalis
<220> FEATURE:
<221> NAME/KEY: CDS
<222> LOCATION: (1)..(1683)

<400> SEQUENCE: 55

| | | | | | | | | | | | | | | | | |
|---|---|---|---|---|---|---|---|---|---|---|---|---|---|---|---|---|
| atg | gct | cca | act | gct | gtt | gat | atc | cat | aac | gag | tac | aaa | cag | aat | gtt | 48 |
| Met | Ala | Pro | Thr | Ala | Val | Asp | Ile | His | Asn | Glu | Tyr | Lys | Gln | Asn | Val | |
| 1 | | | | 5 | | | | | 10 | | | | | 15 | | |

| tcc | aac | gaa | cag | gaa | att | cct | ttc | aac | aaa | act | gaa | aga | aag | tca | tcg | 96 |
|---|---|---|---|---|---|---|---|---|---|---|---|---|---|---|---|---|
| Ser | Asn | Glu | Gln | Glu | Ile | Pro | Phe | Asn | Lys | Thr | Glu | Arg | Lys | Ser | Ser | |
| | | | 20 | | | | | 25 | | | | | 30 | | | |

| att | gca | tct | aaa | tta | gga | ctg | aat | cca | gac | gct | aag | att | cac | tac | aat | 144 |
|---|---|---|---|---|---|---|---|---|---|---|---|---|---|---|---|---|
| Ile | Ala | Ser | Lys | Leu | Gly | Leu | Asn | Pro | Asp | Ala | Lys | Ile | His | Tyr | Asn | |
| | | 35 | | | | | 40 | | | | | 45 | | | | |

| tct | gct | gtt | cct | ata | tta | tac | gaa | gat | ggt | tta | aag | gaa | aaa | ggt | aca | 192 |
|---|---|---|---|---|---|---|---|---|---|---|---|---|---|---|---|---|
| Ser | Ala | Val | Pro | Ile | Leu | Tyr | Glu | Asp | Gly | Leu | Lys | Glu | Lys | Gly | Thr | |
| | 50 | | | | | 55 | | | | | 60 | | | | | |

| acc | att | tcc | tct | tct | ggt | gca | ttg | att | gca | ttc | tct | ggt | tcc | aaa | aca | 240 |
|---|---|---|---|---|---|---|---|---|---|---|---|---|---|---|---|---|
| Thr | Ile | Ser | Ser | Ser | Gly | Ala | Leu | Ile | Ala | Phe | Ser | Gly | Ser | Lys | Thr | |
| 65 | | | | | 70 | | | | | 75 | | | | | 80 | |

| ggt | aga | tct | cca | aag | gac | aaa | aga | att | gtc | gat | gaa | gag | act | tca | aca | 288 |
|---|---|---|---|---|---|---|---|---|---|---|---|---|---|---|---|---|
| Gly | Arg | Ser | Pro | Lys | Asp | Lys | Arg | Ile | Val | Asp | Glu | Glu | Thr | Ser | Thr | |
| | | | | 85 | | | | | 90 | | | | | 95 | | |

| gac | aac | atc | tgg | tgg | ggt | cca | gtc | aat | aag | aag | gtt | gat | gaa | aac | act | 336 |
|---|---|---|---|---|---|---|---|---|---|---|---|---|---|---|---|---|
| Asp | Asn | Ile | Trp | Trp | Gly | Pro | Val | Asn | Lys | Lys | Val | Asp | Glu | Asn | Thr | |
| | | | 100 | | | | | 105 | | | | | 110 | | | |

| tgg | aat | atc | tcg | aaa | tct | aga | gcg | att | gat | tat | ttg | aga | aca | aga | gag | 384 |
|---|---|---|---|---|---|---|---|---|---|---|---|---|---|---|---|---|
| Trp | Asn | Ile | Ser | Lys | Ser | Arg | Ala | Ile | Asp | Tyr | Leu | Arg | Thr | Arg | Glu | |
| | | 115 | | | | | 120 | | | | | 125 | | | | |

| aag | gtt | tac | att | atc | gat | gct | ttt | gct | ggt | tgg | gat | cca | aga | tac | aga | 432 |
|---|---|---|---|---|---|---|---|---|---|---|---|---|---|---|---|---|
| Lys | Val | Tyr | Ile | Ile | Asp | Ala | Phe | Ala | Gly | Trp | Asp | Pro | Arg | Tyr | Arg | |
| | 130 | | | | | 135 | | | | | 140 | | | | | |

| att | aag | gtt | aga | att | gtc | tgt | gct | aga | gct | tac | cat | gct | ttg | ttc | atg | 480 |
|---|---|---|---|---|---|---|---|---|---|---|---|---|---|---|---|---|
| Ile | Lys | Val | Arg | Ile | Val | Cys | Ala | Arg | Ala | Tyr | His | Ala | Leu | Phe | Met | |
| 145 | | | | | 150 | | | | | 155 | | | | | 160 | |

| aag | aat | atg | tta | att | aga | cca | aca | acg | gaa | gaa | tta | aag | aac | ttt | ggt | 528 |
|---|---|---|---|---|---|---|---|---|---|---|---|---|---|---|---|---|
| Lys | Asn | Met | Leu | Ile | Arg | Pro | Thr | Thr | Glu | Glu | Leu | Lys | Asn | Phe | Gly | |
| | | | | 165 | | | | | 170 | | | | | 175 | | |

| gag | cct | gat | ttc | acc | att | tgg | aat | gca | ggt | caa | ttc | cct | gct | aat | gtt | 576 |
|---|---|---|---|---|---|---|---|---|---|---|---|---|---|---|---|---|
| Glu | Pro | Asp | Phe | Thr | Ile | Trp | Asn | Ala | Gly | Gln | Phe | Pro | Ala | Asn | Val | |
| | | | 180 | | | | | 185 | | | | | 190 | | | |

| tac | act | aag | ggt | atg | act | tct | tca | act | tct | gtt | gaa | ata | aat | ttc | aag | 624 |
|---|---|---|---|---|---|---|---|---|---|---|---|---|---|---|---|---|
| Tyr | Thr | Lys | Gly | Met | Thr | Ser | Ser | Thr | Ser | Val | Glu | Ile | Asn | Phe | Lys | |
| | | 195 | | | | | 200 | | | | | 205 | | | | |

| tct | atg | gaa | atg | gtt | atc | cta | ggt | act | gaa | tac | gca | ggt | gaa | atg | aag | 672 |
|---|---|---|---|---|---|---|---|---|---|---|---|---|---|---|---|---|
| Ser | Met | Glu | Met | Val | Ile | Leu | Gly | Thr | Glu | Tyr | Ala | Gly | Glu | Met | Lys | |
| | 210 | | | | | 215 | | | | | 220 | | | | | |

| aaa | ggt | atc | ttt | acc | gtt | atg | ttc | tac | ttg | atg | cca | atc | aga | cac | aag | 720 |
|---|---|---|---|---|---|---|---|---|---|---|---|---|---|---|---|---|
| Lys | Gly | Ile | Phe | Thr | Val | Met | Phe | Tyr | Leu | Met | Pro | Ile | Arg | His | Lys | |
| 225 | | | | | 230 | | | | | 235 | | | | | 240 | |

| gtt | tta | act | tta | cac | tct | tct | gca | aat | caa | ggt | aaa | aag | gat | ggt | gat | 768 |
|---|---|---|---|---|---|---|---|---|---|---|---|---|---|---|---|---|
| Val | Leu | Thr | Leu | His | Ser | Ser | Ala | Asn | Gln | Gly | Lys | Lys | Asp | Gly | Asp | |
| | | | | 245 | | | | | 250 | | | | | 255 | | |

| gtc | aca | tta | ttc | ttt | ggt | tta | tct | ggt | aca | ggt | aaa | aca | acc | ttg | tct | 816 |
|---|---|---|---|---|---|---|---|---|---|---|---|---|---|---|---|---|
| Val | Thr | Leu | Phe | Phe | Gly | Leu | Ser | Gly | Thr | Gly | Lys | Thr | Thr | Leu | Ser | |
| | | | | 260 | | | | | 265 | | | | | 270 | | |

| gca | gat | cct | cat | aga | gaa | ttg | att | ggt | gat | gat | gaa | cat | tgc | tgg | tct | 864 |
|---|---|---|---|---|---|---|---|---|---|---|---|---|---|---|---|---|
| Ala | Asp | Pro | His | Arg | Glu | Leu | Ile | Gly | Asp | Asp | Glu | His | Cys | Trp | Ser | |
| | | | 275 | | | | | 280 | | | | | 285 | | | |

| gat | cat | ggt | gtt | ttc | aac | att | gaa | ggt | gga | tgt | tat | gct | aag | tgt | ttg | 912 |
|---|---|---|---|---|---|---|---|---|---|---|---|---|---|---|---|---|
| Asp | His | Gly | Val | Phe | Asn | Ile | Glu | Gly | Gly | Cys | Tyr | Ala | Lys | Cys | Leu | |
| | | 290 | | | | | 295 | | | | | 300 | | | | |

| gac | tta | tct | gct | gaa | aga | gaa | cct | gag | att | ttc | aat | gca | att | agg | ttt | 960 |
|---|---|---|---|---|---|---|---|---|---|---|---|---|---|---|---|---|

```
Asp Leu Ser Ala Glu Arg Glu Pro Glu Ile Phe Asn Ala Ile Arg Phe
305                 310                 315                 320 gga tct gtc ttg gag aat gtt gtc tat gat cca gtt gat aga act gtt      1008
Gly Ser Val Leu Glu Asn Val Val Tyr Asp Pro Val Asp Arg Thr Val
                325                 330                 335 gac tat tcc gct gct aat gtc act gaa aat act aga tgt gct tat cct      1056
Asp Tyr Ser Ala Ala Asn Val Thr Glu Asn Thr Arg Cys Ala Tyr Pro
            340                 345                 350 atc gac ttt att cct tct gct aag atc cca tgt ctg gca gat tct cat      1104
Ile Asp Phe Ile Pro Ser Ala Lys Ile Pro Cys Leu Ala Asp Ser His
        355                 360                 365 cca aag aat att gtt ctt tta act tgt gat gca aga ggt gtt ttg cca      1152
Pro Lys Asn Ile Val Leu Leu Thr Cys Asp Ala Arg Gly Val Leu Pro
370                 375                 380 cct gtc tcc aag cta act aat gca caa gtc atg tat cac ttt atc tct      1200
Pro Val Ser Lys Leu Thr Asn Ala Gln Val Met Tyr His Phe Ile Ser
385                 390                 395                 400 ggt tac acc tcc aag atg gca ggt acc gaa gtt ggt gtc act gaa cca      1248
Gly Tyr Thr Ser Lys Met Ala Gly Thr Glu Val Gly Val Thr Glu Pro
                405                 410                 415 gaa gca acc ttc tct gca tgt ttt ggt caa cct ttc tta gtt tta cat      1296
Glu Ala Thr Phe Ser Ala Cys Phe Gly Gln Pro Phe Leu Val Leu His
            420                 425                 430 cca atg aaa tac gca caa caa ctc tct gat aaa atg gct gaa cat tct      1344
Pro Met Lys Tyr Ala Gln Gln Leu Ser Asp Lys Met Ala Glu His Ser
        435                 440                 445 tcc acc gct tgg tta ttg aat acc ggt tgg act ggt caa tct tat gtt      1392
Ser Thr Ala Trp Leu Leu Asn Thr Gly Trp Thr Gly Gln Ser Tyr Val
    450                 455                 460 aaa ggt ggt aag aga tgt cca ttg aag tat act aga gca att tta gat      1440
Lys Gly Gly Lys Arg Cys Pro Leu Lys Tyr Thr Arg Ala Ile Leu Asp
465                 470                 475                 480 gct att cac tct ggt gag ctt gca aaa cag gaa ttc gaa aca tac cct      1488
Ala Ile His Ser Gly Glu Leu Ala Lys Gln Glu Phe Glu Thr Tyr Pro
                485                 490                 495 act ttc ggt tta caa gtt cca aaa act tgt cca ggt gtc cca gaa agt      1536
Thr Phe Gly Leu Gln Val Pro Lys Thr Cys Pro Gly Val Pro Glu Ser
            500                 505                 510 gtt ctg aac cca tct aaa cac tgg gct act ggt gaa gct gat ttc aag      1584
Val Leu Asn Pro Ser Lys His Trp Ala Thr Gly Glu Ala Asp Phe Lys
        515                 520                 525 gct gaa gtc act aac ttg gct aaa tta ttt gct gag aac ttt gaa aag      1632
Ala Glu Val Thr Asn Leu Ala Lys Leu Phe Ala Glu Asn Phe Glu Lys
    530                 535                 540 tat tct gca gaa tgt act gca gaa gtt gtt gct gct ggt cct gct tta      1680
Tyr Ser Ala Glu Cys Thr Ala Glu Val Val Ala Ala Gly Pro Ala Leu
545                 550                 555                 560 taa                                                                   1683

<210> SEQ ID NO 56
<211> LENGTH: 560
<212> TYPE: PRT
<213> ORGANISM: Issatchenkia orientalis

<400> SEQUENCE: 56

Met Ala Pro Thr Ala Val Asp Ile His Asn Glu Tyr Lys Gln Asn Val
1               5                   10                  15

Ser Asn Glu Gln Glu Ile Pro Phe Asn Lys Thr Glu Arg Lys Ser Ser
            20                  25                  30
```

-continued

```
Ile Ala Ser Lys Leu Gly Leu Asn Pro Asp Ala Lys Ile His Tyr Asn
            35                  40                  45

Ser Ala Val Pro Ile Leu Tyr Glu Asp Gly Leu Lys Glu Lys Gly Thr
50                  55                  60

Thr Ile Ser Ser Ser Gly Ala Leu Ile Ala Phe Ser Gly Ser Lys Thr
65                  70                  75                  80

Gly Arg Ser Pro Lys Asp Lys Arg Ile Val Asp Glu Thr Ser Thr
                85                  90                  95

Asp Asn Ile Trp Trp Gly Pro Val Asn Lys Lys Val Asp Glu Asn Thr
                100                 105                 110

Trp Asn Ile Ser Lys Ser Arg Ala Ile Asp Tyr Leu Arg Thr Arg Glu
                115                 120                 125

Lys Val Tyr Ile Ile Asp Ala Phe Ala Gly Trp Asp Pro Arg Tyr Arg
130                 135                 140

Ile Lys Val Arg Ile Val Cys Ala Arg Ala Tyr His Ala Leu Phe Met
145                 150                 155                 160

Lys Asn Met Leu Ile Arg Pro Thr Thr Glu Glu Leu Lys Asn Phe Gly
                165                 170                 175

Glu Pro Asp Phe Thr Ile Trp Asn Ala Gly Gln Phe Pro Ala Asn Val
                180                 185                 190

Tyr Thr Lys Gly Met Thr Ser Thr Ser Val Glu Ile Asn Phe Lys
                195                 200                 205

Ser Met Glu Met Val Ile Leu Gly Thr Glu Tyr Ala Gly Glu Met Lys
            210                 215                 220

Lys Gly Ile Phe Thr Val Met Phe Tyr Leu Met Pro Ile Arg His Lys
225                 230                 235                 240

Val Leu Thr Leu His Ser Ser Ala Asn Gln Gly Lys Lys Asp Gly Asp
                245                 250                 255

Val Thr Leu Phe Phe Gly Leu Ser Gly Thr Gly Lys Thr Thr Leu Ser
                260                 265                 270

Ala Asp Pro His Arg Glu Leu Ile Gly Asp Asp Glu His Cys Trp Ser
                275                 280                 285

Asp His Gly Val Phe Asn Ile Glu Gly Gly Cys Tyr Ala Lys Cys Leu
            290                 295                 300

Asp Leu Ser Ala Glu Arg Glu Pro Glu Ile Phe Asn Ala Ile Arg Phe
305                 310                 315                 320

Gly Ser Val Leu Glu Asn Val Val Tyr Asp Pro Val Asp Arg Thr Val
                325                 330                 335

Asp Tyr Ser Ala Ala Asn Val Thr Glu Asn Thr Arg Cys Ala Tyr Pro
                340                 345                 350

Ile Asp Phe Ile Pro Ser Ala Lys Ile Pro Cys Leu Ala Asp Ser His
                355                 360                 365

Pro Lys Asn Ile Val Leu Leu Thr Cys Asp Ala Arg Gly Val Leu Pro
370                 375                 380

Pro Val Ser Lys Leu Thr Asn Ala Gln Val Met Tyr His Phe Ile Ser
385                 390                 395                 400

Gly Tyr Thr Ser Lys Met Ala Gly Thr Glu Val Gly Val Thr Glu Pro
                405                 410                 415

Glu Ala Thr Phe Ser Ala Cys Phe Gly Gln Pro Phe Leu Val Leu His
                420                 425                 430

Pro Met Lys Tyr Ala Gln Gln Leu Ser Asp Lys Met Ala Glu His Ser
            435                 440                 445

Ser Thr Ala Trp Leu Leu Asn Thr Gly Trp Thr Gly Gln Ser Tyr Val
```

```
                    450                 455                 460
Lys Gly Gly Lys Arg Cys Pro Leu Lys Tyr Thr Arg Ala Ile Leu Asp
465                 470                 475                 480

Ala Ile His Ser Gly Glu Leu Ala Lys Gln Glu Phe Glu Thr Tyr Pro
                    485                 490                 495

Thr Phe Gly Leu Gln Val Pro Lys Thr Cys Pro Gly Val Pro Glu Ser
                500                 505                 510

Val Leu Asn Pro Ser Lys His Trp Ala Thr Gly Glu Ala Asp Phe Lys
            515                 520                 525

Ala Glu Val Thr Asn Leu Ala Lys Leu Phe Ala Glu Asn Phe Glu Lys
530                 535                 540

Tyr Ser Ala Glu Cys Thr Ala Glu Val Val Ala Ala Gly Pro Ala Leu
545                 550                 555                 560

<210> SEQ ID NO 57
<211> LENGTH: 1812
<212> TYPE: DNA
<213> ORGANISM: Issatchenkia orientalis
<220> FEATURE:
<221> NAME/KEY: CDS
<222> LOCATION: (1)..(1812)

<400> SEQUENCE: 57 atg aca aaa gat tgc tgt gag gtt aca aag att cca gtg gga gag gag     48
Met Thr Lys Asp Cys Cys Glu Val Thr Lys Ile Pro Val Gly Glu Glu
1               5                   10                  15 gcc aaa gtg acc gtt cct cgt tcc aca aga tta tca gca act ggt cca     96
Ala Lys Val Thr Val Pro Arg Ser Thr Arg Leu Ser Ala Thr Gly Pro
            20                  25                  30 gtt gaa tgt gat tta tct ggt ttc caa gtt ttg aac tct cca ctt ttc    144
Val Glu Cys Asp Leu Ser Gly Phe Gln Val Leu Asn Ser Pro Leu Phe
        35                  40                  45 aac aag ggc act gca ttc act att gca gaa aga gaa gca ttt ggt tta    192
Asn Lys Gly Thr Ala Phe Thr Ile Ala Glu Arg Glu Ala Phe Gly Leu
    50                  55                  60 aac ggg tta ctt cct ccg gtt gta aac act cta gaa gaa caa gtt gag    240
Asn Gly Leu Leu Pro Pro Val Val Asn Thr Leu Glu Glu Gln Val Glu
65                  70                  75                  80 aga agc tat aag caa cta cat ttt ctc aag act cca ttg gca aag aat    288
Arg Ser Tyr Lys Gln Leu His Phe Leu Lys Thr Pro Leu Ala Lys Asn
                85                  90                  95 gac ttt tgc acg tca ttg aga ttg caa aac aag gtt ctg ttt tat agg    336
Asp Phe Cys Thr Ser Leu Arg Leu Gln Asn Lys Val Leu Phe Tyr Arg
            100                 105                 110 tta gtc aag gaa cac att aag gag ttg att cca att gtg tat aca cca    384
Leu Val Lys Glu His Ile Lys Glu Leu Ile Pro Ile Val Tyr Thr Pro
        115                 120                 125 aca gag ggt gat gca att atc gct tat tct gac aga ttc aga aaa cca    432
Thr Glu Gly Asp Ala Ile Ile Ala Tyr Ser Asp Arg Phe Arg Lys Pro
    130                 135                 140 gag ggg tta ttc ctt gat att aca aga cca aat gaa att gat caa aga    480
Glu Gly Leu Phe Leu Asp Ile Thr Arg Pro Asn Glu Ile Asp Gln Arg
145                 150                 155                 160 ctg gaa cag ttt gga gaa gat aaa gat gtg gat tac att gtt ata aca    528
Leu Glu Gln Phe Gly Glu Asp Lys Asp Val Asp Tyr Ile Val Ile Thr
                165                 170                 175 gat tct gaa ggt att cta ggt att ggt gac caa ggt gtt ggc ggt gtc    576
Asp Ser Glu Gly Ile Leu Gly Ile Gly Asp Gln Gly Val Gly Gly Val
            180                 185                 190
```

```
aga atc aca att gca aag gct gct cta atg act gta tgt gct ggt ttg    624
Arg Ile Thr Ile Ala Lys Ala Ala Leu Met Thr Val Cys Ala Gly Leu
        195                 200                 205 cat cca ggt aga gtt gtc tct tgt gtc ttg gac gtt ggc act aac aat    672
His Pro Gly Arg Val Val Ser Cys Val Leu Asp Val Gly Thr Asn Asn
    210                 215                 220 gtg aaa ttg cta gaa gat gat cta tat ctt ggt aac aga ttc cca aga    720
Val Lys Leu Leu Glu Asp Asp Leu Tyr Leu Gly Asn Arg Phe Pro Arg
225                 230                 235                 240 gtt aga ggt aag gag tat gac gat ttt gtg aat aaa act att cgt gca    768
Val Arg Gly Lys Glu Tyr Asp Asp Phe Val Asn Lys Thr Ile Arg Ala
            245                 250                 255 atg aag aag aga ttt cca agt gct gtt att cat ttt gaa gat ttt ggt    816
Met Lys Lys Arg Phe Pro Ser Ala Val Ile His Phe Glu Asp Phe Gly
        260                 265                 270 gtt aca act gct aga cct gtg ttg gaa aga ttc aga gat gaa att cct    864
Val Thr Thr Ala Arg Pro Val Leu Glu Arg Phe Arg Asp Glu Ile Pro
    275                 280                 285 tgc ttt aat gat gac atc caa ggt acc ggc gct gtt gtc atg gct tcg    912
Cys Phe Asn Asp Asp Ile Gln Gly Thr Gly Ala Val Val Met Ala Ser
290                 295                 300 atg gcg gct gct ctt aaa tta acc cat aga aat cta cta gac tcc aaa    960
Met Ala Ala Ala Leu Lys Leu Thr His Arg Asn Leu Leu Asp Ser Lys
305                 310                 315                 320 gtt ttg att tat ggg gct ggt tca gcc ggt ttg ggt att gcc gat caa   1008
Val Leu Ile Tyr Gly Ala Gly Ser Ala Gly Leu Gly Ile Ala Asp Gln
            325                 330                 335 att gtt aat cat atg gtt agc cat ggt gcg act aaa gaa gaa gct aga   1056
Ile Val Asn His Met Val Ser His Gly Ala Thr Lys Glu Glu Ala Arg
        340                 345                 350 agg aag att tac tgt atg gac agg tat ggt ttg att tta aaa ggt atg   1104
Arg Lys Ile Tyr Cys Met Asp Arg Tyr Gly Leu Ile Leu Lys Gly Met
    355                 360                 365 act tcg aat tct cct gct caa gaa gat tat gct cat gat cca aaa gat   1152
Thr Ser Asn Ser Pro Ala Gln Glu Asp Tyr Ala His Asp Pro Lys Asp
370                 375                 380 tgg gaa aat att tca acc act tcg tta gtg gat gtt atc gaa aaa gtc   1200
Trp Glu Asn Ile Ser Thr Thr Ser Leu Val Asp Val Ile Glu Lys Val
385                 390                 395                 400 aag cct act act tta gtt ggg tgc tcc acg caa gcg ggc gct ttc aat   1248
Lys Pro Thr Thr Leu Val Gly Cys Ser Thr Gln Ala Gly Ala Phe Asn
            405                 410                 415 gaa gaa gtc atc aaa aca atg tat aaa cat aat cca aga cca atg att   1296
Glu Glu Val Ile Lys Thr Met Tyr Lys His Asn Pro Arg Pro Met Ile
        420                 425                 430 ttc cca ttg tcc aac cca act aga tta cat gag tgt ttc cct gaa gac   1344
Phe Pro Leu Ser Asn Pro Thr Arg Leu His Glu Cys Phe Pro Glu Asp
    435                 440                 445 gca ctt aaa tgg acc gat ttc aac gct tta gtt gcc act ggt tct cct   1392
Ala Leu Lys Trp Thr Asp Phe Asn Ala Leu Val Ala Thr Gly Ser Pro
450                 455                 460 ttc cca cct gtt gaa ggt cat gtt att tct gaa aat aac aat tgt ttt   1440
Phe Pro Pro Val Glu Gly His Val Ile Ser Glu Asn Asn Asn Cys Phe
465                 470                 475                 480 gcc ttc ccg ggt att ggt cta ggt gca gtg ctc gct aga act act agg   1488
Ala Phe Pro Gly Ile Gly Leu Gly Ala Val Leu Ala Arg Thr Thr Arg
            485                 490                 495 ata tca gac aac atg att tcg gct gcc gtt gac gag cta gct tct ctt   1536
Ile Ser Asp Asn Met Ile Ser Ala Ala Val Asp Glu Leu Ala Ser Leu
        500                 505                 510
```

```
tct cca gct caa aaa gat cct aaa ttg ggc ctt tta cct cca att gag       1584
Ser Pro Ala Gln Lys Asp Pro Lys Leu Gly Leu Leu Pro Pro Ile Glu
            515                 520                 525 gaa atc gac gag acc tct gca aga atc gca act gca gtt atc ttg aag       1632
Glu Ile Asp Glu Thr Ser Ala Arg Ile Ala Thr Ala Val Ile Leu Lys
530                 535                 540 gct gtc gag gaa gga ttt gca aga gta gaa gaa gaa gat tct cca tta       1680
Ala Val Glu Glu Gly Phe Ala Arg Val Glu Glu Glu Asp Ser Pro Leu
545                 550                 555                 560 ggt ggt aaa gtt aaa att cca aga gag ttt gat cca tgt cta aga tgg       1728
Gly Gly Lys Val Lys Ile Pro Arg Glu Phe Asp Pro Cys Leu Arg Trp
                565                 570                 575 gtt aaa gaa cag atg tgg cat cca att tac aga cca atg atc aaa gtc       1776
Val Lys Glu Gln Met Trp His Pro Ile Tyr Arg Pro Met Ile Lys Val
            580                 585                 590 gca cac tca gac aat att cat act cac caa tac taa                       1812
Ala His Ser Asp Asn Ile His Thr His Gln Tyr
                595                 600

<210> SEQ ID NO 58
<211> LENGTH: 603
<212> TYPE: PRT
<213> ORGANISM: Issatchenkia orientalis

<400> SEQUENCE: 58

Met Thr Lys Asp Cys Cys Glu Val Thr Lys Ile Pro Val Gly Glu Glu
1               5                   10                  15

Ala Lys Val Thr Val Pro Arg Ser Thr Arg Leu Ser Ala Thr Gly Pro
            20                  25                  30

Val Glu Cys Asp Leu Ser Gly Phe Gln Val Leu Asn Ser Pro Leu Phe
        35                  40                  45

Asn Lys Gly Thr Ala Phe Thr Ile Ala Glu Arg Glu Ala Phe Gly Leu
    50                  55                  60

Asn Gly Leu Leu Pro Pro Val Val Asn Thr Leu Glu Glu Gln Val Glu
65                  70                  75                  80

Arg Ser Tyr Lys Gln Leu His Phe Leu Lys Thr Pro Leu Ala Lys Asn
                85                  90                  95

Asp Phe Cys Thr Ser Leu Arg Leu Gln Asn Lys Val Leu Phe Tyr Arg
            100                 105                 110

Leu Val Lys Glu His Ile Lys Glu Leu Ile Pro Ile Val Tyr Thr Pro
        115                 120                 125

Thr Glu Gly Asp Ala Ile Ile Ala Tyr Ser Asp Arg Phe Arg Lys Pro
    130                 135                 140

Glu Gly Leu Phe Leu Asp Ile Thr Arg Pro Asn Glu Ile Asp Gln Arg
145                 150                 155                 160

Leu Glu Gln Phe Gly Glu Asp Lys Asp Val Asp Tyr Ile Val Ile Thr
                165                 170                 175

Asp Ser Glu Gly Ile Leu Gly Ile Gly Asp Gln Gly Val Gly Gly Val
            180                 185                 190

Arg Ile Thr Ile Ala Lys Ala Ala Leu Met Thr Val Cys Ala Gly Leu
        195                 200                 205

His Pro Gly Arg Val Val Ser Cys Val Leu Asp Val Gly Thr Asn Asn
    210                 215                 220

Val Lys Leu Leu Glu Asp Asp Leu Tyr Leu Gly Asn Arg Phe Pro Arg
225                 230                 235                 240

Val Arg Gly Lys Glu Tyr Asp Asp Phe Val Asn Lys Thr Ile Arg Ala
```

```
                    245                 250                 255
Met Lys Lys Arg Phe Pro Ser Ala Val Ile His Phe Glu Asp Phe Gly
                260                 265                 270

Val Thr Thr Ala Arg Pro Val Leu Glu Arg Phe Arg Asp Glu Ile Pro
            275                 280                 285

Cys Phe Asn Asp Asp Ile Gln Gly Thr Gly Ala Val Val Met Ala Ser
290                 295                 300

Met Ala Ala Ala Leu Lys Leu Thr His Arg Asn Leu Leu Asp Ser Lys
305                 310                 315                 320

Val Leu Ile Tyr Gly Ala Gly Ser Ala Gly Leu Gly Ile Ala Asp Gln
                325                 330                 335

Ile Val Asn His Met Val Ser His Gly Ala Thr Lys Glu Glu Ala Arg
                340                 345                 350

Arg Lys Ile Tyr Cys Met Asp Arg Tyr Gly Leu Ile Leu Lys Gly Met
            355                 360                 365

Thr Ser Asn Ser Pro Ala Gln Glu Asp Tyr Ala His Asp Pro Lys Asp
        370                 375                 380

Trp Glu Asn Ile Ser Thr Thr Ser Leu Val Asp Val Ile Glu Lys Val
385                 390                 395                 400

Lys Pro Thr Thr Leu Val Gly Cys Ser Thr Gln Ala Gly Ala Phe Asn
                405                 410                 415

Glu Glu Val Ile Lys Thr Met Tyr Lys His Asn Pro Arg Pro Met Ile
            420                 425                 430

Phe Pro Leu Ser Asn Pro Thr Arg Leu His Glu Cys Phe Pro Glu Asp
        435                 440                 445

Ala Leu Lys Trp Thr Asp Phe Asn Ala Leu Val Ala Thr Gly Ser Pro
    450                 455                 460

Phe Pro Pro Val Glu Gly His Val Ile Ser Glu Asn Asn Cys Phe
465                 470                 475                 480

Ala Phe Pro Gly Ile Gly Leu Gly Ala Val Leu Ala Arg Thr Thr Arg
                485                 490                 495

Ile Ser Asp Asn Met Ile Ser Ala Ala Val Asp Glu Leu Ala Ser Leu
            500                 505                 510

Ser Pro Ala Gln Lys Asp Pro Lys Leu Gly Leu Leu Pro Pro Ile Glu
        515                 520                 525

Glu Ile Asp Glu Thr Ser Ala Arg Ile Ala Thr Ala Val Ile Leu Lys
    530                 535                 540

Ala Val Glu Glu Gly Phe Ala Arg Val Glu Glu Asp Ser Pro Leu
545                 550                 555                 560

Gly Gly Lys Val Lys Ile Pro Arg Glu Phe Asp Pro Cys Leu Arg Trp
                565                 570                 575

Val Lys Glu Gln Met Trp His Pro Ile Tyr Arg Pro Met Ile Lys Val
            580                 585                 590

Ala His Ser Asp Asn Ile His Thr His Gln Tyr
        595                 600
```

<210> SEQ ID NO 59
<211> LENGTH: 1620
<212> TYPE: DNA
<213> ORGANISM: Issatchenkia orientalis
<220> FEATURE:
<221> NAME/KEY: CDS
<222> LOCATION: (1)..(1620)

<400> SEQUENCE: 59

```
atg act tta cac aaa aat tcc aac gaa gga gtt caa gct tca ggg ttt      48
Met Thr Leu His Lys Asn Ser Asn Glu Gly Val Gln Ala Ser Gly Phe
1               5                  10                  15 gag ctc caa gat aat ctg gat gtt ccg cat tct aat gca tca ttc caa      96
Glu Leu Gln Asp Asn Leu Asp Val Pro His Ser Asn Ala Ser Phe Gln
            20                  25                  30 agc ttt aaa tcc gac gag gct gaa cag gct cac aat aat gaa cac ttg     144
Ser Phe Lys Ser Asp Glu Ala Glu Gln Ala His Asn Asn Glu His Leu
        35                  40                  45 atg gag aag cct cag ttt aat aag gca aca atc tcc aac tac tgt aaa     192
Met Glu Lys Pro Gln Phe Asn Lys Ala Thr Ile Ser Asn Tyr Cys Lys
    50                  55                  60 aca aga ttt act gag ttg ttc cca aca aag cag tcg atg gct gcc aac     240
Thr Arg Phe Thr Glu Leu Phe Pro Thr Lys Gln Ser Met Ala Ala Asn
65                  70                  75                  80 aag cac ctt ttg aat cct ctt cct ggt tta aga atg att ggt ttc aaa     288
Lys His Leu Leu Asn Pro Leu Pro Gly Leu Arg Met Ile Gly Phe Lys
                85                  90                  95 caa tgg ctc ttg att tta tct ggg ttc ctt gca tgg act tgg gat gcc     336
Gln Trp Leu Leu Ile Leu Ser Gly Phe Leu Ala Trp Thr Trp Asp Ala
            100                 105                 110 tat gat ttc ttt tcg att tct cta aat act gtc caa ttg gct aag gat     384
Tyr Asp Phe Phe Ser Ile Ser Leu Asn Thr Val Gln Leu Ala Lys Asp
        115                 120                 125 ttt gat aag aca gtc aag gat atc acc tgg ggt att act gtt gtt ttg     432
Phe Asp Lys Thr Val Lys Asp Ile Thr Trp Gly Ile Thr Val Val Leu
    130                 135                 140 atg ttg aga tct gtc ggt ggt ttc ttc ttt ggt tac ttg ggt gat aag     480
Met Leu Arg Ser Val Gly Gly Phe Phe Phe Gly Tyr Leu Gly Asp Lys
145                 150                 155                 160 tac ggt aga aaa tgg cct tta att gca aat cta atg tgt gtc tgt ttt     528
Tyr Gly Arg Lys Trp Pro Leu Ile Ala Asn Leu Met Cys Val Cys Phe
                165                 170                 175 ctt gaa atc ggt act gga ttt atc aaa aac tac tcc caa ttc ttg ggt     576
Leu Glu Ile Gly Thr Gly Phe Ile Lys Asn Tyr Ser Gln Phe Leu Gly
            180                 185                 190 gtt agg gct gtt ttc ggt att atg ttg ggt ggt gtc tat ggt aat gcg     624
Val Arg Ala Val Phe Gly Ile Met Leu Gly Gly Val Tyr Gly Asn Ala
        195                 200                 205 gct gca act gcg ttg gat gat tgt cct gca gag gca agg ggc ttt att     672
Ala Ala Thr Ala Leu Asp Asp Cys Pro Ala Glu Ala Arg Gly Phe Ile
    210                 215                 220 tct ggt ttc tta caa caa ggt tac gca ttt ggt tat ttg ttg gct gtt     720
Ser Gly Phe Leu Gln Gln Gly Tyr Ala Phe Gly Tyr Leu Leu Ala Val
225                 230                 235                 240 gtt ttc aaa aga gca att gct gat aat tcc cct cac aga tgg aga gca     768
Val Phe Lys Arg Ala Ile Ala Asp Asn Ser Pro His Arg Trp Arg Ala
                245                 250                 255 atg ttt tgg ttc ggt gct ggt gtc tgt ttc tta att tgt tgc ttc aga     816
Met Phe Trp Phe Gly Ala Gly Val Cys Phe Leu Ile Cys Cys Phe Arg
            260                 265                 270 gct gtc ttg ccg gaa act aag gct ttc caa aga aac aag gaa att gaa     864
Ala Val Leu Pro Glu Thr Lys Ala Phe Gln Arg Asn Lys Glu Ile Glu
        275                 280                 285 agg tat aat gaa gaa cat ggt att cac cag agg tct ttc aag gaa aag     912
Arg Tyr Asn Glu Glu His Gly Ile His Gln Arg Ser Phe Lys Glu Lys
    290                 295                 300 gcc act gct tct ttg aag atc tac tgg ttg atg atc att tac atg gtt     960
Ala Thr Ala Ser Leu Lys Ile Tyr Trp Leu Met Ile Ile Tyr Met Val
305                 310                 315                 320
```

```
ctg tta atg gct ggt ttc aat ttc atg tcc cat ggt tct caa gat tta    1008
Leu Leu Met Ala Gly Phe Asn Phe Met Ser His Gly Ser Gln Asp Leu
            325                 330                 335 tat cca acc tta ttg act gtt aga tat aat ttt agt gat aat gct aca    1056
Tyr Pro Thr Leu Leu Thr Val Arg Tyr Asn Phe Ser Asp Asn Ala Thr
            340                 345                 350 act gtt aca aac tgt gtt gca aat att ggt gca atc aca ggt ggt atc    1104
Thr Val Thr Asn Cys Val Ala Asn Ile Gly Ala Ile Thr Gly Gly Ile
            355                 360                 365 att att gga cat ttc tcg aat ttc att ggt aga aga ttg tcg atc att    1152
Ile Ile Gly His Phe Ser Asn Phe Ile Gly Arg Arg Leu Ser Ile Ile
            370                 375                 380 atc tgc tgt att att ggt ggt gct cta att tat cct tgg gcc ttt gtt    1200
Ile Cys Cys Ile Ile Gly Gly Ala Leu Ile Tyr Pro Trp Ala Phe Val
385                 390                 395                 400 gac aat gca aac att aat gca gga gct ttc ttt tta cag ttc ttt gtg    1248
Asp Asn Ala Asn Ile Asn Ala Gly Ala Phe Phe Leu Gln Phe Phe Val
            405                 410                 415 caa ggt gct tgg ggt gtt gtt cca gtt cat tta tcc gaa ttg gca cca    1296
Gln Gly Ala Trp Gly Val Val Pro Val His Leu Ser Glu Leu Ala Pro
            420                 425                 430 cct gac ttc aaa gcc ttt gtt gtt ggt att gca tac caa ttg ggt aat    1344
Pro Asp Phe Lys Ala Phe Val Val Gly Ile Ala Tyr Gln Leu Gly Asn
            435                 440                 445 ttg gca tcc tct gca agt tcc acc att gaa aca aca att ggt gtg cac    1392
Leu Ala Ser Ser Ala Ser Ser Thr Ile Glu Thr Thr Ile Gly Val His
            450                 455                 460 ttc cca atg act tct cca ggt ggt gaa cca atc ttt gat tat gca aaa    1440
Phe Pro Met Thr Ser Pro Gly Gly Glu Pro Ile Phe Asp Tyr Ala Lys
465                 470                 475                 480 gtt atg gca att ttc gtt ggc tgt gtc ttt gca tat gtg tta ctt atc    1488
Val Met Ala Ile Phe Val Gly Cys Val Phe Ala Tyr Val Leu Leu Ile
            485                 490                 495 aca ttt att ggt cca gag agg aaa tct gtg tcc ttt gag gag cca gtt    1536
Thr Phe Ile Gly Pro Glu Arg Lys Ser Val Ser Phe Glu Glu Pro Val
            500                 505                 510 gat gag gat atc gaa atc aat gaa aaa atc aaa cac aat gaa gaa atc    1584
Asp Glu Asp Ile Glu Ile Asn Glu Lys Ile Lys His Asn Glu Glu Ile
            515                 520                 525 gag gct ggc tct aac ttg gga act tca aga gca taa                    1620
Glu Ala Gly Ser Asn Leu Gly Thr Ser Arg Ala
            530                 535

<210> SEQ ID NO 60
<211> LENGTH: 539
<212> TYPE: PRT
<213> ORGANISM: Issatchenkia orientalis

<400> SEQUENCE: 60

Met Thr Leu His Lys Asn Ser Asn Glu Gly Val Gln Ala Ser Gly Phe
1               5                   10                  15

Glu Leu Gln Asp Asn Leu Asp Val Pro His Ser Asn Ala Ser Phe Gln
            20                  25                  30

Ser Phe Lys Ser Asp Glu Ala Glu Gln Ala His Asn Asn Glu His Leu
        35                  40                  45

Met Glu Lys Pro Gln Phe Asn Lys Ala Thr Ile Ser Asn Tyr Cys Lys
    50                  55                  60

Thr Arg Phe Thr Glu Leu Phe Pro Thr Lys Gln Ser Met Ala Ala Asn
65                  70                  75                  80
```

-continued

```
Lys His Leu Leu Asn Pro Leu Pro Gly Leu Arg Met Ile Gly Phe Lys
                 85                  90                  95

Gln Trp Leu Leu Ile Leu Ser Gly Phe Leu Ala Trp Thr Trp Asp Ala
            100                 105                 110

Tyr Asp Phe Phe Ser Ile Ser Leu Asn Thr Val Gln Leu Ala Lys Asp
            115                 120                 125

Phe Asp Lys Thr Val Lys Asp Ile Thr Trp Gly Ile Thr Val Val Leu
    130                 135                 140

Met Leu Arg Ser Val Gly Phe Phe Gly Tyr Leu Gly Asp Lys
145                 150                 155                 160

Tyr Gly Arg Lys Trp Pro Leu Ile Ala Asn Leu Met Cys Val Cys Phe
                165                 170                 175

Leu Glu Ile Gly Thr Gly Phe Ile Lys Asn Tyr Ser Gln Phe Leu Gly
            180                 185                 190

Val Arg Ala Val Phe Gly Ile Met Leu Gly Gly Val Tyr Gly Asn Ala
        195                 200                 205

Ala Ala Thr Ala Leu Asp Asp Cys Pro Ala Glu Ala Arg Gly Phe Ile
        210                 215                 220

Ser Gly Phe Leu Gln Gln Gly Tyr Ala Phe Gly Tyr Leu Leu Ala Val
225                 230                 235                 240

Val Phe Lys Arg Ala Ile Ala Asp Asn Ser Pro His Arg Trp Arg Ala
                245                 250                 255

Met Phe Trp Phe Gly Ala Gly Val Cys Phe Leu Ile Cys Cys Phe Arg
            260                 265                 270

Ala Val Leu Pro Glu Thr Lys Ala Phe Gln Arg Asn Lys Glu Ile Glu
        275                 280                 285

Arg Tyr Asn Glu Glu His Gly Ile His Gln Arg Ser Phe Lys Glu Lys
    290                 295                 300

Ala Thr Ala Ser Leu Lys Ile Tyr Trp Leu Met Ile Ile Tyr Met Val
305                 310                 315                 320

Leu Leu Met Ala Gly Phe Asn Phe Met Ser His Gly Ser Gln Asp Leu
                325                 330                 335

Tyr Pro Thr Leu Leu Thr Val Arg Tyr Asn Phe Ser Asp Asn Ala Thr
            340                 345                 350

Thr Val Thr Asn Cys Val Ala Asn Ile Gly Ala Ile Thr Gly Gly Ile
        355                 360                 365

Ile Ile Gly His Phe Ser Asn Phe Ile Gly Arg Arg Leu Ser Ile Ile
    370                 375                 380

Ile Cys Cys Ile Ile Gly Gly Ala Leu Ile Tyr Pro Trp Ala Phe Val
385                 390                 395                 400

Asp Asn Ala Asn Ile Asn Ala Gly Ala Phe Phe Leu Gln Phe Val
                405                 410                 415

Gln Gly Ala Trp Gly Val Val Pro Val His Leu Ser Glu Leu Ala Pro
            420                 425                 430

Pro Asp Phe Lys Ala Phe Val Gly Ile Ala Tyr Gln Leu Gly Asn
        435                 440                 445

Leu Ala Ser Ser Ala Ser Ser Thr Ile Glu Thr Thr Ile Gly Val His
    450                 455                 460

Phe Pro Met Thr Ser Pro Gly Gly Glu Pro Ile Phe Asp Tyr Ala Lys
465                 470                 475                 480

Val Met Ala Ile Phe Val Gly Cys Val Phe Ala Tyr Val Leu Leu Ile
                485                 490                 495
```

-continued

```
Thr Phe Ile Gly Pro Glu Arg Lys Ser Val Ser Phe Glu Pro Val
            500                 505                 510

Asp Glu Asp Ile Glu Ile Asn Glu Lys Ile Lys His Asn Glu Glu Ile
        515                 520                 525

Glu Ala Gly Ser Asn Leu Gly Thr Ser Arg Ala
    530                 535

<210> SEQ ID NO 61
<211> LENGTH: 1737
<212> TYPE: DNA
<213> ORGANISM: Issatchenkia orientalis
<220> FEATURE:
<221> NAME/KEY: CDS
<222> LOCATION: (1)..(1737)

<400> SEQUENCE: 61 atg tta ctc aga tca cta aac tct tct gct cgt tgt gtc aaa caa aca     48
Met Leu Leu Arg Ser Leu Asn Ser Ser Ala Arg Cys Val Lys Gln Thr
1               5                   10                  15 acc aga aca aag gtt agg tat ctc agc cac gtc agt ggt gca agc atg     96
Thr Arg Thr Lys Val Arg Tyr Leu Ser His Val Ser Gly Ala Ser Met
                20                  25                  30 gcg aaa cct aca ttg aag aac aac tcg aga gaa tcc aac aaa tcc aga    144
Ala Lys Pro Thr Leu Lys Asn Asn Ser Arg Glu Ser Asn Lys Ser Arg
            35                  40                  45 aac tat cta att gct gct gtg aca gca ttg gct gta tca acc tca att    192
Asn Tyr Leu Ile Ala Ala Val Thr Ala Leu Ala Val Ser Thr Ser Ile
        50                  55                  60 gga gtt gcc gta cat gtg aag gac ccc ttg tat aac gat gct acc ggc    240
Gly Val Ala Val His Val Lys Asp Pro Leu Tyr Asn Asp Ala Thr Gly
65                  70                  75                  80 agt gat tct ccg aga agt ata tct gtt gac gag ttt gtc aag cat aat    288
Ser Asp Ser Pro Arg Ser Ile Ser Val Asp Glu Phe Val Lys His Asn
                85                  90                  95 tca caa aac gac tgt tgg att gca atc aat ggc aag gtt tat gat ttc    336
Ser Gln Asn Asp Cys Trp Ile Ala Ile Asn Gly Lys Val Tyr Asp Phe
            100                 105                 110 act gat ttt att cca aac cat cca ggt ggg gta cct cca tta gtt aat    384
Thr Asp Phe Ile Pro Asn His Pro Gly Gly Val Pro Pro Leu Val Asn
        115                 120                 125 cat gct ggt tat gat ggt act aaa ctt tat gag aaa ttg cat cca aaa    432
His Ala Gly Tyr Asp Gly Thr Lys Leu Tyr Glu Lys Leu His Pro Lys
    130                 135                 140 ggt aca att gag aaa ttc ttg cca aag gat aag ttt ctg ggt gtg tta    480
Gly Thr Ile Glu Lys Phe Leu Pro Lys Asp Lys Phe Leu Gly Val Leu
145                 150                 155                 160 gat ggt gaa gcg cca aaa ttg gaa gca gac tat ttg gtg gac gat gat    528
Asp Gly Glu Ala Pro Lys Leu Glu Ala Asp Tyr Leu Val Asp Asp Asp
                165                 170                 175 gaa caa gag aga ctg gat tat ttg aac aac tta cct cct ttg tca tct    576
Glu Gln Glu Arg Leu Asp Tyr Leu Asn Asn Leu Pro Pro Leu Ser Ser
            180                 185                 190 att cag aat gtt tat gat ttc gaa tac ttg gcc aag aag att tta cct    624
Ile Gln Asn Val Tyr Asp Phe Glu Tyr Leu Ala Lys Lys Ile Leu Pro
        195                 200                 205 aaa gat gcc tgg gca tat tat tct tgt ggt gcc gat gat gaa atc aca    672
Lys Asp Ala Trp Ala Tyr Tyr Ser Cys Gly Ala Asp Asp Glu Ile Thr
    210                 215                 220 atg aga gaa aac cat tat gct tat caa aga gtt tat ttc aga cca aga    720
Met Arg Glu Asn His Tyr Ala Tyr Gln Arg Val Tyr Phe Arg Pro Arg
225                 230                 235                 240
```

```
att tgt gtt gat gtc aag gaa gtt gat act tct tat gaa atg tta ggc    768
Ile Cys Val Asp Val Lys Glu Val Asp Thr Ser Tyr Glu Met Leu Gly
            245                 250                 255 act aaa acc tct gtt cct ttt tat gta tct gcc acc gct ttg gct aaa    816
Thr Lys Thr Ser Val Pro Phe Tyr Val Ser Ala Thr Ala Leu Ala Lys
        260                 265                 270 tta ggc cat cct gat ggt gaa tgc tca att gct aga ggc gct ggt aag    864
Leu Gly His Pro Asp Gly Glu Cys Ser Ile Ala Arg Gly Ala Gly Lys
    275                 280                 285 gaa ggt gtc gtt caa atg att tcg acc ctt tcc tca atg tca tta gat    912
Glu Gly Val Val Gln Met Ile Ser Thr Leu Ser Ser Met Ser Leu Asp
290                 295                 300 gaa att gcc gct gct aga att cca ggt gca acc caa tgg ttc caa tta    960
Glu Ile Ala Ala Ala Arg Ile Pro Gly Ala Thr Gln Trp Phe Gln Leu
305                 310                 315                 320 tac att aat gag gat aga aat gtc gct aaa ggt ctg gtc aaa cat gca   1008
Tyr Ile Asn Glu Asp Arg Asn Val Ala Lys Gly Leu Val Lys His Ala
                325                 330                 335 gaa gac ttg ggt atg aag gct atc ttt ata act gtt gat gct cct tct   1056
Glu Asp Leu Gly Met Lys Ala Ile Phe Ile Thr Val Asp Ala Pro Ser
            340                 345                 350 cta ggt aac aga gaa aag gat aaa aga tta aag ttt gtt aat gac acc   1104
Leu Gly Asn Arg Glu Lys Asp Lys Arg Leu Lys Phe Val Asn Asp Thr
        355                 360                 365 gat gtc gat ttg ggt gat tcc gca gat cga aac agt ggt gct tca aag   1152
Asp Val Asp Leu Gly Asp Ser Ala Asp Arg Asn Ser Gly Ala Ser Lys
    370                 375                 380 gca cta tct tcg ttc att gat gct tct gtc tct tgg aat gac gtc aaa   1200
Ala Leu Ser Ser Phe Ile Asp Ala Ser Val Ser Trp Asn Asp Val Lys
385                 390                 395                 400 gcg gtc aag tcg tgg act aaa ttg cct gtc tta gtt aaa ggt gtt caa   1248
Ala Val Lys Ser Trp Thr Lys Leu Pro Val Leu Val Lys Gly Val Gln
                405                 410                 415 aca gtt gaa gac gtt att gaa gct tac gat gct ggt tgt caa ggt gtt   1296
Thr Val Glu Asp Val Ile Glu Ala Tyr Asp Ala Gly Cys Gln Gly Val
            420                 425                 430 gtt ttg tca aac cac ggt ggt agg caa cta gat act gct cct cct cca   1344
Val Leu Ser Asn His Gly Gly Arg Gln Leu Asp Thr Ala Pro Pro Pro
        435                 440                 445 atc gaa tta tta gct gaa act gtt cca act ttg aag aga ttg ggt aaa   1392
Ile Glu Leu Leu Ala Glu Thr Val Pro Thr Leu Lys Arg Leu Gly Lys
    450                 455                 460 tta aga cca gat ttt gaa att tta att gac ggt ggt gtc aaa aga ggt   1440
Leu Arg Pro Asp Phe Glu Ile Leu Ile Asp Gly Gly Val Lys Arg Gly
465                 470                 475                 480 acc gat att ttg aaa gca gtc gca atc ggt ggc caa gat gtc aga gtt   1488
Thr Asp Ile Leu Lys Ala Val Ala Ile Gly Gly Gln Asp Val Arg Val
                485                 490                 495 tca gtt ggt atg ggt aga cct ttc tta tat gcc aac tct tgc tat ggt   1536
Ser Val Gly Met Gly Arg Pro Phe Leu Tyr Ala Asn Ser Cys Tyr Gly
            500                 505                 510 gaa gca ggt gtt aga aaa tta att caa aat cta aag gat gaa tta gaa   1584
Glu Ala Gly Val Arg Lys Leu Ile Gln Asn Leu Lys Asp Glu Leu Glu
        515                 520                 525 atg gat atg aga ttg ttg ggt gtc act aaa atg gac cag cta tct tcg   1632
Met Asp Met Arg Leu Leu Gly Val Thr Lys Met Asp Gln Leu Ser Ser
    530                 535                 540 aaa cat gtc gat act aaa cgt ttg att ggt aga gat gcg atc aac tat   1680
Lys His Val Asp Thr Lys Arg Leu Ile Gly Arg Asp Ala Ile Asn Tyr
```

```
                545             550             555             560
ttg tat gat aat gta tac agc cca atc gaa acc gtt aaa ttc aac aat    1728
Leu Tyr Asp Asn Val Tyr Ser Pro Ile Glu Thr Val Lys Phe Asn Asn
                565             570             575 gaa gat tga                                                        1737
Glu Asp

<210> SEQ ID NO 62
<211> LENGTH: 578
<212> TYPE: PRT
<213> ORGANISM: Issatchenkia orientalis

<400> SEQUENCE: 62

Met Leu Leu Arg Ser Leu Asn Ser Ser Ala Arg Cys Val Lys Gln Thr
1               5                   10                  15

Thr Arg Thr Lys Val Arg Tyr Leu Ser His Val Ser Gly Ala Ser Met
            20                  25                  30

Ala Lys Pro Thr Leu Lys Asn Asn Ser Arg Glu Ser Asn Lys Ser Arg
        35                  40                  45

Asn Tyr Leu Ile Ala Ala Val Thr Ala Leu Ala Val Ser Thr Ser Ile
    50                  55                  60

Gly Val Ala Val His Val Lys Asp Pro Leu Tyr Asn Asp Ala Thr Gly
65                  70                  75                  80

Ser Asp Ser Pro Arg Ser Ile Ser Val Asp Glu Phe Val Lys His Asn
                85                  90                  95

Ser Gln Asn Asp Cys Trp Ile Ala Ile Asn Gly Lys Val Tyr Asp Phe
            100                 105                 110

Thr Asp Phe Ile Pro Asn His Pro Gly Gly Val Pro Pro Leu Val Asn
        115                 120                 125

His Ala Gly Tyr Asp Gly Thr Lys Leu Tyr Glu Lys Leu His Pro Lys
    130                 135                 140

Gly Thr Ile Glu Lys Phe Leu Pro Lys Asp Lys Phe Leu Gly Val Leu
145                 150                 155                 160

Asp Gly Glu Ala Pro Lys Leu Glu Ala Asp Tyr Leu Val Asp Asp Asp
                165                 170                 175

Glu Gln Glu Arg Leu Asp Tyr Leu Asn Asn Leu Pro Pro Leu Ser Ser
            180                 185                 190

Ile Gln Asn Val Tyr Asp Phe Glu Tyr Leu Ala Lys Lys Ile Leu Pro
        195                 200                 205

Lys Asp Ala Trp Ala Tyr Tyr Ser Cys Gly Ala Asp Asp Glu Ile Thr
    210                 215                 220

Met Arg Glu Asn His Tyr Ala Tyr Gln Arg Val Tyr Phe Arg Pro Arg
225                 230                 235                 240

Ile Cys Val Asp Val Lys Glu Val Asp Thr Ser Tyr Glu Met Leu Gly
                245                 250                 255

Thr Lys Thr Ser Val Pro Phe Tyr Val Ser Ala Thr Ala Leu Ala Lys
            260                 265                 270

Leu Gly His Pro Asp Gly Glu Cys Ser Ile Ala Arg Gly Ala Gly Lys
        275                 280                 285

Glu Gly Val Val Gln Met Ile Ser Thr Leu Ser Ser Met Ser Leu Asp
    290                 295                 300

Glu Ile Ala Ala Ala Arg Ile Pro Gly Ala Thr Gln Trp Phe Gln Leu
305                 310                 315                 320

Tyr Ile Asn Glu Asp Arg Asn Val Ala Lys Gly Leu Val Lys His Ala
                325                 330                 335
```

```
Glu Asp Leu Gly Met Lys Ala Ile Phe Ile Thr Val Asp Ala Pro Ser
            340                 345                 350

Leu Gly Asn Arg Glu Lys Asp Lys Arg Leu Lys Phe Val Asn Asp Thr
        355                 360                 365

Asp Val Asp Leu Gly Asp Ser Ala Asp Arg Asn Ser Gly Ala Ser Lys
    370                 375                 380

Ala Leu Ser Ser Phe Ile Asp Ala Ser Val Ser Trp Asn Asp Val Lys
385                 390                 395                 400

Ala Val Lys Ser Trp Thr Lys Leu Pro Val Leu Val Lys Gly Val Gln
                405                 410                 415

Thr Val Glu Asp Val Ile Glu Ala Tyr Asp Ala Gly Cys Gln Gly Val
            420                 425                 430

Val Leu Ser Asn His Gly Gly Arg Gln Leu Asp Thr Ala Pro Pro Pro
        435                 440                 445

Ile Glu Leu Leu Ala Glu Thr Val Pro Thr Leu Lys Arg Leu Gly Lys
    450                 455                 460

Leu Arg Pro Asp Phe Glu Ile Leu Ile Asp Gly Gly Val Lys Arg Gly
465                 470                 475                 480

Thr Asp Ile Leu Lys Ala Val Ala Ile Gly Gly Gln Asp Val Arg Val
                485                 490                 495

Ser Val Gly Met Gly Arg Pro Phe Leu Tyr Ala Asn Ser Cys Tyr Gly
            500                 505                 510

Glu Ala Gly Val Arg Lys Leu Ile Gln Asn Leu Lys Asp Glu Leu Glu
        515                 520                 525

Met Asp Met Arg Leu Leu Gly Val Thr Lys Met Asp Gln Leu Ser Ser
    530                 535                 540

Lys His Val Asp Thr Lys Arg Leu Ile Gly Arg Asp Ala Ile Asn Tyr
545                 550                 555                 560

Leu Tyr Asp Asn Val Tyr Ser Pro Ile Glu Thr Val Lys Phe Asn Asn
                565                 570                 575

Glu Asp

<210> SEQ ID NO 63
<211> LENGTH: 1698
<212> TYPE: DNA
<213> ORGANISM: Issatchenkia orientalis
<220> FEATURE:
<221> NAME/KEY: CDS
<222> LOCATION: (1)..(1698)
<220> FEATURE:
<221> NAME/KEY: misc_feature
<222> LOCATION: (941)..(941)
<223> OTHER INFORMATION: n is a, c, g, or t
<220> FEATURE:
<221> NAME/KEY: misc_feature
<222> LOCATION: (943)..(943)
<223> OTHER INFORMATION: n is a, c, g, or t

<400> SEQUENCE: 63 atg tta aga tcc cag ttc aaa aac att ttg aaa aat gtt aac aag aac      48
Met Leu Arg Ser Gln Phe Lys Asn Ile Leu Lys Asn Val Asn Lys Asn
1               5                   10                  15 cat tct cta agg aga act ttt act tcc agc acc tca aag gct gga aaa      96
His Ser Leu Arg Arg Thr Phe Thr Ser Ser Thr Ser Lys Ala Gly Lys
            20                  25                  30 aat gct tca tac aat gcc aag att ata tct gca acc gtg gcc tcg att     144
Asn Ala Ser Tyr Asn Ala Lys Ile Ile Ser Ala Thr Val Ala Ser Ile
        35                  40                  45
```

| | | |
|---|---|---|
| gtt gca gca gct ggc tct tat atg ttg gtc cag cct tca cta gct aat<br>Val Ala Ala Ala Gly Ser Tyr Met Leu Val Gln Pro Ser Leu Ala Asn<br>50                         55                     60 | | 192 |
| gat gag gca cag tct gct aat cca act agg aag atc tct gtt gac gaa<br>Asp Glu Ala Gln Ser Ala Asn Pro Thr Arg Lys Ile Ser Val Asp Glu<br>65                     70                    75                    80 | | 240 |
| ttt gtt aaa cac aac cat gcc gat gat tgt tgg atc act gtt aac ggt<br>Phe Val Lys His Asn His Ala Asp Asp Cys Trp Ile Thr Val Asn Gly<br>                   85                    90                    95 | | 288 |
| aac gtc tat gac ttg act gat ttc att tca atg cat cca ggt ggt act<br>Asn Val Tyr Asp Leu Thr Asp Phe Ile Ser Met His Pro Gly Gly Thr<br>         100                     105                    110 | | 336 |
| acc cca ttg att caa aat gca ggt cac gac gca act gaa att tac aac<br>Thr Pro Leu Ile Gln Asn Ala Gly His Asp Ala Thr Glu Ile Tyr Asn<br>         115                     120                    125 | | 384 |
| aag att cat cca aag ggt aca atc gag aac ttc tta cca aag gaa aag<br>Lys Ile His Pro Lys Gly Thr Ile Glu Asn Phe Leu Pro Lys Glu Lys<br>130                        135                    140 | | 432 |
| caa ttg ggt gtt ttg gat ggt gaa gct cct aaa atc gaa gtt gtg ctt<br>Gln Leu Gly Val Leu Asp Gly Glu Ala Pro Lys Ile Glu Val Val Leu<br>145                        150                    155                160 | | 480 |
| gac gaa aag gag aaa cac aga ttg gag ttg ttg aat cat ctc cct gct<br>Asp Glu Lys Glu Lys His Arg Leu Glu Leu Leu Asn His Leu Pro Ala<br>         165                     170                    175 | | 528 |
| ctt tcc aga att caa aac att tat gat ttc gaa cat att gct tct aga<br>Leu Ser Arg Ile Gln Asn Ile Tyr Asp Phe Glu His Ile Ala Ser Arg<br>              180                     185                    190 | | 576 |
| gtt ttg agc gac caa gca tgg aac tac tat tca tgt ggt gcc gaa gat<br>Val Leu Ser Asp Gln Ala Trp Asn Tyr Tyr Ser Cys Gly Ala Glu Asp<br>         195                     200                    205 | | 624 |
| gaa atc acc ttg agg gaa aat cat tat gct tac caa aga atc tac ttt<br>Glu Ile Thr Leu Arg Glu Asn His Tyr Ala Tyr Gln Arg Ile Tyr Phe<br>210                        215                    220 | | 672 |
| aag cca aaa tgt tgt gtc aat gtt gca gaa gtt gat acc tct cat gaa<br>Lys Pro Lys Cys Cys Val Asn Val Ala Glu Val Asp Thr Ser His Glu<br>225                        230                    235                240 | | 720 |
| att tta ggt aca aaa gct tct gtt cct ttc tac gtt tcc gca gcc gct<br>Ile Leu Gly Thr Lys Ala Ser Val Pro Phe Tyr Val Ser Ala Ala Ala<br>         245                     250                    255 | | 768 |
| tct gca aag ttg ggg cac gag gat ggt gaa tgt tcc att gct aga ggt<br>Ser Ala Lys Leu Gly His Glu Asp Gly Glu Cys Ser Ile Ala Arg Gly<br>              260                     265                    270 | | 816 |
| gca ggt aag gaa ggc gtt att caa atg att tct tcc ttc tct tcc aac<br>Ala Gly Lys Glu Gly Val Ile Gln Met Ile Ser Ser Phe Ser Ser Asn<br>         275                     280                    285 | | 864 |
| tct ttg gag gaa att gca gaa tcc aga att cct ggt gca aca caa tgg<br>Ser Leu Glu Glu Ile Ala Glu Ser Arg Ile Pro Gly Ala Thr Gln Trp<br>290                        295                    300 | | 912 |
| ttt caa tta tac gtt aat gaa gac aag gnt ntt gtg aag aag act tta<br>Phe Gln Leu Tyr Val Asn Glu Asp Lys Xaa Xaa Val Lys Lys Thr Leu<br>305                        310                    315                320 | | 960 |
| aaa agg gcc gaa aac ttg ggt atg aag gcc atc ttt gtc act gtg gac<br>Lys Arg Ala Glu Asn Leu Gly Met Lys Ala Ile Phe Val Thr Val Asp<br>         325                     330                    335 | | 1008 |
| gct gct agt aga ggt aat aga gaa aaa gac att aca atg aga att acc<br>Ala Ala Ser Arg Gly Asn Arg Glu Lys Asp Ile Thr Met Arg Ile Thr<br>              340                     345                    350 | | 1056 |
| gaa gat aca gat gag tta ata gac gat tct tct gtt aga gct ggt tct<br>Glu Asp Thr Asp Glu Leu Ile Asp Asp Ser Ser Val Arg Ala Gly Ser<br>         355                     360                    365 | | 1104 |

-continued

| | | |
|---|---|---|
| acc tct ggt gca ttg cca gct ttc att gac aag agg ctg act tgg gat<br>Thr Ser Gly Ala Leu Pro Ala Phe Ile Asp Lys Arg Leu Thr Trp Asp<br>    370                        375                    380 | 1152 | |
| gaa gtt aag gat atc att tca tgg acc aag tta cca gtt ttg ctg aag<br>Glu Val Lys Asp Ile Ile Ser Trp Thr Lys Leu Pro Val Leu Leu Lys<br>385                    390                    395                  400 | 1200 | |
| ggt gtt caa aga act gat gat att gag aag gca att gat att ggt tgt<br>Gly Val Gln Arg Thr Asp Asp Ile Glu Lys Ala Ile Asp Ile Gly Cys<br>                  405                    410                  415 | 1248 | |
| aag ggt gtt gtc ttg tcc aat cat ggt ggt aga caa tta gat act tct<br>Lys Gly Val Val Leu Ser Asn His Gly Gly Arg Gln Leu Asp Thr Ser<br>420                    425                    430 | 1296 | |
| cct cct cca ata gaa gtt atg gct gaa tct gtt cca atc cta aag caa<br>Pro Pro Pro Ile Glu Val Met Ala Glu Ser Val Pro Ile Leu Lys Gln<br>          435                    440                    445 | 1344 | |
| aag ggt aaa ctg gat cca aat ttc agt att ttc gtt gat ggt ggt gtt<br>Lys Gly Lys Leu Asp Pro Asn Phe Ser Ile Phe Val Asp Gly Gly Val<br>    450                      455                    460 | 1392 | |
| aga aga ggt aca gat att ttg aaa gct ttg gct att ggt ggc aga gac<br>Arg Arg Gly Thr Asp Ile Leu Lys Ala Leu Ala Ile Gly Gly Arg Asp<br>465                    470                    475                  480 | 1440 | |
| tgt aaa gtt gct gtt ggt ctg ggt aga cct ttc ctt tat gca aat act<br>Cys Lys Val Ala Val Gly Leu Gly Arg Pro Phe Leu Tyr Ala Asn Thr<br>                  485                    490                    495 | 1488 | |
| ggt tat ggt gaa aag ggt gtc aga aag gcc gtg caa att cta aga gaa<br>Gly Tyr Gly Glu Lys Gly Val Arg Lys Ala Val Gln Ile Leu Arg Glu<br>          500                    505                    510 | 1536 | |
| gaa tta aag gct gac atg aga atg ttg ggc gtt acc tct ttg aac gag<br>Glu Leu Lys Ala Asp Met Arg Met Leu Gly Val Thr Ser Leu Asn Glu<br>    515                      520                    525 | 1584 | |
| cta gac gac tct tac att gac acc aga aga tta cta ggt aga gat gct<br>Leu Asp Asp Ser Tyr Ile Asp Thr Arg Arg Leu Leu Gly Arg Asp Ala<br>530                    535                    540 | 1632 | |
| gtt aac cac ata tac aac aac aac tac tac cca atg tct aag att caa<br>Val Asn His Ile Tyr Asn Asn Asn Tyr Tyr Pro Met Ser Lys Ile Gln<br>545                    550                    555                  560 | 1680 | |
| ttc aaa aac gaa aaa taa<br>Phe Lys Asn Glu Lys<br>                565 | 1698 | |

```
<210> SEQ ID NO 64
<211> LENGTH: 565
<212> TYPE: PRT
<213> ORGANISM: Issatchenkia orientalis
<220> FEATURE:
<221> NAME/KEY: misc_feature
<222> LOCATION: (314)..(314)
<223> OTHER INFORMATION: The 'Xaa' at location 314 stands for Asp, y,
      Ala, or Val.
<220> FEATURE:
<221> NAME/KEY: misc_feature
<222> LOCATION: (315)..(315)
<223> OTHER INFORMATION: The 'Xaa' at location 315 stands for Ile, l,
      Leu, or Phe.

<400> SEQUENCE: 64
```

Met Leu Arg Ser Gln Phe Lys Asn Ile Leu Lys Asn Val Asn Lys Asn
1                 5                      10                     15

His Ser Leu Arg Arg Thr Phe Thr Ser Ser Thr Ser Lys Ala Gly Lys
              20                      25                      30

Asn Ala Ser Tyr Asn Ala Lys Ile Ile Ser Ala Thr Val Ala Ser Ile
        35                      40                      45

```
Val Ala Ala Ala Gly Ser Tyr Met Leu Val Gln Pro Ser Leu Ala Asn
     50                  55                  60

Asp Glu Ala Gln Ser Ala Asn Pro Thr Arg Lys Ile Ser Val Asp Glu
 65                  70                  75                  80

Phe Val Lys His Asn His Ala Asp Asp Cys Trp Ile Thr Val Asn Gly
                     85                  90                  95

Asn Val Tyr Asp Leu Thr Asp Phe Ile Ser Met His Pro Gly Gly Thr
                100                 105                 110

Thr Pro Leu Ile Gln Asn Ala Gly His Asp Ala Thr Glu Ile Tyr Asn
            115                 120                 125

Lys Ile His Pro Lys Gly Thr Ile Glu Asn Phe Leu Pro Lys Glu Lys
130                 135                 140

Gln Leu Gly Val Leu Asp Gly Glu Ala Pro Lys Ile Glu Val Val Leu
145                 150                 155                 160

Asp Glu Lys Glu Lys His Arg Leu Glu Leu Leu Asn His Leu Pro Ala
                165                 170                 175

Leu Ser Arg Ile Gln Asn Ile Tyr Asp Phe Glu His Ile Ala Ser Arg
            180                 185                 190

Val Leu Ser Asp Gln Ala Trp Asn Tyr Tyr Ser Cys Gly Ala Glu Asp
        195                 200                 205

Glu Ile Thr Leu Arg Glu Asn His Tyr Ala Tyr Gln Arg Ile Tyr Phe
    210                 215                 220

Lys Pro Lys Cys Cys Val Asn Val Ala Glu Val Asp Thr Ser His Glu
225                 230                 235                 240

Ile Leu Gly Thr Lys Ala Ser Val Pro Phe Tyr Val Ser Ala Ala Ala
                245                 250                 255

Ser Ala Lys Leu Gly His Glu Asp Gly Glu Cys Ser Ile Ala Arg Gly
            260                 265                 270

Ala Gly Lys Glu Gly Val Ile Gln Met Ile Ser Ser Phe Ser Ser Asn
        275                 280                 285

Ser Leu Glu Glu Ile Ala Glu Ser Arg Ile Pro Gly Ala Thr Gln Trp
    290                 295                 300

Phe Gln Leu Tyr Val Asn Glu Asp Lys Xaa Xaa Val Lys Lys Thr Leu
305                 310                 315                 320

Lys Arg Ala Glu Asn Leu Gly Met Lys Ala Ile Phe Val Thr Val Asp
                325                 330                 335

Ala Ala Ser Arg Gly Asn Arg Glu Lys Asp Ile Thr Met Arg Ile Thr
            340                 345                 350

Glu Asp Thr Asp Glu Leu Ile Asp Asp Ser Ser Val Arg Ala Gly Ser
        355                 360                 365

Thr Ser Gly Ala Leu Pro Ala Phe Ile Asp Lys Arg Leu Thr Trp Asp
    370                 375                 380

Glu Val Lys Asp Ile Ile Ser Trp Thr Lys Leu Pro Val Leu Leu Lys
385                 390                 395                 400

Gly Val Gln Arg Thr Asp Asp Ile Glu Lys Ala Ile Asp Ile Gly Cys
                405                 410                 415

Lys Gly Val Val Leu Ser Asn His Gly Gly Arg Gln Leu Asp Thr Ser
            420                 425                 430

Pro Pro Pro Ile Glu Val Met Ala Glu Ser Val Pro Ile Leu Lys Gln
        435                 440                 445

Lys Gly Lys Leu Asp Pro Asn Phe Ser Ile Phe Val Asp Gly Gly Val
    450                 455                 460
```

```
Arg Arg Gly Thr Asp Ile Leu Lys Ala Leu Ala Ile Gly Gly Arg Asp
465                 470                 475                 480

Cys Lys Val Ala Val Gly Leu Gly Arg Pro Phe Leu Tyr Ala Asn Thr
            485                 490                 495

Gly Tyr Gly Glu Lys Gly Val Arg Lys Ala Val Gln Ile Leu Arg Glu
        500                 505                 510

Glu Leu Lys Ala Asp Met Arg Met Leu Gly Val Thr Ser Leu Asn Glu
    515                 520                 525

Leu Asp Asp Ser Tyr Ile Asp Thr Arg Arg Leu Leu Gly Arg Asp Ala
530                 535                 540

Val Asn His Ile Tyr Asn Asn Tyr Tyr Pro Met Ser Lys Ile Gln
545                 550                 555                 560

Phe Lys Asn Glu Lys
            565

<210> SEQ ID NO 65
<211> LENGTH: 933
<212> TYPE: DNA
<213> ORGANISM: Issatchenkia orientalis
<220> FEATURE:
<221> NAME/KEY: CDS
<222> LOCATION: (1)..(933)

<400> SEQUENCE: 65 atg act ttg aag tcc aaa tca aaa tcc aaa aag aag cac gca tcc tca      48
Met Thr Leu Lys Ser Lys Ser Lys Ser Lys Lys Lys His Ala Ser Ser
1               5                   10                  15 aaa cca ctg gaa tca tct aat aaa atg tcc aaa agt agt gtt gaa cac      96
Lys Pro Leu Glu Ser Ser Asn Lys Met Ser Lys Ser Ser Val Glu His
            20                  25                  30 cat gaa cat acc tca aat aag gaa aat gac cat att tcc ttg cat tcc     144
His Glu His Thr Ser Asn Lys Glu Asn Asp His Ile Ser Leu His Ser
        35                  40                  45 cgc ttg acg aat att gaa cat cag atc atg ggc aaa gta cat aca agt     192
Arg Leu Thr Asn Ile Glu His Gln Ile Met Gly Lys Val His Thr Ser
    50                  55                  60 gat gac ggc gcc tat gtt atc tta gac aac aaa aag tat cct aag tca     240
Asp Asp Gly Ala Tyr Val Ile Leu Asp Asn Lys Lys Tyr Pro Lys Ser
65                  70                  75                  80 gaa tta ttg aag gcc ttt ggt ggt ttt atg aac cct ggt tgg gca gtg     288
Glu Leu Leu Lys Ala Phe Gly Gly Phe Met Asn Pro Gly Trp Ala Val
                85                  90                  95 cct tcc gaa cac aag ttt ggt aat cca gct cct ttg ggt cta tct gca     336
Pro Ser Glu His Lys Phe Gly Asn Pro Ala Pro Leu Gly Leu Ser Ala
            100                 105                 110 ttt gcg tat tgt act ttt gtt gca tct ttg gtc aac atg caa act aga     384
Phe Ala Tyr Cys Thr Phe Val Ala Ser Leu Val Asn Met Gln Thr Arg
        115                 120                 125 cat gtt gaa aat gat gct gtt aat gtc ggt gct gca atg ttt tat ggt     432
His Val Glu Asn Asp Ala Val Asn Val Gly Ala Ala Met Phe Tyr Gly
    130                 135                 140 ggt ttt atc cag ttc att gcc gga ctt tgg gaa ata tcg ctt gaa aac     480
Gly Phe Ile Gln Phe Ile Ala Gly Leu Trp Glu Ile Ser Leu Glu Asn
145                 150                 155                 160 gct ttt ggt ggt ttg gca ttt tgc tct ttt gga ggt tac tgg atg gca     528
Ala Phe Gly Gly Leu Ala Phe Cys Ser Phe Gly Gly Tyr Trp Met Ala
                165                 170                 175 tcg gcc tca aac cat atc ccc tgg ttc cat att gct agc tct tat act     576
Ser Ala Ser Asn His Ile Pro Trp Phe His Ile Ala Ser Ser Tyr Thr
            180                 185                 190
```

```
aca gaa gca gaa ttc aaa tca ggt atg gga ttt ttc tac ctt ggt tgg     624
Thr Glu Ala Glu Phe Lys Ser Gly Met Gly Phe Phe Tyr Leu Gly Trp
            195                 200                 205 cta ctc ttt aca ata atc ttg cta gct tgt tca atc aaa tct acc att     672
Leu Leu Phe Thr Ile Ile Leu Leu Ala Cys Ser Ile Lys Ser Thr Ile
210                 215                 220 tta ttt ttc ctg ttg ttt gtg ctg gtc ttt atg aga ttg ctg tta tta     720
Leu Phe Phe Leu Leu Phe Val Leu Val Phe Met Arg Leu Leu Leu Leu
225                 230                 235                 240 aca tgt tgg aag ttt gcg gac agt cat gcc tgt gag ttt gct gct ggt     768
Thr Cys Trp Lys Phe Ala Asp Ser His Ala Cys Glu Phe Ala Ala Gly
            245                 250                 255 gtt ttc ggt gtt ttg gca tct ctg tta gca tgg tat cat gca tat gca     816
Val Phe Gly Val Leu Ala Ser Leu Leu Ala Trp Tyr His Ala Tyr Ala
        260                 265                 270 ggt att gca aca cct cag aat tct tac tat gtt gtt aat cca aca cct     864
Gly Ile Ala Thr Pro Gln Asn Ser Tyr Tyr Val Val Asn Pro Thr Pro
        275                 280                 285 atg cct gtt att gga tca aag agc aaa gat atg ttt gat tct gac gac     912
Met Pro Val Ile Gly Ser Lys Ser Lys Asp Met Phe Asp Ser Asp Asp
290                 295                 300 ttt gac caa tct tca tct tga                                         933
Phe Asp Gln Ser Ser Ser
305                 310

<210> SEQ ID NO 66
<211> LENGTH: 310
<212> TYPE: PRT
<213> ORGANISM: Issatchenkia orientalis

<400> SEQUENCE: 66

Met Thr Leu Lys Ser Lys Ser Lys Ser Lys Lys His Ala Ser Ser
1               5                   10                  15

Lys Pro Leu Glu Ser Ser Asn Lys Met Ser Lys Ser Ser Val Glu His
            20                  25                  30

His Glu His Thr Ser Asn Lys Glu Asn Asp His Ile Ser Leu His Ser
        35                  40                  45

Arg Leu Thr Asn Ile Glu His Gln Ile Met Gly Lys Val His Thr Ser
    50                  55                  60

Asp Asp Gly Ala Tyr Val Ile Leu Asp Asn Lys Lys Tyr Pro Lys Ser
65                  70                  75                  80

Glu Leu Leu Lys Ala Phe Gly Gly Phe Met Asn Pro Gly Trp Ala Val
                85                  90                  95

Pro Ser Glu His Lys Phe Gly Asn Pro Ala Pro Leu Gly Leu Ser Ala
            100                 105                 110

Phe Ala Tyr Cys Thr Phe Val Ala Ser Leu Val Asn Met Gln Thr Arg
        115                 120                 125

His Val Glu Asn Asp Ala Val Asn Val Gly Ala Ala Met Phe Tyr Gly
    130                 135                 140

Gly Phe Ile Gln Phe Ile Ala Gly Leu Trp Glu Ile Ser Leu Glu Asn
145                 150                 155                 160

Ala Phe Gly Gly Leu Ala Phe Cys Ser Phe Gly Gly Tyr Trp Met Ala
                165                 170                 175

Ser Ala Ser Asn His Ile Pro Trp Phe His Ile Ala Ser Ser Tyr Thr
            180                 185                 190

Thr Glu Ala Glu Phe Lys Ser Gly Met Gly Phe Phe Tyr Leu Gly Trp
        195                 200                 205
```

```
Leu Leu Phe Thr Ile Ile Leu Ala Cys Ser Ile Lys Ser Thr Ile
        210                 215                 220

Leu Phe Phe Leu Leu Phe Val Leu Val Phe Met Arg Leu Leu Leu Leu
225                 230                 235                 240

Thr Cys Trp Lys Phe Ala Asp Ser His Ala Cys Glu Phe Ala Ala Gly
                245                 250                 255

Val Phe Gly Val Leu Ala Ser Leu Leu Ala Trp Tyr His Ala Tyr Ala
            260                 265                 270

Gly Ile Ala Thr Pro Gln Asn Ser Tyr Tyr Val Val Asn Pro Thr Pro
        275                 280                 285

Met Pro Val Ile Gly Ser Lys Ser Lys Asp Met Phe Asp Ser Asp Asp
    290                 295                 300

Phe Asp Gln Ser Ser Ser
305                 310

<210> SEQ ID NO 67
<211> LENGTH: 1134
<212> TYPE: DNA
<213> ORGANISM: Issatchenkia orientalis
<220> FEATURE:
<221> NAME/KEY: CDS
<222> LOCATION: (1)..(1134)

<400> SEQUENCE: 67 atg tta tcc aag acc atc act gct gca ttg agg ggc aat aca act cgt    48
Met Leu Ser Lys Thr Ile Thr Ala Ala Leu Arg Gly Asn Thr Thr Arg
1               5                   10                  15 act gca ttc aga atc aat gcc att aga agt tta gcg atc cca gct att    96
Thr Ala Phe Arg Ile Asn Ala Ile Arg Ser Leu Ala Ile Pro Ala Ile
                20                  25                  30 cca gag aca caa aag ggt gtt atc ttt tat gag aac gga ggt gaa cta   144
Pro Glu Thr Gln Lys Gly Val Ile Phe Tyr Glu Asn Gly Gly Glu Leu
            35                  40                  45 ttt tac aag gac att cca gtt cca aag cca aag cca aat gag att ttg   192
Phe Tyr Lys Asp Ile Pro Val Pro Lys Pro Lys Pro Asn Glu Ile Leu
        50                  55                  60 gtg aat gtc aag tat tct ggt gtt tgt cat acc gat tta cac gca tgg   240
Val Asn Val Lys Tyr Ser Gly Val Cys His Thr Asp Leu His Ala Trp
65                  70                  75                  80 aaa ggt gac tgg cct ttg gcg acc aag ttg cca ttg gtt ggt gga cat   288
Lys Gly Asp Trp Pro Leu Ala Thr Lys Leu Pro Leu Val Gly Gly His
                85                  90                  95 gaa ggt gcc gga gtt gtt gtt gct aag ggg gac aat gtc acc aac ttt   336
Glu Gly Ala Gly Val Val Val Ala Lys Gly Asp Asn Val Thr Asn Phe
            100                 105                 110 gaa att ggc gat tat gcc ggt atc aag tgg ttg aat ggt tca tgt atg   384
Glu Ile Gly Asp Tyr Ala Gly Ile Lys Trp Leu Asn Gly Ser Cys Met
        115                 120                 125 ggg tgt gaa ttt tgc caa caa ggt gca gag cca aac tgt cca cag gcc   432
Gly Cys Glu Phe Cys Gln Gln Gly Ala Glu Pro Asn Cys Pro Gln Ala
130                 135                 140 gac ttg agt ggt tac acc cat gac ggg tcc ttt caa caa tat gcc act   480
Asp Leu Ser Gly Tyr Thr His Asp Gly Ser Phe Gln Gln Tyr Ala Thr
145                 150                 155                 160 gcc gat gct gtt cag gca gcc aag att cct cag ggc act gat ttg gct   528
Ala Asp Ala Val Gln Ala Ala Lys Ile Pro Gln Gly Thr Asp Leu Ala
                165                 170                 175 caa gtt gcg cca att tta tgt gca ggt att act gtc tat aag gct tta   576
Gln Val Ala Pro Ile Leu Cys Ala Gly Ile Thr Val Tyr Lys Ala Leu
```

```
                180                 185                 190
aag act gca gaa tta aga cca ggt caa tgg gtt gcc att tct ggt gct        624
Lys Thr Ala Glu Leu Arg Pro Gly Gln Trp Val Ala Ile Ser Gly Ala
            195                 200                 205 gct gga ggt tta ggt tct ctt gct gtt caa tat gcc aag gcc atg ggt        672
Ala Gly Gly Leu Gly Ser Leu Ala Val Gln Tyr Ala Lys Ala Met Gly
    210                 215                 220 ttg aga gtt ttg ggt att gat ggt ggt gag gag aag ggc aag ttt gca        720
Leu Arg Val Leu Gly Ile Asp Gly Gly Glu Glu Lys Gly Lys Phe Ala
225                 230                 235                 240 aag tct ctt gga gct gaa gtt ttc att gat ttc acc aaa tcc aag gac        768
Lys Ser Leu Gly Ala Glu Val Phe Ile Asp Phe Thr Lys Ser Lys Asp
                245                 250                 255 att gtc aag gat atc caa gag gcc acc aat ggt ggt cca cat ggt gtc        816
Ile Val Lys Asp Ile Gln Glu Ala Thr Asn Gly Gly Pro His Gly Val
            260                 265                 270 att aat gtt tct gtt tct cca gct gct att tct caa agt acc cag tat        864
Ile Asn Val Ser Val Ser Pro Ala Ala Ile Ser Gln Ser Thr Gln Tyr
        275                 280                 285 gtc aga acc ttg ggt aag gtt gtc ctt gtt gga tta cca gcg cat gct        912
Val Arg Thr Leu Gly Lys Val Val Leu Val Gly Leu Pro Ala His Ala
    290                 295                 300 gta tgc gag tct tcg gtt ttc gac cat gtt gtc aag tcg att caa att        960
Val Cys Glu Ser Ser Val Phe Asp His Val Val Lys Ser Ile Gln Ile
305                 310                 315                 320 aga ggc tct tat gtt ggt aac agg gaa gat act agt gag gct att gat       1008
Arg Gly Ser Tyr Val Gly Asn Arg Glu Asp Thr Ser Glu Ala Ile Asp
                325                 330                 335 ttt ttc acc agg ggt tta gtg aag tca cca att aag att gtt ggt ttg       1056
Phe Phe Thr Arg Gly Leu Val Lys Ser Pro Ile Lys Ile Val Gly Leu
            340                 345                 350 agt gag ttg cca aag atc tat gaa ttg atg gag caa ggt aag att tta       1104
Ser Glu Leu Pro Lys Ile Tyr Glu Leu Met Glu Gln Gly Lys Ile Leu
        355                 360                 365 ggc aga tat gtt gtt gac act tcg aaa tga                               1134
Gly Arg Tyr Val Val Asp Thr Ser Lys
    370                 375

<210> SEQ ID NO 68
<211> LENGTH: 377
<212> TYPE: PRT
<213> ORGANISM: Issatchenkia orientalis

<400> SEQUENCE: 68

Met Leu Ser Lys Thr Ile Thr Ala Ala Leu Arg Gly Asn Thr Thr Arg
1               5                   10                  15

Thr Ala Phe Arg Ile Asn Ala Ile Arg Ser Leu Ala Ile Pro Ala Ile
            20                  25                  30

Pro Glu Thr Gln Lys Gly Val Ile Phe Tyr Glu Asn Gly Gly Glu Leu
        35                  40                  45

Phe Tyr Lys Asp Ile Pro Val Pro Lys Pro Lys Asn Glu Ile Leu
    50                  55                  60

Val Asn Val Lys Tyr Ser Gly Val Cys His Thr Asp Leu His Ala Trp
65              70                  75                  80

Lys Gly Asp Trp Pro Leu Ala Thr Lys Leu Pro Leu Val Gly Gly His
            85                  90                  95

Glu Gly Ala Gly Val Val Ala Lys Gly Asp Asn Val Thr Asn Phe
        100                 105                 110
```

-continued

```
Glu Ile Gly Asp Tyr Ala Gly Ile Lys Trp Leu Asn Gly Ser Cys Met
            115                 120                 125

Gly Cys Glu Phe Cys Gln Gln Gly Ala Glu Pro Asn Cys Pro Gln Ala
130                 135                 140

Asp Leu Ser Gly Tyr Thr His Asp Gly Ser Phe Gln Gln Tyr Ala Thr
145                 150                 155                 160

Ala Asp Ala Val Gln Ala Ala Lys Ile Pro Gln Gly Thr Asp Leu Ala
                165                 170                 175

Gln Val Ala Pro Ile Leu Cys Ala Gly Ile Thr Val Tyr Lys Ala Leu
            180                 185                 190

Lys Thr Ala Glu Leu Arg Pro Gly Gln Trp Val Ala Ile Ser Gly Ala
        195                 200                 205

Ala Gly Gly Leu Gly Ser Leu Ala Val Gln Tyr Ala Lys Ala Met Gly
    210                 215                 220

Leu Arg Val Leu Gly Ile Asp Gly Gly Glu Glu Lys Gly Lys Phe Ala
225                 230                 235                 240

Lys Ser Leu Gly Ala Glu Val Phe Ile Asp Phe Thr Lys Ser Lys Asp
                245                 250                 255

Ile Val Lys Asp Ile Gln Glu Ala Thr Asn Gly Gly Pro His Gly Val
            260                 265                 270

Ile Asn Val Ser Val Ser Pro Ala Ala Ile Ser Gln Ser Thr Gln Tyr
        275                 280                 285

Val Arg Thr Leu Gly Lys Val Val Leu Val Gly Leu Pro Ala His Ala
    290                 295                 300

Val Cys Glu Ser Ser Val Phe Asp His Val Val Lys Ser Ile Gln Ile
305                 310                 315                 320

Arg Gly Ser Tyr Val Gly Asn Arg Glu Asp Thr Ser Glu Ala Ile Asp
                325                 330                 335

Phe Phe Thr Arg Gly Leu Val Lys Ser Pro Ile Lys Ile Val Gly Leu
            340                 345                 350

Ser Glu Leu Pro Lys Ile Tyr Glu Leu Met Glu Gln Gly Lys Ile Leu
        355                 360                 365

Gly Arg Tyr Val Val Asp Thr Ser Lys
    370                 375
```

<210> SEQ ID NO 69
<211> LENGTH: 20
<212> TYPE: DNA
<213> ORGANISM: Artificial Sequence
<220> FEATURE:
<223> OTHER INFORMATION: PCR primer

<400> SEQUENCE: 69
tctctggtct tcaaacatgg    20

<210> SEQ ID NO 70
<211> LENGTH: 24
<212> TYPE: DNA
<213> ORGANISM: Artificial Sequence
<220> FEATURE:
<223> OTHER INFORMATION: PCR primer

<400> SEQUENCE: 70
cttcaaagtg gtgcatgcgg tgag    24

<210> SEQ ID NO 71
<211> LENGTH: 20
<212> TYPE: DNA

```
<213> ORGANISM: Artificial Sequence
<220> FEATURE:
<223> OTHER INFORMATION: PCR primer

<400> SEQUENCE: 71
actcttctgc tcgttgtgtc                                                 20

<210> SEQ ID NO 72
<211> LENGTH: 20
<212> TYPE: DNA
<213> ORGANISM: Artificial Sequence
<220> FEATURE:
<223> OTHER INFORMATION: PCR primer

<400> SEQUENCE: 72
gtttgaccag acctttagcg                                                 20

<210> SEQ ID NO 73
<211> LENGTH: 20
<212> TYPE: DNA
<213> ORGANISM: Artificial Sequence
<220> FEATURE:
<223> OTHER INFORMATION: PCR primer

<400> SEQUENCE: 73
caacggcaac agtttacagg                                                 20

<210> SEQ ID NO 74
<211> LENGTH: 1032
<212> TYPE: DNA
<213> ORGANISM: Bacteriophage P1
<220> FEATURE:
<221> NAME/KEY: CDS
<222> LOCATION: (1)..(1032)

<400> SEQUENCE: 74
```

| | | | | | | | | | | | | | | | | |
|---|---|---|---|---|---|---|---|---|---|---|---|---|---|---|---|---|
| atg | tct | aat | tta | ctt | act | gtt | cac | caa | aac | ttg | cct | gca | tta | cca | gtt | 48 |
| Met | Ser | Asn | Leu | Leu | Thr | Val | His | Gln | Asn | Leu | Pro | Ala | Leu | Pro | Val | |
| 1 | | | | 5 | | | | | 10 | | | | | 15 | | |
| gac | gca | acc | tcc | gat | gaa | gtc | aga | aag | aac | ctt | atg | gat | atg | ttt | aga | 96 |
| Asp | Ala | Thr | Ser | Asp | Glu | Val | Arg | Lys | Asn | Leu | Met | Asp | Met | Phe | Arg | |
| | | | 20 | | | | | 25 | | | | | 30 | | | |
| gat | aga | caa | gct | ttc | tcc | gaa | cat | act | tgg | aaa | atg | tta | tta | tcc | gtt | 144 |
| Asp | Arg | Gln | Ala | Phe | Ser | Glu | His | Thr | Trp | Lys | Met | Leu | Leu | Ser | Val | |
| | | 35 | | | | | 40 | | | | | 45 | | | | |
| tgt | aga | tcc | tgg | gcc | gct | tgg | tgt | aaa | ctt | aac | aat | aga | aaa | tgg | ttt | 192 |
| Cys | Arg | Ser | Trp | Ala | Ala | Trp | Cys | Lys | Leu | Asn | Asn | Arg | Lys | Trp | Phe | |
| | 50 | | | | | 55 | | | | | 60 | | | | | |
| cct | gct | gaa | cca | gaa | gac | gtc | aga | gat | tac | tta | ctt | tac | tta | caa | gct | 240 |
| Pro | Ala | Glu | Pro | Glu | Asp | Val | Arg | Asp | Tyr | Leu | Leu | Tyr | Leu | Gln | Ala | |
| 65 | | | | | 70 | | | | | 75 | | | | | 80 | |
| aga | ggt | ttg | gct | gtt | aaa | act | atc | caa | caa | cac | tta | ggt | caa | ttg | aat | 288 |
| Arg | Gly | Leu | Ala | Val | Lys | Thr | Ile | Gln | Gln | His | Leu | Gly | Gln | Leu | Asn | |
| | | | | 85 | | | | | 90 | | | | | 95 | | |
| atg | tta | cac | aga | aga | tcc | ggt | tta | cca | aga | cca | tcc | gat | tcc | aac | gca | 336 |
| Met | Leu | His | Arg | Arg | Ser | Gly | Leu | Pro | Arg | Pro | Ser | Asp | Ser | Asn | Ala | |
| | | | 100 | | | | | 105 | | | | | 110 | | | |
| gtt | tcc | ctt | gtt | atg | aga | aga | att | aga | aaa | gaa | aat | gtt | gac | gct | ggt | 384 |
| Val | Ser | Leu | Val | Met | Arg | Arg | Ile | Arg | Lys | Glu | Asn | Val | Asp | Ala | Gly | |
| | | | | 115 | | | | | 120 | | | | | 125 | | |
| gaa | aga | gct | aaa | caa | gca | tta | gca | ttt | gaa | aga | acc | gat | ttc | gat | caa | 432 |
| Glu | Arg | Ala | Lys | Gln | Ala | Leu | Ala | Phe | Glu | Arg | Thr | Asp | Phe | Asp | Gln | |
| | 130 | | | | | 135 | | | | | 140 | | | | | |

-continued

```
gtt aga tcc tta atg gaa aat tcc gat aga tgt caa gat att aga aac      480
Val Arg Ser Leu Met Glu Asn Ser Asp Arg Cys Gln Asp Ile Arg Asn
145                 150                 155                 160 tta gct ttc tta ggt att gct tac aac aca tta tta aga atc gct gaa      528
Leu Ala Phe Leu Gly Ile Ala Tyr Asn Thr Leu Leu Arg Ile Ala Glu
                165                 170                 175 att gct aga att aga gtt aaa gat att tca aga acc gat ggc ggt aga      576
Ile Ala Arg Ile Arg Val Lys Asp Ile Ser Arg Thr Asp Gly Gly Arg
            180                 185                 190 atg tta atc cac att ggc aga aca aaa acc tta gtc tcc aca gca ggc      624
Met Leu Ile His Ile Gly Arg Thr Lys Thr Leu Val Ser Thr Ala Gly
        195                 200                 205 gtc gaa aaa gca tta tca tta ggt gtt act aaa tta gtt gaa cgt tgg      672
Val Glu Lys Ala Leu Ser Leu Gly Val Thr Lys Leu Val Glu Arg Trp
    210                 215                 220 att tcc gtt tcc ggt gtt gca gat gac cca aac aac tac tta ttc tgt      720
Ile Ser Val Ser Gly Val Ala Asp Asp Pro Asn Asn Tyr Leu Phe Cys
225                 230                 235                 240 cgt gtt aga aaa aat ggt gtt gcc gct cct tcc gct acc tca caa tta      768
Arg Val Arg Lys Asn Gly Val Ala Ala Pro Ser Ala Thr Ser Gln Leu
                245                 250                 255 tcc aca aga gca tta gaa ggc att ttt gaa gct acc cac aga ctt att      816
Ser Thr Arg Ala Leu Glu Gly Ile Phe Glu Ala Thr His Arg Leu Ile
            260                 265                 270 tat ggt gca aaa gac gat tcc ggt caa aga tat tta gct tgg tct ggt      864
Tyr Gly Ala Lys Asp Asp Ser Gly Gln Arg Tyr Leu Ala Trp Ser Gly
        275                 280                 285 cat tcc gct aga gtt ggt gcc gca aga gac atg gca aga gct ggt gtt      912
His Ser Ala Arg Val Gly Ala Ala Arg Asp Met Ala Arg Ala Gly Val
    290                 295                 300 tct att cct gaa att atg caa gcc ggt ggt tgg act aat gtt aac att      960
Ser Ile Pro Glu Ile Met Gln Ala Gly Gly Trp Thr Asn Val Asn Ile
305                 310                 315                 320 gtt atg aac tat atc aga aac tta gat tcc gaa aca ggt gct atg gtt     1008
Val Met Asn Tyr Ile Arg Asn Leu Asp Ser Glu Thr Gly Ala Met Val
                325                 330                 335 aga tta ctt gaa gac ggt gat taa                                     1032
Arg Leu Leu Glu Asp Gly Asp
            340
```

<210> SEQ ID NO 75
<211> LENGTH: 343
<212> TYPE: PRT
<213> ORGANISM: Bacteriophage P1

<400> SEQUENCE: 75

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
            85                  90                  95

Met Leu His Arg Arg Ser Gly Leu Pro Arg Pro Ser Asp Ser Asn Ala

```
            100                 105                 110
Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
        130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
                180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
        210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
                260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
        290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
        340
```

<210> SEQ ID NO 76
<211> LENGTH: 34
<212> TYPE: DNA
<213> ORGANISM: Artificial Sequence
<220> FEATURE:
<223> OTHER INFORMATION: PCR primer

<400> SEQUENCE: 76
gaaaggatcc atgtctaatt tacttactgt tcac        34

<210> SEQ ID NO 77
<211> LENGTH: 41
<212> TYPE: DNA
<213> ORGANISM: Artificial Sequence
<220> FEATURE:
<223> OTHER INFORMATION: PCR primer

<400> SEQUENCE: 77
gaaattaatt aacttaatca ccgtcttcaa gtaatctaac c        41

<210> SEQ ID NO 78
<211> LENGTH: 34
<212> TYPE: DNA
<213> ORGANISM: Artificial Sequence
<220> FEATURE:
<223> OTHER INFORMATION: PCR primer

<400> SEQUENCE: 78
gaaaatgcat gcaacggcaa catcaatgtc cacg                                    34

<210> SEQ ID NO 79
<211> LENGTH: 35
<212> TYPE: DNA
<213> ORGANISM: Artificial Sequence
<220> FEATURE:
<223> OTHER INFORMATION: PCR primer

<400> SEQUENCE: 79
gaaagtcgac ggtaaggccc gggaattcag cttgc                                   35

<210> SEQ ID NO 80
<211> LENGTH: 33
<212> TYPE: DNA
<213> ORGANISM: Artificial Sequence
<220> FEATURE:
<223> OTHER INFORMATION: PCR primer

<400> SEQUENCE: 80
aaaaaaacgc gtatgtcaac tgtggaagat cac                                     33

<210> SEQ ID NO 81
<211> LENGTH: 40
<212> TYPE: DNA
<213> ORGANISM: Artificial Sequence
<220> FEATURE:
<223> OTHER INFORMATION: PCR primer

<400> SEQUENCE: 81
aaaaaacctg caggttaagc tgctggcgct tcatctttgg                              40

<210> SEQ ID NO 82
<211> LENGTH: 23
<212> TYPE: DNA
<213> ORGANISM: Artificial Sequence
<220> FEATURE:
<223> OTHER INFORMATION: PCR primer

<400> SEQUENCE: 82
cagagagagg aagaagttgg aac                                                23

<210> SEQ ID NO 83
<211> LENGTH: 24
<212> TYPE: DNA
<213> ORGANISM: Artificial Sequence
<220> FEATURE:
<223> OTHER INFORMATION: PCR primer

<400> SEQUENCE: 83
gtacagagaa cttgtaaaca attc                                               24

<210> SEQ ID NO 84
<211> LENGTH: 32
<212> TYPE: DNA
<213> ORGANISM: Artificial Sequence
<220> FEATURE:
<223> OTHER INFORMATION: PCR primer

<400> SEQUENCE: 84
taatgggtac accatacggt ggattcccag ag                                      32

<210> SEQ ID NO 85
<211> LENGTH: 32

<212> TYPE: DNA
<213> ORGANISM: Artificial Sequence
<220> FEATURE:
<223> OTHER INFORMATION: PCR primer

<400> SEQUENCE: 85
ctctgggaat ccaccgtatg gtgtacccat ta                          32

<210> SEQ ID NO 86
<211> LENGTH: 94
<212> TYPE: DNA
<213> ORGANISM: Artificial Sequence
<220> FEATURE:
<223> OTHER INFORMATION: PCR primer

<400> SEQUENCE: 86
aatattctat tattatatat tttcttccca ataaaacaaa ataaaacaaa acacagcaaa    60
acacaaaaat cctggaattc gcccttacat atgg                              94

<210> SEQ ID NO 87
<211> LENGTH: 90
<212> TYPE: DNA
<213> ORGANISM: Artificial Sequence
<220> FEATURE:
<223> OTHER INFORMATION: PCR primer

<400> SEQUENCE: 87
tatagattgt aaagtagacg taaagtttag taattcattt taatgttcat tttacattca    60
gatgtcatta cggctcgtgc tatattcttg                                   90

<210> SEQ ID NO 88
<211> LENGTH: 90
<212> TYPE: DNA
<213> ORGANISM: Artificial Sequence
<220> FEATURE:
<223> OTHER INFORMATION: PCR primer

<400> SEQUENCE: 88
attctattat tatatttt cttcccaata aacaaaata aacaaaaca cagcaaaaca        60 caaaaatcct ggaattcgcc cttacatatg                                   90

<210> SEQ ID NO 89
<211> LENGTH: 20
<212> TYPE: DNA
<213> ORGANISM: Artificial Sequence
<220> FEATURE:
<223> OTHER INFORMATION: PCR primer

<400> SEQUENCE: 89
gcgcatccat attttggcgg                                             20

<210> SEQ ID NO 90
<211> LENGTH: 20
<212> TYPE: DNA
<213> ORGANISM: Artificial Sequence
<220> FEATURE:
<223> OTHER INFORMATION: PCR primer

<400> SEQUENCE: 90
ggagtgacac aacctgaaag                                             20

<210> SEQ ID NO 91
<211> LENGTH: 20
<212> TYPE: DNA

```
<213> ORGANISM: Artificial Sequence
<220> FEATURE:
<223> OTHER INFORMATION: PCR primer

<400> SEQUENCE: 91
aaaggctgac ggacacaatc                                               20

<210> SEQ ID NO 92
<211> LENGTH: 32
<212> TYPE: DNA
<213> ORGANISM: Artificial Sequence
<220> FEATURE:
<223> OTHER INFORMATION: PCR primer

<400> SEQUENCE: 92
atattagtcg acccttctat cagggaaggg ag                                 32

<210> SEQ ID NO 93
<211> LENGTH: 20
<212> TYPE: DNA
<213> ORGANISM: Artificial Sequence
<220> FEATURE:
<223> OTHER INFORMATION: PCR primer

<400> SEQUENCE: 93
ttggcgcttc accatctaac                                               20

<210> SEQ ID NO 94
<211> LENGTH: 20
<212> TYPE: DNA
<213> ORGANISM: Artificial Sequence
<220> FEATURE:
<223> OTHER INFORMATION: PCR primer

<400> SEQUENCE: 94
ggtgcttcaa aggcactatc                                               20

<210> SEQ ID NO 95
<211> LENGTH: 23
<212> TYPE: DNA
<213> ORGANISM: Artificial Sequence
<220> FEATURE:
<223> OTHER INFORMATION: PCR primer

<400> SEQUENCE: 95
gtgggctaca aatgatacga tgg                                           23

<210> SEQ ID NO 96
<211> LENGTH: 20
<212> TYPE: DNA
<213> ORGANISM: Artificial Sequence
<220> FEATURE:
<223> OTHER INFORMATION: PCR primer

<400> SEQUENCE: 96
tcggccactt gtttattggg                                               20

<210> SEQ ID NO 97
<211> LENGTH: 20
<212> TYPE: DNA
<213> ORGANISM: Artificial Sequence
<220> FEATURE:
<223> OTHER INFORMATION: PCR primer

<400> SEQUENCE: 97
ctgcaggttt gccagcttac                                               20
```

<210> SEQ ID NO 98
<211> LENGTH: 22
<212> TYPE: DNA
<213> ORGANISM: Artificial Sequence
<220> FEATURE:
<223> OTHER INFORMATION: PCR primer

<400> SEQUENCE: 98
gattgtgtat tagtgtattt cg                                              22

<210> SEQ ID NO 99
<211> LENGTH: 42
<212> TYPE: DNA
<213> ORGANISM: Artificial Sequence
<220> FEATURE:
<223> OTHER INFORMATION: PCR primer

<400> SEQUENCE: 99
gaaattgccg ctgctagaat cccaggtgca acccaatggt tc                        42

<210> SEQ ID NO 100
<211> LENGTH: 42
<212> TYPE: DNA
<213> ORGANISM: Artificial Sequence
<220> FEATURE:
<223> OTHER INFORMATION: PCR primer

<400> SEQUENCE: 100
gaaccattgg gttgcacctg ggattctagc agcggcaatt tc                        42

<210> SEQ ID NO 101
<211> LENGTH: 32
<212> TYPE: DNA
<213> ORGANISM: Artificial Sequence
<220> FEATURE:
<223> OTHER INFORMATION: PCR primer

<400> SEQUENCE: 101
gtccaggagt ccatcggttc ctgtcagatg gg                                   32

<210> SEQ ID NO 102
<211> LENGTH: 43
<212> TYPE: DNA
<213> ORGANISM: Artificial Sequence
<220> FEATURE:
<223> OTHER INFORMATION: PCR primer

<400> SEQUENCE: 102
gcgtctagaa ttttgtgtt ttgctgtgtt ttgttttatt ttg                        43

<210> SEQ ID NO 103
<211> LENGTH: 72
<212> TYPE: DNA
<213> ORGANISM: Artificial Sequence
<220> FEATURE:
<223> OTHER INFORMATION: PCR primer

<400> SEQUENCE: 103
ggtaccgcgg ccgcggatcc ctcgaggcct taattaacat ctgaatgtaa aatgaacatt     60
aaaatgaatt ac                                                         72

<210> SEQ ID NO 104
<211> LENGTH: 70
<212> TYPE: DNA

-continued

```
<213> ORGANISM: Artificial Sequence
<220> FEATURE:
<223> OTHER INFORMATION: PCR primer

<400> SEQUENCE: 104
gagctcgcgg ccgcggattc gccgaatcct tttattataa aattatatat tattcttaat    60
tacatatcac                                                          70

<210> SEQ ID NO 105
<211> LENGTH: 45
<212> TYPE: DNA
<213> ORGANISM: Artificial Sequence
<220> FEATURE:
<223> OTHER INFORMATION: PCR primer

<400> SEQUENCE: 105
gatgaacgaa ggtaccgagc tctaagtagt ggtgttggtg aactc                   45

<210> SEQ ID NO 106
<211> LENGTH: 45
<212> TYPE: DNA
<213> ORGANISM: Artificial Sequence
<220> FEATURE:
<223> OTHER INFORMATION: PCR primer

<400> SEQUENCE: 106
attatggtag cggccgcatt tggcaaggcg tatctatata ggagg                   45

<210> SEQ ID NO 107
<211> LENGTH: 45
<212> TYPE: DNA
<213> ORGANISM: Artificial Sequence
<220> FEATURE:
<223> OTHER INFORMATION: PCR primer

<400> SEQUENCE: 107
ttgccaaatg cggccgctac cataatgtat gcgttgagcc tcttg                   45

<210> SEQ ID NO 108
<211> LENGTH: 46
<212> TYPE: DNA
<213> ORGANISM: Artificial Sequence
<220> FEATURE:
<223> OTHER INFORMATION: PCR primer

<400> SEQUENCE: 108
ggttcaatgg gccctaaaag tgttggtgta ttagatgagt ttgtcc                  46

<210> SEQ ID NO 109
<211> LENGTH: 36
<212> TYPE: DNA
<213> ORGANISM: Artificial Sequence
<220> FEATURE:
<223> OTHER INFORMATION: PCR primer

<400> SEQUENCE: 109
ttaattaaca agggcgattt ctgcagatat cggccg                             36

<210> SEQ ID NO 110
<211> LENGTH: 36
<212> TYPE: DNA
<213> ORGANISM: Artificial Sequence
<220> FEATURE:
<223> OTHER INFORMATION: PCR primer

<400> SEQUENCE: 110
```

```
cggccgatat ctgcagaaat cgcccttgtt aattaa                             36
```

<210> SEQ ID NO 111
<211> LENGTH: 22
<212> TYPE: DNA
<213> ORGANISM: Artificial Sequence
<220> FEATURE:
<223> OTHER INFORMATION: PCR primer

<400> SEQUENCE: 111

```
ggaggaatgg aacagtgatg ac                                            22
```

<210> SEQ ID NO 112
<211> LENGTH: 31
<212> TYPE: DNA
<213> ORGANISM: Artificial Sequence
<220> FEATURE:
<223> OTHER INFORMATION: PCR primer

<400> SEQUENCE: 112

```
caagagtatc ccatctgaca ggaaccgatg g                                  31
```

<210> SEQ ID NO 113
<211> LENGTH: 19
<212> TYPE: DNA
<213> ORGANISM: Artificial Sequence
<220> FEATURE:
<223> OTHER INFORMATION: PCR primer

<400> SEQUENCE: 113

```
cttctatagg ttgagaccc                                                19
```

<210> SEQ ID NO 114
<211> LENGTH: 27
<212> TYPE: DNA
<213> ORGANISM: Artificial Sequence
<220> FEATURE:
<223> OTHER INFORMATION: PCR primer

<400> SEQUENCE: 114

```
catcactgtt aaaggaatgg gtaaatc                                       27
```

<210> SEQ ID NO 115
<211> LENGTH: 21
<212> TYPE: DNA
<213> ORGANISM: Artificial Sequence
<220> FEATURE:
<223> OTHER INFORMATION: PCR primer

<400> SEQUENCE: 115

```
gcatctaatg tacgttccaa c                                             21
```

<210> SEQ ID NO 116
<211> LENGTH: 23
<212> TYPE: DNA
<213> ORGANISM: Artificial Sequence
<220> FEATURE:
<223> OTHER INFORMATION: PCR primer

<400> SEQUENCE: 116

```
cgaaaccgtt aaattcaaca atg                                           23
```

<210> SEQ ID NO 117
<211> LENGTH: 33
<212> TYPE: DNA

```
<213> ORGANISM: Artificial Sequence
<220> FEATURE:
<223> OTHER INFORMATION: PCR primer

<400> SEQUENCE: 117
gtttaaacgt acgactcatg gggctttaca aac                                  33

<210> SEQ ID NO 118
<211> LENGTH: 53
<212> TYPE: DNA
<213> ORGANISM: Artificial Sequence
<220> FEATURE:
<223> OTHER INFORMATION: PCR primer

<400> SEQUENCE: 118
gagctcagcg gccgctcata tgaagtgttg cagttgtttt cttcttaata aag            53

<210> SEQ ID NO 119
<211> LENGTH: 50
<212> TYPE: DNA
<213> ORGANISM: Artificial Sequence
<220> FEATURE:
<223> OTHER INFORMATION: PCR primer

<400> SEQUENCE: 119
catatgagcg gccgctgagc tctctagagt ccctctaatt cttcctgttg                50

<210> SEQ ID NO 120
<211> LENGTH: 38
<212> TYPE: DNA
<213> ORGANISM: Artificial Sequence
<220> FEATURE:
<223> OTHER INFORMATION: PCR primer

<400> SEQUENCE: 120
gtttaaacca gtgatcgagc actcatttat acgagatg                             38

<210> SEQ ID NO 121
<211> LENGTH: 31
<212> TYPE: DNA
<213> ORGANISM: Artificial Sequence
<220> FEATURE:
<223> OTHER INFORMATION: PCR primer

<400> SEQUENCE: 121
aaaaaaacgc gtatgcctca ttctatcaac g                                    31

<210> SEQ ID NO 122
<211> LENGTH: 36
<212> TYPE: DNA
<213> ORGANISM: Artificial Sequence
<220> FEATURE:
<223> OTHER INFORMATION: PCR primer

<400> SEQUENCE: 122
aaaaaacctg caggttacaa actcaaaccg tttctg                               36

<210> SEQ ID NO 123
<211> LENGTH: 26
<212> TYPE: DNA
<213> ORGANISM: Artificial Sequence
<220> FEATURE:
<223> OTHER INFORMATION: PCR primer

<400> SEQUENCE: 123
caaaacaact gtcccctatg tacatc                                          26
```

<210> SEQ ID NO 124
<211> LENGTH: 35
<212> TYPE: DNA
<213> ORGANISM: Artificial Sequence
<220> FEATURE:
<223> OTHER INFORMATION: PCR primer

<400> SEQUENCE: 124
ctgaagttga acaaatttat gccacgcagc ttttc                          35

<210> SEQ ID NO 125
<211> LENGTH: 19
<212> TYPE: DNA
<213> ORGANISM: Artificial Sequence
<220> FEATURE:
<223> OTHER INFORMATION: PCR primer

<400> SEQUENCE: 125
gagtgacaca acctgaaag                                            19

<210> SEQ ID NO 126
<211> LENGTH: 24
<212> TYPE: DNA
<213> ORGANISM: Artificial Sequence
<220> FEATURE:
<223> OTHER INFORMATION: PCR primer

<400> SEQUENCE: 126
gtacagagaa cttgtaaaca attc                                      24

<210> SEQ ID NO 127
<211> LENGTH: 39
<212> TYPE: DNA
<213> ORGANISM: Artificial Sequence
<220> FEATURE:
<223> OTHER INFORMATION: PCR primer

<400> SEQUENCE: 127
catgcatgca tgtctagata aaatgttagc tgctagatc                      39

<210> SEQ ID NO 128
<211> LENGTH: 43
<212> TYPE: DNA
<213> ORGANISM: Artificial Sequence
<220> FEATURE:
<223> OTHER INFORMATION: PCR primer

<400> SEQUENCE: 128
catgcatgca tgttaattaa cttaatcctt tggaccaatc atg                 43

<210> SEQ ID NO 129
<211> LENGTH: 30
<212> TYPE: DNA
<213> ORGANISM: Artificial Sequence
<220> FEATURE:
<223> OTHER INFORMATION: PCR primer

<400> SEQUENCE: 129
gagaacttat acgcaccaga acgcctttg                                 30

<210> SEQ ID NO 130
<211> LENGTH: 29
<212> TYPE: DNA
<213> ORGANISM: Artificial Sequence
<220> FEATURE:

<223> OTHER INFORMATION: PCR primer

<400> SEQUENCE: 130
gaggaagttc aaagtatgaa agacgtcag                                              29

<210> SEQ ID NO 131
<211> LENGTH: 180
<212> TYPE: DNA
<213> ORGANISM: Issatchenkia orientalis

<400> SEQUENCE: 131
gtatctgttg ttgttttatt tcctttggaa gtgtataaaa caaacctagt ccccgctttt           60
gtttttctct cacaacccctt tagagtaagg attagcttgg tatctatttt ttattttcgt          120
tgaaacaagt ttagtcaggt gcttgaaaca caaccaaaca agtaataagt ttgacataga           180

<210> SEQ ID NO 132
<211> LENGTH: 180
<212> TYPE: DNA
<213> ORGANISM: Issatchenkia orientalis

<400> SEQUENCE: 132
ttgtttccct tcgctttaac tcctatcaat aatacattca aaacttagta ttactgatgc           60
tgttacgact actaatacta ttgctactac caatactatt cacttctcta tctattttag          120
atatatatgc atatagtcat ttttctcttt tttttttga tatctatact ctacactata           180

<210> SEQ ID NO 133
<211> LENGTH: 379
<212> TYPE: DNA
<213> ORGANISM: Artificial Sequence
<220> FEATURE:
<223> OTHER INFORMATION: RIOR43690 upstream/downstream construct

<400> SEQUENCE: 133
gtatctgttg ttgttttatt tcctttggaa gtgtataaaa caaacctagt ccccgctttt           60
gtttttctct cacaacccctt tagagtaagg attagcttgg tatctatttt ttattttcgt          120
tgaaacaagt ttagtcaggt gcttgaaaca caaccaaaca agtaataagt ttgacataga           180
catatgaaaa aaagagctct tgtttccctt cgctttaact cctatcaata atacattcaa           240
aacttagtat tactgatgct gttacgacta ctaatactat tgctactacc aatactattc           300
acttctctat ctattttaga tatatatgca tatagtcatt ttttcttttt tttttttgat           360
atctatactc tacactata                                                       379

<210> SEQ ID NO 134
<211> LENGTH: 1138
<212> TYPE: DNA
<213> ORGANISM: Schizosaccharomyces pombe

<400> SEQUENCE: 134
cggtttgaac accattggca agattgttta catcttacaa atcttttgt tttctctttt            60
tggctcttgt atgttgtttc gtttcatcaa gtatccatct accattaagg actcttggaa          120
tcatcacttg gaaaagttgt ttatcgcaac ttgtttgtta tctatttcca cattcatcga          180
catgttagct atctatgctt atccagatac cggtgaatgg atggtctggg tcattagaat          240
cttatactac atcatgtcg ctgtctcttt catctactgt gttatggcct ttttcaccat           300
tttcaacaat catgtttaca ctattgaaac tgcttctcca gcttggattt tgccaatctt          360
ccctccaatg atctgtggtg tcattgctgg tgctgttaac tccacccaac ctgctcacca          420

```
attgaaaaac atggtcattt tcggtatctt gtttcaaggt ttaggttttt gggtttacct    480 tttactttc gccgttaatg tttgagatt cttcacagtc ggtttagcaa agccacaaga    540
tagaccaggt atgtttatgt tcgttggtcc accagctttc tctggtttag cattgattaa    600
cattgcaaga ggtgcaatgg gctcaagacc ttacattttc gttggtgcaa actcttccga    660
atacttaggt tttgtctcaa ccttcatggc catttcatc tggggtttag ccgcatggtg    720
ttattgctta gctatggttt ccttccttgc cggctttttc actagagcac cattgaaatt    780
cgcttgtggt tggttcgctt tcatctttcc aaatgttggt tttgttaact gtactatcga    840
aatcggcaag atgattgatt ctaaggcttt tcaaatgttt ggtcacatca ttggtgttat    900
cttgtgtatt caatggattt tgttaatgta cttaatggtt agagcattcc ttgttaatga    960
cttgtgctat cctggtaaag acgaagatgc cacccacca ccaaagccaa acactggtgt   1020
cttaaaccca actttcccac cagagaaggc tccagcatca ttagagaagg ttgatactca   1080
tgttacatca acaggtggtg aatccgatcc tccatcttcc gaacatgaat ccgttaa      1138
```

<210> SEQ ID NO 135
<211> LENGTH: 400
<212> TYPE: DNA
<213> ORGANISM: Schizosaccharomyces pombe

<400> SEQUENCE: 135

```
aaacgcgtat gggtgaattg aaagagattt tgaaacaaag atatcatgaa ttacttgatt     60
ggaatgttaa ggcaccacat gtccctttat cccagagatt gaagcacttt acttggtcat    120
ggtttgcttg tactatggca accggtggtg ttggtttgat cattggttcc ttcccattca    180
gattctacgg tttgaacacc attggcaaga ttgtttacat cttacaaatc tttttgtttt    240 ctcttttgg ctcttgtatg ttgtttcgtt tcatcaagta tccatctacc attaaggact    300
cttggaatca tcacttggaa aagttgttta tcgcaacttg tttgttatct atttccacat    360
tcatcgacat gttagctatc tatgctcctg caggaatcct                          400
```

<210> SEQ ID NO 136
<211> LENGTH: 20
<212> TYPE: DNA
<213> ORGANISM: Artificial Sequence
<220> FEATURE:
<223> OTHER INFORMATION: Primer

<400> SEQUENCE: 136

```
gaagtcatat ttcgacactc                                                 20
```

<210> SEQ ID NO 137
<211> LENGTH: 44
<212> TYPE: DNA
<213> ORGANISM: Artificial Sequence
<220> FEATURE:
<223> OTHER INFORMATION: PCR primer

<400> SEQUENCE: 137

```
catcaatagg taccgagctc ccgtttcgat gggattccca gaag                      44
```

<210> SEQ ID NO 138
<211> LENGTH: 41
<212> TYPE: DNA
<213> ORGANISM: Artificial Sequence
<220> FEATURE:
<223> OTHER INFORMATION: PCR primer

<400> SEQUENCE: 138
cccctggtgc ggccgctccc ttctctaaat ggactgcttg g          41

<210> SEQ ID NO 139
<211> LENGTH: 39
<212> TYPE: DNA
<213> ORGANISM: Artificial Sequence
<220> FEATURE:
<223> OTHER INFORMATION: PCR primer

<400> SEQUENCE: 139
agaagggagc ggccgcacca ggggtttagt gaagtcacc              39

<210> SEQ ID NO 140
<211> LENGTH: 43
<212> TYPE: DNA
<213> ORGANISM: Artificial Sequence
<220> FEATURE:
<223> OTHER INFORMATION: PCR primer

<400> SEQUENCE: 140
acttacaagg gccccataac tgacatttat ggtaaggttg ctc         43

<210> SEQ ID NO 141
<211> LENGTH: 26
<212> TYPE: DNA
<213> ORGANISM: Artificial Sequence
<220> FEATURE:
<223> OTHER INFORMATION: PCR primer

<400> SEQUENCE: 141
caggatcgaa gaatagaagt tgtgtg                            26

<210> SEQ ID NO 142
<211> LENGTH: 24
<212> TYPE: DNA
<213> ORGANISM: Artificial Sequence
<220> FEATURE:
<223> OTHER INFORMATION: PCR primer

<400> SEQUENCE: 142
gaacgtctac aacgaggtga acac                              24

<210> SEQ ID NO 143
<211> LENGTH: 4910
<212> TYPE: DNA
<213> ORGANISM: Artificial Sequence
<220> FEATURE:
<223> OTHER INFORMATION: URA3 gene disruption fragment
<220> FEATURE:
<221> NAME/KEY: misc_feature
<222> LOCATION: (1656)..(1656)
<223> OTHER INFORMATION: n is a, c, g, or t
<220> FEATURE:
<221> NAME/KEY: misc_feature
<222> LOCATION: (4312)..(4312)
<223> OTHER INFORMATION: n is a, c, g, or t

<400> SEQUENCE: 143
ctcaaaacta tttaattagt taattgtata aactgtatgt cattataaac agggaaggtt      60
gacattgtct agcggcaatc attgtctcat ttggttcatt aactttggtt ctgttcttgg    120
aaacgggtac caactctctc agagtgcttc aaaaattttt cagcacattt ggttagacat    180
gaactttctc tgctggttaa ggattcagag gtgaagtctt gaacacaatc gttgaaacat    240
ctgtccacaa gagatgtgta tagcctcatg aaatcagcca tttgcttttg ttcaacgatc    300

```
ttttgaaatt gttgttgttc ttggtagtta agttgatcca tcttggctta tgttgtgtgt      360
atgttgtagt tattcttagt atattcctgt cctgagttta gtgaaacata atatcgcctt      420
gaaatgaaaa tgctgaaatt cgtcgacata caattttttca aacttttttt ttttcttggt     480
gcacggacat gttttttaaag gaagtactct ataccagtta ttcttcaccc tgcagggtac     540
gtagcatgca ctcgcaagct gtgccatcgc ccaacggtta attataagaa atcaacatca      600
gccaacaact attttcgtcc ccctcttttc agtggtaacg agcaattaca ttagtaagag      660
actattttct tcagtgattt gtaatttttt ttcagtgatt tgtaattctt tctcgaaata      720
tgcgggctta acttatccgg acattcacta catgcaagga aaaacgagaa ccgcggagat      780
ttcctcagta agtaacaatg atgatctttt tacgcttcat catcactttc caaagttcta      840
agctataagt tcaagcctag atacgctgaa aaactcctga ccaacaatgt aaagaaaaca      900
attacaattg taaggttgaa aacatctaaa aatgaaatat tttattgtac atgcacaccc      960
tgatagtcat tctcttactt catccctgaa agacgtggct gtacaagagt tggaatcgca     1020
aggtcatgag gttaaagtta gtgatcttta tgctcaaaag tggaaggcct caatagaccg     1080
tgacgacttc gagcagcttt tcgcaagaag agaggttaaa aataccccaa gcttcttatg     1140
aagcgtatgc cagaggagca ttaacaaaag acgtaaatca ggaacaggaa aaacttattt     1200
gggcggactt tgtcattttg tcgtttccta tatggtggtc ttctatgccg gctagtcgac     1260
ccctcgacc ccctcgagcg atctcgagat ttgctgcaac ggcaacatca atgtccacgt      1320
ttacacacct acatttatat ctatatttat atttatattt atttatttat gctacttagc     1380
ttctatagtt agttaatgca ctcacgatat tcaaaattga cacccttcaa ctactcccta     1440
ctattgtcta ctactgtcta ctactcctct ttactatagc tgctcccaat aggctccacc     1500
aataggctct gtcaatacat tttgcgccgc cacctttcag gttgtgtcac tcctgaagga     1560
ccatattggg taatcgtgca atttctggaa gagagtgccg cgagaagtga gccccccact     1620
gtaaatcctc gaggggggcat ggagtatggg gcatgnagga tggaggatgg gggggggggg    1680
ggaaaatagg tagcgaaagg acccgctatc accccacccg gagaactcgt tgccgggaag     1740
tcatatttcg acactccggg gagtctataa aaggcgggtt ttgtcttttg ccagttgatg     1800
ttgctgagag gacttgtttg ccgtttcttc cgatttaaca gtatagaatc aaccactgtt     1860
aattatacac gttatactaa cacaacaaaa acaaaaacaa cgacaacaac aacaacaatg     1920
tttgctttct actttctcac cgcatgcacc actttgaagg gtgttttcgg agtttctccg     1980
agttacaatg gtcttggtct caccccacag atgggttggg acagctggaa tacgtttgcc     2040
tgcgatgtca gtgaacagct acttctagac actgctgata gaatttctga cttggggcta     2100
aaggatatgg gttacaagta tgtcatccta gatgactgtt ggtctagcgg cagggattcc     2160
gacggtttcc tcgttgcaga caagcacaaa tttcccaacg gtatgggcca tgttgcagac     2220
cacctgcata ataacagctt tcttttcggt atgtattcgt ctgctggtga gtacacctgt     2280
gctgggtacc ctgggtctct ggggcgtgag gaagaagatg ctcaattctt tgcaaataac     2340
cgcgttgact acttgaagta tgataattgt tacaataaag gtcaatttgg tacaccagac     2400
gtttcttacc accgttacaa ggccatgtca gatgctttga taaaactgg taggcctatt      2460
ttctattctc tatgtaactg gggtcaggat ttgacatttt actggggctc tggtatcgcc     2520
aattcttgga gaatgagcgg agatattact gctgagttca cccgtccaga tagcagatgt     2580
ccctgtgacg gtgacgaata tgattgcaag tacgccggtt ccattgttc tattatgaat      2640
```

-continued

```
attcttaaca aggcagctcc aatggggcaa aatgcaggtg ttggtggttg gaacgatctg      2700
gacaatctag aggtcggagt cggtaatttg actgacgatg aggaaaaggc ccatttctct      2760
atgtgggcaa tggtaaagtc cccacttatc attggtgccg acgtgaatca cttaaaggca      2820
tcttcgtact cgatctacag tcaagcctct gtcatcgcaa ttaatcaaga tccaaagggt      2880
attccagcca caagagtctg gagatattat gtttcagaca ccgatgaata tggacaaggt      2940
gaaattcaaa tgtggagtgg tccgcttgac aatggtgacc aagtggttgc tttattgaat      3000
ggaggaagcg tagcaagacc aatgaacacg accttggaag agattttctt tgacagcaat      3060
ttgggttcaa aggaactgac atcgacttgg gatatttacg acttatgggc aacagagtt      3120 gacaactcta cggcgtctgc tatccttgaa cagaataagg cagccaccgg tattctctac      3180
aatgctacag agcagtctta taaagacggt ttgtctaaga atgatacaag actgtttggc      3240
cagaaaattg gtagtctttc tccaaatgct atacttaaca caactgttcc agctcatggt      3300
atcgccttct ataggttgag accctcggct taagctcaat gttgagcaaa gcaggacgag      3360
aaaaaaaaaa ataatgattg ttaagaagtt catgaaaaaa aaaggaaaaa atactcaaat      3420
acttataaca gagtgattaa ataataaacg gcagtatacc ctatcaggta ttgagatagt      3480 tttattttg taggtatata atctgaagcc tttgaactat tttctcgtat atatcatgga      3540
gtatacattg cattagcaac attgcatact agtcactcgc aagctgtgcc atcgcccaac      3600
ggttaattat aagaaatcaa catcagccaa caactatttt cgtcccctc ttttcagtgg      3660 taacgagcaa ttacattagt aagagactat tttcttcagt gatttgtaat ttttttcag      3720 tgatttgtaa ttcttctcg aaatatgcgg gctwaamtaa tccggacatt cactacatgc      3780
aaggaaaaac gagaaccgcg gagatttcct cagtaagtaa caatgatgat cttttacgc      3840 ttcatcatca ctttccaaag ttctaagcta taagttcaag cctagatacg ctgaaaaact      3900
cctgaccaac aatgtaaaga aaacaattac aattgtaagg ttgaaaacat ctaaaaatga      3960
aatattttat tgtacatgca caccctgata gtcattctct tacttcatcc ctgaaagacg      4020
tggctgtaca agagttggaa tcgcaaggtc atgaggttaa agttagtgat ctttatgctc      4080
aaaagtggaa ggcctcaata gaccgtgacg acwwmaaaaa amaaamrmaa gaagagaggt      4140
taaaaatacc ccaagcttct tatgaagcgt atgccagagg agcattaaca aaagacgtaa      4200
atcaggaaca ggaaaaactt atttgggcgg acttttgtcat tttgtcgttt cctatatggt      4260
ggtcttctat gccggctagc ggccgggcaa caaagcctcc cagatttgat anattttcaa      4320
tttgtgcttt gaatcatgac ttccacctgt ttggtccgca agaacacgta aatgcgcaat      4380
ttgtttctcc cttctgctta aaaaccatgc acctttaata ttatctggaa agataaagaa      4440
cagaattgtt gcgtagaaac aagtagcaga gccgtaaatg agaaaaatat acttccaagc      4500
tggtaatttc ccctttatta gtccaataca gtgtccgaag accccaccaa gaataccagc      4560
aagggtgttg aaatataatg tagatcttag tggttgttct gatttcttcc accacattcc      4620
gctaataatc ataaaagacg gtaatattcc ggcttcaaat acgccaagaa aaaacctcac      4680
ggtaaccaaa ccaccaaagc tatgacatgc agccatgcac ataagtaagc cgccccaaat      4740
gaacaaacaa atagacacaa atttgccaat tctaactcgt ggcaacaaaa aaaggatat      4800 gaactcacct aataaataac cgaaataaaa agtagaagca actgtggaaa attgagaacc      4860
atgtaaattt gtgtcttctt tcaatgtata aacagccgca atacctaggg                4910
```

<210> SEQ ID NO 144
<211> LENGTH: 22

```
<212> TYPE: DNA
<213> ORGANISM: Artificial Sequence
<220> FEATURE:
<223> OTHER INFORMATION: Primer

<400> SEQUENCE: 144
gcaactgatg ttcacgaatg cg                                               22

<210> SEQ ID NO 145
<211> LENGTH: 20
<212> TYPE: DNA
<213> ORGANISM: Artificial Sequence
<220> FEATURE:
<223> OTHER INFORMATION: Primer

<400> SEQUENCE: 145
ttgccgttgc agcaaatctc                                                  20

<210> SEQ ID NO 146
<211> LENGTH: 21
<212> TYPE: DNA
<213> ORGANISM: Artificial Sequence
<220> FEATURE:
<223> OTHER INFORMATION: Primer

<400> SEQUENCE: 146
acggcagtat accctatcag g                                                21

<210> SEQ ID NO 147
<211> LENGTH: 20
<212> TYPE: DNA
<213> ORGANISM: Artificial Sequence
<220> FEATURE:
<223> OTHER INFORMATION: Primer

<400> SEQUENCE: 147
aatgatccat ggtccgagag                                                  20

<210> SEQ ID NO 148
<211> LENGTH: 3704
<212> TYPE: DNA
<213> ORGANISM: Artificial Sequence
<220> FEATURE:
<223> OTHER INFORMATION: PDC gene disruption fragment

<400> SEQUENCE: 148
cccccagttg ttgttgcaat taacaaattt gctaccgaca ccgagaagga aattgagacc        60
attagagaag aagccatcaa ggctggtgca tttgatgctg ttgagtcaga ccattggtca       120
caaggtggta agggtgcaat caagttagct gaggcaattg tacgtgctac cgaggaaaga       180
ccgttggaag aaagtcaacc tcctaactat ctttattcat tagatggttc gttagaagat       240
agactaagaa caattgccac caagatgtat ggagcaaaag atattgaact atctgagttg       300
gccaagaaac agattgaaga gtatgagagt caaggttttg gcaagctgcc tgtttgtatt       360
gcaaagacgc aatattctct ctcccatgat ccaacattga aggtgttcc aaaggatttc       420 atcttcccaa tcagagaagt tagaataagt gcaggagcag gatatttata tgcactagct       480
gcaaagatca tgacaattcc aggtctatca acttatgccg gatttatgaa tgttgaagtc       540
aacgaagatg gtgagattga tggattgttt agtttttat tataaaatta tatattattc       600
ttaattacat atcaccctcc tatcagggaa gggagaaacg aaaatagaga gtgacctatc       660
caagctcggg ggtctaagtt ttaatggccc agggaatcat tactttttt tctcaatcct       720
```

```
tgatggataa aagtattaca tacgtacagg attgtgtatt agtgtatttc gttatatgat    780
taaacaaagt ttatagattg taaagtagac gtaaagttta gtaattcatt ttaatgttca    840
ttttacattc agatggcggc cgcggatcca gatcccccgg ggcgttgaag atctattctc    900
cagcaattaa atttgtgaag aataactggt atagagtact tcctttaaaa acatgtccgt    960
gcaccaagaa aaaaaaaaag tttgaaaaat tgtatgtcga cgaatttcag cattttcatt   1020
tcaaggcgat attatgtttc actaaactca ggacaggaat atactaagaa taactacaac   1080
atacacacaa cataagccaa gatggatcaa cttaactacc aagaacaaca acaatttcaa   1140
aagatcgttg aacaaaagca aatggctgat ttcatgaggc tatctgcaga tacgcggaac   1200
aatcaatcga taatgatttg actgataaag aaaaccatac ttttgtttat gtttattagt   1260
tatcgctttg ctacattaaa aattcacata ctaaagcctt tgttaaacaa cttttttctaa  1320
atcttaagat tttactctat ctagtttttt tggttgtagg tgaacgtaaa gtacctcatt   1380
tatttttttt tttttgcttg tgtaattctt ttcatgctta tttaaactag tgtacatgta   1440
tcaaatcttt gtgtaagaat catttaaatc tgtttaaata agcattccaa ccagcttgtt   1500
ggtatctttt agcttgctct ataggatctc ttccttgacc gtacaaacct ctaccaacaa   1560
ttatgatatc cgttccagtc tttacaactt catcaacagt tctatattgt tgaccaagtg   1620
catcaccttt gtcatctaaa ccaaccccctg gagtcataat gatccagtca aaaccttctt  1680
ctctaccgcc catatcgtgt tgcgcaataa accaatgac aaactcttta tcagatttag    1740
caatttctac tgttttttct gtatattcac catatgctaa agaacccttt gatgataact   1800
cagcaagcat tagcaaacct ctaggttcac tggttgtttc ttgggctgcc tccttcaagc   1860
cagaaacaat acctgcaccc gttacaccat gtgcattagt gatgtcagcc cattcggcaa   1920
tacgaaagac accagattta tattgatttt taacagtgtt accaatatca gcaaattttc   1980
tatcttcaaa aatcataaaa ttatgtttct tggcaagctc cttcaaaggc aacacagttc   2040
cttcatacgt aaaatcagaa acaatatcga tgtgtgtttt aactagacag atgtaaggac   2100
caatagtgtc caaaatagag agaagctttt cagtttcagt aatatccaat gatgcacaaa   2160
ggttagactt cttttcctcc atgatggaga aaagtctcct agcaacaggg gaagtgtgtg   2220
attctgatct ttctttgtat gacgccatcc ttgacaaaca aactacttta ttaaagcgtt   2280
gaagatctat tctccagcaa ttaaatttgt gaagaataac tggtatagag tacttccttt   2340
aaaaacatgt ccgtgcacca agaaaaaaaa aaagtttgaa aaattgtatg tcgacgaatt   2400
tcagcatttt catttcaagg cgatattatg tttcactaaa ctcaggacag gaatatacta   2460
agaataacta caacatacac acaacataag ccaagatgga tcaacttaac taccaagaac   2520
aacaacaatt tcaaaagatc gttgaacaaa agcaaatggc tgatttcatg aggctatgaa   2580
ttctttttatt ataaaattat atattattct taattacata tcacccttct atcagggaag  2640
ggagaaacga aaatagagag tgacctatcc aagcttgggg gtctaagttt taatggccca   2700
gggaatcatt actttttttt ctcaatccctt gatggataaa agtattacat acgtacagga  2760
ttgtgtatta gtgtatttcg ttatatgatt aaacaaagtt tatagattgt aaagtagacg   2820
taaagtttag taattcattt taatgttcat tttacattca gatgttaatt aaggcctcga   2880
gggatccgcg gccgctattt tgtgttttg ctgtgttttg ttttattttg ttttattggg    2940
aagaaaatat ataataatag aatattatat taacaaataa ttaaagaagc tcaactgtta   3000
ttagaataaa tgggttctcc gtgtcctttt tatacgccctt ctccgaaaag aaaaaaacca  3060
tcgtatcatt tgtagcccac gccacccgga aaaaccacca ttgtcctcag cagtccgcaa   3120
```

-continued

```
aaatatggat gcgctcaatc aatttccctc ccccgtcaat gccaaaagga taacgacaca    3180
ctattaagag cgcatcattt gtaaaagccg aggaaggggg atacgctgac cgagacgtct    3240
cgcctcactc tcggagctga gccgccctcc ttaagaaatt catgggaaga acacccttcg    3300
cggcttctga acggctcgcc ctcgtccatt ggtcacctca cagtggcaac taataaggac    3360
attatagcaa tagaaattaa aatggtgcac agaaatacaa taggatcgaa taggatagga    3420
tacaataaga tacggaatat tagactatac tgtgatacgg tacgctacga tacgctacga    3480
tacgatacga tagaggatac cacggatata acgtagtgtt atttttcatt attggggttt    3540
tttttctgtt tgaattttcc acgtcaagag tatcccatct gacaggaacc gatggactcg    3600
tcacagtacc tatcgcccga gttcaatcca tggacgctgc gggtgaagga tcttcgcccg    3660
ctgttggcaa gccatgggat cagggcgtcg ccaagggacg ggcc                    3704
```

<210> SEQ ID NO 149
<211> LENGTH: 22
<212> TYPE: DNA
<213> ORGANISM: Artificial Sequence
<220> FEATURE:
<223> OTHER INFORMATION: Primer

<400> SEQUENCE: 149

```
gaagagacgt acaagatccg cc                                              22
```

<210> SEQ ID NO 150
<211> LENGTH: 47
<212> TYPE: DNA
<213> ORGANISM: Artificial Sequence
<220> FEATURE:
<223> OTHER INFORMATION: Primer

<400> SEQUENCE: 150

```
ggataaaagt attacatacg tacaggattg tgtattagtg tatttcg                   47
```

<210> SEQ ID NO 151
<211> LENGTH: 22
<212> TYPE: DNA
<213> ORGANISM: Artificial Sequence
<220> FEATURE:
<223> OTHER INFORMATION: Primer

<400> SEQUENCE: 151

```
taggaatggt gcatcatcca ac                                              22
```

<210> SEQ ID NO 152
<211> LENGTH: 27
<212> TYPE: DNA
<213> ORGANISM: Artificial Sequence
<220> FEATURE:
<223> OTHER INFORMATION: Primer

<400> SEQUENCE: 152

```
gctggagaat agatcttcaa cgccccg                                         27
```

<210> SEQ ID NO 153
<211> LENGTH: 6392
<212> TYPE: DNA
<213> ORGANISM: Artificial Sequence
<220> FEATURE:
<223> OTHER INFORMATION: PYC gene integration fragment

<400> SEQUENCE: 153

```
ctaagtagtg gtgttggtga actcaagatg gactctttag gtaattatat tcttgaatag      60
ttgtgtaaag cgaatatgca aatagatttg ttttataatt atgcatctct ttgaaagagg     120
tttagaggca aagttcttgc atacaatatt gtgattgttt taatgtcatt cttgattttc     180
ataaagagat taaaaaaaaa aaaaaaaaac ttataaaatt gagtagaacc atttatatat     240
aagacaaaga ttgtctgtat tagtcctcaa cacactaaac cttacatact tagggtaaat     300
ttgctaatag agtgatatgt tcatgagaac tccaacgaca acacaaccac ctatttgcac     360
aacaaacacc attgtcgcac gctgcgcgcc ctagaagtag aaagaaaggg aaatgacatt     420
aagagaatca tacccgtgc ccgtaacgcc gaaaaaatca caccccgtcc cccacacctt      480
aaaacctcaa ccgcttaaca ccgccacacc ctttctcttt ataaacgccg tttgcattac     540
tcattcttct tataaaccgc acccccaaa acgcggaata gcttcaaccc cccaatcaga      600
tatgagtttc ccgggaaacc cgcttttccc gacagcccca caaggggttg gtctataaaa     660
gaggacgttt tccccgtcat cgagattgaa gattcttaca ggcccattta ttcaaattgg     720
agttgattct tcttgtcttt actttcttc tctcttttc ttccttttt aatattatct        780
tttgtcaagc ctggttccct aagttgaact ctcttttctt gtgatcctcc tatatagata    840
cgccttgcca aatgcggccg cgagtccatc ggttcctgtc agatgggata ctcttgacgt     900
ggaaaattca aacagaaaaa aaaccccaat aatgaaaaat aacactacgt tatatccgtg    960
gtatcctcta tcgtatcgta tcgtagcgta tcgtagcgta ccgtatcaca gtatagtcta    1020
atattccgta tcttattgta tcctatccta ttcgatccta ttgtatttca gtgcaccatt    1080
ttaatttcta ttgctataat gtccttatta gttgccactg tgaggtgacc aatggacgag    1140
ggcgagccgt tcagaagccg cgaagggtgt tcttcccatg aatttcttaa ggagggcggc    1200
tcagctccga gagtgaggcg agacgtctcg gtcagcgtat ccccccttcct cggcttttac    1260
aaatgatgcg ctcttaatag tgtgtcgtta tccttttggc attgacgggg gagggaaatt    1320
gattgagcgc atccatattt ttgcggactg ctgaggacaa tggtggtttt tccgggtggc    1380
gtgggctaca aatgatacga tggttttttt cttttcggag aaggcgtata aaaaggacac    1440
ggagaaccca tttattctaa aaacagttga gcttctttaa ttattttttg atataatatt    1500
ctattattat atattttctt cccaataaaa caaataaaa caaaacacag caaaacacaa     1560
aaattctaga taaaatgtca actgtggaag atcactcctc cctacataaa ttgagaaagg    1620
aatctgagat tctttccaat gcaaacaaaa tcttagtggc taatagaggt gaaattccaa    1680
ttagaatttt caggtcagcc catgaattgt caatgcatac tgtggcgatc tattcccatg    1740
aagatcggtt gtccatgcat aggttgaagg ccgacgaggc ttatgcaatc ggtaagactg    1800
gtcaatattc gccagttcaa gcttatctac aaattgacga aattatcaaa atagcaaagg    1860
aacatgatgt ttccatgatc catccaggtt atggtttctt atctgaaaac tccgaattcg    1920
caaagaaggt tgaagaatcc ggtatgattt gggttgggcc tcctgctgaa gttattgatt    1980
ctgttggtga caaggtttct gcaagaaatt tggcaattaa atgtgacgtt cctgttgttc    2040
ctggtaccga tggtccaatt gaagacattg aacaggctaa acagtttgtg gaacaatatg    2100
gttatcctgt cattataaag gctgcatttg gtggtggtgg tagaggtatg agagttgtta    2160
gagaaggtga tgatatagtt gatgctttcc aaagagcgtc atctgaagca aagtctgcct    2220
ttggtaatgg tacttgtttt attgaaagat ttttggataa gccaaaacat attgaggttc    2280
aattattggc tgataattat ggtaacacaa tccatctctt tgaaagagat tgttctgttc    2340
aaagaagaca tcaaaaggtt gttgaaattg cacctgccaa aactttacct gttgaagtta    2400
```

```
gaaatgctat attaaaggat gctgtaacgt tagctaaaac cgctaactat agaaatgctg    2460
gtactgcaga atttttagtt gattcccaaa acagacatta ttttattgaa attaatccaa    2520
gaattcaagt tgaacataca attactgaag aaatcacggg tgttgatatt gttgccgctc    2580
aaattcaaat tgctgcaggt gcatcattgg aacaattggg tctattacaa aacaaaatta    2640
caactagagg ttttgcaatt caatgtagaa ttacaaccga ggatcctgct aagaattttg    2700
ccccagatac aggtaaaatt gaggtttata gatctgcagg tggtaacggt gtcagattag    2760
atggtggtaa tgggtttgcc ggtgctgtta tatctcctca ttatgactcg atgttggtta    2820
aatgttcaac atctggttct aactatgaaa ttgccagaag aaagatgatt agagcttttag   2880 ttgaatttag aatcagaggt gtcaagacca atattccttt cttattggca ttgctaactc    2940
atccagtttt catttcgggt gattgttgga caacttttat tgatgatacc ccttcgttat    3000
tcgaaatggt ttcttcaaag aatagagccc aaaaattatt ggcatatatt ggtgacttgt    3060
gtgtcaatgg ttcttcaatt aaaggtcaaa ttggttttccc taaattgaac aaggaagcag    3120
aaatcccaga tttgttggat ccaaatgatg aggttattga tgtttctaaa ccttctacca    3180
atggtctaag accgtatcta ttaaagtatg gaccagatgc gttttccaaa aaagttcgtg    3240
aattcgatgg ttgtatgatt atggatacca cctggagaga tgcacatcaa tcattattgg    3300
ctacaagagt tagaactatt gatttactga gaattgctcc aacgactagt catgccttac    3360
aaaatgcatt tgcattagaa tgttggggtg gcgcaacatt tgatgttgcg atgaggttcc    3420
tctatgaaga tccttgggag agattaagac aacttagaaa ggcagttcca aatattcctt    3480
tccaaatgtt attgagaggt gctaatggtg ttgcttattc gtcattacct gataatgcaa    3540
ttgatcattt tgttaagcaa gcaaggata atggtgttga tattttcaga gtctttgatg    3600
ctttgaacga tttggaacaa ttgaaggttg gtgttgatgc tgtcaagaaa gccggaggtg    3660
ttgttgaagc tacagtttgt tactcaggtg atatgttaat tccaggtaaa aagtataact    3720
tggattatta tttagagact gttggaaaga ttgtggaaat gggtacccat atttttaggta   3780 ttaaggatat ggctggcacg ttaaagccaa aggctgctaa gttgttgatt ggctcgatca    3840
gatcaaaata ccctgacttg gttatccatg tccatacca tgactctgct ggtaccggta     3900
tttcaactta tgttgcatgc gcattggcag gtgccgacat tgtcgattgt gcaatcaatt    3960
cgatgtctgg tttaacctct caaccttcaa tgagtgcttt tattgctgct ttagatggtg    4020
atatcgaaac tggtgttcca gaacattttg caagacaatt agatgcatac tgggcagaaa    4080
tgagattgtt atactcatgt ttcgaagccg acttgaaggg accagaccca gaagtttata    4140
aacatgaaat tccaggtgga cagttgacta acctaatctt ccaagcccaa caagttggtt    4200
tgggtgaaca atgggaagaa actaagaaga agtatgaaga tgctaacatg ttgttgggtg    4260
atattgtcaa ggttaccccca acctccaagg ttgttggtga tttagcccaa tttatggttt    4320
ctaataaatt agaaaagaa gatgttgaaa acttgctaa tgaattagat ttcccagatt      4380
cagttcttga tttctttgaa ggattaatgg gtacaccata tggtggattc ccagagcctt    4440
tgagaacaaa tgtcatttcc ggcaagagaa gaaaattaaa gggtagacca ggtttagaat    4500
tagaaccttt caacctcgag gaaatcagag aaaatttggt ttccagattt ggtccaggta    4560
ttactgaatg tgatgttgca tcttataaca tgtatccaaa ggtttacgag caatatcgta    4620
aggtggttga aaaatatggt gatttatctg ttttaccaac aaaagcattt ttggctcctc    4680
caactattgg tgaagaagtt catgtggaaa ttgagcaagg taagacttttg attattaagt   4740
```

```
tattagccat ttctgacttg tctaaatctc atggtacaag agaagtatac tttgaattga    4800
atggtgaaat gagaaaggtt acaattgaag ataaaacagc tgcaattgag actgttacaa    4860
gagcaaaggc tgacggacac aatccaaatg aagttggtgc gccaatggct ggtgtcgttg    4920
ttgaagttag agtgaagcat ggaacagaag ttaagaaggg tgatccatta gccgttttga    4980
gtgcaatgaa aatggaaatg gttatttctg ctcctgttag tggtagggtc ggtgaagttt    5040
ttgtcaacga aggcgattcc gttgatatgg gtgatttgct tgtgaaaatt gccaaagatg    5100
aagcgccagc agcttaatta attctgtctt tgattttctt atgttattca aacatctgc     5160 cccaaaatct aacgattata tatattccta cgtataactg tatagctaat tattgattta    5220
tttgtacata aaaaccacat aaatgtaaaa gcaagaaaaa aataactaa ggagaaggat      5280 caatatctca tttataatgc tcgccaaagc agcgtacgtg aatttttaatc aagcatcaa     5340 caaatcttgc aacttggtta tatcgcttct tcacccactc acccgctttt ctacattgtt    5400
gaacacaaat atatacaggg gtatgtctca aggtcaagtg cagtttcaac agagactacc    5460
tcaaggtacc tcttcagaaa tgcagaactt cactcttgat cagattttct ccgaattaaa    5520
ggtttaaaca tagcctcatg aaatcagcca tttgcttttg ttcaacgatc ttttgaaatt    5580
gttgttgttc ttggtagtta agttgatcca tcttggctta tgttgtgtgt atgttgtagt    5640
tattcttagt atattcctgt cctgagttta gtgaaacata atatcgcctt gaaatgaaaa    5700
tgctgaaatt cgtcgacata caattttca aactttttt ttttcttggt gcacggacat      5760
gtttttaaag gaagtactct ataccagtta ttcttcacaa atttaattgc tggagaatag    5820
atcttcaacg ctttaataaa gtagtttgtt tgtcaaggat ggcgtcatac aaagaaagat    5880
cagaatcaca cacttcccct gttgctagga acttttctc catcatggag gaaagaagt     5940 ctaaccttttg tgcatcattg gatattactg aaactgaaaa gcttctctct attttggaca   6000
ctattggtcc ttacatctgt ctagttaaaa cacacatcga tattgtttct gattttacgt    6060
atgaaggaac tgtgttgcct ttgaaggagc ttgccaagaa acataatttt atgattttg     6120 aagatagaaa atttgctgat attggtaaca ctgttaaaaa tcaatataaa tctggtgtct    6180
tccgtattgc cgaatgggct gacatcacta atgcacatgg tgtaacgggt gcaggtattg    6240
tttctggctt gaaggaggca gcccaagaaa caaccagtga acctagaggt ttgctaatgc    6300
ttgctgagtt atcatcaaag ggttctttag catatggtga atatacagaa aaaacagtag    6360
aaattgctaa atctgataaa gagtttgttg ag                                  6392
```

<210> SEQ ID NO 154
<211> LENGTH: 22
<212> TYPE: DNA
<213> ORGANISM: Artificial Sequence
<220> FEATURE:
<223> OTHER INFORMATION: Primer

<400> SEQUENCE: 154

```
gcaggtgctt caggtcaatt cg                                               22
```

<210> SEQ ID NO 155
<211> LENGTH: 4886
<212> TYPE: DNA
<213> ORGANISM: Artificial Sequence
<220> FEATURE:
<223> OTHER INFORMATION: MAE gene integration fragment

<400> SEQUENCE: 155

```
ctttgaagga gcttgccaag aaacataatt ttatgatttt tgaagataga aaatttgctg      60
```

-continued

```
atattggtaa cactgttaaa aatcaatata aatctggtgt cttccgtatt gccgaatggg      120
ctgacatcac taatgcacat ggtgtaacgg gtgcaggtat tgtttctggc ttgaaggagg      180
cagcccaaga aacaaccagt gaacctagag gtttgctaat gcttgctgag ttatcatcaa      240
agggttcttt agcatatggt gaatatacag aaaaaacagt agaaattgct aaatctgata      300
aagagtttgt cattggtttt attgcgcaac acgatatggg cggtagagaa gaaggttttg      360 actgatcat tatgactcca gggggttggtt tagatgacaa aggtgatgca cttggtcaac       420
aatatagaac tgttgatgaa gttgtaaaga ctggaacgga tatcataatt gttggtagag       480
gtttgtacgg tcaaggaaga gatcctatag agcaagctaa aagataccaa caagctggtt       540
ggaatgctta tttaaacaga tttaaatgat tcttacacaa agatttgata catgtacact       600
agtttaaata agcatgaaaa gaattacaca agcaaaaaaa aaaaaataaa tgaggtactt       660
tacgttcacc tacaaccaaa aaaactagat agagtaaaat cttaagattt agaaaaagtt       720
gtttaacaaa ggctttagta tgtgaatttt taatgtagca aagcgataac taataaacat       780
aaacaaaagt atggtttctt ttatcagtca aatcattatc gattgattgt tccgcgtatc       840
tgcagatagc ctcatgaaat cagccatttg cttttgttca acgatcttt gaaattgttg        900 ttgttcttgg tagttaagtt gatccatctt ggcttatgtt gtgtgtatgt tgtagttatt       960
cttagtatat tcctgtcctg agtttagtga aacataatat cgccttgaaa tgaaaatgct      1020
gaaattcgtc gacatacaat ttttcaaact ttttttttt cttggtgcac ggacatgttt       1080
ttaaaggaag tactctatac cagttattct tcacaaattt aattgctgga gaatagatct      1140
tcaacgcgtt taaacagcaa tttgaggaag gaataggaga aggagaagca atttctagga      1200
aagagcaagg tgtgcaacag catgctctga atgatatttt cagcaatagt tcagttgaag      1260
aacctgttgg cgtatctaca tcacttccta caaacaacac cacgaattgc gtccgtggtg      1320
acgcaactac gaatggcatt gtcaatgcca atgccagtgc acatacacgt gcaagtccca      1380 ccggttcct gcccggctat ggtagagaca agaaggacga taccggcatc gacatcaaca       1440
gtttcaacag caatgcgttt ggcgtcgacg cgtcgatggg gctgccgtat ttggatttgg      1500
acgggctaga tttcgatatg gatatggata tggatatgga tatggagatg aatttgaatt      1560
tagatttggg tcttgatttg gggttggaat taaaagggga taacaatgag ggttttcctg      1620
ttgatttaaa caatggacgt gggaggtgat tgatttaacc tgatccaaaa ggggtatgtc      1680
tattttttag agtgtgtctt tgtgtcaaat tatggtagaa tgtgtaaagt agtataaact      1740
ttcctctcaa atgacgaggt ttaaaacacc ccccgggtga gccgagccga gaatggggca      1800
attgttcaat gtgaaataga agtatcgagt gagaaacttg ggtgttggcc agccaagggg      1860
gaaggaaaat ggcgcgaatg ctcaggtgag attgttttgg aattgggtga agcgaggaaa      1920
tgagcgaccc ggaggttgtg actttagtgg cggaggagga acgggaggaa aaggccaaga      1980
gggaaagtgt atataagggg gagcaatttg ccaaccagga tagaattgga tgagttataa      2040
ttctactgta tttattgtat aatttatttc tccttttata tcaaacacat acaaaacac       2100 acaaaacata caaacataca cagctagcat gggtgaattg aaagagattt tgaaacaaag      2160
atatcatgaa ttacttgatt ggaatgttaa ggcaccacat gtcccttat cccagagatt       2220 gaagcacttt acttggtcat ggtttgcttg tactatggca accggtggtg ttggtttgat      2280
cattggttcc ttcccattca gattctacgg tttgaacacc attggcaaga ttgtttacat      2340
cttacaaatc ttttttgtttt ctcttttttgg ctcttgtatg ttgtttcgtt tcatcaagta    2400
```

```
tccatctacc attaaggact cttggaatca tcacttggaa aagttgttta tcgcaacttg    2460
tttgttatct atttccacat tcatcgacat gttagctatc tatgcttatc cagataccgg    2520
tgaatggatg gtctgggtca ttagaatctt atactacatc tatgtcgctg tctctttcat    2580
ctactgtgtt atggccttt tcaccatttt caacaatcat gtttacacta ttgaaactgc     2640
ttctccagct tggattttgc caatcttccc tccaatgatc tgtggtgtca ttgctggtgc    2700
tgttaactcc acccaacctg ctcaccaatt gaaaaacatg gtcattttcg gtatcttgtt    2760
tcaaggttta ggttttgggg tttaccttt acttttcgcc gttaatgttt tgagattctt    2820
cacagtcggt ttagcaaagc cacaagatag accaggtatg tttatgttcg ttggtccacc    2880
agctttctct ggtttagcat tgattaacat tgcaagaggt gcaatgggct caagacctta    2940
cattttcgtt ggtgcaaact cttccgaata cttaggtttt gtctcaacct tcatggccat    3000
tttcatctgg ggtttagccg catggtgtta ttgcttagct atggtttcct tccttgccgg    3060
ctttttcact agagcaccat tgaaattcgc ttgtggttgg ttcgcttca tctttccaaa     3120
tgttggtttt gttaactgta ctatcgaaat cggcaagatg attgattcta aggcttttca    3180
aatgtttggt cacatcattg gtgttatctt gtgtattcaa tggatttttgt taatgtactt    3240
aatggttaga gcattccttg ttaatgactt gtgctatcct ggtaaagacg aagatgcaca    3300
cccaccacca aagccaaaca ctggtgtctt aaacccaact ttcccaccag agaaggctcc    3360
agcatcatta gagaaggttg atactcatgt tacatcaaca ggtggtgaat ccatcctcc     3420
atcttccgaa catgaatccg tttaaggcgc gccatctaat agtttaatca cagcttatag    3480
tctactatag ttttcttttt taaacattgt tgtatttgt cccccccctc taattgatga     3540
tgattatcct ataagaatcc aataaaacga tggaaactaa taccctctcc tttgtcatgt    3600
ggtctttagt atttcttgaa cattggctct gatttctcga cttatagtc ctattaaaat     3660
cgctgttagt tctcgatcgt tgtatctcgt ttcttgtctc tttggtggat gattttgcgt    3720
gcgaacatgt tttttccct ttctctcacc atcatcgtgt agttcttgtc accatccccc     3780
ccacccttc cttctctcat tgattctata agagcttatc cacagaggtg cagtaacgag     3840
gtagtttaac cttcgagtgg atcaaaatgt cacacaggcc tgcggccgct accataatgt    3900
atgcgttgag cctcttgcac cttctttatt aggaaatcag ttgaaaaatt tccggattgt    3960
ctttattatt ggcccatttt tttttggtca cacctttatt tttgtacact tctcgggcaa    4020
agcaaaaact atagtaccgg ataggccttt ataaaactcc agtgtgtatg attttagttg    4080
gtgtgccatc tacacgttct cttagtttct ttatcatgtc acagaaagca agcatgcaaa    4140
cccttacaaa aaataacaac atacaaatgc ctaaacaact ggactataat gatggtgagt    4200
cagttacgaa aagagcaagt gggttaatac gatttcgtaa gggacagtct gaggaagact    4260
acaattttca aaaggagcag ttctggtcca cgggtccttt agtacagaat cacacatttg    4320
tgactgaatt tgttgaaaag tttattgaaa acacaattag tgaagattat tcaatcacag    4380
atagatcgaa aatagaacgt gaaacaatca tacacggatt ggagaagctg tattttcaaa    4440
gggaatatga gcgatgtcta aaagatgttc aactattgaa ggacaatatc gataagttca    4500
atcctaattt ggatcttaat gaaaagaatt tataatgagc tgaattatat tcttggatg     4560
tgcatcaaaa agatccatga gagtaacgaa aagaaactgg gggaaatcta ataatttaca    4620
atttcaatat acacttctat atcctttaat gtaatggctt tataaataaa cacgaacttc    4680
tacagcaccg acgtttcttt ttcttaccag ctccctcttct tcttcttctt cttcttcttc    4740
ttcttcttct tcttcttctt cttcttcttc ttcttcttct ttcttaccat cattgccatt    4800
```

```
ttcctttttt cttatttgct cttgatcctc tgtttttca atttggacaa actcatctaa    4860
tacaccaaca cttttagggc ccccgc                                         4886

<210> SEQ ID NO 156
<211> LENGTH: 22
<212> TYPE: DNA
<213> ORGANISM: Artificial Sequence
<220> FEATURE:
<223> OTHER INFORMATION: Primer

<400> SEQUENCE: 156
cagcagcacc acaaactgta ac                                               22

<210> SEQ ID NO 157
<211> LENGTH: 20
<212> TYPE: DNA
<213> ORGANISM: Artificial Sequence
<220> FEATURE:
<223> OTHER INFORMATION: Primer

<400> SEQUENCE: 157
tcttctctac cgcccatatc                                                  20

<210> SEQ ID NO 158
<211> LENGTH: 23
<212> TYPE: DNA
<213> ORGANISM: Artificial Sequence
<220> FEATURE:
<223> OTHER INFORMATION: Primer

<400> SEQUENCE: 158
tgaatgggag gcatgaatcg cag                                              23

<210> SEQ ID NO 159
<211> LENGTH: 20
<212> TYPE: DNA
<213> ORGANISM: Artificial Sequence
<220> FEATURE:
<223> OTHER INFORMATION: Primer

<400> SEQUENCE: 159
cacagaggtg cagtaacgag                                                  20

<210> SEQ ID NO 160
<211> LENGTH: 4115
<212> TYPE: DNA
<213> ORGANISM: Artificial Sequence
<220> FEATURE:
<223> OTHER INFORMATION: I. orientalis FUM gene integration fragment

<400> SEQUENCE: 160 aattcttga aggagcttgc caagaaacat aattttatga ttttgaaga tagaaaattt      60 gctgatattg gtaacactgt taaaaatcaa tataaatctg gtgtcttccg tattgccgaa    120
tgggctgaca tcactaatgc acatggtgta acgggtgcag gtattgtttc tggcttgaag    180
gaggcagccc aagaaacaac cagtgaacct agaggtttgc taatgcttgc tgagttatca    240
tcaaagggtt ctttagcata tggtaatat acagaaaaaa cagtagaaat tgctaaatct    300
gataaagagt ttgtcattgg ttttattgcg caacacgata tgggcggtag agaagaaggt    360
tttgactgga tcattatgac tccaggggtt ggtttagatg acaaaggtga tgcacttggt    420
caacaatata gaactgttga tgaagttgta aagactggaa cggatatcat aattgttggt    480
```

-continued

```
agaggtttgt acggtcaagg aagagatcct atagagcaag ctaaaagata ccaacaagct   540
ggttggaatg cttatttaaa cagatttaaa tgattcttac acaaagattt gatacatgta   600
cactagttta aataagcatg aaaagaatta cacaagcaaa aaaaaaaaaa taaatgaggt   660
actttacgtt cacctacaac caaaaaaact agatagagta aaatcttaag atttagaaaa   720
agttgtttaa caaaggcttt agtatgtgaa ttttttaatgt agcaaagcga taactaataa   780
acataaacaa aagtatggtt ttctttatca gtcaaatcat tatcgattga ttgttccgcg   840
tatctgcaga tagcctcatg aaatcagcca tttgcttttg ttcaacgatc ttttgaaatt   900
gttgttgttc ttggtagtta agttgatcca tcttggctta tgttgtgtgt atgttgtagt   960
tattcttagt atattcctgt cctgagttta gtgaaacata atatcgcctt gaaatgaaaa  1020
tgctgaaatt cgtcgacata caattttca aactttttt ttttcttggt gcacggacat  1080 gttttttaaag gaagtactct ataccagtta ttcttcacaa atttaattgc tggagaatag  1140
atcttcaacg cgtttcctcg acatttgctg caacggcaac atcaatgtcc acgtttacac  1200
acctacattt atatctatat ttatatttat atttatttat ttatgctact agcttctat  1260 agttagttaa tgcactcacg atattcaaaa ttgacaccct tcaactactc cctactattg  1320
tctactactg tctactactc ctctttacta tagctgctcc caataggctc caccaatagg  1380
ctctgtcaat acattttgcg ccgccaccct tcaggttgtg tcactcctga aggaccatat  1440
tgggtaatcg tgcaatttct ggaagagagt ccgcgagaag tgaggccccc actgtaaatc  1500
ctcgaggggg catggagtat ggggcatgga ggatggagga tggggggggg ggggggaaa  1560 ataggtagcg aaaggacccg ctatcacccc acccggagaa ctcgttgccg ggaagtcata  1620
tttcgacact ccggggagtc tataaaaggc gggttttgtc ttttgccagt tgatgttgct  1680
gagaggactt gtttgccgtt tcttccgatt taacagtata gaatcaacca ctgttaatta  1740
tacacgttat actaacacaa caaaaacaaa aacaacgaca acaacaacaa catctagata  1800
aaatgttagc tgctagatca ttaaaggcaa gaatgtcaac aagagctttc tcaactacct  1860
caattgcaaa aagaatcgaa aaagatgcat ttggtgacat tgaagtccca aatgagaaat  1920 attgggggtgc tcaaactcaa agatctttac aaaatttcaa aattggtggt aagagagaag  1980
ttatgccaga accaatcatc aaatcttttg gtattttaaa gaaggctact gctaagatca  2040
atgctgagtc tggtgcttta gacccaaagt tatctgaagc catccaacaa gctgcaaccg  2100
aagtttatga aggtaaacta atggaccatt tcccattagt tgtctttcaa accggttctg  2160
gtactcaatc taacatgaat gccaatgaag tcatctctaa tagagcaatt gaaatcttgg  2220
gtggtgaatt aggctctaaa actccagtcc atcctaatga tcatgttaat atgtcccaat  2280
cttctaatga tactttccct actgtcatgc atattgcagc agttacagaa gtttcatccc  2340
atttattacc agaattaact gcactaagag atgcattgca aaagaaatcc gatgaattta  2400
agaatattat caaaatcggt agaacccatt tacaagatgc aactccttta actttaggtc  2460
aagaattttc tggttatgtt caacaatgta ctaatggtat caaaagaatc gaaattgctc  2520
ttgaacattt gagatactta gctcaaggtg gtactgccgt tggtactggt cttaacacca  2580
agaaaggttt tgctgaaaag gttgcaaatg aagtcactaa attgactggt ttacaattct  2640
ataccgctcc aaataaattc gaagcccttg cagctcacga tgctgttgtt gaaatgtctg  2700
gtgctttgaa taccgttgca gtctcattat tcaaaatcgc tcaagatatc agatatttgg  2760
gttccggccc aagatgtggt tatggtgaat tggcttacc agaaaatgaa ccaggttctt  2820
ccatcatgcc gggtaaagtt aacccaactc aaaaacgaagc tttgactatg ctttgtaccc  2880
```

```
aagtctttgg taaccactct tgtattacct ttgcaggtgc ttcaggtcaa ttcgaattga      2940
atgtctttaa gccagttatg atctccaact tgttatcttc tattaggtta ttaggtgatg      3000
gttgtaattc ttttagaatc cactgtgttg aaggtatcat tgcaaatacc gacaagattg      3060
ataaattact acatgaatct ctcatgttag ttactgcttt gaacccacac attggttacg      3120
ataaggcttc caagattgca agaatgcac acaagaaggg cttgacattg aaacaatctg       3180
cattggaatt aggttacttg accgaagaac aattcaatga atgggttaga ccagaaaaca      3240
tgattggtcc aaaggattaa gttaattaac atctgaatgt aaaatgaaca ttaaaatgaa      3300
ttactaaact ttacgtctac tttacaatct ataaactttg tttaatcata taacgaaata      3360
cactaataca caatcctgta cgtatgtaat acttttatcc atcaaggatt gagaaaaaaa      3420
agtaatgatt ccctgggcca ttaaaactta gaccccaag cttggatagg tcactctcta       3480
ttttcgtttc tcccttccct gatagaaggg tgatatgtaa ttaagaataa tatataattt      3540
tataataaaa gcggccgcct cccttctcta aatggactgc ttggataact tggaccccct     3600
tcccatttta tagtcattct cttccccctc attttcccac tattcccaac aatgaccatc      3660
tctccacctt gtttccccat tcttcctgct ctacctggtg ggggtgtttc accccattaa      3720
cggtcggatt ccgctgtgga gatggctctg gccttttcc cattccttcc ccccctcaat       3780
cttctccatg cggggaaaaa aaattttat ccataaacaa ccaaaccggc ggctcaacgg       3840
ggggtttata ctgacagaaa tggggtcaat acacccactg actgtacccg ctctaatctt     3900
aagctttccc ccccccctcc tgtattaacg gcgcggagtg cccgcagcgc caatggaga     3960 aggcgcgcag tggggatgc ccagggaggg gacaggtaca cgcacaggcc atgccaacac      4020
cgcatagacg tgcgacctcc tctccccac tgcagagctg ccttttcgg acacactccg      4080 tgcaagagga ctcggccggc tcggcttttc tgccg                                4115

<210> SEQ ID NO 161
<211> LENGTH: 6527
<212> TYPE: DNA
<213> ORGANISM: Artificial Sequence
<220> FEATURE:
<223> OTHER INFORMATION: PYC gene inserter fragment

<400> SEQUENCE: 161
ctaaaagtgt tggtgtatta gatgagtttg tccaaattga aaaacagag gatcaagagc         60 aaataagaaa aaaggaaaat ggcaatgatg gtaagaaaga agaagaagaa gaagaagaag        120
aagaagaaga agaagaagaa gaagaagaag aagaagaaga agaggagctg gtaagaaaaa        180
gaaacgtcgg tgctgtagaa gttcgtgttt atttataaag ccattacatt aaaggatata       240
gaagtgtata ttgaaattgt aaattattag atttccccca gtttctttc gttactctca        300 tggatctttt tgatgcacat ccaagaaata taattcagct cattataaat tcttttcatt       360
aagatccaaa ttaggattga acttatcgat attgtccttc aatagttgaa catcttttag      420
acatcgctca tattcccttt gaaaatacag cttctccaat ccgtgtatga ttgtttcacg      480
ttctattttc gatctatctg tgattgaata atcttcacta attgtgtttt caataaactt      540
ttcaacaaat tcagtcacaa atgtgtgatt ctgtactaaa ggacccgtgg accgaaactg     600
ctccttttga aaattgtagt cttcctcaga ctgtccctta cgaaatcgta ttaacccact     660
tgctcttttc gtaactgact caccatcatt atagtccagt tgtttaggca tttgtatgtt      720
gttatttttt gtaagggttt gcatgcttgc tttctgtgac atgataaaga aactaagaga       780
```

```
acgtgtagat ggcacaccaa ctaaaatcat acacactgga gttttataaa ggcctatccg    840
gtactatagt ttttgctttg cccgagaagt gtacaaaaat aaaggtgtga ccaaaaaaaa    900
atgggccaat aataaagaca atccggaaat ttttcaactg atttcctaat aaagaaggtg    960
caagaggctc aacgcataca ttatggtagc ggccgcgagt ccatcggttc ctgtcagatg   1020
ggatactctt gacgtggaaa attcaaacag aaaaaaaacc ccaataatga aaataacac    1080 tacgttatat ccgtggtatc ctctatcgta tcgtatcgta gcgtatcgta gcgtaccgta   1140
tcacagtata gtctaatatt ccgtatctta ttgtatccta tcctattcga tcctattgta   1200
tttcagtgca ccatttttaat ttctattgct ataatgtcct tattagttgc cactgtgagg   1260
tgaccaatgg acgagggcga gccgttcaga agccgcgaag ggtgttcttc ccatgaattt   1320
cttaaggagg gcggctcagc tccgagagtg aggcgagacg tctcggtcag cgtatccccc   1380
ttcctcggct tttacaaatg atgcgctctt aatagtgtgt cgttatcctt ttggcattga   1440
cgggggaggg aaattgattg agcgcatcca tattttttgcg gactgctgag gacaatggtg   1500 gttttccgg gtggcgtggg ctacaaatga tacgatggtt ttttcttt cggagaaggc   1560 gtataaaaag gacacggaga acccattat tctaaaaaca gttgagcttc tttaattatt   1620
ttttgatata atattctatt attatatatt ttcttcccaa taaaacaaaa taaaacaaaa   1680
cacagcaaaa cacaaaaatt ctagataaaa tgtcaactgt ggaagatcac tcctccctac   1740
ataaattgag aaaggaatct gagattcttt ccaatgcaaa caaaatctta gtggctaata   1800
gaggtgaaat tccaattaga attttcaggt cagcccatga attgtcaatg catactgtgg   1860
cgatctattc ccatgaagat cggttgtcca tgcataggtt gaaggccgac gaggcttatg   1920
caatcggtaa gactggtcaa tattcgccag ttcaagctta tctacaaatt gacgaaatta   1980
tcaaaatagc aaaggaacat gatgtttcca tgatccatcc aggttatggt ttcttatctg   2040
aaaactccga attcgcaaag aaggttgaag aatccggtat gatttgggtt gggcctcctg   2100
ctgaagttat tgattctgtt ggtgacaagg tttctgcaag aaatttggca attaaatgtg   2160
acgttcctgt tgttcctggt accgatggtc caattgaaga cattgaacag gctaaacagt   2220
ttgtggaaca atatgttat cctgtcatta taaaggctgc atttggtggt ggtggtagag   2280
gtatgagagt tgttagagaa ggtgatgata tagttgatgc tttccaaaga gcgtcatctg   2340
aagcaaagtc tgcctttggt aatggtactt gttttattga agatttttg gataagccaa   2400 aacatattga ggttcaatta ttggctgata attatggtaa cacaatccat ctctttgaaa   2460
gagattgttc tgttcaaaga agacatcaaa aggttgttga aattgcacct gccaaaactt   2520
tacctgttga agttagaaat gctatattaa aggatgctgt aacgttagct aaaaccgcta   2580
actatagaaa tgctggtact gcagaatttt tagttgattc ccaaaacaga cattatttta   2640
ttgaaattaa tccaagaatt caagttgaac atacaattac tgaagaaatc acgggtgttg   2700
atattgttgc cgctcaaatt caaattgctg caggtgcatc attggaacaa ttgggtctat   2760
tacaaaacaa aattacaact agaggttttg caattcaatg tagaattaca accgaggatc   2820
ctgctaagaa ttttgcccca gatacaggta aaattgaggt ttatagatct gcaggtggta   2880 acgtgtcag attagatggt ggtaatgggt ttgccggtgc tgttatatct cctcattatg   2940
actcgatgtt ggttaaatgt tcaacatctg gttctaacta tgaaattgcc agaagaaaga   3000
tgattagagc tttagttgaa tttagaatca gaggtgtcaa gaccaatatt cctttcttat   3060
tggcattgct aactcatcca gttttcattt cgggtgattg ttggacaact tttattgatg   3120
ataccccttc gttattcgaa atggtttctt caaagaatag agcccaaaaa ttattggcat   3180
```

```
atattggtga cttgtgtgtc aatggttctt caattaaagg tcaaattggt ttccctaaat   3240
tgaacaagga agcagaaatc ccagatttgt tggatccaaa tgatgaggtt attgatgttt   3300
ctaaaccttc taccaatggt ctaagaccgt atctattaaa gtatggacca gatgcgtttt   3360
ccaaaaaagt tcgtgaattc gatggttgta tgattatgga taccacctgg agagatgcac   3420
atcaatcatt attggctaca agagttagaa ctattgattt actgagaatt gctccaacga   3480
ctagtcatgc cttacaaaat gcatttgcat tagaatgttg gggtggcgca acatttgatg   3540
ttgcgatgag gttcctctat gaagatcctt gggagagatt aagacaactt agaaaggcag   3600
ttccaaatat tccttccaa atgttattga gaggtgctaa tggtgttgct tattcgtcat   3660
tacctgataa tgcaattgat cattttgtta agcaagcaaa ggataatggt gttgatattt   3720
tcagagtctt tgatgctttg aacgatttgg aacaattgaa ggttggtgtt gatgctgtca   3780
agaaagccgg aggtgttgtt gaagctacag tttgttactc aggtgatatg ttaattccag   3840
gtaaaaagta taacttggat tattatttag agactgttgg aaagattgtg gaaatgggta   3900
cccatatttt aggtattaag gatatggctg gcacgttaaa gccaaaggct gctaagttgt   3960
tgattggctc gatcagatca aaataccctg acttggttat ccatgtccat acccatgact   4020
ctgctggtac cggtatttca acttatgttg catgcgcatt ggcaggtgcc gacattgtcg   4080
attgtgcaat caattcgatg tctgttttaa cctctcaacc ttcaatgagt gcttttattg   4140
ctgctttaga tggtgatatc gaaactggtg ttccagaaca ttttgcaaga caattagatg   4200
catactgggc agaaatgaga ttgttatact catgtttcga agccgacttg aagggaccag   4260
acccagaagt ttataaacat gaaattccag gtggacagtt gactaaccta atcttccaag   4320
cccaacaagt tggtttgggt gaacaatggg aagaaactaa gaagaagtat gaagatgcta   4380
acatgttgtt gggtgatatt gtcaaggtta ccccaacctc caaggttgtt ggtgatttag   4440
cccaatttat ggtttctaat aaattagaaa aagaagatgt tgaaaaactt gctaatgaat   4500
tagatttccc agattcagtt cttgatttct ttgaaggatt aatgggtaca ccatatggtg   4560
gattcccaga gcctttgaga acaaatgtca tttccggcaa gagaagaaaa ttaagggta   4620
gaccaggttt agaattagaa cctttcaacc tcgaggaat cagagaaaat ttggtttcca   4680
gatttggtcc aggtattact gaatgtgatg ttgcatctta taacatgtat ccaaaggttt   4740
acgagcaata tcgtaaggtg gttgaaaaat atggtgattt atctgtttta ccaacaaaag   4800
cattttggc tcctccaact attggtgaag aagttcatgt ggaaattgag caaggtaaga   4860
ctttgattat taagttatta gccatttctg acttgtctaa atctcatggt acaagagaag   4920
tatactttga attgaatggt gaaatgagaa aggttacaat tgaagataaa acagctgcaa   4980
ttgagactgt tacaagagca aaggctgacg gacacaatcc aaatgaagtt ggtgcgccaa   5040
tggctggtgt cgttgttgaa gttagagtga agcatggaac agaagttaag aagggtgatc   5100
cattagccgt tttgagtgca atgaaaatgg aaatggttat ttctgctcct gttagtggta   5160
gggtcggtga agttttttgtc aacgaaggcg attccgttga tatgggtgat ttgcttgtga   5220
aaattgccaa agatgaagcg ccagcagctt aattaattct gtctttgatt ttcttatgtt   5280
attcaaaaca tctgccccaa aatctaacga ttatatatat tcctacgtat aactgtatag   5340
ctaattattg atttatttgt acataaaaac cacataaatg taaaagcaag aaaaaaaata   5400
actaaggaga aggatcaata tctcatttat aatgctcgcc aaagcagcgt acgtgaattt   5460
taatcaagac atcaacaaat cttgcaactt ggttatatcg cttcttcacc cactcacccg   5520
```

| | |
|---|---|
| cttttctaca ttgttgaaca caaatatata caggggtatg tctcaaggtc aagtgcagtt | 5580 |
| tcaacagaga ctacctcaag gtacctcttc agaaatgcag aacttcactc ttgatcagat | 5640 |
| tttctccgaa ttaaaggttt aaacatagcc tcatgaaatc agccatttgc ttttgttcaa | 5700 |
| cgatcttttg aaattgttgt tgttcttggt agttaagttg atccatcttg cttatgttg | 5760 |
| tgtgtatgtt gtagttattc ttagtatatt cctgtcctga gtttagtgaa acataatatc | 5820 |
| gccttgaaat gaaaatgctg aaattcgtcg acatacaatt tttcaaactt ttttttttc | 5880 |
| ttggtgcacg gacatgtttt taaaggaagt actctatacc agttattctt cacaaattta | 5940 |
| attgctggag aatagatctt caacgcttta ataaagtagt ttgtttgtca aggatggcgt | 6000 |
| catacaaaga aagatcagaa tcacacactt cccctgttgc taggagactt ttctccatca | 6060 |
| tggaggaaaa aagtctaac ctttgtgcat cattggatat tactgaaact gaaaagcttc | 6120 |
| tctctatttt ggacactatt ggtccttaca tctgtctagt aaaacacac atcgatattg | 6180 |
| tttctgattt tacgtatgaa ggaactgtgt tgcctttgaa ggagcttgcc aagaaacata | 6240 |
| attttatgat ttttgaagat agaaaatttg ctgatattgg taacactgtt aaaaatcaat | 6300 |
| ataaatctgg tgtcttccgt attgccgaat gggctgacat cactaatgca catggtgtaa | 6360 |
| cgggtgcagg tattgtttct ggcttgaagg aggcagccca agaacaacc agtgaaccta | 6420 |
| gaggtttgct aatgcttgct gagttatcat caaagggttc tttagcatat ggtgaatata | 6480 |
| cagaaaaaac agtagaaatt gctaaatctg ataaagagtt tgttgag | 6527 |

<210> SEQ ID NO 162
<211> LENGTH: 3863
<212> TYPE: DNA
<213> ORGANISM: Artificial Sequence
<220> FEATURE:
<223> OTHER INFORMATION: MDH gene integration fragment

<400> SEQUENCE: 162

| | |
|---|---|
| ccataactga catttatggt aaggttgctc gttgtaatgt agtgttgtgt ggtatggtat | 60 |
| tatagtataa aatagtatat caataatata tcggagtata tatggtataa tagtatgaag | 120 |
| tatagcacat tgtaccatgt cgtggagcat attatggtat tacgtggttt ggcatagtat | 180 |
| actatagtat tatagagttg tattgtacta taaagcagtg ttgtttctgg atactacact | 240 |
| aacgtatagt gtactacagt tttgtatagt atagtctagc gtatcagagt tgtactgcag | 300 |
| catcgtgtag tatgctacat tgaactcctc atgtcgcatc ttatattatc gtattgatct | 360 |
| catcttatct tatcatatca tattatttca tttcatttcg ttatatactc tactcctcat | 420 |
| cactatacat cccccatgca tatcaatata cataaaaaa cgtcacacca gtacacccaa | 480 |
| gtcagcccat catttcgaag tgtcaacaac atatctgcct aaaatcttac cttgctccat | 540 |
| caattcatag atctttggca actcactcaa accaacaatc ttaattggtg acttcactaa | 600 |
| accccctggtg cggccgcgga tccctcgaga ttggtagttc tttccccctc tcaagctggc | 660 |
| gtgaaatgca accttacggc gtctacgtta ctacaaggtc cagaaagtgt aggtattgct | 720 |
| actattttta tttttattg gttctggaga aatgcagaca gtcaatgaac caactgtct | 780 |
| caatatgcat ctatgcacat gcacacacac acacatcaca ggtaccccta caaagagagg | 840 |
| tctcttgata atgtttcatt accacgtggc atccccccc ccccccccaa taaacaagtg | 900 |
| gccgagttcc cctgttgcag aggaggacaa aaaaccgct ggtgttggta ccattatgca | 960 |
| gcaactagca caacaaacaa ccgacccaga catacaaatc aacaacactt cgccaaagac | 1020 |
| acccttttcca gggaggatcc actcccaacg tctctccata atgtctctgt tggcccatgt | 1080 |

```
ctctgtcgtt gacaccgtaa ccacaccaac caacccgtcc attgtactgg gatggtcgtc    1140
catagacacc tctccaacgg ggaacacctc attcgtaaac cgccaaggtt accgttcctc    1200
ctgactcgcc ccgttgttga tgctgcgcac ctgtggttgc ccaacatggt tgtatatcgt    1260
gtaaccacac caacacatgt gcagcacatg tgtttaaaag agtgtcatgg aggtggatca    1320
tgatggaagt ggactttacc acttgggaac tgtctccact cccgggaaga aaagacccgg    1380
cgtatcacgc ggttgcctca atggggcaat ttggaaggag aaatataggg aaaatcacgt    1440
cgctctcgga cggggaagag ttccagacta tgaggggggg gggtggtata taaagacagg    1500
agatgtccac ccccagagag aggaagaagt tggaacttta aagagagag ataactttcc     1560 ccagtgtcca tcaatacaca accaaacaca aactctatat ttacacatat aaccccctct    1620
ctagataaaa tggttaaagt tacagtttgt ggtgctgctg gtggtattgg tcaacccctt    1680
tctttactct tgaagcaatc ctctcacatt actcacttat ctctttatga tatcgttaat    1740
actcctggtg ttgctgctga tcttagtcat atcgatacca aatccaaggt cactggtcat    1800
gtaggtgctg ctcaacttga agaagctatc aaggattctg atgttgtcgt tattcccgct    1860
ggtgtcccaa gaaagccagg tatgacgcgt gatgatcttt tcaagattaa tgctggtatt    1920
gtacgtgatt tggctacagc tgctgcaaag tacgctccaa aggccttcat gtgtatcatt    1980
tctaacccag tcaactcgac tgtcccaatc gttactgaag tattcaaaca gcacaatgtt    2040
tatgacccca aaagaatctt tggtgtaaca acacttgata ttgttcgtgc atccaccttt    2100
gtatccgaat tgattggagg tgaacctaat tcacttcgtg ttcccgtcat ggtggtcac    2160 agcggcgtaa ccatcttacc tttactctca caggtccccg gcattgaaaa gttaaaccaa    2220
gaacaaattg agaaggtaac tcatcgtatt caatttggtg gcgatgaagt tgtcaaggcc    2280
aaggatggtg ctggttctgc cactctttcc atggcttatg ctggtgctcg ttttgctaca    2340
aacatcattg aggctgcttt tgctggaaag aagggcattg ttgaatgtac ctatgttcaa    2400
ttggatgctg ataaatctgg tgcccaatct gtcaaggatt tggttggtag tgaacttgaa    2460
tatttctctg ttcccgttga attgggtcct agtggtgttg aaaagatttt acccattgga    2520
aacgttaatg aatatgaaaa gaagttgttg aacgaggctt ctcctgaatt aaaaaccaac    2580
attgataaag gttgtacttt tgttactgaa ggctcaaagt tgtaattaat taatttattt    2640
tactagttta tttttgctcc tgagaatagg attacaaaca cttaaagtct ttaattacaa    2700
ctatatataa tattctgttg gttttcttga attggttcgc tgcgattcat gcctcccatt    2760
caccaaaggt ggagtgggaa ataacggttt tactgcggta attagcagag gcaagaacag    2820
gatacacttt ttgatgataa atctgtatta tagtcgagcc tatttaggaa atcaaatttt    2880
cttgtgttta cttttcaaat aaataatgtt cgaaaatttt tactttactc cttcatttaa    2940
ctataccaga cgttatatca tcaacacctt ctgaccatat acagctcaag atgtttaaga    3000
gtctgttaaa ttttttcaat ccatttcatg gagtaccagg aggtgctaca aaaggaattc    3060
atagcctcat gaaatcagcc atttgctttt gttcaacgat cttttgaaat tgttgttgtt    3120
cttggtagtt aagttgatcc atcttggctt atgttgtgtg tatgttgtag ttattcttag    3180
tatattcctg tcctgagttt agtgaaacat aatatcgcct tgaaatgaaa atgctgaaat    3240
tcgtcgacat acaattttc aaacttttt ttttcttgg tgcacggaca tgtttttaaa       3300
ggaagtactc tataccagtt attcttcaca aatttaattg ctggagaata gatcttcaac    3360
gctttaataa agtagtttgt ttgtcaagga tggcgtcata caaagaaaga tcagaatcac    3420
```

```
acacttcccc tgttgctagg agactttct ccatcatgga ggaaaagaag tctaaccttt    3480
gtgcatcatt ggatattact gaaactgaaa agcttctctc tattttggac actattggtc    3540
cttacatctg tctagttaaa acacacatcg atattgtttc tgattttacg tatgaaggaa    3600
ctgtgttgcc tttgaaggag cttgccaaga aacataattt tatgattttt gaagatagaa    3660
aatttgctga tattggtaac actgttaaaa atcaatataa atctggtgtc ttccgtattg    3720
ccgaatgggc tgacatcact aatgcacatg gtgtaacggg tgcaggtatt gtttctggct    3780
tgaaggaggc agcccaagaa acaaccagtg aacctagagg tttgctaatg cttgctgagt    3840
tatcatcaaa gggttcttta gca                                             3863
```

<210> SEQ ID NO 163
<211> LENGTH: 4760
<212> TYPE: DNA
<213> ORGANISM: Artificial Sequence
<220> FEATURE:
<223> OTHER INFORMATION: MAE gene integration fragment

<400> SEQUENCE: 163

```
aattctttga aggagcttgc caagaaacat aatttatga ttttgaaga tagaaaattt      60 gctgatattg gtaacactgt taaaaatcaa tataaatctg gtgtcttccg tattgccgaa   120
tgggctgaca tcactaatgc acatggtgta acgggtgcag gtattgtttc tggcttgaag   180
gaggcagccc aagaaacaac cagtgaacct agaggtttgc taatgcttgc tgagttatca   240
tcaaagggtt ctttagcata tggtaatat acagaaaaaa cagtagaaat tgctaaatct   300
gataaagagt ttgtcattgg ttttattgcg caacacgata tgggcggtag agaagaaggt   360
tttgactgga tcattatgac tccagggggtt ggtttagatg acaaaggtga tgcacttggt   420
caacaatata gaactgttga tgaagttgta aagactggaa cggatatcat aattgttggt   480
agaggtttgt acggtcaagg aagagatcct atagagcaag ctaaaagata ccaacaagct   540
ggttggaatg cttatttaaa cagatttaaa tgattcttac acaagatttt gatacatgta   600
cactagttta ataagcatg aaaagaatta cacaagcaaa aaaaaaaaa taaatgaggt   660 actttacgtt cacctacaac caaaaaaact agatagagta aaatcttaag atttagaaaa   720
agttgtttaa caaaggcttt agtatgtgaa ttttaatgt agcaaagcga taactaataa   780
acataaacaa aagtatggtt ttctttatca gtcaaatcat tatcgattga ttgttccgcg   840
tatctgcaga tagcctcatg aaatcagcca tttgcttttg ttcaacgatc ttttgaaatt   900
gttgttgttc ttggtagtta agttgatcca tcttggctta tgttgtgtgt atgttgtagt   960
tattcttagt atattcctgt cctgagttta gtgaaacata atatcgcctt gaaatgaaaa  1020
tgctgaaatt cgtcgacata caattttca aacttttttt ttttcttggt gcacggacat  1080 gttttttaaag gaagtactct ataccagtta ttcttcacaa atttaattgc tggagaatag  1140
atcttcaacg cgtttaaaca gcaatttgag gaaggaatag gagaaggaga agcaatttct  1200
aggaaagagc aaggtgtgca acagcatgct ctgaatgata ttttcagcaa tagttcagtt  1260
gaagaacctg ttggcgtatc tacatcactt cctacaaaca acaccacgaa ttgcgtccgt  1320
ggtgacgcaa ctacgaatgg cattgtcaat gccaatgcca gtgcacatac acgtgcaagt  1380
cccaccggtt ccctgcccgg ctatggtaga acaagaagg acgataccgg catcgacatc  1440
aacagtttca acagcaatgc gtttggcgtc gacgcgtcga tggggctgcc gtatttggat  1500
ttggacgggc tagatttcga tatggatatg gatatggata tggatatgga gatgaatttg  1560
aatttagatt tgggtcttga tttggggttg gaattaaaag gggataacaa tgagggtttt  1620
```

```
cctgttgatt taaacaatgg acgtgggagg tgattgattt aacctgatcc aaaagggta    1680 tgtctatttt ttagagtgtg tctttgtgtc aaattatggt agaatgtgta aagtagtata    1740
aactttcctc tcaaatgacg aggtttaaaa cacccccgg gtgagccgag ccgagaatgg     1800
ggcaattgtt caatgtgaaa tagaagtatc gagtgagaaa cttgggtgtt ggccagccaa    1860
gggggaagga aaatggcgcg aatgctcagg tgagattgtt ttggaattgg gtgaagcgag    1920
gaaatgagcg acccggaggt tgtgacttta gtggcgagg aggaacggga ggaaaaggcc     1980
aagagggaaa gtgtatataa gggggagcaa tttgccaacc aggatagaat tggatgagtt    2040
ataattctac tgtatttatt gtataattta tttctccttt tatatcaaac acattacaaa    2100
acacacaaaa catacaaaca tacacagcta gcatgggtga attgaaagag atttttgaaac   2160 aaagatatca tgaattactt gattggaatg ttaaggcacc acatgtccct ttatcccaga    2220
gattgaagca ctttacttgg tcatggtttg cttgtactat ggcaaccggt ggtgttggtt    2280
tgatcattgg ttccttccca ttcagattct acggtttgaa caccattggc aagattgttt    2340
acatcttaca aatcttttg ttttctcttt ttggctcttg tatgttgttt cgtttcatca     2400
agtatccatc taccattaag gactcttgga atcatcactt ggaaaagttg tttatcgcaa    2460
cttgtttgtt atctatttcc acattcatcg acatgttagc tatctatgct tatccagata    2520
ccggtgaatg gatggtctgg gtcattagaa tcttatacta catctatgtc gctgtctctt    2580
tcatctactg tgttatggcc ttttcacca ttttcaacaa tcatgtttac actattgaaa     2640
ctgcttctcc agcttggatt ttgccaatct tccctccaat gatctgtggt gtcattgctg    2700
gtgctgttaa ctccacccaa cctgctcacc aattgaaaaa catggtcatt ttcggtatct    2760
tgtttcaagg tttaggtttt tgggtttacc ttttactttt cgccgttaat gttttgagat    2820
tcttcacagt cggtttagca aagccacaag atagaccagg tatgtttatg ttcgttggtc    2880
caccagcttt ctctggttta gcattgatta acattgcaag aggtgcaatg ggctcaagac    2940
cttacatttt cgttggtgca aactcttccg aatacttagg ttttgtctca accttcatgg    3000
ccattttcat ctggggttta gccgcatggt gttattgctt agctatggtt tccttccttg    3060
ccggcttttt cactagagca ccattgaaat tcgcttgtgg ttggttcgct ttcatctttc    3120
caaatgttgg ttttgttaac tgtactatcg aaatcggcaa gatgattgat tctaaggctt    3180
ttcaaatgtt tggtcacatc attggtgtta tcttgtgtat tcaatggatt ttgttaatgt    3240
acttaatggt tagagcattc cttgttaatg acttgtgcta tcctggtaaa gacgaagatg    3300
cacacccacc accaaagcca aacactggtg tcttaaaccc aactttccca ccagagaagg    3360
ctccagcatc attagagaag gttgatactc atgttacatc aacaggtggt gaatccgatc    3420
ctccatcttc cgaacatgaa tccgtttaag gcgcgccatc taatagttta atcacagctt    3480
atagtctact atagttttct ttttaaaca ttgttgtatt ttgtccccc cctctaattg     3540 atgatgatta tcctataaga atccaataaa acgatgaaa ctaataccct ctcctttgtc     3600
atgtggtctt tagtatttct tgaacattgg ctctgatttc tcgactttat agtcctatta    3660
aaatcgctgt tagttctcga tcgttgtatc tcgtttcttg tctctttggt ggatgatttt    3720
gcgtgcgaac atgttttttt ccctttctct caccatcatc gtgtagttct tgtcaccatc    3780
ccccccaccc cttccttctc tcattgattc tataagagct tatccacaga ggtgcagtaa    3840
cgaggtagtt taaccttcga gtggatcaaa atgtcacaca ggcctgcggc cgcatttggc    3900
aaggcgtatc tatataggag gatcacaaga aaagagagtt caacttaggg aaccaggctt    3960
```

```
gacaaaagat aatattaaaa aaggaagaaa aagagagaaa gaaagtaaag acaagaagaa    4020
tcaactccaa tttgaataaa tgggcctgta agaatcttca atctcgatga cggggaaaac    4080
gtcctctttt atagaccaac cccttgtggg gctgtcggga aaagcgggtt tcccgggaaa    4140
ctcatatctg attgggggt tgaagctatt ccgcgttttg ggggtgcgg tttataagaa    4200 gaatgagtaa tgcaaacggc gtttataaag agaaggggtg tggcggtgtt aagcggttga    4260
ggttttaagg tgtgggggac ggggtgtgat tttttcggcg ttacgggcac ggggtatgat    4320
tctcttaatg tcatttccct ttctttctac ttctagggcg cgcagcgtgc gacaatggtg    4380
tttgttgtgc aaataggtgg ttgtgttgtc gttggagttc tcatgaacat atcactctat    4440
tagcaaattt accctaagta tgtaaggttt agtgtgttga ggactaatac agacaatctt    4500
tgtcttatat ataaatggtt ctactcaatt ttataagttt ttttttttt tttttaatct    4560 ctttatgaaa atcaagaatg acattaaaac aatcacaata ttgtatgcaa gaactttgcc    4620
tctaaacctc tttcaaagag atgcataatt ataaaacaaa tctatttgca tattcgcttt    4680
acacaactat tcaagaatat aattacctaa agagtccatc ttgagttcac caacaccact    4740
acttagagct cggtacccgc                                                4760
```

<210> SEQ ID NO 164
<211> LENGTH: 4174
<212> TYPE: DNA
<213> ORGANISM: Artificial Sequence
<220> FEATURE:
<223> OTHER INFORMATION: I. orientalis FUM gene integration fragment

<400> SEQUENCE: 164

```
gaattctttg aaggagcttg ccaagaaaca taattttatg attttgaag atagaaaatt      60 tgctgatatt ggtaacactg ttaaaaatca atataaatct ggtgtcttcc gtattgccga    120
atgggctgac atcactaatg cacatggtgt aacgggtgca ggtattgttt ctggcttgaa    180
ggaggcagcc caagaaacaa ccagtgaacc tagaggtttg ctaatgcttg ctgagttatc    240
atcaaagggt tctttagcat atggtgaata tacagaaaaa acagtagaaa ttgctaaatc    300
tgataaagag tttgtcattg gttttattgc gcaacacgat atgggcggta gagaagaagg    360
ttttgactgg atcattatga ctccaggggt tggtttagat gacaaaggtg atgcacttgg    420
tcaacaatat agaactgttg atgaagttgt aaagactgga acggatatca taattgttgg    480
tagaggtttg tacggtcaag gaagagatcc tatagagcaa gctaaaagat accaacaagc    540
tggttggaat gcttatttaa acagatttaa atgattctta cacaaagatt tgatacatgt    600
acactagttt aaataagcat gaaaagaatt acacaagcaa aaaaaaaaaa ataaatgagg    660
tactttacgt tcacctacaa ccaaaaaaac tagatagagt aaaatcttaa gatttagaaa    720
aagttgttta acaaaggctt tagtatgtga attttttaatg tagcaaagcg ataactaata    780
aacataaaca aaagtatggt tttctttatc agtcaaatca ttatcgattg attgttccgc    840
gtatctgcag atagcctcat gaaatcagcc atttgctttt gttcaacgat cttttgaaat    900
tgttgttgtt cttggtagtt aagttgatcc atcttggctt atgttgtgtg tatgttgtag    960
ttattcttag tatattcctg tcctgagttt agtgaaacat aatatcgcct tgaaatgaaa   1020
atgctgaaat tcgtcgacat acaatttttc aaactttttt ttttcttgg tgcacggaca   1080 tgttttaaa ggaagtactc tataccagtt attcttcaca aatttaattg ctggagaata   1140
gatcttcaac gcgtttcctc gacatttgct gcaacggcaa catcaatgtc cacgtttaca   1200
cacctacatt tatatctata tttatattta tatttattta tttatgctac ttagcttcta   1260
```

```
tagttagtta atgcactcac gatattcaaa attgacaccc ttcaactact ccctactatt   1320
gtctactact gtctactact cctcttact  atagctgctc ccaataggct ccaccaatag   1380
gctctgtcaa tacattttgc gccgccacct ttcaggttgt gtcactcctg aaggaccata   1440
ttgggtaatc gtgcaatttc tggaagagag tccgcgagaa gtgaggcccc cactgtaaat   1500
cctcgagggg gcatggagta tggggcatgg aggatggagg atggggggg  ggggggggaa   1560
aataggtagc gaaaggaccc gctatcaccc cacccggaga actcgttgcc gggaagtcat   1620
atttcgacac tccggggagt ctataaaagg cgggttttgt cttttgccag ttgatgttgc   1680
tgagaggact tgtttgccgt ttcttccgat ttaacagtat agaatcaacc actgttaatt   1740
atacacgtta tactaacaca acaaaaacaa aaacaacgac aacaacaaca acatctagat   1800
aaaatgttag ctgctagatc attaaaggca agaatgtcaa caagagcttt ctcaactacc   1860
tcaattgcaa aagaatcga  aaaagatgca tttggtgaca ttgaagtccc aaatgagaaa   1920
tattggggtc tcaaactca  aagatcttta caaaatttca aaattggtgg taagagagaa   1980
gttatgccag aaccaatcat caaatctttt ggtatttaa  agaaggctac tgctaagatc   2040
aatgctgagt ctggtgcttt agacccaaag ttatctgaag ccatccaaca agctgcaacc   2100
gaagtttatg aaggtaaact aatggaccat ttcccattag ttgtctttca aaccggttct   2160
ggtactcaat ctaacatgaa tgccaatgaa gtcatctcta atagagcaat tgaaatcttg   2220
ggtggtgaat taggctctaa aactccagtc catcctaatg atcatgttaa tatgtcccaa   2280
tcttctaatg atactttccc tactgtcatg catattgcag cagttacaga gtttcatcc    2340
catttattac cagaattaac tgcactaaga gatgcattgc aaaagaaatc cgatgaattt   2400
aagaatatta tcaaaatcgg tagaacccat ttacaagatg caactccttt aactttaggt   2460
caagaatttt ctggttatgt tcaacaatgt actaatggta tcaaaagaat cgaaattgct   2520
cttgaacatt tgagatactt agctcaaggt ggtactgccg ttggtactgg tcttaacacc   2580
aagaaaggtt ttgctgaaaa ggttgcaaat gaagtcacta aattgactgg tttacaattc   2640
tataccgctc aaataaaatt cgaagccctt gcagctcacg atgctgttgt tgaaatgtct   2700
ggtgctttga ataccgttgc agtctcatta ttcaaaatcg ctcaagatat cagatatttg   2760
ggttccggcc caagatgtgg ttatggtgaa ttggctttac cagaaaatga accaggttct   2820
tccatcatgc cgggtaaagt taacccaact caaaacgaag ctttgactat gctttgtacc   2880
caagtctttg gtaaccactc ttgtattacc tttgcaggtg cttcaggtca attcgaattg   2940
aatgtctta  agccagttat gatctccaac ttgttatctt ctattaggtt attaggtgat   3000
ggttgtaatt cttttagaat ccactgtgtt gaaggtatca ttgcaaatac cgacaagatt   3060
gataaattac tacatgaatc tctcatgtta gttactgctt tgaacccaca cattggttac   3120
gataaggctt ccaagattgc aaagaatgca cacaagaagg gcttgacatt gaaacaatct   3180
gcattggaat taggttactt gaccgaagaa caattcaatg aatgggttag accagaaaac   3240
atgattggtc caaaggatta agttaattaa catctgaatg taaaatgaac attaaaatga   3300
attactaaac tttacgtcta ctttacaatc tataaacttt gtttaatcat ataacgaaat   3360
acactaatac acaatcctgt acgtatgtaa tactttattc catcaaggat tgagaaaaaa   3420
aagtaatgat tccctgggcc attaaaactt agaccccccaa gcttggatag gtcactctct  3480
attttcgttt ctcccttccc tgatagaagg gtgatatgta attaagaata atatataatt   3540
ttataataaa agcggccgca ccaggggttt agtgaagtca ccaattaaga ttgttggttt   3600
```

| | | |
|---|---|---|
| gagtgagttg ccaaagatct atgaattgat ggagcaaggt aagattttag gcagatatgt | 3660 | |
| tgttgacact tcgaaatgat gggctgactt gggtgtactg gtgtgacgtt tttatgtgta | 3720 | |
| tattgatatg catgggggat gtatagtgat gaggagtaga gtatataacg aaatgaaatg | 3780 | |
| aaataatatg atatgataag ataagatgag atcaatacga taatataaga tgcgacatga | 3840 | |
| ggagttcaat gtagcatact acacgatgct gcagtacaac tctgatacgc tagactatac | 3900 | |
| tatacaaaac tgtagtacac tatacgttag tgtagtatcc agaaacaaca ctgctttata | 3960 | |
| gtacaataca actctataat actatagtat actatgccaa accacgtaat accataatat | 4020 | |
| gctccacgac atggtacaat gtgctatact tcatactatt ataccatata tactccgata | 4080 | |
| tattattgat atactatttt atactataat accataccac acaacactac attacaacga | 4140 | |
| gcaaccttac cataaatgtc agttatggcc gcgg | 4174 | |

<210> SEQ ID NO 165
<211> LENGTH: 6874
<212> TYPE: DNA
<213> ORGANISM: Artificial Sequence
<220> FEATURE:
<223> OTHER INFORMATION: FRD gene integration fragment

<400> SEQUENCE: 165

| | | |
|---|---|---|
| aaacctccgt tatgtatgtt tgtacccaaa agaatgcgc tatattagtt taatcttttta | 60 | |
| taaacccgga attataaaaa tacagttagg aataaagtaa tagaaagatg aacaacgggc | 120 | |
| ctaaaaagac taatgtgttg tggatcggaa tgtttcgaat agagtattaa agttatgctt | 180 | |
| tcttttcttt ttgaacatgc ttggtattac tttgatatgc aaaagatatc gacaaattga | 240 | |
| aaatggtttt gatgtctata gatgtggcat ggtaaggttc atttcaattt agcaaatatc | 300 | |
| agacgagctc agcggccgcg gatccctcga ggagtccatc ggttcctgtc agatgggata | 360 | |
| ctcttgacgt ggaaaattca aacagaaaaa aaccccaat aatgaaaaat aacactacgt | 420 | |
| tatatccgtg gtatcctcta tcgtatcgta tcgtagcgta tcgtagcgta ccgtatcaca | 480 | |
| gtatagtcta atattccgta tcttattgta tcctatccta ttcgatccta ttgtatttca | 540 | |
| gtgcaccatt ttaatttcta ttgctataat gtccttatta gttgccactg tgaggtgacc | 600 | |
| aatggacgag ggcgagccgt tcagaagccg cgaagggtgt tcttcccatg aatttcttaa | 660 | |
| ggagggcggc tcagctccga gagtgaggcg agacgtctcg gtcagcgtat ccccctttcct | 720 | |
| cggcttttac aaatgatgcg ctcttaatag tgtgtcgtta tccttttggc attgacgggg | 780 | |
| gagggaaatt gattgagcgc atccatattt ttgcggactg ctgaggacaa tggtggtttt | 840 | |
| tccgggtggc gtgggctaca aatgatacga tggtttttt cttttcggag aaggcgtata | 900 | |
| aaaaggacac ggagaaccca tttattctaa aaacagttga gcttctttaa ttattttttg | 960 | |
| atataatatt ctattattat atatttttctt cccaataaaa caaaataaaa caaaacacag | 1020 | |
| caaaacacaa aaattctaga atggctgatg gcaaaacctc tgcatcagtt gttgctgttg | 1080 | |
| atgctgaacg tgccgctaag gaaagagatg cagcagctag agctatgttg caaggtggtg | 1140 | |
| gtgtctctcc tgctggcaag gcacaattgt tgaaaaaggg tttggttcac actgttccat | 1200 | |
| ataccttaaa ggttgtcgtc gcagatccaa aggaaatgga gaaggcaact gctgacgcag | 1260 | |
| aagaggtttt acaagctgca tttcaagtcg tcgacaccct tttgaacaac tttaacgaaa | 1320 | |
| actcagaagt ttcaagagtc aataggttgg cagttggtga ggaacatcaa atgtctgaaa | 1380 | |
| cattgaaaca cgtcatggcc tgttgtcaaa aggtttatca ttcctccaga ggtgtttttg | 1440 | |
| acccagcagt tggtccatta gtccgtgaac ttagagaagc tgctcacaag ggtaaaactg | 1500 | |

```
ttccagccga aagagttaat gatttgttat ccaaatgtac ccttaatgca tctttttcaa    1560
ttgatatgtc cagaggtatg attgcaagga agcatccaga cgccatgttg gatttgggtg    1620
gtgtcaacaa gggttatggt atcgactaca ttgttgaaca cttaaactct ttgggttatg    1680
atgatgtctt tttcgaatgg ggtggtgatg ttagagcatc cggcaaaaac cagttatctc    1740
aaccttgggc tgttggtatt gttagaccac ctgccttggc cgacattaga actgttgtcc    1800
cagaggacaa aagatccttt atccgtgtcg tcagattgaa caacgaagct attgctacct    1860
ctggtgatta tgagaatttg gttgaaggtc ctggttctaa ggtttactct tccaccttca    1920
atccaacttc caaaaacttg ttggaaccta ccgaagcagg tatggctcaa gtttctgtca    1980
agtgttgctc atgtatctac gctgatgctt tagcaacagc agctttgttg aaaaacgatc    2040
ctgctgccgt tagaaggatc ttagataact ggagatatgt cagagatact gttactgact    2100
acaccactta cacaagggaa ggtgaaagag ttgctaagat gttggaaatt gctaccgaag    2160
atgctgaaat gagagcaaag agaatcaagg gctctttacc agcaagagtt atcattgttg    2220
gtggtggttt ggccggttgt tccgcagcta tcgaagcagc taactgtggc gcccacgtca    2280
tcttgttaga aaaggaacca aagttaggtg gtaactctgc aaaggctacc tccggtatca    2340
acgcctgggg tactagagca caagcaaaac aaggtgtcat ggacggcggc aagttttcg     2400 aaagagatac ccatagatcc ggcaagggtg gtaattgcga tccatgcctt gttaagactt    2460
tgtccgttaa gtcctctgat gcagttaagt ggttatctga attaggtgtt ccattgactg    2520
ttttgtctca attaggtggt gcttcaagga acgttgtca ccgtgcacca gataagtctg     2580
atggtacacc agtcccagtt ggtttcacca ttatgaaaac ccttgaaaac cacattgtca    2640
acgatttgtc cagacatgtt acagttatga caggtattac cgtcacagct ttagaatcta    2700
catcaagagt cagacctgat ggtgttttag tcaagcatgt tactggtgtt cacttgattc    2760
aggcatctgg tcaatctatg gttttgaatg cagacgctgt tatcttagct actggtggtt    2820
tctccaatga tcatacccca aactccctt tacaacaata cgccccacag ttgtcatctt     2880
ttccaacaac caatggtgtc tgggcaactg gcgatggtgt taagatggct tccaagttgg    2940
gtgtcgcctt agttgatatg gataaggtcc aattacatcc taccggcttg ttagacccaa    3000
aagatccatc taatagaacc aagtatcttg gtccagaggc cttaagaggt tccggcggtg    3060
tcttgttaaa caaaaacggt gaaagatttg ttaatgaatt agacttaaga tctgttgtct    3120
ctcaagctat catcgcacaa gataatgagt acccaggctc tggtggttcc aagttcgcat    3180
actgtgtttt gaacgaaact gcagcaaagt tattcggcaa aaacttcctt ggtttctact    3240
ggaatagatt aggtctttc caaaaggttg attccgttgc tggtttagct aagttgattg     3300
gttgtccaga agctaatgtt gttgctacat tgaagcaata tgaggagtta tcttccaaaa    3360
agcttaatcc ttgtccattg actggcaagt ctgtctttcc ttgtgtttta ggcactcaag    3420
gtccatacta tgttgccttg gttacccccat ccattcacta cactatgggt ggttgtttga   3480 tttcccatc tgctgagatg caaccattg acaactctgg tgttactcct gtcagacgtc      3540
caatcttagg cttattcggt gctggtgaag ttactggcgg tgtccatggt ggtaacagat    3600
taggcggtaa ctctttgtta gaatgtgttg ttttcggcaa gatcgctggt gacagagctg    3660
caaccatctt gcaaaagaaa aacaccggct tatcaatgac agaatggtct actgtcgtct    3720
taagagaagt tagagaaggt ggtgtctatg gtgctggttc cagagttttg aggtttaaca    3780
tgcctggtgc attacagaga actggtttag ctttaggtca attcatcggt atcagaggtg    3840
```

```
attgggacgg tcacagattg atcggttact attctccaat cactttacct gatgatgttg    3900
gtgttattgg tatcttagct agagcagaca agggtagatt ggcagaatgg atttctgcat    3960
tgcagccagg tgacgctgtt gagatgaagg cctgcggtgg tcttatcatt gacagaagat    4020
tcgctgaaag acatttcttt ttccgtggtc ataagatcag aaagttggcc cttatcggtg    4080
gtggtactgg tgttgcacca atgttacaaa tcgtcagagc tgctgtcaaa aagccatttg    4140
tcgattcaat tgagtccatt cagttcatct atgctgcaga ggatgttttcc gagcttacat    4200
acagaacctt acttgaatct tacgaagagg aatatggttc agaaaagttt aagtgtcact    4260
tcgttttgaa taacccacca gctcaatgga ctgacggtgt tggtttcgtt gatactgcat    4320
tgttgagatc cgcagttcaa gcaccatcaa atgatttgct tgttgcaatt tgtggtccac    4380
caatcatgca aagagcagtt aagggtgcat tgaaaggttt aggttacaat atgaatcttg    4440
ttagaaccgt tgacgaaact gaaccaccat cataattaat taacatctga atgtaaaatg    4500
aacattaaaa tgaattacta aactttacgt ctactttaca atctataaac tttgtttaat    4560
catataacga aatacactaa tacacaatcc tgtacgtatg taatacttttt atccatcaag    4620
gattgagaaa aaaaagtaat gattccctgg gccattaaaa cttagacccc caagcttgga    4680
taggtcactc tctattttcg tttctccctt ccctgataga agggtgatat gtaattaaga    4740
ataatatata attttataat aaaagaattc atagcctcat gaaatcagcc atttgctttt    4800
gttcaacgat cttttgaaat tgttgttgtt cttggtagtt aagttgatcc atcttggctt    4860
atgttgtgtg tatgttgtag ttattcttag tatattcctg tcctgagttt agtgaaacat    4920
aatatcgcct tgaaatgaaa atgctgaaat tcgtcgacat acaattttc aaactttttt    4980
tttttcttgg tgcacggaca tgttttaaa ggaagtactc tataccagtt attcttcaca    5040
aatttaattg ctggagaata gatcttcaac gctttaataa agtagtttgt ttgtcaagga    5100
tggcgtcata caaagaaaga tcagaatcac acacttcccc tgttgctagg agacttttct    5160
ccatcatgga ggaaaagaag tctaacccttt gtgcatcatt ggatattact gaaactgaaa    5220
agcttctctc tattttggac actattggtc cttacatctg tctagttaaa acacacatcg    5280
atattgtttc tgattttacg tatgaaggaa ctgtgttgcc tttgaaggag cttgccaaga    5340
aacataattt tatgattttt gaagatagaa atttgctga tattggtaac actgttaaaa    5400
atcaatataa atctggtgtc ttccgtattg ccgaatgggc tgacatcact aatgcacatg    5460
gtgtaacggg tgcaggtatt gtttctggct tgaaggaggc agcccaagaa acaaccagtg    5520
aacctagagg tttgctaatg cttgctgagt tatcatcaaa gggttcttta gcatatggtg    5580
aatatacaga aaaaacagta gaaattgcta atctgataa agagtttgtc attggttta    5640
ttgcgcaaca cgatatgggc ggtagagaag aaggttttga ctggatcatt atgactccag    5700
gggttggttt agatgacaaa ggtgatgcac ttggtcaaca atatagaact gttgatgaag    5760
ttgtaaagac tggaacggat atcataattg ttggtagagg tttgtacggt caaggaagag    5820
atcctataga gcaagctaaa agataccaac aagctggttg gaatgcttat ttaaacagat    5880
ttaaatgatt cttacacaaa gatttgatac atgtacacta gtttaaataa gcatgaaaag    5940
aattacacaa gcaaaaaaaa aaaataaat gaggtacttt acgttcacct acaaccaaaa    6000
aaactagata gagtaaaatc ttaagattta gaaaagttg tttaacaaag ctttagtat    6060
gtgaattttt aatgtagcaa agcgataact aataaacata acaaaagta tggttttctt    6120
tatcagtcaa atcattatcg attgattgtt ccgcgtatct gcagatagcc tcatgaaatc    6180
agccatttgc ttttgttcaa cgatcttttg aaattgttgt tgttcttggt agttaagttg    6240
```

```
atccatcttg gcttatgttg tgtgtatgtt gtagttattc ttagtatatt cctgtcctga    6300
gtttagtgaa acataatatc gccttgaaat gaaaatgctg aaattcgtcg acatacaatt    6360
tttcaaactt ttttttttc ttggtgcacg gacatgtttt taaaggaagt actctatacc    6420
agttattctt cacaaattta attgctggag aatagatctt caacgccccg ggggatctgg    6480
atccgcggcc gctcatatgt ttgaaggtat tatcactgct gttgatttac gttcttgaaa    6540
actgcacgga taatattcac aatactaaca ataaagaaga ctcattgtgg aaggtgactc    6600
aatcatgcta gaaagctggg gaataaagg cacttttata gtagccacat tttggttcaa    6660
aagaatataa aggaaaaaaa aatattttcc agtgaaaaag aaaagactct ttctccgaga    6720
agccgagttt ctacgaggcc ttgttgagtc ataggggacc tctgtggttg actccggctt    6780
attacgtgaa tcatcggggg agccgcaccg tttgtccgcg acaggagaaa acgcaaggag    6840
tcaaacatta aattggtagg cactaccgag gttt                               6874
```

<210> SEQ ID NO 166
<211> LENGTH: 987
<212> TYPE: DNA
<213> ORGANISM: Rhizopus delemar
<220> FEATURE:
<221> NAME/KEY: CDS
<222> LOCATION: (1)..(987)

<400> SEQUENCE: 166

```
atg gtt aaa gtt aca gtt tgt ggt gct gct ggt ggt att ggt caa ccc       48
Met Val Lys Val Thr Val Cys Gly Ala Ala Gly Gly Ile Gly Gln Pro
1               5                  10                  15 ctt tct tta ctc ttg aag caa tcc tct cac att act cac tta tct ctt       96
Leu Ser Leu Leu Leu Lys Gln Ser Ser His Ile Thr His Leu Ser Leu
            20                  25                  30 tat gat atc gtt aat act cct ggt gtt gct gct gat ctt agt cat atc      144
Tyr Asp Ile Val Asn Thr Pro Gly Val Ala Ala Asp Leu Ser His Ile
        35                  40                  45 gat acc aaa tcc aag gtc act ggt cat gta ggt gct gct caa ctt gaa      192
Asp Thr Lys Ser Lys Val Thr Gly His Val Gly Ala Ala Gln Leu Glu
    50                  55                  60 gaa gct atc aag gat tct gat gtt gtc gtt att ccc gct ggt gtc cca      240
Glu Ala Ile Lys Asp Ser Asp Val Val Val Ile Pro Ala Gly Val Pro
65                  70                  75                  80 aga aag cca ggt atg acg cgt gat gat ctt ttc aag att aat gct ggt      288
Arg Lys Pro Gly Met Thr Arg Asp Asp Leu Phe Lys Ile Asn Ala Gly
                85                  90                  95 att gta cgt gat ttg gct aca gct gct gca aag tac gct cca aag gcc      336
Ile Val Arg Asp Leu Ala Thr Ala Ala Ala Lys Tyr Ala Pro Lys Ala
            100                 105                 110 ttc atg tgt atc att tct aac cca gtc aac tcg act gtc cca atc gtt      384
Phe Met Cys Ile Ile Ser Asn Pro Val Asn Ser Thr Val Pro Ile Val
        115                 120                 125 act gaa gta ttc aaa cag cac aat gtt tat gac ccc aaa aga atc ttt      432
Thr Glu Val Phe Lys Gln His Asn Val Tyr Asp Pro Lys Arg Ile Phe
    130                 135                 140 ggt gtt aca aca ctt gat att gtt cgt gca tcc acc ttt gta tcc gaa      480
Gly Val Thr Thr Leu Asp Ile Val Arg Ala Ser Thr Phe Val Ser Glu
145                 150                 155                 160 ttg att gga ggt gaa cct aat tca ctt cgt gtt ccc gtc att ggt ggt      528
Leu Ile Gly Gly Glu Pro Asn Ser Leu Arg Val Pro Val Ile Gly Gly
                165                 170                 175 cac agc ggc gta acc atc tta cct tta ctc tca cag gtc ccc ggc att      576
His Ser Gly Val Thr Ile Leu Pro Leu Leu Ser Gln Val Pro Gly Ile
```

```
His Ser Gly Val Thr Ile Leu Pro Leu Leu Ser Gln Val Pro Gly Ile
                180                 185                 190 gaa aag tta aac caa gaa caa att gag aag gta act cat cgt att caa      624
Glu Lys Leu Asn Gln Glu Gln Ile Glu Lys Val Thr His Arg Ile Gln
            195                 200                 205 ttt ggt ggc gat gaa gtt gtc aag gcc aag gat ggt gct ggt tct gcc      672
Phe Gly Gly Asp Glu Val Val Lys Ala Lys Asp Gly Ala Gly Ser Ala
210                 215                 220 act ctt tcc atg gct tat gct ggt gct cgt ttt gct aca aac atc att      720
Thr Leu Ser Met Ala Tyr Ala Gly Ala Arg Phe Ala Thr Asn Ile Ile
225                 230                 235                 240 gag gct gct ttt gct gga aag aag ggc att gtt gaa tgt acc tat gtt      768
Glu Ala Ala Phe Ala Gly Lys Lys Gly Ile Val Glu Cys Thr Tyr Val
                245                 250                 255 caa ttg gat gct gat aaa tct ggt gcc caa tct gtc aag gat ttg gtt      816
Gln Leu Asp Ala Asp Lys Ser Gly Ala Gln Ser Val Lys Asp Leu Val
            260                 265                 270 ggt agt gaa ctt gaa tat ttc tct gtt ccc gtt gaa ttg ggt cct agt      864
Gly Ser Glu Leu Glu Tyr Phe Ser Val Pro Val Glu Leu Gly Pro Ser
        275                 280                 285 ggt gtt gaa aag att tta ccc att gga aac gtt aat gaa tat gaa aag      912
Gly Val Glu Lys Ile Leu Pro Ile Gly Asn Val Asn Glu Tyr Glu Lys
290                 295                 300 aag ttg ttg aac gag gct tct cct gaa tta aaa acc aac att gat aaa      960
Lys Leu Leu Asn Glu Ala Ser Pro Glu Leu Lys Thr Asn Ile Asp Lys
305                 310                 315                 320 ggt tgt act ttt gtt act gaa ggc taa                                  987
Gly Cys Thr Phe Val Thr Glu Gly
                325

<210> SEQ ID NO 167
<211> LENGTH: 328
<212> TYPE: PRT
<213> ORGANISM: Rhizopus delemar

<400> SEQUENCE: 167

Met Val Lys Val Thr Val Cys Gly Ala Ala Gly Gly Ile Gly Gln Pro
1               5                   10                  15

Leu Ser Leu Leu Leu Lys Gln Ser Ser His Ile Thr His Leu Ser Leu
            20                  25                  30

Tyr Asp Ile Val Asn Thr Pro Gly Val Ala Ala Asp Leu Ser His Ile
        35                  40                  45

Asp Thr Lys Ser Lys Val Thr Gly His Val Gly Ala Ala Gln Leu Glu
    50                  55                  60

Glu Ala Ile Lys Asp Ser Asp Val Val Ile Pro Ala Gly Val Pro
65                  70                  75                  80

Arg Lys Pro Gly Met Thr Arg Asp Asp Leu Phe Lys Ile Asn Ala Gly
                85                  90                  95

Ile Val Arg Asp Leu Ala Thr Ala Ala Lys Tyr Ala Pro Lys Ala
            100                 105                 110

Phe Met Cys Ile Ile Ser Asn Pro Val Asn Ser Thr Val Pro Ile Val
        115                 120                 125

Thr Glu Val Phe Lys Gln His Asn Val Tyr Asp Pro Lys Arg Ile Phe
    130                 135                 140

Gly Val Thr Thr Leu Asp Ile Val Arg Ala Ser Thr Phe Val Ser Glu
145                 150                 155                 160

Leu Ile Gly Gly Glu Pro Asn Ser Leu Arg Val Pro Val Ile Gly Gly
                165                 170                 175
```

```
His Ser Gly Val Thr Ile Leu Pro Leu Leu Ser Gln Val Pro Gly Ile
            180                 185                 190

Glu Lys Leu Asn Gln Glu Gln Ile Glu Lys Val Thr His Arg Ile Gln
        195                 200                 205

Phe Gly Gly Asp Glu Val Val Lys Ala Lys Asp Gly Ala Gly Ser Ala
    210                 215                 220

Thr Leu Ser Met Ala Tyr Ala Gly Ala Arg Phe Ala Thr Asn Ile Ile
225                 230                 235                 240

Glu Ala Ala Phe Ala Gly Lys Lys Gly Ile Val Glu Cys Thr Tyr Val
                245                 250                 255

Gln Leu Asp Ala Asp Lys Ser Gly Ala Gln Ser Val Lys Asp Leu Val
            260                 265                 270

Gly Ser Glu Leu Glu Tyr Phe Ser Val Pro Val Glu Leu Gly Pro Ser
        275                 280                 285

Gly Val Glu Lys Ile Leu Pro Ile Gly Asn Val Asn Glu Tyr Glu Lys
    290                 295                 300

Lys Leu Leu Asn Glu Ala Ser Pro Glu Leu Lys Thr Asn Ile Asp Lys
305                 310                 315                 320

Gly Cys Thr Phe Val Thr Glu Gly
                325

<210> SEQ ID NO 168
<211> LENGTH: 4127
<212> TYPE: DNA
<213> ORGANISM: Artificial Sequence
<220> FEATURE:
<223> OTHER INFORMATION: MDH gene integration fragment

<400> SEQUENCE: 168
gttaacccgt tcgatgggga ttcccagaag tggatactat actgtctgca atgcactaca      60
ctctaaaaaa gtattataca ttaccataca ttagcaaatc accaatactc tgcactgttt     120
cagtgtgtgc acattgctac ccaattggga aatcgcaggg aaaatgagac accccctcca     180
ttcgtattac gtaagacaat atcagggctg ccgaattcgg cagaaaagcc gagccggccg     240
agtcctcttg cacggagtgt gtccgaaaag ggcagctctg cagtggggga gaggaggtcg     300
cacgtctatg cggtgttggc atggcctgtg cgtgtacctg tcccctccct gggcatcccc     360
cactgcgcgc cttctccatt gggcgctgcg ggcactccgc gccgttaata caggaggggg     420
gggggaaagc ttaagattag agcgggtaca gtcagtgggt gtattgaccc catttctgtc     480
agtataaacc ccccgttgag ccgccggttt ggttgtttat ggataaaatt ttttttttccc     540 cgcatggaga agattgaggg ggggaaggaa tgggaaaaag gccagagcca tctccacagc     600
ggaatccgac cgttaatggg gtgaaacacc cccaccaggt agagcaggaa gaatggggaa     660
acaaggtgga gagatggtca ttgttgggaa tagtgggaaa atgaggggga agagaatgac     720
tataaaatgg gaaggggggtc caagttatcc aagcagtcca tttagagaag ggagcggccc     780
ctattggtag ttctttcccc ctctcaagct ggcgtgaaat gcaaccttac ggcgtctacg     840
ttactacaag gtccagaaag tgtaggtatt gctactattt ttattttttta ttggttctgg     900 agaaatgcag acagtcaatg aacacaactg tctcaatatg catctatgca catgcacaca     960
cacacacatc acaggtaccc ctacaaagag aggtctcttg ataatgtttc attaccacgt    1020
ggcatccccc ccccccccccc caataaacaa gtggccgagt tccctgttg cagaggagga    1080 caaaaaaacc gctggtgttg gtaccattat gcagcaacta gcacaacaaa caaccgaccc    1140
```

```
agacatacaa atcaacaaca cttcgccaaa gacacccttt ccagggagga tccactccca    1200
acgtctctcc ataatgtctc tgttggccca tgtctctgtc gttgacaccg taaccacacc    1260
aaccaacccg tccattgtac tgggatggtc gtccatagac acctctccaa cggggaacac    1320
ctcattcgta aaccgccaag gttaccgttc ctcctgactc gccccgttgt tgatgctgcg    1380
cacctgtggt tgcccaacat ggttgtatat cgtgtaacca caccaacaca tgtgcagcac    1440
atgtgtttaa aagagtgtca tggaggtgga tcatgatgga agtggacttt accacttggg    1500
aactgtctcc actcccggga agaaaagacc cggcgtatca cgcggttgcc tcaatggggc    1560
aatttggaag gagaaatata gggaaaatca cgtcgctctc ggacggggaa gagttccaga    1620
ctatgagggg ggggggtggt atataaagac aggagatgtc cacccccaga gagaggaaga    1680
agttggaact ttagaagaga gagataactt tccccagtgt ccatcaatac acaaccaaac    1740
acaaactcta tatttacaca tataacccce tctctagaat ggttaaagtt acagtttgtg    1800
gtgctgctgg tggtattggt caaccccttt ctttactctt gaagcaatcc tctcacatta    1860
ctcacttatc tctttatgat atcgttaata ctcctggtgt tgctgctgat cttagtcata    1920
tcgataccaa atccaaggtc actggtcatg taggtgctgc tcaacttgaa gaagctatca    1980
aggattctga tgttgtcgtt attcccgctg gtgtcccaag aaagccaggt atgacgcgtg    2040
atgatctttt caagattaat gctggtattg tacgtgattt ggctacagct gctgcaaagt    2100
acgctccaaa ggccttcatg tgtatcattt ctaacccagt caactcgact gtcccaatcg    2160
ttactgaagt attcaaacag cacaatgttt atgaccccaa agaatctttt ggtgtaacaa    2220
cacttgatat tgttcgtgca tccacccttg tatccgaatt gattggaggt gaacctaatt    2280
cacttcgtgt tcccgtcatt ggtggtcaca gcggcgtaac catcttacct ttactctcac    2340
aggtccccgg cattgaaaag ttaaaccaag aacaaattga gaaggtaact catcgtattc    2400
aatttggtgg cgatgaagtt gtcaaggcca aggatggtgc tggttctgcc actcttttcca    2460 tggcttatgc tggtgctcgt tttgctacaa acatcattga ggctgctttt gctggaaaga    2520
agggcattgt tgaatgtacc tatgttcaat ggatgctga taaatctggt gcccaatctg    2580
tcaaggattt ggttggtagt gaacttgaat atttctctgt tcccgttgaa ttgggtccta    2640
gtggtgttga aaagatttta cccattggaa acgttaatga atatgaaaag aagttgttga    2700
acgaggcttc tcctgaatta aaaaccaaca ttgataaagg ttgtactttt gttactgaag    2760
gctcaaagtt gtaattaatt aatttatttt actagtttat ttttgctcct gagaatagga    2820
ttacaaacac ttaaagtctt taattacaac tatatataat attctgttgg ttttcttgaa    2880
ttggttcgct gcgattcatg cctcccattc accaaaggtg gagtgggaaa taacggtttt    2940
actgcggtaa ttagcagagg caagaacagg atacactttt tgatgataaa tctgtattat    3000
agtcgagcct atttaggaaa tcaaatttttc ttgtgtttac ttttcaaata aataatgttc    3060
gaaaattttt actttactcc ttcatttaac tataccagac gttatatcat caacaccttc    3120
tgaccatata cagctcaaga tgtttaagag tctgttaaat ttttcaatc catttcatgg    3180 agtaccagga ggtgctacaa aaggaattca tagcctcatg aaatcagcca tttgcttttg    3240
ttcaacgatc ttttgaaatt gttgttgttc ttggtagtta agttgatcca tcttggctta    3300
tgttgtgtgt atgttgtagt tattcttagt atattcctgt cctgagttta gtgaaacata    3360
atatcgcctt gaaatgaaaa tgctgaaatt cgtcgacata caatttttca aactttttt    3420 ttttcttggt gcacggacat gttttttaaag gaagtactct ataccagtta ttcttcacaa    3480
atttaattgc tggagaatag atcttcaacg ctttaataaa gtagtttgtt tgtcaaggat    3540
```

```
ggcgtcatac aaagaaagat cagaatcaca cacttcccct gttgctagga gacttttctc    3600
catcatggag gaaaagaagt ctaacctttg tgcatcattg gatattactg aaactgaaaa    3660
gcttctctct attttggaca ctattggtcc ttacatctgt ctagttaaaa cacacatcga    3720
tattgtttct gattttacgt atgaaggaac tgtgttgcct ttgaaggagc ttgccaagaa    3780
acataatttt atgattttg aagatagaaa atttgctgat attggtaaca ctgttaaaaa    3840
tcaatataaa tctggtgtct tccgtattgc cgaatgggct gacatcacta atgcacatgg    3900
tgtaacgggt gcaggtattg tttctggctt gaaggaggca gcccaagaaa caaccagtga    3960
acctagaggt ttgctaatgc ttgctgagtt atcatcaaag ggttctttag catatggtga    4020
atatacagaa aaaacagtag aaattgctaa atctgataaa gagtttgtca ttggttttat    4080
tgcgcaacac gatatgggcg gtagagaaga aggttttgac tccgcgg                  4127
```

<210> SEQ ID NO 169
<211> LENGTH: 6874
<212> TYPE: DNA
<213> ORGANISM: Artificial Sequence
<220> FEATURE:
<223> OTHER INFORMATION: FRD gene integration fragment

<400> SEQUENCE: 169

```
aaacctcggt agtgcctacc aatttaatgt ttgactcctt gcgttttctc ctgtcgcgga      60
caaacggtgc ggctcccccg atgattcacg taataagccg gagtcaacca cagaggtccc     120
ctatgactca acaaggcctc gtagaaactc ggcttctcgg agaaagagtc ttttcttttt     180
cactggaaaa tattttttt tcctttatat tcttttgaac caaaatgtgg ctactataaa     240
agtgccttta ttccccagct tttctagcat gattgagtca ccttccacaa tgagtcttct     300
ttattgttag tattgtgaat attatccgtg cagttttcaa gaacgtaaat caacagcagt     360
gataatacct tcaaacatat gagcggccgc ggatccctcg aggagtccat cggttcctgt     420
cagatgggat actcttgacg tggaaaattc aaacagaaaa aaaccccaa taatgaaaaa     480 taacactacg ttatatccgt ggtatcctct atcgtatcgt atcgtagcgt atcgtagcgt     540
accgtatcac agtatagtct aatattccgt atcttattgt atcctatcct attcgatcct     600
attgtatttc agtgcaccat tttaatttct attgctataa tgtccttatt agttgccact     660
gtgaggtgac caatggacga gggcgagccg ttcagaagcc gcgaagggtg ttcttcccat     720
gaatttctta aggagggcgg ctcagctccg agagtgaggc gagacgtctc ggtcagcgta     780 tccccctcc tcggctttta caaatgatgc gctcttaata gtgtgtcgtt atcctttgg     840 cattgacggg ggagggaaat tgattgagcg catccatatt tttgcggact gctgaggaca     900
atggtggttt ttccgggtgg cgtgggctac aaatgatacg atggtttttt tcttttcgga     960
gaaggcgtat aaaaaggaca cggagaaccc atttattcta aaaacagttg agcttcttta    1020
attatttttt gatataatat tctattatta tatattttct tcccaataaa acaaaataaa    1080
acaaaacaca gcaaaacaca aaaattctag aatggctgat ggcaaaacct ctgcatcagt    1140
tgttgctgtt gatgctgaac gtgccgctaa ggaaagagat gcagcagcta gagctatgtt    1200
gcaaggtggt ggtgtctctc ctgctggcaa ggcacaattg ttgaaaaagg gtttggttca    1260
cactgttcca tataccttaa aggttgtcgt cgcagatcca aaggaaatgg agaaggcaac    1320
tgctgacgca gaagaggttt tacaagctgc atttcaagtc gtcgcacccc ttttgaacaa    1380 cttttaacgaa aactcagaag tttcaagagt caataggttg gcagttggtg aggaacatca    1440
```

```
aatgtctgaa acattgaaac acgtcatggc ctgttgtcaa aaggtttatc attcctccag   1500
aggtgttttt gacccagcag ttggtccatt agtccgtgaa cttagagaag ctgctcacaa   1560
gggtaaaact gttccagccg aaagagttaa tgatttgtta tccaaatgta cccttaatgc   1620
atcttttcca attgatatgt ccagaggtat gattgcaagg aagcatccag acgccatgtt   1680
ggatttgggt ggtgtcaaca agggttatgg tatcgactac attgttgaac acttaaactc   1740
tttgggttat gatgatgtct ttttcgaatg gggtggtgat gttagagcat ccggcaaaaa   1800
ccagttatct caaccttggg ctgttggtat tgttagacca cctgccttgg ccgacattag   1860
aactgttgtc ccagaggaca aaagatcctt tatccgtgtc gtcagattga acaacgaagc   1920
tattgctacc tctggtgatt atgagaattt ggttgaaggt cctggttcta aggtttactc   1980
ttccaccttc aatccaactt ccaaaaactt gttggaacct accgaagcag gtatggctca   2040
agtttctgtc aagtgttgct catgtatcta cgctgatgct ttagcaacag cagctttgtt   2100
gaaaaacgat cctgctgccg ttagaaggat cttagataac tggagatatg tcagagatac   2160
tgttactgac tacaccactt acacaaggga aggtgaaaga gttgctaaga tgttggaaat   2220
tgctaccgaa gatgctgaaa tgagagcaaa gagaatcaag ggctctttac cagcaagagt   2280
tatcattgtt ggtggtggtt tggccggttg ttccgcagct atcgaagcag ctaactgtgg   2340
cgcccacgtc atcttgttag aaaaggaacc aaagttaggt ggtaactctg caaaggctac   2400
ctccggtatc aacgcctggg gtactagagc acaagcaaaa caaggtgtca tggacggcgg   2460
caagttttc gaaagagata cccatagatc cggcaagggt ggtaattgcg atccatgcct   2520
tgttaagact ttgtccgtta agtcctctga tgcagttaag tggttatctg aattaggtgt   2580
tccattgact gttttgtctc aattaggtgg tgcttcaagg aaacgttgtc accgtgcacc   2640
agataagtct gatggtacac cagtcccagt tggtttcacc attatgaaaa cccttgaaaa   2700
ccacattgtc aacgatttgt ccagacatgt tacagttatg acaggtatta ccgtcacagc   2760
tttagaatct acatcaagag tcagacctga tggtgtttta gtcaagcatg ttactggtgt   2820
tcacttgatt caggcatctg gtcaatctat ggttttgaat gcagacgctg ttatcttagc   2880
tactggtggt ttctccaatg atcatacccc aaactccctt ttacaacaat acgcccacca   2940
gttgtcatct tttccaacaa ccaatggtgt ctgggcaact ggcgatggtg ttaagatggc   3000
ttccaagttg ggtgtcgcct tagttgatat ggataaggtc caattacatc ctaccggctt   3060
gttagaccca aaagatccat ctaatagaac caagtatctt ggtccagagg ccttaagagg   3120
ttccggcggt gtcttgttaa acaaaaacgg tgaaagattt gttaatgaat tagacttaag   3180
atctgttgtc tctcaagcta tcatcgcaca agataatgag tacccaggct ctggtggttc   3240
caagttcgca tactgtgttt tgaacgaaac tgcagcaaag ttattcggca aaaacttcct   3300
tggtttctac tggaatagat taggtctttt ccaaaaggtt gattccgttg ctggtttagc   3360
taagttgatt ggttgtccag aagctaatgt tgttgctaca ttgaagcaat atgaggagtt   3420
atcttccaaa aagcttaatc cttgtccatt gactggcaag tctgtctttc cttgtgtttt   3480
aggcactcaa ggtccatact atgttgcctt ggttaccca tccattcact acactatggg   3540
tggttgtttg atttccccat ctgctgagat gcaaaccatt gacaactctg tgttactcc   3600
tgtcagacgt ccaatcttag gcttattcgg tgctggtgaa gttactggcg tgtccatgg   3660
tggtaacaga ttaggcggta actctttgtt agaatgtgtt gttttcggca agatcgctgg   3720
tgacagagct gcaaccatct tgcaaaagaa aaacaccggc ttatcaatga cagaatggtc   3780
tactgtcgtc ttaagagaag ttagagaagg tggtgtctat ggtgctggtt ccagagtttt   3840
```

```
gaggtttaac atgcctggtg cattacagag aactggttta gcttaggtc aattcatcgg     3900
tatcagaggt gattgggacg gtcacagatt gatcggttac tattctccaa tcactttacc   3960
tgatgatgtt ggtgttattg gtatcttagc tagagcagac aagggtagat tggcagaatg   4020
gatttctgca ttgcagccag gtgacgctgt tgagatgaag gcctgcggtg gtcttatcat   4080
tgacagaaga ttcgctgaaa gacatttctt tttccgtggt cataagatca gaaagttggc   4140
ccttatcggt ggtggtactg gtgttgcacc aatgttacaa atcgtcagag ctgctgtcaa   4200
aaagccattt gtcgattcaa ttgagtccat tcagttcatc tatgctgcag aggatgtttc   4260
cgagcttaca tacagaacct tacttgaatc ttacgaagag gaatatggtt cagaaaagtt   4320
taagtgtcac ttcgttttga ataacccacc agctcaatgg actgacggtg ttggtttcgt   4380
tgatactgca ttgttgagat ccgcagttca agcaccatca aatgatttgc ttgttgcaat   4440
ttgtggtcca ccaatcatgc aaagagcagt taagggtgca ttgaaaggtt taggttacaa   4500
tatgaatctt gttagaaccg ttgacgaaac tgaaccacca tcataattaa ttaacatctg   4560
aatgtaaaat gaacattaaa atgaattact aaactttacg tctactttac aatctataaa   4620
ctttgtttaa tcatataacg aaatacacta atacacaatc ctgtacgtat gtaatacttt   4680
tatccatcaa ggattgagaa aaaaagtaa tgattccctg gccattaaa acttagaccc     4740
ccaagcttgg ataggtcact ctctattttc gtttctccct tccctgatag aagggtgata   4800
tgtaattaag aataatatat aatttataa taaaagaatt catagcctca tgaaatcagc    4860
catttgcttt tgttcaacga tcttttgaaa ttgttgttgt tcttggtagt taagttgatc   4920
catcttggct tatgttgtgt gtatgttgta gttattctta gtatattcct gtcctgagtt   4980
tagtgaaaca taatatcgcc ttgaaatgaa aatgctgaaa ttcgtcgaca tacaattttt   5040
caaactttt tttttcttg gtgcacggac atgtttttaa aggaagtact ctataccagt     5100
tattcttcac aaatttaatt gctggagaat agatcttcaa cgctttaata agtagtttg    5160
tttgtcaagg atggcgtcat acaaagaaag atcagaatca cacacttccc ctgttgctag   5220
gagacttttc tccatcatgg aggaaaagaa gtctaacctt tgtgcatcat tggatattac   5280
tgaaactgaa aagcttctct ctattttgga cactattggt ccttacatct gtctagttaa   5340
aacacacatc gatattgttt ctgattttac gtatgaagga actgtgttgc cttttgaagga 5400
gcttgccaag aaacataatt ttatgatttt tgaagataga aaatttgctg atattggtaa   5460
cactgttaaa aatcaatata aatctggtgt cttccgtatt gccgaatggg ctgacatcac   5520
taatgcacat ggtgtaacgg gtgcaggtat tgtttctggc ttgaaggagg cagcccaaga   5580
aacaaccagt gaacctagag gtttgctaat gcttgctgag ttatcatcaa agggttcttt   5640
agcatatggt gaatatacag aaaaaacagt agaaattgct aaatctgata aagagtttgt   5700
cattggtttt attgcgcaac acgatatggg cggtagagaa gaaggttttg actggatcat   5760
tatgactcca ggggttggtt tagatgacaa aggtgatgca cttggtcaac aatatagaac   5820
tgttgatgaa gttgtaaaga ctggaacgga tatcataatt gttggtagag gtttgtacgg   5880
tcaaggaaga gatcctatag agcaagctaa aagataccaa caagctggtt ggaatgctta   5940
tttaaacaga tttaaatgat tcttacacaa agatttgata catgtacact agtttaaata   6000
agcatgaaaa gaattacaca agcaaaaaaa aaaaataaa tgaggtactt tacgttcacc     6060
tacaaccaaa aaactagat agagtaaaat cttaagattt agaaaagtt gtttaacaaa     6120
ggctttagta tgtgaatttt taatgtagca aagcgataac taataaacat aaacaaagt    6180
```

-continued

```
atggttttct ttatcagtca aatcattatc gattgattgt tccgcgtatc tgcagatagc    6240
ctcatgaaat cagccatttg cttttgttca acgatctttt gaaattgttg ttgttcttgg    6300
tagttaagtt gatccatctt ggcttatgtt gtgtgtatgt tgtagttatt cttagtatat    6360
tcctgtcctg agtttagtga aacataatat cgccttgaaa tgaaaatgct gaaattcgtc    6420
gacatacaat ttttcaaact ttttttttt cttggtgcac ggacatgttt ttaaaggaag     6480
tactctatac cagttattct tcacaaattt aattgctgga gaatagatct tcaacgcccc    6540
gggggatctg gatccgcggc cgctgagctc gtctgatatt tgctaaattg aaatgaacct    6600
taccatgcca catctataga catcaaaacc attttcaatt tgtcgatatc ttttgcatat    6660
caaagtaata ccaagcatgt tcaaaaagaa aagaaagcat aactttaata ctctattcga    6720
aacattccga tccacaacac attagtcttt ttaggcccgt tgttcatctt tctattactt    6780
tattcctaac tgtattttta taattccggg tttataaaag attaaactaa tatagcgcat    6840 tcttttggg tacaaacata cataacggag gttt                                 6874
```